US010138504B2

(12) United States Patent
Sillers et al.

(10) Patent No.: US 10,138,504 B2
(45) Date of Patent: Nov. 27, 2018

(54) PRODUCTION OF MALONYL-COA DERIVED PRODUCTS VIA ANAEROBIC PATHWAYS

(75) Inventors: William Ryan Sillers, Lebanon, NH (US); Shital A. Tripathi, Berkeley, CA (US); Arthur J. Shaw, IV, Grantham, NH (US); Aaron Argyros, White River Junction, VT (US); David A. Hogsett, Grantham, NH (US)

(73) Assignee: Lallemand Hungary Liquidity Management LLC, Budapest (HU)

( * ) Notice: Subject to any disclaimer, the term of this patent is extended or adjusted under 35 U.S.C. 154(b) by 75 days.

(21) Appl. No.: 13/814,616

(22) PCT Filed: Aug. 5, 2011

(86) PCT No.: PCT/US2011/046869
§ 371 (c)(1),
(2), (4) Date: Aug. 23, 2013

(87) PCT Pub. No.: WO2012/019175
PCT Pub. Date: Feb. 9, 2012

(65) Prior Publication Data
US 2013/0323766 A1    Dec. 5, 2013

Related U.S. Application Data

(60) Provisional application No. 61/371,582, filed on Aug. 6, 2010.

(51) Int. Cl.
*C12P 7/18* (2006.01)
*C12N 1/22* (2006.01)
*C12N 9/88* (2006.01)
*C12N 9/10* (2006.01)
*C12P 7/64* (2006.01)
*C12P 17/18* (2006.01)

(52) U.S. Cl.
CPC .............. *C12P 17/182* (2013.01); *C12N 1/22* (2013.01); *C12N 9/1018* (2013.01); *C12N 9/88* (2013.01); *C12P 7/6409* (2013.01); *G01N 2333/91034* (2013.01)

(58) Field of Classification Search
CPC .......... C12N 1/22; C12N 9/1018; C12N 9/88; C12P 7/6409; C12P 17/182; G01N 2333/91034
See application file for complete search history.

(56) References Cited

U.S. PATENT DOCUMENTS

| 5,252,466 | A | 10/1993 | Cronan, Jr. |
| 5,487,987 | A | 1/1996 | Frost et al. |
| 5,616,496 | A | 4/1997 | Frost et al. |
| 6,852,517 | B1 | 2/2005 | Suthers et al. |
| 7,011,959 | B1 | 3/2006 | Santi et al. |
| 7,186,541 | B2 | 3/2007 | Gokarn et al. |
| 7,393,676 | B2 | 7/2008 | Gokarn et al. |
| 7,638,316 | B2 | 12/2009 | Gokarn et al. |
| 7,799,545 | B2 | 9/2010 | Burgard et al. |
| 7,846,712 | B2 | 12/2010 | Zhang et al. |
| 8,034,591 | B2 | 10/2011 | Winkler et al. |
| 8,048,654 | B2 * | 11/2011 | Berry et al. ................. 435/134 |
| 8,048,976 | B2 | 11/2011 | McPhee |
| 8,062,871 | B2 | 11/2011 | Burgard et al. |
| 8,076,120 | B2 | 12/2011 | Gokarn et al. |
| 8,088,607 | B2 | 1/2012 | Burgard et al. |
| 8,097,439 | B2 | 1/2012 | Alibhai et al. |
| 8,217,128 | B2 | 7/2012 | McPhee |
| 8,247,201 | B2 | 8/2012 | Tajima et al. |
| 9,029,124 | B2 * | 5/2015 | Robertson et al. ........ 435/257.2 |
| 9,410,131 | B2 * | 8/2016 | Milo ................... C12N 9/0006 |
| 2004/0076982 | A1 | 4/2004 | Gokarn et al. |
| 2007/0184524 | A1 | 8/2007 | Gokarn et al. |

(Continued)

FOREIGN PATENT DOCUMENTS

| JP | WO 2009/072562_MT | * 6/2009 | ............... C12P 7/46 |
| WO | WO 95/07996 A1 | 3/1995 | |

(Continued)

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Kimchi-Sarfaty et al., A "Silent" polymorphism in the MDR1 gene changes substrate specificty. Science, 2007, vol. 315: 525-528.*

(Continued)

*Primary Examiner* — Ganapathirama Raghu
(74) *Attorney, Agent, or Firm* — Nutter McClennen & Fish LLP

(57) ABSTRACT

The present invention provides for novel metabolic pathways to convert biomass and other carbohydrate sources to malonyl-CoA derived products, such as hydrocarbons and other bioproducts, under anaerobic conditions and with the net production of ATP. More specifically, the invention provides for a recombinant microorganism comprising one or more native and/or heterologous enzymes that function in one or more engineered metabolic pathways to achieve conversion of a carbohydrate source to, e.g., long-chain hydrocarbons and hydrocarbon derivatives, wherein the one or more native and/or heterologous enzymes is activated, upregulated, downregulated, or deleted. The invention also provides for processes to convert biomass to malonyl-CoA derived products which comprise contacting a carbohydrate source with a recombinant microorganism of the invention.

30 Claims, 72 Drawing Sheets

Specification includes a Sequence Listing.

(56) References Cited

U.S. PATENT DOCUMENTS

| | | | |
|---|---|---|---|
| 2008/0076167 A1 | 3/2008 | Gokarn et al. | |
| 2008/0092829 A1 | 4/2008 | Renninger et al. | |
| 2008/0261287 A1 | 10/2008 | Winkler et al. | |
| 2008/0293060 A1 | 11/2008 | Schirmer et al. | |
| 2009/0053783 A1 | 2/2009 | Gokarn et al. | |
| 2009/0275097 A1 | 11/2009 | Sun et al. | |
| 2009/0305364 A1 | 12/2009 | Burgard et al. | |
| 2010/0056714 A1 | 3/2010 | McPhee | |
| 2010/0056743 A1 | 3/2010 | McPhee | |
| 2010/0068773 A1* | 3/2010 | Marx et al. | C12P 7/62 435/135 |
| 2010/0071259 A1 | 3/2010 | Hu et al. | |
| 2010/0105955 A1 | 4/2010 | Alibhai et al. | |
| 2010/0105963 A1 | 4/2010 | Hu | |
| 2010/0297716 A1 | 11/2010 | Tajima et al. | |
| 2010/0317822 A1 | 12/2010 | Boussie et al. | |
| 2010/0317823 A1 | 12/2010 | Boussie et al. | |
| 2010/0317825 A1 | 12/2010 | Boussie et al. | |
| 2010/0330626 A1 | 12/2010 | Burgard et al. | |
| 2011/0059485 A1 | 3/2011 | Caiazza et al. | |
| 2011/0125118 A1 | 5/2011 | Lynch | |
| 2011/0144377 A1 | 6/2011 | Eliot et al. | |
| 2011/0195466 A1 | 8/2011 | Burgard et al. | |
| 2011/0218318 A1 | 9/2011 | Boussie et al. | |
| 2011/0306790 A1 | 12/2011 | Murphy et al. | |
| 2012/0135481 A1* | 5/2012 | Jessen et al. | 435/141 |

FOREIGN PATENT DOCUMENTS

| | | |
|---|---|---|
| WO | WO 01/16346 A1 | 3/2001 |
| WO | WO 02/42418 A2 | 5/2002 |
| WO | WO 2006/009434 A1 | 1/2006 |
| WO | WO 2009/035595 A1 | 3/2009 |
| WO | WO 2009/072562 A1 | 6/2009 |
| WO | WO 2009/151728 A2 | 12/2009 |
| WO | WO 2010/144862 A2 | 12/2010 |
| WO | WO 2011/003034 A2 | 1/2011 |
| WO | WO 2011/063055 A2 | 5/2011 |
| WO | WO 2011/094457 A1 | 8/2011 |
| WO | WO 2011/140386 A2 | 11/2011 |

OTHER PUBLICATIONS

Kisselev L., Polypeptide release factors in prokaryotes and eukaryotes: same function, different structure. Structure, 2002, vol. 10: 8-9.*
Nackley et al., Human Caechol-O-Methyltransferase haplotypes modulate protein expression by altering mRNA secondary structure. Science, 2006, vol. 314: 1930-1933.*
Sauna et al., Silent polymorhisms speak: How they affect pharmacogenomics and the treatment of cancer. Cancer Res., 2007, vol. 67(20): 9609-9612.*
Seffernick et al., Melamine deaminase and Atrazine chlorohydrolase: 98 percent identical but functionally different. J. Bacteriol., 2001, vol. 183 (8): 2405-2410.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
Bar-Even et al., Design and analysis of synthetic carbon fixation pathways. PNAS, 2010, vol. 107 (19): 8889-8894.*
Enzyme Entry 2.1.3.1; one page downloaded from http://enzyme.expasy.org/ on Sep. 10, 2016.*
Murtif et al., Mutagenesis affecting carboxyl terminus of the biotinyl subunit of of transcarboxylase. The J. Biol. Chem., 1987, vol. 262 (24): 11813-11816.*
Shenoy et al., Effect of mutations at Met-88 and Met-90 on the biotination of apo 1.3S subunit of transcarboxylase. FASEB J., 1988, vol. 2: 2505-2511.*
Deok et al., Influence of gluconeogenic phosphoenolpyruvate carboxykinase (PCK) expression on succinic acid fermentation in *Escherichia coli* under high bicarbonate condition. J. Microbiol. Biotechnol., 2006, vol. 16(9): 1448-1452. (Year: 2006).*
Houwen et al., Enzymatic evidence for involvement of methylmalonyl-CoA pathway in propionate oxidation by Syntrophobacter wolinii. Arch Microbiol., 1990, vol. 155: 52-55. (Year: 1990).*
Millard et al., Enhanced production of succinic acid by overexpression of phosphoenolpyruvate carboxylase in *Escherichia coli*. Appl. Environ. Microbiol., 1996, vol. 62(5): 18108-1810. (Year: 1996).*
Aklujkar, M., et al., "The genome of *Geobacter bemidjiensis*, exemplar for the subsurface Glade of *Geobacter* species that predominate in Fe(III)-reducing subsurface environments," *BMC Genomics* 11:490, BioMed Central, England (Sep. 2010); 18 pages.
Aldai, N., et al., "Gas-liquid chromatographic method for analysing complex mixtures of fatty acids including conjugated linoleic acids (cis9trans11 and trans10cis12 isomers) and long-chain (n-3 or n-6) polyunsaturated fatty acids Application to the intramuscular fat of beef meat," *Journal of Chromotography A* 1110:133-39, Elsevier B.V., Netherlands (2006).
An, J.H. and Kim, Y. S., "A gene cluster encoding malonyl-CoA decarboxylase (MatA), malonyl-CoA synthetase (MatB) and a putative dicarboxylate carrier protein (MatC) in *Rhizobium trifolii*—Cloning, sequencing, and expression of the enzymes in *Escherichia coli*," *Eur. J. Biochem.* 257:395-402, FEBS, England (1998).
Van Beilen, J. B., et al., "Analysis of *Pseudomonas putida* alkane-degradation gene clusters and flanking insertion sequences: evolution and regulation of the alk genes," *Microbiol.* 147:1621-30, SGM, England (2001).
Beller, H. R., et al., "Genes Involved in Long-Chain Alkene Biosynthesis in *Micrococcus luteus*," *Appl. Environ. Microbiol.* 76(4):1212-23, American Society for Microbiology, United States (Feb. 2010); published ahead of print on Dec. 28, 2009.
Berrís-Rivera, S. J., et al., "Metabolic Engineering of *Escherichia coli*: Increase of NADH Availability by Overexpressing on $NAD^+$-Dependent Formate Dehyrodgenase," *Met. Eng.* 4:217-29, Elsevier Science, United States (2002).
Black, P. N. and Dirusso, C. C., "Transmembrane Movement of Exogenous Long-Chain Fatty Acids: Proteins, Enzymes, and Vectorial Esterification," *Microbiol. Mol. Biol. Rev.* 67(3):454-72, American Society for Microbiology, United States (2003).
Burgard, A. P., et al., "OptKnock: A Bilevel Programming Framework for Identifying Gene Knockout Strategies for Microbial Strain Optimization," *Biotech. Bioeng.* 84(6):647-57, Wiley Periodicals, Inc., United States (2003).
Carey, P. R., et al., "Transcarboxylase: One of Nature's Early Nanomachines," *IUBMB Life* 56(10):575-83, IUBMB, England (2004).
Davis, M. S. and Cronan, Jr., J. E., "Inhibition of *Escherichia coli* Acetyl Coenzyme A Carboxylase by Acyl-Acyl Carrier Protein," *J. Bacteriol.* 183(4):1499-1503, American Society for Microbiology, United States (2001).
Davis, M. S., et al., "Overproduction of Acetyl-CoA Caboxylase Activity Increases the Rate of Fatty Acid Biosynthesis in *Escherichia coli*," *J. Biol. Chem.* 275(37):28593-98, The American Society for Biochemistry and Molecular Biology, Inc., United States (2000).
Falentin, H., et al., "The Complete Genome of *Propionibacterium freudenreichii* CIRM-BIA1$^T$, a Hardy Actinobacterium with Food and Probiotic Applications," *PLOS One* 5(7): e11748, Public Library of Science, United States (Jul. 2010); 12 pages.
Heath, R. J. and Rock, C. O., "Regulation of Fatty Acid Elongation and Initiation by Acyl-Acyl Carrier Protein in *Escherichia coli*," *J. Biol. Chem.* 271(4):1833-36, The American Society for Biochemistry and Molecular Biology, Inc., United States (1996).
Höpner, T. and Knappe, J., "Determination with Formate Dehyorgenase," in Bergmeyer H. U. ed, *Methods of Enzymatic Analysis*, Ed 2, vol. 3, pp. 15515-1555, Academic Press, New York (1974).
Hügler, M., et al., "Malonyl-Coenzyme A Reductase from *Chloroflexus aurantiacus*, a Key Enzyme of the 3-Hydroxypropionate Cycle for

(56) References Cited

OTHER PUBLICATIONS

Autotrophic $CO_2$ Fixation," *J. Bacteriol.* 184(9):2402-10, American Society for Microbiology, United States (2002).
Inui, H., et al., "Wax ester fermentation in *Euglena gracilis,*" *FEBS Lett.* 150(1):89-93, Elsevier Biomedical Press, Netherlands (1982).
Inui, H., et al., "Fatty acid synthesis in mitochondria of *Euglena gracilis,*" *Eur. J. Biochem.* 142:121-26, FEBS, England (1984).
Jenke-Kodama, H., et al., "Evolutionary Implications of Bacterial Polyketide Synthases," *Mol. Biol. Evol.* 22(10):2027-39, Oxford University Press, England (2005).
Jeppsson, M., et al., "Reduced Oxidative Pentose Phosphate Pathway Flux in Recombinant Xylose-Utilizing *Saccharomyces cerevisiae* Strains Improves the Ethanol Yield from Xylose," *Appl. Environ. Microbiol.* 68(4):1604-09, American Society for Microbiology, United States (2002).
Kalscheuer, R. and Steinbüchel, A., "A Novel Bifunctional Wax Ester Synthase/Acyl-CoA:Diacylglycerol Acyltransferase Mediates Wax Ester and Triacylglycerol Biosynthesis in *Acinetobacter calcoaceticus* ADP1," *J. Biol. Chem.* 278(10):8075-82, The American Society for Biochemistry and Molecular Biology, Inc., United States (2003).
Kalscheuer., R., et al., "Microdiesel: *Escherichia coli* engineered for fuel Production," *Microbiol.* 152:2529-36, SGM, Great Britain (2006).
Karhumaa, K., et al., "Comparison of the xylose reductase-xylitol dehydrogenase and the xylose isomerase pathways for xylose fermentation by recombinant *Saccharomyces cerevisiae,*" *Microb. Cell. Fact.* 6:5, BioMed Central Ltd., England (2007); 10 pages.
Kieboom, J., et al., "Identification and Molecular Characterization of an Efflux Pump Involved in *Pseudomonas putida* S12 Solvent Tolerance," *J. Biol. Chem.* 273(1):85-91, The American Society for Biochemistry and Molecular Biology, Inc., United States (1998).
Kim, Y., et al., "Construction of an *Escherichia coli* K-12 Mutant for Homoethanologenic Fermentation of Glucose or Xylose without Foreign Genes," *Appl. Environ. Microbiol.* 73(6):1766-71, American Society for Microbiology, United States (2007); published ahead of print on Jan. 26, 2007.
Kosaka, T., et al., "The genome of *Pelotomaculum thermopropionicum* reveals niche-associated evolution in anaerobic microbiota," *Genome Res.* 18:442-48, Cold Spring Harbor Laboratory Press, United States (2008).
Kuyper M., et al., "Evolutionary engineering of mixed-sugar utilization by a xylose-fermenting *Saccharomyces cerevisiae* strain." *FEMS Yeast Res.* 5:925-34, Elsevier B.V., Netherlands (2005).
Kuyper M., et al., "Metabolic engineering of a xylose-isomerase-expressing *Saccharomyces cerevisiae* strain for rapid anaerobic xylose fermentation," *FEMS Yeast Res.* 5:399-409, Elsevier B.V., Netherlands (2005).
Kuyper M., et al., "Minimal metabolic engineering of *Saccharomyces cerevisiae* for efficient anaerobic xylose fermentation: a proof of principle," *FEMS Yeast Res.* 4:655-64, Elsevier B.V., Netherlands (2004).
Leal, T.F. and De Sá-Nogueira, I., "Purification, characterization and functional analysis of an endo-arabinanase (AbnA) from *Bacillus subtilis,*" *FEMS Microbiol. Lett.* 241:41-48, Elsevier B.V., Netherlands (2004).
Li, S-J. and Cronan, Jr., J. E., "Growth Rate Regulation of *Escherichia coli* Acetyl Coenzyme A Carboxylase, Which Catalyzes the First Committed Step of Lipid Biosynthesis," *J. Bacteriol.* 175(2):332-40, American Society for Microbiology, United States (1993).
Li, N., et al., "Conversion of Fatty Aldehydes to Alka(e)nes and Formate by a Cyanobacterial Aldehyde Decarbonylase: Cryptic Redox by an Unusual Di-metal Oxygenase," *J. Am. Chem. Soc.* 133(16):6158-61, ACS Publications, United States (Epub Apr. 2012).
Liang, S.-T., et al., "Activities of Constitutive Promoters in *Escherichia coli,*" *J. Mol Bio.* 292:19-37, Academic Press, United States (1999).
Liu, X., et al., "Two novel metal-independent long-chain alkyl alcohol dehydrogenases from *Geobacillus thermodenitrificans* NG80-2," *Microbiol.* 155:2078-85, SGM, Great Britain (2009).

Magnuson, K., et al., "Regulation of Fatty Acid Biosynthesis in *Escherichia coli,*" *Microbiol. Rev.* 57(3):522-42, American Society for Microbiology, United States (1993).
Matte, A., et al., "Structure and Mechanism of Phosphoenolpyruvate Carboxykinase," *J. Biol. Chem.* 272(13):8105-08, The American Society for Biochemistry and Molecular Biology, Inc., United States (1997).
Mota, L. J., et al., "Mode of action of AraR, the key regulator of L-arabinose metabolism in *Bacillus subtilis,*" *Mol. Microbiol.* 33(3):476-89, Blackwell Science Ltd., England (1999).
Mota, L. J., et al., "Control of the Arabinose Regulon in *Bacillus subtilis* by AraR In Vivo: Crucial Roles of Operators, Cooperativity, and DNA Looping," *J. Bacteriol.* 183(14):4190-201, American Society for Microbiology, United States (2001).
Nakamura, Y., et al. "Codon usage tabulated from international DNA sequence databases: status for the year 2000," *Nucl. Acids Res.* 28(1):292, Oxford University Press, England (2000).
National Microbial Pathogen Data Resource, SEED Subsystem: L-Arabinose_utilization, accessed at http://www.nmpdr.org/FIG/subsys.cgi?user=&ssa_name=L-Arabinose_utilization&request=show_ssa, accessed on Jun. 11, 2013.
Neumann, G., et al., "Prediction of the Adaptability of *Pseudomonas putida* DOT-TIE to a Second Phase of a Solvent for Economically Sound Two-Phase Biotransformations," *Appl. Environ. Microbiol.* 71(11):6606-12, American Society for Microbiology, United States (2005).
Pelletier, E., et al.,"'*Candidatus* Cloacamonas Acidaminovorans': Genome Sequence Reconstruction Provides a First Glimpse of a New Bacterial Division," *J. Bacteriol.* 190(7):2572-79, American Society for Microbiology, United States (2008).
Peralta-Yahya, P. P. and Keasling, J. D., "Advanced biofuel production in microbes," *Biotechnol. J.* 5:147-62, Wiley-VCH Verlag GmbH & Co. KGaA, Germany (Feb. 2010).
Picataggio, S., et al., "Metabolic Engineering of *Candida tropicalis* for the Production of Long-Chain Dicarboxylic Acids," *Bio/Technology* 10:894-98, Nature Pub. Co., United States (1992).
Rathnasingh, C., et al., "Development and Evaluation of Efficient Recombinant *Escherichia coli* Strains for the Production of 3-Hydroxypropionic Acid From Glycerol," *Biotech. Bioeng.* 104(4):729-39, Wiley Periodicals, Inc., United States (2009).
Rathnasingh, C., et al., "Production of 3-hydroxy,ropionic acid via malonyl-CoA pathway using recombinant *Escherichia coli* strains," *J. Biotech.* 157:633-40, Elsevier B.V., Netherlands (2012).
Reiser, S. and Somerville, C., "isolation of Mutants of *Acinetobacter calcoaceticus* Deficient in Wax Ester Synthesis and Complementation of One Mutation with a Gene Encoding a Fatty Acyl Coenzyme A Reductase," *J. Bacteriol.* 179(9):2969-75, American Society for Microbiology, United States (1997).
Rodolfi, L., et al., "Microalgae for Oil: Strain Selection, Induction of Lipid Synthesis and Outdoor Mass Cultivation in a Low-Cost Photobioreactor," *Biotech. Bioeng.* 102(1):100-12, Wiley Periodicals, Inc., United States (2009).
Sá-Nogueira I., et al., "The *Bacillus subtilis* L-arabinose (ara) operon: nucleotide sequence, genetic organization and expression," *Microbiol.* 143:957-69, SGM, Great Britain (1997).
Sauer, U., "Evolutionary Engineering of Industrially Important Microbial Phenotypes," *Advances in Biochemical Engineering/Biotechnology* 73:129-69, Spenger-Verlag, Germany (2001).
Schleif, R., "Regulation of the L-arainose operon of *Escherichia coli,*" *Trends Genet.* 16(12):559-65, Elsevier Science Ltd., England (2000).
Shanks, R. M. Q., et al., "*Saccharomyces cerevisiae*-Based Molecular Tool Kit for Manipulation of Genes from Gram-Negative Bacteria," *Appl. Environ. Microbiol.* 72(7):5027-36, American Society for Microbiology, United States (2006).
Shaw, A. J. et al., "Natural Competence in *Thermoanaerobacter* and *Thermoanaerobacterium* Species," *Appl. Environ. Microbiol.* 76(14):4713-19, American Society for Microbiology, United States (Jul. 2010); published ahead of print on May 14, 2010.
Steen, E. J., et al., "Microbial production of fatty-acid-derived fuels and chemicals from plant biomass," *Nature* 463:559-62, Macmillan Publishers Limited, England (Jan. 2010).

(56) References Cited

OTHER PUBLICATIONS

Sukovich, D. J., et al., "Widespread Head-to-Head Hydrocarbon Biosynthesis in Bacteria and Role of OleA," *Appl. Environ. Microbiol.* 76(12):3850-62, American Society for Microbiology, United States (Jun. 2010); published ahead of print on Apr. 23, 2010.

Suwannakham, S. and Yang, S-T., "Enhanced Propionic Acid Fermentation by *Propionibacterium acidipropionici* Mutant Obtained by Adaptation in a Fibrous-Bed Bioreactor," *Biotech. Bioeng.* 91(3):325-37, Wiley Periodicals, Inc., United States (2005).

Tsuruta, H., et al., "High-Level Production of Amorpha-4,11-Diene, a Precursor of the Antimalarial Agent Artemisinin, in *Escherichia coli*," *PLOS One* 4(2):e4489, Public Library of Science, United States (2009); 12 pages.

Vanhanen S., et al., "A Consensus Sequence for Long-chain Fatty-acid Alcohol Oxidases from *Candida* Identifies a Family of Genes Involved in Lipid ω-Oxidation in Yeast with Homologues in Plants and Bacteria," *J. Biol. Chem.* 275(6):4445-52, The American Society for Biochemistry and Molecular Biology, Inc., United States (2000).

Wahlen, B. D., et al., "Purification, Characterization, and Potential Bacterial Wax Production Role of an NADPH-Dependent Fatty Aldehyde Reductase from *Marinobacter aquaeolei* VT8," *Appl. Environ. Microbiol.* 75(9):2758-64, American Society for Microbiology, United States (2009); published ahead of print on Mar. 6, 2009.

Van Walsum, G. P. and Lynd, L. R., "Allocation of ATP to Synthesis of Cells and Hydrolytic Enzymes in Cellulolytic Fermentative Microorganisms: Bioenergetics, Kinetics, and Bioprocessing," *Biotech. Bioeng.* 58(2-3):316-20, John Wiley & Sons, Inc., United States (1998).

Wang, L., et al., "Isolation and characterization of a novel thermophilic *Bacillus* strain degrading long-chain n-alkanes," *Extremophiles* 10:347-56, Springer-Verlag, Germany (2006).

Watanabe, S., et al., "Cloning, Expression, and Characterization of Bacterial L-Arabinose 1-Dehydrogenase Involved in an Alternative Pathway of L-Arabinose Metabolism," *J. Biol. Chem.* 281(5):2612-23, The American Society for Biochemistry and Molecular Biology, Inc., United States (2006).

Whited, G. M., et al., "Development of a gas-phase bioprocess for isoprene-monomer production using metabolic pathway engineering," *Industrial Biotechnology* 6(3):152-63, Mary Ann Liebert, Inc., United States (Jun. 2010).

Wood, H. G. and Stjernholm, R., "Transcarboxylase, II. Purification and Properties of Methylmalonyl-Oxaloacetic Transcarboxylase," *PNAS.* 47:289-303, National Academy of Sciences, United States (1961).

Yan, Y. and Liao, J. C., "Engineering metabolic systems for production of advanced fuels," *J. Ind. Microbiol. Biotechnol.* 36:471-79, Springer, England (2009).

Zelle R. M., et al., "Phosphoenolpyruvate Carboxykinase as the Sole Anaplerotic Enzyme in *Saccharomyces cerevisae*," *Appl. Environ. Microbiol.* 76(16):5383-89, American Society for Microbiology, United States (Aug. 2010); published ahead of print on Jun. 25, 2010.

Zhang, X at al., "Metabolic evolution of energy-conserving pathways for succinate production in *Escherichia coli*," *PNAS.* 106(48):20180-85, National Academy of Sciences, United States (2009).

International Search Report for International Application No. PCT/US2011/046869, European Patent Office, Netherlands, dated Feb. 24, 2012; 9 pages.

Accession No. AAS20429, NCBI Database, Hugler, M. and Fuchs, G., accessed at www.ncbi.nlm.nih.gov/protein/AAS20429, accessed on Jun. 11, 2013; 2 pages.

Accession No. YP_001636209.1, NCBI Database, Copeland, A., et al., accessed at www.ncbi.nlm.nih.gov/protein/YP_001636209.1, accessed on Jun. 11, 2013; 3 pages.

Accession No. YP_002570540, NCBI Database, Lucas, S., et al., accessed at www.ncbi.nlm.nih.gov/protein/YP_002570540, accessed on Jun. 11, 2013; 3 pages.

Accession No. YP_002462600, NCBI Database, Lucas, S., et al., accessed at www.ncbi.nlm.nih.gov/protein/YP_002462600, accessed on Jun. 11, 2013; 3 pages.

Accession No. ZP_07684596.1, NCBI Database, Kuznetsov, B. B. and Beletsky, A. V., accessed at www.ncbi.nlm.nih.gov/protein/ZP_07684596.1?report=genpept, accessed on Jun. 11, 2013; 2 pages.

Accession No. YP_001433009, NCBI Database, Copeland, A., et al., accessed at www.ncbi.nlm.nih.gov/protein/YP_001433009, accessed on Jun. 11, 2013; 3 pages.

Accession No. YP_001277512, NCBI Database, Copeland, A., et al., accessed at www.ncbi.nlm.nih.gov/protein/YP_001277512, accessed on Jun. 11, 2013; 3 pages.

Accession No. ZP_01039179.1, NCBI Database, Falkowski, P., et al., accessed at www.ncbi.nlm.nih.gov/protein/ZP_01039179.1?report=genpept, accessed on Jun. 11, 2013; 2 pages.

Accession No. ZP_04957196.1, NCBI Database, Amann, R., et al., accessed at www.ncbi.nlm.nih.gov/protein/ZP_04957196.1?report=genpept, accessed on Jun. 11, 2013; 2 pages.

Accession No. U00096.2, NCBI Database, Blattner, F.R., et al., accessed at www.ncbi.nlm.nih.gov/nuccore/U00096, accessed on Jun. 11, 2013; 119 pages.

\* cited by examiner

Figure 1
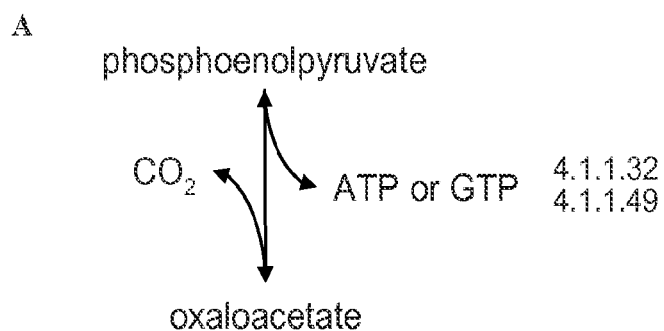
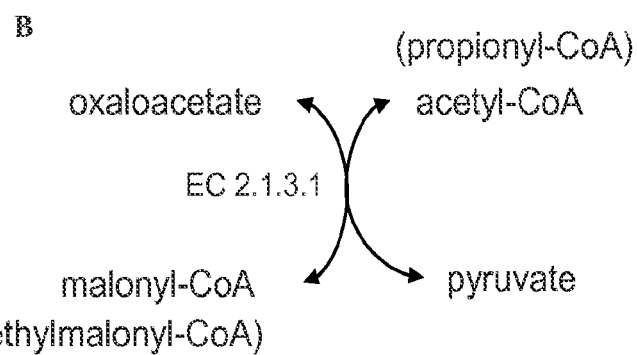

Figure 2
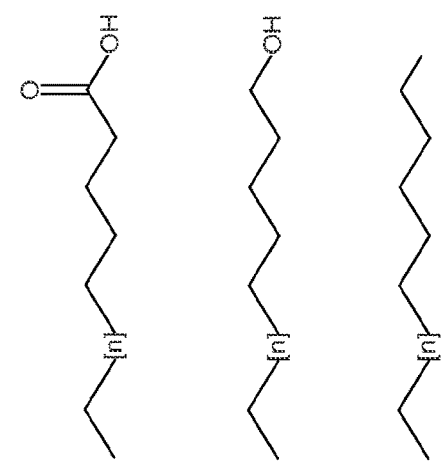
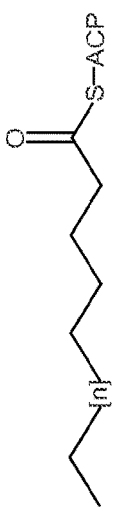
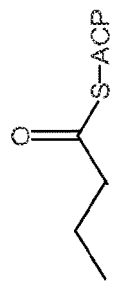

Figure 7A

Transcarboxylase 5S subunit

```
                                         1                                                50
SEQ. ID NO. 11:   Pfreud 5S       (1)    MSPREIEVSE....VG....LV..RDAHQS..MAT..AMED..GACA........
SEQ. ID NO. 19:   Pacnes 5S       (1)    --------MSPRKIGV..DLV..RDAHQS..IAT..AMED..VDACA........
SEQ. ID NO. 25:   Cthe_0701       (1)    -----------MAKVKI....T..RDAHQS..IAT..RIEE..LPIIDKL....
SEQ. ID NO. 33:   Tsacch or1888   (1)    -----------MSKIKI..ETV..RDAHQS..LATR..TDE..LPI..EKL...

51                                               100
SEQ. ID NO. 11:   Pfreud 5S      (51)    W.V...GGAT.............NEDEWER...TFRKLMPNS...OM..RGQN...G.
SEQ. ID NO. 19:   Pacnes 5S      (43)    W.V...GGAT.............NEDEWER...TFRKLLPNSR..OM..RGQN...G.
SEQ. ID NO. 25:   Cthe_0701      (41)    H.L....GGA............NEDEWER....I.SHCK..TP..OM..RGQN...G.
SEQ. ID NO. 33:   Tsacch or1888  (41)    ..I....GGAT..AC.M..L.NEDEWER...L.KKALKKTP..OM..RGQN...G.

101                                              150
SEQ. ID NO. 11:   Pfreud 5S     (101)    R....V.DR.V....NGMDV...DA..N...MAHAMAAV.KA....A.
SEQ. ID NO. 19:   Pacnes 5S     (93)     R....V.DK.V.KS..NGMDV...DA..N...LEHAMAAV.K......
SEQ. ID NO. 25:   Cthe_0701     (91)     K..AL.VVEY.V..KSVA..C..III......ETAIKAC..KF..G..
SEQ. ID NO. 33:   Tsacch or1888 (91)     K...P.VW...I....VE..GIDII....DA..V..LEVPIKS..A..

151                                              200
SEQ. ID NO. 11:   Pfreud 5S     (151)    GTIG..IS.V.TVEGYV..G..LI..GADS..ILK..AAIL.KQPA.E..
SEQ. ID NO. 19:   Pacnes 5S     (143)    GTIG..TS.I.TPESFV..R.I..GADS...K.AAL.KQPA.E..
SEQ. ID NO. 25:   Cthe_0701     (141)    GTVC..ISL.V..LELP..DAKT..VE..GADS..VK.LAG..L.Y..
SEQ. ID NO. 33:   Tsacch or1888 (141)    A.IV..VSEV...DHY..KVKS..QD.GADS..CI.DY.SGI..Y..

201                                              250
SEQ. ID NO. 11:   Pfreud 5S     (201)    AI..D.YGQF..Q....S...VT.VSLM.ATAGV..V.DT.SMSLG
SEQ. ID NO. 19:   Pacnes 5S     (193)    GIKENH-P.VQ......S..VTLVLQ.ATAGV.W..TS.SMSLG
SEQ. ID NO. 25:   Cthe_0701     (191)    AL.ENV--KVP..I.....SV.SMTY.KAT.AG..V..D.A.S.MSM.TS
SEQ. ID NO. 33:   Tsacch or1888 (191)    S..K.AL--Y.P..........LA.SMTYL.AT.DG..V..G.DT.AT.SLAL.TS 251                                              300
SEQ. ID NO. 11:   Pfreud 5S     (251)    .NP..SV.EM...G..T..I...YDR.HK..RDH..KAIRPYKKKFESKTLVDT
SEQ. ID NO. 19:   Pacnes 5S     (242)    .NF..SLVEM...G.E..R...MDR.L..RDH..KVKEKYKKKFESKTLVNT
SEQ. ID NO. 25:   Cthe_0701     (239)    QPP....LVAT..KG..P..D..LLD..S..AD...PLKEKYI.EGLLDVKVM
SEQ. ID NO. 33:   Tsacch or1888 (239)    QPA..S.VAA..K...Y.D..G...L..A....VVKQ..HK..D..MSLLMS 301                                              350
SEQ. ID NO. 11:   Pfreud 5S     (301)    ---S-I.KS..I..PGGMLS..ME.Q..RAQ..EDKMD..MA..VERVR.KAA...T.
SEQ. ID NO. 19:   Pacnes 5S     (292)    ---N-I..S..T..PGGMLS..ME.Q...AQL.GDRMDE..MK..VERVR.KD...Y.
SEQ. ID NO. 25:   Cthe_0701     (289)    GVDVNTLKY..V..PGGMLS..N..V.SQ.KC..NAVDK..EEV.L.VPRV..DR.YP.
SEQ. ID NO. 33:   Tsacch or1888 (289)    -VDVKAL..S..L..PGGMLS..N.VGQ.KQQN.L.KY.D..LK..VPRV...DI..P.

351                                              400
SEQ. ID NO. 11:   Pfreud 5S     (347)    LV.T..S.Q..VGTOAV..NV..MG----.RMTG..FADTMI..TT.CA.PADRP..V
SEQ. ID NO. 19:   Pacnes 5S     (338)    LV.T..S.I..VGTOAV..NV.LMENGS..NLTA..FADLMI...K.PIGELNPEI
SEQ. ID NO. 25:   Cthe_0701     (339)    LV.F...CI..VGTOAVLN..VT.-ER..MV..K..SKALTKG..KGR..FAPVNPEV
SEQ. ID NO. 33:   Tsacch or1888 (338)    LV.T...C..VGVOAL..L..V.-ERK..IV...KDYVK....K.MPPAPI.SD..

401                                              450
SEQ. ID NO. 11:   Pfreud 5S     (395)    VKLAE..QSGK.F..TQ..PAD.ILP..EWEEQ...EAAALKGFNGT..EDV.T..A.
SEQ. ID NO. 19:   Pacnes 5S     (388)    V..MAKKCTGKEF..DC..PAD.ILE..EWD.LV.QAK..L.GFDG..EDV.T.NA.
SEQ. ID NO. 25:   Cthe_0701     (388)    QKKILK--..EF..TV..PADTE..ELD..IRN---EMKEYLEQ..DDV.E.Q..
SEQ. ID NO. 33:   Tsacch or1888 (387)    RKKIIG--...EV..SK..PAD..L...LDE..KN---EIKEFIEQ..DDV.SYA.

451                                              500
SEQ. ID NO. 11:   Pfreud 5S     (445)    ..QVPV...PH..AEGPHSVALTDAQLKA...GDEKSLAVAGPVTYNVVG
SEQ. ID NO. 19:   Pacnes 5S     (438)    ..G.V.PK....F..AQGFKSVAMTEAQLKA.K..G-TGAAGIAGPVNYNVTVG
SEQ. ID NO. 25:   Cthe_0701     (433)    ...Q.VEK..F..YR.KAQKYL.TEPDM..Y..NRVHPV------------
SEQ. ID NO. 33:   Tsacch or1888 (432)    ...Q.VRR..FEY..QAKKYPIDSTLLNI..ERVHPI------------

501      511
SEQ. ID NO. 11:   Pfreud 5S     (495)    GTVREVTVQQA
SEQ. ID NO. 19:   Pacnes 5S     (487)    GNSHQVT.EPA
SEQ. ID NO. 25:   Cthe_0701     (466)    -----------
SEQ. ID NO. 33:   Tsacch or1888 (465)    -----------
```

Figure 7B

Transcarboxylase 1.3S subunit

```
                                    1                                                 50
SEQ. ID NO. 8:   Pfreud 1.3S   (1)  -MKLKVT TGTA  L DVDKSHENFMGTILFGGG GGAPAPRAA GAG-
SEQ. ID NO. 19:  Pacnes 1.3S   (1)  -MELKVT N VA  D DVDKTANAPMAPILFGGAG--- PMKASGGG-
SEQ. ID NO. 33:  Cthe_0700     (1)  MK  LI  GNQ   EEIR GASAPQVT STP AAPAPGPAPA E KT
SEQ. ID NO. 31:  Tsacch or0947 (1)  MK TIVT GKK   E EVK  VA EKKAKE TAAKNA ASVKSK---
                                    51                                                100
SEQ. ID NO. 8:   Pfreud 1.3S   (49) --------AGKAGEGEIP  LA  TVSKILV  D  KA QV  V  AMK 
SEQ. ID NO. 19:  Pacnes 1.3S   (46) --------AGKAGEGEVP  LA  VAKTLVA  D  KA QVI T  AMK 
SEQ. ID NO. 33:  Cthe_0700     (51) AAPKKDS VPAGATAIK  MF  IL TRV  D  KK QVI T  AMK 
SEQ. ID NO. 31:  Tsacch or0947 (48) QVEV N--EVK GF IN  MP  IL VKTSQ    RR  VI T  AMK 
                                    101                              132
SEQ. ID NO. 8:   Pfreud 1.3S   (92)  T NA T   VE VI   RDA  QG  QG    IG
SEQ. ID NO. 19:  Pacnes 1.3S   (89)  T NA A  TVK IL  AVGDA QG  QG  VALG
SEQ. ID NO. 33:  Cthe_0700    (101)   VA N  TVASIN SKGAS NV  V  VSLK
SEQ. ID NO. 31:  Tsacch or0947 (96)   T SS YD TIISIN SKGAS NT  V  LYLK
```

Figure 7C

Transcarboxylase 12S subunit (N-terminus)

```
                                              1                                                  50
SEQ. ID NO. 14:  Pfreud 12S-N    (1)   MAENNNIKLASTMEGRVEQ AE RQVIEA   G  RVE H    Q A E
SEQ. ID NO. 17:  Pacnes 12S      (1)   MAEKKPIKLADTMAGRIEQ AD RH VEL   DRL  D  A A E
SEQ. ID NO. 21:  Cthe_0699       (1)   ---------MDKV KIGL REKLAQVEQ   AEKTA H DA M A E
SEQ. ID NO. 29:  Tsacch or0945   (1)   ---------MSID    L RREMVLE   LDKVE H  GKL A E
                                              51                                                 100
SEQ. ID NO. 14:  Pfreud 12S-N   (51)   LNN   PHS D VGAFRKH TTL  G D AVV AD VT GRGT  L RP  
SEQ. ID NO. 17:  Pacnes 12S     (51)   I N   AYS D VGAFRKH TTL  V A  V A  VT GRAT  L R HI
SEQ. ID NO. 21:  Cthe_0699      (41)   IQA   F  V I  FV T  ID    KKV G  VT YGS  G L   V
SEQ. ID NO. 29:  Tsacch or0945  (41)   IY       V I  AYV L CID G    QF E  VT YGT  D GRL  IV
                                              101                                                150
SEQ. ID NO. 14:  Pfreud 12S-N  (101)   AS  Q    M G AG QST VV TMEQALLT   ELFFY DSCGAR QE   
SEQ. ID NO. 17:  Pacnes 12S    (101)   AS  Q    M G AG QST VV TMEQSLLT   PLFFY DSCGAR QE   
SEQ. ID NO. 21:  Cthe_0699     (91)    AA  Q     G S  E MA K I DMAMKM   FIS  DSCGAP  E L
SEQ. ID NO. 29:  Tsacch or0945 (91)    YA  Q    V G S L Y LA K I KI DMALKM   I G  DSCGAR QE GV
                                              151                                                200
SEQ. ID NO. 14:  Pfreud 12S-N  (151)   S   V   M  A VKL GV VR  A I A   GGA  G AL DT  M --K A
SEQ. ID NO. 17:  Pacnes 12S    (151)   S   V KM  YA VKL GV VR  A I A   GGA K AL DT  M --K A
SEQ. ID NO. 21:  Cthe_0699     (141)   A   G    IYR  LA   I  Q  SV    GGA V  P L DT  MVDKTS
SEQ. ID NO. 29:  Tsacch or0945 (141)   A   G V  I FR  LA   V  Q  SV    GGA V  P L DT  MVDKTS
                                              201                                                250
SEQ. ID NO. 14:  Pfreud 12S-N  (200)   V   GG V  K V  GE  TADE GGA E MA   GN   VAEDDDA E IA
SEQ. ID NO. 17:  Pacnes 12S    (200)   V   GG V  K V  GE VTADD GGA  MST GNE   VAEDDDA VL IA
SEQ. ID NO. 21:  Cthe_0699     (191)   Q   GG V  K V  GE DV FE  GGAET NSI VA TRS   E  CIEQI
SEQ. ID NO. 29:  Tsacch or0945 (191)   Q   GG V  K A  GE V SAEE GG  SIT STK  VA  RAE DEECLKM
                                              251                                                300
SEQ. ID NO. 14:  Pfreud 12S-N  (250)   K  ILS       DEEAS VN N  VSPNTE -  RD V  LDG  G  VRDVHIA
SEQ. ID NO. 17:  Pacnes 12S    (250)   K  ILS    N  PEDAQISN ND VSPQ E -  RD V  LDG  G  VRDVIS
SEQ. ID NO. 21:  Cthe_0699     (241)   KK ISY   N  LSD PIVPTQD  I RITDNI VD   QD N P  MMEI T
SEQ. ID NO. 29:  Tsacch or0945 (241)   R  ILS Y   N  LEDPPQLAT DD   RFSDR IE  D  PN   D REV S
                                              301                                                350
SEQ. ID NO. 14:  Pfreud 12S-N  (299)   K   EDYL  AGY T L VTA A V  R  V  VAN    MS    INA 
SEQ. ID NO. 17:  Pacnes 12S    (299)   KI  WDYL V AGW TV IVTA A V  RL V  VAN   KMS   L IAS
SEQ. ID NO. 21:  Cthe_0699     (291)   V    D F   I QK  A N IIG G MN GT V  VANQE K AA G V NS 
SEQ. ID NO. 29:  Tsacch or0945 (291)    L  VY L  SQAMYA N ITA A A RL N K VC  LAN  KVLA G   AS
                                              351                                                400
SEQ. ID NO. 14:  Pfreud 12S-N  (349)   KAA  V T  S   N LVQLV  P   VG  YG  I RHG    YAYS 
SEQ. ID NO. 17:  Pacnes 12S    (349)   KAA   IT   PN L LVQL V    VG  YG  I RHGA    YS 
SEQ. ID NO. 21:  Cthe_0699     (341)   KAA  VR  A  N  IIT   V G L GVG  H  VI  HGA L AYA S 
SEQ. ID NO. 29:  Tsacch or0945 (341)   KAS  TR   A N   LLNIV  P     N  YG  I RHGAAM YA S 
                                              401                                                450
SEQ. ID NO. 14:  Pfreud 12S-N  (399)   ATVP ITVVL KA GG  I A C RL GADA   AV  AETAVM A F AAN 
SEQ. ID NO. 17:  Pacnes 12S    (399)   ATVP KITVVL KA GGS  A C  RL GADA  A  GA AVM GA DAAN 
SEQ. ID NO. 21:  Cthe_0699     (391)   ATW   LVIV KA GG  I A NSK  GADM   V  ETAVM PI CAA T
SEQ. ID NO. 29:  Tsacch or0945 (391)   ATVP VTLIVR KA GGA   AM  SK   GAP F   AW  ETAVM   CAAN I
                                              451                                                500
SEQ. ID NO. 14:  Pfreud 12S-N  (449)   I  RKE  KAAR D  DAM  AE K    E   NA NT  V   GQ DV I   AD  R
SEQ. ID NO. 17:  Pacnes 12S    (449)   I RR   KDSED  AT AAKN   RNA  T  V  A R QVD ID AD  RR
SEQ. ID NO. 21:  Cthe_0699     (441)   I KKD   AAAD   MET  K  L   R K      A   V  I  AT  I
SEQ. ID NO. 29:  Tsacch or0945 (441)   V K P KSSDD VAT NEK I  RENG A   R AAR G  VID VL QF  RP
                                              501              526
SEQ. ID NO. 14:  Pfreud 12S-N  (499)   KIAS  LEMYAT  QT   A KK CNF C
SEQ. ID NO. 17:  Pacnes 12S    (499)   KITA  LETYAT  QS  A K  GV  C
SEQ. ID NO. 21:  Cthe_0699     (491)   RLTS  LEMLAS       A KK N  L
SEQ. ID NO. 29:  Tsacch or0945 (491)   RLT   MLMS  S   KK  GNF  V
```

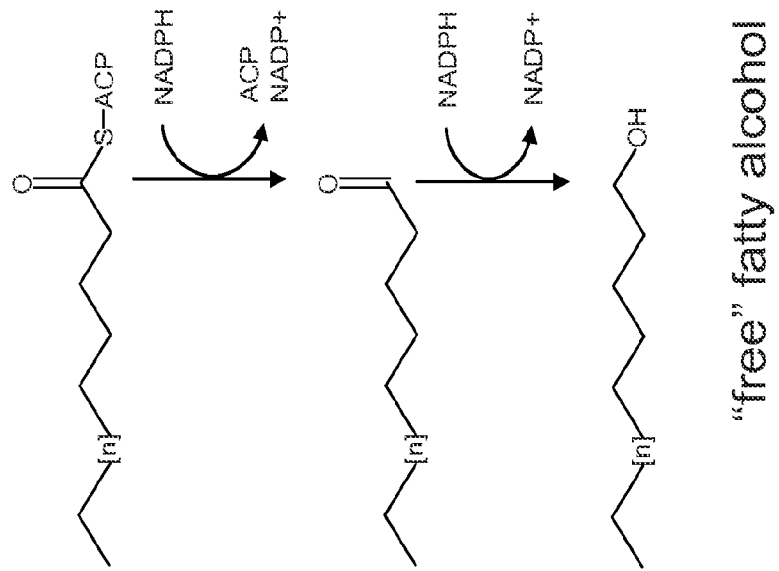
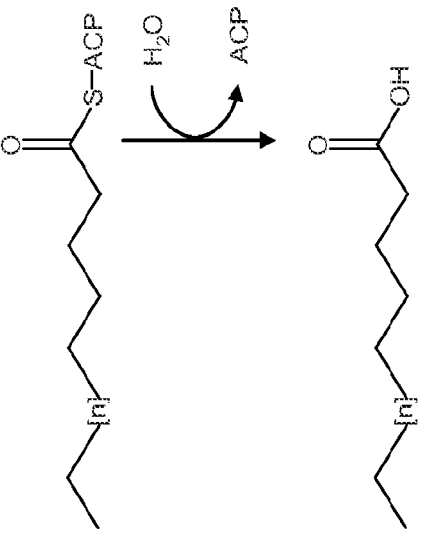
Figure 13

Figure 21
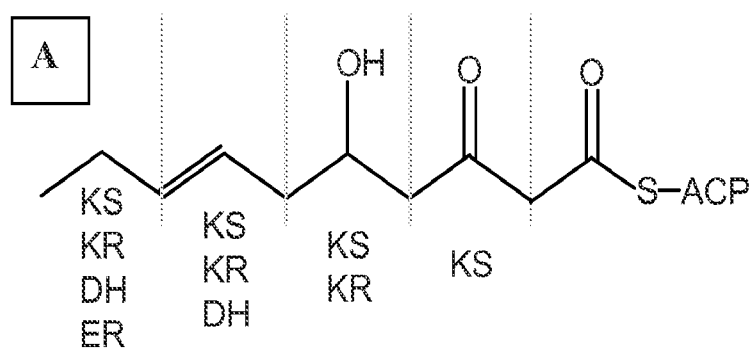
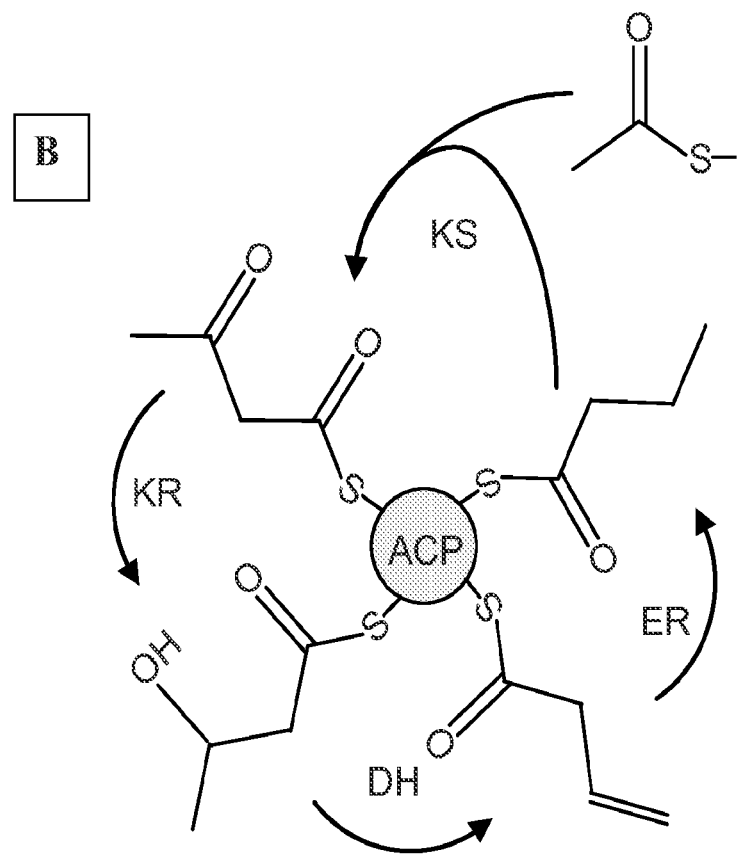

Figure 22A

|        | pMU690 | pMU3061 | pMU3062 | pMU3063 | pMU3064 |
|--------|--------|---------|---------|---------|---------|
| Sum    | 45     | 154     | 201     | 39      | 54      |
| 12:0   | 0.00   | 49.53   | 2.82    | 0.25    | 0.25    |
| 14:0   | 1.94   | 1.88    | 70.37   | 3.57    | 1.76    |
| 14:1   | 0.00   | 15.92   | 2.56    | 0.16    | 0.14    |
| 15:0   | 0.00   | 0.00    | 0.43    | 0.14    | 0.00    |
| 15:1   | 0.00   | 0.00    | 0.00    | 0.00    | 0.00    |
| 16:0   | 21.87  | 5.39    | 19.30   | 12.41   | 20.21   |
| 16:1w5 | 0.00   | 0.00    | 0.00    | 0.00    | 0.00    |
| 16:1w7 | 5.74   | 4.01    | 75.74   | 6.28    | 5.57    |
| 17:0   | 0.49   | 0.38    | 0.52    | 0.37    | 0.34    |
| 17:1   | 5.76   | 1.85    | 3.21    | 4.93    | 5.72    |
| 18:0   | 1.76   | 1.94    | 1.72    | 1.37    | 2.19    |
| 18:1w9 | 0.37   | 0.54    | 0.16    | 0.14    | 0.17    |
| 18:1w7 | 5.73   | 10.16   | 7.53    | 5.36    | 12.13   |
| 18:2w6 | 0.00   | 0.36    | 7.65    | 0.34    | 0.35    |
| 20:0   | 0.00   | 0.00    | 0.00    | 0.00    | 0.00    |
| 20:1w9 | 0.00   | 0.00    | 0.49    | 0.00    | 0.27    |
| 20:2w6 | 0.00   | 0.00    | 3.64    | 0.00    | 0.00    |
| 20:3w6 | 0.00   | 0.00    | 1.33    | 0.00    | 0.00    |
| 20:5w3 | 0.00   | 0.00    | 1.05    | 0.00    | 0.00    |
| 22:0   | 0.00   | 0.00    | 0.00    | 0.00    | 0.00    |
| 22:1w9 | 0.30   | 0.13    | 0.29    | 0.23    | 0.22    |
| 24:0   | 0.00   | 0.00    | 0.00    | 0.00    | 0.00    |
| other  | 0.57   | 61.53   | 2.05    | 3.72    | 4.42    |

Figure 27
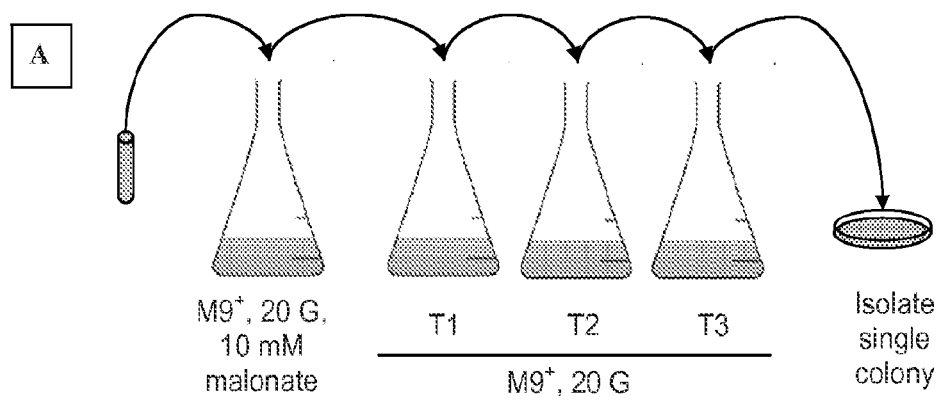
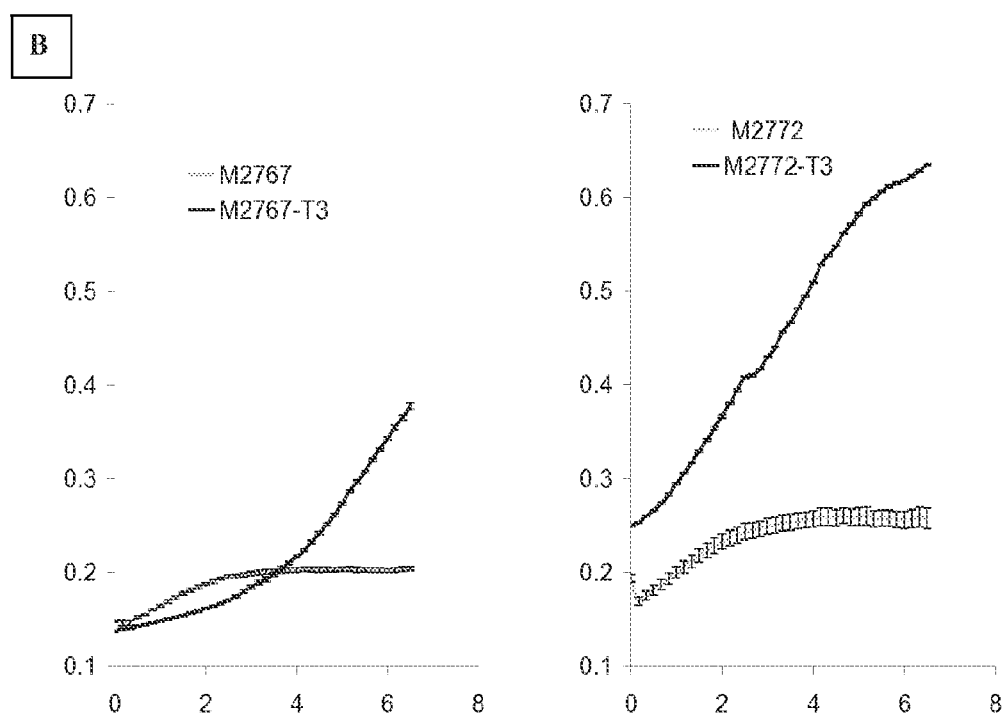
|  | μmax | SD |
|---|---|---|
| M2767 | 0.005 | 0.00 |
| M2767-T3 | 0.24 | 0.00 |
|  | μmax | SD |
|---|---|---|
| M2772 | 0.01 | 0.00 |
| M2772-T3 | 0.18 | 0.00 |

Figure 31

12S subunits

| | | | 1 | 50 |
|---|---|---|---|---|
| SEQ. ID NO. 67: | D.propionicus_12S | (1) | ----------MSTKEKLEIEQKEAKALLEGQDNDNIIISQGRYR | |
| SEQ. ID NO. 51: | C.kroppenstedtii_12S | (1) | MSEQ---PHDPSMPEHGELLKERNIRLLEQAFLEPKGDRIKCCR | |
| SEQ. ID NO. 14: | P.feudenreichii_12S | (1) | MAENNNLKLASTIEGRVEQEAKQRQVIEACGERRVEKEIIQIKQZR | |
| SEQ. ID NO. 59: | G.bemidjiensis_12S | (1) | ----------MSIEEKKRAINEKFSEIKLEGRSKIDOGEQESITR | |
| SEQ. ID NO. 37: | C.bescii_12S | (1) | ----------MTINIGREICKEEAILKLEESVTKKKQSKKLER | |
| SEQ. ID NO. 45: | C.cellulolyticum_12S | (1) | ----------MSQIEKEQKINMEKTIAKEEQKEAKPIADGESEAR | |
| SEQ. ID NO. 31: | C.thermocellum_12S | (1) | ----------MDKVEKGLIEKKLACYEQICAEEIAKEIDAGKMTR | |
| SEQ. ID NO. 29: | T.saccharolyticum_12S | (1) | ----------MSIDDRKEDILRKEEMILEGEGLLKYEKEQKEGIR | |
| | Consensus | (1) |     MSM EKI QLKEKR KI GGG DKIDKQHA GKLTARER | |
| | | | 51 | 100 |
| SEQ. ID NO. 67: | D.propionicus_12S | (41) | QLEIEPGILYEAKLEAGYNGVEIKFFSDGIVTGKIACGKPVVI | |
| SEQ. ID NO. 51: | C.kroppenstedtii_12S | (48) | TKILEDDAQTGMEAKGTTLGEPADAPALIVIGGSALYEPFINA | |
| SEQ. ID NO. 14: | P.feudenreichii_12S | (51) | DNNIIEPHSGDVGAFRNRTTLGELDRAVVEADSEVIGEPLEHA | |
| SEQ. ID NO. 59: | G.bemidjiensis_12S | (41) | TEAPILKDSEQKIGIFARRTNGGAGKEIGEVLEASEIGEMVIE | |
| SEQ. ID NO. 37: | C.bescii_12S | (39) | IEYDILPGSINEILMEELDKQEFYGLEEVIGESTINEKVFV | |
| SEQ. ID NO. 45: | C.cellulolyticum_12S | (41) | IHLIIEDNSDVEDAFIESEKPTEKQRKKLPSIRFVVKEKVPV | |
| SEQ. ID NO. 31: | C.thermocellum_12S | (41) | ICAHILENSEVLDIFIVYETGISILPEDKKAKVPGDLIVVIT | |
| SEQ. ID NO. 29: | T.saccharolyticum_12S | (41) | IYKILEDSEVDIEAVDEITLIEEEQKPGEEVIGSTEPSSLIVE | |
| | Consensus | (51) | I  LLDE SF EIDAFVEHRC DFGMDK KVPGDGVVTGYGTI GR VHV | |
| | | | 101 | 150 |
| SEQ. ID NO. 67: | D.propionicus_12S | (91) | YEDGIVESTIGGSLGEMHAEICKLKVMEGMKNGIPVIGLNDSGGARIEGLD | |
| SEQ. ID NO. 51: | C.kroppenstedtii_12S | (98) | AQDFSVIGGSAGEMRQNKIVAMMKASATTIEFVFLIDSGGAR... | |
| SEQ. ID NO. 14: | P.feudenreichii_12S | (101) | AIQDITVIGGSAGETGDIVQAHLGELRTSTIEFFYDSGGARIEEIDID | |
| SEQ. ID NO. 59: | G.bemidjiensis_12S | (91) | ACQIIVIGGSLAGETSGDIVQAHLGELRTSTIEFFDSGGARIEEIDID | |
| SEQ. ID NO. 37: | C.bescii_12S | (89) | YEQDIKSTIGSLGEMHAEKICYVLDIAIEYECIVEISNDSGGARIEEID | |
| SEQ. ID NO. 45: | C.cellulolyticum_12S | (91) | SSEQDIVVIGGSGEMHAEEITATVDIGMNGARILIIDSGGAEIEGID | |
| SEQ. ID NO. 31: | C.thermocellum_12S | (91) | AEQDIIVIGGSEYEARKITLYMDMGLEMKAEIEINDSGGAEEIGID | |
| SEQ. ID NO. 29: | T.saccharolyticum_12S | (91) | YEDDFTVIGGSIGEMHAKIEKEVMDMLKGMPFIGINDSGGAEIEGID | |
| | Consensus | (101) | AAQDFTVIGGSLGEMHA KI KVMDMALK G PFIGINDSGGARIQEGID | |
| | | | 151 | 200 |
| SEQ. ID NO. 67: | D.propionicus_12S | (141) | ALSGYGDIEYKLRTVLASGVIPGGYSVIMGPCAGGAVYSPAFTDDIIMQKIQS | |
| SEQ. ID NO. 51: | C.kroppenstedtii_12S | (148) | ISGYGRIKRNVLASGVIPOISVIMGPAGGAVSPAFTDEIIMTKIA | |
| SEQ. ID NO. 14: | P.feudenreichii_12S | (151) | RGEGKMIFRYNVLASGVIPOALLAGECAGGAVSPALDDEIIMTKIA | |
| SEQ. ID NO. 59: | G.bemidjiensis_12S | (141) | AEGGKIFYRNVLASGVIPOMLEGAGGAVSPAEIDDFIILMTAKIA | |
| SEQ. ID NO. 37: | C.bescii_12S | (139) | ILSGYGDIIINEVIASAAILIGGAGGAVYSPALDDFIIVDRISS | |
| SEQ. ID NO. 45: | C.cellulolyticum_12S | (141) | MIGYGDILLYENNILASGVIPGISVILGPAGGAVYSPADIDDFVDDTSS | |
| SEQ. ID NO. 31: | C.thermocellum_12S | (141) | MIGYGDIFYRNVLASGVIPVSVIMGPAGGAVYSPAFDDFIIMVKTS | |
| SEQ. ID NO. 29: | T.saccharolyticum_12S | (141) | MSGYGDINFRNIKNVLASGVIPGVIMGSAGGAVSPAEDDDFIIMMVEKTS | |
| | Consensus | (151) | ALSGYGDIFYRNVLASGVIPQISVIMGPCAGGAVYSPALTDFIIMVDKTS | |
| | | | 201 | 250 |
| SEQ. ID NO. 67: | D.propionicus_12S | (191) | YEFITGEKVIIKSEVILNESIVIGEOAAMFEESYEAAEDEEEOYE | |
| SEQ. ID NO. 51: | C.kroppenstedtii_12S | (197) | NIFGEEIKRVIGSVTGKEAEEEEANAMETKSSNIFFVARDBKAAELEA | |
| SEQ. ID NO. 14: | P.feudenreichii_12S | (200) | RLYGEEPIKSVDVTALESEIGEEANMAISSNIPFTABDBEAAELEA | |
| SEQ. ID NO. 59: | G.bemidjiensis_12S | (190) | REYEGEVIKSVEARGETISALEIGEPLSONNHTAREVAENNLVEERKC | |
| SEQ. ID NO. 37: | C.bescii_12S | (189) | NEFGEELIKSVGELSEFLEEGAYITEFKFVADEEADDYHLLQMY | |
| SEQ. ID NO. 45: | C.cellulolyticum_12S | (191) | NEVPVGEIIKAVSEVISEDEREDVTATIEEIAREKSSEEECLEDK | |
| SEQ. ID NO. 31: | C.thermocellum_12S | (191) | QMFITGPOVIKSVIGEDVSAEEELGGADTHSNIEINIERUSSSKECIEQI | |
| SEQ. ID NO. 29: | T.saccharolyticum_12S | (191) | QMFITGPQVIKAVSGVGAEEELGADVIEEIEKRVATTERAMSKECLEKKA | |
| | Consensus | (201) | QMFITGPQVIKSVTGEDVSAEELGGADTHSS SGVAHPVAE DEEAI II | |
| | | | 251 | 300 |
| SEQ. ID NO. 67: | D.propionicus_12S | (241) | KESEYDONEEENEFDAPCDGPYTKRSRLFNSKELKEDNPAAEVNKVS | |
| SEQ. ID NO. 51: | C.kroppenstedtii_12S | (247) | QEELILAQTEELIIKDPDEEEVEPDSSMRIEEVEDGPKEYKEPRER | |
| SEQ. ID NO. 14: | P.feudenreichii_12S | (250) | KEMIVQILRQTIEEBASFYNENN-DVSPNTENRTEBIDGKENKKRNDES | |
| SEQ. ID NO. 59: | G.bemidjiensis_12S | (240) | KEMIVVIQLITEDPQEESD-MIVPDKINSMEYSQKLREEEKFQK | |
| SEQ. ID NO. 37: | C.bescii_12S | (239) | KEINVGEESEEDEFIMSEESEKEFVPEENEIOEPNAIFEEEEY | |
| SEQ. ID NO. 45: | C.cellulolyticum_12S | (241) | KIVELKSPPDNPSETMYYGVSDAADKLAESDNSMEEESKRPLIFDLSIK | |
| SEQ. ID NO. 31: | C.thermocellum_12S | (241) | KEEIVEEESEGPEVIIFPTIDKNRRITDNIVYEEIIOSNRPIDMEESE | |
| SEQ. ID NO. 29: | T.saccharolyticum_12S | (241) | KELIEELIEDEEDELQAADDDINFSDPINEIELSDSPKKPIEEIVEEE | |
| | Consensus | (251) | KKLLSFLP NNLEDPP V SDD I R D L DIIP D NKAYDMKDVIT | |
| | | | 301 | 350 |
| SEQ. ID NO. 67: | D.propionicus_12S | (291) | ETAENSIIIGKKNFAPKVLVIGYGKARVIGFEARVGESYYKVLDDSE | |
| SEQ. ID NO. 51: | C.kroppenstedtii_12S | (296) | KLVYGDELFIVQAGVIARIIAVREIVGFAREINGESVGEIEGOVEETAS | |
| SEQ. ID NO. 14: | P.feudenreichii_12S | (299) | ELWGDVLEVKAGIATKVTADEIVIGFARINGESVGIEDGCEDEEHNAS | |
| SEQ. ID NO. 59: | G.bemidjiensis_12S | (289) | EIGGDFLEIEQPLFEANEKIVGEARIMRSLGEVEINOPEKVEAS | |
| SEQ. ID NO. 37: | C.bescii_12S | (289) | KEVNQEFLEVQPYEANIVEIGFANINGESVGIVANAKVLDYSSS | |
| SEQ. ID NO. 45: | C.cellulolyticum_12S | (291) | EKVDGDFLVQAFARNIVIGIGFARINGESVIANIPKEMAGSPLDINSS | |
| SEQ. ID NO. 31: | C.thermocellum_12S | (291) | SEIVNENEIFESEIVAAGNEDIVEGEFARINGRSIEINENPKIVEAGVEDINSS | |
| SEQ. ID NO. 29: | T.saccharolyticum_12S | (291) | EKVDEEVILESIMAGSEVILEFANINGEREVGIEANOPKEMAGEEDINAS | |
| | Consensus | (301) | KIVD GDFLEVQA FAQNIVIGFARINGRSVGIVANQPKVMAGVLDINAS | |

```
                                           451                                              500
SEQ. ID NO. 25:       Cthermocellum_5S    (415) -NEMSYLEQDEVISSAKLEVAEPESKQYEK---------------AQ
SEQ. ID NO. 49:       Ccellulolyticum_5S  (415) -EAVKDYIEQDEVISSAKLEVAEPESKQEI---------------ED
SEQ. ID NO. 63:       Gbemidjiensis_5S    (418) ALPLEGCDGSDEVLTYALEEVAPEEATES---------------EG
SEQ. ID NO. 55:       Ckroppenstedtii_5S  (430) ADELDGTDGSDEVLENALEEVAPGEEKTEP---------------QG
SEQ. ID NO. 11:       Pfreudenreichii_5S  (426) AAALEGENGTEEEVLTYALEEVAFVEEEHEA---------------EG
SEQ. ID NO. 71: Dpropionicus_5S_1.3S      (447) -KEIGELAKDIEEVLEKAEEVTEKELEWEYGITPAPPEVKPLTLEDVK
SEQ. ID NO. 41:       Cbescii_5S          (414) -EKIKEYIEKQEEVTYICLEQLEENEKLEF---------------AK
SEQ. ID NO. 33:       Tsaccharolyticum_5S (414) -NEIKEYIEQEEVISYALEEVAPAEEPEYEQ---------------AK
                      Consensus           (451)  EIKEYIEQDEDVLTYALFPQVA KFF   R                 E
                                           501                                              550
SEQ. ID NO. 25:       Cthermocellum_5S    (448) KYKVEPDMVDYENRVHPV----------------------------
SEQ. ID NO. 49:       Ccellulolyticum_5S  (448) KDKATAPASDEIKPEVVAAISAVVNEMGERDGTQYRIGNISKLNQNQNRW
SEQ. ID NO. 63:       Gbemidjiensis_5S    (452) PRNLGRDPVTGASETSIPEGHPGKITGPVTYTVTLSGQPHKVTVAPYGQE
SEQ. ID NO. 55:       Ckroppenstedtii_5S  (464) PKNVGKTKELEREEAKASGDATAIREPIMKVTTGGRSHTVSVEPA---
SEQ. ID NO. 11:       Pfreudenreichii_5S  (460) PHSVALTDESLK-AEAKGDEKSLAVAGPVTENENVGTVRENTVQQA---
SEQ. ID NO. 71: Dpropionicus_5S_1.3S      (496) KEDELVAKAKAGELIEPKPAAPEKTANVRTENVFVDGEYFNGEVDPTGDF
SEQ. ID NO. 41:       Cbescii_5S          (447) KYKVDADLVGNKVYPV------------------------------
SEQ. ID NO. 33:       Tsaccharolyticum_5S (447) KYKVDSTLNIEERVHPI-----------------------------
                      Consensus           (501) KYKV   VQ  K                  Y V  G   V V
                                           551                                              600
SEQ. ID NO. 25:       Cthermocellum_5S    (466) --------------------------------------------------
SEQ. ID NO. 49:       Ccellulolyticum_5S  (498) SLYGMLDRFRTKI-------------------------------------
SEQ. ID NO. 63:       Gbemidjiensis_5S    (502) --------------------------------------------------
SEQ. ID NO. 55:       Ckroppenstedtii_5S  (511) --------------------------------------------------
SEQ. ID NO. 11:       Pfreudenreichii_5S  (506) --------------------------------------------------
SEQ. ID NO. 71: Dpropionicus_5S_1.3S      (546) QPMVAAAPRPAAPAAAPKAAAPAAAAPAAAPKAAAPAAAAPAPAAVEGGT
SEQ. ID NO. 41:       Cbescii_5S          (464) --------------------------------------------------
SEQ. ID NO. 33:       Tsaccharolyticum_5S (465) --------------------------------------------------
                      Consensus           (551)
                                           601                                              650
SEQ. ID NO. 25:       Cthermocellum_5S    (466) --------------------------------------------------
SEQ. ID NO. 49:       Ccellulolyticum_5S  (511) --------------------------------------------------
SEQ. ID NO. 63:       Gbemidjiensis_5S    (502) --------------------------------------------------
SEQ. ID NO. 55:       Ckroppenstedtii_5S  (511) --------------------------------------------------
SEQ. ID NO. 11:       Pfreudenreichii_5S  (506) --------------------------------------------------
SEQ. ID NO. 71: Dpropionicus_5S_1.3S      (596) PLLAPMPGMIVKNLVNVGDAVKAGDPILVLEAMKMENNLGSPCDGTVKAL
SEQ. ID NO. 41:       Cbescii_5S          (464) --------------------------------------------------
SEQ. ID NO. 33:       Tsaccharolyticum_5S (465) --------------------------------------------------
                      Consensus           (601)
                                           651      668
SEQ. ID NO. 25:       Cthermocellum_5S    (466) ------------------
SEQ. ID NO. 49:       Ccellulolyticum_5S  (511) ------------------
SEQ. ID NO. 63:       Gbemidjiensis_5S    (502) ------------------
SEQ. ID NO. 55:       Ckroppenstedtii_5S  (511) ------------------
SEQ. ID NO. 11:       Pfreudenreichii_5S  (506) ------------------
SEQ. ID NO. 71: Dpropionicus_5S_1.3S      (646) NFGSGDSVAKDTVLAIIG
SEQ. ID NO. 41:       Cbescii_5S          (464) ------------------
SEQ. ID NO. 33:       Tsaccharolyticum_5S (465) ------------------
                      Consensus           (651)
```

Figure 31 cont.

1.3S subunits

```
                                          1                                                  50
SEQ. ID NO. 31: Tsaccharolyticum_1.3S  (1)  MKEEIEVVNGKKIDVEVEEIKVEVASEKKAKEDTEAKNESDASVKSK---
SEQ. ID NO.  9: Pfreudenreichii_1.3S   (1)  -MKLFKVVNGTAYEVEVVDKSHENPMGTILFGGGTGGEPAPRAEGGAG-
SEQ. ID NO. 53: Ckroppenstedtii_1.3S   (1)  -MELTEVVNGVPKSELEVEHEERPTLGTIITGGNSN-SPTPTAPTTES-
SEQ. ID NO. 61: Gbemidjiensis_1.3S     (1)  -VQLTEIEDGKKIRVEEVEEGEEVRTEGAFPPTETMQEYPVYSEHPEAT
SEQ. ID NO. 39: Cbescii_1.3S           (1)  MRKEKVKIESQEEVEEEEIGVENATSVVPRPKIGHFEPKQEKHEDKEK-
SEQ. ID NO. 47: Ccellulolyticum_1.3S   (1)  MSKEIIKVENGTPVEVEMEEVGGGRPISAAPKLRAEKPGHTSAAKEAQP--
SEQ. ID NO. 23: Cthermocellum_1.3S     (1)  MKEELIRVVNGNQYEVEVEERDGASAPQVTLSTPEAAFEPSPAPEQFEKT
                             Consensus (1)  M KF VTVNG  YDVEVEEI  E           A     A      T
                                          51                                                 100
SEQ. ID NO. 31: Tsaccharolyticum_1.3S  (48) --QVEVKMEVKDETENGEEIEEEIDVKESQEETVERGDVLLIEEAMKME
SEQ. ID NO.  9: Pfreudenreichii_1.3S   (49) --------AGKEGEGEIPAPLAETVSKEIKEEETVAEQTVLVEEAMKME
SEQ. ID NO. 53: Ckroppenstedtii_1.3S   (48) --------VQGVSENEVTAPLAESVSKVIVEEEQATTAGEIEVVEAMKME
SEQ. ID NO. 61: Gbemidjiensis_1.3S     (50) PPLAAPTPASESEKICREELAEVEKIVAQVEQHLEMNIDEVEEAMKME
SEQ. ID NO. 39: Cbescii_1.3S           (50) ----QSPVLSEDKNEEVVEQEEEEVRELKSEEDVVDANEPVELEAMKME
SEQ. ID NO. 47: Ccellulolyticum_1.3S   (49) --------QAGKEGDEAAEEETPVLEKVAIEDEVEKGQVLLEEAMKME
SEQ. ID NO. 23: Cthermocellum_1.3S     (51) AAPKKDSTVPEGEIEKEEEEIVERVNQEEITKKEQVEELEEAMKME
                             Consensus (51)        A A SI APLPGTVLKILV  GD VK GDVLLILEAMKME
                                          101                     133
SEQ. ID NO. 31: Tsaccharolyticum_1.3S  (96)  ...
SEQ. ID NO.  9: Pfreudenreichii_1.3S   (92)  ...
SEQ. ID NO. 53: Ckroppenstedtii_1.3S   (91)  ...
SEQ. ID NO. 61: Gbemidjiensis_1.3S    (100)  ...
SEQ. ID NO. 39: Cbescii_1.3S           (96)  ...
SEQ. ID NO. 47: Ccellulolyticum_1.3S   (91)  ...
SEQ. ID NO. 23: Cthermocellum_1.3S    (101)  ...
                             Consensus (101) NEITAP DGKV AI V  G AVQ GDLLL IA
```

12S C-term subunit

```
                                              1                                                  50
SEQ. ID NO. 57: Ckroppenstedtii_12Scterm   (1) MNTDNASSAELSQLLARLSNQVEKLSRNVTKLENEVAAEKQRSDEEEPEE
SEQ. ID NO. 16: Pfreudenreichii_12Scterm   (1) -------------MADEEEKDLMIATLNKRVASLESELGSEQS-DTQGVTEE
SEQ. ID NO. 27: Cthermocellum_12Scterm     (1) ------------------------------------MKEQENEE
SEQ. ID NO. 35: Tsaccharolyticum_12Scterm  (1) -------------------------------------MEEENEE
SEQ. ID NO. 43: Cbescii_12Scterm           (1) ---------------------------MYAQVSTISTETEE
SEQ. ID NO. 69: Dpropionicus_12Scterm      (1) ------------------------------MAKENKKMAAAEAAV
SEQ. ID NO. 65: Gbemidjiensis_12Scterm     (1) ----------------------------VDEEEMEQEHDPEETPEE
                                 Consensus (1)                                    L        I EE
                                              51                                                 100
SEQ. ID NO. 57: Ckroppenstedtii_12Scterm  (51) EIAESAAVSEYMGHRETVEAEHFLE-----HRSESQQEEQAEQHEEKWQ
SEQ. ID NO. 16: Pfreudenreichii_12Scterm  (39) ETAESAAVAAYLENDESAEVEHFAP-----SPNEVREEERAEQNHEIR-
SEQ. ID NO. 27: Cthermocellum_12Scterm     (9) EELAEEAAEAELETREPEYKLVERSFERIPQTSPVESATEKIEREERSM--
SEQ. ID NO. 35: Tsaccharolyticum_12Scterm  (8) EVAVEEAAELYEAFGEYEKNFREKVIERVDSNMPFEERKAEGLYNQMR-----
SEQ. ID NO. 43: Cbescii_12Scterm          (15) EEACIEAEKEEHIVMEE--EQYEITNITEEQE----QNKEVKGAEEMEENQEQMF
SEQ. ID NO. 69: Dpropionicus_12Scterm     (16) NAYLEEQEEEEAYEQEQLLAAESEAPAG------PSIEEAIAEROQDEENFRRLI
SEQ. ID NO. 65: Gbemidjiensis_12Scterm    (17) EEMVEEEEAEYEEGETVRIERARFVDPN--LINAEGQSSEEVVEQASHNLR
                                 Consensus (51)  IL  ISAAIAAYLGN G  K  V    K        W   GR LM  S
                                              101
SEQ. ID NO. 57: Ckroppenstedtii_12Scterm  (96) -----
SEQ. ID NO. 16: Pfreudenreichii_12Scterm  (83) -----
SEQ. ID NO. 27: Cthermocellum_12Scterm    (57) -----
SEQ. ID NO. 35: Tsaccharolyticum_12Scterm (53) -----
SEQ. ID NO. 43: Cbescii_12Scterm          (60) YRWR-
SEQ. ID NO. 69: Dpropionicus_12Scterm     (61) QMKAF
SEQ. ID NO. 65: Gbemidjiensis_12Scterm    (65) R----
                                 Consensus (101)
``` fdh1::Badoles ADH PFL rc flanks
25779 bp

FDH2:: Badoles ADH PFL
25358 bp

Figure 46

```
                                         1                                                50
SEQ. ID NO. 1:     AAS20429       (1)   ------MS GT    GRL  KIALITGGAGNIGSEITRRFLAEGATVVISGRN RA
SEQ. ID NO. 296:   YP_001277512   (1)   ---MSTTRRHD    VAL  GAGN  EV  TRRF      VVIT    VE
SEQ. ID NO. 295:   YP_001433009   (1)   ------MSTVR    VAL  GAGN  EV  TRRF      VIT     AE
SEQ. ID NO. 297:   ZP_01039179    (1)   -MSKEGNAARG    VAL  AGLN ELS AHAR      VNT      TEE
SEQ. ID NO. 298:   ZP_04957196    (1)   MNTETRTQSG  DK VVIL AGN   YISESLE ANL MT        EF
SEQ. ID NO. 294:   ZP_07684596    (1)   ------MFNT ND  AL   ACT   EV  TRRY         MA    RD
SEQ. ID NO. 293:   YP_002462600   (1)   ------MS G     AKI  GAGN  ESM TRRF   A   VIIS    SA
SEQ. ID NO. 291:   YP_001636209   (1)   ------MSTG     AKI  GAGN  ESL TRRF  AG   VIIS    RA
SEQ. ID NO. 292:   YP_002570540   (1)   ------MSTG     AKI  GAGN  ESL TRRF  AG   VIIS    RA
                   Consensus      (1)         MS  GRL  GKIALITGGAGNIGSEITRRFLAEGATVVISGRN 51                                              100
SEQ. ID NO. 1:     AAS20429       (45)   KT ALAERMCAEAGV PAKRIDL VMDGSDP AVRAGIAAIVAP----
SEQ. ID NO. 296:   YP_001277512   (48)   KLAAYRRE IDE RIAPERVVALP  GSD AQV AALAQ  HGGADVPTP
SEQ. ID NO. 295:   YP_001433009   (45)   K AVYRREL IDE VAPERVVALP  GSD AQV AGVA   HCCTDVPIP
SEQ. ID NO. 297:   ZP_01039179    (50)   RIS AR QSIADTG APERIDTA VID GN  SIR AMA LE E YG------
SEQ. ID NO. 298:   ZP_04957196    (51)   K  FVT  VEG G-FDRDN LIAI  SAKAD C  EIVP  TNNH G-----
SEQ. ID NO. 294:   ZP_07684596    (44)   K DRYR KIT  HALPERVAVR  GSSNAEV    G  AVVA H------
SEQ. ID NO. 293:   YP_002462600   (45)   KLA LADRT SEA  PAKE DLE VM    D A V  G  AATIG---
SEQ. ID NO. 291:   YP_001636209   (45)   KT LAERM AEAGV PAKRIDLE VMCGSD AV  AGI AIVAR----
SEQ. ID NO. 292:   YP_002570540   (45)   KT LAERMCAEAGV PAKRIDLE VMCGSDP AVRAGI AIVAR----
                   Consensus      (51)   KL A  ERLIAEAGV ERIDL VMDGSDP AVRAGIAAIVA 101                                             150
SEQ. ID NO. 1:     AAS20429       (88)   H   IDI VNNAG A QRKL  IPLTEA  EGPE ETL  SIANLLGMG
SEQ. ID NO. 296:   YP_001277512   (98)   LKR DI VNNAC S PRRS VDL EPS VHFP I LAQAVG VGVA
SEQ. ID NO. 295:   YP_001433009   (95)   LR  DI VNNAC S PRR  VDL EPS VQFP S LA QVG LVGIT
SEQ. ID NO. 297:   ZP_01039179    (95)   R---DI INNAG   K F HNV LS PQEME A G  VRD AMI LGVT
SEQ. ID NO. 298:   ZP_04957196    (95)   --N DI VNNAGGG R    DI FSE RIAR GDD  MLI AAM LTA A
SEQ. ID NO. 294:   ZP_07684596    (87)   E   DI LNN   ARQR PA  LRS  QADIT F  AU SIG  LIGIT
SEQ. ID NO. 293:   YP_002462600   (88)   HG  IDI VNNAC T QRR AEI NET DPDLD E ALS SVA LLGMA
SEQ. ID NO. 291:   YP_001636209   (88)   H   IDI VNNAC S AQRP AE ILTEA  GPGAE TH AGIA LGMG
SEQ. ID NO. 292:   YP_002570540   (88)   H   IDI VNNAC S AQRR AE IDTEA  GPGAE TH AGIA LLGMG
                   Consensus      (101)  G  IDILVNNAGSAGARRRL EIPLTES  ELGPGDEETL  SIANLLGMA 151                                             200
SEQ. ID NO. 1:     AAS20429       (137)  H MR AAP  MP G  V IN  T  SRTE Y GRI YV PKAAL NT L
SEQ. ID NO. 296:   YP_001277512   (147)  QNLT  AAMYE P G SIIN  ST D GRI AVV PKAAV N  SGL
SEQ. ID NO. 295:   YP_001433009   (144)  QNLT  AAM S  SG VIN  S  SRCR A AL A A DGL
SEQ. ID NO. 297:   ZP_01039179    (143)  HNMA IVAE  P VGAM I  S SHER C  T V A NS  SNG
SEQ. ID NO. 298:   ZP_04957196    (143)  HNMT IAV SE GSIV N  S SRKT V  PT LV SG A SIGI
SEQ. ID NO. 294:   ZP_07684596    (136)  VTI   AA FL E PG SI V  S   R  VI VKTA  HA  LA
SEQ. ID NO. 293:   YP_002462600   (137)  HLMR  LE  P AIIN IS S AE    V VRTAI  NE T  IA
SEQ. ID NO. 291:   YP_001636209   (137)  HLMR AE    P VG VIN  S SRAE C  I TR AL N SGL
SEQ. ID NO. 292:   YP_002570540   (137)  HLMR IAAP  VG VIN  S SRAE    V TK ALN SQL
                   Consensus      (151)  WNLMRIAAPHMP GSAVINVSTIFSRTEYYGRIPYVVPKAALNALSQ AA 201                                             250
SEQ. ID NO. 1:     AAS20429       (187)  E   AP    VNT  GP  S   V G N      D        NT
SEQ. ID NO. 296:   YP_001277512   (197)  DCVR    VNT  GP  T H V    LKG E E   SG  R
SEQ. ID NO. 295:   YP_001433009   (194)  DC  RG   VNT  GP  T  VP    LKG    T    SG  R
SEQ. ID NO. 297:   ZP_01039179    (193)  S  CPKG   IVNTVEGP  S  D V  AAND VQS  KDI AV TG
SEQ. ID NO. 298:   ZP_04957196    (193)  KE  GEH   VN T   GP  S  D V     QSA     SQD  RDI
SEQ. ID NO. 294:   ZP_07684596    (186)  T    R    VNT   GP  S    D    RVV     PGS DG  FCA
SEQ. ID NO. 293:   YP_002462600   (187)  D C R     VNT  GP  S R   V  M  LKR     SG  EA
SEQ. ID NO. 291:   YP_001636209   (187)  DIC A     VNV  GP  E S     V         SG   H  T
```

Figure 46 cont.

```
SEQ ID NO. 292:  YP_002570540  (187)  RELG RG IRVNTIFPGPIESDRIRTVFQRMD LKG PEGDTA    FL   M
                 Consensus      (201)  RELG RG IRVNTIFPGPIESDRIRTVFQRMD LKG PEGDTA    FL   M
                                       251                                                  300

SEQ. ID NO. 1:    AAS20429       (236)
SEQ. ID NO. 296:  YP_001277512   (246)
SEQ. ID NO. 295:  YP_001433009   (243)
SEQ. ID NO. 297:  ZP_01039179    (242)
SEQ. ID NO. 298:  ZP_04957196    (243)
SEQ. ID NO. 294:  ZP_07684596    (235)
SEQ. ID NO. 293:  YP_002462600   (236)
SEQ. ID NO. 291:  YP_001636209   (236)
SEQ. ID NO. 292:  YP_002570540   (236)
                  Consensus      (251) RL RAN QG LEKRFPS  DVA  AVFLASEESAALSGETIEVTHGMELP
                                       301                                              350

SEQ. ID NO. 1:    AAS20429       (286)
SEQ. ID NO. 296:  YP_001277512   (296)
SEQ. ID NO. 295:  YP_001433009   (293)
SEQ. ID NO. 297:  ZP_01039179    (292)
SEQ. ID NO. 298:  ZP_04957196    (293)
SEQ. ID NO. 294:  ZP_07684596    (285)
SEQ. ID NO. 293:  YP_002462600   (286)
SEQ. ID NO. 291:  YP_001636209   (286)
SEQ. ID NO. 292:  YP_002570540   (286)
                  Consensus      (301)  S TSLLARPDLRTIDASGRTTLICAGDQIEEAMALTGMLRTCGAEVII
                                        351                                              400

SEQ. ID NO. 1:    AAS20429       (336)
SEQ. ID NO. 296:  YP_001277512   (346)
SEQ. ID NO. 295:  YP_001433009   (343)
SEQ. ID NO. 297:  ZP_01039179    (342)
SEQ. ID NO. 298:  ZP_04957196    (343)
SEQ. ID NO. 294:  ZP_07684596    (335)
SEQ. ID NO. 293:  YP_002462600   (336)
SEQ. ID NO. 291:  YP_001636209   (336)
SEQ. ID NO. 292:  YP_002570540   (336)
                  Consensus      (351) GFRS AALAQFE  L E R LAGA         PILL LDP DP TID
                                       401                                              450

SEQ. ID NO. 1:    AAS20429       (379)
SEQ. ID NO. 296:  YP_001277512   (396)
SEQ. ID NO. 295:  YP_001433009   (393)
SEQ. ID NO. 297:  ZP_01039179    (380)
SEQ. ID NO. 298:  ZP_04957196    (380)
SEQ. ID NO. 294:  ZP_07684596    (378)
SEQ. ID NO. 293:  YP_002462600   (379)
SEQ. ID NO. 291:  YP_001636209   (379)
SEQ. ID NO. 292:  YP_002570540   (379)
                  Consensus      (401)   FDW G EN GGIHAAVILPAS  HEPA SVIEVDDE V  FL DEIVG
                                         451                                             500

SEQ. ID NO. 1:    AAS20429       (428)
SEQ. ID NO. 296:  YP_001277512   (445)
SEQ. ID NO. 295:  YP_001433009   (442)
SEQ. ID NO. 297:  ZP_01039179    (430)
SEQ. ID NO. 298:  ZP_04957196    (429)
SEQ. ID NO. 294:  ZP_07684596    (426)
SEQ. ID NO. 293:  YP_002462600   (427)
SEQ. ID NO. 291:  YP_001636209   (427)
SEQ. ID NO. 292:  YP_002570540   (427)
                  Consensus      (451) TIVIASRLARYWQ   L PGA A  PRVIFLSNPADQNGN YG I SAAI
                                       501                                              550

SEQ. ID NO. 1:    AAS20429       (478)
SEQ. ID NO. 296:  YP_001277512   (491)
SEQ. ID NO. 295:  YP_001433009   (488)
SEQ. ID NO. 297:  ZP_01039179    (476)
SEQ. ID NO. 298:  ZP_04957196    (475)
```

Figure 46 cont.

```
SEQ. ID NO. 294:   ZP_07684596   (476)  [shaded] EQLIRVWRHEAELDY R A   D      L AVWANQIVRFAN ELENLEFA
SEQ. ID NO. 293:   YP_002462600  (477)  [shaded]
SEQ. ID NO. 291:   YP_001636209  (477)  [shaded]
SEQ. ID NO. 292:   YP_002570540  (477)  [shaded]
                   Consensus     (501)  EQLIRVWRHEAELDY R A   D      L AVWANQIVRFAN ELENLEFA 551                                              600
SEQ. ID NO.   1:   AAS20429      (526)  [shaded]
SEQ. ID NO. 296:   YP_001277512  (540)  [shaded]
SEQ. ID NO. 295:   YP_001433009  (537)  [shaded]
SEQ. ID NO. 297:   ZP_01039179   (519)  [shaded]
SEQ. ID NO. 298:   ZP_04957196   (518)  [shaded]
SEQ. ID NO. 294:   ZP_07684596   (526)  [shaded]
SEQ. ID NO. 293:   YP_002462600  (525)  [shaded]
SEQ. ID NO. 291:   YP_001636209  (525)  [shaded]
SEQ. ID NO. 292:   YP_002570540  (525)  [shaded]
                   Consensus     (551)  CAW A LL  S  R  I  EI  L  IPANISATTGAR ASVGWAESLIGLHLGKV 601                                              650
SEQ. ID NO.   1:   AAS20429      (576)  [shaded]
SEQ. ID NO. 296:   YP_001277512  (590)  [shaded]
SEQ. ID NO. 295:   YP_001433009  (587)  [shaded]
SEQ. ID NO. 297:   ZP_01039179   (569)  [shaded]
SEQ. ID NO. 298:   ZP_04957196   (568)  [shaded]
SEQ. ID NO. 294:   ZP_07684596   (576)  [shaded]
SEQ. ID NO. 293:   YP_002462600  (575)  [shaded]
SEQ. ID NO. 291:   YP_001636209  (575)  [shaded]
SEQ. ID NO. 292:   YP_002570540  (575)  [shaded]
                   Consensus     (601)  ALITGGSAGIGGQIGRLLALSGARVMLAARD   KLEQMRAMIVSEL EVG 651                                              700
SEQ. ID NO.   1:   AAS20429      (626)  [shaded]
SEQ. ID NO. 296:   YP_001277512  (640)  [shaded]
SEQ. ID NO. 295:   YP_001433009  (637)  [shaded]
SEQ. ID NO. 297:   ZP_01039179   (619)  [shaded]
SEQ. ID NO. 298:   ZP_04957196   (618)  [shaded]
SEQ. ID NO. 294:   ZP_07684596   (626)  [shaded]
SEQ. ID NO. 293:   YP_002462600  (625)  [shaded]
SEQ. ID NO. 291:   YP_001636209  (625)  [shaded]
SEQ. ID NO. 292:   YP_002570540  (625)  [shaded]
                   Consensus     (651)  Y DVE RV I PGCDVSDEEQLE LVERTL  FG VDYLINNAGIAGAEE 701                                              750
SEQ. ID NO.   1:   AAS20429      (676)  [shaded]
SEQ. ID NO. 296:   YP_001277512  (690)  [shaded]
SEQ. ID NO. 295:   YP_001433009  (687)  [shaded]
SEQ. ID NO. 297:   ZP_01039179   (669)  [shaded]
SEQ. ID NO. 298:   ZP_04957196   (668)  [shaded]
SEQ. ID NO. 294:   ZP_07684596   (676)  [shaded]
SEQ. ID NO. 293:   YP_002462600  (675)  [shaded]
SEQ. ID NO. 291:   YP_001636209  (675)  [shaded]
SEQ. ID NO. 292:   YP_002570540  (675)  [shaded]
                   Consensus     (701)  MVIDMPVEAWRHTLFANLISNYSLMRKLAPLMK QGSGYVLNVSSYFGGE 751                                              800
SEQ. ID NO.   1:   AAS20429      (726)  [shaded]
SEQ. ID NO. 296:   YP_001277512  (740)  [shaded]
SEQ. ID NO. 295:   YP_001433009  (737)  [shaded]
SEQ. ID NO. 297:   ZP_01039179   (719)  [shaded]
SEQ. ID NO. 298:   ZP_04957196   (718)  [shaded]
SEQ. ID NO. 294:   ZP_07684596   (726)  [shaded]
SEQ. ID NO. 293:   YP_002462600  (725)  [shaded]
SEQ. ID NO. 291:   YP_001636209  (725)  [shaded]
SEQ. ID NO. 292:   YP_002570540  (725)  [shaded]
                   Consensus     (751)  KYAAIPYPNRADYAVSKAGQRAMAEVFARFLGPEIQINAIAPGPVEGDRL 801                                              850
SEQ. ID NO.   1:   AAS20429      (776)  [shaded]
SEQ. ID NO. 296:   YP_001277512  (790)  [shaded]
```

Figure 46 cont.

```
SEQ. ID NO. 295:  YP_001433009  (787)  [aligned sequence block]
SEQ. ID NO. 297:  ZP_01039179   (769)
SEQ. ID NO. 298:  ZP_04957196   (768)
SEQ. ID NO. 294:  ZP_07684596   (776)
SEQ. ID NO. 293:  YP_002462600  (775)
SEQ. ID NO. 291:  YP_001636209  (775)
SEQ. ID NO. 292:  YP_002570540  (775)
                  Consensus     (801)  RGTGERPGLF RRARLILENKRLNELHAALIAA R D   M ELL   LL
                                       851                                              900

SEQ. ID NO. 1:    AAS20429      (826)
SEQ. ID NO. 296:  YP_001277512  (839)
SEQ. ID NO. 295:  YP_001433009  (836)
SEQ. ID NO. 297:  ZP_01039179   (818)
SEQ. ID NO. 298:  ZP_04957196   (816)
SEQ. ID NO. 294:  ZP_07684596   (826)
SEQ. ID NO. 293:  YP_002462600  (825)
SEQ. ID NO. 291:  YP_001636209  (825)
SEQ. ID NO. 292:  YP_002570540  (825)
                  Consensus     (851)  NDVAAL Q PAAP  LR LA RFRS GDPAASSSSPLLNRSIA KLLARL
                                       901                                              950

SEQ. ID NO. 1:    AAS20429      (876)
SEQ. ID NO. 296:  YP_001277512  (889)
SEQ. ID NO. 295:  YP_001433009  (886)
SEQ. ID NO. 297:  ZP_01039179   (868)
SEQ. ID NO. 298:  ZP_04957196   (865)
SEQ. ID NO. 294:  ZP_07684596   (876)
SEQ. ID NO. 293:  YP_002462600  (875)
SEQ. ID NO. 291:  YP_001636209  (875)
SEQ. ID NO. 292:  YP_002570540  (875)
                  Consensus     (901)  NGGYILPAD FA L              PPDPPFTRAQIDREARKVRDGI
                                       951                                             1000

SEQ. ID NO. 1:    AAS20429      (915)
SEQ. ID NO. 296:  YP_001277512  (928)
SEQ. ID NO. 295:  YP_001433009  (925)
SEQ. ID NO. 297:  ZP_01039179   (918)
SEQ. ID NO. 298:  ZP_04957196   (907)
SEQ. ID NO. 294:  ZP_07684596   (916)
SEQ. ID NO. 293:  YP_002462600  (914)
SEQ. ID NO. 291:  YP_001636209  (914)
SEQ. ID NO. 292:  YP_002570540  (914)
                  Consensus     (951)  MGMLYLQRMPTEFDVALATVYYLADRNVSGETFHPSGGLRYERTPTGGEL
                                       1001                                            1050

SEQ. ID NO. 1:    AAS20429      (965)
SEQ. ID NO. 296:  YP_001277512  (978)
SEQ. ID NO. 295:  YP_001433009  (975)
SEQ. ID NO. 297:  ZP_01039179   (968)
SEQ. ID NO. 298:  ZP_04957196   (957)
SEQ. ID NO. 294:  ZP_07684596   (966)
SEQ. ID NO. 293:  YP_002462600  (964)
SEQ. ID NO. 291:  YP_001636209  (964)
SEQ. ID NO. 292:  YP_002570540  (964)
                  Consensus     (1001) FG PSPERLA L GSTVYLIGEHLTEHL LLARAYLERYGA  VVLI BT
                                       1051                                            1100

SEQ. ID NO. 1:    AAS20429      (1015)
SEQ. ID NO. 296:  YP_001277512  (1028)
SEQ. ID NO. 295:  YP_001433009  (1025)
SEQ. ID NO. 297:  ZP_01039179   (1018)
SEQ. ID NO. 298:  ZP_04957196   (1007)
SEQ. ID NO. 294:  ZP_07684596   (1016)
SEQ. ID NO. 293:  YP_002462600  (1014)
SEQ. ID NO. 291:  YP_001636209  (1014)
SEQ. ID NO. 292:  YP_002570540  (1014)
                  Consensus     (1051) E GAE MR LL DHV AGRLMIIVAGDQIEAAID AI   YGRPGPVVSTP
```

Figure 46 cont.

```
                                        1101                                    1150
SEQ. ID NO. 1:        AAS20429    (1065)
SEQ. ID NO. 296:   YP_001277512   (1078)
SEQ. ID NO. 295:   YP_001433009   (1075)
SEQ. ID NO. 297:    ZP_01039179   (1068)
SEQ. ID NO. 298:    ZP_04957196   (1055)
SEQ. ID NO. 294:    ZP_07684596   (1066)
SEQ. ID NO. 293:   YP_002462600   (1064)
SEQ. ID NO. 291:   YP_001636209   (1064)
SEQ. ID NO. 292:   YP_002570540   (1064)
                      Consensus   (1101)  FRPLPS PLVGRKDSDWSTVLS AEFAELCE QLTHHFRVARKIAL DGA
                                        1151                                    1200
SEQ. ID NO. 1:        AAS20429    (1115)
SEQ. ID NO. 296:   YP_001277512   (1127)
SEQ. ID NO. 295:   YP_001433009   (1124)
SEQ. ID NO. 297:    ZP_01039179   (1112)
SEQ. ID NO. 298:    ZP_04957196   (1105)
SEQ. ID NO. 294:    ZP_07684596   (1116)
SEQ. ID NO. 293:   YP_002462600   (1114)
SEQ. ID NO. 291:   YP_001636209   (1114)
SEQ. ID NO. 292:   YP_002570540   (1114)
                      Consensus   (1151)  SL LVTPETTA STTEQFALANFVKTTLHAFTATIGVESERTA RILVNQ
                                        1201                                    1250
SEQ. ID NO. 1:        AAS20429    (1165)
SEQ. ID NO. 296:   YP_001277512   (1177)
SEQ. ID NO. 295:   YP_001433009   (1174)
SEQ. ID NO. 297:    ZP_01039179   (1162)
SEQ. ID NO. 298:    ZP_04957196   (1155)
SEQ. ID NO. 294:    ZP_07684596   (1166)
SEQ. ID NO. 293:   YP_002462600   (1164)
SEQ. ID NO. 291:   YP_001636209   (1164)
SEQ. ID NO. 292:   YP_002570540   (1164)
                      Consensus   (1201)  VDLTRRARAEEPRDP E QQELERFIEAVLLVTAPLP EADSRY GRIHR
                                        1251
SEQ. ID NO. 1:        AAS20429    (1215)
SEQ. ID NO. 296:   YP_001277512   (1227)
SEQ. ID NO. 295:   YP_001433009   (1224)
SEQ. ID NO. 297:    ZP_01039179   (1212)
SEQ. ID NO. 298:    ZP_04957196   (1205)
SEQ. ID NO. 294:    ZP_07684596   (1216)
SEQ. ID NO. 293:   YP_002462600   (1214)
SEQ. ID NO. 291:   YP_001636209   (1214)
SEQ. ID NO. 292:   YP_002570540   (1214)
                      Consensus   (1251)  GRAITV
```

PRODUCTION OF MALONYL-COA DERIVED PRODUCTS VIA ANAEROBIC PATHWAYS

CROSS-REFERENCE TO RELATED APPLICATIONS

This application is the National Stage of International Application Number PCT/US2011/046869, filed Aug. 5, 2011, which claims the benefit of U.S. Provisional Application No. 61/371,582, filed Aug. 6, 2010, which are incorporated by reference herein.

REFERENCE TO A SEQUENCE LISTING SUBMITTED ELECTRONICALLY VIA EFS-WEB

The content of the electronically submitted sequence listing (Name: SequenceListing.ascii.txt; Size:448,649 bytes; and Date of Creation: Feb. 5, 2013) is herein incorporated by reference in its entirety.

BACKGROUND OF THE INVENTION

Depleting petroleum reserves, recurrent energy crises, increasing demand, and climate change have provided significant impetus in the search for sustainable technologies to replace petroleum as a source of fuels and chemical feedstocks. Long chain fatty acids and other derivatives are commercially attractive as fuel and chemical feedstocks because they can directly replace crude petroleum (as "biocrude"), which is composed primarily of alkanes, alkenes, and aromatic hydrocarbons. In particular, cellulosic biomass is a preferred source of generating long chain fatty acids and other derivatives for use as fuel and chemical feedstocks, which are compatible with existing petroleum refining and distribution and can substitute for diesel, gasoline, jet fuel, and other derivatives of crude oil.

Currently, commercial and academic efforts are focused on bio-based petroleum replacement fuels made from microorganisms such as microalgae and that require aerobic microbial production. Algae bio-petroleum can appear as a very attractive option because fuel production occurs directly from sunlight and $CO_2$. However, algal volumetric productivities are 100-fold lower than fermentative processes, requiring significantly higher biorefinery capital expenditures. See Liliana et al., *Biotechnology and Bioengineering* 102:100-12 (2009). In addition, lower capital algal options, such as open pond culturing, have many technical hurdles to clear before commercial deployment despite decades of research into the issue.

Other efforts are underway to produce fatty acid compounds from sugars and plant biomass, but all current methods require oxygen to be supplied during fermentation, and are not full consolidated bioprocessing (CBP) processes. Unlike traditional ethanol fermentations, aerobic biofuel synthesis routes feature product formation which is uncoupled from ATP generation and cell growth. Uncoupling of product formation from cell growth simplifies metabolic engineering and has allowed for rapid development of first generation biocatalysts. However, there is a price to be paid for aerobic production when the technology is scaled up to meet industrial needs. First, there are significant costs associated with scaling-up aerobic fermentations, such as, those due to the need for aeration and heat removal. In practice, these constraints limit the size of aerobic fermentors, with those used in anaerobic fuel ethanol production being an order of magnitude larger. Second, although maximum theoretical product yields from an aerobic process are only slightly lower than an anaerobic process, in practice it is extraordinarily difficult to approach this maximum since there is no biological incentive for microbes to reach high product yields.

To reach the best aerobic process hydrocarbon yields to date, researchers have resorted to high cell density fermentation, which resulted in product yields between 30-40% of the theoretical maximum. See Tsuruta et al., *PLoS ONE* 4:e4489 (2009); Whited et al., *Industrial Biotechnology* 6:152-163 (2010). While these yields may be quite acceptable for pharmaceutical or specialty chemical production, fuel biorefinery process models have shown that fermentation yields lower than 85% of theoretical result in unattractive process economics. However, an anaerobic, oxygen-free fermentation not only creates higher product yields, but also removes many significant scale-up problems associated with aerobic fermentation. Hydrocarbon fuel production also has process benefits compared to ethanol fuel production, such as a lower product recovery cost and a lower product toxicity to fermenting organisms. The latter could result in smaller fermentation volumes needed to reach equivalent productivities.

An anaerobic biocatalyst requires a higher degree of metabolic pathway integration to couple product formation with ATP generation, NAD(P)H regeneration, and cell growth. However, once these requirements are met, natural evolutionary forces can be harnessed to increase product yields and productivities, driving them towards theoretical maxima. See Burgard et al., *Biotechnology and Bioengineering* 84:647-57 (2003); Sauer, *Advances in Biochemical Engineering/Biotechnology* 73:129-69 (2001). Higher yields, combined with a lower-cost path for scale-up, make an anaerobic process a preferred option for developing microbes to produce fungible biofuels. The invention describes a method to produce long chain fatty acids and their derivatives in an organism or consortia of organisms in a CBP process that is anaerobic.

Integral to the process of producing any end product, including those that can be produced using the methods of the invention, is an adequate supply of metabolic substrates. Malonyl-CoA is such a key metabolic precursor for the biological synthesis of various bioproducts, including, but not limited to, fatty acid derived long chain hydrocarbon compounds such as fatty alcohols, fatty aldehydes, fatty acids, wax esters, and alkanes. However, the biosynthesis of malonyl-CoA is known to occur through only a few mechanisms in vivo—namely from acetyl-CoA, carbon dioxide, and ATP by acetyl-CoA carboxylase (acc, EC 6.4.1.2) or from malonate, CoA, and ATP by malonyl-CoA synthetase (matB) (An and Kim, *Eur. J. Biochem.* 257:395-402 (1998)). Yet, both of these mechanisms require the consumption of ATP to drive the reaction towards malonyl-CoA. In contrast, to produce fatty acid derived hydrocarbons, or any other bioproducts that use malonyl-CoA as a precursor, anaerobically at high yield, the route to malonyl-CoA should result in a net production of ATP. The invention describes recombinant microorganisms, pathways, and methods for producing desired end-products from malonyl-CoA precursors with a net production of ATP.

BRIEF SUMMARY OF THE INVENTION

The recombinant microorganisms and methods of the invention use metabolic pathways that allow for the production of malonyl-CoA derived products, such as hydrocarbons and hydrocarbon derivatives and other bioproducts, under anaerobic conditions. The metabolic pathways allow for the production of long chain compounds, including, e.g., chain lengths from four carbon atoms up to 40 or more carbon atoms per molecule, and cellular growth in the absence of oxygen or other mechanisms to generate cellular energy (ATP) besides fermentative metabolism.

An aspect of the invention is the ability to produce long chain compounds at high yield with an anaerobic process rather than with an aerobic process. Anaerobic production results in a higher product yield, easier scalability, and better process thermodynamics. For lignocellulosic biomass conversion, an anaerobic process is even more desirable, as the requirement for oxygen transfer in a medium with suspended solids is highly unattractive from an engineering perspective. Additional advantages include, but are not limited to:

1) Production of a direct (fungible) replacement for petroleum;
2) Lower separation costs from a dilute aqueous fermentation as a result of the immiscible nature of long chain hydrocarbons compared to fully miscible shorter chain compounds;
3) Greater downstream product diversity and flexibility; and
4) Potentially lower product toxicity for fermenting organism which will allow for reduced fermentor volume and lower capital costs in a cellulosic biomass process.

One aspect of the invention relates to a recombinant microorganism comprising one or more native and/or heterologous enzymes that function in one or more engineered metabolic pathways to convert a carbohydrate source to a hydrocarbon, wherein the one or more native and/or heterologous enzymes is activated, upregulated, downregulated, or deleted. In certain embodiments, the conversion of a carbohydrate source to a hydrocarbon is under anaerobic conditions. In certain embodiments, the conversion of a carbohydrate source to a hydrocarbon is under microaerophilic conditions.

In certain embodiments, the one or more engineered metabolic pathways produce net ATP. In some embodiments, the one or more engineered metabolic pathway produces at least about 0.5 net ATP; at least about 1.0 net ATP; at least about 1.5 net ATP; or at least about 2.0 net ATP. In other embodiments the net ATP production is at least about at least about 0.1 net ATP; at least about 0.2 net ATP; at least about 0.3 net ATP; at least about 0.4 net ATP; at least about 0.5 net ATP; at least about 0.6 net ATP; at least about 0.7 net ATP; at least about 0.8 net ATP; at least about 0.9 net ATP; at least about 1.0 net ATP; 1.1 net ATP; at least about 1.2 net ATP; at least about 1.3 net ATP; at least about 1.4 net ATP; at least about 1.5 net ATP; at least about 1.6 net ATP; at least about 1.7 net ATP; at least about 1.8 net ATP; at least about 1.9 net ATP; or at least about 2.0 net ATP.

In particular aspects of the invention, the hydrocarbon produced by the recombinant microorganism is an alkane, an alkene, a hydrocarbon derivative, or a combination of any of these hydrocarbons. In some embodiments, the hydrocarbon produced is selected from the group consisting of an alkane; an alkene; an alkyne; a hydrocarbon derivative; and combinations of these hydrocarbons. In certain aspects, the hydrocarbon derivative is an aldehyde; an alcohol; an ester; a fatty acid; an unsaturated fatty acid; a branched-chain fatty acid; a branched methoxy fatty acid; a multi-methyl branched acid; a divinyl-ether fatty acid; a w-phenylalkanoic acid; or a dicarboxylic acid. In some embodiments, the hydrocarbon derivative is selected from the group consisting of an aldehyde; an alcohol; an ester; a fatty acid; an unsaturated fatty acid; a branched-chain fatty acid; a branched methoxy fatty acid; a multi-methyl branched acid; a divinyl-ether fatty acid; a w-phenylalkanoic acid; a dicarboxylic acid; and combinations of these hydrocarbon derivatives.

In certain aspects of the invention, the hydrocarbon or hydrocarbon derivative produced by the recombinant microorganism comprises a carbon backbone of $C_4$-$C_{40}$. In some embodiments, the hydrocarbon or hydrocarbon derivative comprises a carbon backbone selected from the group consisting of $C_6$-$C_{36}$; $C_8$-$C_{32}$; $C_{10}$-$C_{28}$; $C_{12}$-$C_{24}$; $C_{14}$-$C_{22}$; $C_{16}$-$C_{20}$; and combinations thereof. In other embodiments, the hydrocarbon or hydrocarbon derivative comprises a carbon backbone selected from the group consisting of $C_{12}$; $C_{14}$; $C_{16}$; $C_{18}$; $C_{20}$; $C_{22}$; $C_{24}$; and combinations of thereof. In one embodiment, the hydrocarbon or hydrocarbon derivative comprises a carbon backbone of $C_{16}$.

In some aspects of the invention, the carbohydrate source converted to a hydrocarbon is from biomass or from carbohydrates, such as a sugar or a sugar alcohol. In one embodiment, the carbohydrate source converted to a hydrocarbon is a lignocellulosic material. In some embodiments, the carbohydrate is a monosaccharides (e.g., glucose, fructose, galactose, xylose, arabinose, rhamnose, galacturonic acid, xylitol, sorbitol, or ribose), a disaccharide (e.g., sucrose, cellobiose, maltose, or lactose), an oligosaccharide (e.g., xylooligomers, cellodextrins, or maltodextrins), or a polysaccharide (e.g., xylan, cellulose, starch, mannan, or pectin).

In a particular aspect of the invention, one of the engineered metabolic pathways in the recombinant microorganism comprises the conversion of oxaloacetate and acetyl-CoA to malonyl-CoA and pyruvate. In one embodiment, the oxaloacetate and acetyl-CoA is converted to malonyl-CoA and pyruvate by a transcarboxylase. In some embodiments, the transcarboxylase is encoded by a heterologous transcarboxylase polynucleotide. In certain embodiments, the transcarboxylase is encoded by a polynucleotide from a *Thermoanaerobacter* species, *P. freudenreichii*, *P. acnes*, or *C. thermocellum*. In one embodiment, the transcarboxylase is genetically modified In another aspect of the invention, one of the engineered metabolic pathways comprises the conversion of phosphoenolpyruvate to oxaloacetate. In one embodiment, the phosphoenolpyruvate is converted to oxaloacetate by a phosphoenolpyruvate carboxykinase. In some embodiments, the phosphoenolpyruvate carboxykinase is encoded by a heterologous phosphoenolpyruvate carboxykinase polynucleotide. In certain embodiments, the phosphoenolpyruvate carboxykinase is encoded by a polynucleotide from a *Thermoanaerobacter* species, *E. coli*, *S. cerevisiae*, or *C. thermocellum*.

In other aspects of the invention, one of the engineered metabolic pathways further comprises at least one of the following steps: conversion of malonyl-CoA to malonyl-ACP; conversion of malonyl-ACP to an acyl-ACP; conversion of an $acyl_n$-ACP to a β-keto $ester_{n+2}$-ACP; conversion of a β-keto $ester_{n+2}$-ACP to a β-D-$hydroxyacyl_{n+2}$-ACP; conversion of a β-D-$hydroxyacyl_{n+2}$-ACP to a trans-2-unsaturated $acyl_{n+2}$-ACP; or conversion of a trans-2-unsaturated $acyl_{n+2}$-ACP to an $acyl_{n+2}$-ACP.

In some aspects of the invention, one of the engineered metabolic pathways further comprises the conversion of pyruvate and CoA-SH into acetyl-CoA and $CO_2$ and NAD(P)H.

In some aspects of the invention, one or more of the native enzymes in the engineered metabolic pathways are downregulated or deleted. In certain embodiments, the downregulated or deleted native enzyme is an enzyme involved in central metabolism. In some embodiments, the downregulated or deleted native enzyme is selected from the group consisting of a pyruvate kinase; a hydrogenase; a lactate dehydrogenase; a phosphotransacetylase; an acetate kinase; an acetaldehyde dehydrogenase; an alcohol dehydrogenase; a pyruvate formate lyase; a pyruvate decarboxylase; an enzyme involved in degradation of fatty acids and their derivatives; and combinations of thereof.

In some aspects of the invention, the microorganism is a thermophilic or a mesophilic bacterium. In certain embodiments, the thermophilic or mesophilic bacterium is a species of the genera *Escherichia, Propionibacterium, Thermoanaerobacterium, Thermoanaerobacter, Clostridium, Geobacillus, Saccharococcus, Paenibacillus, Bacillus, Caldicellulosiruptor, Anaerocellum, Anoxybacillus, Klebsiella, Lactobacillus, Lactococcus,* or *Corynebacterium*. In other embodiments, the microorganism is a bacterium selected from the group consisting of: *E. coli* strain B, strain C, strain K, strain W, *Shewanella, Propionibacterium acnes, Propionibacterium freudenreichii, Propionibacterium shermanii, Propionibacterium pentosaceum, Propionibacterium arabinosum, Clostridium acetobutylicum, Clostridium beijerinckii, Thermoanaerobacterium thermosulfurigenes, Thermoanaerobacterium aotearoense, Thermoanaerobacterium polysaccharolyticum, Thermoanaerobacterium zeae, Thermoanaerobacterium xylanolyticum, Thermoanaerobacterium saccharolyticum, Thermoanaerobium brockii, Thermoanaerobacterium thermosaccharolyticum, Thermoanaerobacter thermohydrosulfuricus, Thermoanaerobacter ethanolicus, Thermoanaerobacter brocki, Clostridium thermocellum, Clostridium clariflavum, Clostridium cellulolyticum, Clostridium phytofermentans, Clostridium straminosolvens, Geobacillus thermoglucosidasius, Geobacillus stearothermophilus, Saccharococcus caldoxylosilyticus, Saccharoccus thermophilus, Paenibacillus campinasensis, Bacillus flavothermus, Anoxybacillus kamchatkensis, Anoxybacillus gonensis, Caldicellulosiruptor acetigenus, Caldicellulosiruptor saccharolyticus, Caldicellulosiruptor kristjanssonii, Caldicellulosiruptor owensensis, Caldicellulosiruptor lactoaceticus, Lactobacillus thermophilus, Lactobacillus bulgaricus, Lactococcus lactis,* and *Anaerocellum thermophilum*. In one embodiment, recombinant microorganism is selected from the group consisting of *Clostridium thermocellum,* and *Thermoanaerobacterium saccharolyticum.*

Another aspect of the invention relates to a process for converting a carbohydrate source to a hydrocarbon comprising contacting the carbohydrate source with a recombinant microorganism of the invention. In some embodiments, the carbohydrate source comprises lignocellulosic biomass. In certain embodiments, the lignocellulosic biomass is selected from the group consisting of grass, switch grass, cord grass, rye grass, reed canary grass, mixed prairie grass, miscanthus, sugar-processing residues, sugarcane bagasse, sugarcane straw, agricultural wastes, rice straw, rice hulls, barley straw, corn cobs, cereal straw, wheat straw, canola straw, oat straw, oat hulls, corn fiber, stover, soybean stover, corn stover, forestry wastes, recycled wood pulp fiber, paper sludge, sawdust, hardwood, softwood, agave, and combinations thereof. In other embodiments, the carbohydrate source comprises a carbohydrate. In certain embodiments, the carbohydrate is a sugar, a sugar alcohol, or a mixture thereof.

In some aspects of the invention, the hydrocarbon produced by the recombinant microorganism is secreted.

Another aspect of the invention relates to an engineered metabolic pathway for producing a hydrocarbon from consolidated bioprocessing media.

One aspect of the invention relates to a recombinant microorganism comprising a native and/or heterologous enzyme that converts oxaloacetate and acetyl-CoA to malonyl-CoA and pyruvate, wherein said one or more native and/or heterologous enzymes is activated, upregulated, downregulated, or deleted. In some embodiments, the microorganism produces a hydrocarbon. In some embodiments, the enzyme is a transcarboxylase. In one embodiment, the transcarboxylase is encoded by a polynucleotide from a *Thermoanaerobacter* species, *P. freudenreichii P. acnes,* or *C. thermocellum*. In another embodiment, the transcarboxylase is genetically modified.

In some embodiments, the genetic modification produces an altered catalytic activity and/or an altered substrate specificity to improve the conversion of a substrate to a product as compared to the native enzyme. In some embodiments, the genetic modification alters catalytic activity and/or substrate specificity to provide a genetically modified polypeptide that converts a substrate to a product that is not catalyzed by the native enzyme in vivo, or is catalyzed at only minimal turnover.

BRIEF DESCRIPTION OF THE DRAWINGS/FIGURES

FIG. 1A depicts the conversion of phosphoenolpyruvate to oxaloacetate catalyzed by an enzyme from EC 4.1.1.32 or 4.1.1.49.

FIG. 1B depicts the conversion of oxaloacetate and acetyl-CoA to malonyl-CoA and pyruvate catalyzed by an enzyme from EC 2.1.3.1.

FIG. 2 depicts three steps in the synthesis of hydrocarbons and hydrocarbon derivatives.

FIG. 7A is an alignment of the transcarboxylase 5S subunits from *P. freudenreichii, P. acnes, C. thermocellum,* and *T. saccharolyticum.*

FIG. 7B is an alignment of the transcarboxylase 1.3S subunits from *P. freudenreichii, P. acnes, C. thermocellum,* and *T. saccharolyticum.*

FIG. 7C is an alignment of the transcarboxylase 12S subunit (N-terminus) from *P. freudenreichii, P. acnes, C. thermocellum,* and *T. saccharolyticum.*

FIG. 13 depicts the final step of the anaerobic fatty acid pathway.

Figure 20:
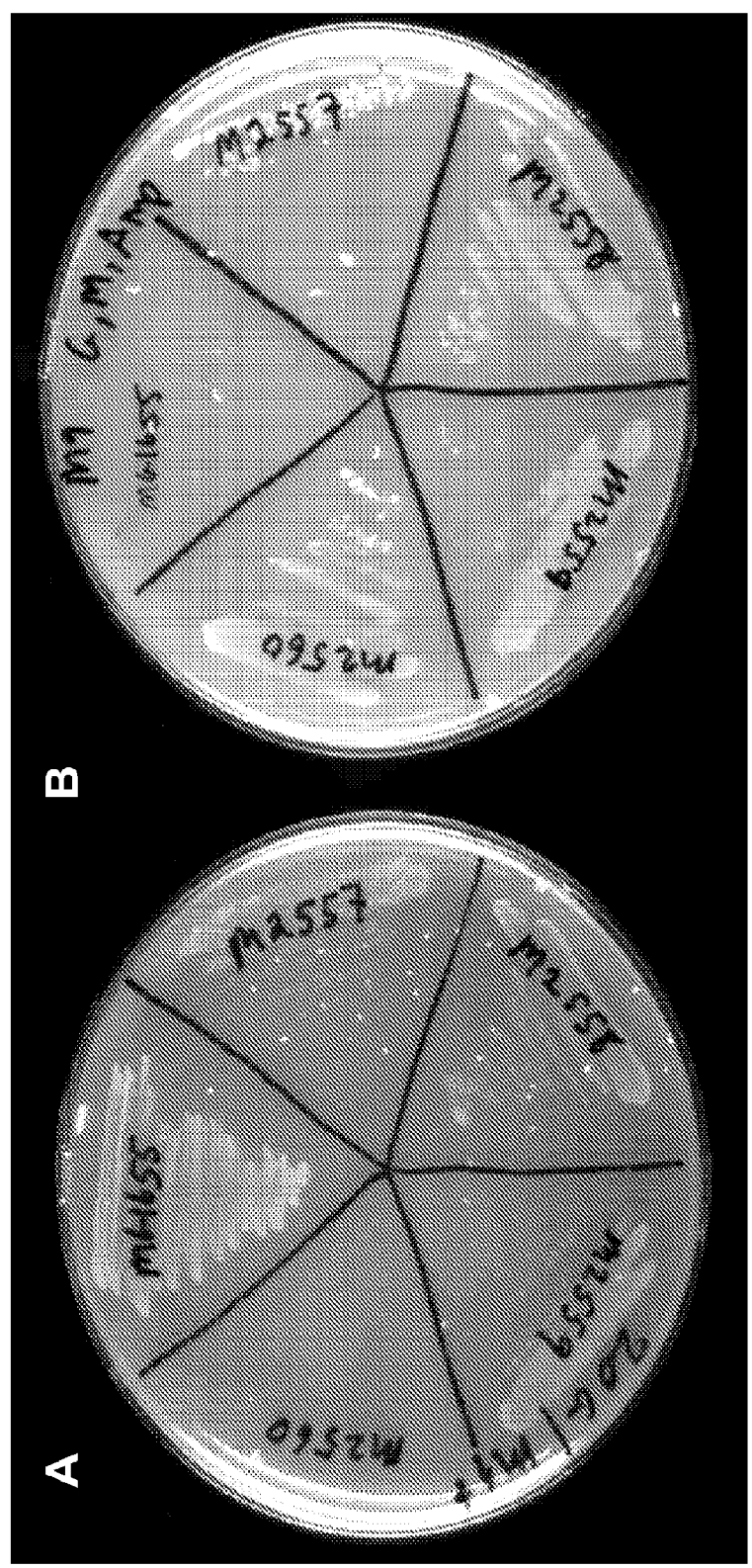

FIG. 20 demonstrates growth of transformants containing putative transcarboxylases on selective media.

FIG. 21A depicts polyketide chain synthesis, which proceeds by the addition or condensation of different functional groups to an acyl-ACP chain using a combination of enzymatic activities per two-carbon chain extension.

FIG. 21B depicts fatty acid chain synthesis, which proceeds by four enzymatic steps per two-carbon chain extension.

FIG. 22A depicts the total fatty acid content (shown in µg/mL) for *E. coli* strain M2933 carrying different acyl-ACP chain termination enzymes.

Figure 22B:
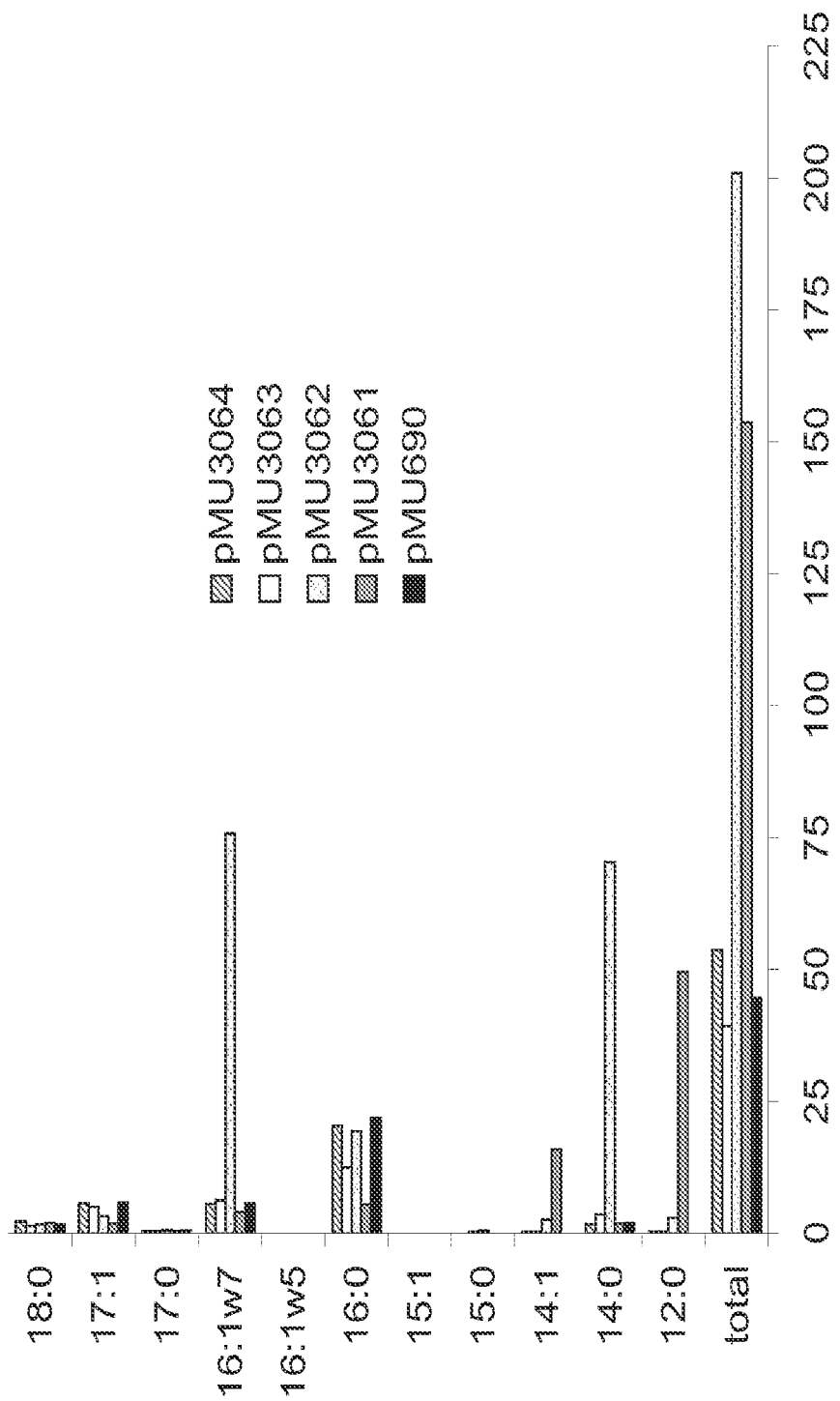

FIG. 22B is a graphical representation of the data from FIG. 22A.

Figure 23:
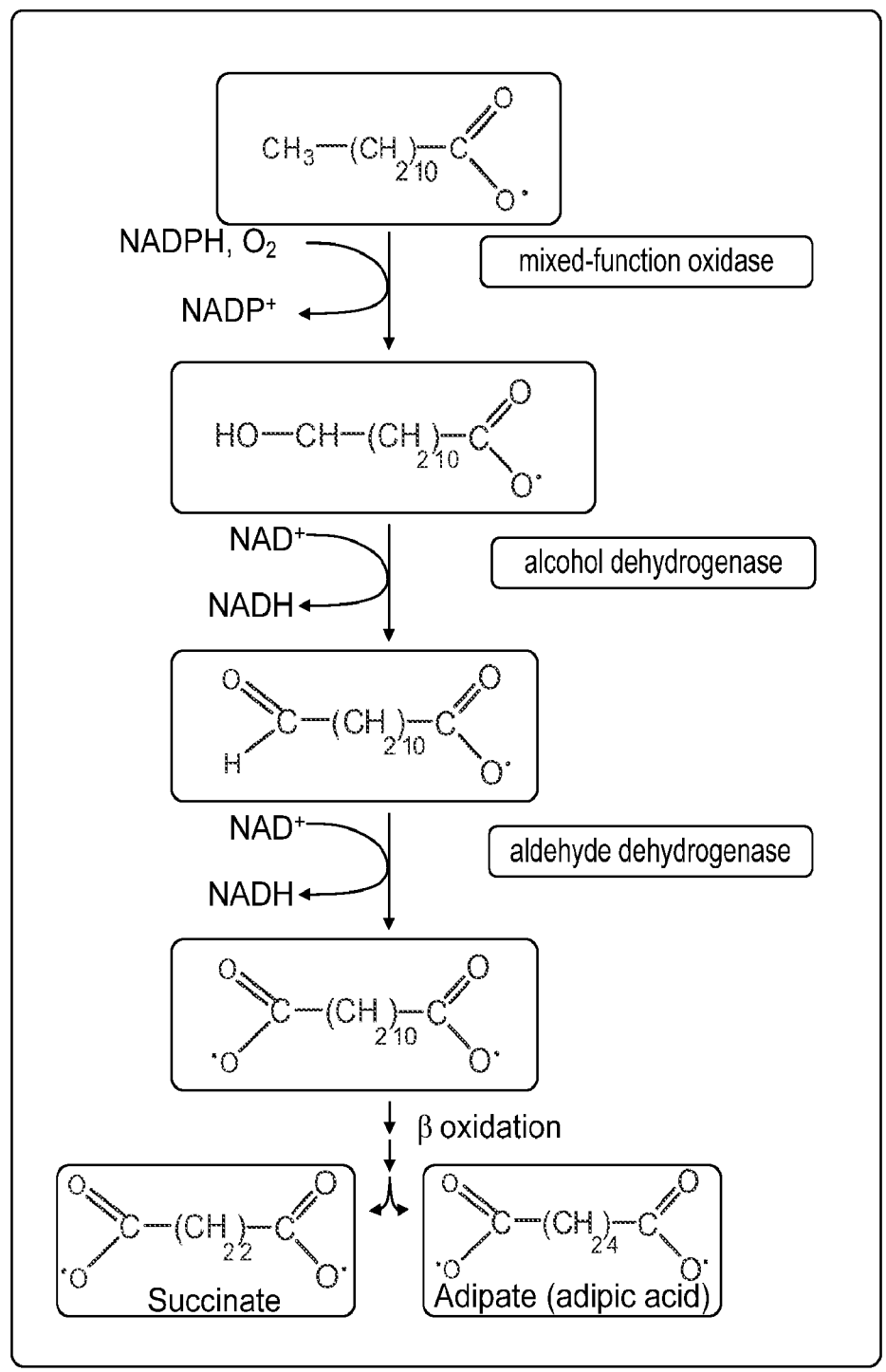

FIG. 23 depicts the synthesis of succinate and adipate using omega oxidation.

Figure 24:
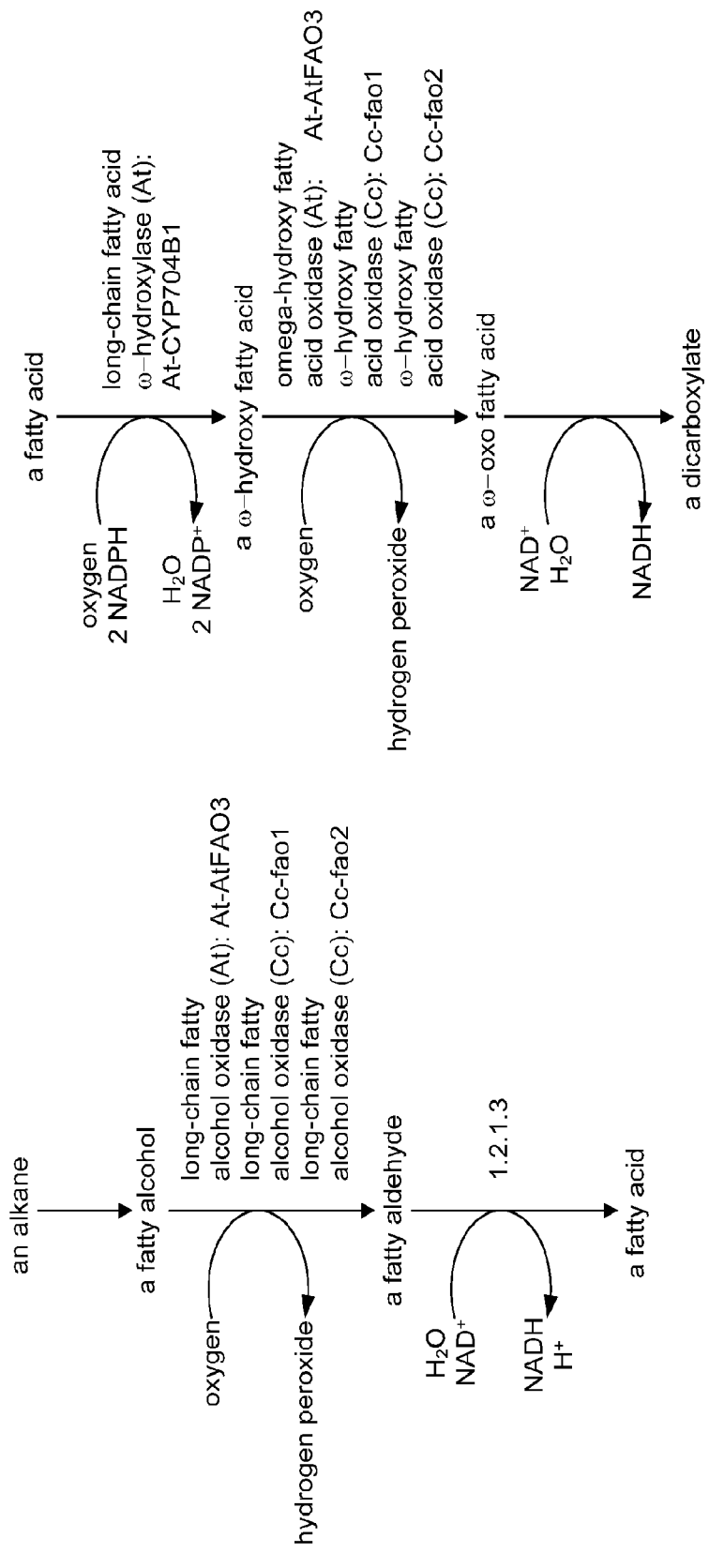

FIG. 24 depicts the synthesis of a dicarboxylate using omega oxidation.

Figure 25:
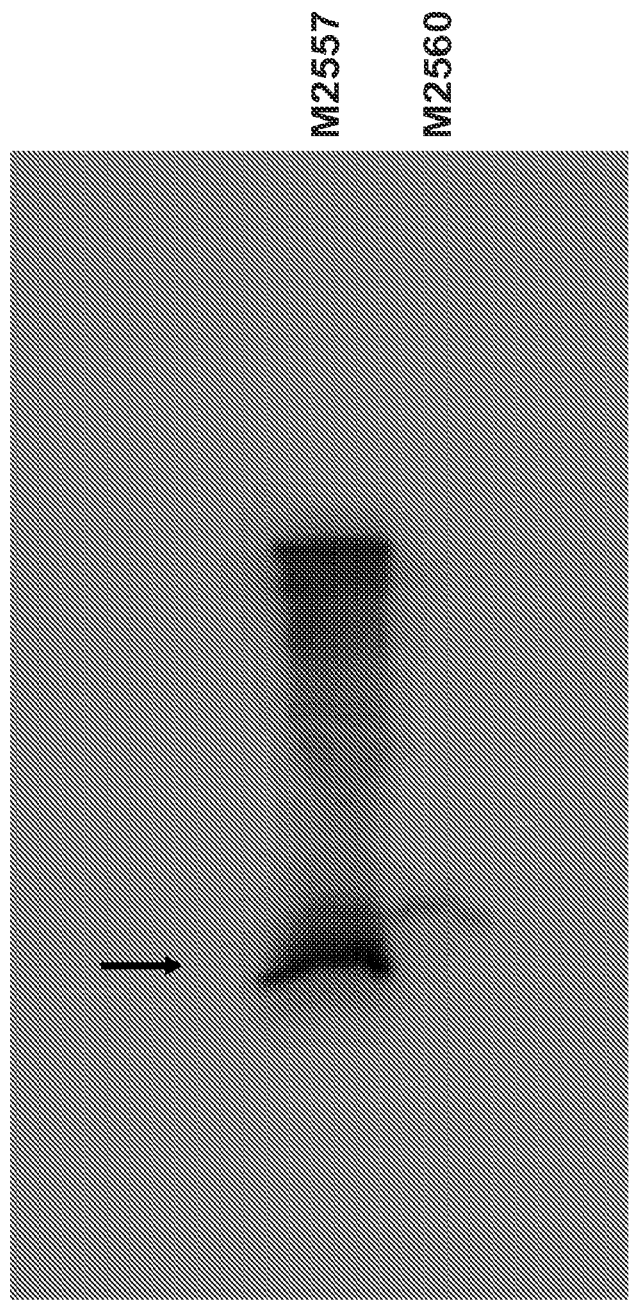

FIG. 25 is a western blot demonstrating the presence of biotinylated enzyme in construct M2557 but not in M2560.

Figure 26A:
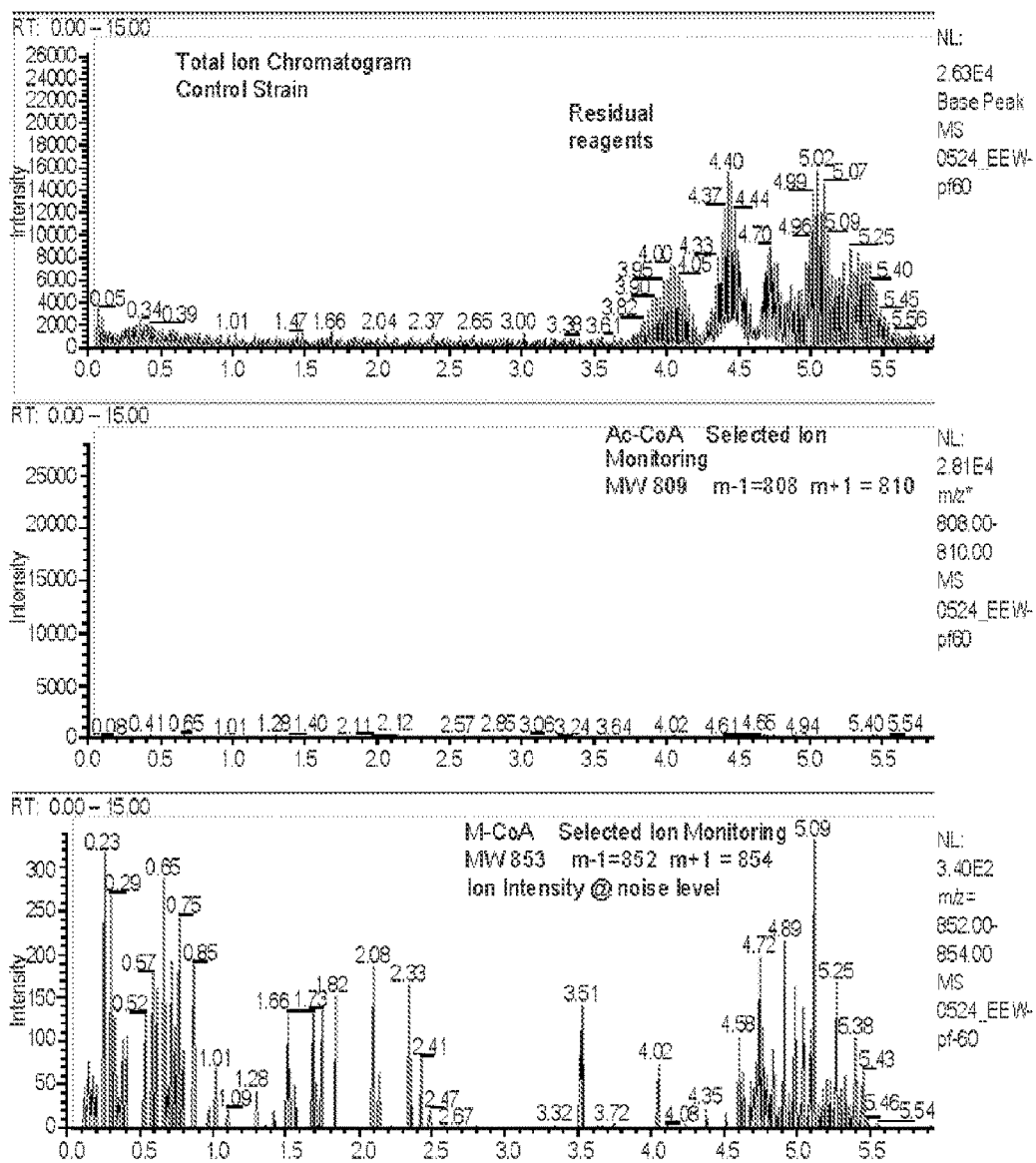
Figure 26A:
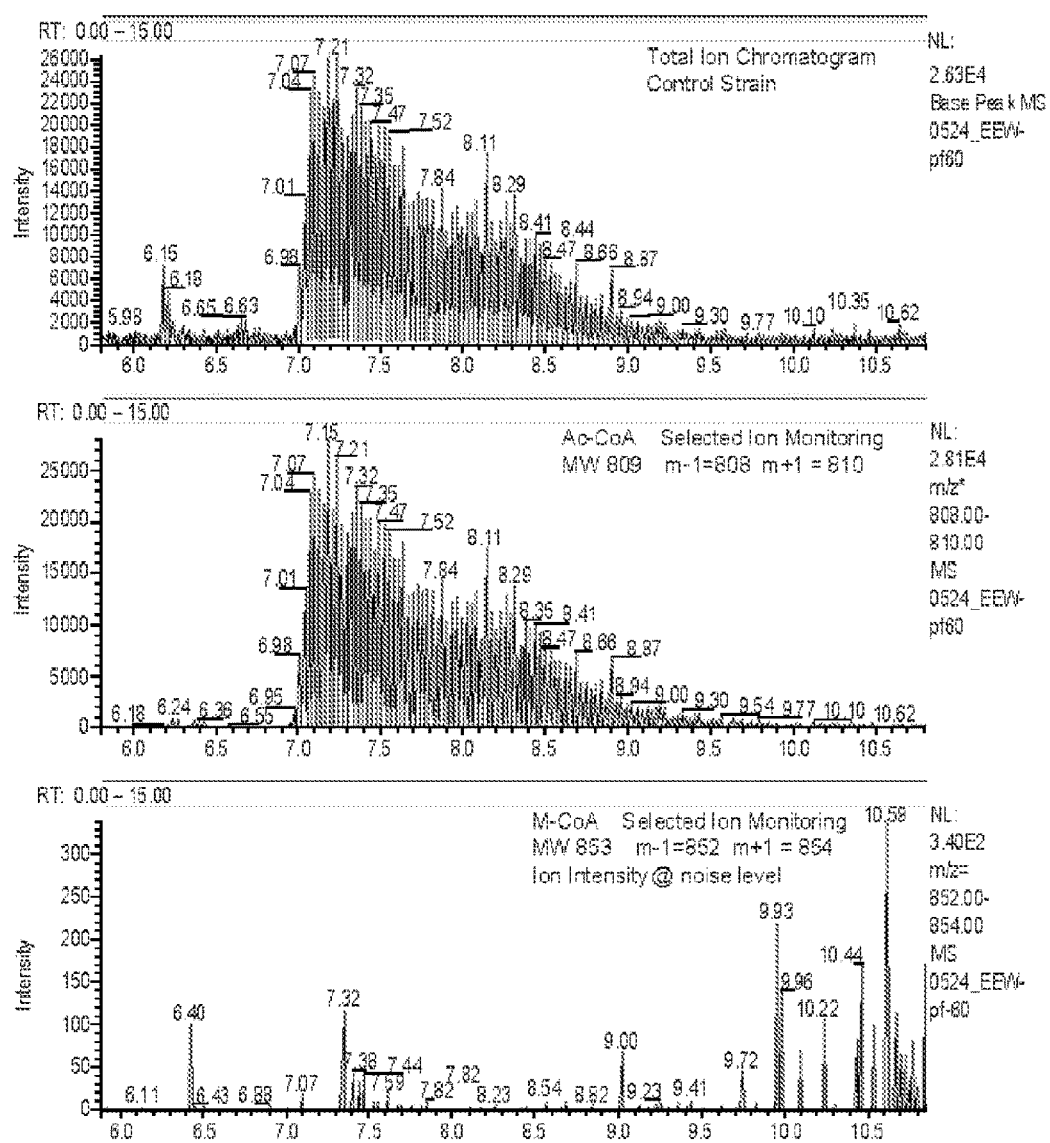
Figure 26A:
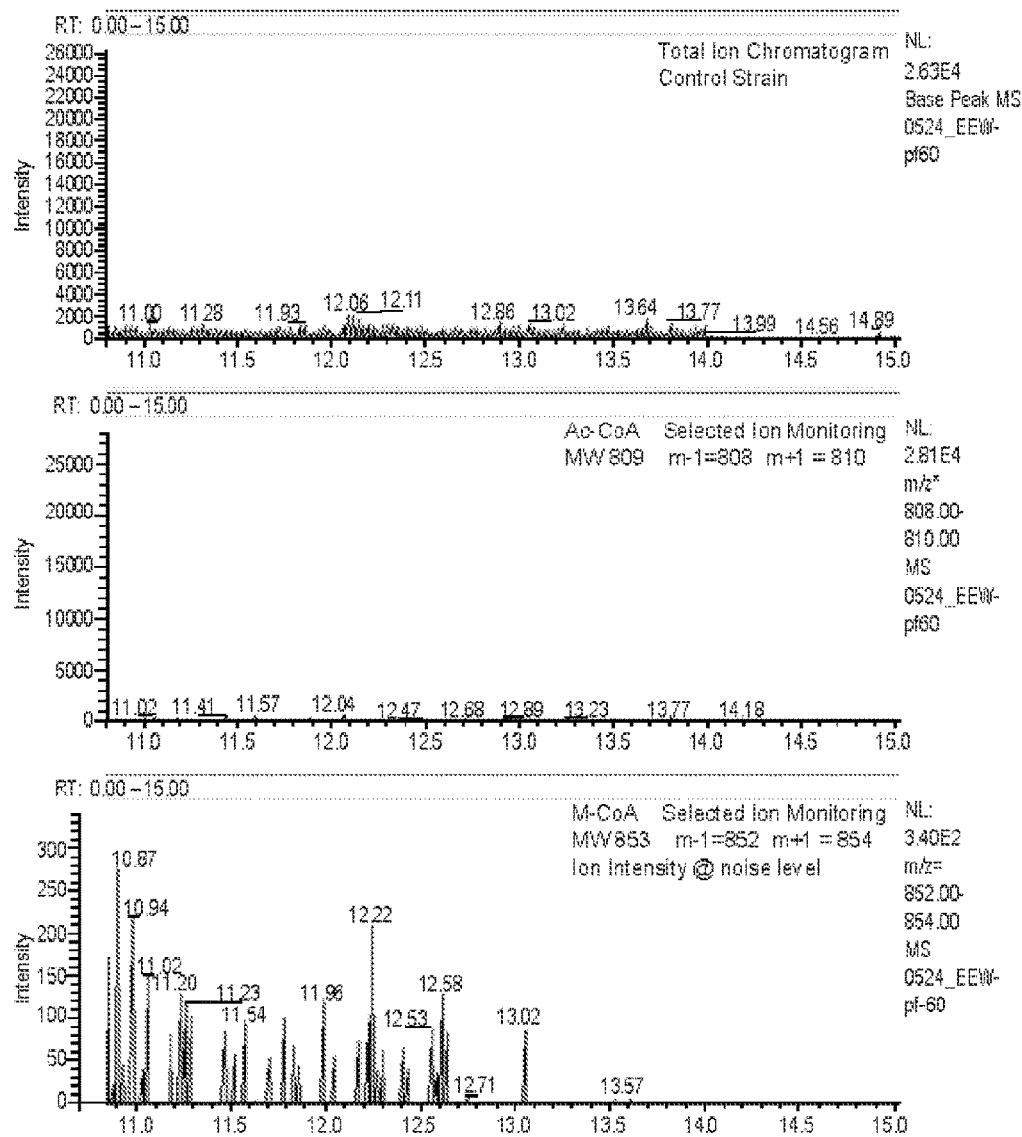

FIG. 26A depicts a mass spectrum of the transcarboxylase assay products for the negative control sample.

Figure 26B:
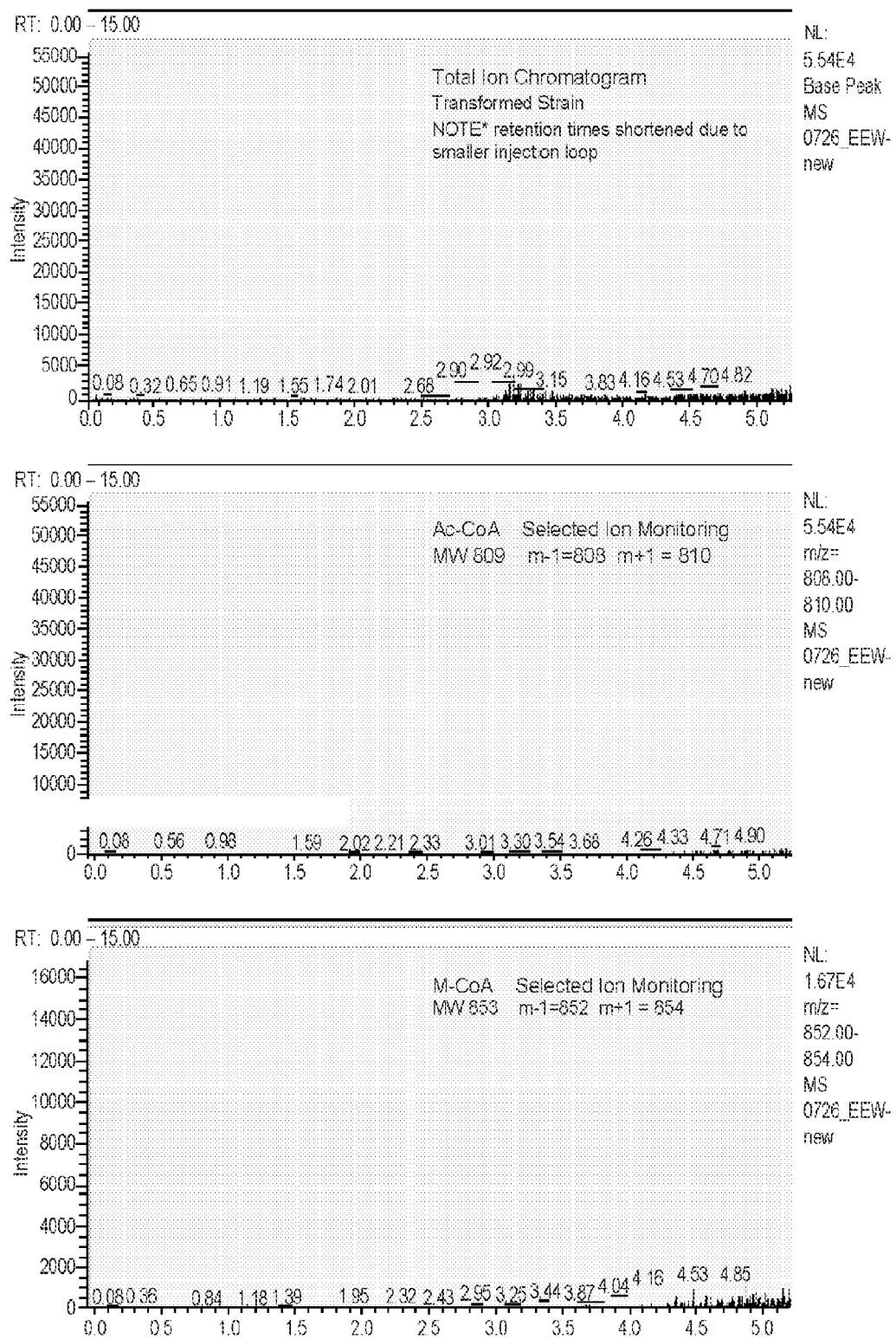
Figure 26B:
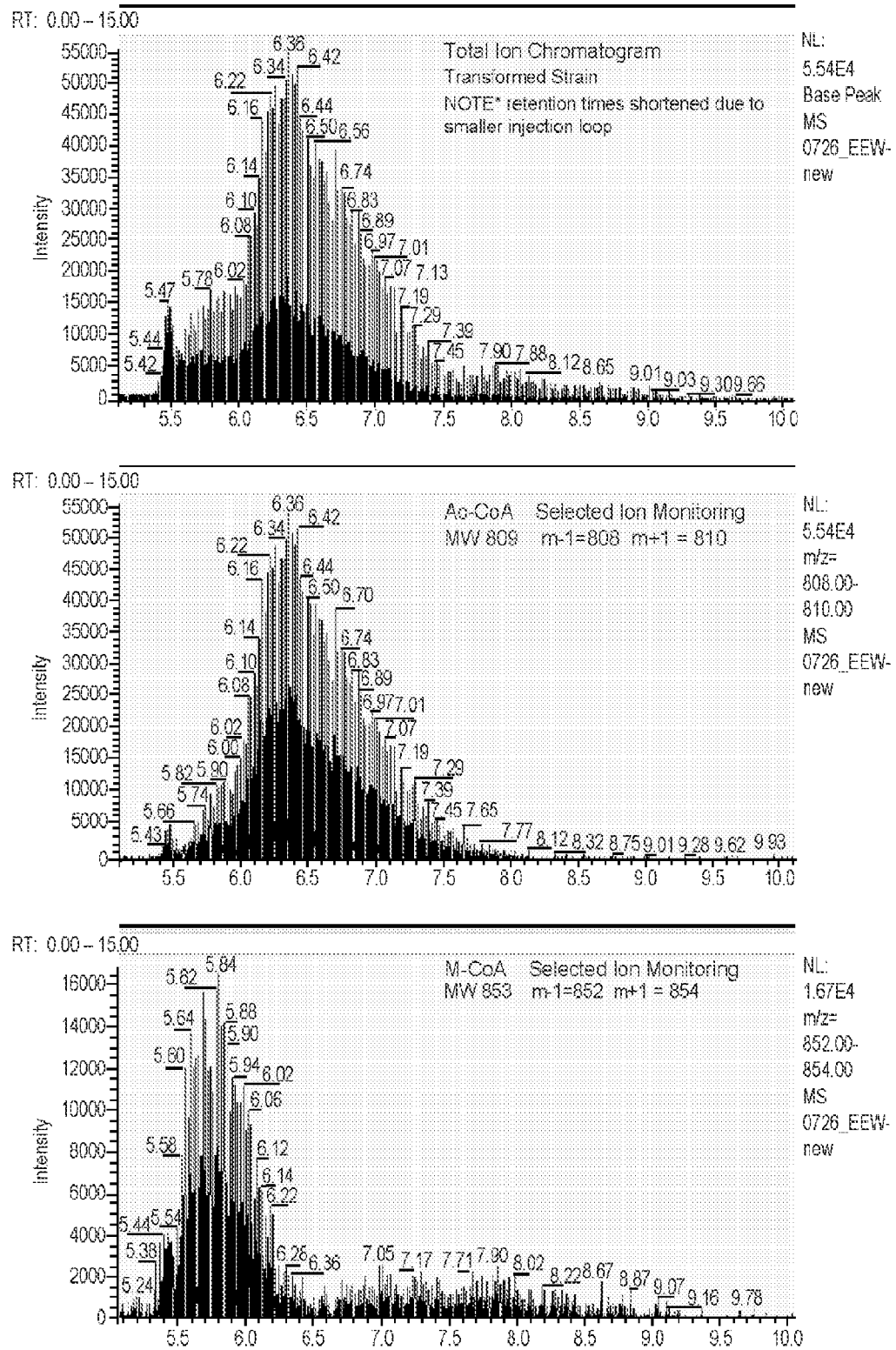
Figure 26B:
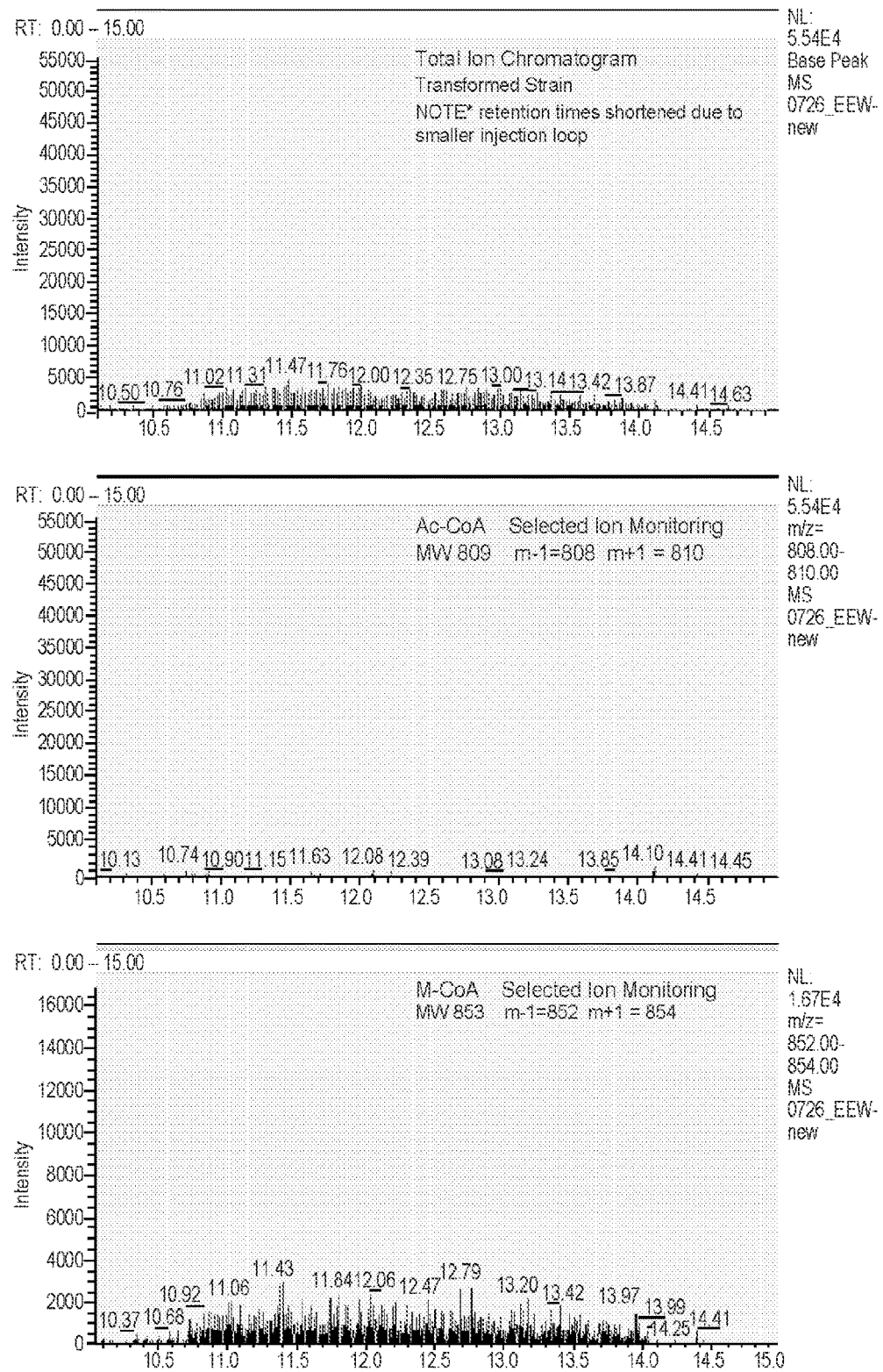

FIG. 26B depicts a mass spectrum of the transcarboxylase assay products for the transcarboxylase sample.

FIG. 27 depicts a schematic for the use of the accC:: matBC *E. coli* strain M2470 to select for more efficient malonyl-CoA production by transcarboxylases.

Figure 28:
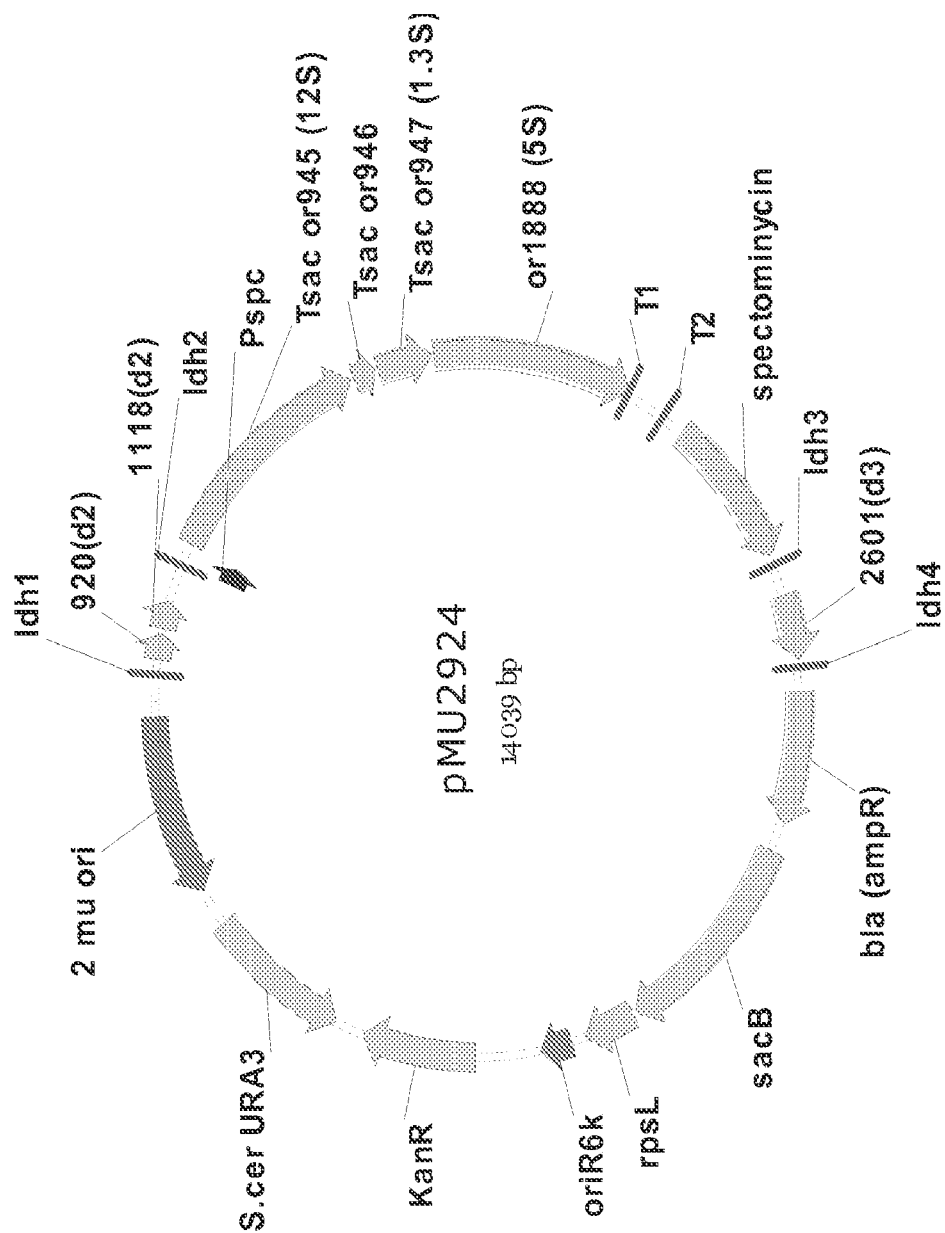

FIG. 28 depicts the vector pMU2924.

Figure 29:
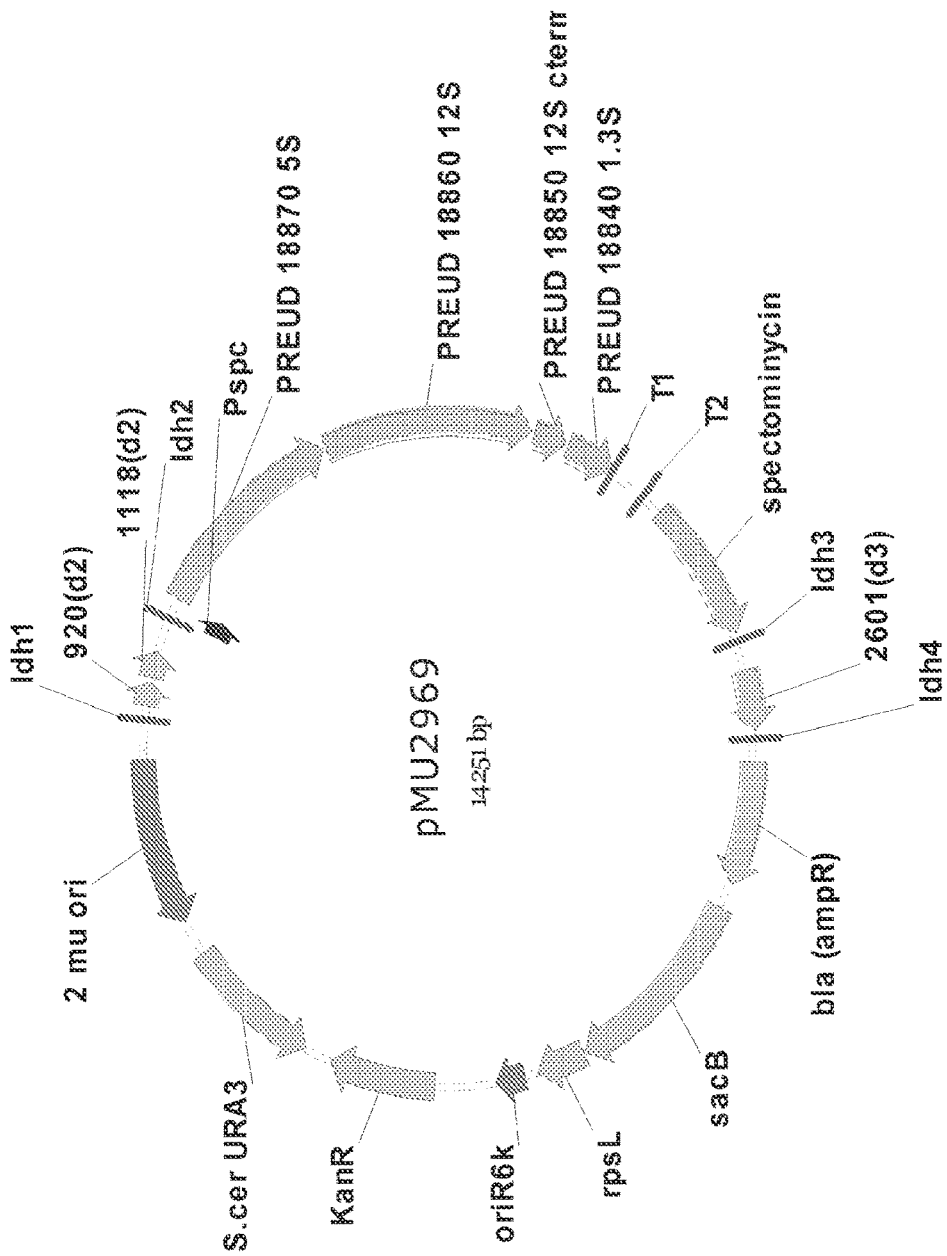

FIG. 29 depicts the vector pMU2969.

Figure 30:
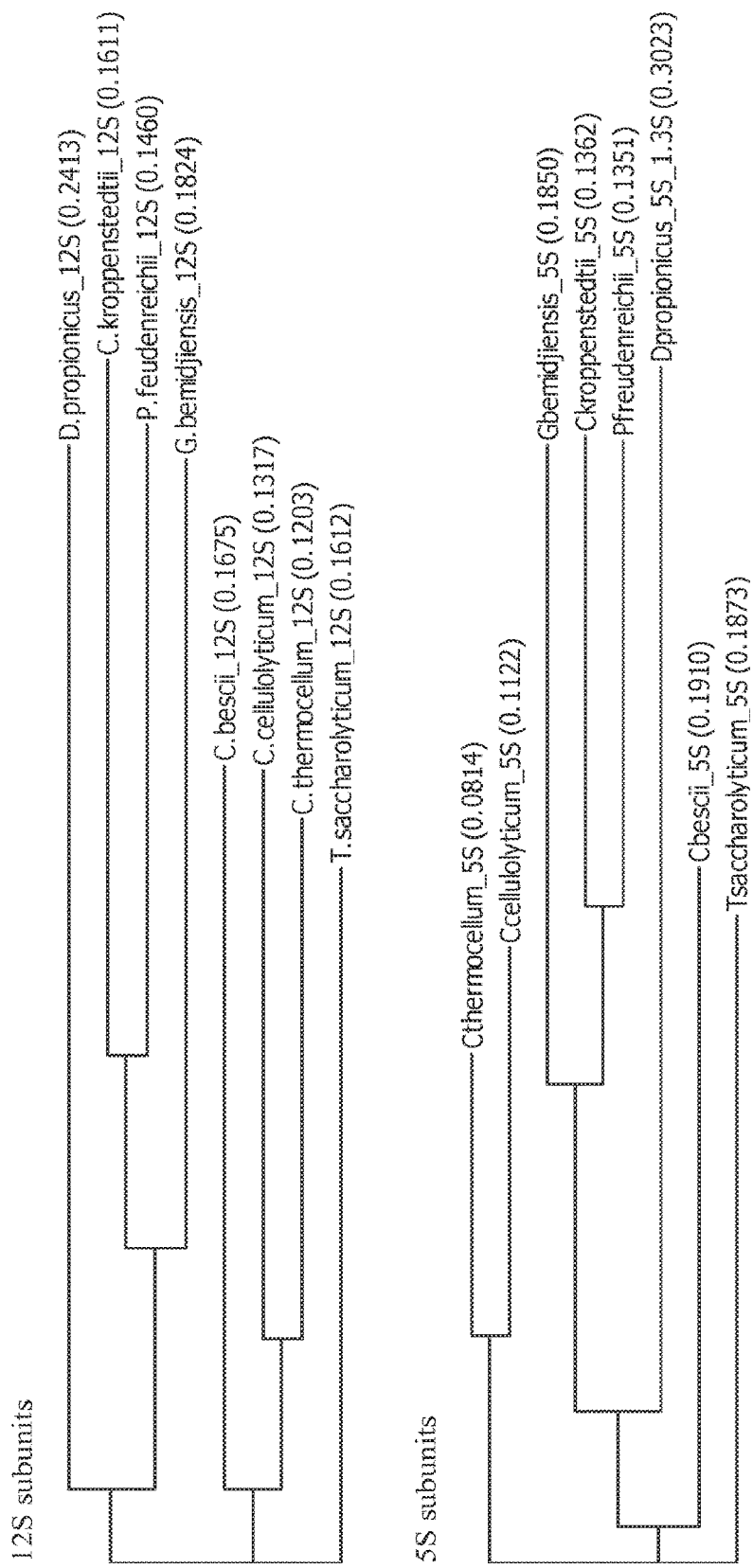
Figure 30:
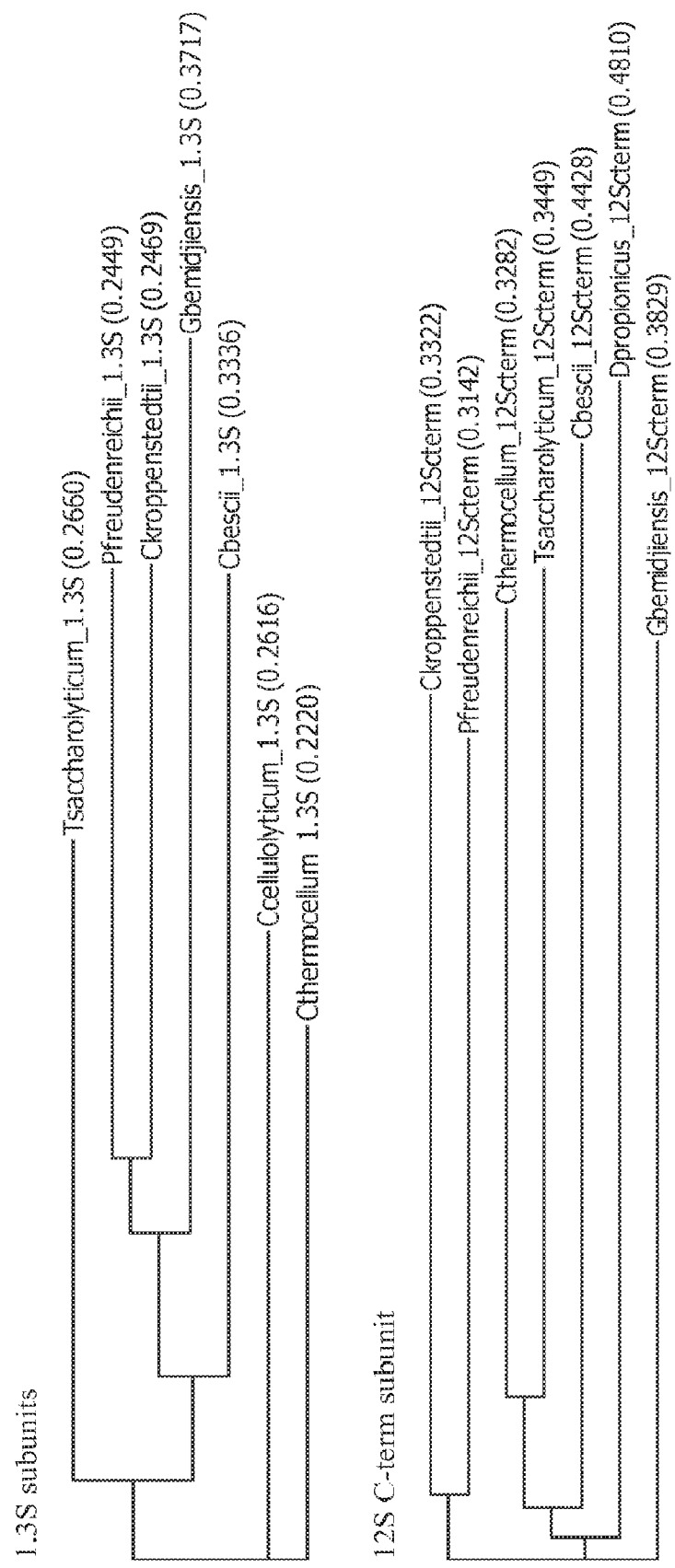

FIG. 30 is a phylogenetic tree depicting relatedness between 12S, 5S, 1.3S, and 12S C-term subunits of transcarboxylases from *D. propionicus, C. kroppenstedtii, P. fuedenreichii, G. bemidjiensis, C. bescii, C. Cellulolyticum, C. thermocellum,* and *T. saccharolyticum*.

Figure 31:
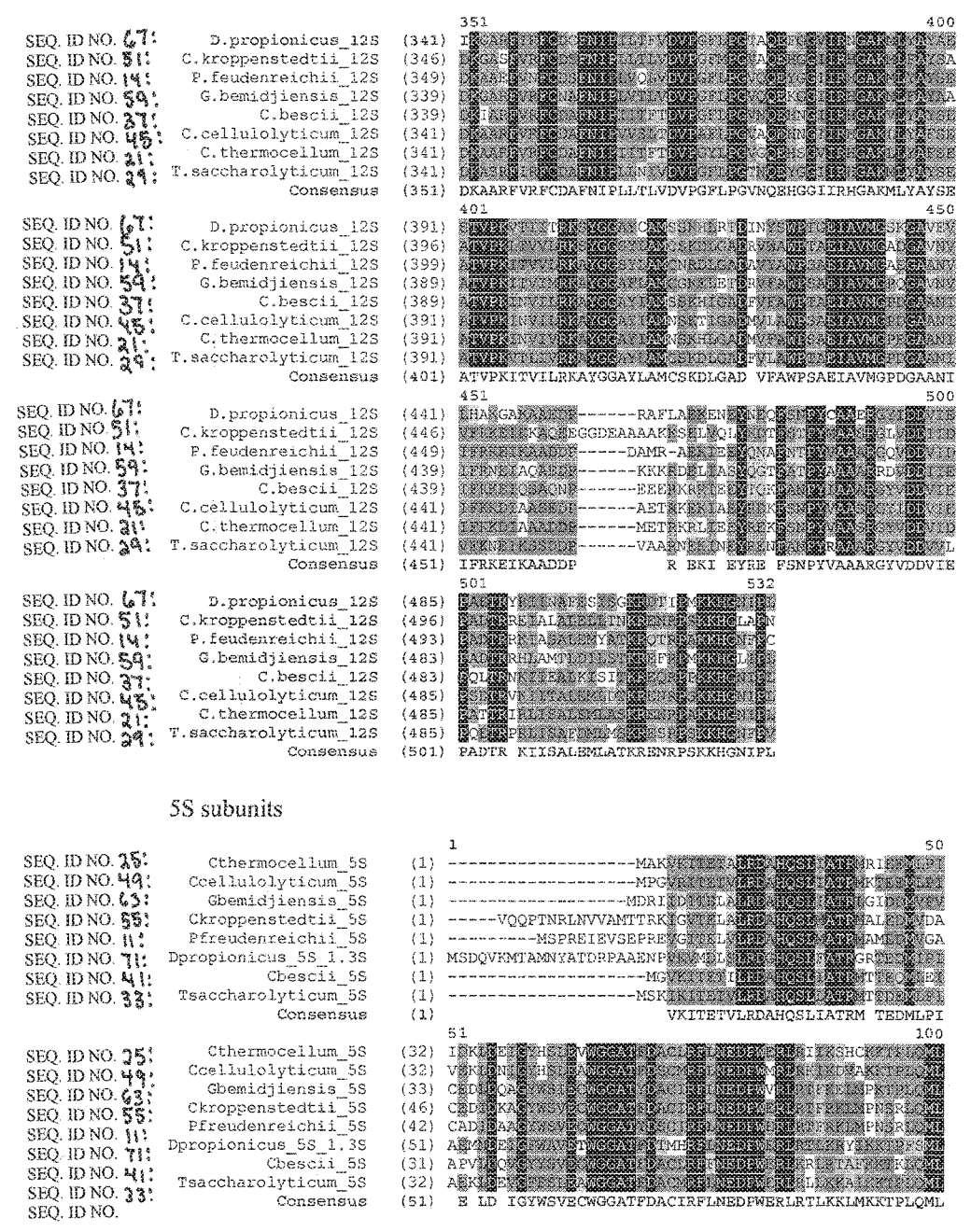
Figure 31:
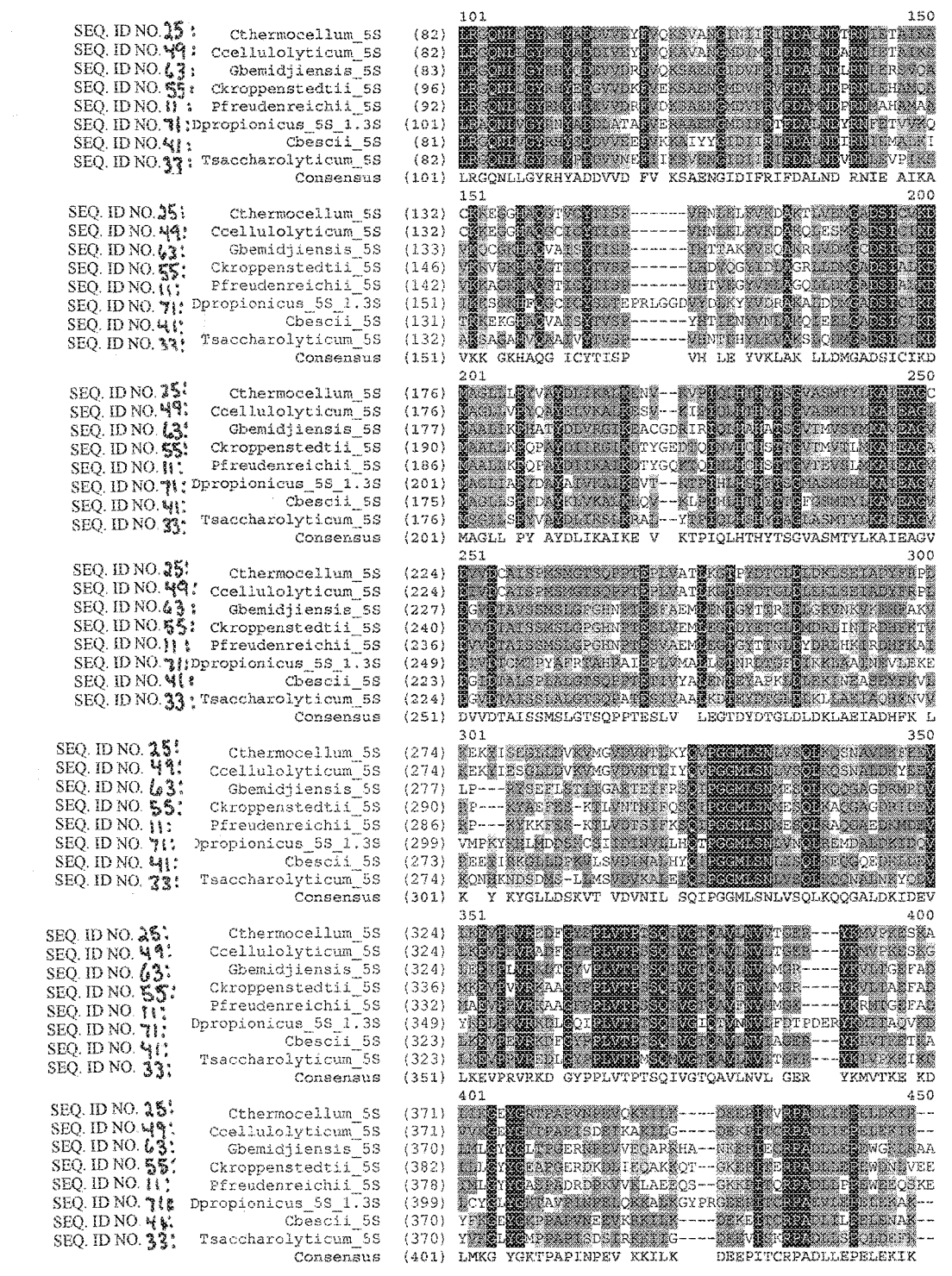

FIG. 31 is an alignment of the transcarboxylase subunits from *D. propionicus, C. kroppenstedtii, P. fuedenreichii, G. bemidjiensis, C. bescii, C. Cellulolyticum, C. thermocellum,* and *T. saccharolyticum*.

Figure 32:
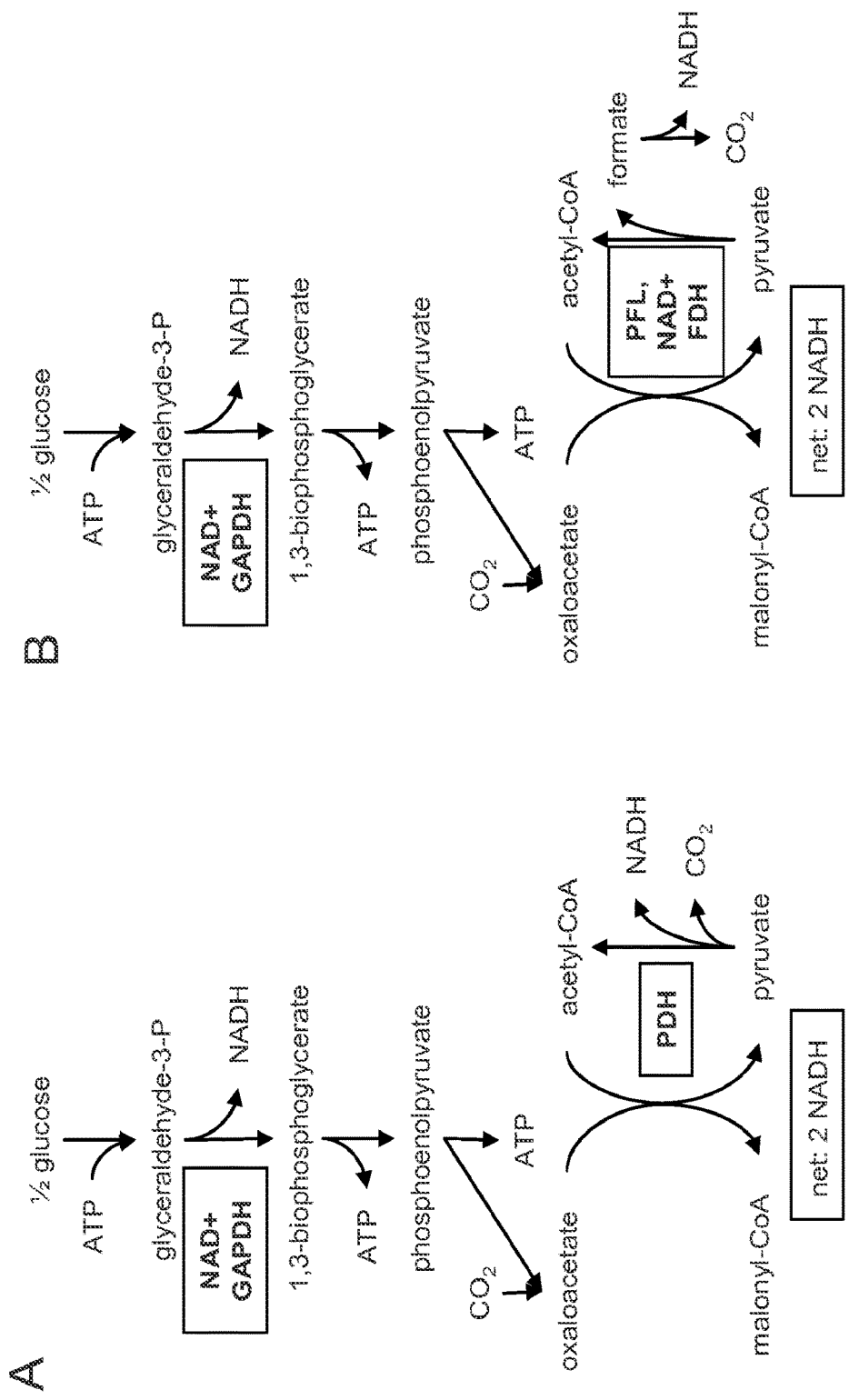
Figure 32:
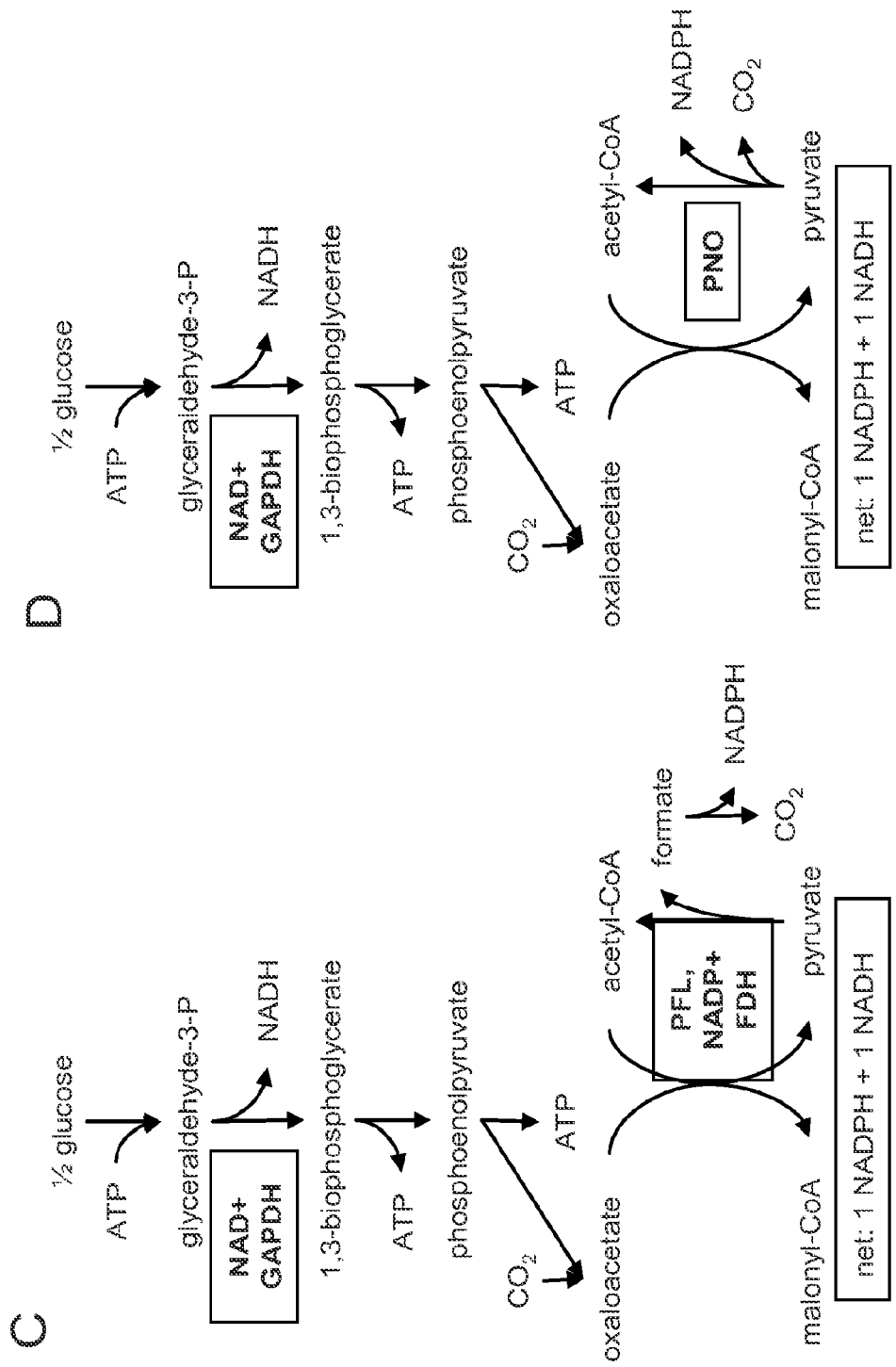
Figure 32:
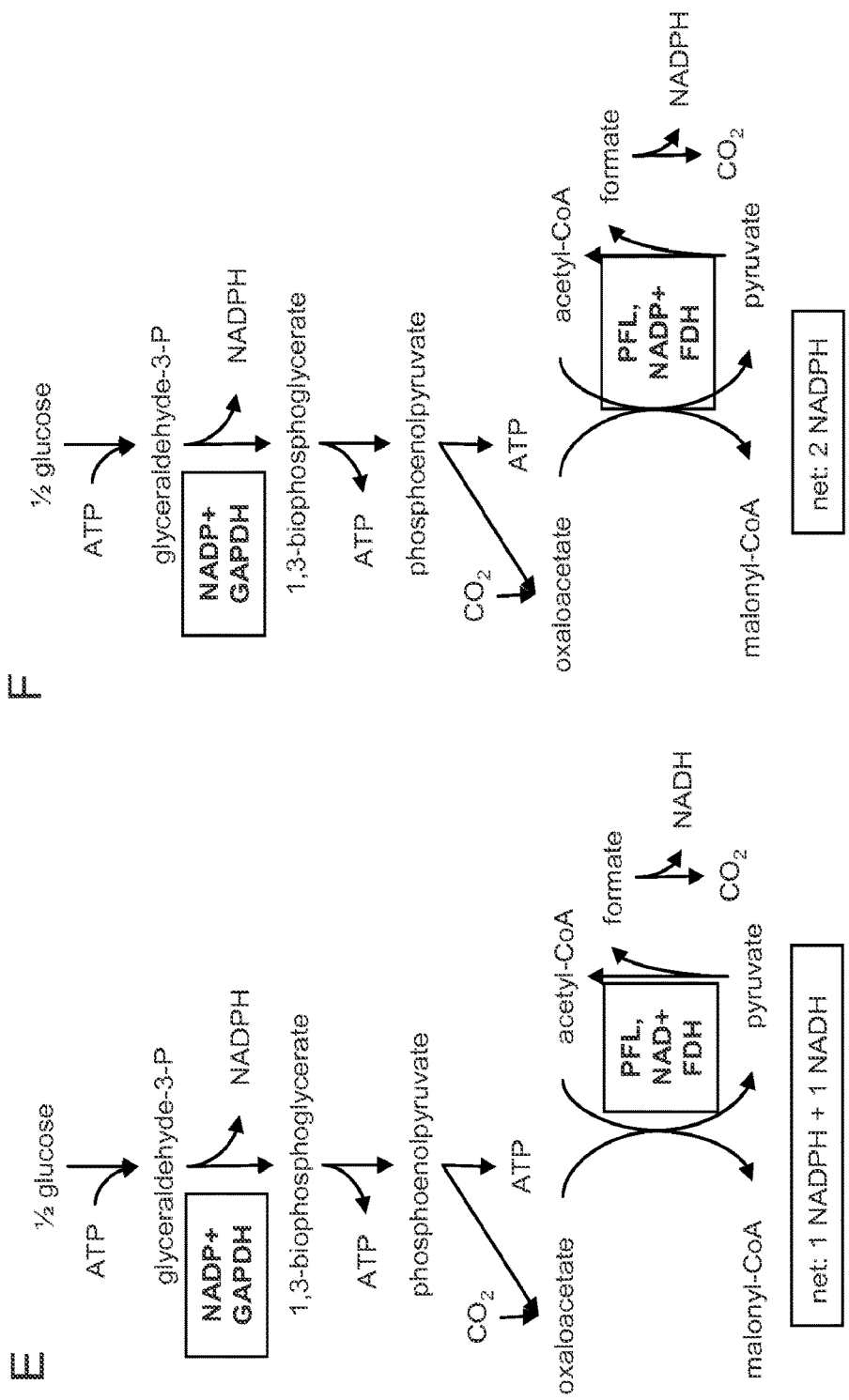
Figure 32:
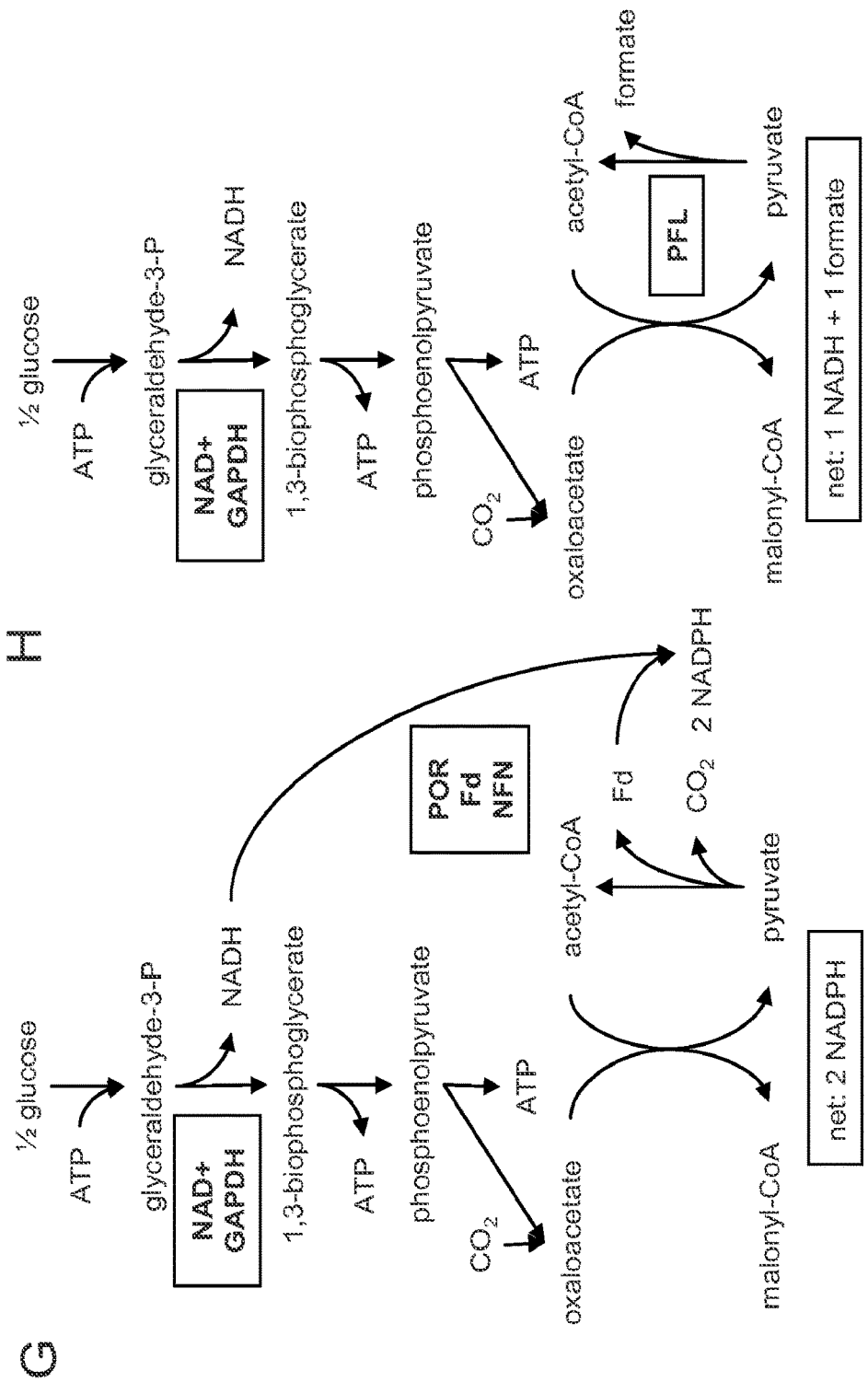
Figure 32:
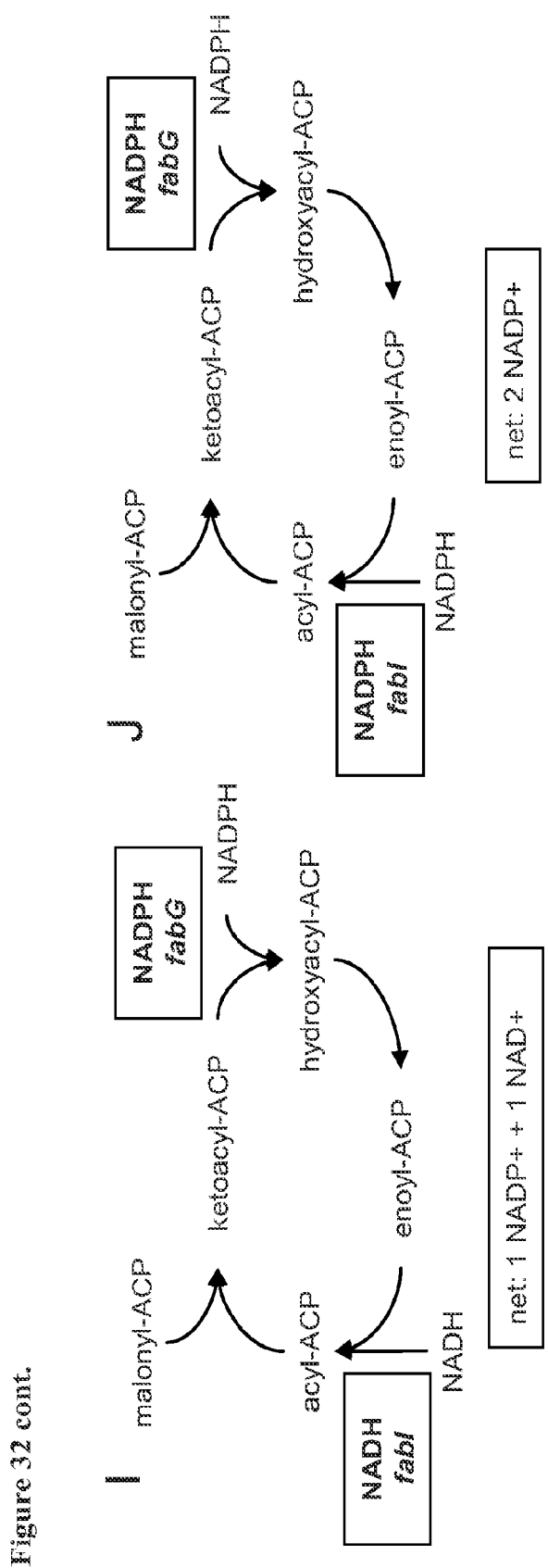
Figure 32:
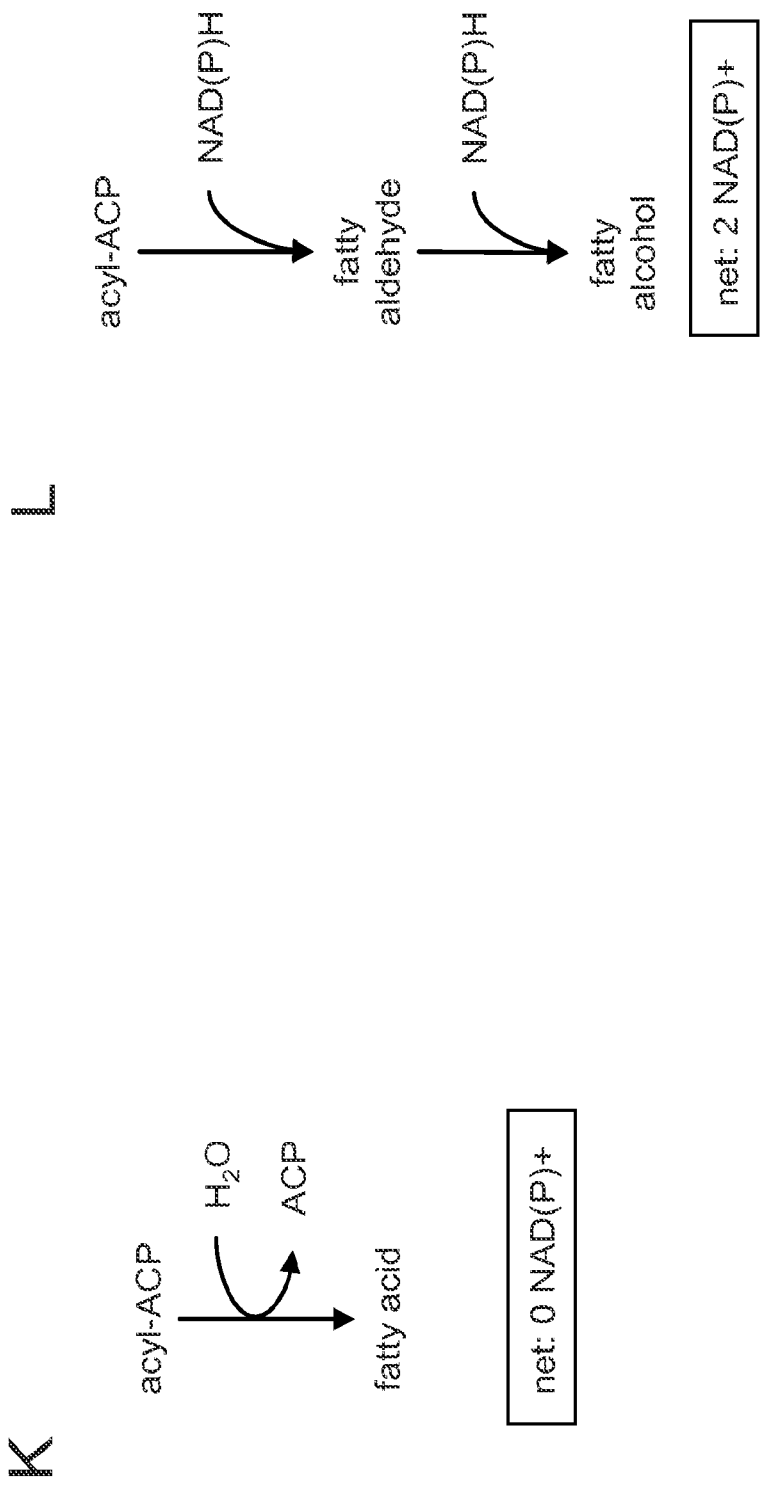

FIG. 32 depicts different schematic routes that correspond to co-factor pathway selection presented in Table 10.

Figure 33:
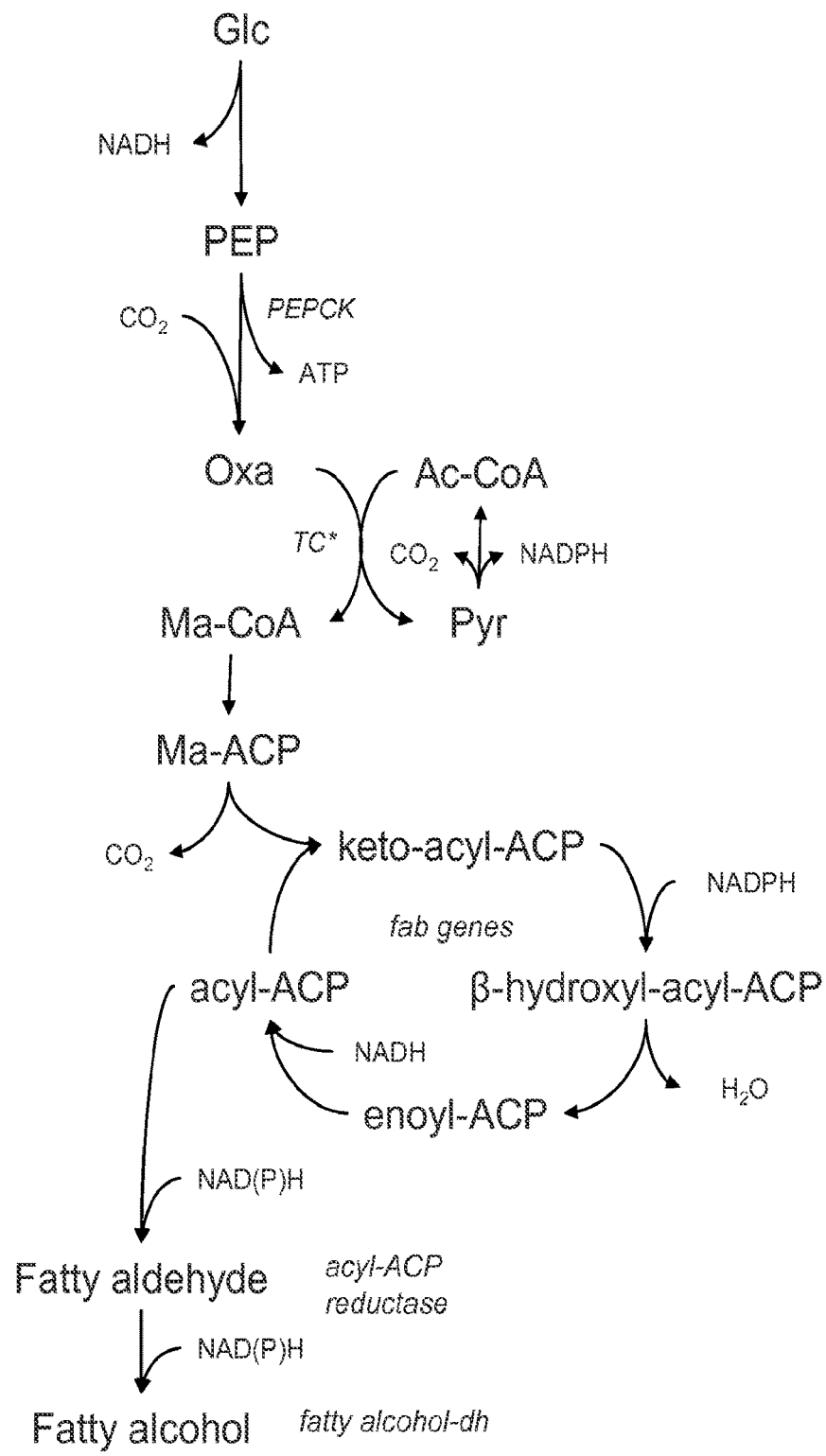

FIG. 33 depicts a pathway for the conversion of glucose to fatty aldehyde or fatty alcohol.

Figure 34:
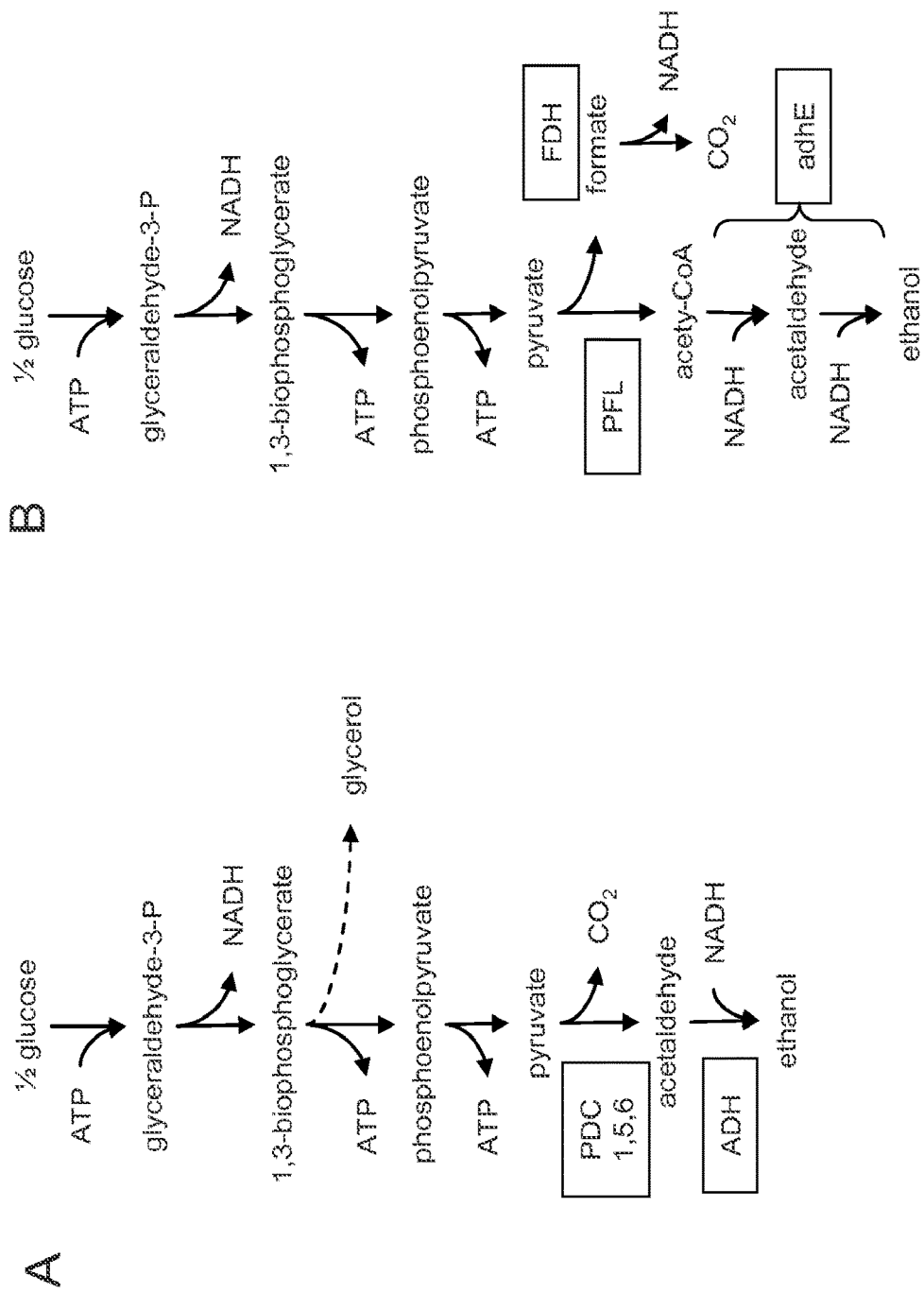
Figure 34:
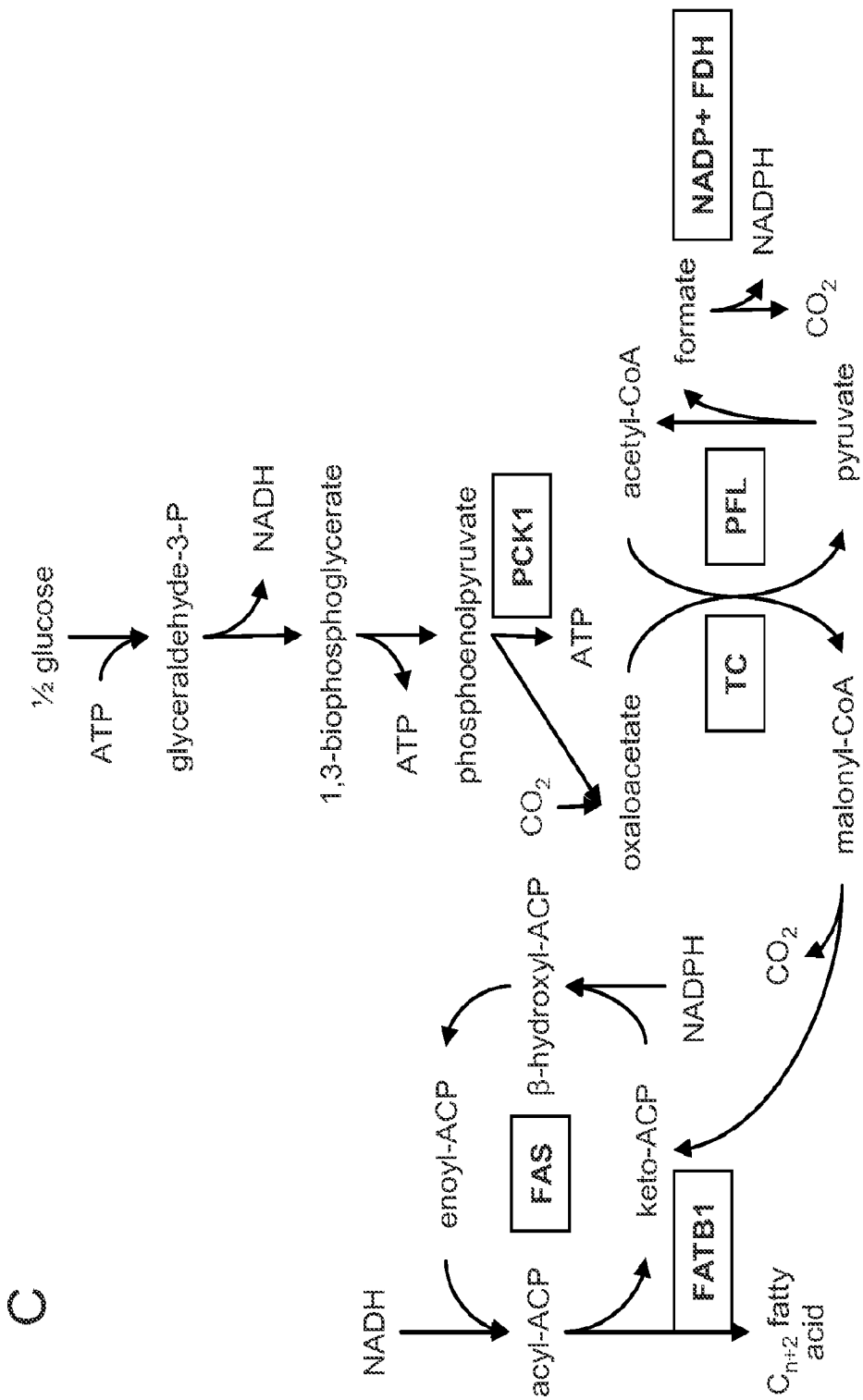

FIG. 34 depicts the pathways for the conversion of the fermentative metabolism of *S. cerevisiae* from the native pyruvate decarboxylase (pdc) based ethanol pathway (A) to an intermediary pyruvate formate lyase and alcohol/aldehyde dehydrogenase (pfl adhE) based ethanol pathway (B), and finally to a transcarboxylase based palmitic acid pathway (C).

Figure 35:
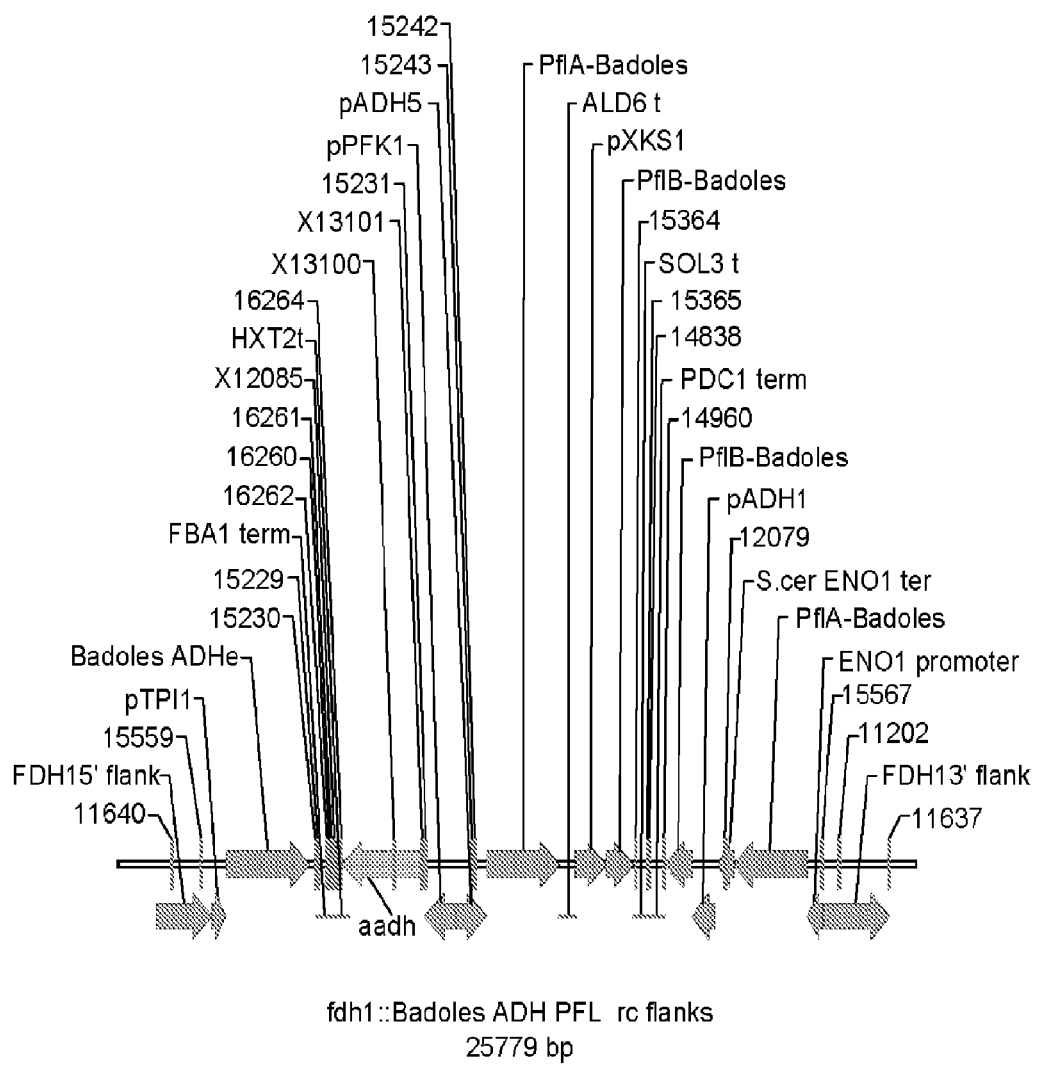

FIG. 35 depicts an integration design which deletes FDH1 and replaces the gene with two copies of ADH and two copies of PFL.

Figure 36:
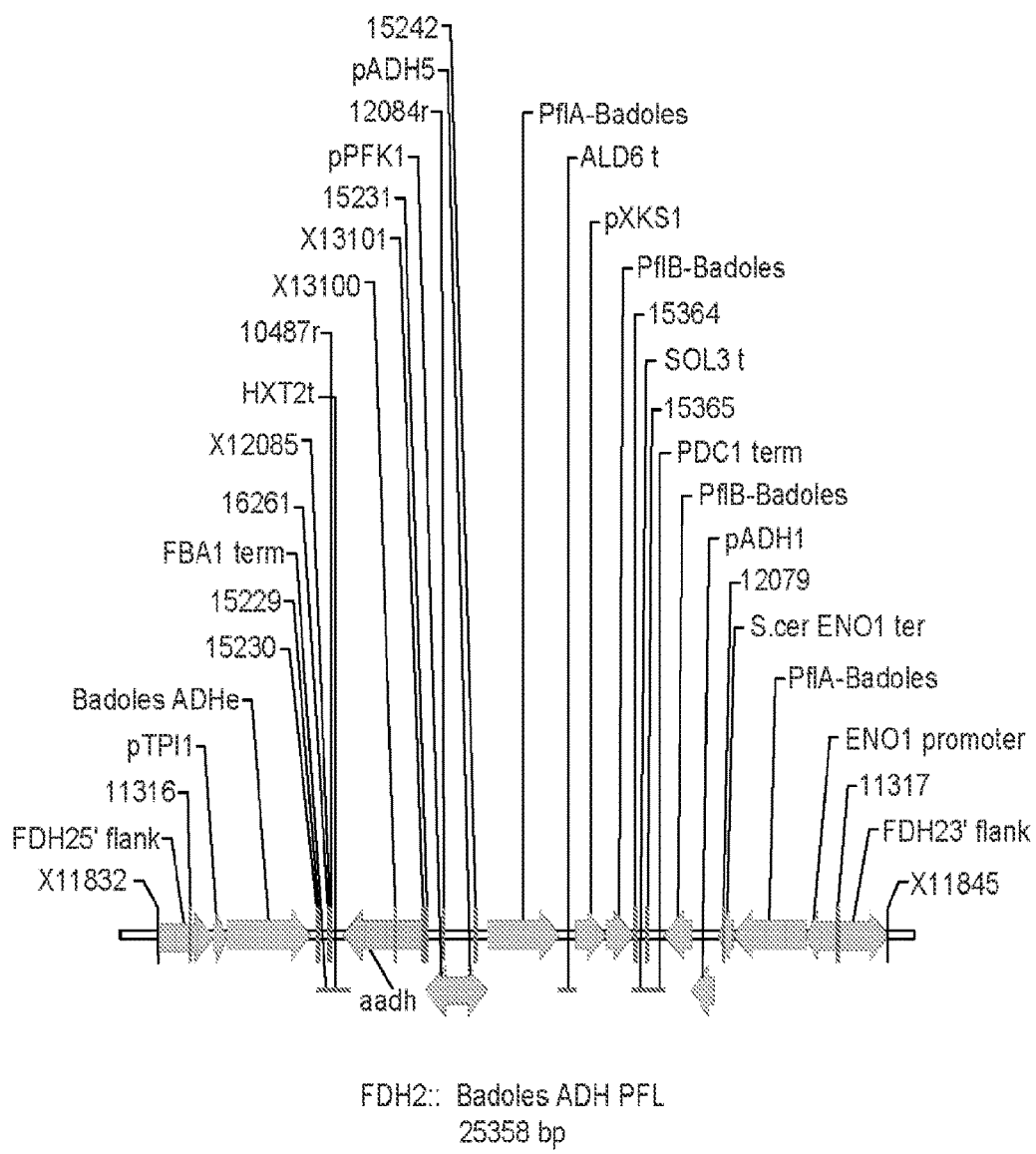

FIG. 36 depicts an integration design which deletes FDH2 and replaces the gene with two copies of ADH and two copies of PFL.

Figure 37:
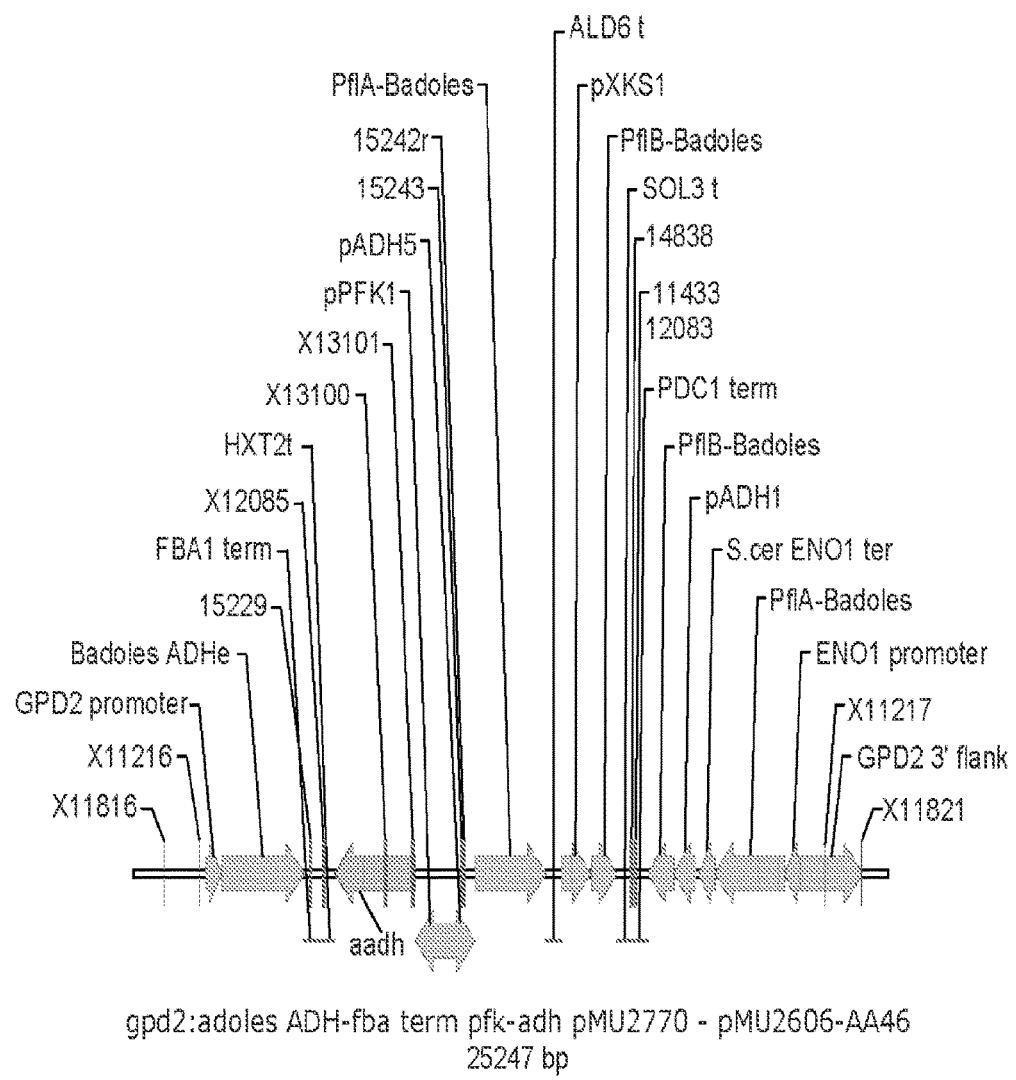

FIG. 37 depicts an integration design which deletes GPD2 and replaces the gene with two copies of ADH and two copies of PFL.

Figure 38:
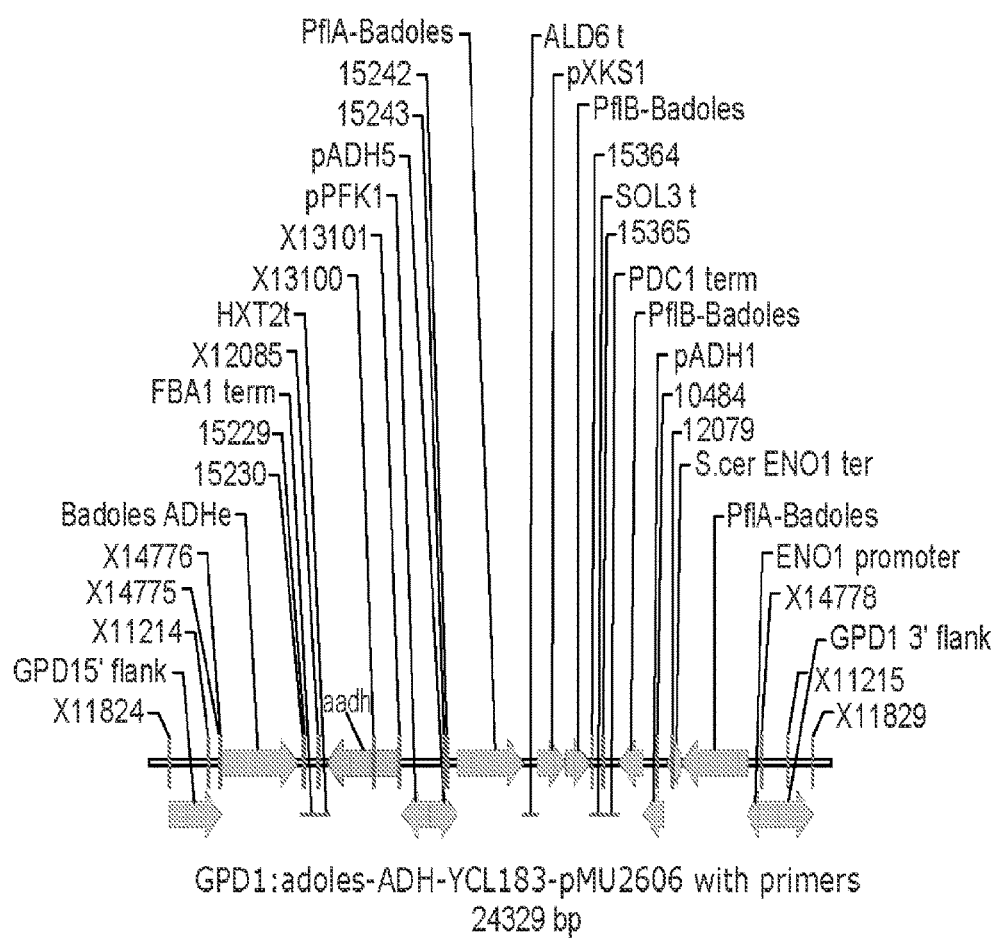

FIG. 38 depicts an integration design which deletes GPD1 and replaces the gene with two copies of ADH and two copies of PFL.

Figure 39:
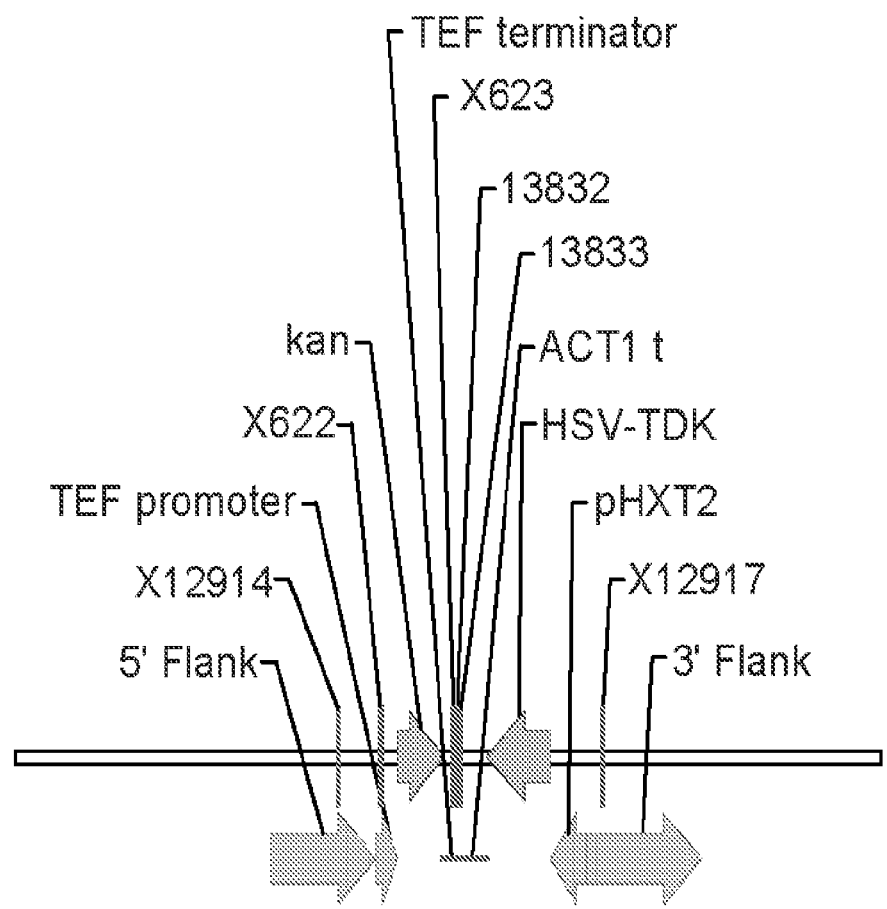

FIG. 39 depicts an integration design which deletes PDC5 and replaces a counter selective gene HSV-TDK and an antibiotic marker (Kan).

Figure 40:
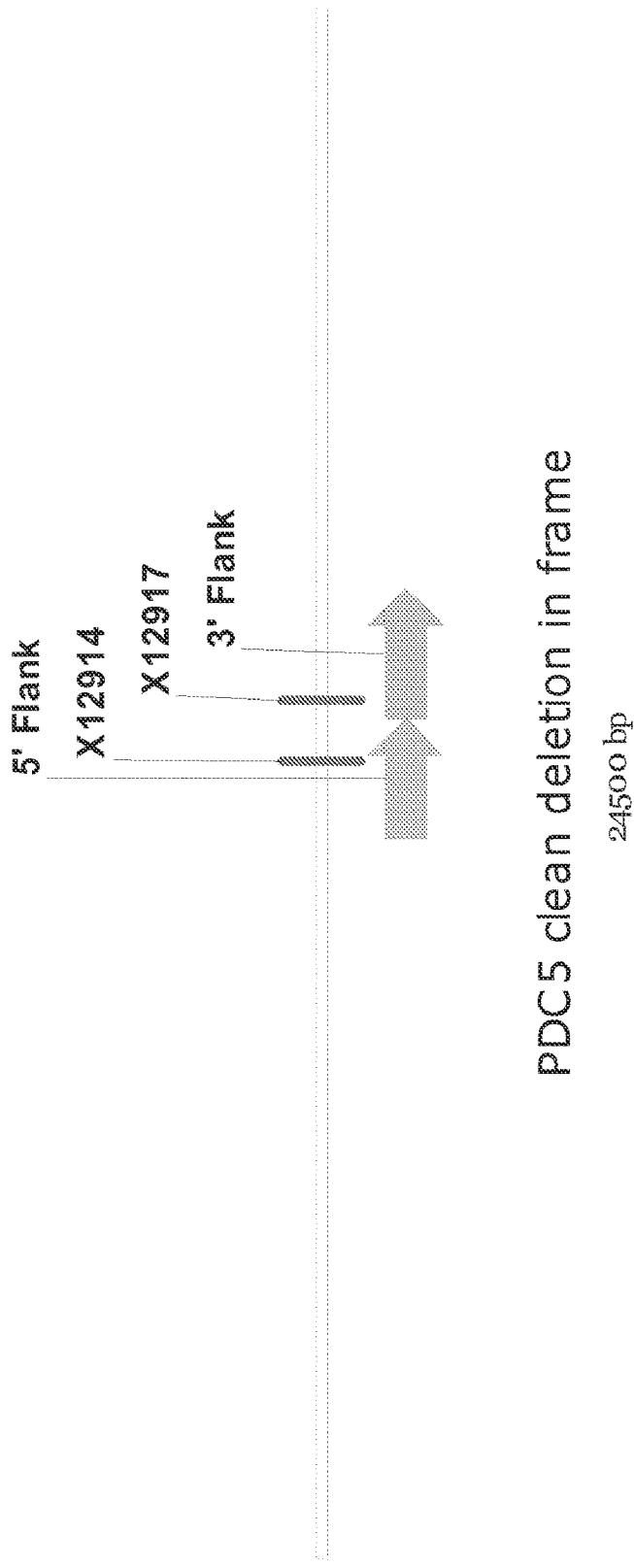

FIG. 40 depicts an integration design which removes the marker shown in FIG. 39 resulting in a clean deletion of PDC5.

Figure 41:
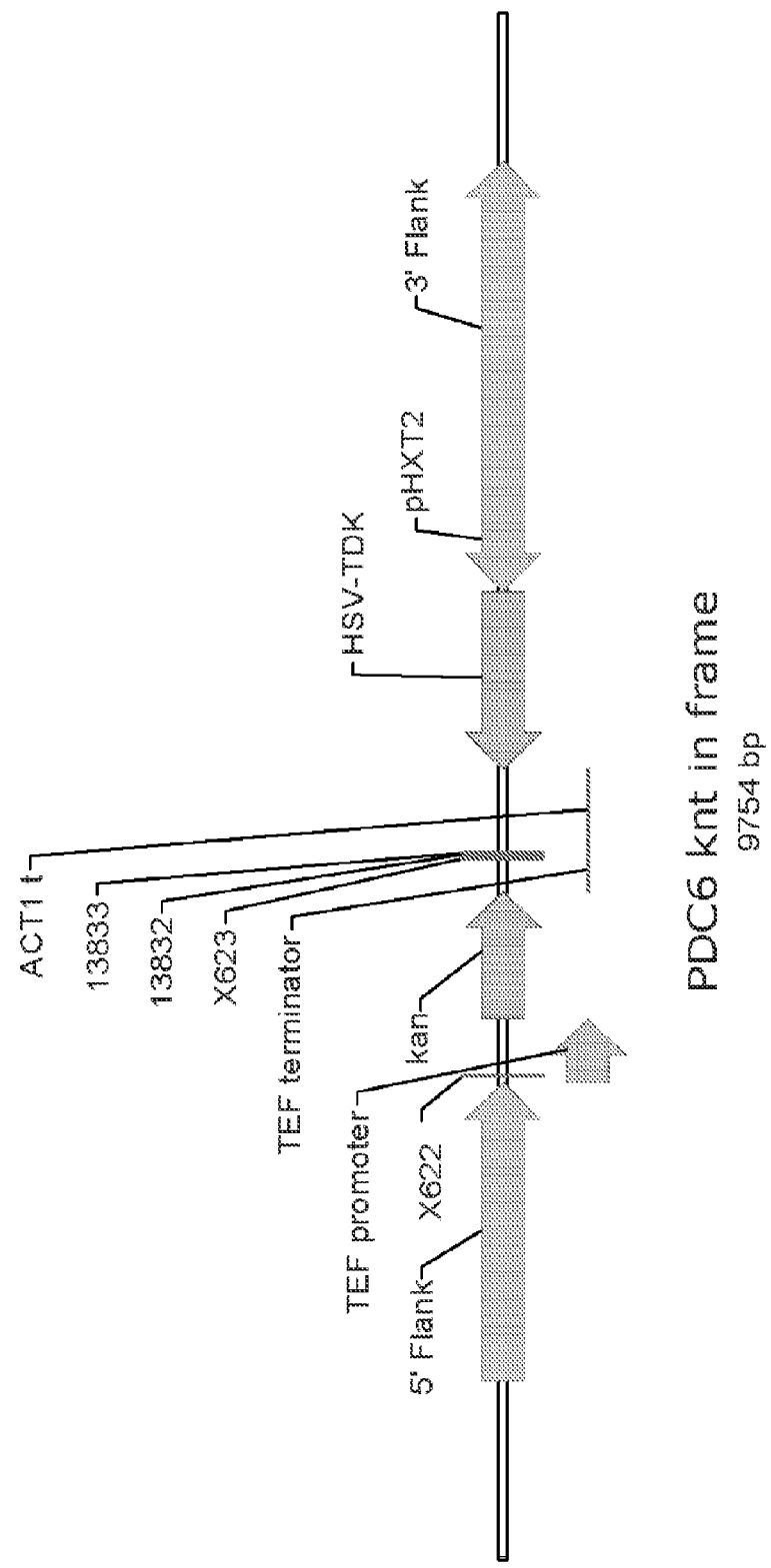

FIG. 41 depicts an integration design which deletes PDC6 and replaces a counter selective gene HSV-TDK and an antibiotic marker (Kan).

Figure 42:
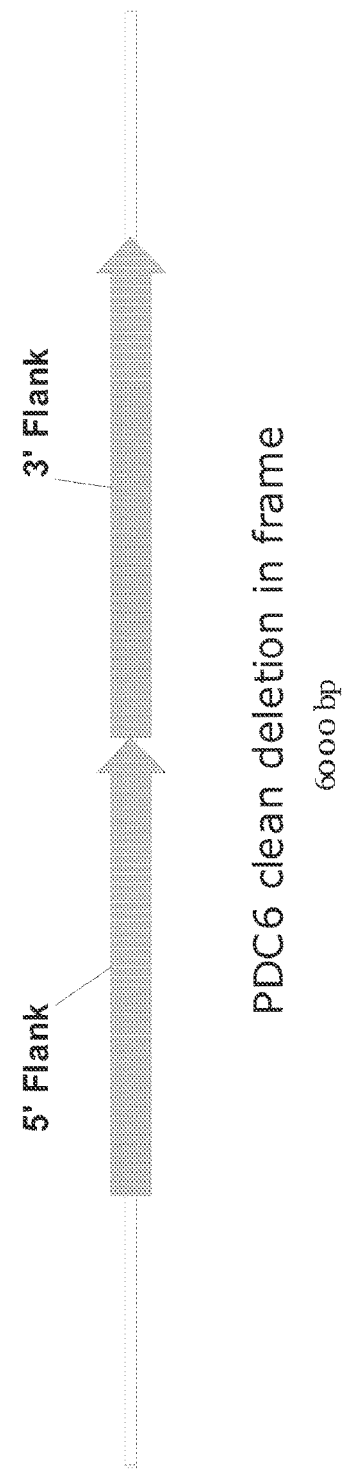

FIG. 42 depicts an integration design which removes the marker shown in FIG. 41 resulting in a clean deletion of PDC6.

Figure 43:
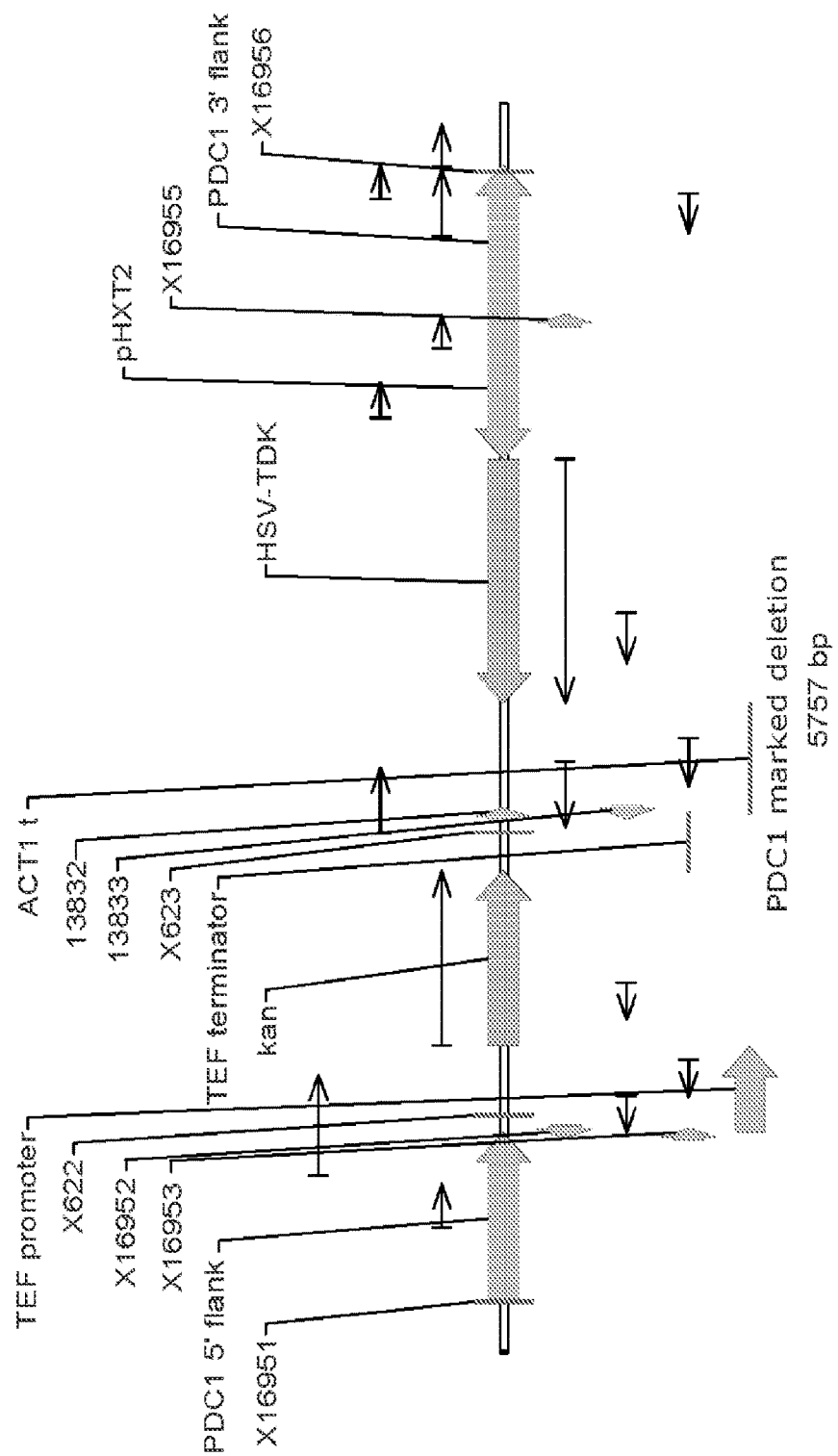

FIG. 43 depicts an integration design which deletes PDC1 and replaces it with a counter selective gene HSV-TDK and an antibiotic marker (Kan).

Figure 44:
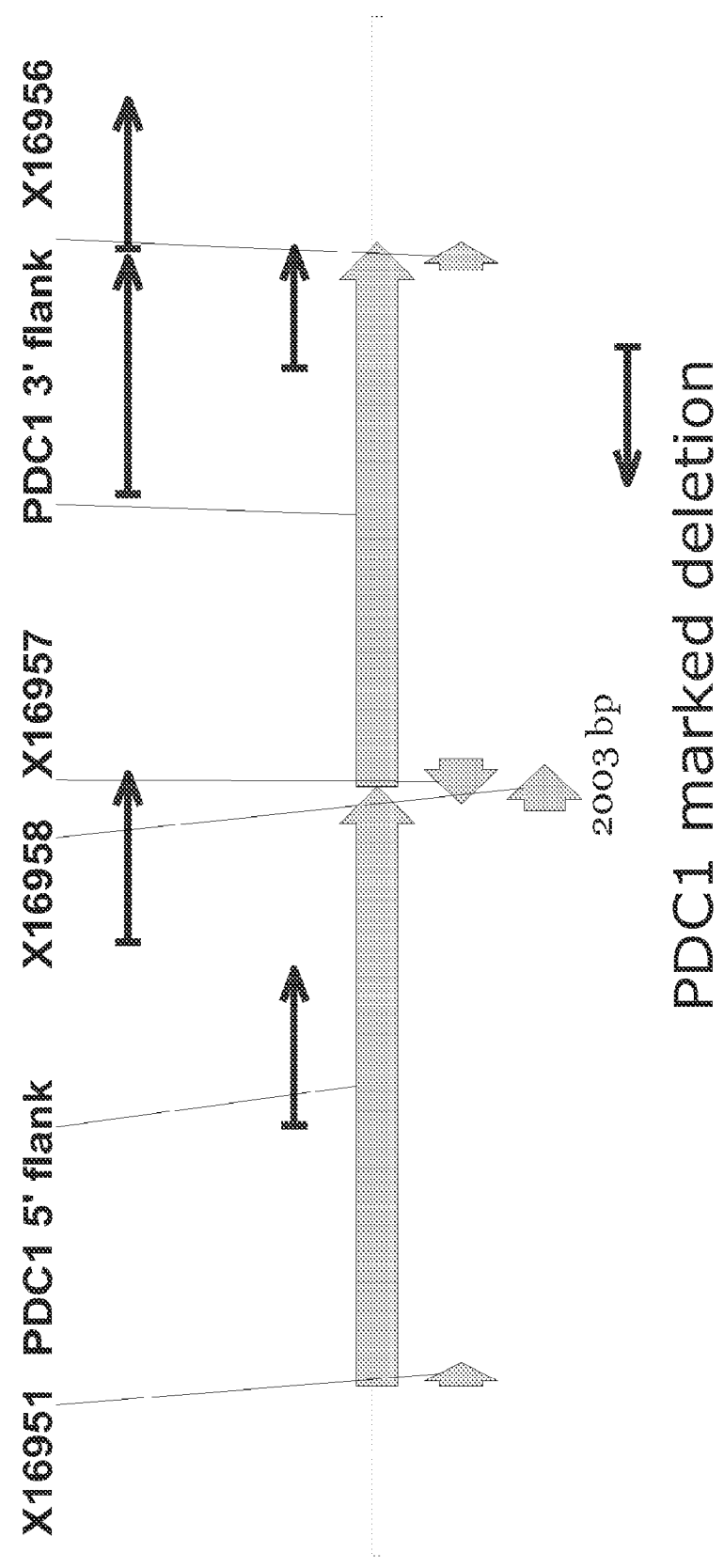

FIG. 44 depicts an integration design which removes the marker shown in FIG. 41 resulting in a clean deletion of PDC1.

Figure 45:
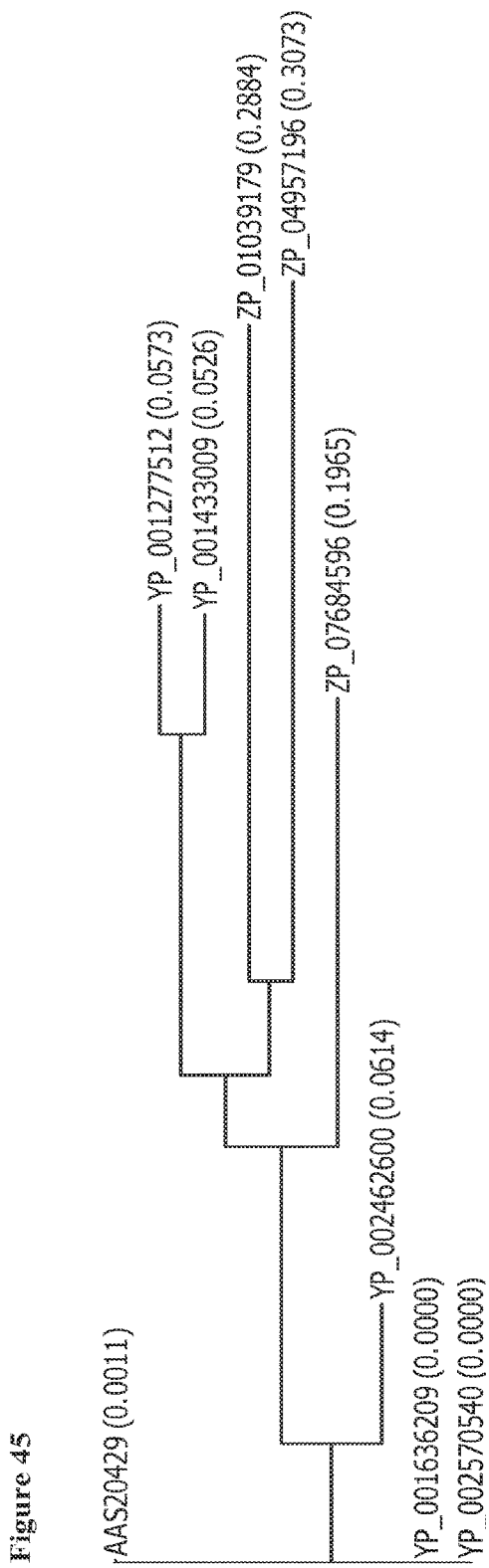

FIG. 45 is a phylogenetic tree depicting relatedness between bifunctional malonyl-CoA reductases from *C. aurantiacus, C. aurantiacus* J-10-fl, *Chloroflexus* sp. Y-400-fl, *C. aggregans* DSM 9485, *O. trichoides* DG6, *R. castenholzii* DSM 13941, *R. oseiflexus* sp. RS-1, *Erythrobacter* sp. NAP1, and gamma proteobacterium NOR51-B.

FIG. 46 is an alignment of bifunctional malonyl-CoA reductases from *C. aurantiacus, C. aurantiacus* J-10-fl, *Chloroflexus* sp. Y-400-fl, *C. aggregans* DSM 9485, *O. trichoides* DG6, *R. castenholzii* DSM 13941, *R. oseiflexus* sp. RS-1, *Erythrobacter* sp. NAP1, and gamma proteobacterium NOR51-B.

DETAILED DESCRIPTION OF THE INVENTION

Definitions

The indefinite articles "a" and "an" preceding an element or component of the invention are intended to include plurals of the element or component, e.g., one or at least one of the element or component, unless the context is such that only the singular form is intended.

The term "heterologous" when used in reference to a polynucleotide, a gene, a polypeptide, or an enzyme refers to a polynucleotide, gene, polypeptide, or an enzyme not normally found in the host organism. "Heterologous" also includes a native coding region, or portion thereof, that is reintroduced into the source organism in a form that is different from the corresponding native gene, e.g., not in its natural location in the organism's genome. The heterologous polynucleotide or gene may be introduced into the host organism by, e.g., gene transfer. A heterologous gene may include a native coding region that is a portion of a chimeric gene including non-native regulatory regions that is reintroduced into the native host. Foreign genes can comprise native genes inserted into a non-native organism, or chimeric genes.

The term "heterologous polynucleotide" is intended to include a polynucleotide that encodes one or more polypeptides or portions or fragments of polypeptides. A heterologous polynucleotide may be derived from any source, e.g., eukaryotes, prokaryotes, viruses, or synthetic polynucleotide fragments.

The terms "promoter" or "surrogate promoter" is intended to include a polynucleotide that can transcriptionally control a gene-of-interest that it does not transcriptionally control in nature. In certain embodiments, the transcriptional control of a surrogate promoter results in an increase in expression of the gene-of-interest. In certain embodiments, a surrogate promoter is placed 5' to the gene-of-interest. A surrogate promoter may be used to replace the natural promoter, or may be used in addition to the natural promoter. A surrogate promoter may be endogenous with regard to the host cell in which it is used, or it may be a heterologous polynucleotide sequence introduced into the host cell, e.g., exogenous with regard to the host cell in which it is used.

The terms "gene(s)" or "polynucleotide" or "polynucleotide sequence(s)" are intended to include nucleic acid molecules, e.g., polynucleotides which include an open reading frame encoding a polypeptide, and can further include non-coding regulatory sequences, and introns. In addition, the terms are intended to include one or more genes that map to a functional locus. In addition, the terms are intended to include a specific gene for a selected purpose. The gene may be endogenous to the host cell or may be recombinantly introduced into the host cell, e.g., as a plasmid maintained episomally or a plasmid (or fragment thereof) that is stably integrated into the genome. In addition to the plasmid form, a gene may, for example, be in the form of linear DNA. The term gene is also intended to cover all copies of a particular gene, e.g., all of the DNA sequences in a cell encoding a particular gene product.

The term "transcriptional control" is intended to include the ability to modulate gene expression at the level of transcription. In certain embodiments, transcription, and thus gene expression, is modulated by replacing or adding a surrogate promoter near the 5' end of the coding region of a gene-of-interest, thereby resulting in altered gene expression. In certain embodiments, the transcriptional control of one or more genes is engineered to result in the optimal expression of such genes, e.g., in a desired ratio. The term also includes inducible transcriptional control as recognized in the art.

The term "expression" is intended to include the expression of a gene at least at the level of mRNA production.

The term "expression product" is intended to include the resultant product, e.g., a polypeptide, of an expressed gene.

The term "polypeptide" is intended to encompass a singular "polypeptide," as well as plural "polypeptides," and refers to a molecule composed of monomers (amino acids) linearly linked by amide bonds (also known as peptide bonds). The term "polypeptide" refers to any chain or chains of two or more amino acids and does not refer to a specific length of the amino acids. Thus, peptides, dipeptides, tripeptides, oligopeptides, "protein," "amino acid chain," "enzyme," or any other term used to refer to a chain or chains of two or more amino acids, are included within the definition of "polypeptide," and the term "polypeptide" may be used instead of, or interchangeably with, any of these terms. A polypeptide may be derived from a natural biological source or produced by recombinant technology. It may be generated in any manner, including by chemical synthesis.

The term "increased expression" is intended to include an alteration in gene expression at least at the level of increased mRNA production and, preferably, at the level of polypeptide expression. The term "increased production" is intended to include an increase in the amount of a polypeptide expressed, in the level of the enzymatic activity of the polypeptide, or a combination thereof, as compared to the native production of, or the enzymatic activity of, the polypeptide.

The terms "activity," "activities," "enzymatic activity," and "enzymatic activities" are used interchangeably and are intended to include any functional activity normally attributed to a selected polypeptide when produced under favorable conditions. Typically, the activity of a selected polypeptide encompasses the total enzymatic activity associated with the produced polypeptide. The polypeptide produced by a host cell and having enzymatic activity may be located in the intracellular space of the cell, cell-associated, secreted into the extracellular milieu, or a combination thereof. Techniques for determining total activity as compared to secreted activity are described herein and are known in the art.

The term "secreted" is intended to include the movement of polypeptides to the periplasmic space or extracellular milieu. The term "increased secretion" is intended to include situations in which a given polypeptide is secreted at an increased level (i.e., in excess of the naturally-occurring amount of secretion). In certain embodiments, the term "increased secretion" refers to an increase in secretion of a given polypeptide that is at least about 10% or at least about 100%, 200%, 300%, 400%, 500%, 600%, 700%, 800%, 900%, 1000%, or more, as compared to the naturally-occurring level of secretion.

The term "secretory polypeptide" is intended to include any polypeptide(s), alone or in combination with other polypeptides, that facilitate the transport of another polypeptide from the intracellular space of a cell to the extracellular milieu. In certain embodiments, the secretory polypeptide(s) encompass all the necessary secretory polypeptides sufficient to impart secretory activity to a Gram-negative or Gram-positive host cell or to a yeast host cell. Typically, secretory proteins are encoded in a single region or locus that may be isolated from one host cell and transferred to another host cell using genetic engineering. In certain embodiments, the secretory polypeptide(s) are derived from any bacterial cell having secretory activity or any yeast cell having secretory activity. In certain embodiments, the secretory polypeptide(s) are derived from a host cell having Type II secretory activity. In certain embodiments, the host cell is a thermophilic bacterial cell. In certain embodiments, the host cell is a yeast cell.

The term "derived from" is intended to include the isolation (in whole or in part) of a polynucleotide segment from an indicated source or the purification of a polypeptide from an indicated source. The term is intended to include, for example, direct cloning, PCR amplification, or artificial synthesis from or based on a sequence associated with the indicated polynucleotide source.

By "thermophilic" is meant an organism that thrives at a temperature of about 45° C. or higher.

By "mesophilic" is meant an organism that thrives at a temperature of about 20-45° C.

Certain embodiments of the present invention provide for the "insertion," (e.g., the addition, integration, incorporation, or introduction) of certain genes or particular polynucleotide sequences within thermophilic or mesophilic microorganisms, which insertion of genes or particular polynucleotide sequences may be understood to encompass "genetic modification(s)" or "transformation(s)" such that the resulting strains of said thermophilic or mesophilic microorganisms may be understood to be "genetically modified" or "transformed." In certain embodiments, strains may be of bacterial, fungal, or yeast origin.

In certain embodiments, the polynucleotide sequences of the invention are genetically modified such that the encoded enzyme is engineered to alter catalytic activity and/or alter substrate specificity to improve the conversion of a substrate to a product as compared to the native enzyme. In certain aspects, the genetic modification alters catalytic activity and/or substrate specificity to provide an encoded enzyme that converts a substrate to a product that is not catalyzed by the native enzyme in vivo, or is catalyzed at only minimal turnover. Techniques to genetically modify polynucleotides are known in the art and include, but are not limited to, alteration, insertion, and/or deletion of one or more nucleic acids in the polynucleotide. Such techniques to alter, insert, and/or delete nucleic acids include, but are not limited to, random, site-directed, or saturating mutagenesis.

Certain embodiments of the present invention provide for the "inactivation" or "deletion" of certain genes or particular polynucleotide sequences within thermophilic or mesophilic microorganisms, which "inactivation" or "deletion" of genes or particular polynucleotide sequences may be understood to encompass "genetic modification(s)" or "transformation(s)" such that the resulting strains of said thermophilic or mesophilic microorganisms may be understood to be "genetically modified" or "transformed." In certain embodiments, strains may be of bacterial, fungal, or yeast origin.

The term "consolidated bioprocessing" or "CBP" is intended to include a processing strategy for cellulosic biomass that involves consolidating into a single process step, four biologically-mediated events: enzyme production, hydrolysis, hexose fermentation, and pentose fermentation. Implementing this strategy requires development of microorganisms that both utilize cellulose, hemicellulosics, and other biomass components while also producing a product of interest at sufficiently high yield and concentrations. The feasibility of CBP is supported by kinetic and bioenergetic analysis. See van Walsum and Lynd (1998) *Biotech. Bioeng.* 58:316.

The term "CBP organism" is intended to include microorganisms of the invention, e.g., microorganisms that have properties suitable for CBP.

In one aspect of the invention, the genes or particular polynucleotide sequences are inserted to activate the activity for which they encode, such as the expression of an enzyme. In certain embodiments, genes encoding enzymes in the metabolic production of fatty acids may be added to a mesophilic or a thermophilic organism.

In one aspect of the invention, the genes or particular polynucleotide sequences are partially, substantially, or completely deleted, silenced, inactivated, or down-regulated in order to inactivate the activity for which they encode, such as the expression of an enzyme. Deletions provide maximum stability because there is no opportunity for a reverse mutation to restore function. Alternatively, genes can be partially, substantially, or completely deleted, silenced, inactivated, or down-regulated by insertion of nucleic acid sequences that disrupt the function and/or expression of the gene (e.g., P1 transduction or other methods known in the art). The terms "eliminate," "elimination," and "knockout" are used interchangeably with the terms "deletion," "partial deletion," "substantial deletion," or "complete deletion." In certain embodiments, strains of thermophilic or mesophilic microorganisms of interest may be engineered by site directed homologous recombination to knockout the production of organic acids. In still other embodiments, RNAi or antisense DNA (asDNA) may be used to partially, substantially, or completely silence, inactivate, or down-regulate a particular gene of interest.

In certain embodiments, the genes targeted for deletion or inactivation as described herein may be endogenous to the native strain of the microorganism, and may thus be understood to be referred to as "native gene(s)" or "endogenous gene(s)." An organism is in "a native state" if it has not been genetically engineered or otherwise manipulated by the hand of man in a manner that intentionally alters the genetic and/or phenotypic constitution of the organism. For example, wild-type organisms may be considered to be in a native state. In other embodiments, the gene(s) targeted for deletion or inactivation may be non-native to the organism.

Similarly, the enzymes of the invention as described herein can be endogenous to the native strain of the microorganism, and can thus be understood to be referred to as "native" or "endogenous."

The term "upregulated" means increased in activity, e.g., increase in enzymatic activity of the enzyme as compared to activity in a native host organism.

The term "downregulated" means decreased in activity, e.g., decrease in enzymatic activity of the enzyme as compared to activity in a native host organism.

The term "activated" means expressed or metabolically functional.

As used herein, the term "hydrocarbon" is intended to include compounds containing only carbon and hydrogen, such as aliphatic hydrocarbons and aromatic hydrocarbons. Examples of hydrocarbons include, but are not limited to, alkanes, alkenes, or alkynes.

As used herein, the term "hydrocarbon derivative" is intended to include compounds formed by the addition of at least one functional group to a hydrocarbon. Examples of hydrocarbon derivatives include, but are not limited to, aldehydes, alcohols, esters, fatty acids, unsaturated fatty acids, branched-chain fatty acids, branched methoxy fatty acids, multi-methyl branched acids, divinyl-ether fatty acids, w-phenylalkanoic acids, dicarboxylic acids.

The term "carbohydrate source" is intended to include any source of carbohydrate including, but not limited to, biomass or carbohydrates, such as a sugar or a sugar alcohol. "Carbohydrates" include, but are not limited to, monosaccharides (e.g., glucose, fructose, galactose, xylose, arabinose, or ribose), sugar derivatives (e.g., sorbitol, glycerol, galacturonic acid, rhamnose, xylitol), disaccharides (e.g., sucrose, cellobiose, maltose, or lactose), oligosaccharides (e.g., xylooligomers, cellodextrins, or maltodextrins), and polysaccharides (e.g., xylan, cellulose, starch, mannan, alginate, or pectin).

As used herein, the term "microaerophilic" is intended to include conditions in which oxygen is present at lower concentrations than atmospheric oxygen content. A microaerophilic organism is one that requires a lower concentration of oxygen for growth than is present in the atmosphere. Microaerophilic conditions include those in which oxygen is present at less than about 5%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, less than about 95%, or less than about 99% of atmospheric oxygen concentration.

As used herein, the term "malonyl-CoA derived product" or "malonyl-CoA derived bioproduct" is intended to include those products that are synthesized from, derived from, or are used as an intermediate in their synthesis from, malonyl-CoA. The term includes products such as hydrocarbons, hydrocarbon derivatives, polyketides, organic acids, including but not limited to adipic acid and 3-hydroxyproprionate, and any other products from which malonyl-CoA can serve as a precursor.

Metabolic Pathway Engineering

Many bacteria have the ability to ferment simple hexose sugars into a mixture of acidic and pH-neutral products via the process of glycolysis. The glycolytic pathway is abundant and comprises a series of enzymatic steps whereby a six carbon glucose molecule is broken down, via multiple intermediates, into two molecules of the three carbon compound pyruvate. This process results in the net generation of ATP (biological energy supply) and the reduced cofactor NADH.

Pyruvate is an important intermediary compound of metabolism. For example, under aerobic conditions pyruvate may be oxidized to acetyl coenzyme A (acetyl CoA), which then enters the tricarboxylic acid cycle (TCA), which in turn generates synthetic precursors, $CO_2$ and reduced cofactors. The cofactors are then oxidized by donating hydrogen equivalents, via a series of enzymatic steps, to oxygen resulting in the formation of water and ATP. This process of energy formation is known as oxidative phosphorylation.

Under anaerobic conditions (no available oxygen), fermentation occurs in which the degradation products of organic compounds serve as hydrogen donors and acceptors. Excess NADH from glycolysis is oxidized in reactions involving the reduction of organic substrates to products, such as lactate and ethanol. In addition, ATP is regenerated from the production of organic acids, such as acetate, in a process known as substrate level phosphorylation. Therefore, the fermentation products of glycolysis and pyruvate metabolism include a variety of organic acids, alcohols and $CO_2$.

Biomass

Biomass can include any type of biomass known in the art or described herein. The terms "lignocellulosic material," "lignocellulosic substrate," and "cellulosic biomass" mean any type of biomass comprising cellulose, hemicellulose, lignin, or combinations thereof, such as but not limited to woody biomass, forage grasses, herbaceous energy crops, non-woody-plant biomass, agricultural wastes and/or agricultural residues, forestry residues and/or forestry wastes, paper-production sludge and/or waste paper sludge, wastewater-treatment sludge, municipal solid waste, corn fiber from wet and dry mill corn ethanol plants, and sugar-processing residues. The terms "hemicellulosics," "hemicellulosic portions," and "hemicellulosic fractions" mean the non-lignin, non-cellulose elements of lignocellulosic material, such as but not limited to hemicellulose (i.e., comprising xyloglucan, xylan, glucuronoxylan, arabinoxylan, mannan, glucomannan, and galactoglucomannan), pectins (e.g., homogalacturonans, rhamnogalacturonan I and II, and xylogalacturonan), and proteoglycans (e.g., arabinogalactan-protein, extensin, and proline-rich proteins).

In a non-limiting example, the lignocellulosic material can include, but is not limited to, woody biomass, such as recycled wood pulp fiber, sawdust, hardwood, softwood, and combinations thereof; grasses, such as switch grass, cord grass, rye grass, reed canary grass, miscanthus, or a combination thereof; sugar-processing residues, such as but not limited to sugar cane bagasse; agricultural wastes, such as but not limited to rice straw, rice hulls, barley straw, corn cobs, cereal straw, wheat straw, canola straw, oat straw, oat hulls, and corn fiber; stover, such as but not limited to soybean stover, corn stover; succulents, such as but not limited to, Agave; and forestry wastes, such as but not limited to, recycled wood pulp fiber, sawdust, hardwood (e.g., poplar, oak, maple, birch, willow), softwood, or any combination thereof. Lignocellulosic material may comprise one species of fiber; alternatively, lignocellulosic material may comprise a mixture of fibers that originate from different lignocellulosic materials. Other lignocellulosic materials are agricultural wastes, such as cereal straws, including wheat straw, barley straw, canola straw and oat straw; corn fiber; stovers, such as corn stover and soybean stover; grasses, such as switch grass, reed canary grass, cord grass, and miscanthus; or combinations thereof.

Paper sludge is also a viable feedstock for lactate or acetate production. Paper sludge is solid residue arising from pulping and paper-making, and is typically removed from process wastewater in a primary clarifier. At a disposal cost of $30/wet ton, the cost of sludge disposal equates to $5/ton of paper that is produced for sale. The cost of disposing of wet sludge is a significant incentive to convert the material for other uses, such as conversion to ethanol. Processes provided by the present invention are widely applicable. Moreover, the saccharification and/or fermentation products may be used to produce ethanol or higher value added chemicals, such as organic acids, aromatics, esters, acetone and polymer intermediates.

Xylose Metabolism

Xylose is a five-carbon monosaccharide that can be metabolized into useful products by a variety of organisms. There are two main pathways of xylose metabolism, each unique in the characteristic enzymes they utilize. One pathway is called the "Xylose Reductase-Xylitol Dehydrogenase" or XR-XDH pathway. Xylose reductase (XR) and xylitol dehydrogenase (XDH) are the two main enzymes used in this method of xylose degradation. XR, encoded by the XYL1 gene, is responsible for the reduction of xylose to xylitol and is aided by cofactors NADH or NADPH. Xylitol is then oxidized to xylulose by XDH, which is expressed through the XYL2 gene, and accomplished exclusively with the cofactor NAD+. Because of the varying cofactors needed in this pathway and the degree to which they are available for usage, an imbalance can result in an overproduction of xylitol byproduct and an inefficient production of desirable ethanol. Varying expression of the XR and XDH enzyme levels have been tested in the laboratory in the attempt to optimize the efficiency of the xylose metabolism pathway.

The other pathway for xylose metabolism is called the "Xylose Isomerase" (XI) pathway. Enzyme XI is responsible for direct conversion of xylose into xylulose, and does not proceed via a xylitol intermediate. Both pathways create xylulose, although the enzymes utilized are different. After production of xylulose both the XR-XDH and XI pathways proceed through enzyme xylulokinase (XK), encoded on gene XKS1, to further modify xylulose into xylulose-5-P where it then enters the pentose phosphate pathway for further catabolism.

Studies on flux through the pentose phosphate pathway during xylose metabolism have revealed that limiting the speed of this step may be beneficial to the efficiency of fermentation to ethanol. Modifications to this flux that may improve ethanol production include a) lowering phosphoglucose isomerase activity, b) deleting the GND1 gene, and c) deleting the ZWF1 gene. See Jeppsson et al., *Appl. Environ. Microbiol.* 68:1604-09 (2002). Since the pentose phosphate pathway produces additional NADPH during metabolism, limiting this step will help to correct the already evident imbalance between NAD(P)H and NAD+ cofactors and reduce xylitol byproduct. Another experiment comparing the two xylose metabolizing pathways revealed that the XI pathway was best able to metabolize xylose to produce the greatest ethanol yield, while the XR-XDH pathway reached a much faster rate of ethanol production. See Karhumaa et al., *Microb Cell Fact.* 6:5 (Feb. 5, 2007); see also International Publication No. WO2006/009434, incorporated herein by reference in its entirety.

Arabinose Metabolism

Arabinose is a five-carbon monosaccharide that can be metabolized into useful products by a variety of organisms. L-Arabinose residues are found widely distributed among many heteropolysaccharides of different plant tissues, such as arabinans, arabinogalactans, xylans and arabinoxylans. *Bacillus* species in the soil participate in the early stages of plant material decomposition, and *B. subtilis* secretes three enzymes, an endo-arabanase and two arabinosidases, capable of releasing arabinosyl oligomers and L-arabinose from plant cell.

Three pathways for L-arabinose metabolism in microorganisms have been described. Many bacteria, including *Escherichia coli*, use arabinose isomerase (AraA; E.C. 5.3.1.4), ribulokinase (AraB; E.C. 2.7.1.16), and ribulose phosphate epimerase (AraD; E.C. 5.1.3.4) to sequentially convert L-arabinose to D-xylulose-5-phosphate through L-ribulose and L-ribulose 5-phosphate. See, e.g., Sa-Nogueira I., et al., *Microbiology* 143:957-69 (1997). The D-xylulose-5-phosphate then enters the pentose phosphate pathway for further catabolism. In the second pathway, L-arabinose is converted to L-2-keto-3-deoxyarabonate (L-KDA) by the consecutive action of enzymes arabinose dehydrogenase (ADH), arabinolactone (AL), and arabinonate dehydratase (AraC). See, e.g., Watanabe, S., et al., *J. Biol. Chem.* 281: 2612-2623 (2006). L-KDA can be further metabolized in two alternative pathways: 1) L-KDA conversion to 2-ketoglutarate via 2-ketoglutaric semialdehyde (KGSA) by L-KDA dehydratase and KGSA dehydrogenase or 2) L-KDA conversion to pyruvate and glycolaldehyde by L-KDA aldolase. In the third, fungal pathway, L-arabinose is converted to D-xylulose-5-phosphate through L-arabinitol, L-xylulose, and xylitol, by enzymes such as NAD(P)H-dependent aldose reductase (AR), L-arabinitol 4-dehydrogenase (ALDH), L-xylulose reductase (LXR), xylitol dehydrogenase (XylD), and xylulokinase (XylB). These, and additional proteins involved in arabinose metabolism and regulation may be found at the website of National Microbial Pathogen Data Resource (NMPDR), which is incorporated by reference herein in its entirety.

AraC protein regulates expression of its own synthesis and the other genes of the Ara system. See Schleif, R., *Trends Genet.* 16(12):559-65 (2000). In *E. coli*, the AraC protein positively and negatively regulates expression of the proteins required for the uptake and catabolism of the sugar L-arabinose. Homologs of AraC, such as regulatory proteins RhaR and RhaS of the rhamnose operon, have been identified that contain regions homologous to the DNA-binding domain of AraC (Leal, T. F. and de Sa-Nogueira, I., *FEMS Microbiol Lett.* 241(1):41-48 (2004)). Such arabinose regulatory proteins are referred to as the AraC/XylS family. See also, Mota, L. J., et al., *Mol. Microbiol.* 33(3):476-89 (1999); Mota, L. J., et al., *J. Bacteriol.* 183(14):4190-201 (2001).

In *E. coli*, the transport of L-arabinose across the *E. coli* cytoplasmic membrane requires the expression of either the high-affinity transport operon, araFGH, a binding protein-dependent system on the low-affinity transport operon, araE, or a proton symporter. Additional arabinose transporters include those identified from *K. marxianus* and *P. guilliermondii*, disclosed in U.S. Pat. No. 7,846,712, which is incorporated by reference herein.

In some embodiments, the recombinant microorganisms of the invention have the ability to metabolize arabinose using one or more of the above enzymes.

Vectors and Host Cells

The present invention also relates to vectors which include genes encoding for enzymes of the present invention, as described above, as well as host cells which are genetically engineered with vectors of the invention and the production of polypeptides of the invention by recombinant techniques.

Host cells are genetically engineered (transduced or transformed or transfected) with the vectors of this invention which can be, for example, a cloning vector or an expression vector. The vector can be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The DNA sequence in the expression vector is operatively associated with an appropriate expression control sequence(s) (promoter) to direct mRNA synthesis. Any suitable promoter to drive gene expression in the host cells of the invention can be used. Additionally, promoters known to control expression of genes in prokaryotic or lower eukaryotic cells can be used. The expression vector also contains a ribosome binding site for translation initiation and a transcription terminator. The vector can also include appropriate sequences for amplifying expression, or can include additional regulatory regions.

The vector containing the appropriate selectable marker sequence as used herein, as well as an appropriate promoter or control sequence, can be employed to transform an appropriate thermophilic host to permit the host to express the protein.

Host cells useful in the present invention include any prokaryotic or eukaryotic cells; for example, microorganisms selected from bacterial, algal, and yeast cells. Among host cells thus suitable for the present invention are microorganisms, for example, of the genera *Aeromonas, Aspergillus, Bacillus, Escherichia, Kluyveromyces, Pichia, Rhodococcus, Saccharomyces* and *Streptomyces*.

In some embodiments, the host cells are microorganisms. In one embodiment the microorganism is a yeast. According to the present invention the yeast host cell can be, for example, from the genera *Saccharomyces, Kluyveromyces, Candida, Pichia, Schizosaccharomyces, Hansenula, Kloeckera, Schwanniomyces*, and *Yarrowia*. Yeast species as host cells may include, for example, *S. cerevisiae, S. bulderi, S. barnetti, S. exiguus, S. uvarum, S. diastaticus, K. lactis, K. marxianus*, or *K. fragilis*. In some embodiments, the yeast is selected from the group consisting of *Saccharomyces cer-* evisiae, *Schizzosaccharomyces pombe, Candida albicans, Pichia pastoris, Pichia stipitis, Yarrowia lipolytica, Hansenula polymorpha, Phaffia rhodozyma, Candida utilis, Arxula adeninivorans, Debaryomyces hansenii, Debaryomyces polymorphus, Schizosaccharomyces pombe* and *Schwanniomyces occidentalis*. In one particular embodiment, the yeast is *Saccharomyces cerevisiae*. In another embodiment, the yeast is a thermotolerant *Saccharomyces cerevisiae*. The selection of an appropriate host is deemed to be within the scope of those skilled in the art from the teachings herein.

In some embodiments, the host cell is an oleaginous cell. The oleaginous host cell can be an oleaginous yeast cell. For example, the oleaginous yeast host cell can be from the genera *Blakeslea, Candida, Cryptococcus, Cunninghamella, Lipomyces, Mortierella, Mucor, Phycomyces, Pythium, Rhodosporidum, Rhodotorula, Trichosporon* or *Yarrowia*. According to the present invention, the oleaginous host cell can be an oleaginous microalgae host cell. For example, the oleaginous microalgea host cell can be from the genera *Thraustochytrium* or *Schizochytrium*. Biodiesel could then be produced from the triglyceride produced by the oleaginous organisms using conventional lipid transesterification processes. In some particular embodiments, the oleaginous host cells can be induced to secrete synthesized lipids. Embodiments using oleaginous host cells are advantageous because they can produce biodiesel from lignocellulosic feedstocks which, relative to oilseed substrates, are cheaper, can be grown more densely, show lower life cycle carbon dioxide emissions, and can be cultivated on marginal lands.

In some embodiments, the host cell is a thermotolerant host cell. Thermotolerant host cells can be particularly useful in simultaneous saccharification and fermentation processes by allowing externally produced cellulases and ethanol-producing host cells to perform optimally in similar temperature ranges.

Thermotolerant host cells can include, for example, *Issatchenkia orientalis, Pichia mississippiensis, Pichia mexicana, Pichia farinosa, Clavispora opuntiae, Clavispora lusitaniae, Candida mexicana, Hansenula polymorpha* and *Kluyveromyces* host cells. In some embodiments, the thermotolerant cell is an *S. cerevisiae* strain, or other yeast strain, that has been adapted to grow in high temperatures, for example, by selection for growth at high temperatures in a cytostat.

In some particular embodiments, the host cell is a *Kluyveromyces* host cell. For example, the *Kluyveromyces* host cell can be a *K. lactis, K. marxianus, K. blattae, K. phaffii, K. yarrowii, K. aestuarii, K. dobzhanskii, K. wickerhamii K. thermotolerans,* or *K. waltii* host cell. In one embodiment, the host cell is a *K. lactis*, or *K. marxianus* host cell. In another embodiment, the host cell is a *K. marxianus* host cell.

In some embodiments, the thermotolerant host cell can grow at temperatures above about 30° C., about 31° C., about 32° C., about 33° C., about 34° C., about 35° C., about 36° C., about 37° C., about 38° C., about 39° C., about 40° C., about 41° C. or about 42° C. In some embodiments of the present invention the thermotolerant host cell can produce ethanol from cellulose at temperatures above about 30° C., about 31° C., about 32° C., about 33° C., about 34° C., about 35° C., about 36° C., about 37° C., about 38° C., about 39° C., about 40° C., about 41° C., about 42° C., or about 43° C., or about 44° C., or about 45° C., or about 50° C.

In some embodiments of the present invention, the thermotolerant host cell can grow at temperatures from about 30° C. to 60° C., about 30° C. to 55° C., about 30° C. to 50° C., about 40° C. to 60° C., about 40° C. to 55° C. or about 40° C. to 50° C. In some embodiments of the present invention, the thermotolerant host cell can produce ethanol from cellulose at temperatures from about 30° C. to 60° C., about 30° C. to 55° C., about 30° C. to 50° C., about 40° C. to 60° C., about 40° C. to 55° C. or about 40° C. to 50° C.

In some embodiments, the host cell has the ability to metabolize xylose. Detailed information regarding the development of the xylose-utilizing technology can be found in the following publications: Kuyper M., et al., *FEMS Yeast Res.* 4: 655-64 (2004); Kuyper M., et al., *FEMS Yeast Res.* 5:399-409 (2005); and Kuyper M., et al., *FEMS Yeast Res.* 5:925-34 (2005), which are herein incorporated by reference in their entirety. For example, xylose-utilization can be accomplished in *S. cerevisiae* by heterologously expressing the xylose isomerase gene, XylA, e.g., from the anaerobic fungus *Piromyces* sp. E2, overexpressing five *S. cerevisiae* enzymes involved in the conversion of xylulose to glycolytic intermediates (xylulokinase, ribulose 5-phosphate isomerase, ribulose 5-phosphate epimerase, transketolase and transaldolase) and deleting the GRE3 gene encoding aldose reductase to minimize xylitol production.

The host cells can contain antibiotic markers or can contain no antibiotic markers.

Aspects of the present invention relate to the use of thermophilic and thermotolerant microorganisms as hosts. Their potential in process applications in biotechnology stems from their ability to grow at relatively high temperatures with attendant high metabolic rates, production of physically and chemically stable enzymes, elevated yields of end products, and lower susceptibility to microbial contamination. Major groups of thermophilic bacteria include eubacteria and archaebacteria. Thermophilic eubacteria include: phototropic bacteria, such as cyanobacteria, purple bacteria, and green bacteria; Gram-positive bacteria, such as *Bacillus, Clostridium*, Lactic acid bacteria, and *Actinomyces*; and other eubacteria, such as *Thiobacillus, Spirochete, Desulfotomaculum*, Gram-negative aerobes, Gram-negative anaerobes, and *Thermotoga*. Within archaebacteria are considered Methanogens, extreme thermophiles (an art-recognized term), and *Thermoplasma*. In certain embodiments, the present invention relates to Gram-negative organotrophic thermophiles of the genera *Thermus*, Gram-positive eubacteria, such as genera *Clostridium*, and also which comprise both rods and cocci, genera in group of eubacteria, such as *Thermosipho* and *Thermotoga*, genera of Archaebacteria, such as *Thermococcus, Thermoproteus* (rod-shaped), *Thermofilum* (rod-shaped), *Pyrodictium, Acidianus, Sulfolobus, Pyrobaculum, Pyrococcus, Thermodiscus, Staphylothermus, Desulfurococcus, Archaeoglobus,* and *Methanopyrus*.

Some examples of thermophilic or mesophilic (including bacteria, procaryotic microorganism, and fungi), which may be suitable for the present invention include, but are not limited to: *Clostridium thermosulfurogenes, Clostridium cellulolyticum, Clostridium thermocellum, Clostridium thermohydrosulfuricum, Clostridium thermoaceticum, Clostridium thermosaccharolyticum, Clostridium tarlarivorum, Clostridium thermocellulaseum, Clostridium phytofermentans, Clostridium straminosolvens, Thermoanaerobacterium thermosaccarolyticum, Thermoanaerobacterium saccharolyticum, Thermobacteroides acetoethylicus, Thermoanaerobium brockii, Methanobacterium thermoautotrophicum, Anaerocellum thermophilium, Pyrodictium occultum, Thermoproteus neutrophilus, Thermofilum librum, Thermothrix thioparus, Desulfovibrio thermophilus, Thermoplasma acidophilum, Hydrogenomonas thermophi-* lus, Thermomicrobium roseum, Thermus flavas, Thermus ruber, Pyrococcus furiosus, Thermus aquaticus, Thermus thermophilus, Chloroflexus aurantiacus, Thermococcus litoralis, Pyrodictium abyssi, Bacillus stearothermophilus, Cyanidium caldarium, Mastigocladus laminosus, Chlamydothrix calidissima, Chlamydothrix penicillata, Thiothrix carnea, Phormidium tenuissimum, Phormidium geysericola, Phormidium subterraneum, Phormidium byiahensi, Oscillatoria filiformis, Synechococcus lividus, Chloroflexus aurantiacus, Pyrodictium brockii, Thiobacillus thiooxidans, Sulfolobus acidocaldarius, Thiobacillus thermophilica, Bacillus stearothermophilus, Cercosulcifer hamathensis, Vahlkampfia reichi, Cyclidium citrullus, Dactylaria gallopava, Synechococcus lividus, Synechococcus elongatus, Synechococcus minervae, Synechocystis aquatilus, Aphanocapsa thermalis, Oscillatoria terebriformis, Oscillatoria amphibia, Oscillatoria germinata, Oscillatoria okenii, Phormidium laminosum, Phormidium parparasiens, Symploca thermalis, Bacillus acidocaldarias, Bacillus coagulans, Bacillus thermocatenalatus, Bacillus licheniformis, Bacillus pamilas, Bacillus macerans, Bacillus circulans, Bacillus laterosporus, Bacillus brevis, Bacillus subtilis, Bacillus sphaericus, Desulfotomaculum nigrficans, Streptococcus thermophilus, Lactobacillus thermophilus, Lactobacillus bulgaricus, Bifidobacterium thermophilum, Streptomyces fragmentosporus, Streptomyces thermonitrificans, Streptomyces thermovulgaris, Pseudonocardia thermophila, Thermoactinomyces vulgaris, Thermoactinomyces sacchari, Thermoactinomyces candidas, Thermomonospora curvata, Thermomonospora viridis, Thermomonospora citrina, Microbispora thermodiastatica, Microbispora aerata, Microbispora bispora, Actinobifida dichotomica, Actinobifida chromogena, Micropolyspora caesia, Micropolyspora faeni, Micropolyspora cectivugida, Micropolyspora cabrobrunea, Micropolyspora thermovirida, Micropolyspora viridinigra, Methanobacterium thermoautothropicum, Caldicellulosiruptor acetigenus, Caldicellulosiruptor saccharolyticus, Caldicellulosiruptor kristjanssonii, Caldicellulosiruptor owensensis, Caldicellulosiruptor lactoaceticus, Clostridium clariflavum, E. coli strain B, strain C, strain K, strain W, Shewanella, Propionibacterium acnes, Propionibacterium freudenreichii, Propionibacterium shermanii, Propionibacterium pentosaceum, Propionibacterium arabinosum, Clostridium acetobutylicum, Clostridium beijerinckii, Lactobacillus thermophilus, Lactobacillus bulgaricus, Lactococcus lactis, variants thereof, and/or progeny thereof.

In particular embodiments, the present invention relates to thermophilic bacteria selected from the group consisting of Clostridium cellulolyticum, Clostridium thermocellum, and Thermoanaerobacterium saccharolyticum.

In certain embodiments, the present invention relates to thermophilic bacteria selected from the group consisting of Fervidobacterium gondwanense, Clostridium thermolacticum, Moorella sp., and Rhodothermus marinus.

In certain embodiments, the present invention relates to thermophilic bacteria of the genera Thermoanaerobacterium or Thermoanaerobacter, including, but not limited to, species selected from the group consisting of: Thermoanaerobacterium thermosulfurigenes, Thermoanaerobacterium aotearoense, Thermoanaerobacterium polysaccharolyticum, Thermoanaerobacterium zeae, Thermoanaerobacterium xylanolyticum, Thermoanaerobacterium saccharolyticum, Thermoanaerobium brockii, Thermoanaerobacterium thermosaccharolyticum, Thermoanaerobacter thermohydrosulfuricus, Thermoanaerobacter ethanolicus, Thermoanaerobacter brockii, variants thereof, and progeny thereof.

In certain embodiments, the present invention relates to microorganisms of the genera Geobacillus, Saccharococcus, Paenibacillus, Bacillus, and Anoxybacillus, including, but not limited to, species selected from the group consisting of: Geobacillus thermoglucosidasius, Geobacillus stearothermophilus, Saccharococcus caldoxylosilyticus, Saccharoccus thermophilus, Paenibacillus campinasensis, Bacillus flavothermus, Anoxybacillus kamchalkensis, Anoxybacillus gonensis, variants thereof, and progeny thereof.

In certain embodiments, the present invention relates to mesophilic bacteria selected from the group consisting of Saccharophagus degradans; Flavobacterium johnsoniae; Fibrobacter succinogenes; Clostridium hungatei; Clostridium phytofermentans; Clostridium cellulolyticum; Clostridium aldrichii; Clostridium termitididis; Acetivibrio cellulolyticus; Acetivibrio ethanolgignens; Acetivibrio multivorans; Bacteroides cellulosolvens; Alkalibacter saccharofomentans, variants thereof, and progeny thereof. In certain embodiments, the present invention relates to mesophilic bacteria selected from the group consisting of Escherichia coli, E. coli strain B, strain C, strain K, strain W, Shewanella, Propionibacterium acnes, Propionibacterium freudenreichii, Propionibacterium shermanii, Propionibacterium pentosaceum, Propionibacterium arabinosum, Clostridium acetobutylicum, Clostridium beijerinckii, variants thereof, and progeny thereof.

Codon-Optimized Polynucleotides

The polynucleotides encoding heterologous polypeptides can be codon-optimized. As used herein the term "codon-optimized coding region" means a nucleic acid coding region that has been adapted for expression in the cells of a given organism by replacing at least one, or more than one, or a significant number, of codons with one or more codons that are more frequently used in the genes of that organism.

In general, highly expressed genes in an organism are biased towards codons that are recognized by the most abundant tRNA species in that organism. One measure of this bias is the "codon adaptation index" or "CAI," which measures the extent to which the codons used to encode each amino acid in a particular gene are those which occur most frequently in a reference set of highly expressed genes from an organism.

The CAI of codon optimized sequences of the present invention corresponds to between about 0.8 and 1.0, between about 0.8 and 0.9, or about 1.0. A codon optimized sequence may be further modified for expression in a particular organism, depending on that organism's biological constraints. For example, large runs of "As" or "Ts" (e.g., runs greater than 3, 4, 5, 6, 7, 8, 9, or 10 consecutive bases) can be removed from the sequences if these are known to effect transcription negatively. Furthermore, specific restriction enzyme sites may be removed for molecular cloning purposes. Examples of such restriction enzyme sites include PacI, AscI, BamHI, BglII, EcoRI and XhoI. Additionally, the DNA sequence can be checked for direct repeats, inverted repeats and mirror repeats with lengths of ten bases or longer, which can be modified manually by replacing codons with "second best" codons, i.e., codons that occur at the second highest frequency within the particular organism for which the sequence is being optimized.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 1. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

TABLE 1

The Standard Genetic Code

| | T | C | A | G |
|---|---|---|---|---|
| T | TTT Phe (F) | TCT Ser (S) | TAT Tyr (Y) | TGT Cys (C) |
| | TTC Phe (F) | TCC Ser (S) | TAC Tyr (Y) | TGC Cys (C) |
| | TTA Leu (L) | TCA Ser (S) | TAA Ter | TGA Ter |
| | TTG Leu (L) | TCG Ser (S) | TAG Ter | TGG Trp (W) |
| | | | | |
| C | CTT Leu (L) | CCT Pro (P) | CAT His (H) | CGT Arg (R) |
| | CTC Leu (L) | CCC Pro (P) | CAC His (H) | CGC Arg (R) |
| | CTA Leu (L) | CCA Pro (P) | CAA Gln (Q) | CGA Arg (R) |
| | CTG Leu (L) | CCG Pro (P) | CAG Gln (Q) | CGG Arg (R) |
| | | | | |
| A | ATT Ile (I) | ACT Thr (T) | AAT Asn (N) | AGT Ser (S) |
| | ATC Ile (I) | ACC Thr (T) | AAC Asn (N) | AGC Ser (S) |
| | ATA Ile (I) | ACA Thr (T) | AAA Lys (K) | AGA Arg (R) |
| | ATG Met (M) | ACG Thr (T) | AAG Lys (K) | AGG Arg (R) |
| | | | | |
| G | GTT Val (V) | GCT Ala (A) | GAT Asp (D) | GGT Gly (G) |
| | GTC Val (V) | GCC Ala (A) | GAC Asp (D) | GGC Gly (G) |
| | GTA Val (V) | GCA Ala (A) | GAA Glu (E) | GGA Gly (G) |
| | GTG Val (V) | GCG Ala (A) | GAG Glu (E) | GGG Gly (G) |

Many organisms display a bias for use of particular codons to code for insertion of a particular amino acid in a growing peptide chain. Codon preference or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, it is possible to calculate the relative frequencies of codon usage. Codon usage tables are readily available, for example, at the website of Codon Usage Database, and these tables can be adapted in a number of ways. See Nakamura, Y., et al. "Codon usage tabulated from the international DNA sequence databases: status for the year 2000," *Nucl. Acids Res.* 28:292 (2000). Codon usage tables for yeast, calculated from GenBank Release 128.0 [15 Feb. 2002], are reproduced below as Table 2. This table uses mRNA nomenclature, and so instead of thymine (T) which is found in DNA, the tables use uracil (U) which is found in RNA. The table has been adapted so that frequencies are calculated for each amino acid, rather than for all 64 codons.

TABLE 2

Codon Usage Table for *Saccharomyces cerevisiae* Genes

| Amino Acid | Codon | Number | Frequency per hundred |
|---|---|---|---|
| Phe | UUU | 170666 | 26.1 |
| Phe | UUC | 120510 | 18.4 |
| Leu | UUA | 170884 | 26.2 |
| Leu | UUG | 177573 | 27.2 |
| Leu | CUU | 80076 | 12.3 |
| Leu | CUC | 35545 | 5.4 |
| Leu | CUA | 87619 | 13.4 |
| Leu | CUG | 68494 | 10.5 |
| Ile | AUU | 196893 | 30.1 |
| Ile | AUC | 112176 | 17.2 |
| Ile | AUA | 116254 | 17.8 |
| Met | AUG | 136805 | 20.9 |
| Val | GUU | 144243 | 22.1 |
| Val | GUC | 76947 | 11.8 |
| Val | GUA | 76927 | 11.8 |
| Val | GUG | 70337 | 10.8 |
| Ser | UCU | 153557 | 23.5 |
| Ser | UCC | 92923 | 14.2 |
| Ser | UCA | 122028 | 18.7 |
| Ser | UCG | 55951 | 8.6 |
| Ser | AGU | 92466 | 14.2 |
| Ser | AGC | 63726 | 9.8 |
| Pro | CCU | 88263 | 13.5 |
| Pro | CCC | 44309 | 6.8 |
| Pro | CCA | 119641 | 18.3 |
| Pro | CCG | 34597 | 5.3 |
| Thr | ACU | 132522 | 20.3 |
| Thr | ACC | 83207 | 12.7 |
| Thr | ACA | 116084 | 17.8 |
| Thr | ACG | 52045 | 8.0 |
| Ala | GCU | 138358 | 21.2 |
| Ala | GCC | 82357 | 12.6 |
| Ala | GCA | 105910 | 16.2 |
| Ala | GCG | 40358 | 6.2 |
| Tyr | UAU | 122728 | 18.8 |
| Tyr | UAC | 96596 | 14.8 |
| His | CAU | 89007 | 13.6 |
| His | CAC | 50785 | 7.8 |
| Gln | CAA | 178251 | 27.3 |
| Gln | CAG | 79121 | 12.1 |
| Asn | AAU | 233124 | 35.7 |
| Asn | AAC | 162199 | 24.8 |
| Lys | AAA | 273618 | 41.9 |
| Lys | AAG | 201361 | 30.8 |
| Asp | GAU | 245641 | 37.6 |
| Asp | GAC | 132048 | 20.2 |
| Glu | GAA | 297944 | 45.6 |
| Glu | GAG | 125717 | 19.2 |
| Cys | UGU | 52903 | 8.1 |
| Cys | UGC | 31095 | 4.8 |
| Trp | UGG | 67789 | 10.4 |
| Arg | CGU | 41791 | 6.4 |
| Arg | CGC | 16993 | 2.6 |
| Arg | CGA | 19562 | 3.0 |
| Arg | CGG | 11351 | 1.7 |
| Arg | AGA | 139081 | 21.3 |
| Arg | AGG | 60289 | 9.2 |
| Gly | GGU | 156109 | 23.9 |
| Gly | GGC | 63903 | 9.8 |
| Gly | GGA | 71216 | 10.9 |
| Gly | GGG | 39359 | 6.0 |
| Stop | UAA | 6913 | 1.1 |
| Stop | UAG | 3312 | 0.5 |
| Stop | UGA | 4447 | 0.7 |

By utilizing this or similar tables, one of ordinary skill in the art can apply the frequencies to any given polypeptide sequence, and produce a nucleic acid fragment of a codon-optimized coding region which encodes the polypeptide, but which uses codons optimal for a given species. Codon-optimized coding regions can be designed by various different methods.

In one method, a codon usage table is used to find the single most frequent codon used for any given amino acid, and that codon is used each time that particular amino acid appears in the polypeptide sequence. For example, referring to Table 2 above, for leucine, the most frequent codon is UUG, which is used 27.2% of the time. Thus all the leucine residues in a given amino acid sequence would be assigned the codon UUG.

In another method, the actual frequencies of the codons are distributed randomly throughout the coding sequence. Thus, using this method for optimization, if a hypothetical polypeptide sequence had 100 leucine residues, referring to Table 2 for frequency of usage in the S. cerevisiae, about 5, or 5% of the leucine codons would be CUC, about 11, or 11% of the leucine codons would be CUG, about 12, or 12% of the leucine codons would be CUU, about 13, or 13% of the leucine codons would be CUA, about 26, or 26% of the leucine codons would be UUA, and about 27, or 27% of the leucine codons would be UUG.

These frequencies would be distributed randomly throughout the leucine codons in the coding region encoding the hypothetical polypeptide. As will be understood by those of ordinary skill in the art, the distribution of codons in the sequence can vary significantly using this method; however, the sequence always encodes the same polypeptide.

When using the methods above, the term "about" is used precisely to account for fractional percentages of codon frequencies for a given amino acid. As used herein, "about" is defined as one amino acid more or one amino acid less than the value given. The whole number value of amino acids is rounded up if the fractional frequency of usage is 0.50 or greater, and is rounded down if the fractional frequency of use is 0.49 or less. Using again the example of the frequency of usage of leucine in human genes for a hypothetical polypeptide having 62 leucine residues, the fractional frequency of codon usage would be calculated by multiplying 62 by the frequencies for the various codons. Thus, 7.28 percent of 62 equals 4.51 UUA codons, or "about 5," i.e., 4, 5, or 6 UUA codons, 12.66 percent of 62 equals 7.85 UUG codons or "about 8," i.e., 7, 8, or 9 UUG codons, 12.87 percent of 62 equals 7.98 CUU codons, or "about 8," i.e., 7, 8, or 9 CUU codons, 19.56 percent of 62 equals 12.13 CUC codons or "about 12," i.e., 11, 12, or 13 CUC codons, 7.00 percent of 62 equals 4.34 CUA codons or "about 4," i.e., 3, 4, or 5 CUA codons, and 40.62 percent of 62 equals 25.19 CUG codons, or "about 25," i.e., 24, 25, or 26 CUG codons.

Randomly assigning codons at an optimized frequency to encode a given polypeptide sequence, can be done manually by calculating codon frequencies for each amino acid, and then assigning the codons to the polypeptide sequence randomly. Additionally, various algorithms and computer software programs are readily available to those of ordinary skill in the art. For example, the "EditSeq" function in the Lasergene Package, available from DNAstar, Inc., Madison, Wis., the backtranslation function in the Vector NTI Suite, available from InforMax, Inc., Bethesda, Md., and the "backtranslate" function in the GCG—Wisconsin Package, available from Accelrys, Inc., San Diego, Calif. In addition, various resources are publicly available to codon-optimize coding region sequences, e.g., the "backtranslation" function at the website of Eurofins Genomics and the "backtranseq" function available at the website of EMBOSS explorer. Constructing a rudimentary algorithm to assign codons based on a given frequency can also easily be accomplished with basic mathematical functions by one of ordinary skill in the art.

A number of options are available for synthesizing codon optimized coding regions designed by any of the methods described above, using standard and routine molecular biological manipulations well known to those of ordinary skill in the art. In one approach, a series of complementary oligonucleotide pairs of 80-90 nucleotides each in length and spanning the length of the desired sequence is synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides is designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they are ligated together and cloned into a standard bacterial cloning vector, for example, a TOPO® vector available from Invitrogen Corporation, Carlsbad, Calif. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

In additional embodiments, a full-length polypeptide sequence is codon-optimized for a given species resulting in a codon-optimized coding region encoding the entire polypeptide, and then nucleic acid fragments of the codon-optimized coding region, which encode fragments, variants, and derivatives of the polypeptide are made from the original codon-optimized coding region. As would be well understood by those of ordinary skill in the art, if codons have been randomly assigned to the full-length coding region based on their frequency of use in a given species, nucleic acid fragments encoding fragments, variants, and derivatives would not necessarily be fully codon optimized for the given species. However, such sequences are still much closer to the codon usage of the desired species than the native codon usage. The disadvantage of this approach is that synthesizing codon-optimized nucleic acid fragments encoding each fragment, variant, and derivative of a given polypeptide, although routine, would be time consuming and would result in significant expense.

Transposons

To select for foreign DNA that has entered a host it is preferable that the DNA be stably maintained in the organism of interest. With regard to plasmids, there are two processes by which this can occur. One is through the use of replicative plasmids. These plasmids have origins of replication that are recognized by the host and allow the plasmids to replicate as stable, autonomous, extrachromosomal elements that are partitioned during cell division into daughter cells. The second process occurs through the integration of a plasmid onto the chromosome. This predominately happens by homologous recombination and results in the insertion of the entire plasmid, or parts of the plasmid, into the host chromosome. Thus, the plasmid and selectable marker (s) are replicated as an integral piece of the chromosome and segregated into daughter cells. Therefore, to ascertain if plasmid DNA is entering a cell during a transformation event through the use of selectable markers requires the use of a replicative plasmid or the ability to recombine the plasmid onto the chromosome. These qualifiers cannot always be met, especially when handling organisms that do not have a suite of genetic tools.

One way to avoid issues regarding plasmid-associated markers is through the use of transposons. A transposon is a mobile DNA element, defined by mosaic DNA sequences that are recognized by enzymatic machinery referred to as a transposase. The function of the transposase is to randomly insert the transposon DNA into host or target DNA. A selectable marker can be cloned onto a transposon by standard genetic engineering. The resulting DNA fragment can be coupled to the transposase machinery in an in vitro reaction and the complex can be introduced into target cells by electroporation. Stable insertion of the marker onto the chromosome requires only the function of the transposase machinery and alleviates the need for homologous recombination or replicative plasmids.

The random nature associated with the integration of transposons has the added advantage of acting as a form of mutagenesis. Libraries can be created that comprise amalgamations of transposon mutants. These libraries can be used in screens or selections to produce mutants with desired phenotypes. For instance, a transposon library of a CBP organism could be screened for the ability to produce more ethanol, or less lactic acid and/or more acetate.

Hydrocarbon Synthesis

Hydrocarbons consist of carbon and hydrogen and include aliphatic hydrocarbons and aromatic hydrocarbons. Non-limiting examples of hydrocarbons include, alkanes, alkenes, alkynes, and hydrocarbon derivatives. The latter of which includes those compounds formed by the addition of at least one functional group to a hydrocarbon. Examples of hydrocarbon derivatives include, but are not limited to, aldehydes, alcohols, esters, fatty acids, unsaturated fatty acids, branched-chain fatty acids, branched methoxy fatty acids, multi-methyl branched acids, divinyl-ether fatty acids, w-phenylalkanoic acids, dicarboxylic acids.

Hydrocarbons produced by the recombinant microorganisms and methods of the invention include carbon backbones of at least 4 carbons and up to 40 or more carbons. Such chain lengths are referred to as long-chain hydrocarbons. In certain aspects, the chain lengths include $C_6$-$C_{36}$; $C_8$-$C_{32}$; $C_{10}$-$C_{28}$; $C_{12}$-$C_{24}$; $C_{14}$-$C_{22}$; or $C_{16}$-$C_{20}$. In some embodiments, the chain length comprises a carbon backbone of $C_{12}$, $C_{14}$, $C_{16}$, $C_{18}$, $C_{20}$, and/or $C_{22}$. In further embodiments, the chain length comprises a carbon backbone of $C_{16}$.

To produce hydrocarbons and hydrocarbon derivatives according to the invention, the following stoichiometric equations provide examples of an electron-balanced process.

Fatty Acid: $2C_6H_{12}O_6 \rightarrow C_8H_{16}O_2 + 4CO_2 + 2H_2O + 2H_2$

Fatty Alcohol: $2C_6H_{12}O_6 \rightarrow C_8H_{18}O + 4CO_2 + 3H_2O$

N-alkane: $2C_6H_{12}O_6 + O_2 \rightarrow C_7H_{16} + 5CO_2 + 4H_2O$

Wax ester: $4C_6H_{12}O_6 \rightarrow C_6H_{32}O_2 + 8CO_2 + 6H_2O + 2H_2$

Figure 6:
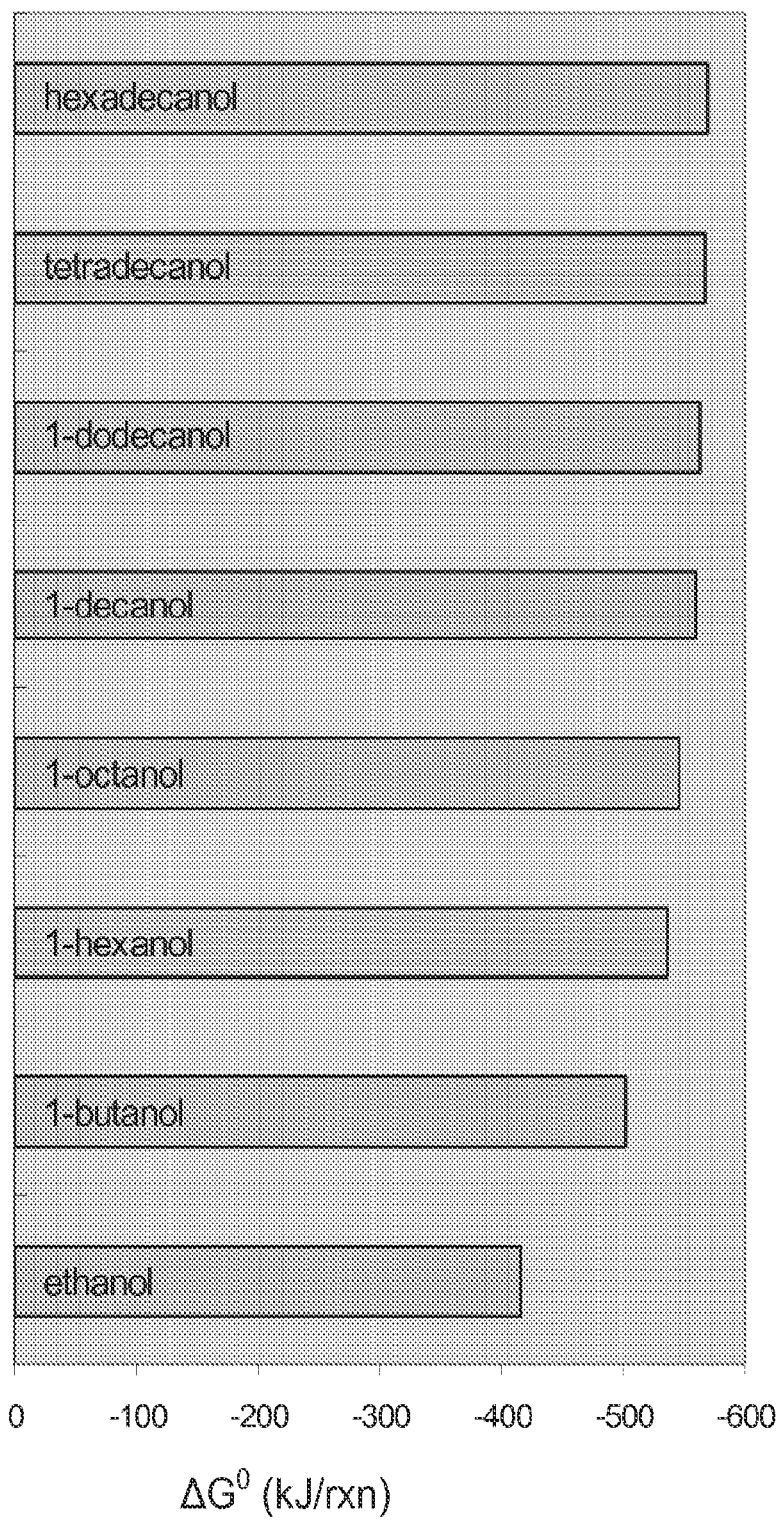
FIG. 6 depicts the Gibbs free energy change for the conversion of glucose into the specified alcohols.

The synthesis of hydrocarbons becomes more thermodynamically favorable as the chain length increases (see FIG. 6 (values derived from Stull et al., The Chemical Thermodynamics of Organic Compounds, Wiley, New York, N.Y. (1969))). For example, the stoichiometry for the production of a fatty alcohol proceeds according to the following equation, where n is the number of glucose molecules and x is the number of carbon atoms in the saturated fatty alcohol.

$n\text{Glucose} \rightarrow (4n/x)C_x\text{alcohol} + 2nCO_2 + n[2-(4/x)]H_2O$

As can be seen, the number of $H_2O$ molecules generated increases as chain length increases. This helps contribute to a more overall thermodynamically favorable reaction. Gibbs free energy changes per 2 glucose molecules (n=2) for specific alcohols are shown in FIG. 6.

The Gibbs free energy change for the production of heptane, accounting for the requirement of elemental oxygen for the conversion of a fatty aldehyde to alkane by aldehyde decarbonylase (Li et al., *JACS*, 133:6158-6161 (2011)) is:

$2\text{Glucose} + O_2 \rightarrow 1\text{heptane} + 5CO_2 + 4H_2O$ $\Delta G° = -1044.0$ kJ/reaction The Gibbs free energy change for the production of octanal is:

$2\text{Glucose} \rightarrow 1\text{octanal} + 4CO_2 + 3H_2O + H_2$ $\Delta G° = -512.2$ kJ/reaction Other sugars, including, but not limited to, xylose or arabinose, have a similar Gibbs free energy change as glucose. While some steps in the production of hydrocarbons or hydrocarbon derivatives can be slightly unfavorable, e.g., aldolase or triosephosphate isomerase in glycolysis, the overall reaction will be thermodynamically favorable when the final steps include chain termination steps, e.g., acid, aldehyde, alcohol, and/or ester formation. The very low aqueous concentrations of the final hydrocarbons or hydrocarbon derivatives will further drive the thermodynamic equilibrium towards product formation.

Polyketide Synthesis

Polyketides are a structurally and functionally diverse family of natural products that possess a wide range of biological and pharmacological properties. Such properties include, but are not limited to, antibiotic, antitumor, antifungal, and immunosuppressive activities. Jenke-Kodama, H., et al., *Mol. Biol. Evol.* 22(10):2027-39 (2005). Polyketides are synthesized as secondary metabolites in bacteria, fungi, plants, and animals by different classes of polyketide synthases (PKS), which resemble the classes of fatty acid synthases. Id. Polyketide synthesis proceeds by the addition or condensation of different functional groups to an acyl-ACP chain. See FIG. 21. And while fatty acid elongation includes four enzymatic steps per two carbon chain extension (KS (ketosynthase), KR (ketoreductase), DH (dehydratase), ER (enoyl reductase)) (FIG. 21B), PKS elongation can include a combination of enzymatic activities, e.g., (KS), (KS, KR), (KS, KR, DH), or (KS, KR, DH, ER), at each step (FIG. 21A). Malonyl-CoA produced by the recombinant microorganisms and pathways of the invention can be used as a metabolic precursor for polyketides.

Organic Acid Synthesis

Malonyl-CoA produced by the recombinant microorganisms and pathways of the invention can be used as a metabolic precursor for number of bioproducts. For example, the organic acid 3-hydroxypropionic acid ("3-HP"), also known as 3-hydroxypropanoate, is used in the production of various industrial chemicals such as renewable polyesters, acrylic acid, malonic acid, and co-polymers with lactic acid. Although 3-HP can be produced by organic chemical synthesis, it is desirable to use bio-alternative methods that allow for more cost effective, efficient, and renewable production. While some microorganisms are known to produce 3-HP (see, e.g., WO 01/16346; WO 02/42418; US 2011/0144377; US 2011/0125118, each of which is incorporated by reference herein), few biological systems have been developed that would result in its efficient production. Production of malonyl-CoA at high yield via transcarboxylase in an anaerobic process would allow for efficient high yield 3-hydroxypropionic acid production using a suitable enzymatic pathway from malonyl-CoA to 3-hydroxypropionic acid and a suitable redox system to generate NADPH during carbohydrate deconstruction. See, e.g., redox systems are "F" and "G" in Table 10.

Enzymes employed for the production of 3-HP by the recombinant microorganisms and methods of the invention include 1) malonyl-CoA reductase (EC 1.2.7.5), 2) 3-hydroxypropionate dehydrogenase (EC 1.1.1.59 and EC 1.1.1.298), and 3) a bifunctional enzyme which harbors aldehyde dehydrogenase and alcohol dehydrogenase domains (Hügler et al., *J. Bacteriol.* 184:2402-2410 (2002)).

The following example pathways demonstrate the production of 3-HP from a malonyl-CoA metabolic precursor using the above-referenced enzymes:

1) Malonyl CoA Reductase (EC 1.2.1.75)

Malonate semialdehyde+coenzyme *A*+NADP(+) <=>malonyl-CoA+NADPH 2a) 3-Hydroxypropionate Dehydrogenase (EC 1.1.1.59)

3-hydroxypropanoate+NAD(+)<=>Malonate semialdehyde+NADH 2b) 3-Hydroxypropionate Dehydrogenase (EC 1.1.1.298)

3-hydroxypropanoate+NADP(+)<=>Malonate semialdehyde+NADPH 3) bifunctional dehydrogenase (aldehyde-alcohol)

malonyl-CoA+NADPH+H⁺→malonate semialdehyde+NADP⁺+CoA malonate semialdehyde (3-oxopropanoate)+NADPH+H⁺→3-hydroxypropionate+NADP⁺

The sequence of a malonyl-CoA reductase from *Chloroflexus aurantiacus* is provided below:

```
C. aurantiacus Malonyl-CoA Reductase
(amino acid sequence; >gi|42561982|gb|AAS20429.1)
                                          (SEQ ID NO: 1)
MSGTGRLAGKIALITGGAGNIGSELTRRFLAEGATVI1SGRNRAKLTALA

ERMQAEAGVPAKRIDLEVMDGSDPVAVRAGIEAIVARHGQIDILVNNAGS

AGAQRRLAEIPLTEAELGPGAEETLHASIANLLGMGWHLMRIAAPHMPVG

SAVINVSTIFSRAEYYGRIPYVTPKAALNALSQLAARELGARGIRVNTIF

PGPIESDRIRTVFQRMDQLKGRPEGDTAHHFLNTMRLCRANDQGALERRF

PSVGDVADAAVFLASAESAALSGETIEVTHGMELPACSETSLLARTDLRT

IDASGRTTLICAGDQIEEVMALTGMLRTCGSEVIIGFRSAAALAQFEQAV

NESRRLAGADFTPPIALPLDPRDPATIDAVFDWGAGENTGGIHAAVILPA

TSHEPAPCVIEVDDERVLNFLADEITGTIVIASRLARYWQSQRLTPGARA

RGPRVIFLSNGADQNGNVYGRIQSAAIGQLIRVWRHEAELDYQRASAAGD

HVLPPVWANQIVRFANRSLEGLEFACAWTAQLLHSQRHINEITLNIPANI

SATTGARSASVGWAESLIGLHLGKVALITGGSAGIGGQIGRLLALSGARV

MLAARDRHKLEQMQAMIQSELAEVGYTDVEDRVHIAPGCDVSSEAQLADL

VERTLSAFGTVDYLINNAGIAGVEEMVIDMPVEGWRHTLFANLISNYSLM
```

```
RKLAPLMKKQGSGYILNVSSYFGGEKDAAIPYPNRADYAVSKAGQRAMAE

VFARFLGPEIQINAIAPGPVEGDRLRGTGERPGLFARRARLILENKRLNE

LHAALIAAARTDERSMHELVELLLPNDVAALEQNPAAPTALRELARRFRS

EGDPAASSSSALLNRSIAAKLLARLHNGGYVLPADIFANLPNPPDPFFTR

AQIDREARKVRDGIMGMLYLQRMPTEFDVAMATVYYLADRNVSGETFHPS

GGLRYERTPTGGELFGLPSPERLAELVGSTVYLIGEHLTEHLNLLARAYL

ERYGARQVVMIVETETGAETMRRLLHDHVEAGRLMTIVAGDQIEAAIDQA

ITRYGRPGPVVCTPFRPLPTVPLVGRKDSDWSTVLSEAEFAELCEHQLTH

HFRVARKIALSDGASLALVTPETTATSTTEQFALANFIKTTLHAFTATIG

VESERTAQRILINQVDLTRRARAEEPRDPHERQQELERFIEAVLLVTAPL

PPEADTRYAGRIHRGRAITV
```

Additional malonyl-CoA reductase enzyme examples include, but are not limited to, those from *Chloroflexus* sp., *Oscillochloris* sp., *Roseiflexus* sp., and marine gamma proteobacterium. See, e.g., Hügler et al., *J. Bacteriol.* 184:2402-2410 (2002); Rathnasingh, C., et al., *Biotech. Bioeng.* 104(4) (2009); Rathnasingh, C., et al., "Production of 3-hydroxypropionic acid via malonyl-CoA pathway using recombinant *Escherichia coli* strains," *J. Biotech.* (Epub Jun. 23, 2011). A phylogenetic tree and an alignment of several malonyl-CoA reductase enzymes is shown in FIGS. 45 and 46. These alignments were made using malonyl-CoA reductase enzymes from *Chloroflexus aurantiacus* (GenBank Accession No. AAS20429; SEQ ID NO:1); *Chloroflexus aurantiacus* J-10-fl (GenBank Accession No. YP_001636209; SEQ ID NO:291); *Chloroflexus* sp. Y-400-fl (GenBank Accession No. YP_002570540; SEQ ID NO:292); *Chloroflexus aggregans* DSM 9485 (GenBank Accession No. YP_002462600; SEQ ID NO:293); *Oscillochloris trichoides* DG6 (GenBank Accession No. ZP_07684596; SEQ ID NO:294); *Roseiflexus castenholzii* DSM 13941 (GenBank Accession No. YP_001433009; SEQ ID NO:295); *Roseiflexus* sp. RS-1 (GenBank Accession No. YP_001277512; SEQ ID NO:296); *Erythrobacter* sp. NAP1 (GenBank Accession No. ZP_01039179; SEQ ID NO:297); gamma proteobacterium NOR51-B (GenBank Accession No. ZP_04957196 SEQ ID NO:298).

Another product that can be produced from a malonyl-CoA metabolic precursor, and/or as an end-product of the fatty acid syntheses described herein, is adipic acid. Adipic acid is a six-carbon dicarboxylic acid, which is used as a chemical intermediate in the synthesis of polymers, such as polyamides (nylons), polyurethanes, and plasticizers, as well as a food acidulant. Chemical synthesis of adipic acid uses various noxious chemicals for oxidation and/or hydration of ketoalcohols or cyclohexanes, which present environmental safety and energy input concerns. Engineering a biological system to produce adipic acid from a carbohydrate source can avoid these concerns and provide a renewable means for producing adipic acid-derived products.

Attempts at the bioproduction of adipic acid have used alternative synthetic pathways, catalysts, substrates, intermediates, and/or recombinant microorganisms. See, e.g., WO2011/003034, WO1995/007996, WO2009/151728, and WO2010/144862, each of which is incorporated by reference herein. In particular, WO2011/003034 discloses the synthesis of adipic acid from, inter alia, fatty acids, fatty alcohols, alkanes, and oils, but does not, however, disclose the synthesis of adipic acid from a malonyl-CoA metabolic precursor. The pathways of the invention for producing malonyl-CoA can be used to produce a $C_{12}$ fatty acid or fatty alcohol, which can be further engineered to produce adipic acid via omega oxidation using. See, e.g., FIGS. 23 and 24 ("At" is *Arabidopsis thaliana*; "Cc" is *Candida cloacae*); WO2011/003034; Vanhanen S., et al., *J. Biol. Chem.* 275 (6):4445-52 (2000); Picataggio, S., et al., *Bio/Technology* 10(8):894-98 (1992). To accommodate the oxidation of the fatty acid or fatty alcohol, either a facultative anaerobe (e.g., *E. coli* or *S. cerevisiae*) can be engineered to include an adipic acid pathway that can be switched to aerobic conditions after a pool of malonyl-CoA or fatty acids/alcohols is synthesized, or a facultative anaerobe or aerobe comprising an adipic acid pathway can be engineered to use in tandem or in series with a recombinant microorganism of the invention that produces fatty acids or fatty alcohols.

To generate adipic acid from a fatty acid or fatty alcohol using omega oxidation pathway, enzymes such as, e.g., a mixed function oxidase to hydroxylate the omega carbon and alcohol and aldehyde dehydrogenases to oxidate the introduced hydroxyl group, can be used.

Phosphoenolpyruvate Carboxykinase

Phosphoenolpyruvate carboxykinase (PEPCK) includes those enzymes that catalyze the conversion of phosphoenolpyruvate (PEP) to oxaloacetate (see FIG. 1A) and that correspond to Enzyme Commission Number 4.1.1.49 or 4.1.1.32. See, e.g., Matte, A., et al., *J. Biol. Chem.* 272: 8105-08 (1997). The reaction is reversible and is used in succinic acid producing bacteria to convert PEP to oxaloacetate. *E. coli* can mutate to use PEPCK when flux is directed primarily to succinic acid. PEPCK requires $Mg^{2+}$ as a co-factor. A number of ATP and GTP using enzymes have been described, including, e.g., a GTP-utilizing PEPCK in *C. thermocellum* and ATP-utilizing PEPCK in *T. saccharolyticum*, *T. tengcongensis*, *E. coli* and *S. cerevisiae*.

PEPCKs have been classified according to nucleotide specificity, i.e., those that are ATP-dependent and those that are GTP- or ITP-dependent. Within each group, the species show significant amino acid sequence identity, in the range of 40-80%, and share similar nucleotide and oxaloacetate binding "consensus motifs" between the groups, including key conserved residues at or near the active sites. See Matte, A., et al., *J. Biol. Chem.* 272:8105-08 (1997). Additional structural characterizations have been described in, e.g., Matte, A., et al., *J. Biol. Chem.* 272:8105-08 (1997). Examples of PEPCK sequences include:

```
C. thermocellum PEPCK (GTP)
>Cthe_2874
                                                                  (SEQ ID NO: 2)
atgacatcaacaaacatgacaaaaaacaaaaaactgctggattgggttaaggaaatggctgaaatgtgtcagcctgatgaaattt
attggtgcgatggttcggaggaagaaaatgagcgcttgataaagttgatggtggattcaggtttggctacgcctttgaatcctgaa
aagcgacctggatgttatctcttccgcagcgatccgtccgacgttgcccgtgttgaggacagaactttattgcatccaaaaccaa
agaagatgcaggacctacaaacaactggatagatccggttgagctcaaggcaactatgaaagagttgtacaagggttgtatgaa
gggaagaacaatgtatgttattcctttctccatgggacctatcggttcacccatttcaaaaatcggcgttgaattgaccgacagccct
tatgttgttgttaacatgcgcattatgactcgcataggcaaggctgtgttggatcagctcggagaagacggagattttgtaccttgtc
tccactcagtcggtgctccgctcaaagagggagaaaaggataaaggttggccatgcgcaccaatcgaaaagaaaatacataagc
cacttcccggaagaaaggactatatggtcatatggttccgatacggtggaaatgcgcttttaggaaagaaatgctttgcacttcgt
attgcatctgttatggcacgtgacgaaggttggcttgctgaacacatgcttatccttcgcataacagaccctgaaggaaacaagac
atatgttacaggtgctttcccaagcgcatgcggaaagacgaacctggctatgcttattcctacaattcccggatggaaagttgaaa
caatcggtgacgatattgcatggatgagatttggaaaagacggccgtttgtatgctatcaacctgaagcaggattcttggtgttg
ctccgggtacatccatggattcaaatccgaacgcaatgcataacaattaagaaaaatactatatttacaaacgttgcattgactgatg
acggcgatgtttggtgggaaggcatcggaactgaaccgccggctcatctcatagactggcagggtaaagactggactcctgatt
ccggaactttggcagcacatcccaacggacgttttacagcacctgcaagtcagtgccctgtaattgctcctgaatgggaggatcc
ggaaggtgtgccgatttcagcaatccttatcggtggacgcctccgaacaccattccgcttgttcatgaaagcttttgactggaacc
atggtgtattcatgggttcaatcatgggttctgaaattacggctgccgcaatttcaaacaaaatcggacaggtacgccgtgacccg
tttgctatgctgccttcataggctacaacgtaaatgactatttgcagcactggttgaacatgggtaccaagactgacccaagcaag
cttcccaagatattctatgtaaactggttccgcaaggacagcaacggtaaatggttgtggcctggatacggtgaaaacagccgtgt
tctcaagtggattgttgaaagagtcaacggaaaaggtaaagcagtaaagacacctataggatatatgcctacagttgacgctatc
gacacaaccggccttgatgtaagcaaagaggatatggaagaactcttgagcgttaacaaagaacagtggctccaggaagttga
gtcaataaaagaacattataagtcatacggagaaaaactgccgaaagaattgtgggcacaattggaggctcttgaacaacgtttg
aaagagtataacggttaa T. saccharolyticum PEPCK
>or2173
                                                                  (SEQ ID NO: 3)
ATGATTATGAAAAAATCAAAGAAATGTTTCAATCTGAATATTGACGACAAAG
AAACCTTGAATACTTTTGGAAGTTCGAGAGGAGAATTGTTTATGATAGATTTA
GATGATGTATTTAAAAATTCTGGCAGTATTCTTTACAATTTACCTGTTTCAGA
TTTGATAGAGGAAGCCATAAGAAATAATGAAGGGAAATTGTTAGAAAATGGT
GCATTAGATGTTTTTACAGGTAAATATACGGGAAGAATACCAAAAGATAAAT
ACATTGTAAATGAAGAATCTATTCATAATGATATTTGGTGGGAAAATAATAA
TTCAATGGAAAAAGAAAATTTTATTAGAGTTTTAAACAGAGTAATTGATTATT
TAAAAAAGAGCAGAAAATTGTATGTTTTTAAAGGTTTTGTTGGCGCAGACCC
GCGATATAGATATCAAGTAACCGTTATTAATGAATATGCCTATCAAAACGCTT
TTGTACATCAATTATTTATTAATCCTAAAAATGAAGAAGAACTTAAAAAGGA
ATCCGATTTTACAGTTATTTGTGTGCCGAATTTTTTAGCTGATCCAATTTATGA
TGGAACTAATTCTGAGGCATTTATTATTATAAGTTTTGAAGAAAAATTAATTT
TAATTGGTGGAACAAGATATTCAGGAGAAATAAAAAAATCTGTCTTCACAAT
GATGAATTATTTGATGTTAAAAAGGAATGTACTGCCTATGCATTGTGCAGCTA
ATATAGGTTCCAATAATGATACAGCGCTTTTTTTTGGGTTGTCGGGAACCGGC
AAGCAACTTTATCAACGGATCCAGAAAGATTTTTAATTGGCGACGATGAAC
ATGGATGGTCTTCACATGGAATTTTTAATTTTGAGGGTGGATGCTATGCAAAG
TGTATAAATTTATCCCCATATAATGAACCTGAAATATGGAATGCAATTAGATT
TGGAACAATTTTAGAAAATGTTATTTATGATGTAAATAATATGCCAGTCTATA
CAAGTAGTAAAATAACTGAAAATACAAGAGCTTCATATCCACTTGAGTACAT
CCCTAGGAAAGCGTCAAATGGCATTGGCGGTAATCCTAAAATTATATTTTTCT
```

-continued

TGGCAGCCGATGCTTTTGGAGTATTGCCTCCAATTTCTAAGCTGACAAATGAA
CAGGCTGTTGACTATTTCTTATTAGGATATACGAGCAAAATACCAGGAACAG
AAAAGGGAATTTGCGAACCACAAGCAACGTTTTCATCATGTTTTGGAGCACC
ATTTTTGCCATCATATCCAATGAGGTATGCTGAATTGTTAAAGAAAAAAATCG
CAGAAAATGATTCAGTTGTTTATTTAATAAATACTGGATGGATAGGTGGACA
TTATGGAATTGGCAAAAGGATAGATTTAAAATACACAAGAGAAATCATAAAA
AATGTTTTAAATGGTGAATTGGAAAAAGCAAAATTTAAAAAAGATACAGTAT
TTGATTTGATGATACCAGAAAAGTGCAATAACATTCCAGATGAATTATTAGA
TCCTATAAAAACATGGGAAGACAAAAATGATTACTTCCAAACTGCTAATAAT
TTATTATCTGCATTTAAAGCGAGATTAGATTATATAAAAAATGGGATTCATCA
ATAA

*E. coli* K12 PEPCK (ATP)

(SEQ ID NO: 4)

ATGCGCGTTAACAATGGTTTGACCCCGCAAGAACTCGAGGCTTATGGTATCA
GTGACGTACATGATATCGTTTACAACCCAAGCTACGACCTGCTGTATCAGGA
AGAGCTCGATCCGAGCCTGACAGGTTATGAGCGCGGGGTGTTAACTAATCTG
GGTGCCGTTGCCGTCGATACCGGGATCTTCACCGGTCGTTCACCAAAAGATA
AGTATATCGTCCGTGACGATACCACTCGCGATACTTTCTGGTGGGCAGACAA
AGGCAAAGGTAAGAACGACAACAAACCTCTCTCTCCGGAAACCTGGCAGCAT
CTGAAAGGCCTGGTGACCAGGCAGCTTTCCGGCAAACGTCTGTTCGTTGTCG
ACGCTTTCTGTGGTGCGAACCCGGATACTCGTCTTTCCGTCCGTTTCATCACC
GAAGTGGCCTGGCAGGCGCATTTTGTCAAAAACATGTTTATTCGCCCGAGCG
ATGAAGAACTGGCAGGTTTCAAACCAGACTTTATCGTTATGAACGGCGCGAA
GTGCACTAACCCGCAGTGGAAGAACAGGGTCTCAACTCCGAAAACTTCGTG
GCGTTTAACCTGACCGAGCGCATGCAGCTGATTGGCGGCACCTGGTACGGCG
GCGAAATGAAGAAAGGGATGTTCTCGATGATGAACTACCTGCTGCCGCTGAA
AGGTATCGCTTCTATGCACTGCTCCGCCAACGTTGGTGAGAAGGCGATGTT
GCGGTGTTCTTCGGCCTTTCCGGCACCGGTAAAACCACCCTTTCCACCGACCC
GAAACGTCGCCTGATTGGCGATGACGAACACGGCTGGGACGATGACGGCGTG
TTTAACTTCGAAGGCGGCTGCTACGCAAAAACTATCAAGCTGTCGAAAGAAG
CGGAACCTGAAATCTACAACGCTATCCGTCGTGATGCGTTGCTGGAAAACGT
CACCGTGCGTGAAGATGGCACTATCGACTTTGATGATGGTTCAAAAACCGAG
AACACCCGCGTTTCTTATCCGATCTATCACATCGATAACATTGTTAAGCCGGT
TTCCAAAGCGGGCCACGCGACTAAGGTTATCTTCCTGACTGCTGATGCTTTCG
GCGTGTTGCCGCCGGTTTCTCGCCTGACTGCCGATCAAACCCAGTATCACTTC
CTCTCTGGCTTCACCGCCAAACTGGCCGGTACTGAGCGTGGCATCACCGAAC
CGACGCCAACCTTCTCCGCTTGCTTCGGCGCGGCATTCCTGTCGCTGCACCCG
ACTCAGTACGCAGAAGTGCTGGTGAAACGTATGCAGGCGGCGGGCGCGCAG
GCTTATCTGGTTAACACTGGCTGGAACGGCACTGGCAAACGTATCTCGATTA
AAGATACCCGCGCCATTATCGACGCCATCCTCAACGGTTCGCTGGATAATGC
AGAAACCTTCACTCTGCCGATGTTTAACCTGGCGATCCCAACCGAACTGCCG
GGCGTAGACACGAAGATTCTCGATCCGCGTAACACCTACGCTTCTCCGGAAC
AGTGGCAGGAAAAAGCCGAAACCCTGGCGAAACTGTTTATCGACAACTTCGA
TAAATACACCGACACCCCTGCGGGTGCCGCGCTGGTAGCGGCTGGTCCGAAA
CTGTAA

*S. cerevisiae* PEPCK (ATP)

(SEQ ID NO: 5)

ATGTCCCCTTCTAAAATGAATGCTACAGTAGGATCTACTTCCGAAGTTGAACA
AAAAATCAGACAAGAATTGGCTCTTAGTGACGAAGTCACCACCATCAGACGC
AATGCTCCAGCTGCCGTTTTGTATGAAGATGGTCTAAAAGAAAATAAAACTG
TCATTTCATCAAGCGGTGCATTGATCGCTTATTCCGGTGTTAAAACCGGAAGA
TCTCCAAAGGACAAACGTATTGTTGAAGAACCTACCTCGAAAGACGAAATTT
GGTGGGGTCCGGTCAATAAACCATGTTCTGAAAGAACATGGTCTATCAACCG
TGAAAGAGCTGCAGATTACTTGAGAACAAGAGACCACATTTATATTGTCGAT
GCATTTGCAGGATGGGATCCAAAATACAGAATCAAAGTCCGCGTTGTTTGTG
CCAGGGCTTACCACGCTTTATTCATGACAAATATGCTTATTAGACCTACAGAA
GAAGAATTAGCCCATTTTGGAGAACCTGATTTTACTGTCTGGAACGCTGGTCA
GTTCCCAGCCAATTTACACACCCAGGATATGTCTTCAAAGAGTACTATAGAA
ATTAACTTCAAAGCAATGGAAATGATCATTTAGGTACCGAATACGCCGGTG
AAATGAAAAAAGGTATTTTCACAGTTATGTTTTACTTGATGCCTGTGCACCAT
AACGTTTTAACTTTGCACTCTTCCGCCAACCAGGGTATTCAAAACGGTGACGT
TACTTTATTCTTTGGCCTAAGTGGTACCGGGAAAACCACTTTATCCGCAGACC
CACATAGATTGTTGATCGGCGATGATGAACATTGTTGGTCCGACCATGGTGTC
TTCAATATCGAAGGTGGTTGTTACGCCAAGTGTATTAATTTATCTGCCGAAAA
GGAGCCTGAAATTTTCGACGCTATCAAGTTTGGTTCTGTATTAGAAAACGTTA
TCTATGACGAGAAGTCGCATGTAGTCGACTATGACGACTCTTCTATTACTGAA
AATACTAGATGTGCCTACCCAATTGACTACATTCCAAGTGCCAAGATTCCATG
TTTGGCGGACTCTCATCCCAAAGAACATTATCCTGCTAACTTGTGATGCTTCGG
GTGTTTTACCACCAGTATCTAAATTGACTCCTGAACAAGTCATGTACCATTTC
ATCTCTGGTTACACTTCTAAAATGGCTGGTACTGAGCAAGGTGTCACTGAACC
TGAACCAACATTTTCATCTTGTTTCGGACAACCCTTCCTAGCCTTGCACCCTAT
TAGATACGCAACCATGTTAGCTACAAAGATGTCTCAACATAAAGCTAATGCG
TACTTAATCAACACCGGCTGGACTGGTTCTTCCTACGTATCTGGTGGTAAACG
TTGCCCATTGAAGTACACAAGGGCCATTCTGGATTCTATTCATGATGGTTCGT
TAGCCAATGAAACGTACGAAACTTTACCGATTTTCAATCTTCAAGTACCTACC
AAGGTTAACGGTGTTCCAGCTGAGCTTTTGAATCCTGCTAAAAACTGGTCTCA
AGGTGAATCCAAATACAGAGGTGCAGTTACCAACTTGGCCAACTTGTTTGTTC
AAAATTTCAAGATTTATCAAGACAGAGCCACACCAGATGTATTAGCCGCTGG
TCCTCAATTCGAGTAA

Transcarboxylase

The conversion of oxaloacetate and acetyl-CoA to pyruvate and malonyl-CoA allows for the anaerobic high yield production of fatty acid derived hydrocarbons. This reaction has not been reported to occur in vivo. However, an in vitro substrate specificity study for fraction-purified (S)-methylmalonyl-CoA:pyruvate carboxytransferase (a transcarboxylase, "Me-TC," E.C. 2.1.3.1) showed the ability of this enzyme to utilize oxaloacetate and acetyl-CoA as substrates. See Wood and Stjernholm, *PNAS* 47:289-303 (1961). The in vitro reaction occurred at one half the velocity of the enzyme's natural substrates, oxaloacetate and propionyl-CoA, however, and the ability of the enzyme to produce malonyl-CoA in its native organism (*Propionibacterium shermanii*) was not determined. Me-TC enzymes are known to be present in other Propionibacteria (e.g., *Propionibacterium freudenreichii* and *Propionibacterium acnes*), which ferment carbohydrates and lactate to propionate and acetate, and in obligately syntrophic bacteria such as *Pelotomaculum thermopropionicum, Candidatus Cloacamonas acidaminovorans*, and *Geobacter bemidjiensis*, which convert propionate and other medium chain organic acids and alcohols to acetate and hydrogen or reduced metals. Falentin et al., *PLOS one* 5(7): e11748 (2010); Kosaka et al., *Genome Res.* 18:442-448 (2008); Pelletier et al., *J. Bact.* 190:2572-2579 (2008); Aklujkar et al., *BMC Genomics* 11:490 (2010).

As used herein, transcarboxylase (TC) includes enzymes that catalyze the conversion of oxaloacetate and acetyl-CoA to malonyl-CoA and pyruvate (see FIG. 1B) and that correspond to Enzyme Commission Number 2.1.3.1 (methylmalonyl-CoA carboxyltransferase). In vivo, TC also catalyzes the conversion of methylmalonyl-CoA and pyruvate to oxaloacetate and propionyl-CoA. The reaction is reversible and requires co-factors such as Biotin, Co, or $Zn^{2+}$. TC consists of 3-4 subunits encoding domains for: a 5S subunit, a 12S subunit, and a 1.3S subunit; a 12S C-terminal subunit may also be present. See Carey et al., *IUBMB Life* 56:575-83 (2004). TC enzymatic activity has been observed in *Propionibacterium* species such as *Propionibacterium freudenreichii* and *Propionibacterium acnes, Bacteroides fragilis, Veillonella parvula, Veillonella gazogenes, Pelotomaculum thermopropionicum, Candidatus Cloacamonas acidaminovorans*, and *Geobacter bemidjiensis*. See Falentin et al., *PLoS One* 5:e11748 (2010); Kosaka et al., *Genome Res.* 18:442-448 2008 (2008); Pelletier et al., *J. Bact.* 190:2572-2579 (2008); and Aklujkar et al., *BMC Genomics* 11:490 (2010). Based on similarity to TC enzymes, high similarity TC genes have been identified in *Thermoanaerobacter* strains (*T. saccharolyticum* or0945, or0947, and or1888), *C. thermocellum* (Cthe_0699, Cthe_0700, and Cthe_0701), *Caldicellulosiruptor bescii, Clostridium cellulolyticum*, and *Corynebacterium kroppenstedtii*. Protein engineering, either across all subunits or on a specific subunit, using techniques known to those in the art, can be employed to increase enzymatic activity towards malonyl-CoA generation.

An alignment of *C. thermocellum* and *T. saccharolyticum* homologs of TC from *Propionibacterium freudenreichii* CIRM-BIA1 and *Propionibacterium acnes* is shown in FIGS. 7A-7C. Additional sequences of TC include:

```
Propionibacterium freudenreichii subsp. shermanii CIRM-BIA1
Transcarboxylase
>PFREUD_18840 (1.3S subunit nucleotide sequence)
Antisense strand:
                                                              (SEQ ID NO: 6)
tcagccgatc ttgatgagac cctgaccgcc ctgcacggcg tcacgctcct tgacaaggac cttctcgacc ttgccgtcgg
tgggagcgtt gatctcggtc tccatcttca tggcctcgag aacgagcacg gtctgaccag ccttgaccgt gtcaccctcc
ttcacgagga tcttggagac ggtgccggcc agcggagcgg gaatctcgcc ctctccggcc ttaccggcgc
ctgcgccacc tgctgcgcgc ggtgccggcg cgccgccggt gccgccgccg aacaggatgg tgcccatcgg
gttttcgtgt gacttgtcga cgtcaacgtc aacgtcatac gcagtgccgt tgactgttac cttcagtttc at Sense strand:
                                                              (SEQ ID NO: 7)
atgaaactgaaggtaacagtcaacggcactgcgtatgacgttgacgttgacgtcgacaagtcacacgaaaacccgatgggcac
catcctgttcggcggcggcaccggcggcgcgccggcaccgcgcgcagcaggtggcgcaggcgccggtaaggccggaga
gggcgagattcccgctccgctggccggcaccgtctccaagatcctcgtgaaggagggtgacacggtcaaggctggtcagacc
gtgctcgttctcgaggccatgaagatggagaccgagatcaacgctcccaccgacggcaaggtcgagaaggtccttgtcaagga
gcgtgacgccgtgcagggcggtcagggtctcatcaagatcggc >PFREUD_18840 (1.3S subunit amino acid sequence)
                                                              (SEQ ID NO: 8)
MKLKVTVNGTAYDVDVDVDKSHENPMGTILFGGGTGGAPAPRAAGGAGAGKA
GEGEIPAPLAGTVSKILVKEGDTVKAGQTVLVLEAMKMETEINAPTDGKVEKVL
VKERDAVQGGQGLIKIG >PFREUD_18870 (5S subunit nucletotide sequence)
Antisense strand:
                                                              (SEQ ID NO: 9)
tcacgcctgc tgaacggtga cttcgcggac ggttccgccc acgttcacgt tgtaggtgac gggaccggcc
acggcgagcg acttctcgtc gccctcggcc tcggccttca gctgggcatc ggtgagagcc acgctgtgcg
ggccctcggc gcgatgctcg aagaagaccg gagcgacctg cgggaacagt gcataggtga gcacgtcctc
gtcggtgccg ttgaagccct tgagggccgc ggcctccttg gactgctcct cccactcggg gggcagcaga
tcggccgggc gctgggtgat cggcttcttg ccggactgct cctcggccaa cttgaccacc ttcggatcgc gatcggccgg
gctggcgccg tagtagccga gcatgatgtc ggcgaactcg ccggtcatcc tcttgtactc gcccatcatc acgttgaaca
cggcctgcgt gccgacgatc tggctggacg gggtgaccag gggcgggaag ccggcggcct tgcggacgcg
cggcacctct gccatgacct cgtccatctt gtcctcggcg ccctgggcgc gcagctgcga ctccatgttg gagagcatgc
cgccggggat ctgcgacttg aagatcgagg tgtcgacaag cgtcttcgac tcgaacttct tgtacttcgg gcggatggcc
ttgaagtgat cgcggatctt gtgcaggcga tcgtagtcaa ggttggtggt gtacccggtg ccctcgagca tctcggcaac
cgactcggtg gggttgtggc ccgggccgag cgacatggac gagatgccgg tgtcgacgac gtcgacgccg
gcctcgatgg ccttcatgag ggagacctcg gtgacacccg tggtggagtg gcagtgcagg ttgatctgcg tcttctggcc
gtaggtgtcc ttgatggcct tgatgatgtc gtaggccggc tgcggcttga gcagggcggc catgtccttc agggcgatgg
aatcagcacc catgtcgagc agctgaccag caagcttgac atagccctca acggtgtgga ccgggctgat
cgtgtagcaa atggtgccct gcgcgtgctt gccggccttc ttgacggcag ccatggcgtg cgccatgttg cggggatcat
```

-continued

```
tcatgcgtc gaagacacgg aacacgtcca tgccgttctc agccgacttg tcgacgaagc gatcgacgac ctcgtcgttg
tagtggcggt aacccagcag gttctggcca cgcagcagca tctggagacg gctgttgggc atcagcttgc
ggaacgtgcg cagacgctcc caaggatcct cgttgaggaa gcggatacac gagtcatacg tggcaccacc
ccaacactcc actgaccagt acccggcagc atcaatgtct gcacaggcgc cgaccatgtc ttccattgcc attcgtgtgg
ccatcaggct ctgatgggca tcgcgcagca cgagctcggt gataccaacc tcgcgcggct cggaaacctc aatttctcgc
ggactcat
```

Sense strand:

(SEQ ID NO: 10)

```
atgagtccgcgagaaattgaggtttccgagccgcgcgaggttggtatccaccgagctcgtgctgcgcgatgcccatcagagcct
gatggccacacgaatggcaatggaagacatggtcggcgcctgtgcagacattgatgctgccgggtactggtcagtggagtgtt
ggggtggtgccacgtatgactcgtgtatccgcttcctcaacgaggatccttgggagcgtctgcgcacgttccgcaagctgatgcc
caacagccgtctccagatgctgctgcgtggccagaacctgctgggttaccgccactacaacgacgaggtcgtcgatcgcttcgt
cgacaagtccgctgagaacggcatggacgtgttccgtgtcttcgacgccatgaatgatccccgcaacatggcgcacgccatgg
ctgccgtcaagaaggccgcaagcacgcgcagggcaccatttgctacacgatcagcccggtccacaccgttgagggctatgt
caagcttgctggtcagctgctcgacatgggtgctgattccatcgccctgaaggacatggccgccctgctcaagccgcagccgg
cctacgacatcatcaaggccatcaaggacacctacggccagaagacgcagatcaacctgcactgccactccaccacgggtgtc
accgaggtctccctcatgaaggccatcgaggccggcgtcgacgtcgtcgacactcgtccatgtcgctcggccggg
ccacaaccccaccgagtcggttgccgagatgctcgagggcaccgggtacaccaccaaccttgactacgatcgcctgcacaag
atccgcgatcacttcaaggccatccgcccgaagtacaagaagttcgagtcgaagacgcttgtcgacacctcgatcttcaagtcgc
agatccccggcggcatgctctccaacatggagtcgcagctgcgcgcccagggcgccgaggacaagatggacgaggtcatgg
cagaggtgccgcgcgtccgcaaggccgcgggtttcccgcccctggtcaccccgcagatcgtcggcacgcaggccg
tgttcaacgtgatgatgggcgagtacaagaggatgaccggcgagttcgccgacatcatgctcggctactacgcgcgccagccg
gccgatcgcgatccgaaggtggtcaagttggccgaggagcagtccggcaagaagccgatcacccagcgcccggccgatctg
ctgccccccgagtgggaggagcagtccaaggaggccgcgccctcaagggcttcaacggcaccgacgaggacgtgctcac
ctatgcactgttcccgcaggtcgctccggtcttcttcgagcatcgccgcgagggcccgcacagcgtggctctcaccgatgccca
gctgaaggccgaggccgagggcgacgagaagtcgctcgccgtggccggtcccgtcacctacaacgtgaacgtgggcggaa
ccgtccgcgaagtcaccgttcagcaggcgtga
```

>PFREUD_18870 (5S subunit amino acid sequence)

(SEQ ID NO: 11)

MSPREIEVSEPREVGITELVLRDAHQSLMATRMAMEDMVGACADIDAAGYWSV
ECWGGATYDSCIRFLNEDPVVERLRTFRKLMPNSRLQMLLRGQNLLGYRHYNDE
VVDRFVDKSAENGMDVFRVFDAMNDPRNMAHAMAAVKKAGKHAQGTICYTIS
PVHTVEGYVKLAGQLLDMGADSIALKDMAALLKPQPAYDIIKAIKDTYGQKTQI
NLHCHSTTGVTEVSLMKAIEAGVDVVDTAISSMSLGPGHNPTESVAEMLEGTGY
TTNLDYDRLHKIRDHFKAIRPKYKKFESKTLVDTSIFKSQIPGGMLSNMESQLRA
QGAEDKMDEVMAEVPRVRKAAGFPPLVTPSSQIVGTQAVFNVMMGEYKRMTG
EFADIMLGYYGASPADRDPKVVKLAEEQSGKKPITQRPADLLPPEWEEQSKEAA
ALKGFNGTDEDVLTYALFPQVAPVFFEHRAEGPHSVALTDAQLKAEAEGDEKSL
AVAGPVTYNVNVGGTVREVTVQQA

>PFREUD_18860 (12S subunit nucleotide sequence)
Antisense strand:

(SEQ ID NO: 12)

```
tcagcagggg aagtttccat gcttcttcgc cgggcgggtc tgacgcttgg tggcgtacat ctccagggcg gaagcaatct
ttcgacgggt atcagccggg tcaatcacgt cgtcgacctg accgccggcg acccagcacgt acggcgtgtt
gaacgcgttc tggtactcct cgatcttctc ggcgcgcatg gcgtcggat cgtcggcagc cttgatctcc ttgcggaaga
tcacatttgc cgcaccctcg cgcgcccatca ccgcaatctc ggcgctgggc caggcgtaca cggcgtcggc
accaaggtca cggttgcaca tggccaggta ggagccgccg taggccttgc ggagcaccac ggtgatcttc
ggcacggtgg cctcggagta ggcgtacagc atcttcgcgc catggccgaga gatgccgccg tactcctgct
gcacgccggg caggaagccc ggcacgtcga ccagctgcac cagcgggatg ttgaacgaat cgcagaaatt
cacgaattcg gcggccttgt cagaggcgtt gatgtcgagg caacccgaca tcaccgacgg ctgattggcc
acgatgccca ccgaacgacc attgaccggg gcgaaggcgg tcacgaggtt ggtggcatag ccggccttga
cctcgaggta gtcaccccag tcgacgatct tggcaatgac atcgcgcacg tcatagccct tcttgccgtc aatcggaacg
atgtcgcgca gctcggtatt ggggcgtgacg tcattgttcg ggttgacgaa ggatgcttcc tcagtgttgt tctgcggaag
gaagctcagc agcttcttgg caatgagctc cgccggcgtcg tcgtcctcgg ccacgaagtg gatattgccc
gagatgccca tatgggcctc agcgccaccg agttcgtcag cggtgacatc ctcgccggtg accgacttga
tgacctgggg gcccgtgatg aacatatggg ccttcttggt catgatgatg aagtcagtca gtgccggcga atacgaggcg
ccaccggcac aggggccggc aatgatggcg atctgccgga cgacgcccga cagcttcacg ttggcgaaga
acatcttgcc gtaaccgctc agcgagtcga tgccctcctg gatccgggcg ccgcccgaat cgtagaagaa
caggaagggc gtgccggtga gcagcgcctg ttccatcgtc tcgacgacct tcgtggactg cgtctcgcca
gccgaaccac ccatgaccgt gaagtcctgg gacgcggcgt gcacgggacg accaaggatg gtgccacggc
cggtgaccac gccatctgcc gggacgacgg cctttgtccat gccgaacacg gtggtgcggt gcttgcggaa
agcgccgacc tcgtcgaacg aatgggggatc gagcaggttg ttcaggcgct cacgagcggt ctgcttaccc tgggaatgtt
gcttctcgac gcgacgttcg ccgccaccgg cttcgatcac ctggcgctgc tctgcgagct gctccacgcg accttccatg
gtgctggcga gcttcaaatt gttgttttca gccat
```

Sense Strand:

(SEQ ID NO: 13)

```
atggctgaaaacaacaatttgaagctcgccagcaccatggaaggtcgcgtggagcagctcgcagagcagcgccaggtgatcg
aagccgggtggcggcgaacgtcgtcgcgagaagcaacattcccaggtaagcaagatgttcttgagcgcctgaacaacctgc
tcgatcccattcgttcgacgaggtcggcgctttccgcaagcaccgccaccacgttgttcggcatggacaaggccgtcgtcccgg
cagatgtcgctggtcaccggccgtggcaccatccttggtcgtcccgtgcacgccgcgtcccaggacttcacggtcatgggtggtt
cggctggcgagacgcagtccacgaaggtcgtcgagacgatggaacaggcgctgctcaccggcacgcccttcctgttcttctac
gattcgggcggcgcccggatccaggaggggcatcgactcgctcgagcggttacggcaagatgttcttcgccaacgtgaagctgtc
gggcgtcgtgccgcagatcgccatcattgccgcccctgtgccggtggcgcctcgtattcgcgcggcactgactgacttcatcatc
atgaccaagaaggcccatatgttcatcacgggccccaggtcatcaagtcggtcaccggcgaggatgtcaccgctgacgaact
cggtggcgctgaggccatatggccatctcgggcaatatccacttcgtggccgaggacgacgacgccgcggagctcattgcc
aagaagctgctgagcttccttccgcagaacaacactgaggaagcatccttcgtcaacccgaacaatgacgtcagccccaatacc
gagctgcgcgacatcgttccgattgacggcaagaagggctatgacgtgcgcgatgtcattgccaagatcgtcgactggggtga
```

-continued

```
ctacctcgaggtcaaggccggctatgccaccaacctcgtgaccgccttcgcccgggtcaatggtcgttcggtgggcatcgtggc
caatcagccgtcggtgatgtcgggttgcctcgacatcaacgcctctgacaaggccgccgaattcgtgaatttctgcgattcgttca
acatcccgctggtgcagctggtcgacgtgccgggcttcctgcccggcgtgcagcaggagtacggcggcatcattcgccatggc
gcgaagatgctgtacgcctactccgaggccacgtgccgaagatcaccgtggtgctccgcaaggcctacggcggctcctacct
ggccatgtgcaaccgtgaccttggtgccgacgccgtgtacgcctggcccagcgccgagattgcggtgatgggcgccgagggt
gcggcaaatgtgatcttccgcaaggagatcaaggctgccgacgatcccgaccgccatgcgcgccgagaagatcgaggagtac
cagaacgcgttcaacacgccgtacgtggccgccgcccgcggtcaggtcgacgacgtgattgacccggctgatacccgtcgaa
agattgcttccgccctggagatgtacgccaccaagcgtcagacccgcccggcgaagaagcatggaaacttcccctgc
```

\>PFREUD_18860 (12S subunit amino acid sequence)

(SEQ ID NO: 14)

```
MAENNNLKLASTMEGRVEQLAEQRQVIEAGGGERRVEKQHSQGKQTARERLNN
LLDPHSFDEVGAFRKHRTTLFGMDKAVVPADGVVTGRGTILGRPVHAASQDFTV
MGGSAGETQSTKVVETMEQALLTGTPPFLFFYDSGGARIQEGIDSLSGYGKMFFA
NVKLSGVVPQIAIIAGPCAGGASYSPALTDFIIMTKKAHMFITGPQVIKSVTGEDV
TADELGGAEAHMAISGNIHFVAEDDDAAELIAKKLLSFLPQNNTEEASFVNPNND
VSPNTELRDIVPIDGKKGYDVRDVIAKIVDWGDYLEVKAGYATNLVTAFARVNG
RSVGIVANQPSVMSGCLDINASDKAAEFVNFCDSFNIPLVQLVDVPGFLPGVQQE
YGGIIRHGAKMLYAYSEATVPKITVVLRKAYGGSYLAMCNRDLGADAVYAWPS
AEIAVMGAEGAANVIFRKEIKAADDPDAMRAEKIEEYQNAFNTPYVAAARGQV
DDVIDPADTRRKIASALEMYATKRQTRPAKKHGNFPC
```

\>P. freudenreichii_(12S_C-term nucleotide sequence)

(SEQ ID NO: 15)

```
atggctgatgaggaagagaaggacctgatgatcgccacgctcaacaagcgcgtcgcgtcattggagtct
gagttgggttcactccagagcgataccagggtgtcaccgaggacgtactgacggccatttcggccgcc
gttgcggcctatctcggcaacgatggatcggctgaggtcgtccatttcgccccgagcccgaactgggtcc
gcgagggtcgtcgggctctgcagaaccattccattcgt
```

\>P. freudenreichii_(12S_C-term amino acid sequence)

(SEQ ID NO: 16)

```
MADEEEKDLMIATLNKRVASLESELGSLQSDTQGVTEDVLTAISAAVAAYLGND
GSAEVVHFAPSPNWVREGRRALQNHSIR
```

*Propionibacterium acnes* SK137 Transcarboxylase
P. acnes (12S subunit)

(SEQ ID NO: 17)

```
atggctgagaagaaaccaatcaagctggccgataccatggccggccggatcgagcagctcgccgacgagcgccacgctgtg
gagcttggcggggcggaggatcgcctgcaaaagcagcgtgaacaggcaagcgaacagacccgtgaacggatcgacaacct
cgttgatgcttattccttcgatgaggtgggtgcgttccgtaagcaccgccaccaccctttttcggcatggacaaggccgaagttcccg
ccgacggcgtagtcaccggtcgtgcgaccatccatggtcgcccggtccacatcgcgtctcaggacttcaccgtcatgggtgggt
cggctggcgagacccagtcgacgaaggtcgtcgagacgatggaacagtccctgctgaccggcactccgtttctgttcttctatga
ctcggggacgcccgaattcaagaaggcatcgactcgctgtcccgggtacggcaagatgttcttcgccgaacgtcaagctgtcgg
gcgtcgtgccgcagatcgccatcattgctggcccctgcgccggcggcgcctcctattcccgccctgaccgacttcatcatcat
gacgaagaaggcccacatgttcattacggccccggagtcatcaagtcggttaccggtgaggaggtgactgctgacgacctgg
gtggtgcggatgcgcacatgtccacctcgggcaatatccacttcgtggccgaagatgacgacgccgcagtgctcatcgcgcag
aagttgctgagcttcctgccgcaaaacaacactgaggacgcccagatctccaacccaatgacgatgtctccccgcagcctgag
ctgcgcgacatcgttccgctggatggtaagaaggggctacgacgtccgcgacgtcatctccaagatcgtcgactggggcgacta
cctagaggtcaaggccggttgggcgaccaacatcgtcaccgcctttgcccgggtcaatggtcgtaccgtcggcatcgtggcca
accagccgaaggtgatgtcgggttgccttgacatcaatgcttcggacaaggctgccgagttcattaccttctgcgactcgttcaat
attccgttggtgcagttggttgacgttcctggcttcctgcctggtgtccagcaggatacggccggcatcatccgccacggccgga
agatgctgtatgcctactccgaggccaccgtcccgaagatcaccgtggtgctgcgtaaggcttacggcggctcctaccttgccat
gtgcaaccgtgacctgggtgctgacgccgctatgcctggccgagcgcggagattgcggtgatgggcgccgatggcgctgcc
aacgtcatttttccgtcgccagatcaaggactctgaggatcccgcagccaccgtgccgcgaagatcgaggagtaccgcaacgc
cttcaacacgccttacgtggctgccgcccgtggacaggttgacgacgtgatcgatccgcggacacccgtcgcaagatcaccg
ccgctctggagacctacgccactaagcgtcagtcccgtccggccaagaagcacgcgcatgccttgctga
```

P. acnes (5S subunit)

(SEQ ID NO: 18)

```
atgagtccacgaaagattggcgttaccgagctcgtgctccgcgacgcgcatcagagcctgcttgccactcgcatggccatgga
ggacatggttgatgcctgtgccgacattgatgcggcaggcttctggtccgttgaatgctggggcggagctaccttcgattcttgca
tccgattcctcaacgaagacccatgggagcgtctgcgtactttccgcaagctgctgccgaactcccggttgcagatgctgctgcg
tggccaaaaccttctgggctaccgccactacaacgacgaggtcgtcgacaagtttgtcgagaagtcggccgagaacggcatgg
acgtgttccgggtgttcgacgtctgaaagatcctcgcaacctttgagcacgcgatggccgtcaaggagcgcgaccgcaagcac
gccagggcaccatctgctacaccacttccccgattcacaccccagagagcttcgtcaagcaggccgatcgtctcatcgacatg
ggtgccgactcgatcgccttcaaggacatggctgctttgctcaagccgcagcctgcctacgacatcatcaagggcattaaggag
aaccatccgacgtgcagatcaacctgcactgccactccaccacgggcgtcaccctggtcaccctgcagaaggccatcgagg
ctggtgtcgacgtcgtcgacaccgctatctcgtcgatgtcgctcggccggggcacaacccaaccggtctttggtcgagatgct
cgagggcaccgagtacaccaccggcctcgacatggatcgcctgctcaagatccgcgaccacttcaaggaagttgcgtccgaag
tacaagaagttcgagtcgaagacgctggtcaacaccaacatcttccagtcccagatcccgggcgaatgctctccaacatggag
tcccagctcgaggcccagggtgctggagaccgcatggatgaggtcatgaaggaggtgccgcgcgttcgtaaggatgccggct
accccgccgctgtcacccgtctccccagatcgtgggaaccccaggcggtgttcaacgtcctggtcgagcgcaatggtttcgtacaaga
acctcactgccgagtttgccgacctcatgcttggctactacgcaagccatggcgagctcaatcccgatcgttcgagatggc
caagaagcagaccggcaaggagccgatcgactgccgtcccgccgacctgctcgagcctgagtggaccagctggtcgagca
ggccaagagtcttgagggcttcgacggctccgacgaggacgttcttaccaacgccctgttcccgggagttgccccgaagttcct
caaggaacgcgcacagggccccgaagagcgtcgcgatgaccgaggcacagctgaaggccgagaaggaaggcaccggcgc
tgccggcatcgccgaccgtcaactacaacgtgacggtcggtggcaacagccaccaggtgaccgtcgagcctgcgtga
```

P. acnes (1.3S subunit)

(SEQ ID NO: 19)

```
atgaagctcaaggtgaccgtcaatgacgtcgcatacgacgttgacgttgacgttgataagaccgccaatgcgccgatggcgcc
```

-continued

```
gatcctctttggtggcggcgccggcggcccgatgaaggcatccggtggcggccgccggtaaggccggtgagggcgaggttcc
cgcaccgctagctgggactgttgccaagatcctggtggccgaaggagatgccgtcaaggccggtcaggtgctcctgaccctcg
aggccatgaagatggagaccgagatcaatgccccggcggacggaaccgtcaagggatcctggtggctgtcggtgacgccg
tccagggtggtcagggcctggtggctctgggctga
```

*C. thermocellum* Transcarboxylase
>Cthe_0699 (12S subunit nucleotide sequence)

(SEQ ID NO: 20)

```
atggacaaagtagacaagatcggccttctccgtgaaaaactggcccaggttgaacagggcggaggagctgaaaaaatcgcaa
aacagcatgatgccggaaaaatgacagcaagagaaagaatccaggctttatttgatgaaaacagctttgttgagatcgacacattt
gttgagacaagaagcattgacttcgatatgcaaaaaaagaaagtcccgggagacggtgttgtaacagggtatggttccatagac
ggacgtctggtctttgttgcggcgcaggacttactgtaatcggtgggtctttgggtgaaatgcatgccgcaaaaatcaccaaagt
aatggacatggcaatgaaaatgggcgcaccgtttataagcattaatgattccggcggtgcaagaattgaagaaggaattgacgc
actcaaggggatttggagatatcttctacagaaatacttttggcttcaggtgtaattccccagatttcagttatcatgggaccatgcgca
ggcggagcggtatattctcctgcaataaccgactttatatttatggttgacaaaaccagtcagatgtttataacgggacccccaggta
attaagtccgtaaccggagaagacgtgacttttgaaaaacttggcggtgcggaaacccacaactccataagcggtgttgctcact
tcagaagttcaagtgaaaaagaatgtatagagcaaatcaaaaagcttattagttatcttcctgataacaatctttccgatgttccgatt
gttccaactcaggatgacataaacagaattactgacaacattctgcgatatcattccgcaggactccaacaagccttatgacatgat
ggaaataatcacttccgtagttgacaacggtgacttttttgaaattcaaaaagactttgcaaaaaacattataataggtttcggcaga
atgaacggcggaaccgtcggtatagtggcaaatcagccaaaagttgccgcaggggttttggatgtgaactcctctgacaaagcc
gcaaggtttgttcgtttctgtgatgcgttcaacattccaattataacctttaccgatgtaccggggtatctgcccggagtaggccagg
agcacagcggagtaataagacacggtgcaaagcttcttttatgctttctctgaagccaccgttccaaaaatcaatgttattgtcagaa
aagcttacggcggtgcatatattgccatgaacagcaagcacctggagcggacatggtatttgcgtggccttcggcggaaattgc
agttatgggaccggaaggtgcggcaaacatcattttcaagaaagatatagctgctgccgatgacccaatggaaacaagaaaga
ggctcattgaagaatatcgtgaaaaattctccaatccgtatgttgcagcttcaagggggtatgttgatgatgtaattgatccggcaac
aacaaggataagactgattagtgcccttgaaatgcttgcaagtaagagagaaaacagacctgccaaaaagcatggaaatattcc
attataa
```

>C. thermocellum_(12S subunit amino acid sequence)

(SEQ ID NO: 21)

```
MDKVDKIGLLREKLAQVEQGGGAEKIAKQHDAGKMTARERIQALFDENSFVEID
TFVETRSIDFDMQKKKVPGDGVVTGYGSIDGRLVFVAAQDFTVIGGSLGEMHAA
KITKVMDMAMKMGAPFISINDSGGARIEEGIDALKGFGDIFYRNTLASGVIPQISV
IMGPCAGGAVYSPAITDFIFMVDKTSQMFITGPQVIKSVTGEDVTFEKLGGAETH
NSISGVAHFRSSSEKECIEQIKKLISYLPDNNLSDVPIVPTQDDINRITDNLVDIIPQD
SNKPYDMMEIITSVVDNGDFFEIQKDFAKNIIGFGRMNGGTVGIVANQPKVAAG
VLDVNSSDKAARFVRFCDAFNIPIITFTDVPGYLPGVGQEHSGVIRHGAKLLYAFS
EATVPKINVIVRKAYGGAYIAMNSKHLGADMVFAWPSAEIAVMGPEGAANIIFK
KDIAAADDPMETRKRLIEEYREKFSNPYVAASRGYVDDVIDPATTRIRLISALEM
LASKRENRPAKKHGNIPL
```

>Cthe_0700 (1.3S subunit nucleotide sequence)

(SEQ ID NO: 22)

```
atgaaaaagttttttgataaaggtaaacggaaatcaatatgaggttgaagttgaagaaatcagagacggtgcttcagcaccacagg
ttactctcagcacaccttcggctgcacctgcctttaccggcaccggctcaggaaacgaaaacagctgcaccaaagaaagac
agcacagtaccggcaggtgctacggcaattaaagctccgatgccgggtaccatactcgacattcgtgtaaatcaaggggatacg
gtaaagaaaggccaagttctttttaattcttgaagcaatgaagatggaaaatgaaatagttgctccaaatgacggtacagttgcatca
attaatgtttcaaaggggtgcatctgtaaacgtcggagaggttcttgtctcattaaaatag
```

>C. thermocellum_(1.3S subunit amino acid sequence)

(SEQ ID NO: 23)

```
MKKFLIKVNGNQYEVEVEEIRDGASAPQVTLSTPSAAPAPSPAPAQETKTAAPKK
DSTVPAGATAIKAPMPGTILDIRVNQGDTVKKGQVLLILEAMKMENEIVAPNDG
TVASINVSKGASVNVGEVLVSLK
```

>Cthe_0701 (5S subunit nucleotide sequence)

(SEQ ID NO: 24)

```
atggctaaggtaaaaattaccgaaacggcgctgagggatgcccatcaatctctcattgcaacaagaatgagaatagaagagatg
cttcctatcatagataaactggacgagatcggttatcattctttggaggtatggggcggtgcaacctttgatgcctgcctgagattttt
gaatgaagacccgtgggaaaggcttagaattataaaaagccactgcaagaaaactcccctttaagaggccagaat
ctttggggttacaagcattatgccgatgacgttgtgagtacttttgtacaaaagagcgttgcaaacggtataaacataataagaatttt
cgacgccttgaatgacaccagaaatatagaaactgcaatcaaagcctgcaaaaagaaggcggtcatgctcagggaacggtat
gttatacaataagtcccgttcacaatcttgaacttttgtcaaagatgcaaagacttcttgtggaaatgggagctgactccatatgcgt
aaaggatatggcaggactttctgcttccatatgttgcatatgaaggcaattgaggcagggtgcgatgttgttggactgcgctatctc
accaatgtcaatgggaacatcccagcctccgacagaacccttgtggcaaccttaaaaggcacgccgtacgataccggacttga
cctggataaattaagtgaaatcgcagactacttcagacctctcaaagaaaagtatatttcagaaggacttcttgatgtaaaggttatg
ggagttgacgtaaacactctcaaatatccaggtacccggtggaatgctttcaagcattggtgtctcagttaaagcagtccaatgcggt
tgataaattcgaagaggttctgaaagaagtgccaagagtaagaagaagacttcggatatcctccgttggttacacactacaagcag
attgtaggtactcaggcagttttaaatgtggtaacgggtgaaagatacaaatggttccaaaagaatccaaggcactgatcaagg
gtgaatacggcagaacaccggctccggtcaaccctgaagttcagaagaagattttaaaagatgaagagccgattacagttagac
ctgctgatttgatagagcccgagcttgacaagatcagaaatgaaatgaaagaatacctgaacaagacgaggacgttttgtccta
tgcactgttccccgcaggtggcagaagaagttcttccaatacaggaaagctcaaaaatataagatagaaccggacatggtcgattac
gaaaacagggttcatccggtttaa
```

>C. thermocellum_(5S subunit amino acid sequence)

(SEQ ID NO: 25)

```
MAKVKITETALRDAHQSLIATRMRIEEMLPIIDKLDEIGYHSLEVWGGATFDACL
RFLNEDPWERLRIIKSHCKKTPLQMLLRGQNLLGYKHYADDVVEYFVQKSVAN
GINIIRIFDALNDTRNIETAIKACKKEGGHAQGTVCYTISPVHNLELFVKDAKTLV
EMGADSICVKDMAGLLLPYVAYDLIKALKENVKVPIQLHTHYTSGVASMTYLK
```

-continued

AIEAGCDVVDCAISPMSMGTSQPPTEPLVATLKGTPYDTGLDLDKLSEIADYFRP
LKEKYISEGLLDVKVMGVDVNTLKYQVPGGMLSNLVSQLKQSNAVDKFEEVLK
EVPRVREDFGYPPLVTPTSQIVGTQAVLNVVTGERYKMVPKESKALIKGEYGRTP
APVNPEVQKKILKDEEPITVRPADLIEPELDKIRNEMKEYLEQDEDVLSYALFPQV
AEKFFQYRKAQKYKIEPDMVDYENRVHPV

>C. thermocellum_(12S_C-term nucleotide sequence) (SEQ ID NO: 26)

```
atgaaagagcaaataaatgaagaaattattctggcaatatcagcggccattgctgctttggaaacaagacccggatacaagcttgt
agtaagatcatttaaaagaataccccaaacttctcctgtatggtccgctacaggaaaaatcgagagaatcagaagaagtatg
```

>C. thermocellum 12S_C-term amino acid sequence (SEQ ID NO: 27)

MKEQINEEIILAISAAIAALETRPGYKLVVRSFKRIPQTSPVWSATGKIERIRRSM

T. saccharolyticum Transcarboxylase
>or0945 (12S subunit nucleotide sequence) (SEQ ID NO: 28)

```
atgtcaatagatgataggattgaagaccttcttagaagaagagagatggttttagaaggcggtggtttagataaagtagagaaaca
acaccaaagggaaagcttaccgcaagagaggatatacaagcttttagatgaagatagctttgtggaaatagatgcgtatgtt
gagcacaggtgtattgactttggcatggaaaagcaaaggatacctggcgaaggcgtagtgacagggtatgggacgatagatgg
aaggcttgtctacgtttatgcacaggattttacggttttaggagcatcagccgtatcatgcaaagaaaatcacaaaaatcat
ggatatggctttaaagatgggagcaccgctcattggattaaatgattccggaggtgccagaatacaggaaggcgtcgatctttat
cgggatatggcaacatattttcagaaacacgctggcatcaggcgtaataccgcaaatatcggtgataatggggcccagcgctg
gaggtgcagtttattcgcctgctcttactgactttatattcatggtagacaagacaagtcagatgtttataactggaccgcaggtcata
aaagccgtcacaggtgaagatgtttcggcagaggagctggtggatcgattactcacagcacgaaaagcggtgtggcgcattt
agggctgaaaacgacgaagagtgtttgaagatgtgaggaagctattaagttaccttccatcaaacaatttggaagatccgccac
agttggcgacagatgacgacataaacagattttccgataggcttattgagataatcccagatagtcctaataagccatacgatatga
agaagtaatttcggaaatagtggatgaaggcgtgtattttgaatcacaggcaatgtatgcgcaaaacataataacggcatttgca
aggcttaatggaaggacggtagggataatagcaaatcagcctaaagttttggctggatgtctcgacatcaatgcgtctgataagg
catcgaggtttataaggttttgcgatgcatttaacatcccgcttctcaatatagtagatgtttccaggattttttgcctggaacgaatcaa
gagtacggtggaataatacgccatggggcaaagatgttgtacgcttactctgaggctacagtgccaaaagtgactccttcattgtga
ggaaagcttatggcggtgcttaccttgccatgtgcagcaaagacttaggagctgattttgtttggcatggcctactgctgaaatag
cggtcatgggacctgatggggcagcaaacatcgtgttaaaaatgaaataaaatcgtctgatgatcctgtggctgcaagaaatga
aaagataaatgagtacaggagaatttcgcaaatccatacagggcagcagcgagaggatgtagatgatgtagttctgccgca
agagacgagacctcgcctcatctcggcgttcgatatgcttatgagcaaaagggagtcaaggcccagcaaaaagcatggcaattt
tcctgttttaa
```

>T. saccharolyticum_(12S subunit amino acid sequence) (SEQ ID NO: 29)

MSIDDRIEDLLRRREMVLEGGGLDKVEKQHQKGKLTARERIYKLLDEDSFVEIDA
YVEHRCIDFGMEKQRIPGEGVVTGYGTIDGRLVYVYAQDFTVLGGSLGEYHAKK
ITKIMDMALKMGAPLIGLNDSGGARIQEGVDALSGYGNIFFRNTLASGVIPQISVI
MGPSAGGAVYSPALTDFIFMVDKTSQMFITGPQVIKAVTGEDVSAEELGGSITHS
TKSGVAHFRAENDEECLKMVRKLLSYLPSNNLEDPPQLATDDDINRFSDRLIEIIP
DSPNKPYDMKEVISEIVDEGVYFESQAMYAQNIITAFARLNGRTVGIIANQPKVL
AGCLDINASDKASRFIRFCDAFNIPLLNIVDVPGFLPGTNQEYGGIIRHGAKMLYA
YSEATVPKVTL1VRKAYGGAYLAMCSKDLGADFVLAWPTAEIAVMGPDGAANI
VFKNEIKSSDDPVAARNEKINEYRENFANPYRAAARGYVDDVVLPQETRPRLISA
FDMLMSKRESRPSKKHGNFPV

>or0947 (1.3S subunit nucleotide sequence) (SEQ ID NO: 30)

```
atgaaaaaatttatagtaactgtcaatggaaaaaaatacgatgtggaagtagaagaagtaaaagtcgacgtggcaagtgagaaa
aaagcaaaagaagatactgctgctaaaaatgcgtcagatgcaagtgtaaaaagcaaacaggttgaagtaaaaaacgaagtcaa
agacggtttctcaatcaatgcaccgatgccgggaactatattggatgtcaaaataagccaaggccagactgtcagacgaggcga
tgtgcttttaatactggaagccatgaagatggaaaatgaaatcacgtcaccttacgatggcacaataatatccataaatgtttcaaaa
ggtgcctctgtaaatacaggcgatgtgcttttgtacttaaaatga
```

>T. saccharolyticum_(1.3S subunit amino acid sequence) (SEQ ID NO: 31)

MKKFIVTVNGKKYDVEVEEVKVDVASEKKAKEDTAAKNASDASVKSKQVEVK
NEVKDGFSINAPMPGTILDVKISQGQTVRRGDVLLILEAMKMENEITSPYDGTIISI
NVSKGASVNTGDVLLYLK

>or1888 (5S subunit nucleotide sequence) (SEQ ID NO: 32)

```
atgtctaagataaaaataacggagactgttttaagagatgcacatcaatcgttgctggcaaccagaatgacaaccgatgaaatgct
tcctatagcagaaaattagatgaagttggtttttttctcgctggaagcatggggcggtgctacatttgatgcatgtatgagattttga
atgaagacccatgggaaagattaagacttttaaagaaggcgattaagaagacacctcttcaaatgcttttaagaggtcaaaatttac
tcggatataaacactatcccgatgatgtcgtaaatgaatttataataaaatctgttgaaaatggtatagatataataagaatttttgatg
cgttaaatgatgtgagaaatttagaagtgccaataaaatctgcaaaaagtgcgatgtgctgtacaggcagctattgtatatacag
ttagtcctgtacataatacagatcattatttgaaagtggcaaagtctcttcaagatgggtgcggattccatatgcattaaggatatg
tctgaatattatcaccctatgttgcatacgatttgattaaatctctgaaaagagcactttacacgccaattcaactgcatagccattat
acagcaggactggcttcaatgacttatttaaaagccatagaagctggtgtagacggggttgatacagctatttcttcgcttgccttag
gaacatcacaaccagctacagaatcaatcgtggctgcattagaagatacagaatatgatcagggctagatttaaaattgcttgct
gagatagctcagcattttaatgtagtcaaacagaatcacaaaaatgacagcgatatgtcttttgcttatgtctgttgatgtttaaagcatt
agaaagtcaaatccaggggaatgttatcaaattttggtttcacagctaaagcagcagaatgcattaaacaaatatcaagacgtct
tgaaagaagttccaagggtacgcgaagatttgggatatcctcctcttgttactccaatgagccagatggttggaacccaggctgttt
taaatgttattacagggagagatataaaatcgttcctaaagaaatttaaagattatgtcaaaggtttatatgggatgccaccagctcc
aatttcagattctatacgaaagaaaataatcggcgatgaagaagtaatttcaaagaggccagcagatttactaagtcctcaattgga
```

-continued tgaatttaaaaatgagataaaggaatttatagagcaagatgaagatgttttatcatatgcattatttcctcaagtagcaagaagattttt
cgagtataggcaagccaaaaaatacagaattgattcaacattattaaatatcgaagaaagggttcatccgatataa >T. saccharolyticum_(5S subunit amino acid sequence)

(SEQ ID NO: 33)

MSKIKITETVLRDAHQSLLATRMTTDEMLPIAEKLDEVGFFSLEAWGGATFDAC
MRFLNEDPWERLRLLKKAIKKTPLQMLLRGQNLLGYKHYPDDVVNEFIIKSVEN
GIDIIRIFDALNDVRNLEVPIKSAKSAGAHVQAAIVYTVSPVHNTDHYLKVAKSL
QDMGADSICIKDMSGILSPYVAYDLIKSLKRALYTPIQLHSHYTAGLASMTYLKA
IEAGVDGVDTAISSLALGTSQPATESIVAALKDTEYDTGLDLKLLAEIAQHFNVV
KQNHKNDSDMSLLMSVDVKALESQIPGGMLSNLVSQLKQQNALNKYQDVLKE
VPRVREDLGYPPLVTPMSQMVGTQAVLNVITGERYKIVPKEIKDYVKGLYGMPP
APISDSIRKKIIGDEEVISKRPADLLSPQLDEFKNEIKEFIEQDEDVLSYALFPQVAR
RFFEYRQAKKYRIDSTLLNIEERVHPI

>T. saccharolyticum_(12S_C-term nucleotide sequence)

(SEQ ID NO: 34)

atggaagagataaatgaagaaatagttgctgtcattgaagctgcgatttacgcggcatttggtcagtacgaaaagaatttccgcat
caaggtaataaagagagtggactcaaatatgccggaatggagaaaagctggcctttacaatcagatgagatag >T. saccharolyticum_(12S_C-term amino acid sequence)

(SEQ ID NO: 35)

MEEINEEIVAVIEAAIYAAFGQYEKNFRIKVIKRVDSNMPEWRKAGLYNQMR

*Caldicellulosiruptor bescii* DSM 6725 Transcarboxylase
>C. bescii_(12S subunit nucleotide sequence)

(SEQ ID NO: 36)

atgacaaacaagctcagagagctcaagcaaaagagagaaagaatactaaagcttggtggagaagataaaataaaaaacagc
atgatagcaaaaaacttacttgtagagagagaatagaatatttcacttgaccctggaagcttcaatgaaatagatatgtttgttgaaca
cagatgtcaagaatttgatatgaaagatacatttgtcccctgtgatggtgttgtaacgggttatggaacaatcaatggcagaaaagtt
tttgtttatgctcaagattttacttcgataggcggttctcttggcgatgcatgcaaaaaagatttgtaaagttttggacttagcattaa
aatatggttgtccagtgataggtataaatgattctgtggtgcaagaattcaagaaggtgttgatgcattagcaggatggtgaaa
tcttctatagaaataccatggcatcaggtgtaattccacaaattgcagctataatgggacttgtgcaggtggagctgtatactctcc
tgctattatggattttatttttatggtggacaaaaccagccaaatgtttgttacaggacctcaggttataaaagctgtgactggagagg
agatatccttttgaagagctggtggcgcttacactcacagctcaaagagttgctcatttattgcagaggatgagtatcacct
acttgatatgataaagtatttattgtcgtttatacctcaaataacatgaagacccaccttttataatgtcatctgattcagaaaaaga
tttgttcccgagctcgaaaatataattccgcaagagccaaacaaagcttatgatgtaaaagaaataatttataaagtagtagacaac
caagaattttttagaagtacaaccttattttgctcaaaatgctgttgtaggatttggtagaataggggcttagcgtaggaattgtagc
aaatcagcccaaagtgaacgctggagtgcttgattatgattcgtctgacaagatagcacgttttgtaagatttttgtgatgcttttaata
ttcccataataacatttacagacgtgcctggattttttgccaggtgttaaccaagacacaatggaataattcgtcatgggctaagg
ttttgtatgcatactcagaggcaacagttccaaagatataatgtaattttgagaaaagcatatggtggggcttacattgcaatgagca
gcaaacacattggtgcagactttgtgtttgcatggccaactgccgagatagctgttatgggaccagatgcgcagcaaatattata
tttagaaaagagatacaaagcgctcaaaatcccgaagaggaaagaaaaaaggatagaagagtatactcaaaagtttgcaaat
ccatacattgcagctgcccgtgggtatgttgacgatgtgattgagccacacgttacccgtaacaaaatcattgaggcgctcaaat
ttccattacaaaaagagagcaaaggcccccaaaaaagcatggcaatattccatta >C. bescii_(12S subunit amino acid sequence)

(SEQ ID NO: 37)

MTNKLRELKQKRERILKLGGEDKIKKQHDSKKLTCRERIEYLLDPGSFNEIDMFV
EHRCQEFDMKDTFVPCDGVVTGYGTINGRKVFVYAQDFTSIGGSLGEMHAKKIC
KVLDLALKYGCPVIGINDSGGARIQEGVDALAGYGEIFYRNTMASGVIPQIAAIM
GPCAGGAVYSPAIMDFIFMVDKTSQMFVTGPQVIKAVTGEEISFEELGGAYTHSS
KSGVAHFIAEDEYHLLDMIKYLLSFIPSNNMEDPPFIMSSDSEKRFVPELENIIPQE
PNKAYDVKEIIYKVVDNQEFLEVQPYFAQNAVVGFGRIGGFSVGIVANQPKVNA
GVLDYDSSDKIARFVRFCDAFNIPIITFTDVPGFLPGVNQEHNGIIRHGAKVLYAY
SEATVPKINVILRKAYGGAYIAMSSKHIGADFVFAWPTAEIAVMGPDGAANIIFR
KEIQSAQNPEEERKRRIEEYTQKFANPYIAAARGYVDDVIEPQLTRNKIIEALKISI
TKREQRPPKKHGNIPL

>C. bescii_(1.3S subunit nucleotide sequence)

(SEQ ID NO: 38)

atgagaaagttcaaggtgaagatcaatagccaagaatttgttgtagaagtggaagaaataggagttgaaaatgctacttctgtcgt
gccaaggcctaagattggccattttgagccaaaacaggaaaaacatgaggataaaacaaaacaaagccctgtactttcttctgat
aaaaattcggttgttgcccagctccgggtactattgtaaggctgctaaaaagtgaaggtgatgttgttgatgcaaatgaacctgtttt
aattcttgaagccatgaaaatggaaaataactgcacctgtcaaaggaaaaattaaaagaatacatgtaaaggaagggca
gaaggtagcaaaaggagatttgctatttgaaatagag >C. bescii_(1.3S subunit amino acid sequence)

(SEQ ID NO: 39)

MRKFKVKINSQEFVVEVEEIGVENATSVVPRPKIGHFEPKQEKHEDKTKQSPVLS
SDKNSVVAQLPGTIVRLLKSEGDVVDANEPVLILEAMKMENEITAPVKGKIKRIH
VKEGQKVAKGDLLFEIE

>C. bescii (5S subunit nucleotide sequence)

(SEQ ID NO: 40)

atgggggtaaaaataacagaaacaatactcagagatgctcatcagtcactcattgcaacccgcatgacaactgaacagatgcttg
agattgctcctgtgcttgaccaagttggttattattcggttgagtgctgggcggtgctacatttgatgcgtgtctgaggttttcaatg
aagacccatgggaaagattaaaaagactgagaactgcttttaaaaagacaaagctccagatgcttcttcgaggcaaaatcttgtt
gggtatagacattattctgatgatgttgttgaagagtttgtaaaaaaggccatatactatggcattgatattataagaatatttgatgca
cttaatgacatccggaatattgaaatggctctaaaaataacaaaaaaagaaaaggacatgcccaggttgccatatcatacactgt
ctcacccttatcatactattgaaaactatgtaaatttggcaaaacaaatagaagaactggggcagactcaatttgtataaaagacatg -continued

```
gctgggcttctctctccatttgatgcttataaacttgtaaaagcgttaaaagagcaggtaaaacttcctattcatcttcatacacactac
accacaggatttggatcaatgacatatttgaaagctgtcgaagcaggtgtggatggtattgacacggctttatctccgcttgcactg
ggcacatcccagcctccaaccgaaacaattgtatatgcacttgaaaatacagaatatgctccaaaacttgatttagaaaagatcaa
cgaggcaagcgaatattttaaagtactcagagaagaatatataagaaagggcttcttgacccgaaagtattaagtgttgatataa
acgctcttcattatcaaatacctggtggaatgctatcaaatcttatttctcagctaaaagaacaagggcaggaagacaagttagatg
aggttttaaaagaggtacctgaggttcgaaaagattttggatatccgccacttgtaactcctacgagtcaaattgtgggaacacaag
ctgttttgaatgttatagcaggtgagagatacaaacttgtcacaaaagaaacaaaagcatattttaaaggtgagtatggaaaacctc
cagctcctgtgaatgaagaggtaaaaagaaaaatcttgaaagacgaaaaagagataacctgcagacctgcagatttgattttgcc
agagcttgaaaatgcaaagaaaagattaaggagtatattgaaaatgatactgatgtggtaacttactgtttattccctcaacttgca
gaaaattttttcaaattaaggttcgcaaaaaaatacaaggttgacgctgatcttgttcagggtaacaaagtgtatcctgtg
```

>C. bescii_(5S subunit amino acid sequence)

(SEQ ID NO: 41)

```
MGVKITETILRDAHQSLIATRMTTEQMLEIAPVLDQVGYYSVECWGGATFDACL
RFFNEDPWERLKRLRTAFKKTKLQMLLRGQNLVGYRHYSDDVVEEFVKKAIYY
GIDIIRIFDALNDIRNIEMALKITKKEKGHAQVAISYTVSPYHTIENYVNLAKQIEE
LGADSICIKDMAGLLSPFDAYKLVKALKEQVKLPIHLHTHYTTGFGSMTYLKAV
EAGVDGIDTALSPLALGTSQPPTETIVYALENTEYAPKLDLEKTNEASEYFKVLRE
EYIRKGLLDPKVLSVDINALHYQIPGGMLSNLISQLKEQGQEDKLDEVLKEVPEV
RKDFGYPPLVTPTSQIVGTQAVLNVIAGERYKLVTKETKAYFKGEYGKPPAPVN
EEVKRKILKDEKEITCRPADLILPELENAKEKIKEYIENDTDVVTYCLFPQLAENFF
KLRFAKKYKVDADLVQGNKVYPV
```

>C. bescii_(12S_C-term nucleotide sequence)

(SEQ ID NO: 42)

```
atgtatgctcaggtcagtactatttcaaccattacaaaagaagaacttgcttgtatttgtgcatgtctgcacattgtgatgggtgaagg
tcaatataaaattaccaacataactaaacagcaaaacaagtgggtcaaaggtgcaagagaaatgatgctcaatcagtcacagatg
ttttatagatggagg
```

>C. bescii_(12S_C-term amino acid sequence)

(SEQ ID NO: 43)

```
MYAQVSTISTITKEELACICACLHIVMGEGQYKITNITKQQNKWVKGAREMMLN
QSQMFYRWR
```

*Clostridium cellulolyticum* H10 ATCC 35319 Transcarboxylase
>C. cellulolyticum_(12S subunit nucleotide sequence)

(SEQ ID NO: 44)

```
atgtcacaaattgaaaagatacaaatttaaaaaacatgaaaaaaactatagctaaaggcggcggagaagagaaaatagcaaaa
agacacgcagatggaaagctttctgccagagaaagaatccatttgttgtttgatgaaaacagttttgttgaggtagatgcattcatag
aatccagatgctttgactttggtatgcagaagaagaaacttccaggtgacggggttgttaccggttacggaacagttaatggcaga
aaggtctttgtttcatcacaggactttactgttataggcggttcattgggagagatgcacgcaaagaaaattacaaaggttatggata
tggctctgaaaatgggagcaccgttcatagccattaatgattccggcggagctcgtattgaggaaggtctggatgctcttcaggtt
acggagatattttttacaggaatactcttgcatcaggcgttattccgcagatatcagtaataatggggccatgtgcaggtggtgcgg
tatattccccggccataactgatttttatattcatggtggaaaaaacaagtcagatgtttattacaggcccacaggtaataaagtctgtt
acgggtgaagatgtatcagttgaaaatctgggaggtgcagatgttcatactgctacaagcggtgtagcacatttcaaatcttcaag
cgaagaagagtgtatagaagatataaagaggcttttaagttttattcccgataataatgtatcagatactatgtactacggagtgtctg
atgctgccgacagattagccgaaagcctcaacagcattattccagaagagtcaaacaagccatatgacatgtttgacgtaatagc
agaagtagtagatgatggagatttctttgaagttcagagttatttctctcagaatataatcggatttgcaagaatgaatggcaga
agtgttggtattgttgcaaaccagcctaagataatggcagggtcactagatatgaacgcggctgataaggcggcacgtttcgttcg
tttctgtgatgcatttaatattcctgtcgtttcattaaccgatgtacctgcattcctgccegggtagcccaggagcataacggcataa
tacgtcacggtgcaaaactcctatatgctttctctgaagcaacagtaccaaagataaatgttattcttagaaaggcatatggaggag
catatattgctatgaacagtaaaacaataggtgccgatatggtttggcatggccatcagctgaattcagttatgggacctgacg
gagcagcaaatattatatttaaaaaggatattgctgcgtcggaagatccagcagaaaccagaaaggaaaagattgccggaatata
gagataaattctcaaatcctttatgctagcagcatcaagagggtatattgatgatgttatcgagcctttctgaaaccagagtaaaaattat
aactgctctggaaatgctggatacaaagagggaaaacaggccttcaaaaaaacatggaaacattccgcta
```

>C. cellulolyticum_(12S subunit amino acid sequence)

(SEQ ID NO: 45)

```
MSQIEKIQNLKNMKKTIAKGGGEEKIAKRHADGKLSARERIHLLFDENSFVEVDA
FIESRCFDFGMQKKKLPGDGVVTGYGTVNGRKVFVSSQDFTVIGGSLGEMHAKK
ITKVMDMALKMGAPFIAINDSGGARIEEGLDALSYGDIFYRNTLASGVIPQISVI
MGPCAGGAVYSPAITDFIFMVEKTSQMFITGPQVIKSVTGEDVSVENLGGADVHT
ATSGVAHFKSSSEEECIEDIKRLLSFIPDNNVSDTMYYGVSDAADRLAESLNSIIPE
ESNKPYDMFDVIAEVVDDGDFFEVQSYFSQNIIIGFARMNGRSVGIVANQPKIMA
GSLDMNAADKAARFVRFCDAFNIPVVSLTDVPAFLPGVAQEHNGIIRHGAKLLY
AFSEATVPKINVILRKAYGGAYIAMNSKTIGADMVLAWPSAEIAVMGPDGAANII
FKKDIAASEDPAETRKEKIAEYRDKFSNPYVAASRGYIDDVIEPSETRVKIITALE
MLDTKRENRPSKKHGNIPL
```

>C. cellulolyticum_(1.3S subunit nucleotide sequence)

(SEQ ID NO: 46)

```
atgagtaaatatataataaaggtaaacgaactccttatgaagtagaggttgaagaagtgggcggggaaggcccatttcagct
gctccaaagctaagagctaccaagccgggacatacctctgctgcaaaagcagcacagccgcaggcaggtaaagcaggtgat
gttgctgctccaatgccgggaactgttttaaaggtaaaggttgctatcggtgatgaagtaaagaaggggcaggtactttaatactt
gaagctatgaaaatggagaatgaaatagttgctccggctgacggtaaagttacggcgttaaacgtcgaggccggaaagtctgtt
actgctggagaactaatggtgtctatagcc
```

-continued

>C. cellulolyticum_(1.3S subunit amino acid sequence)

(SEQ ID NO: 47)

MSKYIIKVNGTPYEVEVEEVGGGRPISAAPKLRATKPGHTSAAKAAQPQAGKAG
DVAAPMPGTVLKVKVAIGDEVKKGQVLLILEAMKMENEIVAPADGKVTALNVE
AGKSVTAGELMVSIA

>C. cellulolyticum_(5S subunit nucleotide sequence)

(SEQ ID NO: 48)

```
atgccaggcgtaagaattacggaaacagttttaagagatgctcaccagtcccttatagcaaccagaatgaagaccgaagaaatg
cttccaattgttgagaagcttgacaatattggttaccattcactggaagcttggggcggagctacttttgactcatgtatgagattttttg
aatgaagatccatggatgagacttagaaaaataaaagatgttgcaaagaaaacacctctgcaaatgcttcttaggggccagaacc
ttttaggatacaaacactatgccgatgatatagttgagtactttgttcagaaggctgttgcaaacggcatggacattatgagaatattc
gatgcactaaatgatgccaggaatatcgagacgcaattaaggcactgataaaaggaaaggcggccatgctcagggctgtatttgc
tatactataagtcctgttcacaatcttgagcttttttgtaaaagatgcaaagcagttggagagcatgggagcagattctatctgtataaa
agacatggccggacttctggtgccgtatcaggcttatgaactggtaaaggctttgaaagaaagtgtaaagataccgatacaattgc
acactcactatactagcggtgtagcatctatgacgtatttgaaggctatagaagcaggtatagatattgttgactgtgcaatttcacct
atgtcaatgggaacgtcacagccgcctacagagcctttggtggcaactttaaagggaactgattttcgatactggactggatttgga
aaaactcagtgaaattgcagactattcagacccccttaaagaaaaatatattgagagcggactattagacgttaaggtaatgggtgt
tgacgttaacactcttatttatcaggtacctggtggaatgctttcaaatcttgttcacaattgaagcagtcaaatgctttggataaatat
gaagaggttctcaaggaagttcccagagtaagagccgattcggctatcctccgcttgtaacaccatcaagtcagatagttggtac
ccaagcggtacttaatgtattgactggtgagagatacaagatgtaccaaaggaatcaaaaggcgttgtaaagggggaatacgg
taaaaccctgcacctattagtgatgaaataaaagctaagattctgggcgatgaaaagcctataacatgcagacctgctgaccta
ttgaacctgagcttgaaaagattagagaagctgttaaggattatatagagcaggatgaagatgtactttcatacgcaatgcttcctc
aggttgccgagaagttctttaaacagcgtattgaggatagaaataaggctactgcacccgcatcagacgaaataaaacccgaag
ttgtagcggcaatatcagccgtagtaaacgaaatgggcgaaagacggcacacagtacagaatcggaaatatctctaagttga
accagaatcagaacagatggagtctgtatggtatgcttgatagattcagaacaaaaatt
```

>C. cellulolyticum_(5S subunit amino acid sequence)

(SEQ ID NO: 49)

MPGVRITETVLRDAHQSLIATRMKTEEMLPIVEKLDNIGYHSLEAWGGATFDSC
MRFLNEDPWMRLRKIKDVAKKTPLQMLLRGQNLLGYKHYADDIVEYFVQKAV
ANGMDIMRIFDALNDARNIETAIKACKKEGGHAQGCICYTISPVHNLELFVKDAK
QLESMGADSICIKDMAGLLVPYQAYELVKALKESVKIPIQLHTHYTSGVASMTYL
KAIEAGIDIVDCAISPMSMGTSQPPTEPLVATLKGTDFDTGLDLEKLSEIADYFRPL
KEKYIESGLLDVKVMGVDVNTLIYQVPGGMLSNLVSQLKQSNALDKYEEVLKE
VPRVRADFGYPPLVTPSSQIVGTQAVLNVLTGERYKMVPKESKGVVKGEYGKTP
APISDEIKAKILGDEKPITCRPADLIEPELEKIREAVKDYIEQDEDVLSYAMLPQVA
EKFFKQRIEDRNKATAPASDEIKPEVVAAISAVVNEMGERDGTQYRIGNISKLNQ
NQNRWSLYGMLDRFRTKI

*Corynebacterium kroppenstedtii* DSM 44385Transcarboxylase
>C. kroppenstedtii_(12S subunit nucleotide sequence)

(SEQ ID NO: 50)

```
atgagtgagcaacctcacgatcccagcatgcctgagcgcctcggacagctggaagaagaaag

-continued catcatcactggtggcaacagcaacgggccaacacccaccgccgccacctcatctgtccagggtgtcagcgccaattcgg
tcacggcacccctggctggttccgtcagcaaggtgcttgtggaggaaggccaagccatcacggccggcgaagtgatcgttgtc
cttgaagccatgaagatggaaaccgaaattacggcccccaacgacggcaccgtcaccgcgcttcacgtgcaacccggcgacg
ccgttcagggtggacagtctctgctggagatcggggac >C. kroppenstedtii_(1.3S subunit amino acid sequence)

(SEQ ID NO: 53)

MKLTVTVNGVPYSVDVEVEHEERPTLGTIITGGNSNGPTPTAPTTSSVQGVSANS
VTAPLAGSVSKVLVEEGQAITAGEVIVVLEAMKMETEITAPNDGTVTALHVQPG
DAVQGGQSLLEIGD

>C. kroppenstedtii_(5S subunit nucleotide sequence)

(SEQ ID NO: 54)

atgaccacgcgaaaaattggagtgaccgaactggctctgcgtgatgctcaccagagcctcatggcaacacgcatggccctcga
agacatggtcgatgcctgtgaggatatagacaaagccgggtactggagcgtggaatgctggggcggggcaaccttcgacgcc
tgcattcgcttcctgaacgaagacccgtgggagagactgcgcacattccgcaagctcatgcccaactcacgccttcagatgctg
cttcgtggccagaatcttctgggataccgtcactacgaggacggcgtcgtcgataagtttgttgaaaaatccgctgaaaacggcat
ggacgtcttcagggttttcgacgcgctcaacgacccccgcaacctcgagcacgccatgcaagctgtgaaaaaagtgggcaagc
acgcgcagggcaccatctgctacaccgtgtccccgctacacgacgtgcagggctacattgatctagcagggcgtttgctggaca
tgggcgcggattcgatcgcgctcaaagacatggcagcgctgctcaaaccacagcccgcctacgacattatccgtggcattaag
gacacctacggcgaggatacgcagatcaacgtccactgccactccaccaccggcgtcacgatggtcaccctcatgaaggccat
tgaagccggtgcggatgtcgtcgacaccgccatttcctccatgtccctcggcccagggcataacccccaccgagtctctcgtcga
aatgctcgaaggaaccgactacgagaccgggcttgacatggatcggctcattaacatccgcgaccacttcaagacagtgcgcc
cgaagtacgcggagtttgagtcgaaaacactggtcaacaccaatattttccaatcgcagattccgggcggaatgctctccaacat
ggaatcgcagctcaaagcccagggcgcgggcgaccgtatcgacgaggtcatgaaagaagtccccgtcgttcggaaagctgc
cggatacccgccgttggtgacgccatcgtcccagatcgtcggcacccaggccgtgttcaacgtgctgatgggccgctacaaag
tactcacggctgaattcgccgacctcctcctcgggtactacggcgaagcaccaggtgagagggataaagacctcatcgagcaa
gccaagaagcagaccggcaaagagcccatcaccgagcgtcctgctgacctccttgagcccgaatgggacaacctggttgagg
aagctgacgaactcgacggcaccgacgggtccgacgaagacgtcctcacaaacgccctgttcccgcaggtcgcgcccgggatt
cttcaagactcgccccgacggcccgaagaacgtcggcaagactaaggaacagctcgagcgcgaagaggcgaaggcctccg
gcgacgccactgccatccgcgaaccgattatgtacaaagtcaccacaggcggccgcagccacactgtctccgtggaacccgca >C. kroppenstedtii_(5S subunit amino acid sequence)

(SEQ ID NO: 55)

MTTRKIGVTELALRDAHQSLMATRMALEDMVDACEDIDKAGYWSVECWGGAT
FDACIRFLNEDPWERLRTFRKLMPNSRLQMLLRGQNLLGYRHYEDGVVDKFVE
KSAENGMDVFRVFDALNDPRNLEHAMQAVKKVGKHAQGTICYTVSPLHDVQG
YIDLAGRLLDMGADSIALKDMAALLKPQPAYDIIRGIKDTYGEDTQINVHCHSTT
GVTMVTLMKAIEAGADVVDTAISSMSLGPGHNPTESLVEMLEGTDYETGLDMD
RLINIRDHFKTVRPKYAEFESKTLVNTNIFQSQIPGGMLSNMESQLKAQGAGDRI
DEVMKEVPVVRKAAGYPPLVTPSSQIVGTQAVFNVLMGRYKVLTAEFADLLLG
YYGEAPGERDKDLIEQAKKQTGKEPITERPADLLEPEWDNLVEEADELDGTDGS
DEDVLTNALFPQVAPGFFKTRPDGPKNVGKTKEQLEREEAKASGDATAIREPIM
YKVTTGGRSHTVSVEPA

>C. kroppenstedtii_(12S_C-term subunit nucleotide sequence)

(SEQ ID NO: 56)

atgaatacagacaatgcatcctctgctgaactcagtcagttgttggcccgcctgtccaaccaggtagaaaagctctcccgcaacg
tcaccaagctcgaaaatgaagttgcggcactgaagcagcgctctgacgaggaaattcctgaagatgtcttgattgcgatcagtgc
ggccgtatccgcctacatgggtaaccgcggaaccgtgcgcgcagttcacttcttgcgccatcgcagctggtcacagcaaggtc
ggcaggcagttcagcacaaggcgaaatggcaa >C. kroppenstedtii_(12S_C-term subunit amino acid sequence)

(SEQ ID NO: 57)

MNTDNASSAELSQLLARLSNQVEKLSRNVTKLENEVAALKQRSDEEIPEDVLIAI
SAAVSAYMGNRGTVRAVHFLRHRSWSQQGRQAVQHKAKWQ

*Geobacter bemidjiensis* BEM(T) Transcarboxylase
>G. bemidjiensis_(12S subunit nucleotide sequence)

(SEQ ID NO: 58)

atgtccatagaagagaagataaaagcgctgaacgacaagaagagcaagctgaagctgggcggcgggcgctcgaagatcgac
cagcagcacgcccagggaagcctgaccgcccgggagcggatagaggcgctggtggacaaggacagcttccaggaaatcg
gcatcttcgccaggcaccgctgcaccaatttcggcatggccgggaaggaactgccggccgaaggggtggtcaccggcgcag
ggagcgtgggcgggaggatggtgcacctggcgagccaggatttcaccgtcgccgggggatcggcgggcgaggtgcacagc
gacaagatcgtgcaggcgatgctggggtcgctgaagaccggaaccccccttcgtcttcatgaacgattccggcggcgccaggat
ccaggaagggatcgactcgttagccggctacggcaaggtcttctaccacaacgtgatgctcagcggggtggtgccgcagatct
cgctcatctgcggcccctgtgccgggggcgcggcctacagcccggcgctcaccgatttcatcatccagaccgccaaggcgcg
catgttcatcaccggcccttccgtgatcaaggaggcgaccggcgaagagatcagcgccgaggagctgggagggccactgtc
gcagatgaaccatagcggcgtagcccatttcgtggcggagaacgacctggtggcgcttcgcatctgcaagaagctcctttccta
cctcccctccaacaacatcgaggacccgccgcagttggaaagcgacgacgtcatcgtcccggacaagacgttgaacagcatc
gtgccgtcggagcagaagaaggcctacgacgtgaggaacgtgatcacgcgcctgatcgacggcggcgacttcctggaggtg
cagcctctgttcgctgccaacatcgtggtcgggttcggcaggatactcgggcggagcgtcggcatcgtcgccaatcagccgtc
ggtcttggcgggggcgctggacatcaacgcttcggacaagggagccaggttcgtccggttctgcaacgccttcaacatcccgct
ggtgaccctggtggacgttccgggttttctccccggggtacagcaggagaagggggggatcatccgccacggcgccaagatg
ctcttcgcctacgccgcggccaccgtcccgaagataaccgtcatcatgcgcaaggcgtacggcggcgccttcctcgccatgtg
cggcaaggagttggagaccgatcgggttttcgcctggcccagcgccgagatcgcggtcatgggaccgcagggagcggtcaa
cgtcatcttccggaacgagatcgcccaggcggaagatcccaagaaaaagcgcgacgagctgatcgcttcttaccagggaacct
tcgccactccctatgcggccgcggcacgccgcgatgtggacgacatcatcgagcccgccgatacgaggcgccacctcgccat
gacgctggacatcctgagcaccaagcgcgaattcaggcccatgaagaagcatggcctcattccgctg -continued

>G. bemidjiensis_(12S subunit amino acid sequence)

(SEQ ID NO: 59)

MSIEEKIKALNDKKSKLKLGGGRSKIDQQHAQGSLTARERIEALVDKDSFQEIGIF
ARHRCTNFGMAGKELPAEGVVTGAGSVGGRMVHLASQDFTVAGGSAGEVHSD
KIVQAMLGSLKTGTPFVFMNDSGGARIQEGIDSLAGYGKVFYHNVMLSGVVPQI
SLICGPCAGGAAYSPALTDFIIQTAKARMFITGPSVIKEATGEEISAEELGGPLSQM
NHSGVAHFVAENDLVALRICKKLLSYLPSNNIEDPPQLESDDVIVPDKTLNSIVPS
EQKKAYDVRNVITRLIDGGDFLEVQPLFAANIVVGFGRILGRSVGIVANQPSVLA
GALDINASDKGARFVRFCNAFNIPLVTLVDVPGFLPGVQQEKGGIIRHGAKMLFA
YAAATVPKITVIMRKAYGGAFLAMCGKELETDRVFAWPSAEIAVMGPQGAVNV
IFRNEIAQAEDPKKKRDELIASYQGTFATPYAAAARRDVDDIIEPADTRRHLAMT
LDILSTKREFRPMKKHGLIPL

>G. bemidjiensis_(1.3S subunit nucleotide sequence)

(SEQ ID NO: 60)

gtgcaactgaccatgaccattgacggaaagaaataccgggtggacgtagaagtcgaggaaggggaagaggtgcgtacggaa
ggggccttccctcccaccgcgactatgcaggcgtacccggtgtattcggcgcatccaaccgcgaccccgccgctggccgcgc
cgaccccggcctccagttcggaaaagatctgccgcagtcccatcgcggggtggttttcaagatcgtggcgcaggtgggtcaa
cacctggagatgaacgacctgctggtcgtcctcgaggcgatgaagatggagaccaacatcaccgcgcacatgtccgggaagg
tggaaaagattctggtttccgtgggcgaagcggtgcagcctggacaggcaattgccgaatttgcc >G. bemidjiensis_(1.3S subunit amin acid sequence)

(SEQ ID NO: 61)

VQLTMTIDGKKYRVDVEVEEGEEVRTEGAFPPTATMQAYPVYSAHPTATPPLAA
PTPASSSEKICRSPIAGVVFKIVAQVGQHLEMNDLLVVLEAMKMETNITAHMSG
KVEKILVSVGEAVQPGQAIAEFA

>G. bemidjiensis_(5S subunit nucleotide sequence)

(SEQ ID NO: 62)

atggaccgcattatcgacataaccgaactggctctgcgcgacgcgcaccagagcctatcgctacgaggctcgggatagacga
catggttccggtgtgcgaggacctggaccaggcgggctactggtccatcgagtgctgggcggggccacctatgacgcctgc
atccgctttctcaacgaagatccgtgggtgaggcttaggaccttcaaggagctgatgccgaaaacccgctgcagatgcttttgc
gggggcagaaccttttgggataccggcattaccaggacgaggtggtggaccggttcgtccagaagagcgccgagaacggcat
cgacgtgttccggatcttcgatgcgctgaacgatctgaggaacctggagcggctcgtccaggcggtgaagcagtgcggaaag
cacgcgcaggtcgccatctcctataccatcagccccattcacaccacggcgaaattcgtggagcaggcgaagcgcctggtcga
catggggtgcgactccatctgcatcaaggacatggcggcgctgatcaagccgcacgcgacatacgacctggtgagagggatc
aaagaggcctgcggcgaccggatccggatacagctgcatgcgcacgccaccagcggcgtgaccatggtgagttacatgaag
gcggtggaggcgggcgtggacggcgtggacaccgcggtttccatgagcctcgggccggacacaaccccgacggaga
gctttgcggagatgctggaaaatacgggctacaccacgcgcatcgacctcggccgggtgaacaaggtgaaggagcatttcgc
caaggtgctccccaggtactcagaattcctctccaccatcaccggcgcggagacggagatcttcaggagccagattccaggcg
ggatgctttccaacatggagagccagttgaagcagcaggggctggggaccggatgcgcgacgtgctggaagagataccgc
tggtgagaaaggacacgggataacgtcccgctggtaacccgaccagccgacatcgtcgggacccaggcggtgctgaacgtatt
gatgggcgctacaaggtgctgaccggcgagttcgccgacctgatgctcggctactacggcctcacgccgggagaacggaa
cccggaggtggtggagcaggcgcgccgccacgcgaataaggagccgatagagtgccgccccgcagatctattggagccgg
aatggggcaagctgcgggcggcggcgctcccccttggagggttgcgacggcagcgacgaggacgtgctcacctacgccctctt
tccgcaggtggccgccgaagttcttcgccacgaggagtgaaggaccccgaaacctggggcgcgatcccgtcaccggagcttcg
gaaaccagcattcccgaagggcacccccggaagatcaccggcccgtcacctacacggtcacccttgagcgggcagccgcac
aaggtgacggttgcaccctacgccaggaat >G. bemidjiensis_(5S subunit amino acid sequence)

(SEQ ID NO: 63)

MDRIIDITELALRDAHQSLIATRLGIDDMVPVCEDLDQAGYWSIECWGGATYDA
CIRFLNEDPWVRLRTFKELMPKTPLQMLLRGQNLLGYRHYQDEVVDRFVQKSA
ENGIDVFRIFDALNDLRNLERSVQAVKQCGKHAQVAISYTISPIHTTAKFVEQAK
RLVDMGCDSICIKDMAALIKPHATYDLVRGIKEACGDRIRIQLHAHATSGVTMVS
YMKAVEAGVDGVDTAVSSMSLGPGHNPTESFAEMLENTGYTTRIDLGRVNKVK
EHFAKVLPRYSEFLSTITGAETEIFRSQIPGGMLSNMESQLKQQGAGDRMRDVLE
EIPLVRKDTGYVPLVTPTSQIVGTQAVLNVLMGRYKVLTGEFADLMLGYYGLTP
GERNPEVVEQARRHANKEPIECRPADLLEPEWGKLRAAALPLEGCDGSDEDVLT
YALFPQVAPKFFATRSEGPRNLGKDPVTGASETSIPEGHPGKITGPVTYTVTLSGQ
PHKVTVAPYGQE

>G. bemidjiensis_(12S_C-term subunit nucleotide sequence)

(SEQ ID NO: 64)

gtggacgaagagatggagcaggaacacgatccggaaatcacgcccgaactgctgatggtgatgtccgccgcgatagccgcgt
atctgggcaagaccgtgaggataaggcgggccaggttcgtcgacccgaatctgatcaacgcctggggacagtcgagccgcgt
ggtgctgcaggcgtcgcacaacttgaggaga >G. bemidjiensis_(12S_C-term subunit amino acid sequence)

(SEQ ID NO: 65)

VDEEMEQEHDPEITPELLMVMSAAIAAYLGKTVRIRRARFVDPNLINAWGQSSR
VVLQASHNLRR

Desulfobulbus propionicus DSM 2032 Transcarboxylase
>D. propionicus DSM 2032_(12S subunit nucleotide sequence)

(SEQ ID NO: 66)

atgagcacaaaggaaaaattagagcagctaaagcaaaaaggggcaaagccttgctgggcggcggtcaggataaaatcgac
aagatccactcccagggcaaatataccgcccgtgagcgtattcaactcctcctcgacccaggcaccttcgaggaatacgatgctt
tcaagctccatcgctgctacaacttcggcatggaaaaaatcaagttttcggcgacggtatcgtcaccggatatggcaagctggc
cggccggccggtttatatttacgcgcaggacttttcggtcctcgccggttctcttccggaaccttggctgaaaaaatatgcaaaat -continued

```
catggatctgggcatgaaaaacggcattccggtcatcggattgaacgactccggtggcgcccgtatccaggaaggtatcgagg
ccctggcaggatataccgaaatcttcacccgtaatgttctcgcttcgggtgttgttcccagatttccggtgttttcggaccctgcgc
cggtggcgccgtttactctcctgccctgaccgacttcatcatccaggtcaagatccagtcctacatgttcctgacaggtcccaagg
tcgttaagactgtgttaaacgaggacgtcaccaccgagcagttgggtggtgcggccatgcataccaccaagtccggcgtcacc
gactatgctgccgagaacgaggacgacgccattcagtacatcaaggatctgatgagctatttgccgcagaacaatctggagaat
cctccggatgcccccctgcgacgatccgatcacccgccgctccgaactgctcaacgacatcattccggacaacccgaatgccgc
ctacgacatgaaaaaggtcatcaccgagacggcagacaacggtatcttctttgaaatcaagaagaatttcgctccgaacatcgtc
atcggttttgcccgttatggtggcaaggctattggcatcgttgccaaccagccgtcctactacgccggtgttctcgacatcgattcct
cgatcaaggtgcccgcttcatccgcttctgcgactgcttcaacattccgatccttaccttcgtcgacgtccctggcttcctgcccg
gcactgcacaggaattcggcggcgttatccgcaacggcgccaagatgctgtatgcctacgccgaatcgacagtgccaaaggta
acgattattacccgtaaatcctatggcggcgcctactcgctcatgtcgtccaagcacctgcgaaccgatatcaactactcctggcc
gaccggtgaaatcgccgttatgggctccaaggcgcggtcgaagtcctgcacgcaagggcgctaaagcagcagaagatcc
cagagcgttcctggccgaaaaagaaaacgagtacaacgagcagttctccaatccatattgtcgggccgagcgtggctatatcga
cgatgtcattgaaccggccgaaaccaggtaccgtatcatcaacgcgtttgagtcgatctctggaaagcgtgacacgatcccgatg
aagaaacacggcaatatcccgctg
```

>D. propionicus DSM 2032_(12S subunit amino acid sequence)

(SEQ ID NO: 67)

```
MSTKEKLEQLKQKRAKALLGGGQDKIDKIHSQGKYTARERIQLLLDPGTFEEYD
APFKLHRCYNFGMEKIKFFGDGIVTGYGKLAGRPVYIYAQDFSVLAGSLSGTLAE
KICKIMDLGMKNGIPVIGLNDSGGARIQEGIEALAGYTEIFTRNVLASGVVPQISG
VFGPCAGGAVYSPALTDFIIQVKIQSYMFLTGPKVVKTVLNEDVTTEQLGGAAM
HTTKSGVTDYAAENEDDAIQYIKDLMSYLPQNNLENPPDAPCDDPITRRSELLND
IIPDNPNAAYDMKKVITETADNGIFFEIKKNFAPNIVIGFARYGGKAIGIVANQPSY
YAGVLDIDSSIKGARFIRFCDCFNIPILTFVDVPGFLPGTAQEFGGVIRNGAKMLY
AYAESTVPKVTIITRKSYGGAYCAMSSKHLRTDINYSWPTGEIAVMGSKGAVEV
LHAKGAKAAEDPRAFLAEKENEYNEQFSNPYCAAERGYIDDVIEPAETRYRIINA
FESISGKRDTIPMKKHGNIPL
```

>D. propionicus DSM 2032_(12S_c-terminal nucleotide sequence)

(SEQ ID NO: 68)

```
atggcaaaaatgaacaaaaaaatggctgcggcccttgcagccgttaatgcctacctgatgcaggaagaggaggcggcatacca
ggcccagttgctggctgccaaatctgttgcaccagccggggccaagcttatgggcaattgccggccgtcaggatatcatgaatttc
cgcaggctgattcaaatgaaagccttc
```

>D. propionicus DSM 2032_(12S_c-terminal amino acid sequence)

(SEQ ID NO: 69)

```
MAKMNKKMAAALAAVNAYLMQEEEAAYQAQLLAAKSVAPAGPSLWAIAGRQ
DIMNFRRLIQMKAF
```

>D. propionicus DSM 2032_(5S_1.3S_fusion nucleotide sequence)

(SEQ ID NO: 70)

```
atgagcgaccaagtgaaaatgaccgccatgaattatgcaactgaccggcctgctgcagaaaatccggtcaaagttatggacttg
agccttcgtgacggccaccagtctctgttcgccaccgcgggcgcaccgaggacatgattccgatcgcggaaatgatggacga
gatcggcttctgggcagttgagacctggggtggcgccacctttgacaccatgcaccgcttcctcaacgaggaccgtgggagc
gtctccgcaccctgaaacgttacatcaagaagacccccttctccatgttgctgcgcgcgcagaacctggttggataccgtaactat
gccgatgacttggccaccgcctttgttgagcgcgctgccgagaacggtatggatatcttccggaccttgacgccctcaacgatta
ccgtaacttcgagacgtgttaaacagatcaagaagagcggcaagcacttccagggttgtatttgctattcgctgaccgaaccg
cgtctgggcggggatgtttatgacctgaagtactatgtcgaccgcgccaaagcgcttgacgacatgggcgctgactccatctgc
atcaaggacatggccggtctgatcgcccatacgacgcctacgccatcgtcaaggctatcaaggaagtcaccaagacccgat
ccacctgcacagccacttccacctctggtatggcgtccatgagtcatctgaaggccattgaggctggcgtagatatcgttgacacct
gcatgaccccgtacgctttccgtaccgccatccggccatcgagccgttggtcatggccctgctcggcaccaaccgcgacacc
ggttcgacatcaagaaactggccgccatcaacgaggtgctagagaaagaggttatgccgaaatacaagcaccctcatggatga
ctccaagtgctcaatcatcgatatcaacgttcttctccatcagacccgggcggcatgctctccaacctggtcaaccagttgcgtg
agatggatgctctggacaagatcgatcaggtctacaaagagctgccgaaagttcggaaagacctcggccagattccgctggta
ccccgaccagccagatcgttggcatccagaccgtgaacaacgtgctgtttgacactcctgatgagcgctacaagatgatcaccg
cccaggtcaaagacctgtgctacggtctctatggtaaaaccgctgtgccgatcaaccctgaactgcagaagaaggctctgaaag
gctatccgcgcggtgaagagcgcgatcacctgccgtccggcagaggtgcttgaacccaaggtgcttgcacctgccgcgctcggctc
tggcgatctcgccaaggatatcgatgacttggtactctacgccatctacccggtcaccgggaagaagttccttgagtggaagtat
ggcattaccccggcaccgcccgaagtcaagccgctcacccttgaggatgtcaagaagcgtgatgaactggtggccaaggcca
aggctggcaagctcatcgagcccaagccgctgctccggagaagaccgctaacgttcggaccttcaacgtcttcgtcgacggt
gagtatttcaacgttgaggtcgacccgaccggtgacttccagccgatggtcgccgctgctccgcggcctgccgcacctgccgct
gcaccgaaagctgctgcacctgccgctgctgcacctgctgccgccgccgaaggctgctgcacctgccgccgccgctccggctc
cagccgctgttgagggaggaaccccgctgttggccccccatgccggcctgcaagaatctggtcaatgttggtgatgcgg
tcaaagctggcgaccccatcctcgttcttgaggccatgaagatggagaacaatctcggttctccgtgcgatggtactgtgaaggc
gcttaattttggcagcggtgactcggttgccaaggataccgtcctggcaatcatcggga
```

>D. propionicus DSM 2032_(5S_1.3S_fusion amino acid sequence)

(SEQ ID NO: 71)

```
MSDQVKMTAMNYATDRPAAENPVKVMDLSLRDGHQSLFATRGRTEDMIPIAE
MMDEIGFWAVETWGGATFDTMHRFLNEDPWERLRTLKRYIKKTPFSMLLRAQN
LVGYRNYADDLATAFVERAAENGMDIFRTFDALNDYRNFETVVKQIKKSGKHF
QGCICYSLTEPRLGGDVYDLKYYVDRAKALDDMGADSICIKDMAGLIAPYDAY
AIVKAIKEVTKTPIHLHSHFTSGMASMSHLKAIEAGVDIVDTCMTPYAFRTAHPAI
EPLVMALLGTNRDTGFDIKKLAAINEVLEKEVMPKYKHLMDDSKCSIIDINVLLH
QTPGGMLSNLVNQLREMDALDKIDQVYKELPKVRKDLGQIPLVTPTSQIVGIQTV
NNVLFDTPDERYKMITAQVKDLCYGLYGKTAVPINPELQKKALKGYPRGEEPIT
CRPAEVLEPELEKAKKEIGDLAKDIDDLVLYAIYPVTGKKFLEWKYGITPAPPEV
KPLTLEDVKKRDELVAKAKAGKLIEPKPAAPEKTANVRTFNVFVDGEYFNVEVD
```

-continued

```
PTGDFQPMVAAAPRPAAPAAAAPKAAAPAAAAPAAAPKAAAPAAAAPAPAAVE
GGTPLLAPMPGMIVKNLVNVGDAVKAGDPILVLEAMKMENNLGSPCDGTVKAL
NFGSGDSVAKDTVLAIIG
```

Engineered Pathways to Produce Hydrocarbons and Other Malonyl-CoA Derived Products Production of a bio-product at high yield requires a balanced chemical equation describing the conversion of substrate to product and a thermodynamically feasible reaction with a negative change in Gibbs free energy. Long chain hydrocarbons, e.g., those that have carbon backbones of at least four carbons and up, derived from fatty acids satisfy both of these requirements. For example, production of a $C_{16}$ fatty alcohol can be described by the following equation:

$$4C_6H_{12}O_6 \rightarrow C_{16}H_{34}O + 8CO_2 + 7H_2O$$

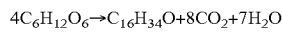

Production of a $C_{16}$ fatty alcohol results in a Gibbs free energy change of −285 kJ/mol glucose. For comparison, production of ethanol results in a Gibbs free energy change of −208 kJ/mol glucose.

The present invention describes the engineering of a recombinant microorganism to convert a native fatty acid biosynthetic pathway into a fermentative pathway, i.e., one that generates net positive ATP and is redox neutral. As shown below, a native fatty acid pathway generates zero net ATP, which stems from the mechanism of producing malonyl-CoA, the acyl-ACP chain precursor used to increase chain length. Malonyl-CoA is formed from the conversion of one glucose into two acetyl-CoA, which produces two ATP and four NAD(P)H. However, ATP is required to produce malonyl-CoA from acetyl-CoA, which results in a net zero ATP balance. In the synthetic route shown below, malonyl-CoA formation is accomplished without the concomitant use of ATP.

Native Pathway: Glucose+CoA→2Malonyl-CoA+ 2NADH+2NAD(P)H

Synthetic Pathway: Glucose+CoA→2Malonyl-CoA+ 2ATP+2NADH+2NAD(P)H

In either case, the NAD(P)H produced during malonyl-CoA synthesis is balanced via reduction of the growing acyl-ACP chain.

Figure 3:
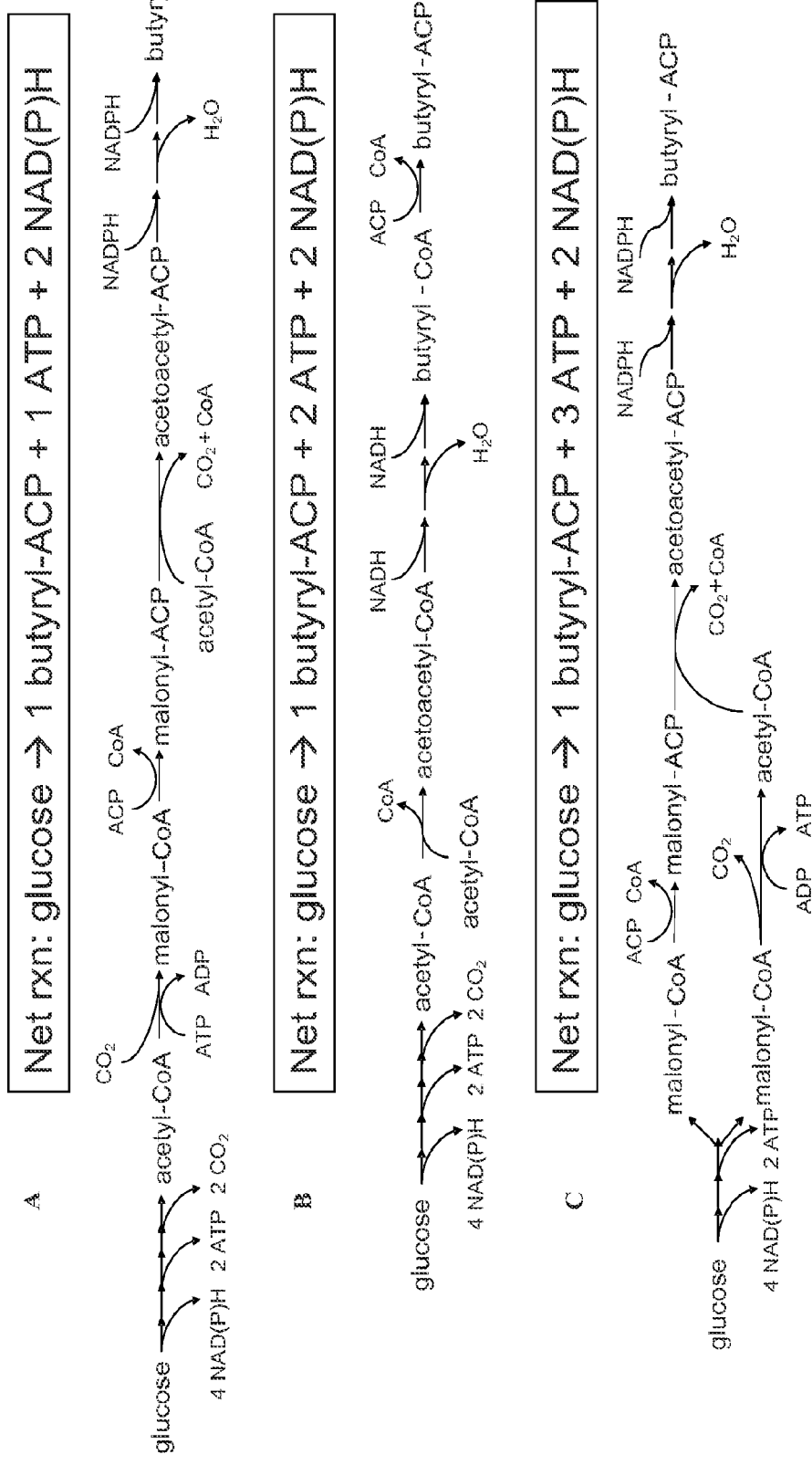
FIG. 3A depicts the net reaction and a native pathway for the conversion of glucose to butyryl-ACP.
FIG. 3B depicts the net reaction and a Clostridial pathway for the conversion of glucose to butyryl-ACP.
FIG. 3C depicts the net reaction and a pathway for the conversion of glucose to butyryl-ACP using a transcarboxylase catalyst.

The synthetic pathways described herein proceed according to three steps: chain initiation, chain extension, and chain termination (see FIG. 2) and can be carried out in aerobic or anaerobic conditions. In some embodiments, the synthetic pathways produce a hydrocarbon and/or a hydrocarbon derivative under anaerobic conditions. In some embodiments, the synthetic pathways produce a polyketide or an organic acid under aerobic or anaerobic conditions. Chain initiation can proceed by one of several options that are ATP positive and in which NAD(P)H is balanced by chain termination and $H_2$ generation (see FIG. 3A-3C).

Figure 4:
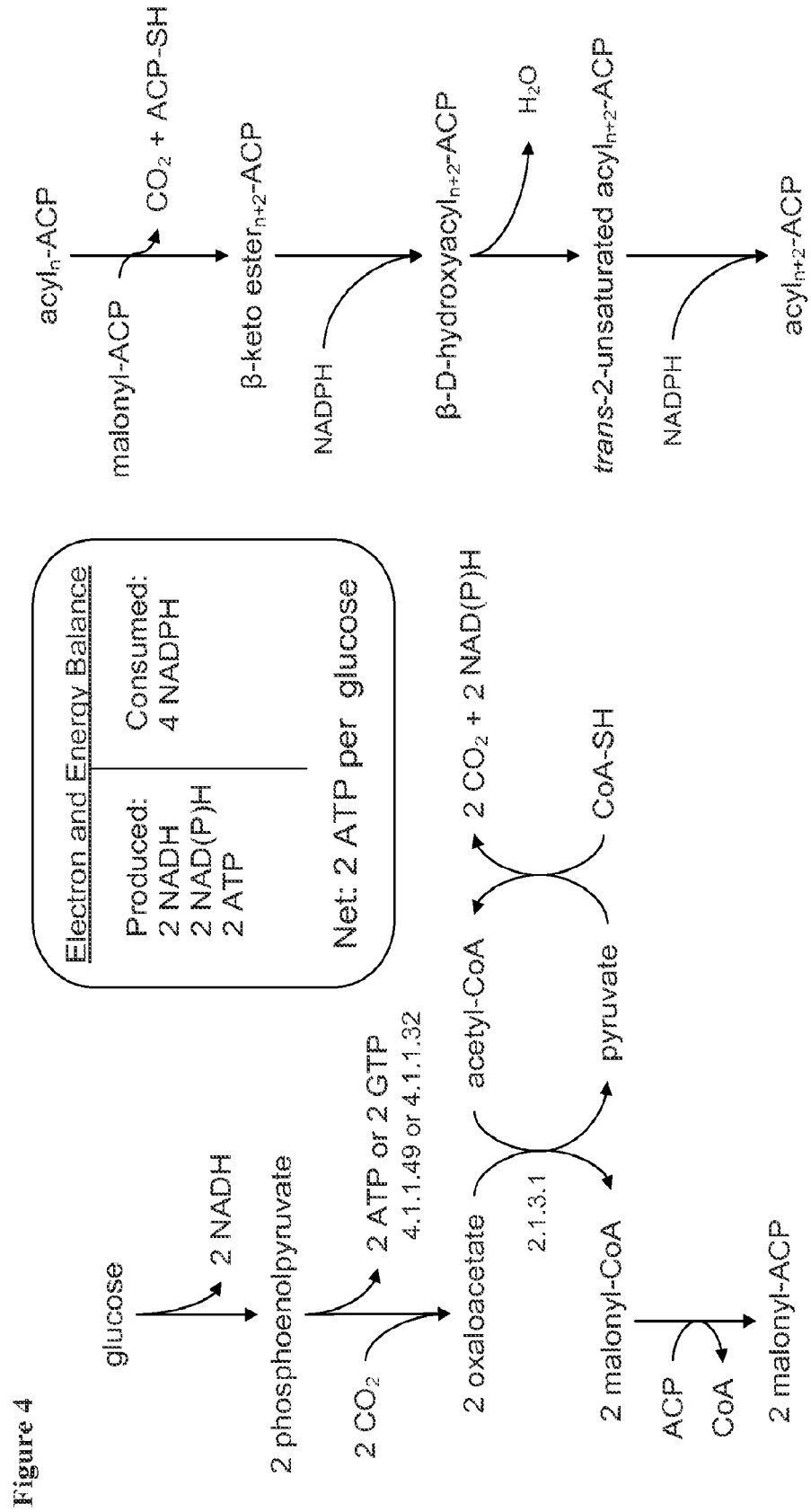
FIG. 4 depicts a pathway for the conversion of glucose to $acyl_{n+2}$-ACP.

In native cells, e.g., E. coli, chain extension proceeds from pyruvate to acetyl-CoA to malonyl-CoA. See Steen et al., Nature 463:559-562 (2010). To conserve ATP during the generation of malonyl-CoA, two enzymes are introduced into the central metabolic network for chain extension: a phosphoenolpyruvate carboxykinase (PEPCK) to convert phosphoenolpyruvate to oxaloacetate and a transcarboxylase (TC) to convert oxaloacetate and acetyl-CoA to malonyl-CoA and pyruvate (see FIG. 4 or FIG. 33). The introduction of these enzymes results in the production of 2 NADH, 2 NAD(P)H, and 2 ATP, resulting in a net production of ATP per carbohydrate, such as but not limited to, glucose. For example, for glucose, the net production of ATP per 6 carbons is about 2. For xylose, the net production of ATP per 5 carbons is about 1.67 ATP. When considering the net production of ATP per hydrocarbon produced rather than sugar consumed, for every 4 carbons of hydrocarbon, the net is about 2 ATP. Thus, for a $C_{16}$ fatty acid, the net ATP is about 8. The conversion of phosphoenolpyruvate to oxaloacetate using PEPCK results in the net production of ATP. See FIG. 4. For example, the net production of ATP in the recombinant microorganisms of the invention includes at least about 0.5 net ATP; at least about 1.0 net ATP; at least about 1.5 net ATP; or at least about 2.0 net ATP during anaerobic growth. The conversion of oxaloacetate and acetyl-CoA to malonyl-CoA and pyruvate by TC then requires the regeneration of acetyl-CoA from the TC-generated pyruvate. The recycling of pyruvate by conversion of pyruvate and CoA-SH into acetyl-CoA and $CO_2$ and NAD(P)H not only facilitates flux in the direction of producing malonyl-CoA, but also generates the reduced NAD(P)H needed to balance redox. Enzymes that can be used to catalyze this pyruvate recycling pathway include, but are not limited to, a pyruvate dehydrogenase, a pyruvate:ferredoxin oxidoreductase and ferredoxin:NAD(P)H oxidoreductase, or a pyruvate formate lyase and formate dehydrogenase.

In addition, competing metabolic pathways can be removed or attenuated. These include, but are not limited to, pyruvate kinase, hydrogenase, lactate dehydrogenase, phosphotransacetylase, acetate kinase, acetaldehyde dehydrogenase, alcohol (ethanol) dehydrogenase, pyruvate formate lyase, pyruvate decarboxylase, and native enzymes involved in the degradation of fatty acids and their derivatives.

PEPCK and TC can be derived from C. thermocellum and T. saccharolyticum or other organisms. Engineering of these enzymes into the recombinant microorganism of the invention may require alteration of substrate specificity to minimize undesirable side reactions. In addition, cofactor specificity in the overall metabolic pathway can be modified, which has been done with other, similar proteins. To increase flux to malonyl-CoA production, native pathways for organic acid and ethanol production can be modified. Each of these engineering steps is within the abilities of those skilled in the art.

The acyl-ACP chain can be extended though the fatty acid biosynthesis (Fab) enzymes present in all organisms that produce fatty acids. These include FabB, FabF, FabG, FabZ, and FabI. Overexpression of these enzymes can benefit hydrocarbon formation; however, the native biosynthetic pathway is largely regulated by the availability of the malonyl-CoA precursor and the accumulation of long-chain fatty acyl-ACP compounds. See Li et al., Journal of Bacteriology 175:332-340 (1993); Davis et al., Journal of Biological Chemistry 275:28593-28598 (2000); Davis and Cronan, Journal of Bacteriology 183; Heath and Rock, Journal of Biological Chemistry 271:1833-1836 (1996)). Supply of sufficient precursor and removal of fatty acyl-ACP via chain termination steps allows for sufficient flux through this chain extension pathway.

Figure 5:
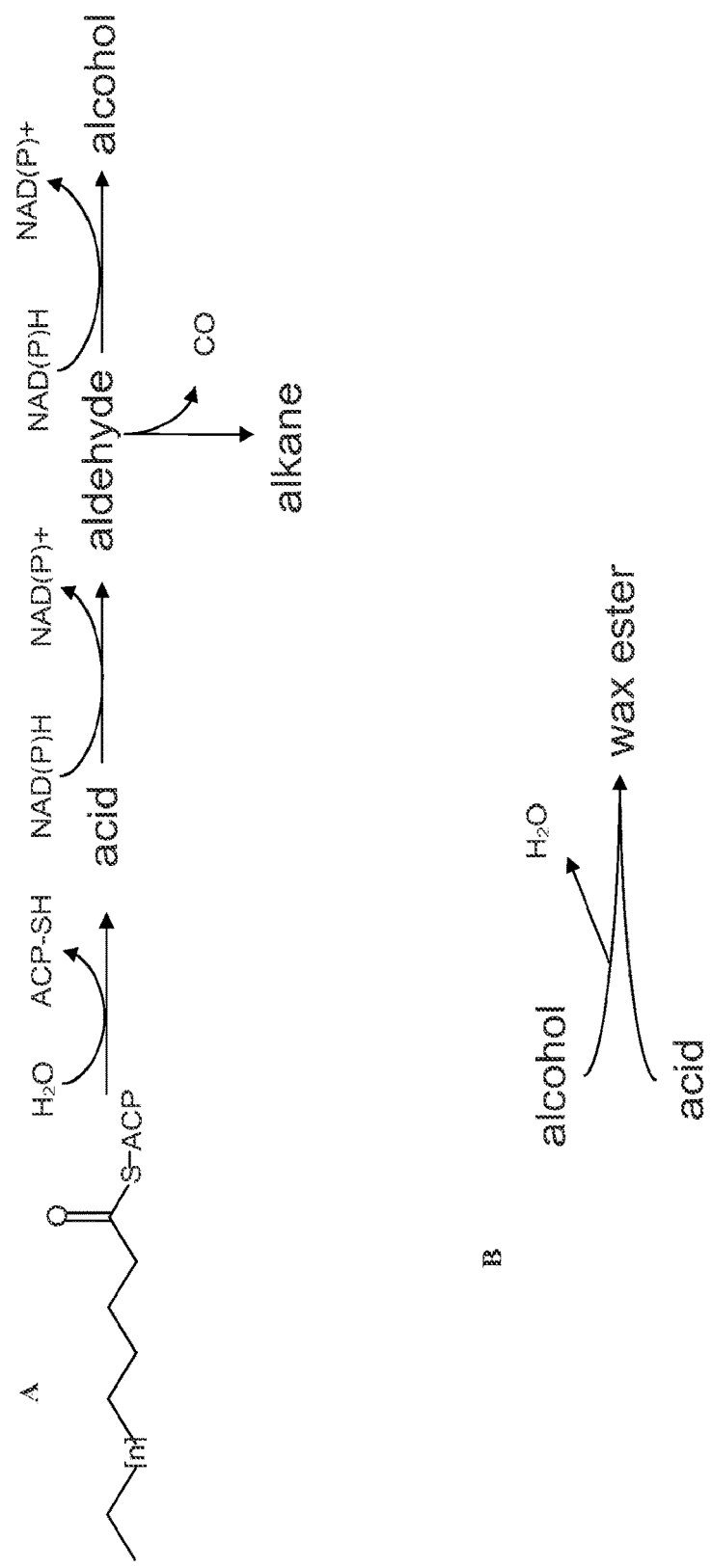
FIG. 5A depicts a pathway for the conversion of a fatty acyl-ACP to a fatty alcohol.
FIG. 5B depicts a pathway for the conversion of an alcohol and an acid to a wax ester.

Once an acyl-ACP chain has reached its desired length, the reaction is terminated and the hydrocarbon product is excreted from the cell. Many chain termination options are available in the art to produce hydrocarbon products or hydrocarbon derivative products, including, but not limited to, fatty acids, alcohols, aldehydes, wax esters, or alkanes (see FIGS. 5A and 5B). See Steen et al., *Nature* 463:559-562 (2010); Sukovich, et al., *Applied and Environmental Microbiology* 76:3850-62 (2010); Kalscheuer and Steinbüchel, *Journal Biological Chemistry* 278:8075-82 (2003); Reiser and Somerville, *Journal of Bacteriology* 179:2969-2975 (1997); Kalscheuer et al., *Microbiology* 152:2529-36 (2006); Beller et al., *Applied and Environmental Microbiology* 76:1212-23 (2010). The termination steps, in concert with chain extension, impart properties on the final compound to mimic petroleum based diesel, gasoline, or jet fuel. For example, production of $C_{14-18}$ fatty alcohols and esters as first generation products can be directly blended to create cellulosic diesel, or serve as a bio-crude that could be converted into other fuels with conventional catalysis technology. Production of fatty alcohols requires expression of a fatty acyl reductase and a fatty aldehyde reductase. See Reiser and Somerville, *Journal of Bacteriology* 179:2969-75 (1997); Steen et al., *Nature* 463:559-562 (2010). Some organisms, such as *E. coli*, have native fatty aldehyde reductase activity, while enzymes such as the jojoba acyl reductase is a bifunctional acyl-ACP/aldehyde reductase. See Reiser and Somerville, *Journal of Bacteriology* 179: 2969-75 (1997). Wax esters can be produced via an acyltransferase in the presence of ethanol or a long-chain alcohol. See Kalscheuer and Steinbüchel, *Journal Biological Chemistry* 278:8075-82 (2003); Reiser and Somerville, *Journal of Bacteriology* 179:2969-2975 (1997); Kalscheuer et al., *Microbiology* 152:2529-36 (2006).

The chain length of the hydrocarbon product or hydrocarbon derivative product is controlled based on, e.g., the specificity of the native organism. See Wang et al., *Extremophiles* 10:347-56 (2006); van Beilen et al., *Microbiology* 147:1621-30 (2001). Based on techniques known in the art, termination enzymes can be screened and engineered to develop hydrocarbon products or hydrocarbon derivative products with the desired chain length. See Steen et al., *Nature* 463:559-562 (2010); Sukovich, et al., *Applied and Environmental Microbiology* 76:3850-62 (2010); Kalscheuer and Steinbüchel, *Journal Biological Chemistry* 278: 8075-82 (2003); Reiser and Somerville, *Journal of Bacteriology* 179:2969-2975 (1997); Kalscheuer et al., *Microbiology* 152:2529-36 (2006); Beller et al., *Applied and Environmental Microbiology* 76:1212-23 (2010).

Hydrocarbon products or hydrocarbon derivative products can exit the cell through a membrane "flip" mechanism. In such a mechanism, the polar hydrophilic-hydrophobic compound enters the lipid bi-layer on the intracellular side with the hydrophilic head pointing towards the inside of the cell, flips over so that the hydrophilic head points outside of the cell, and then exits the bi-layer into the extracellular environment. See Black and DiRusso, *Microbiology and Molecular Biology Reviews* 67:454-472 (2003). Alternatively, to ensure efflux from the recombinant microorganism, high efficiency hydrophobic compound efflux transporters can be engineered, although at a cost of one ATP per molecule extruded. See Kieboom et al., *Journal of Biological Chemistry* 273:85-91 (1998). Such mechanisms allow for collection of the hydrocarbon products or hydrocarbon derivative products in the fermentation medium, in addition to other products naturally secreted or expelled by the host cell.

As hydrocarbon products or hydrocarbon derivative products accumulate in the fermentation media, the products can form a 2-phase organic layer after saturating the aqueous fermentation volume. See Neumann et al., *Applied and Environmental Microbiology* 71:6606-612 (2005). At saturating concentrations, toxicity correlates to the "minimum membrane concentration" of a compound, which is a function of the octanol/water partition coefficient and the aqueous solubility. Generally, as chain length increases, compounds become less toxic.

Product recovery and product toxicity are independent of substrate concentration. This provides the advantages that either a minimal pretreatment can be run at low fermentor solids or, when using refined material, the refined material can be run at very high solids without product toxicity to the fermenting organisms. In addition, because the hydrocarbon products are insoluble, product recovery can be at low cost. This means that the hydrocarbon products can be readily purified for use in fuels and chemical feedstocks.

EXEMPLIFICATION

The invention now being generally described, it will be more readily understood by reference to the following examples, which are included merely for purposes of illustration of certain aspects and embodiments of the present invention, and are not intended to limit the invention.

Example 1

The present prophetic example describes the engineering of a recombinant microorganism to convert a native fatty acid biosynthetic pathway into a fermentative pathway, i.e., one that generates net positive ATP and is redox neutral during anaerobic growth.

1.1 Production of Hexadecanol in *T. saccharolyticum*

Gene overexpression and gene deletion followed by evolutionary engineering will be performed to create a strain producing 1-hexadecanol.

The strain *T. saccharolyticum* JW/SL-YS485 has an established transformation system based on a natural competence protocol. See Shaw et al., *Applied and Environmental Microbiology* 76:4713-4719 (2010). Recombinant DNA, either linear or plasmid based, can be introduced with the following protocol.

1.1.1 *T. saccharolyticum* Transformation Protocol

Prior to use, petri dishes, 50 mL and 15 mL conical falcon tubes, and pipet tips are all placed in the anaerobic chamber at least overnight. Transformations are performed in an anaerobic chamber by inoculation of 10 mL liquid medium M122 (pH 6.1 or 6.7—there is less precipitation at pH 6.1 and it facilitates OD measurement, but kanamycin selection is better at pH 6.7) with 1-3 µL of a frozen working stock culture of *T. saccharolyticum*, which has been frozen-down when in exponential growth. After mixing, 1 mL aliquots of the 10 mL medium are transferred to tubes containing between 0.25 µg-1 µg DNA. The tubes are then incubated at 55° C. for 16-18 hours (overnight) to an OD of 0.6-1. Maintaining cells past 18 hours in stationary phase can dramatically reduce transformation efficiencies.

Next, 100 µL and 500 µL aliquots of the transformant culture are mixed with 25 mL liquid medium M122 pH 6.7 at 55° C. containing 1.2% agar and kanamycin at 200 µg/mL. The mixture is poured into petri dishes and allowed to solidify at room temperature for 30 minutes, or until completely solid, and the petri dishes are incubated at 55° C. in a moisture retaining container until colony formation (24-48 hours).

1.1.2 Gene Deletion

Figure 8:
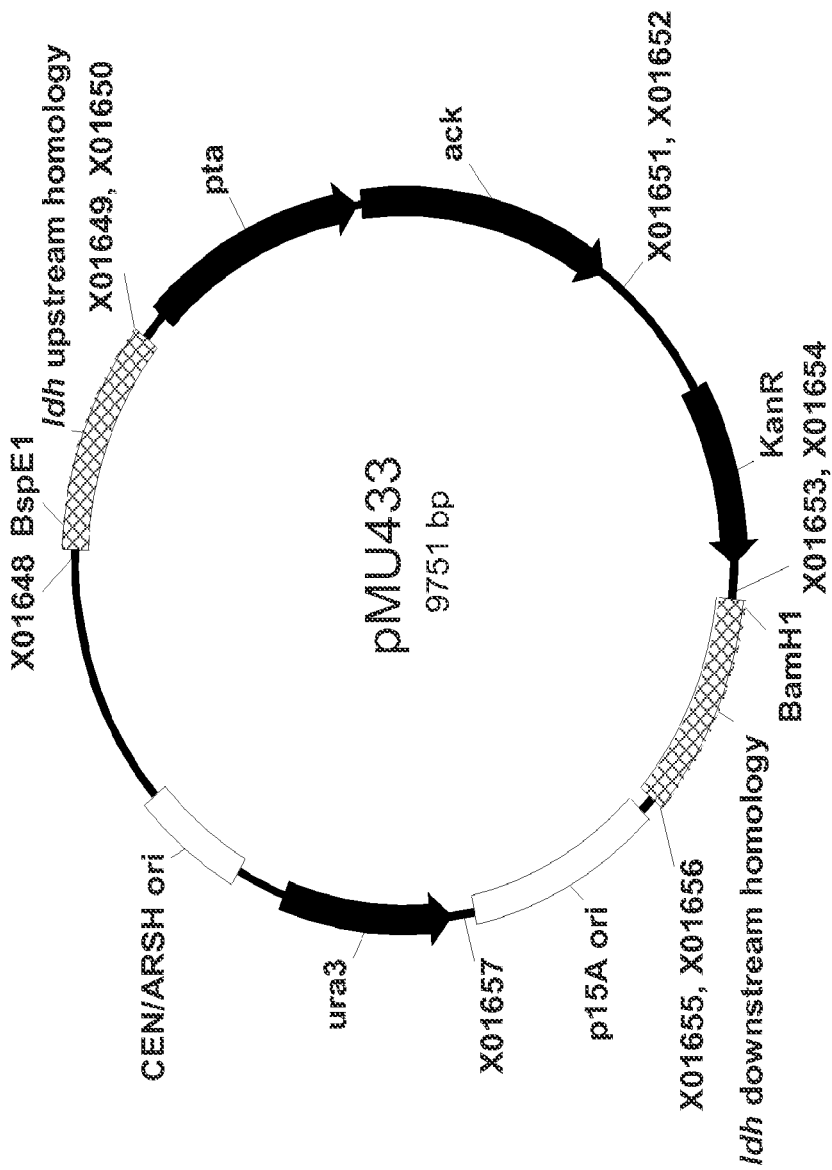
FIG. 8 depicts the vector pMU433.

Gene deletions will be performed with a marker removal system, which allows for clean genomic deletions and marker recycling. The plasmid pMU433 (see FIG. 8) contains the marker removal cassette, namely the pta and ack genes linked to a kanamycin resistance gene. Genes targeted for deletion include L-lactate dehydrogenase, bifunctional alcohol dehydrogenase adhE, pyruvate kinase, pyruvate formate lyase, and phosphotransacetylase and acetate kinase. To construct deletion vectors, homology regions are generated from the target gene sequences from *T. saccharolyticum* and cloned into pMU433.

L-lactate dehydrogenase
(SEQ ID NO: 72)

```
atgagcaaggtagcaataataggatctggttttgtaggtgcaacatcggcatttacgctggcattaagtgggactgtgacagatat
cgtgctggtggatttaaacaaggacaaggctataggcgatgcactggacataagccatggcataccgctaatacagcctgtaaat
gtgtatgcaggtgactacaaagatgtgaaaggcgcagatgtaatagttgtgacagcaggtgctgctcaaaagccgggagagac
acggcttgaccttgtaaagaaaaatacagccatatttaagtccatgatacctgagcttttaaagtacaatgacaaggccatatatttg
attgtgacaaatcccgtagatatactgacgtacgttacatacaagatttctggacttccatggggcagagttttttggttctggcaccg
ttcttgacagctcaaggtttagatacctttttaagcaagcactgcaatatagatccgagaaatgtccacggaaggataatcggcgag
catggtgacacagagtttgcagcatggagcataacaaacatatcgggtatatcatttaatgagtactgcagcatatgcggacgcgt
ctgcaacacaaatttcagaaaggaagtagaagaagaagtcgtaaatgctgcttacaagataatagacaaaaaggtgctacata
ctatgctgtggcagttgcagtaagaaaggattgtggagtgcatcttaagagatgaaaattccatcctcacagtatcatctccattaaat
ggacagtacggcgtgaaagatgtttcattaagcttgccatctatcgtaggcaggaatggcgttgccaggattttggacttgcctttat
ctgacgaagaagtggagaagtttaggcattcagcaagtgtcatggcagatgtcataaaacaattagatata
```

Bifunctional alcohol dehydrogenase adhE
(SEQ ID NO: 73)

```
atggcaacgacaaaaacggaattagacgttcagaagcagatagatctacttgtgtcaagagcacaagaggctcagaaaaaattc
atgtcttacacgcaagagcaaatcgacgcaatagttaaggcaatggctttagcaggcgttgacaaacacgtagagctggcaaag
atggcgtacgaagagacaaaaatgggtgtatacgaagataagtaacaaaaaatctcttcgcaacagatacgtgtaccacgac
ataaaaaatgaaaagactgtaggaatcataaacgagaacatagaagaaaactacatggaagtggcagaaccgataggcgtaat
tgccggtgtcacacctgtcacaaacccaacatctaccacgatgtttaaatgcttaatatccataaagacgcgaaatcctataatattc
agcttccatccaaaggcaataaagtgcagcatcgcagcagccaaagtgatgtatgaagctgcactaaaggcaggcgcacctga
aggatgcataggatggatagaaacgccatcaattgaggccacacagcttctcatgacacatccaggcgtatcgctgatccttgca
acgggcggtgcaggaatggtaaaagcggcatacagctcaggaaaaccggcattaggcgtaggtcctggcaatgtgccatgct
acatcgaaaaatcagcaaacataaagagggcgtgtatcggatctcatactaagcaagacatttgacaatggagtaatatgcgcatc
agagcaggccgtaataatagacgaggaaatagcagatgaagtcaaaaagcttatgaaagaatacggctgctacttcttaaacaa
agatgaaataaagaagcttgagaaatttgcaattgatgagcaaagctgcgccatgagccctgcagtggtaggtcagccagcgg
cgaagattgctgaaatggcaggcttcaaagtccccgaaggcacaaagatattagtggcagagtacgaaggagtaggtccaaaa
tatcctctatcaagggagaaactaagcccgattcttgcttgctacaccgtcaaagactacaatgaaggaatcaaaaagtgcgagg
aaatgactgaattcggaggtttaggccactctgctgtaatacactctgaaaatcaaaacgtcataaatgaatttgcaaggcgagtcc
gcacaggaagacttatcgtaaattccatcatcacagggagcaataggagatatatacaatacaaacacgccatcacttacatta
ggctgtggttctatgggaagaaactcaacgacagacaatattaagcgtcaagaaccttttgaatattaagcgtgtcgtgataaggaa
tgatagaatgaaatggttcaagattccaccgaagatttactttgaaagcgggtcactccagtacctgtgcaaagtcaaaagaaaaa
aagcgtttatcgtcacagatccattcatggttaagcttggcttcgtagacaaagtgacatatcaattagacaaagcaaacatcgaat
acgaaatattctcagaagtagagccagatccatctgttgacacagtcatgaacggcgtaaaaataatgaattcgtacaatcctgac
ttaataatcgctgtaggcggtggctctgcaatagacgcagcaaaggaatgtggcttttctacgaatatcctgatacagagtttgaa
acattgaggcttaaatttgcagacatcagaaaaagggcatttaagttcccagaacttggcaaaaaagcgctattcatcgcaatacc
gacaacaagcggcacaggctcagaagtgacagcatttgccgtaataaccgacaaaaagagaaacatcaagtatccactggca
gactacgaacttacacctgacatagccataatagatcctgaccttacaaagactgtaccgccatctgtaacagcagacacaggca
tggatgtgctgacacacgccatagaagcatacgtatcagtaatggcatcagcatacaacagatgcactggcggaaaaggctataa
agatcgtatttgaatacctgccaaggctctataaaaacggcaatgatgaagaagcccgcgaaaagatgcacaatgcttcctgcat
ggctggtatggcattcacaaatgcattcttaggaataaaccacagcatggcacacatactgggcggaaagttccacataccacac
ggaagagcaaatgcaatacttctgccgtatgtaataaggtacaatgcagaaaaacctacaaagtttgtggcattcccacaatacga
atatccaaaagcagcagaaagatatgcggaaatcgccaaattcttaggactgcctgctttcaactgttgaagaaggcgtagaaag
cttaatagaagctataaagaacctcatgaaagagcttaacattccgcttacacttaaagacgccggcatcaacaaagaacagtttg
aaaaagaaatagaggaaatgtcagacatcgccttcaacgatcagtgcacagggacaaacccgagaatgcctctcacaaaagaa
attgcagagatctacagaaaagcatacggtgca
```

Pyruvate kinase
(SEQ ID NO: 74)

```
atgcgtagaactaagataatatgcacgattggtcctgccagtgaaaaatatgagatattgaaagagcttatagaaagcggtcttaat
atttgcaggttgaattttcacatggggatcatgaagagcatggaagcagaatagacaatattataaagattagagaagaacttaag
ctgcctattgcaattatgcttgctgatacaaaagggcctgaaataaggactgcagatttaaaggcggtgttgcagagcttaaagaag
gccagacatttacgataacatcaagggaaattgaaggagataacactatttgttctgtttcatacaaggggcttcctcaagatgtgg
agagaggttctcgcatattgattgatgacggattagtatcattgaaagtcaatgacgtaaaaggtgaagatatagtatgcactgtgg
agaattctggtacaataggtgatcacaaaggtgtaaatgtacctggtacaaagcttaatttgcctgccataacgcaaaaagacgtg
gatgatatagagttttggaataaaaaaaggaaatcgacatgattgcagcgtcttttgtcagaaaagcagcagatgtaattgccataag
gagattgttagaagacaatgacgctggccatatacttatcatatcaaaaattgaaaatcgcgaaggcgtagaaaatattgacgaaa
taatcaaagtctctgatggcataatggtagcccgcggcgatttgggtgtcgaaattcctatagaggaaatacctatcgttcagaaaa
ggataattgaaaaatgcaacaaagcaggtaaccagtagttactgctacacagatgcttgactctatgataagaaatccaaggcc
aacaagggcagaagtaacagatgtagccaatgctatattgatgcgactgatgcgataatgttgtctggtgaaacagcgcaagg
caaatatcctgtagaggcttttaagacgatgtcaaagatagctgaaaagattgagacgtatataaattacaaagaaatttagataa
aaatgtggattacaatatttctatgcaaatgccataagccatgctacgtgcactaccgcgagagatataggcgcaactgccattat
tacatctacaatatcaggttatactgcgagaatggtgtctaagtatagaccgtcagcacctataatagcagtgacgccaaacaaag
atgttgcaagaaggcttagcatcgtgtggggtgtacatccattgatatcacaggaagtcaattctacagatgaaatgataagaagtat
cagtaaatacggctttaaatgaaggattaattcgaaatggcgatattgtagtaatatcggcaggaataacctgtcgcgactacaggc
acaacaaatatgttgaaggttcatattgtgggagatgtaatagtaaaaggcacaggcataggcactaaatccataagtggtgttgtt
tccatcataagagatccatacaaggacaaagataagttcagagaaggagatatcatcgttgctcaaaaaactgaaagggattatat
gcctataattgagaaggcttcagctatcataacagaagaaggtggactaacgtcccatgctgcaatagttggattgaactatggatt
acctgtcattgtaggctgtgaaggagtaacttcaaagcttaagatggaatgacggtaactctcgatactgccagaggattggtct
acaaaggtatagtgaatataaaatag
```

Pyruvate formate lyase
(SEQ ID NO: 75)

```
atgatcaatgaatggcgcgggtttcaggagggcaaatggcaaaagactattgacgttcaagattttatccagaaaaattacacatt
atacgaaggcgatgatagtttttagaagggcctacagaaaagactattaagctttggaacaaagttcttgagctaatgaaggaag
```

-continued

```
aactgaaaaaaggtgtgttagatattgatacaaaaactgtatcgtctataacatcccatgatgcggggtatatagacaaagatcttg
aggaaatagttggattgcagacagacaaacctcttaaaagagctataatgccttacggtggcataagaatggtcaaaaaagcttg
cgaagcttatggatataaagtggacccaaaagtagaagagatatttacgaagtacagaaagacccacaatgatggtgtatttgat
gcatatactccagaaataagagcagcaagacatgccggcataataacaggtcttccagatgcatatggcagaggaagaatcata
ggtgattacagaaagagttgctctttatggaattgatagactcatcgaagaaaaggaaaaagaaaaaacttgagcttgattacgatga
atttgatgaagcaactattcgcttgagagaagaattgacagaacagataaaagcattaaacgaaatgaaagagatggctttaaagt
acggttatgacatatcaaagcctgcaaaaaatgcaaaagaagctgtgcagtggacttactttgccttccttgctgctataaaggaac
aaaatggtgccgctatgtcgctgggcagagtatctacttttttagatatatacattgaaagagatcttaaagaaggaacattgacag
agaaacaagcacaagagttaatggatcacttttgtcatgaagcttagaatggtgaggttcttaaggactcctgattacaatgaactatt
tagtggcgatcctgtttgggtgactgaatcaattggcggtgtaggcgtagacggaagacctcttgtcactaaaaattcattcaggat
attaaatactttatataacttaggtcctgcacctgagccaaacttgacggttttatggtccaaaaacctcctgaaaactttaaaagatt
ctgtgccaaggtatcaatagatacaagttctattcaatatgaaaatgacgacttaatgaggccaatatacaatgacgactatagcat
cgcctgctgtgtgtcagctatgaagacgggagaacagatgcaattttttggagcaagggcaaatctcgcgaaggcgctactgtat
gctataaacggcggtatcgatgaaaggtataaaacgcaagtggcaccaaaaatttaatcctataacgtctgagtatttagactacgat
gaggtaatggcagcatatgacaatatgtragagtggcttgcaaaagtgtatgttaaagctatgaatataatacactacatgcacgat
aaatacgcttatgaaagatcccttatggctttgcatgatagagacatcgtaaggacgatggcttttggaatcgcaggtctttctgttg
cggcagattcgttaagcgccataaagtatgctaaagtaaaagccataagagatgaaaatggcatagcaatagattatgaagtgga
aggagatttccctaagtttggcaatgatgatgacaggggttgactcaatagcagttgacattgtagaaagattcatgaataagcttaa
aaagcacaagacttacagaaactctataccaacactgtctgttttgacaataacgtcaaatgtggtgtacggcaaaaagacgggt
gctacacctgacggaagaaaagcgggagaaccttttgcgccaggcgcaaatccgatgcacggcagagatacaaaaggtgcc
atagcatcaatgaattcagtatcaaaaatacctttatgacagttcattggatggtatatcatacacatttacgattgtaccaaatgcgctt
ggcaaggatgacgaagataaaattaataatcttgtaggactattagatggatatgcatttaatgcggggcaccacataaacatcaa
tgttttaaacagagatatgttgcttgatgctatggagcatcctgaaaaatatccgcagcttactataagggtttcagggtatgctgtca
atttcaataaattaacgagagagcaacagttggaggttatatcccgcacttttcacgaatctatg
```

Phosphotransacetylase and acetate kinase (SEQ ID NO: 76)

```
gtgtatacaatatatttcttcttagtaagaggaatgtataaaaataaatattttaaaggaagggacgatcttatgagcattattcaaaac
atcattgaaaaagctaaaagcgataaaaagaaaattgttctgccagaaggtgcagaacccaggacattaaaagctgctgaaata
gtttaaaagaagggattgcagatttagtgcttcttggaaatgaagatgagataagaaatgctgcaaaagacttggacatatccaaa
gctgaaatcattgaccctgtaaagtctgaaatgtttgataggtatgctaatgatttctatgagttaaggaagaacaaaggaatcacgt
tggaaaaagccagagaaacaatcaaggataatatctattttggatgtatgatggttaaagaaggttatgctgatggattggtatctg
gcgctattcatgctactgcagatttattaagacctgcatttcagataattaaaacggctccaggagcaaagatagtatcaagctttttt
ataatggaagtgcctaattgtgaatatggtgaaaatggtgtattcttgtttgctgattgtgcggtcaacccatcgcctaatgcagaag
aacttgcttctattgccgtacaatctgctaatactgcaagaatttgttgggctttgaaccaaaagttgccatgctatcattttctacaa
aaggtagtgcatcacatgaattagtagataaagtaagaaaagcgacagagatagcaaaagaaattgatgccagatgttgctatcga
cggtgaattgcaattggatgctgctcttgttaaagaagttgcagagctaaaagcgccgggaagcaaagttgcgggatgtgcaaat
gtgcttatattccctgatttacaagctggtaatataggatataagcttgtacagaggttagctaaggcaaatgcaattggacctataa
cacaaggaatgggtgcaccggttaatgatttatccaaggaggtgcagctatagagatattgttgacgtaatagcaacaacagctgtg
caggctcaataaaatgtaaagtatggaggatgaaaattatgaaaatactggttattaattgcggaagttcttcgctaaaatatcaact
gattgaatcaactgatggaaatgtgttggcaaaaggccttgctgaaagaatcggcataaatgattccatgttgacacataatgctaa
cggagaaaaaatcaagatataaaaaaagacatgaaagatcacaaagacgcaataaaattggttttagatgctttggtaaacagtgac
tacggcgttataaaagatatgtctgagatagatgctgtaggacatagatggttgttcacggaggagaatcttttacatcatcagttctca
taaatgatgaagtgttaaaagcgataacagattgcatagaattagctccactgcacaatcctgctaatatagaaggaattaaagctt
gccagcaaatcatgccaaacgttccaatggtggcggtatttgatacagcctttcatcagacaatgcctgattatgcatatctttatcc
aataccttatgaatactacacaaagtacaggattagaagatatggatttcatggcacatcgcataaatatgtttcaaatagggctgca
gagattttgaataaaacctattgaagatttgaaaatcataacttgtcactttggaaatggctccagcattgctgctgtcaaatatggtaa
atcaattgacacaagcatgggatttacaccattagaaggtttggctatgggtacacgatctggaagcatagacccatccatcatttc
gtatcttatggaaaagaaaatataagcgctgaagaagtagtaaatatattaaataaaaaatctggtgtttacggtatttcaggaata
agcagcgattttagagacttagaagatgccgcctttaaaaatggagatgaaagagctcagttggctttaaatgtgtttgcatatcga
gtaaagaagacgattggcgcttatgcagcagctatgggaggcgtcgatgtcattgtatttacagcaggtgttggtgaaaatggtcc
tgagatacgagaatttatacttgatggattagagtttttagggttcagcttggataaagaaaaaaataaagtcagaggaaaagaaac
tattatatctacgccgaattcaaaagttagcgtgatggttgtgcctactaatgaagaatacatgattgctaaagatactgaaaagatt
gtaaagagtataaaa
```

For knockout vector construction, the 0.8-1.2 kb flanking regions (with primers) on both sides of target are first identified. Once identified, the new flanking regions are used to replace the L-ldh flanking regions in pMU433 using in silico analysis. Yeast-mediated ligation primers (4 total) for the two new flanking regions are made by adding to the targeting primers 5' regions homologous to DNA segments labeled "X01648," "X01649," "X01654," and "X01655" on pMU433 shown in Table 3. Total primer length should be about 55-65 bp.

Next, the flanking regions from *T. saccharolyticum* YS485 genomic DNA are PCR amplified. PCR cleanup is not necessary if correct product was highly amplified.

TABLE 3

Primers for Knockout Vector Construction

| X01648 (SEQ ID NO: 77) | GTCTTTCGACTGAG CCTTTCGTTTTATT TGATGCCTGG | pMU433 construction |

TABLE 3-continued

Primers for Knockout Vector Construction

| X01649 (SEQ ID NO: 78) | AATTGTAGAATACA ATCCCACTTCACAA ATGGGCACG | pMU433 construction |
| X01654 (SEQ ID NO: 79) | AGGGGTCCCGAGCG CCTACGAGGAATTT GTATCG | pMU433 construction |
| X01655 (SEQ ID NO: 80) | CCGTCAGTAGCTGA ACAGGAGGGACAGC TGATAGA | pMU433 construction |

About 100-200 ng pMU433 per yeast transformation is then digested with BamH1/BspE1. Allowing digestion to proceed to completion helps reduce background during yeast transformation.

The digested DNA is transformed into ura3—*S. cerevisiae* (Invitrogen INVSc1 cat#C81000 or equivalent) following the "Lazy bones" yeast transformation protocol. See Shanks et al., *Applied and Environmental Microbiology* 72:5027-5036 (2006). Briefly, about 100 ng digested plasmid and 10-50 μL of each PCR amplified flanking region are mixed. Prior purification is not necessary for either plasmid or PCR unless there are BamH1/BspE1 sites in the flanking regions. Other yeast transformation protocols can suitably be used. To control for background, a plasmid only control can be used.

The transformed yeast are plated on SD-URA plates (SD Medium-URA MP Biomedicals #4812-075 or equivalent) and incubated at 30° C. The plates are incubated for 3-5 days and then yeast total DNA is harvested from plates containing colonies. If cell mass is low, the colonies can be streaked on a new plate to increase the number of colonies. Yeast DNA is isolated using the "Smash and Grab" protocol (see Shanks et al., *Applied and Environmental Microbiology* 72:5027-5036 (2006)), or an equivalent protocol.

Next, competent *E. coli* are transformed with 1-5 μL of yeast total DNA and selected on 50 or 100 Kan LB plates.

dilution of the first round products to approximately 1 ng/μL. This dilution is used as a template; and the upstream flanking region 5' primer and downstream flanking region 3' primer are used for amplification. If necessary, optimization of annealing temperature or $MgCl_2$ can be performed. Alternatively, TOPO cloning (Invitrogen) or other known techniques can be used to make the second construct.

Following a PCR clean-up, 2-3 μg of the vector product is then used to transform *T. saccharolyticum*.

1.1.3 Gene Insertion

To create a metabolic route to I-hexadecanol, native and/or recombinant genes are overexpressed. The native PEPCK and TC genes are overexpressed via insertion of high level promoters in front of the coding sequence for these genes. This is accomplished through the pMU433-based marker cycling system, except that the recombinant promoter region will remain behind after the marker is removed. High expression level promoter regions can be chosen, without limitation, from any of the following promoters:

```
adhE promoter
                                                             (SEQ ID NO: 81)
tcatataagtgtaaggtgattgttaaatgaataacaaaaattatttacatcacacagtccaaaattcaattcattcaagcgaatttcctg
ttgaaatgcttgaaaaactgatacaatcacctgaaatgtagagatttattgttaataaattaacacggaggtgtttatt cbp promoter
                                                             (SEQ ID NO: 82)
gagtcgtgactaagaacgtcaaagtaattaacaatacagctattttttctcatgcttttacccattcataaaatttaattttatcgttatcat
aaaaaattatagacgttatattgcttgccgggatatagtgctgggcattcgttggtgcaaaatgttcggagtaaggtggatattgattt
gcatgttgatctattgcattgaaatgattagttatccgtaaatattaattaatcatatcataaattaattatatcataattgttttgacgaatg
aaggtttttggataaattatcaagtaaaggaacgctaaaaattttggcgtaaaatatcaaaatgaccacttgaattaatatggtaaagt
agatataatattttggtaaacatgccttcagcaaggttagattagctgtttccgtataaattaaccgtatggtaaaacggcagtcaga
aaataagtcataagattccgttatgaaaatatacttcggtagttaataataagagatatgaggtaagagatacaagataagagata
taaggtacgaatgtataagatggtgcttttaggcacactaaataaaaaacaaataaacgaaaattttaaggaggacgaaag pta promoter
                                                             (SEQ ID NO: 83)
gtattctacaattaaacctaatacgctcataatatgcgcctttctaaaaaattattaattgtacttattattttataaaaaatatgttaaaatg
taaaatgtgtatacaatatatttcttcttagtaagaggaatgtataaaaatatattttaaaggaagggacgatctt hyd promoter
                                                             (SEQ ID NO: 84)
ataagcgaaagggtaaattgctttgatttagatgatttgaatatggtagtcgactggatgtgcaagtaaagaaaacatatcaaattag
tcgggattatcagaaaataaaaaaattttttatttttaactgttaaaaaaataattaacatatggtataataattatgtcctattttgcaatttt
aaagattaattttttttaaaaggagggtattag hfs promoter
                                                             (SEQ ID NO: 85)
gctgtaattgtccttgatgacgataggaagataaacattccaacaaaatatatcccagcaatattgctgaagaagatgccatagat
attttcattggatgtcaatgaaagaggacgaaaattaaaaaagttgattgaagaatcaagggaggaagactaattttttaatttttttaa
cgttaattgttaataaattaactattgtttacacactttcttttatgtaataaaataattgtatacagtatacgg ech promoter
                                                             (SEQ ID NO: 86)
tactgaatggagaaactgcacaaaaagcttgttgacggcagcagaggagattattcctctgctattttttgtgggaaaaactgcaaa
attcattgaaatattgttaaataataaacaaaattaattaatattaaatacaattgacttatcatttaattagatttataatcaaaatgggtat
ttaaaaatgtatacaatatataatattcattaaatgaaataaagaaggagtgaaaaa
```

Colonies are screened to verify the constructs. 2-5 μg total plasmid DNA is then used for *T. saccharolyticum* transformations.

A second vector for gene deletion/marker removal is constructed using in silico analysis to place the two flanking regions adjacent to each other. Overlapping regions are added to the two adjacent primers on the flanking regions to obtain about 40 kb of homology between the regions when amplified.

Using two rounds of PCR amplification, the flanking regions can be connected. The first PCR amplification is a traditional amplification, and the second amplification is a Next, recombinant genes encoding a fatty acyl-ACP reductase and hexadecanal dehydrogenase from organisms such as *Acinetobacter calcoaceticus* and *Geobacillus thermodenitrificans* (see Reiser and Somerville, *Journal of Bacteriology* 179:2969-2975 (1997); Liu et al., *Microbiology* 155:2078-2085 (2009)) are identified (see below). These recombinant genes can be integrated into the genome, driven by a high level expression promoter, or expressed via a replicating plasmid such as pMU131 (see WO 2009/035595).

Nucleotide sequence of *Acinetobacter* acr1 fatty acyl-ACP (-CoA) reductase
(GenBank# U77680)

(SEQ ID NO: 87)
```
cagaagatat ggttcggtta tcggttggga ttgaacatat tgatgatttg attgcagatctggaacaagc attggccaca
gtttgagcgt aaatttata aaaaacctct gcaattcag aggtttttt atatttgctt tattatcgta tgatgttcat
aattgatcta gcaaataata aaaattagag caattactct aaaaacattt gtaatttcag atacttaaca ctagattttt
taaccaaatc actttagatt aactttagtt ctggaaattt tatttcctt taaccgtctt caatccaaat acaataatga
cagcctttac agtttgatat caatcaggga aaaacgcgtg aacaaaaaac ttgaagctct cttccgagag aatgtaaaag
gtaaagtggc tttgatcact ggtgcatcta gtggaatcgg tttgacgatt gcaaaaagaa ttgctgcggc aggtgctcat
gtattattgg ttgcccgaac ccaagaaaca ctggaagaag tgaaagctgc aattgaacag caagggggac aggcctctat
tttcctttgt gacctgactg acatgaatgc gattgaccag ttatcacaac aaattatggc cagtgtcgat catgtcgatt
tcctgatcaa taatgcaggg cgttcgattc gccgtgccgt acacgagtcg tttgatcgct tccatgattt tgaacgcacc
atgcagctga attactttgg tgcggtacgt ttagtgttaa atttactgcc acatatgattaagcgtaaaa atggccagat
catcaatatc agctctaggt gtgtattggc caatgcgacccgttttctg cttatgtcgc gtctaaagct gcgctggatg
ccttcagtcg ctgtctttca gccgaggtac tcaagcataa aatctcaatt acctcgattt atatgccatt ggtgcgtacc
ccaatgatcg cacccaccaa aatttataaa tacgtgccca cgctttcccc agaagaagcc gcagatctca ttgtctacgc
cattgtgaaa cgtccaacac gtattgcgac gcacttgggt cgtctggcgt caattaccta tgccatcgca ccagacatca
ataatattct gatgtcgatt ggatttaacc tattcccaag ctcaacggct gcactgggtg aacaggaaaa attgaatctg
ctacaacgtg cctatgcccg cttgttccca ggcgaacact ggtaaattt ataaagaag cctctcatac cgagaggctt
ttttatggtt acgaccatca gccagattta gaggaaattg acttttcctg tttttacatc ataaatcgca ccaacaatat
caatttcttt gcgatccagc atatctttaa gtacagaact atgctgaata atgtattgaa tattatagtg aacattcata
gcagtcacct gatcaataaa tgctttgctt aattcacgcg gtgcataat atcaaataca ctgccaaccg aatgcatgag
tgcccaagc acgtattgga tgtgtggcat ttcctgaata tcggaaatct gcttatgttg caatcttaac tggcatgcgc
tggtgaccgc accacagtcg gtatgtccca aaaccagaat cactttggaa cctttggctt gacaggcaaa
```

Nucleotide sequence of *Geobacillus thermodenitrificans* NG80-2 adh1 (Genbank
Nucleotide CP000557, Protein ABO67118)

(SEQ ID NO: 88)
```
ttacgccttg tgcggctcta cgatcgtccc ggcaaacgcg gcttcgtaaa tcgcacggat gtcggcttcc aacagcggca
acggactgcg ggcaagcaaa cgtttctgtt ggacagcatc tttcgtcaag cttcctagcg cgctttcggg gatgccaaat
cccccaatg ttttcggaat gccgacatcg gcgacgaacc gttctagttc ctcgacgcac cgataagacg cttccacttc
ggacaaaaaa cttgagttgc cgccaagcgc gttgaaaata tcggccattc tcttcgtaca gctttgacgg atgtagccca
tcacatacgg caacagcaca gcattcgatt caccatgagc gatatgaaac tgaccaccga gcggataagc
gagcgcatgc acaccggcta ccccggcgtt gaaaaatgcc aagccggcca aataactgcc gttcgccata
tcaatgcgcg cctgtttgtc cgaaccgttg gccaccgctt tgcgcagtga gcgtgaaatc agccgaatag cggcaacggc
caatccatcc gatgttgggc tcgcattgac cgacacatac gcctcaactg catgggtgag tgcatcaatt cccgttgcgg
ccgttacccg cggtggaacg gaaacggtca gctgcggatc aacgatcgcg acgtcggcca ataagtaatc
gtgcgtcacg acatctttcg tcgtttccaa agacaagaca gagatgtttg tcacttccga cccggtgccc gatgtcgtgg
gaatcaaaat tttcggcaac ccttttttct caagtgttcg cgttcctgtc aaatttaaat agtcagcgac cgagccatca
tgcaccgcca aaacagccgc cagtttcgcc aaatccagcg cgctgccacc accaacaccg atgacaaggt
caaactttcc gtcgcgggca aacgccactg ccttttcccc tgtctcaagc ggcggctctg gcacaacatc cgtatacaca
tgcacgctat acccttcttg acggagcggg gacgtcactt gatcgactag gccgatcttc acaagcatcg ggtcggtaat
caccaaaata tgttttgctc ccaaccgctt cacttcagga actaactggt caagcgctcc ccagccgaca tggctgagcg
gcggaaagac aatgcgggct acactcat
```

Nucleotide sequence of *Geobacillus thermodenitrificans* NG80-2 adh1 (Genbank
Nucleotide CP000557, Protein ABO68223)

(SEQ ID NO: 89)
```
ttataaagac gcacgcaaaa tggcgagcac atcatcacga tttaacgttt tgaaacggcc aaactcacca aacgccatcg
ctttatccgc catcagctcg agattttcct cgccgatgcc ataatcagcc aatcgagacg gcgccccgag gctcgaccaa
aacgcgccaa accgctcgat gccctcaagc gccacgtcgc gctccgtttt gcccgtcgga tcgacgtcaa
agacgcgcac cgccagttgg gcgaaacggc tgacattttc atcaagcaca tgtttcatcc aattcgggaa caaaatggcc
aatcccccgg cgtgcgggat atcgtataca gcagagaccg catgctcgat atcatgcgtc gcccaatcac
cgcgcacgcc catttgcaaa aagccgttta aggcgatcgt gcccgagtac atgatcgtct cgcgcagctc gtagttctct
aagtcgtcaa ccaattttgg cgccgcctca atgaccgttt ttaacactgc ctcgcacatc cggtcttgca gcggcgtgtt
cggcgtatga tggaaatatt gctcaaacac atgggacatc atatcgacga tgccgtaaac ggtatggtct ttcggcaccg
tcatcgtgta cgtcggatcc aaaatcgaaa attgcgggaa tgtcaccggg ctgccccagc cgtattttc tttcgtctcc
caattggtga tcaccgatcc ggcgttcatt tccgagccgg tcgctgccag cgtcaggacc gtcccaaacg gcaacgcctc
agtgacagtc gctttttcg taatgaactc ccacggatcg ccatcaaact tcgcgccggc tgcaatcgct ttcgtacagt
cgatcacact gccgccgcca acggcaagca aaaattcaat tccttcccgt ctgcaaatgt ctacccctttt tttgacggtc
gaaaggcgcg ggtcggttc gacgcctggc agttcaacga cttcggcgcc aatgtccgtc aataggctca tgacttcatc
atatagtccg tttcgtttaa tgctgccgcc cccatagaca agcagcactt ttttgccata tttcggcact tcttctttga
gctgctcaat ttgtcctctc ccaaaaatga gtttggtcgg attgcgaaac gtaaaatttt gcat
```

1.1.4 Selection and Optimization of Engineered Strains

The engineered strain is cultured continuously via any of several methods, including chemostat, pH-auxostat, or serial batch transfer, to select for naturally occurring mutations that impart a benefit upon cellular growth and 1-hexadecanol formation. Because ATP generation and NAD(P)H regeneration are both coupled to 1-hexadecanol formation in the engineered strain, evolutionary forces will select for cells that are better able to carry out this conversion.

1.1.5 Detection of 1-Hexadecanol 1-hexadecanol formation in cultured engineered strains is detected via gas chromatography-mass spectrometry (GC/MS) with or without an extraction step prior to analysis. See Steen et al., *Nature* 463:559-562 (2010); Aldai et al., *Journal of Chromatography* 1110:133-139 (2006).

Example 2

2.1 Diverting Central Metabolic Flux Through Oxaloacetate in *E. coli*

Figure 9:
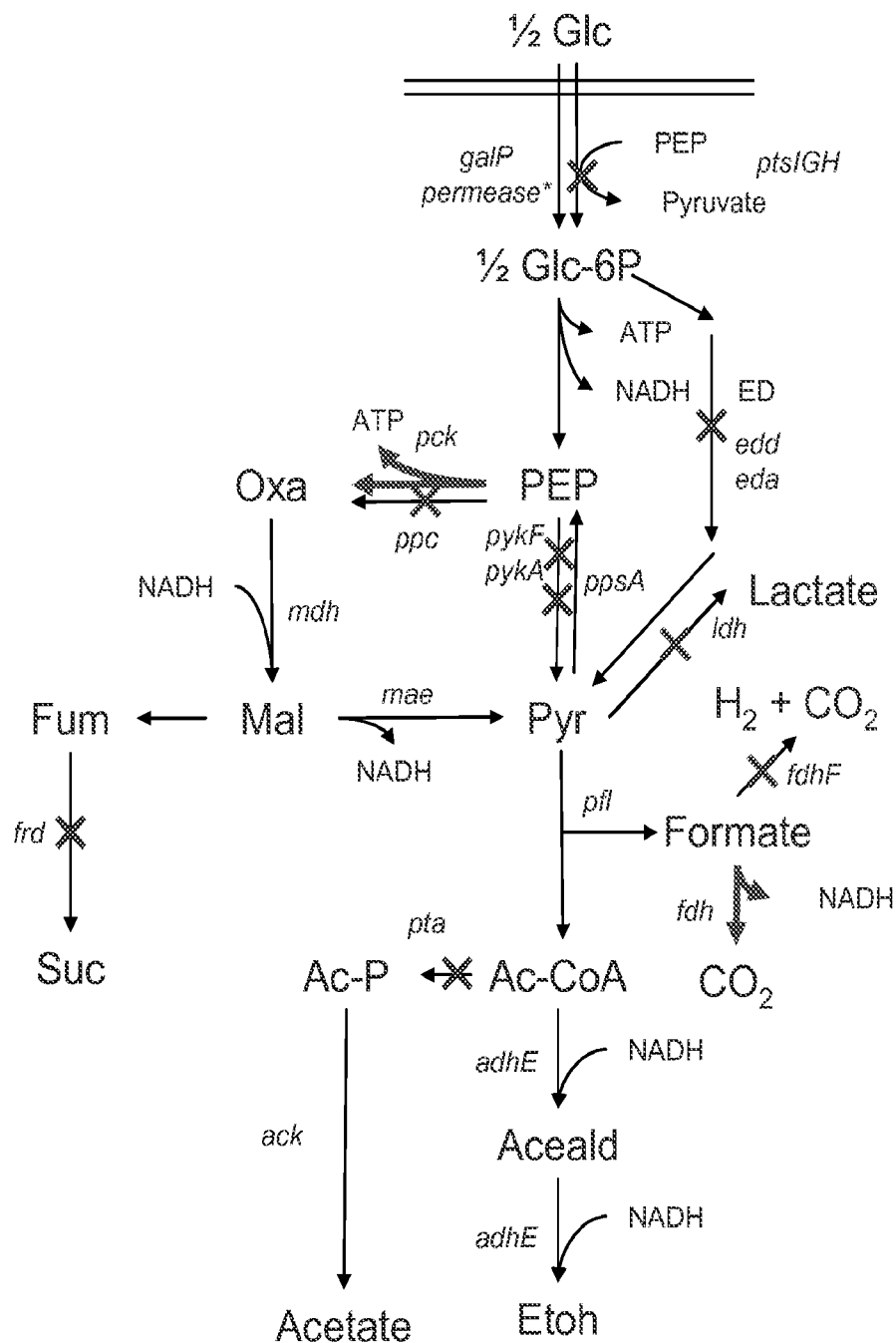
FIG. 9 depicts gene knockout and overexpression strategy to route anaerobic central metabolic flux through oxaloacetate as a key intermediate. Abbreviations: Glc—glucose, Glc-6P—glucose-6-phosphate, PEP—phosphoenolpyruvate, Oxa—oxaloacetate, Fum—fumarate, Mal—malate, Pyr—pyruvate, Ac-CoA—acetyl-CoA, Ac-P—acetyl-phosphate, Aceald—acetaldehyde, Etoh—ethanol.

This example describes engineering the central metabolic flux in *Escherichia coli* so that the majority of glycolytic flux passes from phosphoenolpyruvate to oxaloacetate rather than from phosphoenolpyruvate to pyruvate. See FIG. 9. This is accomplished via a series of gene deletions that inactivate competing pathways and gene overexpressions that activate desired pathways. Target genes are shown in Table 4. A set of minimal target gene deletions is shown in Table 5.

TABLE 4

Targets for Gene Inactivation

| E. coli gene name | description | locus tag[a] |
|---|---|---|
| edd | 6-phosphogluconate dehydratase | b1851 |
| ldhA | lactate dehydrogenase | b1380 |
| pta | phosphate acetyltransferase | b2297 |
| adhE | acetaldehyde dehydrogenase/alcohol dehydrogenase | b1241 |
| frdABCD | fumarate reductase (anaerobic) | b4151-b4154 |
| fdhF | formate dehydrogenase-H | b4079 |
| ppc | phosphoenolpyruvate carboxylase | b3956 |
| pykA | pyruvate kinase | b1854 |
| pykF | pyruvate kinase | b1676 |
| mdh | malate dehydrogenase | b3236 |
| maeA | malic enzyme NADH | b1479 |
| maeB | malic enzyme NADPH | b2463 |
| fadE | acyl coenzyme A dehydrogenase | b0221 |
| ptsI | PEP-protein phosphotransferase of PTS system | b2416 |
| pflB | pyruvate formate lyase | b0903 |
| aceEF | pyruvate dehydrogenase | b0114 |
| poxB | pyruvate oxidase | b0871 |
| mgsA | methylglyoxal synthase | b0963 |
| ppsA | phosphoenolpyruvate synthase | b1702 |

[a]locus tag numbers are given for the genome sequence of E. coli MG1655, which can be accessed via Genbank (Accession No. U00096) or the Kyoto Encyclopedia of Genes and Genomes (KEGG).

TABLE 5

Minimal Targets for Gene Inactivation

| gene name | description | locus tag |
|---|---|---|
| ldhA | lactate dehydrogenase | b1380 |
| pta | phosphate acetyltransferase | b2297 |
| adhE | acetaldehyde dehydrogenase/alcohol dehydrogenase | b1241 |
| pykA | pyruvate kinase | b1854 |
| pykF | pyruvate kinase | b1676 |
| mdh | malate dehydrogenase | b3236 |
| ptsI | PEP-protein phosphotransferase of PTS system | b2416 |

2.1.1 Deletion and Overexpression of Target Genes

Figure 11:
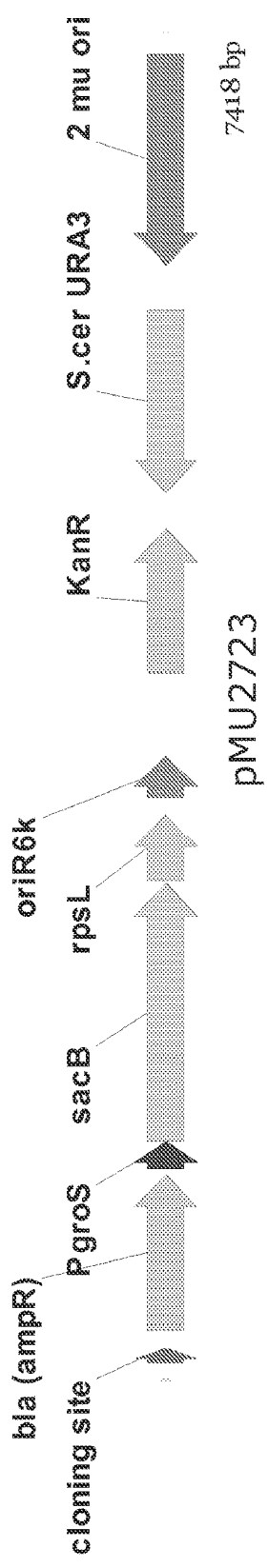
FIG. 11 depicts the vector pMU2723 used to construct gene knockouts and chromosomal integrations in *E. coli*.

In order to perform gene modifications (either deletion or overexpression) in *E. coli* to redirect metabolic flux through oxaloacetate, 500 bp to 2000 bp flanking regions upstream and downstream of a target gene were amplified via PCR using primers (Table 6) and ligated into pMU2723 (FIG. 11) using standard molecular biology methods. See Shanks et al., *AEM* 72: 5027-5036 (2006). The pta::fdh and Pspc pckA promoter exchange modifications were performed by placement of the heterologous DNA (fdh or Pspc) between the two homologous flanking regions of the target gene, with appropriate design to allow either expression of fdh from the native pta promoter, or heterologous expression of the native pckA4 gene. The protocol used is described briefly below.

The starting strain, M2162 or subsequent progeny, was grown overnight in 8 mL of LB medium at 37° C. Two 500 mL baffled flasks, each containing 150 mL of LB, were pre-incubated at 37° C. and then inoculated with 2 mL of the overnight culture. These cultures were incubated at 37° C. with shaking until the OD reached 0.5 to 0.8 (checked OD every 20 min. after 2 hrs). The flasks were then placed in an ice bath for about 15 minutes after which the cultures were transferred to six 50 mL conical tubes. The tubes were spun at 4000 rpm for 8 minutes in a clinical swinging bucket centrifuge at 4° C. Following centrifugation, the supernatant was removed, about 10 mL of ice cold water was added to each tube, and the pellets were resuspended and transferred to two 50 mL tubes which were balanced to 50 mL with ice cold water. The tubes were centrifuged for 8 minutes in the conditions described above. The supernatants were removed and the pellets were resuspended with about 200 µL of cold water, after which 80 µL of the resuspended cells were transferred to a cold 1 mm gap cuvette which contained 2-4 µL of pre-added plasmid DNA targeting the gene of interest. The cuvette was electropulsed using an exponential decay pulse, 1.8 kV voltage, 25 µF capatance, 200Ω resistance, and a 1 mm gap cuvette method. 1 mL of SOC medium was added to the cuvette and the entire volume was then transferred to a 14 mL falcon tube and incubated at 37° C. for 1 hour. 250 µL of cells were removed, plated on LB plates containing 50 µg/mL kanamycin, and incubated at 37° C. for 24-48 hours. Colony PCR was performed on kanamycin resistant colonies using one internal and one external primer to the site of integration with primers listed in Table 8. Two positive colonies we re-streaked on 50 µg/mL kanamycin plates and incubated overnight at 37° C. Two colonies were selected and grown in 5 mL of LB medium, either for 8 hours or overnight at 37° C. Serial dilutions of 1:10, 1:100, and 1:1000 of each LB culture were prepared, and 20 µL of each dilution was plated on 10% w/v sucrose+500 µg/mL streptomycin plates. The plates were incubated overnight at either 37° C. or 42° C. Colony PCR was performed on 7 colonies from each initial LB culture with two primers, as listed in Table 8, external to the site of integration. Two positive colonies were re-streaked on 500 µg/mL streptomycin plates and incubated at 37° C. overnight. One colony from each plate was selected and re-patched on a kanamycin 50 µg/mL plate and a streptomycin 500 µg/mL plate. The patches that grew on the streptomycin but not the kanamycin plates were then used to make culture collection stocks.

TABLE 6

Primers Used to Create Gene Deletion and Gene Overexpression Plasmids for Routing Metabolic Flux Through Oxaloacetate

| Primer # | SEQ ID NO: | Primer sequence | Description |
|---|---|---|---|
| X12312 | 90 | TTTTGTCTGTCTTAATTTTTGGTATCATTATAGGATCTATGTAACCCAGGAAGCGGCAA | pta 1 |
| X12313 | 91 | ACGAGATTACTGCTGCTGTGCAGACTTTGCGTTCCATTGCACGGATCA | pta 2 |
| X12314 | 92 | TGATCCGTGCAATGGAACGCAAAGTCTGCACAGCAGCAGTAATCTCGT | pta 3 |
| X12315 | 93 | GATAACAATTTCACACAGGAAACAGCTATGACCATACGGCCTCTTCTCCCATACCGGT | pta 4 |

TABLE 6-continued

Primers Used to Create Gene Deletion and Gene Overexpression
Plasmids for Routing Metabolic Flux Through Oxaloacetate

| Primer # | SEQ ID NO: | Primer sequence | Description |
|---|---|---|---|
| X12316 | 94 | TTTTGTCTGTCTTAATTTTTGGTATCATTATAGGAACGCAGTTGCTGGATATCAGAGGT | ldh 1 |
| X12317 | 95 | TACTGGTCAGAGCTTCTGCTGTCAACTCGTTCACCTGTTGCAGGTACT | ldh 2 |
| X12318 | 96 | AGTACCTGCAACAGGTGAACGAGTTGACAGCAGAAGCTCTGACCAGTA | ldh 3 |
| X12319 | 97 | GATAACAATTTCACACAGGAAACAGCTATGACCATTTGGGATGTGTGCATTACCCAACG | ldh 4 |
| X12320 | 98 | TTTTGTCTGTCTTAATTTTTGGTATCATTATAGGATACTGGTAAACGTCTGCCGACCAA | edd 1 |
| X12321 | 99 | ACAGCTTAGCGCCTTCTACAGCTTCGCGCGAACGTTCAATGATTCGAT | edd 2 |
| X12322 | 100 | ATCGAATCATTGAACGTTCGCGCGAAGCTGTAGAAGGCGCTAAGCTGT | edd 3 |
| X12323 | 101 | GATAACAAT1TCACACAGGAAACAGCTATGACCATGCTGACATTGGCTATCCCTGCATT | edd 4 |
| X12324 | 102 | TTTTGTCTGTCTTAATTTTTGGTATCATTATAGGAGCGGGTCAATTTCCAGATAACGCA | frd 1 |
| X12325 | 103 | TCAGGAACAGGAATACGCGACCAAGATCGGCTTGAAAGGTTTGCACGA | frd 2 |
| X12326 | 104 | TCGTGCAAACCTTTCAAGCCGATCTTGGTCGCGTATTCCTGTTCCTGA | frd 3 |
| X12327 | 105 | GATAACAATTTCACACAGGAAACAGCTATGACCATGCGAAACATGCACTGCCTTACCTT | frd 4 |
| X12328 | 106 | TTTTGTCTGTCTTAATTTTTGGTATCATTATAGGATGGACCGAATGGACGATGGAGTTT | pfl 1 |
| X12329 | 107 | AGAATGCCTTTCACGCGTTCCATGTCGTTGCTTTATAGACACCCGCCT | pfl 2 |
| X12330 | 108 | AGGCGGGTGTCTATAAAGCAACGACATGGAACGCGTGAAAGGCATTCT | pfl 3 |
| X12331 | 109 | GATAACAATTTCACACAGGAAACAGCTATGACCATTTCCGTTAACGATACGCTTCGGGT | pfl 4 |
| X12332 | 110 | TTTTGTCTGTCTTAATTTTTGGTATCATTATAGGAATTCAAACGTTATGCCCGACGCTG | ppc 1 |
| X12333 | 111 | AGCGGGTCGGTGTAAATATTCCGTTCCTTGATGGTTTCTCCCAGCACT | ppc 2 |
| X12334 | 112 | AGTGCTGGGAGAAACCATCAAGGAACGGAATATTTACACCGACCCGCT | ppc 3 |
| X12335 | 113 | GATAACAATTTCACACAGGAAACAGCTATGACCATTTGAAATTAGCCAGTGGCGGCAAG | ppc 4 |
| X12336 | 114 | TTTTGTCTGTCTTAATTTTTGGTATCATTATAGGACAGCCGCTACATTAAAGGCACCAA | ptsI 1 |
| X12337 | 115 | CCAGCAGCGGCAGATCAAATTCAATGGCGGTTCGACTTTAGCCTGTAT | ptsI 2 |
| X12338 | 116 | ATACAGGCTAAAGTCGAACCGCCATTGAATTTGATCTGCCGCTGCTGG | ptsI 3 |
| X12339 | 117 | GATAACAATTTCACACAGGAAACAGCTATGACCATATGGTTTAGCGGCTATTTGCGTGC | ptsI 4 |
| X12340 | 118 | TTTTGTCTGTCTTAATTTTTGGTATCATTATAGGATGGCGAATGGCACTCCCTATGTTA | pykA 1 |
| X12341 | 119 | TGACAATCACCAGGTCACCAGACATCCGAATGAAATAACGCCGCGATG | pykA 2 |
| X12342 | 120 | CATCGCGGCGTTATTTCATTCGGATGTCTGGTGACCTGGTGATTGTCA | pykA 3 |
| X12343 | 121 | GATAACAATTTCACACAGGAAACAGCTATGACCATTGTTGATGAGATGTTTGCCACCGC | pykA 4 |
| X12344 | 122 | TTTTGTCTGTCTTAATTTTTGGTATCATTATAGGAATGCTGTACGTAATACGCCTGCGA | pykF 1 |

TABLE 6-continued

Primers Used to Create Gene Deletion and Gene Overexpression
Plasmids for Routing Metabolic Flux Through Oxaloacetate

| Primer # | SEQ ID NO: | Primer sequence | Description |
|---|---|---|---|
| X12345 | 123 | TCTTTAACAAGCTGCGGCACAACGATGGGAGAAACTTGCTTTCTGGGC | pykF 2 |
| X12346 | 124 | GCCCAGAAAGCAAGTTTCTCCCATCGTTGTGCCGCAGCTTGTTAAAGA | pykF 3 |
| X12347 | 125 | GATAACAATTTCACACAGGAAACAGCTATGACCATATCTTTAGCAGCCTGAACGTCGGA | pykF 4 |
| X13802 | 126 | TTATAGGTTAATGTCATGATAATAATGGTTTCTTCCGTCAAAGGGCAAATCACCGAAA | fdhF 1 |
| X13803 | 127 | GGGTTCCGCGCACATTTCCCCGAAAAGTGCCACCACTCGGAATAACCGGTTCGGGAAA | fdhF 2 |
| X13804 | 128 | CGCCTTCTATCGCCTTCTTGACGAGTTCTTCTGATACGACAAAGCGTTCGTCGCTTCA | fdhF 3 |
| X13805 | 129 | ACTGTTGGGAAGGGCGATCGGTGCGGGCCTCTTCGAATGAAGCCCAGTTCGCCCATTT | fdhF 4 |
| X14576 | 130 | TTATAGGTTAATGTCATGATAATAATGGTTTCTTGCGGATGCGAAGGCTTTGTTGTAT | Pspc pckA 1 |
| X14577 | 131 | TGGGTAGAAAAAATAAACGGCTCAGATTCCTGTCACGAAACGGTTGCT | Pspc pckA 2 |
| X14578 | 132 | AGCAACCGTTTCGTGACAGGAATCTGAGCCGTTTATTTTTTCTACCCA | Pspc pckA 3 |
| X14579 | 133 | GGTCAAACCATTGTTAACGCGCATTTTAGTGCTCCGCTAATGTCAACT | Pspc pckA 4 |
| X14580 | 134 | AGTTGACATTAGCGGAGCACTAAAATGCGCGTTAACAATGGTTTGACC | Pspc pckA 5 |
| X14581 | 135 | GGGTTCCGCGCACATTTCCCCGAAAAGTGCCACCTAGAAGCGATACCTTTCAGCGGCA | Pspc pckA 6 |
| X14588 | 136 | TTATAGGTTAATGTCATGATAATAATGGTTTCTTTCTATGTAACCCAGGAAGCGGCAA | pta::fdh3 1 |
| X14589 | 137 | TGGGTAGAAAAAATAAACGGCTCACTTTGCGTTCCATTGCACGGATCA | pta::fdh3 2 |
| X14590 | 138 | TGATCCGTGCAATGGAACGCAAAGTGAGCCGTTTATTTTTTCTACCCA | pta::fdh3 3 |
| X14591 | 139 | ATAAAGAACTAAGACAATCTTCATTTTAGTGCTCCGCTAATGTCAACT | pta::fdh3 4 |
| X14592 | 140 | AGTTGACATTAGCGGAGCACTAAAATGAAGATTGTCTTAGTTCTTTAT | pta::fdb3 5 |
| X14593 | 141 | ACGAGATTACTGCTGCTGTGCAGACTATTTCTTATCGTGTTTACCGTA | pta::fdh3 6 |
| X14594 | 142 | TACGGTAAACACGATAAGAAATAGTCTGCACAGCAGCAGTAATCTCGT | pta::fdh3 7 |
| X14595 | 143 | GGGTTCCGCGCACATTTCCCCGAAAAGTGCCACCACGGCCTCTTCTCCCATACCAAAT | pta::fdh3 8 |
| X15570 | 144 | TTATAGGTTAATGTCATGATAATAATGGTTTCTTGCGATCCGTAGCAGACACCATAA | maeA 1 |
| X15571 | 145 | GAATACTGCGCCAGCGTTTCACTTCGTTCCGCTTGTTCTTCGATGGTT | maeA 2 |
| X15572 | 146 | AACCATCGAAGAACAAGCGGAACGAAGTGAAACGCTGGCGCAGTATTC | maeA 3 |
| X15573 | 147 | GGGTTCCGCGCACATTTCCCCGAAAAGTGCCACCCATCAATGGCGATCACTTTGGCGT | maeA 4 |
| X15574 | 148 | TTATAGGTTAATGTCATGATAATAATGGTTTCTTAATTGACCGCCAGTTTGTCACACG | maeB 1 |
| X15575 | 149 | TCGCCGTGCAITTCACCATCAATCGAGCGCGGCGACAACTTCAATAAA | maeB 2 |
| X15576 | 150 | TTTATTGAAGTTGTCGCCGCGCTCGATTGATGGTGAAATGCACGGCGA | maeB 3 |
| X15577 | 151 | GGGTTCCGCGCACATTTCCCCGAAAAGTGCCACCGCCATAAATCACCAATGCACCGCT | maeB 4 |
| X15578 | 152 | TTATAGGTTAATGTCATGATAATAATGGTTTCTTCAGCTGGCAGGCAGTAAACCATTT | mdh 1 |
| X15579 | 153 | TCAAATGCGCTCAGGGTACCGATATTCTGAACCTGAAGGCAGTTGGGT | mdh 2 |

TABLE 6-continued

Primers Used to Create Gene Deletion and Gene Overexpression Plasmids for Routing Metabolic Flux Through Oxaloacetate

| Primer # | SEQ ID NO: | Primer sequence | Description |
|---|---|---|---|
| X15580 | 154 | ACCCAACTGCCTTCAGGTTCAGAATATCGGTACCCTGAGCGCATTTGA | mdh 3 |
| X15581 | 155 | GGGTTCCGCGCACATTTCCCCGAAAAGTGCCACCACTGGCGGTTTACCTACCATTCCA | mdh 4 |
| X15586 | 156 | TTATAGGTTAATGTCATGATAATAATGGTTTCTTTCGACATCGCTATTGTCACCACCA | adhE 1 |
| X15587 | 157 | TTTCGGAAGTTTGTGCCACAACATAATGCTCTCCTGATAATGTTAAAC | adhE 2 |
| X15588 | 158 | GTTTAACATTATCAGGAGAGCATTATGTTGTGGCACAAACTTCCGAAA | adhE 3 |
| X15589 | 159 | GGGTTCCGCGCACATTTCCCCGAAAAGTGCCACCCCAAGTGGTCGGCAATTTCAGCAT | adhE 4 |

Figure 10:
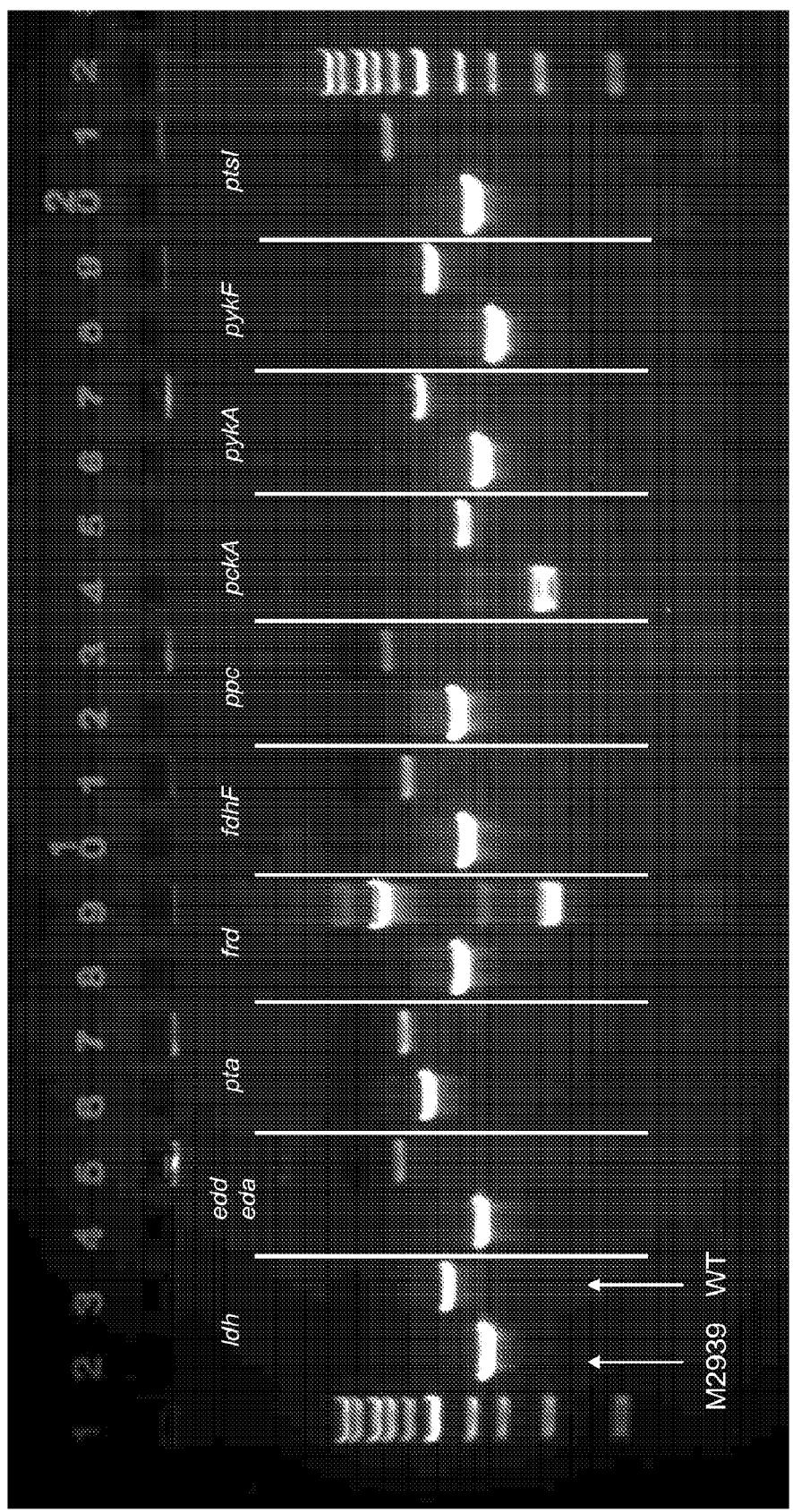
FIG. 10 is an agarose gel image showing deletions and overexpressions of target genes in the *E. coli* chromosome to redirect metabolic flux through oxaloacetate.

Gene modifications were confirmed on an agarose gel. See FIG. 10 and Table 7. Primers external to each region of interest were used to amplify DNA (Table 8), which was subsequently run on an agarose gel and stained with ethidium bromide to visualize DNA length. The ladder shown in lanes 1 and 22 of FIG. 10 is New England Biolabs 1 kb. DNA was amplified from strains M2939 (deletion and overexpression strain) and M2162 (wildtype). See Table 9 for a description of the bacterial strains.

TABLE 7

Predicted Size of Wildtype and Modified Target Genes

| Target | WT length (bp) | KO length (bp) |
|---|---|---|
| ldhA | 2686 | 1855 |
| ldhA | 2686 | 1855 |
| edd | 4343 | 1931 |
| pta::fdh | 3992 | 3186 |
| frd | 5358 | 2241 |
| fdhF | 3927 | 2141 |
| ppc | 4739 | 2321 |
| pckA (promoter exchange) | 2003 | 1053/958* |
| pykA | 3204 | 1803 |
| pykF | 2863 | 1594 |
| ptsI | 4418 | 1938 |

*after psiI restriction digest of PCR product to distinguish the wildtype (2003 bp) and promoter exchange (2011 bp) alleles.

TABLE 8

Primers Used to Verify Genome Alterations

| Primer # | SEQ ID NO: | Primer sequence | Description |
|---|---|---|---|
| X12354 | 160 | TTGCTGTATTTGACACCGCGTTCC | pta ext 1 |
| X12355 | 161 | TTTCACGAAAGAAGCGGTCGGACT | pta ext 2 |
| X12356 | 162 | GGCAAGTTTAACGTCGCAGTAGCA | ldh ext 1 |
| X12357 | 163 | TTTATGGCGGTGTCGTTTGGCTTG | ldh ext 2 |
| X12358 | 164 | ATATCTGGAAGAAGAGGGCGCGAA | edd ext 1 |
| X12359 | 165 | GATGCATTACGCCGTGTGGTTGAA | edd ext 2 |
| X12360 | 166 | AACAGCAATTGTAGCAGCGTGTCG | frd ext 1 |
| X12361 | 167 | TTGTTTGCCAGCATCACGATACCC | frd ext 2 |

TABLE 8-continued

Primers Used to Verify Genome Alterations

| Primer # | SEQ ID NO: | Primer sequence | Description |
|---|---|---|---|
| X12362 | 168 | CTGGGCGTTTATGCTTGCCGTATT | pfl ext 1 |
| X12363 | 169 | AGTCGTCAGTTGTGAGCTCGACTT | pfl ext 2 |
| X12364 | 170 | TATTCACGGTGGCGACGCTTCTAA | ppc ext 1 |
| X12365 | 171 | CGCCTGTTGCAGGATTTCAATGGT | ppc ext 2 |
| X12366 | 172 | AAAGCGTTAGGTGCAAACCTGGTG | pts ext 1 |
| X12367 | 173 | ATTGCCGTGCCTGCTATCAAACAG | pts ext 2 |
| X12368 | 174 | GCTATGGCACTGGAAGCCAATGTT | pykA ext 1 |
| X12369 | 175 | AGAACGTAGTGAAGCTGAACGCGA | pykA ext 2 |
| X12370 | 176 | TGAAGCTTACCGCCTCATCCTGAA | pykF ext 1 |
| X12371 | 177 | AGAATGGTGAACCAGAGCAAGGGA | pykF ext 2 |
| X12801 | 178 | GATTGATTACGCGGTGAAAGCGCA | fdh ext 1 |
| X12802 | 179 | ACACCCGGTATCAAACCCTTCCAT | fdh ext 2 |
| X14574 | 180 | CCGTGGCGATTAACGTGAACAACT | pckA ext 1 |
| X14575 | 181 | AGTCGATAGTGCCATCTTCACGCA | pckA ext 2 |
| X15590 | 182 | ACTGTTCCCTTCCCGCGTTTGATA | maeA ext 1 |
| X15591 | 183 | GCATCAACTGCCGAGTTAAACGCA | maeA ext 2 |
| X15592 | 184 | AGGTCGAAGCCAGCTTGATCAGAA | maeB ext 1 |
| X15593 | 185 | CGCTGACGGTTTGTGATAACGCTT | maeB ext 2 |
| X15594 | 186 | TACCTTCTGCTTTGCCCAGTGAGT | mdh ext 1 |
| X15595 | 187 | TGAAGCATTGCTGGTGGGATCTGA | mdh ext 2 |
| X15596 | 188 | AGTGGCACCACACCAATGCTTTCA | adhE ext 1 |
| X15597 | 189 | TGAACGCCAGCTTCACGGATAGAT | adhE ext 2 |

TABLE 8-continued

Primers Used to Verify Genome Alterations

| Primer # | SEQ ID NO: | Primer sequence | Description |
|---|---|---|---|
| X13673 | 300 | ATACGGGATAATACCGCGCCACAT | internal 1 |
| X13674 | 301 | CCATTCGACCACCAAGCGAAACAT | internal 2 |

TABLE 9

Lineage of Strains From M2162 to M2939

| M number | Genotype | Parent |
|---|---|---|
| M2162 | strepR | MG1655 |
| M2264 | strepR, Δedd Δeda | M2162 |
| M2273 | strepR, Δedd Δeda Δldh | M2264 |
| M2348 | strepR, Δedd Δeda Δldh Δppc | M2273 |
| M2371 | strepR, Δedd Δeda Δldh Δppc ΔfdhF | M2348 |
| M2379 | strepR, Δedd Δeda Δldh Δppc ΔfdhF Δfrd | M2371 |
| M2492 | strepR, Δedd Δeda Δldh Δppc ΔfdhF Δfrd ΔPpckA::Pspc pckA | M2379 |
| M2590 | strepR, Δedd Δeda Δldh Δppc ΔfdhF Δfrd ΔPpckA::Pspc pckA Δpta::fdh3 | M2492 |
| M2645 | strepR, Δedd Δeda Δldh Δppc ΔfdhF Δfrd ΔPpckA::Pspc pckA Δpta::fdh3 ΔpykF | M2590 |
| M2698 | strepR, Δedd Δeda Δldh Δppc ΔfdhF Δfrd ΔPpckA::Pspc pckA Δpta: fdh3 ΔpykF ΔpykA | M2645 |
| M2939 | strepR, Δedd Δeda Δldh Δppc ΔfdhF Δfrd ΔPpckA::Pspc pckA Δpta::fdh3 ΔpykF ΔpykA ΔptsI | M2909 |

2.2 Creating a Balanced Reduction/Oxidation Pathway During Anaerobic Fatty Acid Production Reduction and oxidation (redox) reactions play a key role in catabolic metabolism, allowing the transfer of electrons from one compound to another, and in the process, creating free energy for use elsewhere in cellular metabolism. To facilitate transfer of electrons from one compound to another, cells use redox co-factors to shuttle electrons. Several compounds and proteins can function as redox co-factors—the most relevant for anaerobic growth on carbohydrates are the nicotinamide adenine dinucleotides NADH and NADPH, and the iron-sulfur protein Ferredoxin (Fd).

Since NADH, NADPH, and Fd function as electron shuttles, they must discharge as many electrons as they accept, i.e., their net electron accumulation is zero. Catabolic metabolism can be thought of in two parts: carbohydrate deconstruction, where electrons are placed onto redox co-factors, and end-product construction, where electrons are removed from redox co-factors. In order for a metabolic pathway to function efficiently and at high yield, the type of co-factors used in carbohydrate deconstruction must balance those used in end product construction.

During carbohydrate deconstruction, which in the anaerobic fatty acid pathway ultimately results in acetyl-CoA, electrons are removed at two steps: the conversion of glyceraldehyde-3-phosphate to 1,3-biphosphoglycerate+2e$^-$ and the conversion of pyruvate to acetyl-CoA+$CO_2$+2e$^-$. In *E. coli*, NAD+ is used as electron acceptor for the first conversion. For the second conversion, *E. coli* employs a NAD+ linked pyruvate dehydrogenase during aerobic growth, and pyruvate formate lyase (pfl) and a formate dehydrogenase directly linked to hydrogen production (fdhF) to produce formate or $H_2$ from the 2e$^-$ removed from pyruvate.

*E. coli* strains have been engineered to produce ethanol from acetyl-CoA at high yield via anaerobic expression of pyruvate dehydrogenase (PDH) (Kim et al., *AEM* 73: 1766-1771 (2007)) or via heterologous expression of NAD+ formate dehydrogenase (Berríos-Rivera et al., *Met Eng* 4:217-229 (2002)). In both wildtype and these engineered *E. coli* strains, NADH is the primary redox co-factor.

In contrast, the electron accepting reactions of fatty acid elongation require either exclusively NADPH or 1:1 stoichiometric levels of NADPH and NADH, depending on the co-factor specificity (NADPH or NADH) of enoyl-ACP reductase.

In order to balance the NADPH necessary for fatty acid elongation, the redox enzymes involved in carbohydrate deconstruction should be engineered to produce NADPH. In Table 10 below, different redox enzyme systems are described that can produce, per ½ glucose molecule, 2 NADH, 1 NADH and 1 NADPH, or 2 NADPH. Use of one of these systems in a host microorganism, or a combination thereof, will allow for an overall balanced co-factor pathway for anaerobic fatty acid production. In addition to, or instead of, using these systems, the enzymes can be modified to have different cofactor specifities.

TABLE 10

Enzymes for an overall balanced co-factor pathway for anaerobic fatty acid production

| FIG. 32 | Carbohydrate deconstruction reactions | Redox enzymes | NADH | NADPH |
|---|---|---|---|---|
| A | ½ glucose -> acetyl-CoA + $CO_2$ + 4e$^-$ | NAD+ GAPDH, PDH | 2 | 0 |
| B | ½ glucose -> acetyl-CoA + $CO_2$ + 4e$^-$ | NAD+ GAPDH, PFL, NAD+ FDH | 2 | 0 |
| C | ½ glucose -> acetyl-CoA + $CO_2$ + 4e$^-$ | NAD+ GAPDH, PFL, NADP+ FDH | 1 | 1 |
| D | ½ glucose -> acetyl-CoA + $CO_2$ + 4e$^-$ | NAD+ GAPDH, PNO | 1 | 1 |
| E | ½ glucose -> acetyl-CoA + $CO_2$ + 4e$^-$ | NADP+ GAPDH, PFL, NAD+ FDH | 1 | 1 |
| F | ½ glucose -> acetyl-CoA + $CO_2$ + 4e$^-$ | NADP+ GAPDH, PFL, NADP+ FDH | 0 | 2 |
| G | ½ glucose -> acetyl-CoA + $CO_2$ + 4e | NAD+ GAPDH, POR, Fd, NFN | 0 | 2 |
| H | ½ glucose -> acetyl-CoA + $CH_2O_2$ + 2e$^-$ | NAD+ GAPDH, PFL | 1 | 0 |
| | End product construction reactions | Redox enzymes | NAD+ | NADP+ |
| I | acetyl-CoA + 4e$-$ + acyl$_{(n)}$-ACP -> acyl$_{(n+2)}$-ACP | FabG (NADPH), FabI (NADH) | 1 | 1 |
| J | acetyl-CoA + 4e$-$ + acyl$_{(n)}$-ACP -> acyl$_{(n+2)}$-ACP | FabG (NADPH), FabI (NADPH) | 0 | 2 |

TABLE 10-continued

Enzymes for an overall balanced co-factor pathway for anaerobic fatty acid production

| | | | | |
|---|---|---|---|---|
| K | acyl$_{(n+2)}$-ACP + 4e– -> acyl alcohol (fatty alcohol) | AcDH, ADH | 0-2 | 0-2 |
| L | acyl$_{(n+2)}$-ACP + H$_2$O -> acyl acid (fatty acid) + 2 CH$_2$O$_2$ | BTE | 0 | 0 |

Abbreviations:
GAPDH—glycerol-3-phosphosate dehydrogenase,
PFL—pyruvate formate lyase,
PDH—pyruvate dehydrogenase,
PNO—pyruvate:NADP+ oxidoreductase,
POR—pyruvate:ferredoxin oxidoreductase,
Fd—ferredoxin,
NFN—NADH ferredoxin:NADP+oxidoreductase,
FabG—β-ketoacyl-ACP reductase,
FabI enoylacyl-ACP reductase,
AAR—acyl-ACP reductase,
ADH—alcohol dehydrogenase,
BTE—acyl-ACP thioesterase,
AdhE—bifunctional acetaldehyde/alcohol dehydrogenase.

Figure 12:
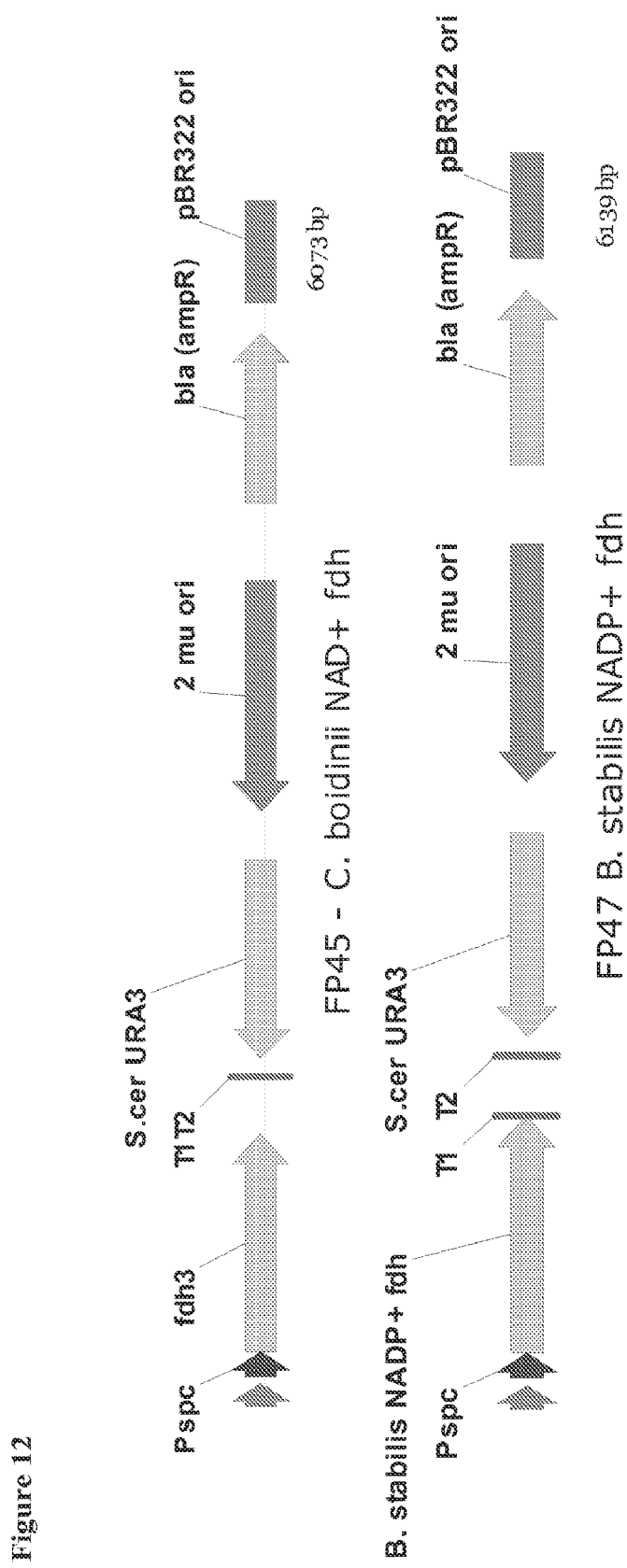
FIG. 12 depicts vectors FP45, FP47, FP66, FP67, FP68, and FP75, which are examples of heterologous redox enzymes designed for expression in *E. coli* to modify the native carbohydrate deconstruction pathway.
Figure 12:
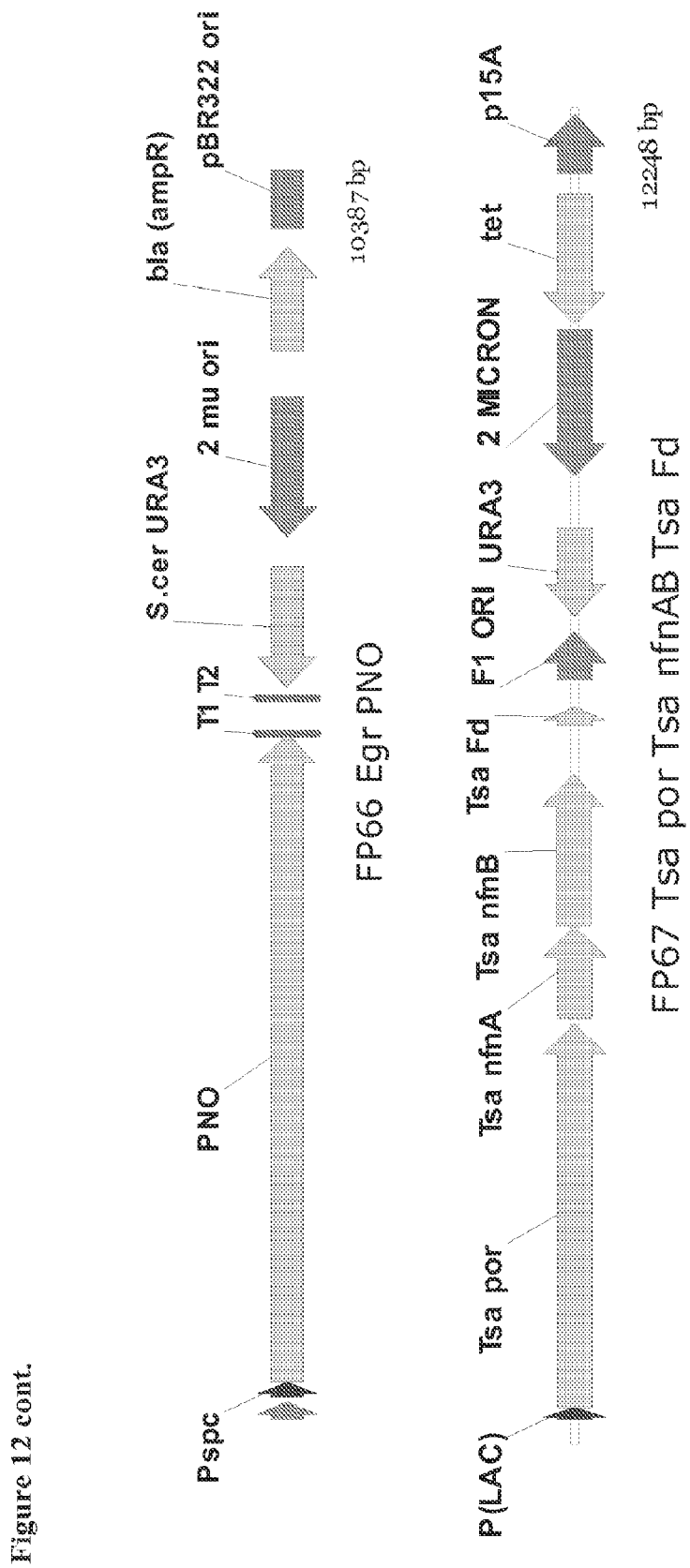
Figure 12:
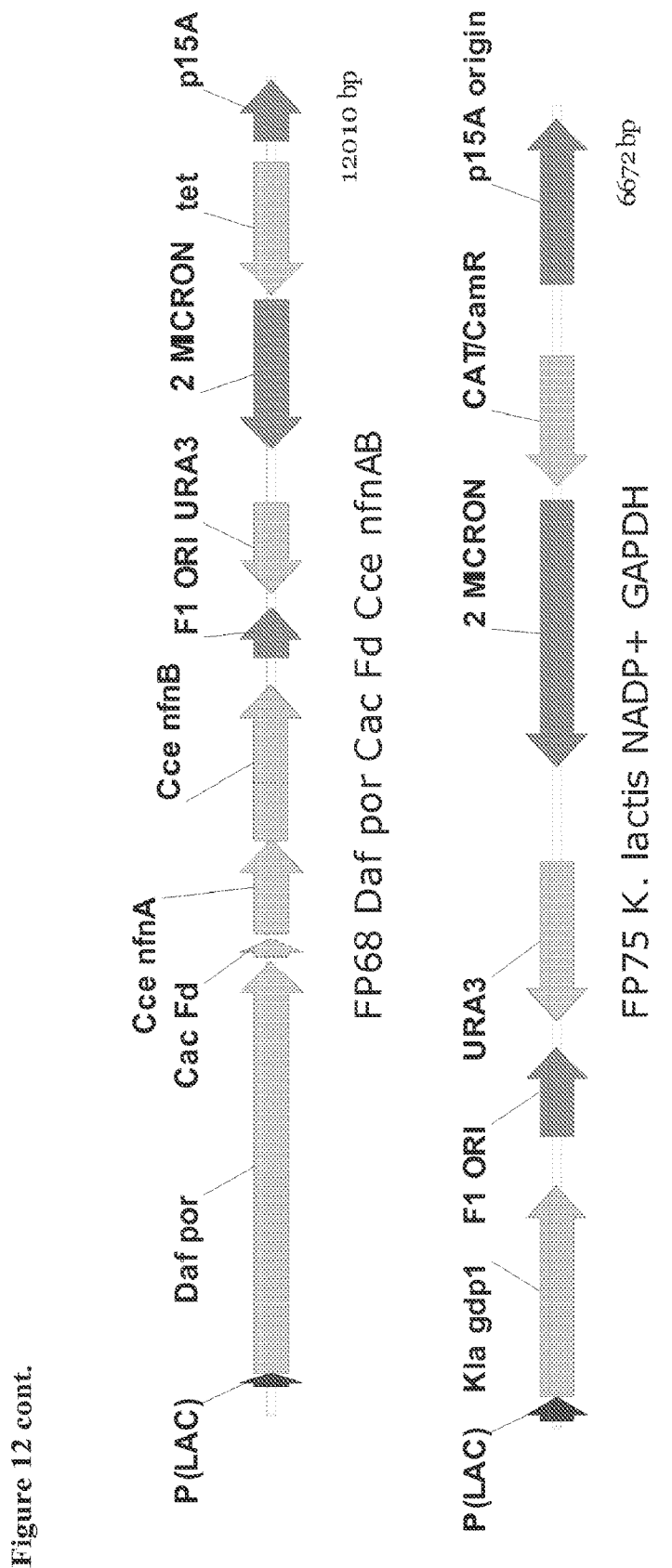

Enzymes used in the carbohydrate deconstruction reactions can be cloned into plasmids for expression in a host strain. For example, plasmids FP45, FP47, FP66, FP67, FP68, and FP75 are examples of heterologous redox enzymes designed for expression in E. coli to modify the native carbohydrate deconstruction pathway. See FIG. 12. Genes or gene operons are cloned under expression of either the constitutively active Pspc ribosomal promoter or the inducible Plac promoter. Cloning was performed via PCR amplification, using the primers listed in Table 11, or direct DNA synthesis of the desired gene products, followed by yeast gap-repair cloning with 30-60 bp homologous flanking regions. See Shanks et al., AEM 72:5027-5036 (2006). Transformed yeasts were selected via growth on SD-ura minimal medium for the presence of the ura3 gene. Plasmids were recovered from ura3+ yeast strains by standard mini-prep (Qiagen) or phenol extract and ethanol precipitation. Crude yeast plasmid preps were then used to transform E. coli TOP10 cells (Invitrogen) using selection with the plasmid appropriate antibiotic, either carbenicillin (100 µg/mL), tetracycline (15 µg/mL), or chloroamphenicol (25 µg/mL). E. coli mini-prepped plasmids were confirmed by restriction digest and agarose gel analysis.

TABLE 11

Primers for the Construction of Redox Balancing Plasmids FP45, FP47, FP67, FP68, and FP75 (FP66 was created from direct DNA synthesis (SEQ ID NO: 206), so no primers were used during its construction)

| Primer # | SEQ ID NO: | Primer sequence | Description |
|---|---|---|---|
| X16072 | 190 | TCTCAGTAGTAGTTGACATTAGCGGAGCACTAAAATGAAGATTGTCTTAGTTCTTTAT | FP45 1 |
| X16073 | 191 | CAGTCTTTCGACTGAGCCTTTCGTTTTACGGCCGCTATTTCTTATCGTGTTTACCGTA | FP45 2 |
| X16082 | 192 | TCTCAGTAGTAGTTGACATTAGCGGAGCACTAAAATGGCAACCGTTCTGTGTGTTCTG | FP47 1 |
| X16083 | 193 | CAGTCTTTCGACTGAGCCTTTCGTTTTACGGCCGTTAGGTCAGACGATAGCTCTGTGC | FP47 2 |
| X16829 | 194 | TGTGAGCGGATAACAATTTCACACAGGAAACAGCTATGTCGAAGGTTATGAAAACCATG | FP67 1 |
| X16064 | 195 | GCTTTCACACCTCCAAGATTTCGTCTAATTTTGTTCAGCAAGCTTCTT | FP67 2 |
| X16065 | 196 | AAGAAGCTTGCTGAACAAAATTAGACGAAATCTTGGAGGTGTGAAAGC | FP67 3 |
| X16830 | 197 | CCTCGAGGTCGACGGTATCGATAAGCTTGATATCTTATTCAGCCTTAATAGCTCCTGTT | FP67 4 |
| X16831 | 198 | TGTGAGCGGATAACAATTTCACACAGGAAACAGCTATGGGAAAGAAAATGATGACGACT | FP68 1 |
| X16075 | 199 | TACACCTCCTTATCTTAATAGGCGTTCTACTTCTTCGTCCGCTTGCTGAG | FP68 2 |
| X16076 | 200 | CTCAGCAAGCGGACGAAGAAGTAGAACGCCTATTAAGATAAGGAGGTGTA | FP68 3 |
| X16077 | 201 | CCCGTCTGATATTTATGGTTCTACGACTTACTCTTGAACTGGAGCTCCTAC | FP68 4 |
| X16078 | 202 | GTAGGAGCTCCAGTTCAAGAGTAAGTCGTAGAACCATAAATATCAGACGGG | FP68 5 |
| X16832 | 203 | CCCTCGAGGTCGACGGTATCGATAAGCTTGATATCCTATTGGTTCTGCCGGATATATAT | FP68 6 |

TABLE 11-continued

Primers for the Construction of Redox Balancing Plasmids FP45, FP47, FP67, FP68, and FP75 (FP66 was created from direct DNA synthesis (SEQ ID NO: 206), so no primers were used during its construction)

| Primer # | SEQ ID NO: | Primer sequence | Description |
| --- | --- | --- | --- |
| X16981 | 204 | TGTGAGCGGATAACAATTTCACACAGGAAACAGCTATGCCCGATATGACAAACGAAT CT | FP75 1 |
| X16982 | 205 | CCCTCGAGGTCGACGGTATCGATAAGCTTGATATCTTAAACACCAGCTTCGAAGTCCTT | FP75 2 |

Sequence of the PNO gene and flanking regions used to create FP66
SEQ ID NO: 206):
tgagccgtttattttttctacccatatccttgaagcggtgttataatgccgcgccctcgatatgggggattttaacgacctgattttcggg tctcagtagtagttgacattagcggagcactaaaatgaaacagagcgttcgtccgattattagcaatgttctgcgtaaagaagttgc cctgtatagcaccattattggtcaggataaaggtaaagaaccgacaggtcgtacctataccagcggtccgaaaccggcaagcca tattgaagttccgcatcatgttaccgttccggcaaccgatcgtaccccgaatccggatgcacagttttttcagagcgttgatggtagc caggcaaccagccatgttgcatatgccctgagcgataccgcatttatctatccgattaccccgagcagcgttatgggtgaactggc agatgtttggatggcacagggtcgtaaaaatgccatggtcaggttgttgatgttcgtgaaatgcagagcgaagccggtgcagcg ggtgcactgcatggtgcactggcagccggtgcgattgcaaccaccttaccgcaagccagggtctgctgctgatgattccgaata tgtataaaatcgcaggcgaactgatgccgagcgttattcatgttgcagcacgtgagctggcaggtcatgcactgagcattttggtg gtcatgcagatgttatggcagttcgtcagaccggtttgggcaatgctgtgtagccataccgttcagcagagccatgatatggcactg attagccatgtggcaaccctgaaaagcagcattccgtttgttcattttttttgatggttttcgcaccagccacgaagtgaacaaaatca aaatgctgccgtatgccgaactgaaaaaactggttccgcctggcaccatggaacagcattgggcacgtagcctgaatccgatgc atccgaccattcgtggcaccaatcagagcgcagatatctattttcagaatatggaaagcgccaaccagtattataccgatctggca gaagttgttcaagaaaccatggatgaagttgcaccgtatattggtcgtcattacaaaatctttgagtatgttggtgcaccggatgcag aagaggtgaccgttctgatgggtagcggtgccaccaccgttaatgaagcagttgatctgctggttaaacgcggtaaaaaagttgg tgcagttctggttcatctgtatcgtccgtggtcaaccaaaagcatttgaaaaagttctgccgaaaaccgtgaaacgtattgcagcact ggatcgttgcaaagaagttaccgcactgggcgaaccgctgtatctggatgttagcgccaccctgaacctgtttccggaacgtcag aatgttaaagttattggtggtcgttatggtctgggtagcaaagattcattccggaacatgcgactggccatttatgcaaatctggcaa gcgaaaatccgattcagcgttttaccgttggtattaccgatgatgttaccggcaccagcgtgccgtttgttaatgaacgtgttgatac cctgccggaaggcacccgtcagtgtgttttttgggggtattggtagtgatggcaccgttggtgcaaatcgtagcgcagttcgtattatt ggtgataatagcgatctgatggtgcaggcgtattttcagtttgatgcatttaaaagcggtggtgttaccagcagccatctgcgttttg gtcctaaaccgattaccgcacagtatctggttaccaatgcagattatattgcctgccactttcaagagtatgtgaaacgttttgatatg ctggatgcaattcgtgaaggtggcacctttgttctgaatagccgttggaccaccgaagatatggaaaaagaaattccggcagatttt cgtcgtaatgtggcacagaaaaaagtgcgctttatatacagttgatgcccgtaaaatttgcgatagctttggtctgggcaaacgcatt aacatgctgatgcaggcatgttttttcaaactgagcggtgttctgccgctggccgaagcacagcgtctgctgaatgaaagcattgtt catgagtatggcaaaaaaggtggtaaagtggtggaaatgaatcaggcagttgttaatgcagtgtttgccggtgatctgcctcaaga agttcaggttccggcagcatgggcaaatgcagttgataccagcacccgcaccccgaccggtattgaatttgttgataaaatcatgc gtccgctgatggatttcaaaggtgatcagctgccggttagcgttatgacaccgggtggtacatttccggttggcaccacccagtat gcaaaacgtgcaattgcggcatttattccgcagtggattccggcaaattgtacccagtgtaattattgcagctatgtttgtccgcatg caaccattcgtccgtttgtgctgaccgatcaagaagtgcagctggcaccggaaagctttgttacccgtaaagcaaaaggtgattat cagggtatgaacttcgtattcaggttgcaccggaagattgtaccggttgtcaggtttgtgttgaaacctgtccggatgatgcactgg aaaatgaccgatgcgtttaccgccacaccggttcagcgtaccaattgggaatttgcaattaaagttccgaatcgtggtacgatgacc -continued

```
gatcgctatagcctgaaaggtagccagtttcagcaaccgctgctggaatttagcggtgcatgtgaaggttgtggtgaaacccgt
atgttaaactgctgacccagctgtttggtgaacgtaccgttattgcaaatgccaccggttgtagcagcatttgggtggtacggcag
gtctggctccgtataccaccaatgcaaaaggtcagggtccggcatggggtaatagcctgtttgaagataatgccgaatttggttttg
gtattgcagttgccaatgcacagaaacgtagccgtgttcgtgattgtattctgcaggccgttgaaaaaaaagtggccgatgaaggt
ctgaccaccctgctggcacagtggctgcaggattggaataccggtgataaaacactgaaatatcaggaccagattattgccggtc
tggcacagcagcgtagtaaagatcctctgctggaacaaatttatggcatgaaagatatgctgccgaatatcagccagtggattatt
ggcggtgatggttgggccaatgatattggctttggtggcctggatcatgttctggcgagcggtcagaatctgaatgttctggtgctg
gataccgaaatgtatagcaatacaggtggtcaggcaagcaaaagcacccatatggcaagcgttgcaaaatttgccctgggtggt
aaacgtaccaacaaaaaaaacctgaccgaaatggccatgagctatggtaatgtttatgttgcaaccgttagccatggtaatatggc
ccagtgtgttaaagcattgttgaagcagaaagctatgatggtccgagcctgattgttggttatgcaccgtgcattgaacatggtctg
cgtgcaggtatggcacgtatggttcaagaatcagaagcagcaattgcaaccggttattggccactgtatcgttttgatccgcgtctg
gcaaccgaaggtaaaaacccgtttcagctggatagcaaacgtattaaaggtaacctgcaagaatatctggatcgccagaatcgtt
atgtgaacctgaaaaaaacaatccgaaaggtgccgatctgctgaaaagccagatggcagataacattacagcacgctttaatcg
ttatcgtcgtatgctggaaggtccgaataccaaagcagcagcaccgagcggtaatcatgtgaccattctgtatggtagtgaaacc
ggtaatagcgaaggtctggcaaaagaactggccaccgattttgaacgtcgtgaatatagcgttgcagttcaggccctggatgatat
tgatgttgcggatctggaaaatatgggctttgttgttattgccgtttcaacctgtggtcagggccagtttccgcgtaatagtcagctgtt
ttggcgtgaactgcagcgtgataaaccggaaggttggctgaaaaatctgaaatacaccgttttggcctgggtgatagcacctatt
acttttattgtcataccgccaaacaaatcgatgcacgtctggcagcgctgggtgcacagcgtgttgttccgattggtttcggtgatga
tggtgatgaagatatgtttcataccggcttcaataattggattccgagcgtttggaatgagctgaaaaccaaaactccggaagaag
cactgtttaccccgtcaattgccgttcagctgaccccgaatgcaacaccgcaggattttcattttgccaaaagcacaccggtgctga
gcattaccggtgcagaacgtattacaccggcagatcatacccgcaattttgttaccattcgttggaaaaccgatctgagctatcagg
ttggtgatagcctgggtgttttccagaaaatacccgtagcgttgttgaagaattcctgcagtattatggcctgaacccgaaagatgt
tattaccattgaaaataaaggctcacgcgaactgccgcattgtatggccgttggtgacctgtttaccaaagttctggatattctgggt
aaaccgaataaccgcttctataaaaccctgagctatttcgccgttgataaagcagaaaagaacgcctgctgaaaattgcagaaat
gggtccggaatatagcaacattctgtcagagatgtatcattatgccgacatctttcatatgtttccgagcgcacgtccgacactgca
gtatctgattgaaatgatcccgaacattaaaccgcgttattatagcattagtagcgcaccgattcatactccgggtgaagtgcatag
cctggttctgattgatacctggattaccctgagcggtaaacatcgtacgggtctgacctgtaccatgctggaacatctgcaggcag
gtcaggtggtggatggttgtattcatccgaccgcaatggaatttccggatcatgaaaaaccggttgttatgtgtgcaatgggttcag
gtctggcaccttttgttgcattctgcgtgaacgtagcaccctgcgtaaacaggtaaaaaaacgggcaatatggcgctgtattttg
gcaatcgttacgaaaaaaccgaatttctgatgaaagaggaactgaaaggccatatcaatgatggtctgctgacactgcgttgtgca
tttagccgtgatgatccgaaaaaaaagtctatgtgcaggatctgatcaaaatggatgaaaaaatgatgtatgattacctggtggttc
agaaaggcagcatgtattgttgtggtagccgtagttttatcaaaccggtgcaagaaagcctgaaacattgttttatgaaagcgggtg
gtctgaccgcagaacaggcagaaaatgaagttattgatatgtttaccacgggtcgctataacattgaagcgtggcggccgtaaaa
cgaaaggctcagtcgaaagactg
```

NAD+ linked fdh from *Candida boidinii* and NADP+ linked fdh from *Burkholderia stabilis* were expressed in *E. coli* TOP10. Biochemical activity measurements were made on cell free extracts, which resulted in the data presented in Table 12 below. The assay was conducted with 50 mM sodium formate and 1.1 mM NAD+ or NADP+ at pH 7.0 in sodium phosphate buffer, as adapted from Hopner, T. and Knappe, J., *Methods of Enzymatic Analysis*, 3:1551-1555 (1974). In a final volume of 1 mL, 0.55 mL of water, 0.375 mL of 200 mM sodium phosphate, pH 7.0, 0.375 mL of 200 mM sodium formate, 0.15 mL of 10.5 mM β-NAD+ or 10.5 mM β-NADP+, and 0.05 mL of crude enzyme prep were added to a 1.5 mL plastic cuvette in the order indicated. Absorbance at 340 nm was recorded for 1 minute with a Shimadzu spectrophotometer, and the rate was used to determine specific activity. Protein concentrations were determined by the Bradford method with BSA as the standard. As expected, fdh from *C. boidinii* preferred NAD+ as a co-factor, while fdh from *B. stabilis* preferred NADP+.

TABLE 12

Biochemical activity of Cell-free Extracts

| plasmid | description | μmol min$^{-1}$ mg$^{-1}$ | |
|---|---|---|---|
| | | NAD+ | NADP+ |
| pMU2726 | empty vector | 0.00 ± 0.00 | 0.00 ± 0.01 |
| FP45 | *C. boidinii* fdh | 0.39 ± 0.04 | 0.01 ± 0.01 |
| FP47 | *B. stabilis* fdh | 0.06 ± 0.00 | 0.31 ± 0.02 |

2.3 Acyl-ACP Chain Termination Enzymes

The final step of the anaerobic fatty acid pathway involves cleavage of the acyl carrier protein (ACP) from the acyl chain, and addition of a functional group to the final carbon of the growing chain (FIG. 13). The chain termination enzyme(s) determine both the terminal functional group and the overall acyl chain length.

Figure 14:
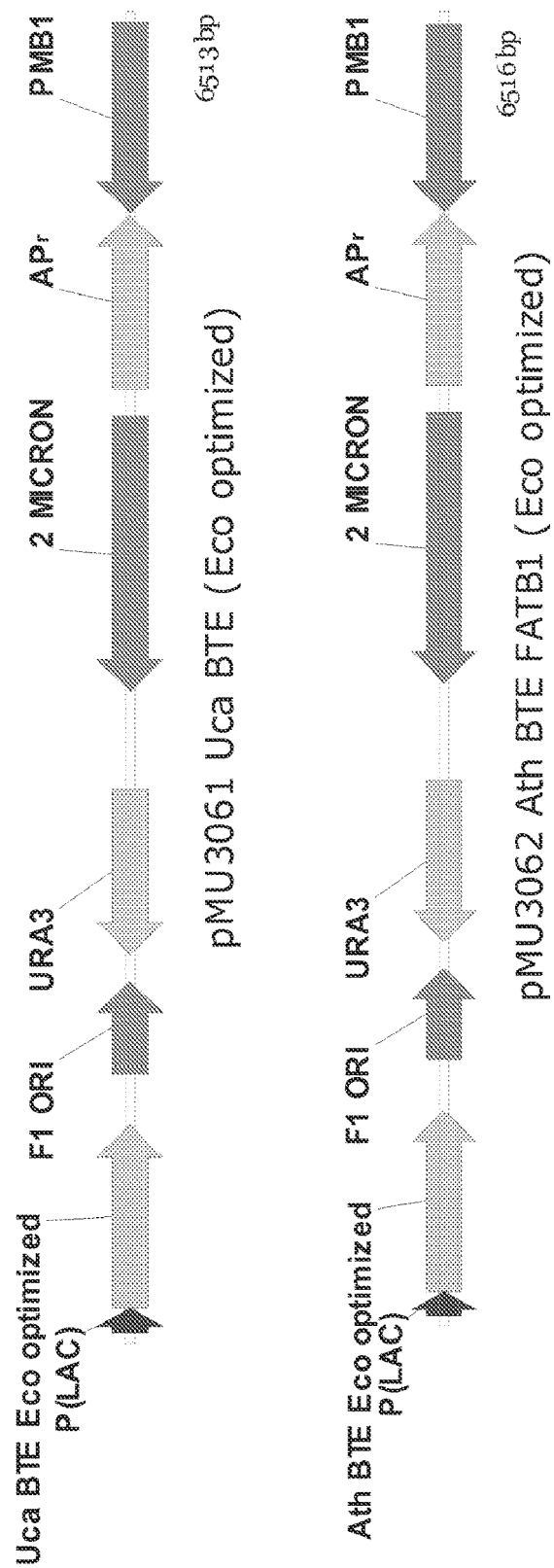
FIG. 14 depicts vectors pMU3061, pMU3062, pMU3063, and pMU3064.
Figure 14:
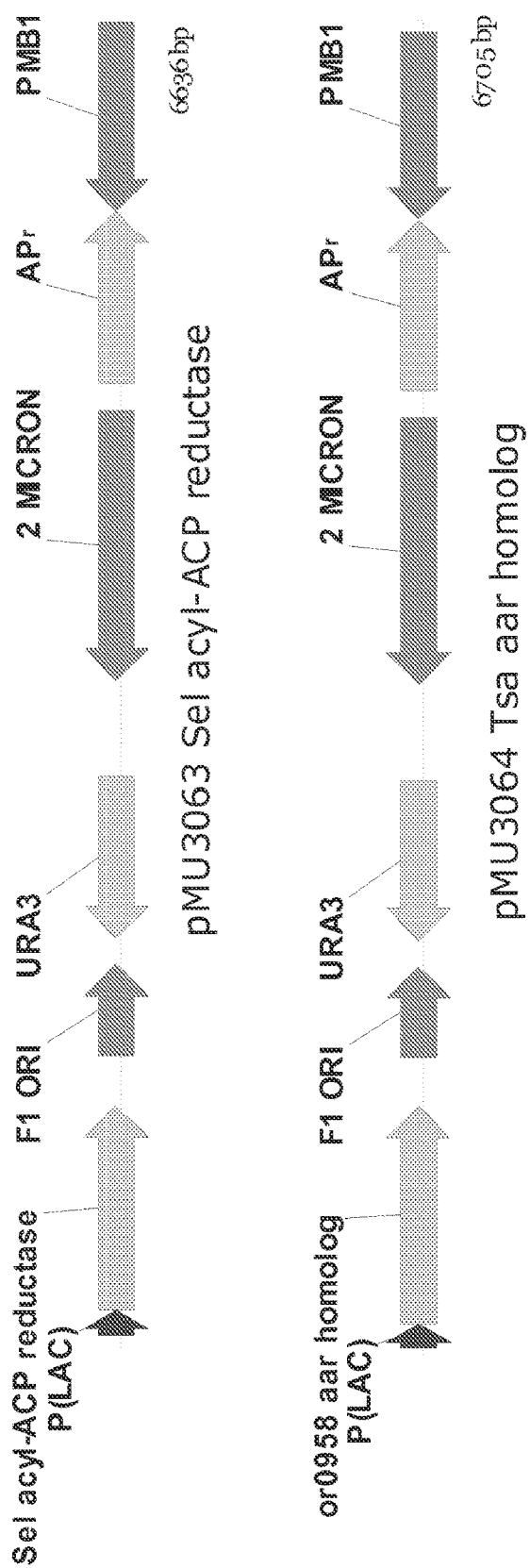

Plasmids encoding an *E. coli* codon optimized C12 acyl-ACP thioesterase (pMU3061), an *E. coli* codon optimized C16 acyl-ACP thioesterase (pMU3062), an acyl-ACP reductase (pMU3063), and an acyl-ACP reductase homolog (pMU3064) have been expressed in *E. coli* strain M2933 harboring a deletion in the acyl-CoA dehydrogenase fadE, an enzyme involved in fatty acid degradation. The expression plasmids used for these enzymes are shown in FIG. 14.

*E. coli* strains were grown to saturation over 48 hours in 5 mL LB medium at 30° C. in aerobic culture tubes containing 100 μg/mL Carbenicillin and 1 mM IPTG. Total fatty acid quantification was performed by lipid extraction followed by methyl ester derivatization and analysis by gas chromatograph with flame ionization detection. Extraction and derivatization was performed by adding 0.5 mL sample to a 13×100 mm glass tube with Teflon coated cap, addition of 4 mL 4% sulfuric acid in methanol followed by vortexing. The samples were then incubated at 70° C. in a water bath for 30 minutes, cooled to room temperature, followed by addition of 2 mL water and 2 mL hexane with vortexing at each step. The hexane layer was transferred to a new tube and dried under nitrogen. 50 μL hexane was then used to re-constitute the fatty acids for gas chromotograph analysis. Total fatty acids for M2933 strains carrying either plasmid pMU960 (empty vector), pMU3061, pMU3062, pMU3063, or pMU3064 are shown in FIGS. 22A and 22B. Individual fatty acids are also shown using a standard naming convention of X:Y, where X is the carbon number and Y is the number of unsaturated bonds.

Example 3

3.1 Methodology to Screen for Transcarboxylase Activity

To confirm that putative transcarboxylase genes have in vivo oxaloacetate:acetyl-CoA carboxytransferase activity, an *E. coli* strain was constructed that requires recombinant production of malonyl-CoA for growth. Wildtype *E. coli* produces malonyl-CoA, a metabolite essential for growth, exclusively via the enzyme acetyl-CoA carboxylase (ACC). ACC is composed of the four subunit genes accA, accB, accC, and accD, which are located at three different loci on the *E. coli* genome.

Because malonyl-CoA is essential, ACC cannot be disrupted directly in wildtype *E. coli* without resulting in a lethal phenotype. To overcome this, a conditional pathway for malonyl-CoA biosynthesis was first introduced into wildtype *E. coli*. This pathway, encoded by matBC from *Rhizobacterium trifolii*, transports exogenous malonate across the cell membrane, and then uses malonate, ATP, and CoA to produce malonyl-CoA, AMP, and PP$_i$. See An and Kim, *Eur. J. Biochem.*, 257:395-402 (1998).

3.1.1 Construction of Strain M2470

Figure 15:
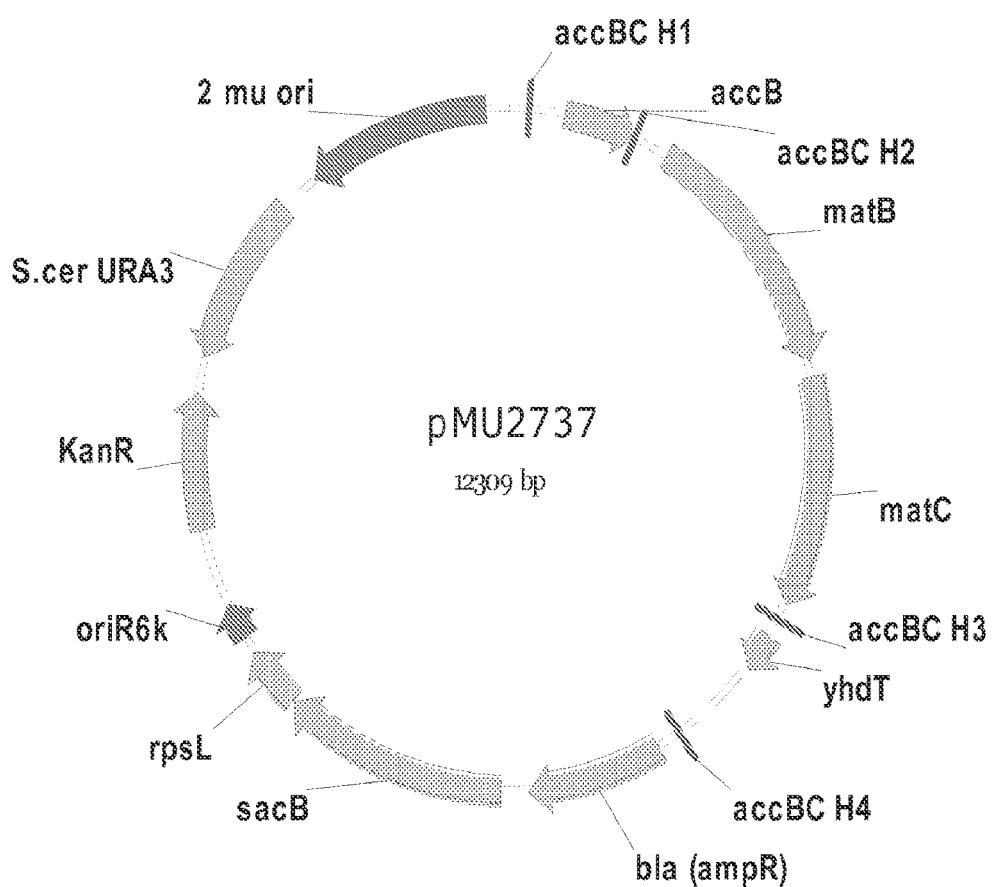
FIG. 15 depicts the vector pMU2737.
Figure 16:
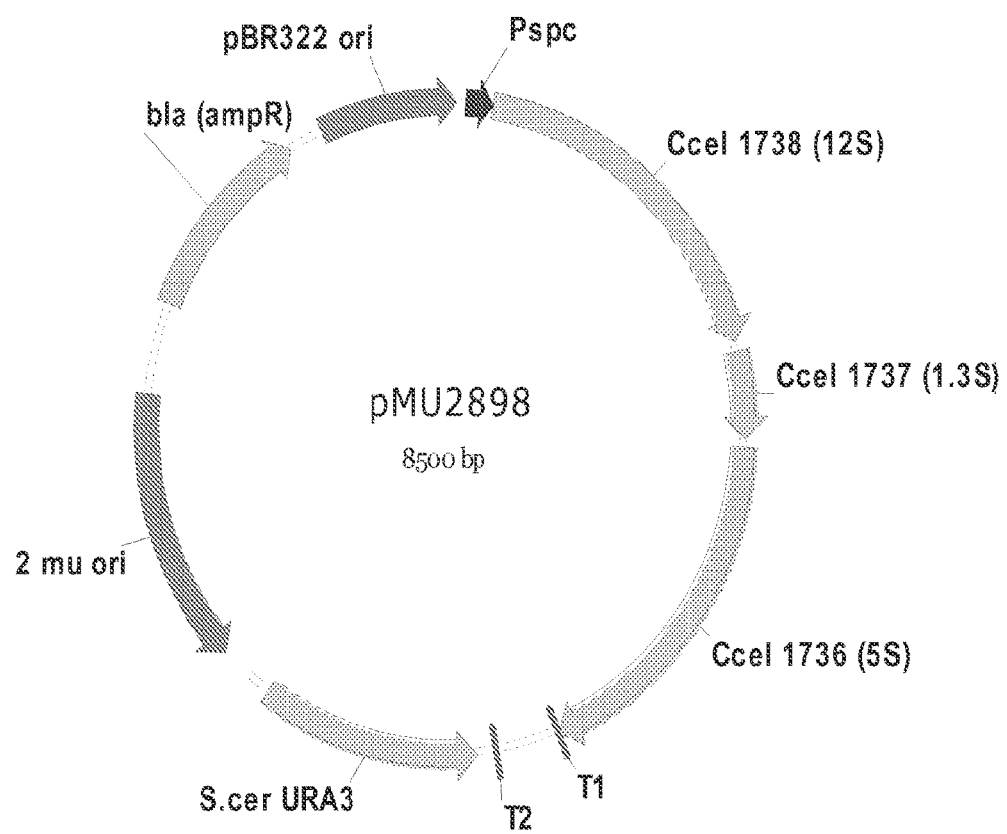
FIG. 16 depicts the vector pMU2898.
Figure 17:
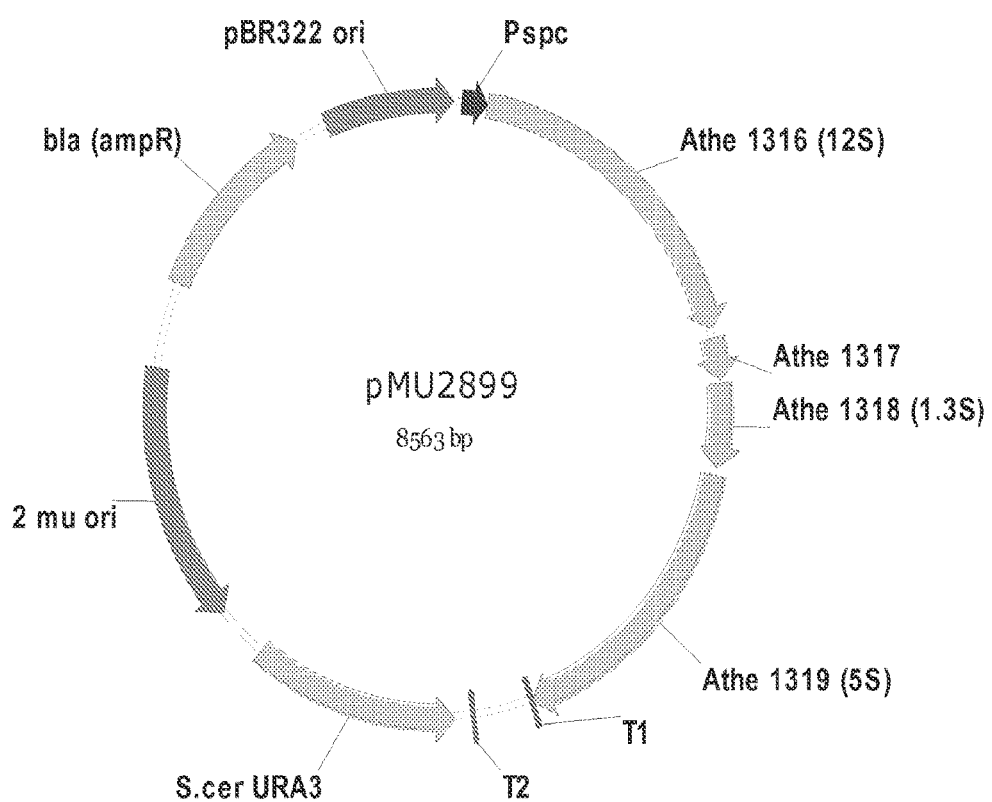
FIG. 17 depicts the vector pMU2899.
Figure 18:
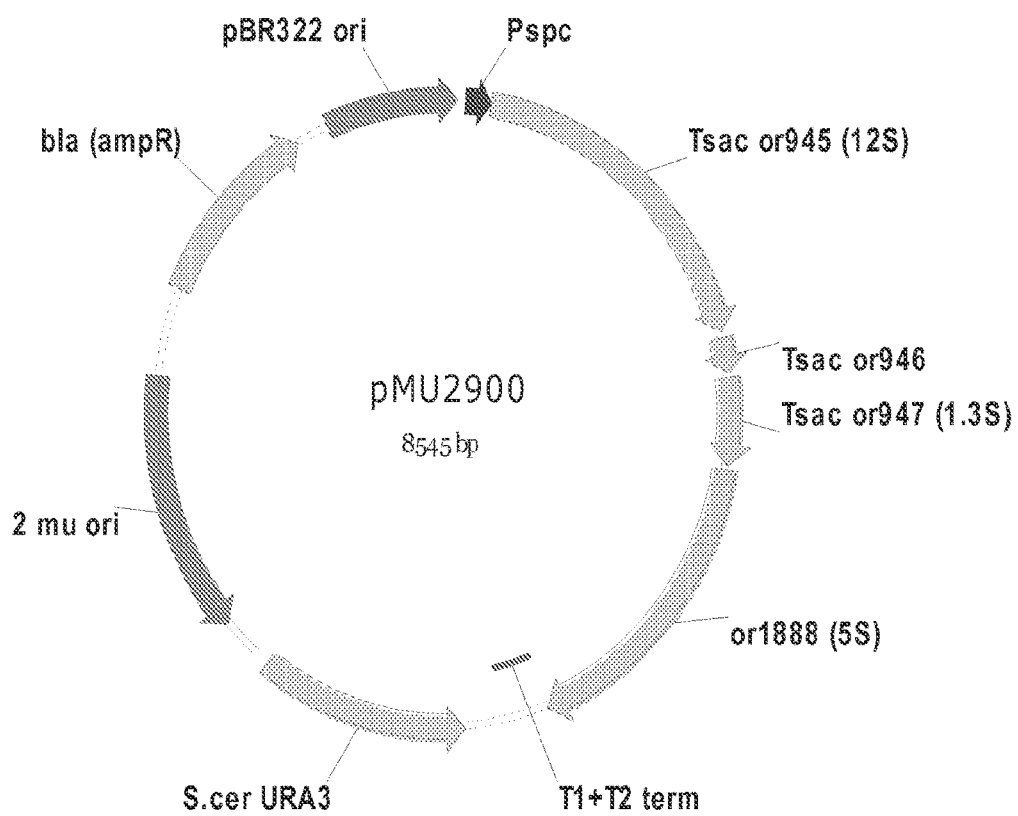
FIG. 18 depicts the vector pMU2900.
Figure 19:
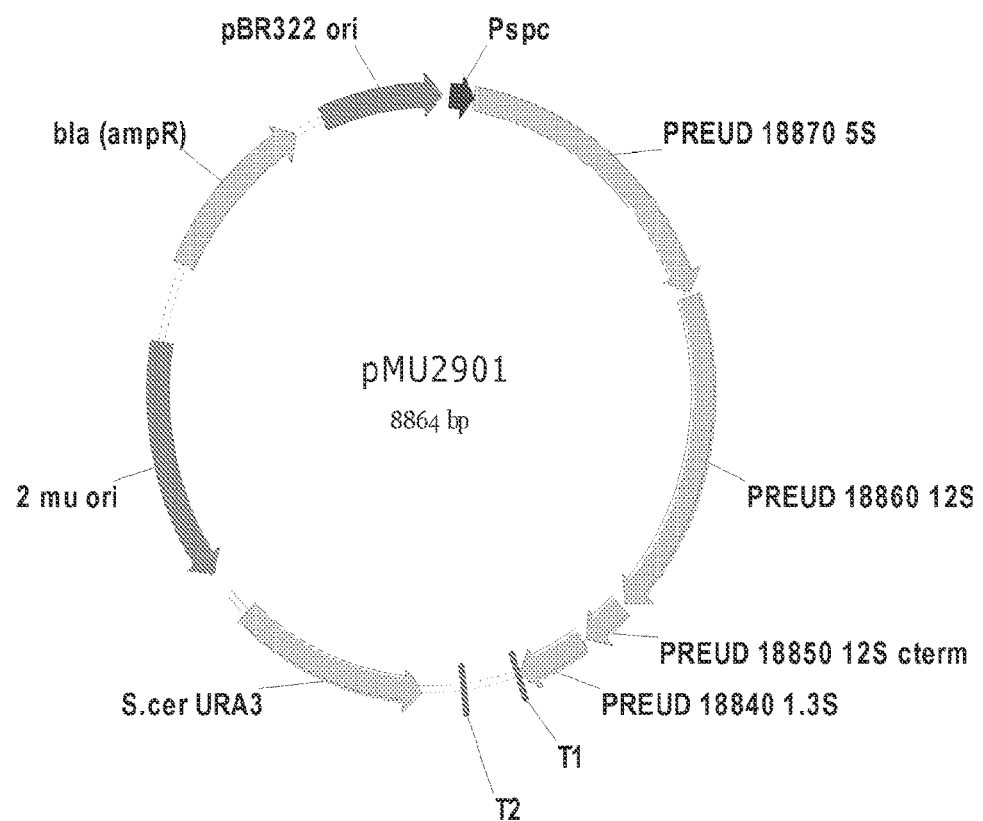
FIG. 19 depicts the vector pMU2901.

Strain M2470 is a ΔaccC::matBC strain built from *E. coli* K12 strain MG1655 (ATCC Accession No. 700926). To construct M2470, plasmid pMU2737 (FIG. 15; SEQ ID NO: 285) was transformed into strain MG1655 with selection on 100 μg/mL ampicillin and 50 μg/mL kanamycin. pMU2737 is a non-replicating plasmid, and confirmation of a single cross over integration was detected via colony PCR. The single cross-over meridiploid contains both a functional and a non-functional copy of accC, as well as the matBC genes, and positive (amp$^R$, kan$^R$) and negative selective (sacB, rpsL) markers. Upon plating on the negative selective condition, 10% w/v sucrose supplemented with 10 mM sodium malonate, the meridiploid resolved exclusively to the wild-type, functional accC gene copy. This suggested that matBC was not able to catalyze the conversion of exogenous malonate to malonyl-CoA at a rate sufficient to allow for observable colony formation. To overcome this, the meridiploid strain was grown aerobically in M9 minimal medium supplemented with 1.4 mM glucose and 10 mM malonate. After two transfers, each lasting ~48 hours in 50 mL of this medium, the culture was re-plated on 10% w/v sucrose supplemented with 10 mM sodium malonate. Upon screening, most (>90%) of the colony isolates now had the non-functional accC copy and matBC genes. An isolate was further purified and designated M2470. It is able to grow only when exogenous malonate is present in the medium.

3.1.2 Construction and Screening of Putative Transcarboxylase Genes

Plasmids pMU2898 (SEQ ID NO:286), pMU2899 (SEQ ID NO:287), pMU2900 (SEQ ID NO:288), and pMU2901 (SEQ ID NO:289) (FIGS. 16-19) were constructed via yeast homologous cloning to express putative transcarboxylases from *Clostridium cellulolyticum* H10 ATCC 35319, *Caldicellulosiruptor bescii* DSM 6725, *Thermoanaerobacterium saccharolyticum* JW/SL-YS485, and *Propionibacterium freudenreichii* CIRM-BIA1$^T$, respectively. Percent consensus and identity positions across the four subunits of these putative transcarboxylases, as well as from *Corynebacterium kroppenstedtii* DSM 44385, *Geobacter bemidjiensis* Bem($^T$), and *Clostridium thermocellum* ATCC 27405, is depicted in Table 13. A phylogenetic tree and alignment of these transcarboxylases, including from *D. propionincus* DSM 2032, is shown in FIGS. 30-31.

TABLE 13

Percent Consensus and Identity Positions Across Putative Transcarboxylases

| | Consensus positions | Identity positions |
|---|---|---|
| 5S subunit | 75.5% | 29.8% |
| 1.3S subunit | 58.6% | 12.0% |
| 12S subunit | 85.0% | 35.0% |
| 12S C-terminal subunit* | 36.5% | 1.9% |

*C. cellulolyticum* does not have a 12S C-terminal subunit

The four putative transcarboxylases were cloned into pMU2727, a replicating vector with the pBR322 origin, amp$^R$, Pspc promoter, and T1T2 terminator. Pspc is a moderately high level constitutive ribosomal promoter. See Liang et al., *J Mol Bio* 292:19-37 (1999).

These plasmids were then transformed into M2470 and transformants were selected on medium containing, per liter, 10 g glucose, 1.48 g disodium malonate, 100 mg ampicillin, 15 g agar, and the modified M9 base medium: 12.8 g Na$_2$HPO$_4$.7H$_2$O, 3 g KH$_2$PO$_4$, 0.5 g NaCl, 1 g NH$_4$Cl, 0.5 g MgSO$_4$, 0.015 g CaCl$_2$, 0.02 g thiamine, 0.02 g CoSO$_4$, 0.02 g ZnSO$_4$, 0.02 g MnSO$_4$, 0.015 g biotin. Transformants were confirmed by plasmid mini-prep, and re-patched onto modified M9 medium plates containing 20 g glucose and 15 g agar per liter ("M9+20 glucose"). If growth was observed on M9+20 glucose plates, colonies were re-grown in either liquid or solid medium of the same composition, and scored for growth and growth rate (Table 14 and FIG. 20A). As a control, transformants were also plated on solid medium comprising M9 base medium, 10 g/L glucose, 10 mM malonate, and 100 g/mL ampicillin (Table 14 and FIG. 20B). The following transformants were isolated and tested for growth: MG1655—wildtype, M2560—ΔaccC::matBC+pMU2727 empty vector (amp$^R$), and M2557, M2558, M2559—ΔaccC::matBC+pMU2900 *T. saccharolyticum* TC (amp$^R$).

TABLE 14

Growth of Transformants Containing Putative Transcarboxylases

| Strain | M9 + 20 glu | M9 + malonate + amp |
| --- | --- | --- |
| MG1655 WT | ++++ | – |
| M2470 | – | +++ |
| M2560 (aka. M2470 + pMU2727) | – | +++ |
| M2557 (aka. M2470 + pMU2900) #1 | +++ | +++ |
| M2558 (aka. M2470 + pMU2900) #2 | +++ | +++ |
| M2559 (aka. M2470 + pMU2900) #3 | +++ | +++ |
| M2470 + pMU2898 | + | +++ |
| M2470 + pMU2899 | ++ | +++ |
| M2470 + pMU2901 | + | +++ |

++++ = visible growth within 24 hours
+++ = visible growth within 48 hours
++ = visible growth within 96 hours
+ = visible growth within 168 hours
– = no visible growth after 200+ hours 3.2 Assays for Recombinant Transcarboxylase and In Vitro Transcarboxylase Activity To determine the presence and activity of the *T. saccharolyticum* transcarboxylase enzyme that was engineered into the *E. coli* ΔaccC::matBC strain and screened using the assay above, several biochemical assays were conducted. Initial evaluation of activity in cell lysate was inconclusive. The *T. saccharolyticum* transcarboxylase enzyme was then purified using the biotin binding domain located in the 1.3S protein. Without wishing to be bound by theory, Streptavidin binding of the 1.3S subunit could co-purify both the 5S and 12S proteins which associate with the 1.3S subunit in the native host. *E. coli* ΔaccC::matBC cells were grown in M9+ medium at 37° C. in aerobic shake flasks to an OD of 6 in 1.8 L total volume and lysed with Y-PER® (Pierce) according to product instructions, in the presence of 100 mM potassium phosphate, pH 6.8, 1 mg/mL reduced glutathione, 1:10,000 dilution of Sigma bacterial protease inhibitors, and 0.5 U/mL DNase I. After 2-3 freeze/thaw cycles, the cells were lysed as determined by microscopic evaluation. The lysate was centrifuged to remove debris and the supernatant was retained for further evaluation of activity. Two constructs were evaluated using this affinity assay, M2557 and M2560, which were either the strain engineered to produce the 12S, 5S, 1.3S, and 12S C-terminal components of the *T. saccharolyticum* transcarboxylase system or the empty vector control strain, respectively (see above).

To determine the presence of the biotin-containing enzyme, the lysates were then purified using monomeric avidin resin with a batch binding protocol (Pierce) according to product instructions. After the sample was incubated with the resin, the protein was eluted from the column with 4 mM biotin. The eluted fractions were analyzed on via Western blot with avidin-HRP as the detection. Samples were run on a 4-20% tris glycine gel then transferred to a PVDF membrane. After overnight blocking in TBS/1% BSA, streptavidin HRP was added. The HRP was detected with ECL chemilunescent and imaged on a chemiluminescent gel doc system. FIG. 25 depicts the results of this affinity assay comparing M2557 and M2560.

The monomeric avidin-purified lysate was purified again with Streptavidin Dynabeads with a batch binding system carried out with 1 mL of lysate mixed with 100 μL of washed streptavidin Dynabeads. After incubation at room temperature for 30 min, the sample was washed with 100 mM potassium phosphate, 1 mg/mL reduced glutathione, pH 6.8 and eluted from the beads by boiling in SDS-PAGE sample buffer. The re-purified lysate was then analyzed via Western Blot as above. The band on the Western Blot that ran at the same location as the one indicated with an arrow in FIG. 25 was sequenced on a Procise N-terminal sequencer. The sequencing data indicated that the N-terminus of the protein was MKKFIVTVNG (SEQ ID NO:299), consistent with the N-terminus of the 1.3S protein.

The enzymatic activity of the monomeric avidin-purified transcarboxylase complex was then assessed using an LC/MS detection assay. The monomeric avidin purified lysate was mixed with oxaloacetate, acetyl CoA and reduced glutathione and incubated at 40° C. for 1.5 hours. The sample was then analyzed by LC/MS using a BioRad 87H column and a Thermo LCQ (HPLC C$_{18}$ column-formate/methanol eluent) ion trap mass spectrometer. The results are shown in FIGS. 26A and 26B. In FIG. 26A, the negative control sample was analyzed. Using selected ion monitoring, acetyl CoA was detected but no malonyl CoA was detected (FIG. 26A, lower two panels). When the transcarboxylase sample was analyzed with selected ion monitoring both acetyl and malonyl CoA (FIG. 26B, lower two panels) were detected thereby indicating that the transcarboxylase enzyme complex was functional.

3.3 Use of *E. Coli* ΔaccC::matBC Strain to Select for Faster-Growing Transcarboxylase-Expressing Strains The *E. coli* accC::matBC strain M2470 can also be used to select for more efficient malonyl-CoA production by transcarboxylases. This selection is based on the principle that malonyl-CoA generation is the rate-limiting factor for growth of this strain. Thus, more efficient generation of malonyl-CoA will result in a faster growing strain which is able to out-compete the remaining culture and dominate the cell population during serial transfer or other continuous or semi-continuous selection systems. See, e.g., FIG. 27A.

First, strain M2470 was transformed with an integrating plasmid (e.g., pMU2924, pMU2969) carrying a transcarboxylase and spectinomycin antibiotic resistance marker flanked by DNA regions homologous to the ldh gene (lactate dehydrogenase). Using kanR, ampR, sacB, and rpsL based selections, the transcarboxylase and specR marker were securely integrated into the genome via two homologous recombination events. During this period, the strain was grown on M9+ base medium with the addition of 2-20 g/L glucose and 1.48 g/L disodium malonate. The medium was prepared at room temperature, adjusted to pH 7.5 with 10 M NaOH or 10 M HCl, and filter sterilized into a pre-sterilized bottle with a 0.22 μm filter. Subsequently, the strain was grown aerobically at 37° C. in 350 mL of M9+ medium with only glucose in a 1 L shake flask. If substantial growth (OD>1) occurred, a 0.1 mL transfer was made to a fresh 350 mL flask, which is repeated 3 times, at which point a small culture volume is plated to isolate a single colony on solid M9+ glucose medium (prepared via addition of 15 g/L melted agar as a 2× stock to 2× liquid media, pre-incubated at 50° C.). See FIG. 27A. This strain is referred to as the 3$^{rd}$ transfer (T3) isolate. Growth rates for the original strain and T3 isolate were then compared in M9+ medium with 20 g/L glucose as the sole carbon and energy source. An increased growth rate indicates an improved ability to generate malonyl-CoA. Plasmids used for this example were pMU2924 (*T. saccharolyticum* TC; FIG. 28; SEQ ID NO:207) and pMU2969 (*P. freudenreichii* TC; FIG. 29; SEQ ID NO:208), which generated strains M2767 and M2772, respectively. Growth rates for the original strain and T3 strain of each are shown in FIG. 27B.

Example 4

4.1 High Yield Palmitic Acid Production in *S. cerevisiae*

The present prophetic example describes the engineering of a recombinant yeast microorganism to convert a native pyruvate decarboxylase (pdc) based ethanol pathway (FIG. 34A) to an intermediary pyruvate formate lyase and alcohol/aldehyde dehydrogenase (pfl adhE) based ethanol pathway (FIG. 34B), and finally to a transcarboxylase based palmitic acid pathway (FIG. 34C).

The genetic modifications described below are used to create a strain capable of anaerobic growth in the absence of functional pyruvate decarboxylase and glycerol-3-phosphate dehydrogenase. To accomplish this, constructs were designed to replace GPD1, GPD2, FDH1, and FDH2 with two copies of a bifunctional alcohol/aldehyde dehydrogenase and two copies of a pyruvate formate lyase, both of which were cloned from *B. adolescentis* (Table 15). See, e.g., PCT/US2011/035416, which is incorporated by reference herein in its entirety, for additional details on the construction of such strain. Additionally, constructs were designed to make deletions of PDC5, PDC6, and PDC1. Either a NAD+ or NADP+ linked formate dehydrogenase is then re-introduced into the strain to create the metabolic pathway shown in (FIG. 34B).

TABLE 15

Coding sequences of pfl and adhE

| GenBank Accession # | Host strain | Gene donor | gene | protein |
|---|---|---|---|---|
| YP_909854 | S. cerevisiae | Bifidobacterioum adolescentis | pflA | pyruvate formate lyase activating enzyme |
| YP_909855 | S. cerevisiae | Bifidobacterioum adolescentis | pflB | pyruvate formate lyase |
| YP_909182 | S. cerevisiae | Bifidobacterioum adolescentis | adhE | alcohol/aldehyde dehydrogenase |

B. adolescentis adhE (amino acid sequence)
(SEQ ID NO: 209)
MADAKKKEEPTKPTPEEKLAAAEAEVDALVKKGLKALDEFEKLDQKQVDH
IVAKASVAALNKHLVLAKMAVEETHRGLVEDKATKNIFACEHVTNYLAGQ
KTVGIIREDDVLGIDEIAEPVGVVAGVTPVTNPTSTAIFKSLIALKTRCP
IIFGFHPGAQNCSVAAAKIVRDAAIAAGAPENCIQWIEHPSIEATGALMK
HDGVATILATGGPGMVKAAYSSGKPALGVGAGNAPAYVDKNVDVVRAAND
LILSKHFDYGMICATEQAIIADKDIYAPLVKELKRRKAYFVNADEKAKLE
QYMFGCTAYSGQTPKLNSVVPGKSPQYIAKAAGFEIPEDATILAAECKEV
GENEPLTMEKLAPVQAVLKSDNKEQAFEMCEAMLKHGAGHTAAIHTNDRD
LVREYGQRMHACRIIWNSPSSLGGVGDIYNAIAPSLTLGCGSYGGNSVSG
NVQAVNLINIKRIARRNNNMQWFKIPAKTYFEPNAIKYLRDMYGIEKAVI
VCDKVMEQLGIVDKIIDQLRARSNRVTFRIIDYVEPEPSVETVERGAAMM
REEFEPDTIIAVGGGSPMDASKIMWLLYEHPEISFSDVREKFFDIRKRAF
KIPPLGKKAKLVCIPTSSGTGSEVTPFAVITDHKTGYKYPITDYALTPSV
AIVDPVLARTQPRKLASDAGFDALTHAFEAYVSVYANDFTDGMALHAAKL
VWDNLAESVNGEPGEEKTRAQEKMHNAATMAGMAFGSAFLGMCHGMAHTI
GALCHVAHGRTNSILLPYVIRYNGSVPEEPTSWPKYNKYIAPERYQEIAK
NLGVNPGKTPEEGVENLAKAVEDYRDNKLGMNKSFQECGVDEDYYWSIID
QIGMRAYEDQCAPANPRIPQIEDMKDIAIAAYYGVSQAEGHKLRVQRQGE
AATEEASERA B. adolescentis pflA (amino acid sequence)
(SEQ ID NO: 210)
MSEHIFRSTTRHMLRDSKDYVNQTLMGGLSGFESPIGLDRLDRIKALKSG
DIGFVHSWDINTSVDGPGTRMTVFMSGCPLRCQYCQNPDTWKMRDGKPVY
YEAMVKKIERYADLFKATGGGITFSGGESMMQPAFVSRVFHAAKQMGVHT
CLDTSGFLGASYTDDMVDDIDLCLLDVKSGDEETYHKVTGGILQPTIDFG
QRLAKAGKKIWVRFVLVPGLTSSEENVENVAKICETFGDALEHIDVLPFH
QLGRPKWHMLNIPYPLEDQKGPSAAMKQRVVEQFQSHGFTVY B. adolescentis pflB (amino acid sequence)
(SEQ ID NO: 211)
MAAVDATAVSQEELEAKAWEGFTEGNWQKDIDVRDFIQKNYTPYEGDESF
LADATDKTKHLWKYLDDNYLSVERKQRVYDVDTHTPAGIDAFPAGYIDSP
EVDNVIVGLQTDVPCKRAMMPNGGWRMVEQAIKEAGKEPDPEIKKIFTKY
RKTHNDGVFGVYTKQIKVARHNKILTGLPDAYGRGRIIGDYRRVALYGVN
ALIKFKQRDKDSIPYRNDFTEPEIEHWIRFREEHDEQIKALKQLINLGNE
YGLDLSRPAQTAQEAVQWTYMGYLASVKSQDGAAMSFGRVSTFFDVYFER
DLKAGKITETDAQEIIDNLVMKLRIVRFLRTKDYDAIFSGDPYWATWSDA
GFGDDGRTMVTKTSFRLLNTLTLEHLGPGPEPNITIFWDPKLPEAYKRFC
ARISIDTSAIQYESDKEIRSHWGDDAAIACCVSPMRVGKQMQFFAARVNS
AKALLYAINGGRDEMTGMQVIDKGVIDPIKPEADGTLDYEKVKANYEKAL
EWLSETYVMALNIIHYMHDKYAYESIEMALHDKEVYRTLGCGMSGLSIAA
DSLSACKYAKVYPIYNKDAKTTPGHENEYVEGADDDLIVGYRTEGDFPLY
GNDDDRADDIAKWVVSTVMGQVKRLPVYRDAVPTQSILTITSNVEYGKAT
GAFPSGHKKGTPYAPGANPENGMDSHGMLPSMFSVGKIDYNDALDGISLT
NTITPDGLGRDEEERIGNLVGILDAGNGHGLYHANINVLRKEQLEDAVEH
PEKYPHLTVRVSGYAVNFVKLTKEQQLDVISRTFHQGAVVD To generate a recombinant yeast microorganism as described in this example, individual molecular components are integratively assembled.

The deletion of the FDH1 gene and replacement with two copies of ADH and two copies of PFL is illustrated in FIG. 35. The primers used to generate the molecular components of this integrative assembly are shown in FIG. 35, Table 16, and Table 26 (below).

TABLE 16

Primers used to generate the integrative assembly of FIG. 35. Each column indicates a PCR fragment that needs to be generated.

| Name | FDH15' Flank rc | pTPI-ADH-FBAt | ADHpPFKrc | PFL-pADH5 | PFL-pENORC | FDH13' Flank rc |
|---|---|---|---|---|---|---|
| Primers | X15559/X15565 | X15564/X14843 | X14844/X14835 | X14836/X14837 | X14838/X15567 | X15566/X15553 |
| Template | S. ce gDNA | pMU2746 | pMU2745 | pMU2770 | pMU2606 | S. ce gDNA |

2) The deletion of the FDH2 gene and replacement with two copies of ADH and two copies of PFL is illustrated in FIG. 36. The primers used to generate the molecular components of this integrative assembly are shown in FIG. 36, Table 17, and Table 26 (below).

TABLE 17

Primers used to generate the integrative assembly of FIG. 36. Each column indicates a PCR fragment that needs to be generated.

| Name | FDH2 5' Flank | FBA(t)-ADH1 | PFK-ADH2 | PFL-F | PFL-R | FDH2 3' Flank |
|---|---|---|---|---|---|---|
| Primers | X16096/X16097 | X16098/X14843 | X14844/X14835 | X14836/X14837 | X14838/X16099 | X16100/X11845 |
| Template | S. ce gDNA | pMU2746 | pMU2745 | pMU2770 | pMU2606 | S. ce gDNA |

3) The deletion of the GPD2 gene and replacement with two copies of ADH and two copies of PFL is illustrated in FIG. 37. The primers used to generate the molecular components of this integrative assembly are shown in FIG. 37, Table 18, and Table 26 (below).

TABLE 18

Primers used to generate the integrative assembly of FIG. 37. Each column indicates a PCR fragment that needs to be generated.

| Name | GPD2 5' flank | FBA(t)-ADH1 | PFK-ADH2 | PFL-F | PFL-R | GPD2 3' flank |
|---|---|---|---|---|---|---|
| Primers | X11816/X14847 | X14845/X14843 | X14844/X14835 | X14836/X14837 | X14838/X14849 | X14850/X11821 |
| Template | S. ce gDNA | YCL150 | YCL149 | pMU2770 | pMU2760 | S. ce gDNA |

4) The deletion of the GPD1 gene and replacement with two copies of ADH and two copies of PFL is illustrated in FIG. 38. The primers used to generate the molecular components of this integrative assembly are shown in FIG. 38, Table 19, and Table 26 (below).

TABLE 19

Primers used to generate the integrative assembly of FIG. 38. Each column indicates a PCR fragment that needs to be generated.

| Name | GPD1 5' flank | FBA(t)-ADH1 | PFK-ADH2 | PFL-F | PFL-R | GPD1 3' flank |
|---|---|---|---|---|---|---|
| Primers | X11824/X14776 | X14775/X14843 | X14844/X14835 | X14836/X14837 | X14838/X14829 | X14778/X11829 |
| Template | S. ce gDNA | pMU2746 | pMU2745 | pMU2770 | pMU2606 | S. ce gDNA |

5) The deletion of the PDC5 gene and replacement with a counter selective gene HSV-TDK and an antibiotic marker (Kan) is illustrated in FIG. 39. The primers used to generate the molecular components of this integrative assembly are shown in FIG. 39, Table 20, and Table 26 (below).

TABLE 20

Primers used to generate the integrative assembly of FIG. 39. Each column indicates a PCR fragment that needs to be generated.

| Name | PDC5 5' Flank | KNT | PDC5 3' Flank |
|---|---|---|---|
| Primers | X16463/X16464 | X16467/X16468 | X16465/X16466 |
| Template | S. ce gDNA | M2543/TB396 | S. ce gDNA |

6) The removal of the marker shown in FIG. 39 resulting in a clean deletion of the PDC5 gene is illustrated in FIG. 40. The primers used to generate the molecular components of this integrative assembly are shown in FIG. 40, Table 21, and Table 26 (below).

TABLE 21

Primers used to generate the integrative assembly of FIG. 40. Each column indicates a PCR fragment that needs to be generated.

| Name | PDC5 5' Flank | PDC5 3' Flank |
|---|---|---|
| Primers | X16463/X16495 | X16494/X16466 |
| Template | S. ce gDNA | S. ce gDNA |

7) The deletion of the PDC6 gene and replacement with a counter selective gene HSV-TDK and an antibiotic marker (Kan) is illustrated in FIG. 41. The primers used to generate the molecular components of this integrative assembly are shown in FIG. 41, Table 22, and Table 26 (below).

TABLE 22

Primers used to generate the integrative assembly of FIG. 41. Each column indicates a PCR fragment that needs to be generated.

| Name | PDC6 5' Flank | KNT | PDC6 3' Flank |
|---|---|---|---|
| Primers | X16471/X16472 | X16475/X16476 | X16473/X16474 |
| Template | S. ce gDNA | M2543/TB396 | S. ce gDNA |

8) The removal of the marker shown in FIG. 41 resulting in a clean deletion of the PDC6 gene is illustrated in FIG. 42. The primers used to generate the molecular components of this integrative assembly are shown in FIG. 42, Table 23, and Table 26 (below).

TABLE 23

Primers used to generate the integrative assembly of FIG. 42. Each column indicates a PCR fragment that needs to be generated.

| Name | PDC6 5' Flank | PDC6 3' Flank |
|---|---|---|
| Primers | X16471/X16497 | X16496/X16474 |
| Template | S. ce gDNA | S. ce gDNA |

9) The deletion of the PDC1 gene and replacement with a counter selective gene HSV-TDK and an antibiotic marker (Kan) is illustrated in FIG. 43. The primers used to generate the molecular components of this integrative assembly are shown in FIG. 43, Table 24, and Table 26 (below).

TABLE 24

Primers used to generate the integrative assembly of FIG. 43. Each column indicates a PCR fragment that needs to be generated.

| Name | PDC1 5' Flank | KNT | PDC1 3' Flank |
|---|---|---|---|
| Primers | X16951/X16952 | X16953/X16954 | X16955/X16956 |
| Template | S. ce gDNA | M2543/TB396 | S. ce gDNA |

10) The removal of the marker shown in FIG. 43 resulting in a clean deletion of the PDC1 gene is illustrated in FIG. 44. The primers used to generate the molecular components of this integrative assembly are shown in FIG. 44, Table 25, and Table 26 (below).

TABLE 25

Primers used to generate the integrative assembly of FIG. 44. Each column indicates a PCR fragment that needs to be generated.

| Name | PDC1 5' Flank | PDC1 3' Flank |
|---|---|---|
| Primers | X16952/X16953 | X16954/X16955 |
| Template | S. ce gDNA | S. ce gDNA |

TABLE 26

Primer sequences used to create the integrative assemblies illustrated in FIGS. 35-44.

| Primer # | SEQ ID NO. | Primer sequence |
|---|---|---|
| X11316 | 212 | GTAATACATCACCTCGATGAAAGAGA |
| X11816 | 213 | GCAGTCATCAGGATCGTAGGAGATAAGCA |
| X11821 | 214 | TCACAAGAGTGTGCAGAAATAGGAGGTGGA |
| X11822 | 215 | GTTGGGGGAAAAAGAGGCAACAGGAAAGATCAGAGACAGCAAGCATTGATAAGGAAGGG |
| X11823 | 216 | CCCTTCCTTATCAATGCTTGCTGTCTCTGATCTTTCCTGTTGCCTCTTTTTCCCCCAAC |
| X11824 | 217 | AAGCCTACAGGCGCAAGATAACACATCAC |
| X11829 | 218 | CTCAGCATTGATCTTAGCAGATTCAGGATCTAGGT |
| X11830 | 219 | TATGTTATCTTTCTCCAATAAATCTAATCTTCATGTAGACTATCAGCAGCAGCAGACAT |
| X11831 | 220 | GATAATATAAAGATGTCTGCTGCTGCTGATAGTCTACATGAAGATTAGATTTATTGGAG |
| X11845 | 221 | TTACTTGTGAAACTGTCTCCGCTATGTCAG |
| X14775 | 222 | CCCCCTCCACAAACACAAATATTGATAATATAAAGATGGCAGACGCAAAGAAGAAGGAA |
| X14778 | 223 | ATTTATTGGAGAAAGATAACATATCATACTTTCC |
| X14829 | 224 | GAAAGTATGATATGTTATCTTTCTCCAATAAATCTAGTCTTCTAGGCGGGTTATCTACT |
| X14835 | 225 | CAAATTCTAACCAACTTCAAAATGACATAGTACCTCATCTATAATTTTTACCCTGATCT |
| X14836 | 226 | AGTTAGATCAGGGTAAAAATTATAGATGAGGTACTATGTCATTTTGAAGTTGGTTAGAA |

TABLE 26-continued

Primer sequences used to create the integrative assemblies illustrated in FIGS. 35-44.

| Primer # | SEQ ID NO. | Primer sequence |
|---|---|---|
| X14837 | 227 | GGTCCATGTAAAATGATTGCTCCAATGATTGAAATTGATTCAGGTCAAAATGGATTCAG |
| X14838 | 228 | ACGTCCCTGAATCCATTTTGACCTGAATCAATTTCAATCATTGGAGCAATCATTTTACA |
| X14843 | 229 | GGTGGAACCATTTACTGTATTTTCAATGTAACGCTAGAGAATAAATTCAAGTTAAAAGA |
| X14844 | 230 | CATCATCTTTTAACTTGAATTTATTCTCTAGCGTTACATTGAAAATACAGTAAATGGTT |
| X15380 | 231 | TAGGTCTAGAGATCTGTTTAGCTTGC |
| X15382 | 232 | GAGACTACATGATAGTCCAAAGA |
| X15546 | 233 | GGACGAGGCAAGCTAAACAGATCTCTAGACCTACTTTATATTATCAATATTTGTGTTTG |
| X15547 | 234 | CCGTTTCTTTTCTTTGGACTATCATGTAGTCTCATTTATTGGAGAAAGATAACATATCA |
| X15548 | 235 | GGACGAGGCAAGCTAAACAGATCTCTAGACCTATGATAAGGAAGGGGAGCGAAGGAAAA |
| X15549 | 236 | CCGTTTCTTTTCTTTGGACTATCATGTAGTCTCCTCTGATCTTTCCTGTTGCCTCTTTT |
| X15552 | 237 | CCGTTTCTTTTCTTTGGACTATCATGTAGTCTCGAGTGATTATGAGTATTTGTGAGCAG |
| X15553 | 238 | ACCAGCGTCTGGTGGACAAACGGCCTTCAAC |
| X15554 | 239 | GGACGAGGCAAGCTAAACAGATCTCTAGACCTAATTAATTTTCAGCTGTTATTTCGATT |
| X15555 | 240 | CCGTTTCTTTTCTTTGGACTATCATGTAGTCTCGAGTGATTATGAGTATTTGTGAGCAG |
| X15559 | 241 | GGAAGGCACCGATACTAGAACTCCG |
| X15564 | 242 | CTAATCAAATCAAAATAACAGCTGAAAATTAATCTACTTATTCCCTTCGAGATTATATC |
| X15565 | 243 | GTTCCTAGATATAATCTCGAAGGGAATAAGTAGATTAATTTTCAGCTGTTATTTTGATT |
| X15566 | 244 | TCGGATCAGTAGATAACCCGCCTAGAAGACTAGGAGTGATTATGAGTATTTGTGAGCAG |
| X15567 | 245 | AAAACTTCTGCTCACAAATACTCATAATCACTCCTAGTCTTCTAGGCGGGTTATCTACT |
| X15870 | 246 | CTAATCAAATCAAAATAACAGCTGAAAATTAATGAGTGATTATGAGTATTTGTGAGCAG |
| X15871 | 247 | AAAACTTCTGCTCACAAATACTCATAATCACTCATTAATTTTCAGCTGTTATTTTGATT |
| X16096 | 248 | CATGGTGCTTAGCAGCAGATGAAAGTGTCA |
| X16097 | 249 | GTTCCTAGATATAATCTCGAAGGGAATAAGTAGATTAATTTTCAGCTGTTATTTCGATT |
| X16098 | 250 | CTAATCAAATCGAAATAACAGCTGAAAATTAATCTACTTATTCCCTTCGAGATTATATC |
| X16099 | 251 | AAAACTTCTGCTCACAAATACTCATAATCACTCCTAGTCTTCTAGGCGGGTTATCTACT |
| X16100 | 252 | TCGGATCAGTAGATAACCCGCCTAGAAGACTAGGAGTGATTATGAGTATTTGTGAGCAG |

TABLE 26-continued

Primer sequences used to create the integrative assemblies illustrated in FIGS. 35-44.

| Primer # | SEQ ID NO. | Primer sequence |
|---|---|---|
| X16463 | 253 | CAGAGTTTGAAGATATCCAAATGGT |
| X16464 | 254 | TTTGTTCTTCTTGTTATTGTATTGTGTTG |
| X16465 | 255 | GCTAATTAACATAAAACTCATGATTCAACG |
| X16466 | 256 | ACATAGGTTTGCAAGCTTTATAATCTG |
| X16467 | 257 | AGAACAACACAATACAATAACAAGAAGAACAAATAGGTCTAGAGATCTGTTTAGCTTGC |
| X16468 | 258 | AAACGTTGAATCATGAGTTTTATGTTAATTAGCGAGACTACATGATAGTCCAAAGAAAA |
| X16469 | 259 | AGAACAACACAATACAATAACAAGAAGAACAAACTACTTATTCCCTTCGAGATTATATC |
| X16470 | 260 | AAACGTTGAATCATGAGTTTTATGTTAATTAGCCTAGTCTTCTAGGCGGGTTATCTACT |
| X16471 | 261 | AAGAATCTGTTAGTTCGAACTCCAG |
| X16472 | 262 | TTTGTTGGCAATATGTTTTTGCTATATTAC |
| X16473 | 263 | GCCATTAGTAGTGTACTCAAACGAA |
| X16474 | 264 | ACGACTCAACATATGTATGTTGCT |
| X16475 | 265 | CACGTAATATAGCAAAAACATATTGCCAACAAATAGGTCTAGAGATCTGTTTAGCTTGC |
| X16476 | 266 | AACAATAATTCGTTTGAGTACACTACTAATGGCGAGACTACATGATAGTCCAAAGAAAA |
| X16477 | 267 | CACGTAATATAGCAAAAACATATTGCCAACAAACTACTTATTCCCTTCGAGATTATATC |
| X16478 | 268 | AACAATAATTCGTTTGAGTACACTACTAATGGCCTAGTCTTCTAGGCGGGTTATCTACT |
| X16951 | 269 | ATGTTCCGCTGATGTGATGTGCAAGATAAAC |
| X16952 | 270 | GAGGCAAGCTAAACAGATCTCTAGACCTATTTGATTGATTTGACTGTGTTATTTTGCGT |
| X16953 | 271 | ATAACCTCACGCAAAATAACACAGTCAAATCAATCAAATAGGTCTAGAGATCTGTTTAG |
| X16954 | 272 | AAAACTTTAACTAATAATTAGAGATTAAATCGCTTAGAGACTACATGATAGTCCAAAGA |
| X16955 | 273 | GTCCCCCCGTTTCTTTTCTTTGGACTATCATGTAGTCTCTAAGCGATTTAATCTCTAAT |
| X16956 | 274 | TCGGTCATTGGGTGAGTTTAAGCATTAGCAGCAATG |
| X16957 | 275 | TAAAACTTTAACTAATAATTAGAGATTAAATCGCTTATTTGATTGATTTGACTGTGTTA |
| X16958 | 276 | CACGCAAAATAACACAGTCAAATCAATCAAATAAGCGATTTAATCTCTAATTATTAGTT |

Heterologous genes for the production of a transcarboxylase based palmitic acid pathway (FIG. 34C) can then be introduced in a yeast microorganism engineered using the above integrative assemblies to replace GPD1, GPD2, FDH1, and FDH2 with two copies of a bifunctional alcohol/aldehyde dehydrogenase and two copies of a pyruvate formate lyase and to delete PDC5, PDC6, and PDC1. Such heterologous genes include, but are not limited to, *S. cerevisiae* NAD+ FDH1 to create the metabolic pathway in (FIG. 34B) and *B. stabilis* NADP+ FDH, *S. cerevisiae* PCK1, *P. freudenreichii* Transcarboxylase (see SEQ ID NOs:6-16), *A. thaliana* FATB1 to create the metabolic pathway in (FIG. 34C). Additional enzymes are identified in PCT/US2011/035416, which is incorporated by reference herein in its entirety. The pathways described herein can be engineered for production of a malonyl-CoA derived product in the yeast cytosol.

>SceNAD+_FDH1

(SEQ ID NO: 277)

```
atgtcgaagggaaaggttttgctggttctttacgaaggtggtaagcatgctgaagagcaggaaaagttattggggtgtattgaaaat
gaacttggtatcagaaatttcattgaagaacagggatacgagttggttactaccattgacaaggaccctgagccaacctcaacggt
agacagggagttgaaagacgctgaaattgtcattactacgccctttttccccgcctacatctcgagaaacaggattgcagaagctc
ctaacctgaagctctgtgtaaccgctggcgtcggttcagacccatgtcgatttagaagctgcaaatgaacggaaaatcacggtcac
cgaagttactggttctaacgtcgtttctgtcgcagagcacgttatggccacaattttggttttgataagaaactataatggtggtcatc
aacaagcaattaatggtgagtgggatattgccggcgtggctaaaaatgagtatgatctggaagacaaaataatttcaacggtaggt
gccggtagaattggatatagggttctggaaagattggtcgcattttaatcgaagaagttactgtactacgactaccaggaactacct
gcggaagcaatcaatagattgaacgaggccagcaagcttttcaatggcagaggtgatattgttcagagagtagagaaattggag
gatatggttgctcagtcagatgttgttaccatcaactgtccattgcacaaggactcaagggggttattcaataaaaagcttatttccca
catgaaagatggtgcatacttggtgaataccgctagaggtgctatttgtgtcgcagaagatgttgccgaggcagtcaagtctggta
aattggctggctatggtggtgatgtctgggataagcaaccagcaccaaaagaccatccctggaggactatggacaataaggacc
acgtgggaaacgcaatgactgttcatatcagtggcacatctctggatgctcaaaagaggtacgctcaggagtaaagaacatcct
aaatagttacttttccaaaaagtttgattaccgtccacaggatattattgtgcagaatggttcttatgccaccagagcttatggacaga
agaaa
```

>SceNAD+_FDH1

(SEQ ID NO: 278)

MSKGKVLLVLYEGGKHAEEQEKLLGCIENELGIRNFIEEQGYELVTTIDKDPEPTS
TVDRELKDAEIVITTPFFPAYISRNRIAEAPNLKLCVTAGVGSDHVDLEAANERKI
TVTEVTGSNVVSVAEHVMATILVLIRNYNGGHQQAINGEWDIAGVAKNEYDLED
KIISTVGAGRIGYRVLERLVAFNPKKLLYYDYQELPAEAINRLNEASKLFNGRGDI
VQRVEKLEDMVAQSDVVTINCPLHKDSRGLFNKKLISHMKDGAYLVNTARGAIC
VAEDVAEAVKSGKLAGYGGDVWDKQPAPKDHPWRTMDNKDHVGNAMTVHIS
GTSLDAQKRYAQGVKNILNSYFSKKFDYRPQDIIVQNGSYATRAYGQKK

>BstabilisNADP+_FDH (SEQ ID NO: 279)

```
atggctaccgttttgtgtgtcttgtatccagatccagttgatggttatccaccacattatgttagagataccattccagttattaccagat
acgctgatggtcaaactgctccaactccagctggtccaccaggttttagaccaggtgaattggttggttctgtttctggtgcttttgggt
ttgagaggttatttggaagctcatggtcatactttgatcgttacctctgataaggatggtccagattctgaattcgaaagaagattgcc
agacgccgatgttgttatttctcaaccattttggccagcttacttgaccgctgaaagaattgctagagcaccaaaattgagattggctt
tgactgctggtattggttctgatcatgttgatttggatgctgctgctagagcccatattactgttgctgaagttactggttccaactctatt
tcagttgccgaacacgttgttatgactacttttggcttgtgctgaaaactacttgccatctcatgctattgctcaacaaggtggttggaat
attgctgattgtgtctctagatcctacgatgttgaaggtatgcatttgtttactgttggtgctggtagaattggtttggctgtttttgagaa
gattgaagccatttggtttacacttgcactacacccaaagacatagattggatgcagctatcgaacaagaattgggtttaacttatca
tgctgatccagcttcattggctgctgctgttgatatagttaacttgcaaatcccattataccccatccaccgaacatttgtttgatgctgct
atgattgctagaatgaagagaggtgcatacttgattaacaccgctaagacgctaaattggttgatagagatgctgttgttagagctgtta
cttctggtcatttggctggttatggtggtgatgtttggttccacaaccagctccagctgatcatccttggagagctatgcctttaatg
gtatgactccacatatctccggtacatctttgtctgctcaagctagatatgctgctggtactttggaaatattgcaatgttggtttgacg
gtagaccaatcagaaacgaatatttgattgtcgacggtggtactttagctggtactggtgctcaatcttacagattaact
```

>BstabilisNADP+_FDH (SEQ ID NO: 280)

MATVLCVLYPDPVDGYPPHYVRDTIPVITRYADGQTAPTPAGPPGFRPGELVGSV
SGALGLRGYLEAHGHTLIVTSDKDGPDSEFERRLPDADVVISQPFWPAYLTAERI
ARAPKLRLALTAGIGSDHVDLAAARAHITVAEVTGSNSISVAEHVVMTTLALV
RNYLPSHAIAQQGGWNIADCVSRSYDVEGMHFGTVGAGRIGLAVLRRLKPFGLH
LHYTQRHRLDAAIEQELGLTYHADPASLAAAVDIVNLQIPLYPSTEHLFDAAMIA
RMKRGAYLINTARAKLVRDAVVRAVTSGHLAGYGGDVWFPQPAPADHPWRA
MPFNGMTPHISGTSLSAQARYAAGTLEILQCWFDGRPIRNEYLIVDGGTLAGTGA
QSYRLT

>ScePCK1

(SEQ ID NO: 281)

```
atgtccccttctaaaatgaatgctacagtaggatctacttccgaagttgaacaaaaaatcagacaagaattggctcttagtgacgaa
gtcaccaccatcagacgcaatgctccagctgccgttttgtatgaagatggtctaaaagaaaataaaactgtcatttcatcaagcggt
gcattgatcgcttattccggtgttaaaaccggaagatctccaaaggacaaacgtattgttgaagaacctacctcgaaagacgaaat
ttggtggggtccggtcaataaaccatgttctgaaagaacatggtctatcaaccgtgcagattacttgagaacaaga
gaccacatttatattgtcgatgcatttgcaggatgggatccaaaatacagaatcaaagtccgcgttgtttgtgccagggcttaccac
gctttattcatgacaaatatgcttattagacctcagaagaagaattagcccattttggagaacctgattttactgtctggaacgctgg
tcagttcccagccaatttacacacccaggatatgtcttcaaagagtactatagaaattaacttcaaagcaatggaaatgatcatttag
gtaccgaatacgccggtgaaatgaaaaaggtattttcacagttatgtttacttgatgcctgtgcaactaacgttttaactttgcact
cttccgccaaccagggtattcaaaacggtgacgttacttattctcttggcctaagtggtaccggaaaaccacttttatccgcagacc
cacatagattgttgatcggcgatgatgaacattgttggtccgaccatggtgtcttcaatatcgaaggtggttgttacgccaagtgtatt
aatttatctgccgaaaggagcctgaaattttcgacgctatcaagtttggttctgtattagaaaacgttatctatgacgagaagtcgca
tgtagtcgactatgacgactcttctattactgaaaatactagatgtgcctacccaattgactacattccaagtgccaagattccatgttt
ggcggactctcatccaaagaacattatcctgctaacttgtgatgcttcgggtgttttaccagcagtatctaaattgactcctgaacaa
gtcatgtaccatttcatctctggttacacttctaaaatggctggtactgagcaaggtgtcactgaacctgaacaacattttcatcttgt
ttcggacaaccctccctagccttgcacccattagatacgcaaccatgttagctacaaagatgtctcaacataaagctaatgcgtact
taatcaaccaccggctggactggttcttcctacgtatctggtggtaaacgttgccattgaagtaccaaaggccatctctggattctat
tcatgatggttcgttagccaatgaaacgtacgaaacttttaccgattttcaatcttcaagtacctaccaaggtttaacggtgttccagctg
agcttttgaatcctgctaaaaactggtctcaaggtgaatccaaatacagaggtcagttaccaacttggccaacttgttttgttcaaaa
tttcaagatttatcaagacagagccacaccagatgtattagccgctggtcctcaattcgag
```

>ScePCK1

(SEQ ID NO: 282)

MSPSKMNATVGSTSEVEQKIRQELALSDEVTTIRRNAPAAVLYEDGLKENKTVIS
SSGALIAYSGVKTGRSPKDKRIVEEPTSKDEIWWGPVNKPCSERTWSINRERAAD
YLRTRDHIYIVDAFAGWDPKYRIKVRVVCARAYHALFMTNMLIRPTEEELAHFG

EPDFTVWNAGQFPANLHTQDMSSKSTIEINFKAMEMIILGTEYAGEMKKGIFTVM
FYLMPVHHNVLTLHSSANQGIQNGDVTLFFGLSGTGKTTLSADPHRLLIGDDEHC
WSDHGVFNIEGGCYAKCINLSAEKEPEIFDAIKFGSVLENVIYDEKSHVVDYDDSS
ITENTRCAYPIDYIPSAKIPCLADSHPKNIILLTCDASGVLPPVSKLTPEQVMYHFIS
GYTSKMAGTEQGVTEPEPTFSSCFGQPFLALHPIRYATMLATKMSQHKANAYLIN
TGWTGSSYVSGGKRCPLKYTRAILDSIHDGSLANETYETLPIFNLQVPTKVNGVP
AELLNPAKNWSQGESKYRGAVTNLANLFVQNFKIYQDRATPDVLAAGPQFE

>Ath_FATB1_mature_peptide (SEQ ID NO: 283)

atgcttgattggaaacctaggcgttctgacatgctggtggatccttttggtatagggagaattgttcaggatggccttgtgttccgtca
gaattttctattaggtcatatgaaataggtgctgatcgctctgcatctatagaaaccgtcatgaatcatctgcaggaaacggcgctta
atcatgttaagactgctggattgcttggagatgggtttggctctacacctgagatgtttaagaagaacttgatatgggttgtcactcgt
atgcaggttgtggttgataaatatcctacttggggagatgttgttgaagtagacacctgggtcagtcaatctggaaagaatggtatg
cgtcgtgattggctagttcgggattgtaatactggagaaaccttaacacgagcatcaagtgtgtgggtgatgatgaataaactgac
aaggagattgtcaaagattcctgaagaggttcgaggggaaatagagcctattttgtgaattctgatcctgtccttgccgaggacag
cagaaagttaacaaaaattgatgacaagactgctgactatgttcgatctggtctcactcctcgatggagtgacctagatgttaacca
gcatgtgaataatgtaaagtacattgggtggatcctggagagtgctccagtgggaataatggagaggcagaagctgaaaagcat
gactctggagtatcggagggaatgcgggagagacagtgtgcttcagtccctcactgcagttacgggttgcgatatcggtaacctg
gcaacagcggggatgtggaatgtcagcatttgctccgactccaggatggagcggaagtggtgagaggaagaacagagtgga
gtagtaaaacaccaacaacaacttggggaactgcaccg >Ath_FATB1_mature_peptide (SEQ ID NO: 284)

MLDWKPRRSDMLVDPFGIGRIVQDGLVFRQNFSIRSYEIGADRSASIETVMNHLQ
ETALNHVKTAGLLGDGFGSTPEMFKKNLIWVVTRMQVVVDKYPTWGDVVEVD
TWVSQSGKNGMRRDWLVRDCNTGETLTRASSVWVMMNKLTRRLSKIPEEVRG
EIEPYFVNSDPVLAEDSRKLTKIDDKTADYVRSGLTPRWSDLDVNQHVNNVKYI
GWILESAPVGIMERQKLKSMTLEYRRECGRDSVLQSLTAVTGCDIGNLATAGDV
ECQHLLRLQDGAEVVRGRTEWSSKTPTTTWGTAP

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

---

SEQUENCE LISTING

<160> NUMBER OF SEQ ID NOS: 301

<210> SEQ ID NO 1
<211> LENGTH: 1220
<212> TYPE: PRT
<213> ORGANISM: C. aurantiacus

<400> SEQUENCE: 1

Met Ser Gly Thr Gly Arg Leu Ala Gly Lys Ile Ala Leu Ile Thr Gly
1               5                   10                  15

Gly Ala Gly Asn Ile Gly Ser Glu Leu Thr Arg Arg Phe Leu Ala Glu
            20                  25                  30

Gly Ala Thr Val Ile Ile Ser Gly Arg Asn Arg Ala Lys Leu Thr Ala
        35                  40                  45

Leu Ala Glu Arg Met Gln Ala Glu Ala Gly Val Pro Ala Lys Arg Ile
    50                  55                  60

Asp Leu Glu Val Met Asp Gly Ser Asp Pro Val Ala Val Arg Ala Gly
65                  70                  75                  80

Ile Glu Ala Ile Val Ala Arg His Gly Gln Ile Asp Ile Leu Val Asn
                85                  90                  95

Asn Ala Gly Ser Ala Gly Ala Gln Arg Arg Leu Ala Glu Ile Pro Leu
            100                 105                 110

-continued

```
Thr Glu Ala Glu Leu Gly Pro Gly Ala Glu Thr Leu His Ala Ser
    115                 120                 125
Ile Ala Asn Leu Leu Gly Met Gly Trp His Leu Met Arg Ile Ala Ala
130                 135                 140
Pro His Met Pro Val Gly Ser Ala Val Ile Asn Val Ser Thr Ile Phe
145                 150                 155                 160
Ser Arg Ala Glu Tyr Tyr Gly Arg Ile Pro Tyr Val Thr Pro Lys Ala
                165                 170                 175
Ala Leu Asn Ala Leu Ser Gln Leu Ala Arg Glu Leu Gly Ala Arg
                180                 185                 190
Gly Ile Arg Val Asn Thr Ile Phe Pro Gly Pro Ile Glu Ser Asp Arg
    195                 200                 205
Ile Arg Thr Val Phe Gln Arg Met Asp Gln Leu Lys Gly Arg Pro Glu
    210                 215                 220
Gly Asp Thr Ala His His Phe Leu Asn Thr Met Arg Leu Cys Arg Ala
225                 230                 235                 240
Asn Asp Gln Gly Ala Leu Glu Arg Arg Phe Pro Ser Val Gly Asp Val
                245                 250                 255
Ala Asp Ala Ala Val Phe Leu Ala Ser Ala Glu Ser Ala Ala Leu Ser
                260                 265                 270
Gly Glu Thr Ile Glu Val Thr His Gly Met Glu Leu Pro Ala Cys Ser
    275                 280                 285
Glu Thr Ser Leu Leu Ala Arg Thr Asp Leu Arg Thr Ile Asp Ala Ser
    290                 295                 300
Gly Arg Thr Thr Leu Ile Cys Ala Gly Asp Gln Ile Glu Glu Val Met
305                 310                 315                 320
Ala Leu Thr Gly Met Leu Arg Thr Cys Gly Ser Glu Val Ile Ile Gly
                325                 330                 335
Phe Arg Ser Ala Ala Ala Leu Ala Gln Phe Glu Gln Ala Val Asn Glu
                340                 345                 350
Ser Arg Arg Leu Ala Gly Ala Asp Phe Thr Pro Pro Ile Ala Leu Pro
    355                 360                 365
Leu Asp Pro Arg Asp Pro Ala Thr Ile Asp Ala Val Phe Asp Trp Gly
    370                 375                 380
Ala Gly Glu Asn Thr Gly Gly Ile His Ala Ala Val Ile Leu Pro Ala
385                 390                 395                 400
Thr Ser His Glu Pro Ala Pro Cys Val Ile Glu Val Asp Asp Glu Arg
                405                 410                 415
Val Leu Asn Phe Leu Ala Asp Glu Ile Thr Gly Thr Ile Val Ile Ala
                420                 425                 430
Ser Arg Leu Ala Arg Tyr Trp Gln Ser Gln Arg Leu Thr Pro Gly Ala
    435                 440                 445
Arg Ala Arg Gly Pro Arg Val Ile Phe Leu Ser Asn Gly Ala Asp Gln
    450                 455                 460
Asn Gly Asn Val Tyr Gly Arg Ile Gln Ser Ala Ala Ile Gly Gln Leu
465                 470                 475                 480
Ile Arg Val Trp Arg His Glu Ala Glu Leu Asp Tyr Gln Arg Ala Ser
                485                 490                 495
Ala Ala Gly Asp His Val Leu Pro Pro Val Trp Ala Asn Gln Ile Val
                500                 505                 510
Arg Phe Ala Asn Arg Ser Leu Glu Gly Leu Glu Phe Ala Cys Ala Trp
    515                 520                 525
Thr Ala Gln Leu Leu His Ser Gln Arg His Ile Asn Glu Ile Thr Leu
```

```
                 530                 535                 540
Asn Ile Pro Ala Asn Ile Ser Ala Thr Thr Gly Ala Arg Ser Ala Ser
545                 550                 555                 560

Val Gly Trp Ala Glu Ser Leu Ile Gly Leu His Leu Gly Lys Val Ala
                565                 570                 575

Leu Ile Thr Gly Gly Ser Ala Gly Ile Gly Gln Ile Gly Arg Leu
                580                 585                 590

Leu Ala Leu Ser Gly Ala Arg Val Met Leu Ala Ala Arg Asp Arg His
                595                 600                 605

Lys Leu Glu Gln Met Gln Ala Met Ile Gln Ser Glu Leu Ala Glu Val
                610                 615                 620

Gly Tyr Thr Asp Val Glu Asp Arg Val His Ile Ala Pro Gly Cys Asp
625                 630                 635                 640

Val Ser Ser Glu Ala Gln Leu Ala Asp Leu Val Glu Arg Thr Leu Ser
                645                 650                 655

Ala Phe Gly Thr Val Asp Tyr Leu Ile Asn Asn Ala Gly Ile Ala Gly
                660                 665                 670

Val Glu Glu Met Val Ile Asp Met Pro Val Glu Gly Trp Arg His Thr
                675                 680                 685

Leu Phe Ala Asn Leu Ile Ser Asn Tyr Ser Leu Met Arg Lys Leu Ala
                690                 695                 700

Pro Leu Met Lys Lys Gln Gly Ser Gly Tyr Ile Leu Asn Val Ser Ser
705                 710                 715                 720

Tyr Phe Gly Gly Glu Lys Asp Ala Ala Ile Pro Tyr Pro Asn Arg Ala
                        725                 730                 735

Asp Tyr Ala Val Ser Lys Ala Gly Gln Arg Ala Met Ala Glu Val Phe
                740                 745                 750

Ala Arg Phe Leu Gly Pro Glu Ile Gln Ile Asn Ala Ile Ala Pro Gly
                755                 760                 765

Pro Val Glu Gly Asp Arg Leu Arg Gly Thr Gly Glu Arg Pro Gly Leu
770                 775                 780

Phe Ala Arg Arg Ala Arg Leu Ile Leu Glu Asn Lys Arg Leu Asn Glu
785                 790                 795                 800

Leu His Ala Ala Leu Ile Ala Ala Ala Arg Thr Asp Glu Arg Ser Met
                        805                 810                 815

His Glu Leu Val Glu Leu Leu Leu Pro Asn Asp Val Ala Ala Leu Glu
                820                 825                 830

Gln Asn Pro Ala Ala Pro Thr Ala Leu Arg Glu Leu Ala Arg Arg Phe
                835                 840                 845

Arg Ser Glu Gly Asp Pro Ala Ala Ser Ser Ser Ala Leu Leu Asn
850                 855                 860

Arg Ser Ile Ala Ala Lys Leu Leu Ala Arg Leu His Asn Gly Gly Tyr
865                 870                 875                 880

Val Leu Pro Ala Asp Ile Phe Ala Asn Leu Pro Asn Pro Pro Asp Pro
                        885                 890                 895

Phe Phe Thr Arg Ala Gln Ile Asp Arg Glu Ala Arg Lys Val Arg Asp
                        900                 905                 910

Gly Ile Met Gly Met Leu Tyr Leu Gln Arg Met Pro Thr Glu Phe Asp
                915                 920                 925

Val Ala Met Ala Thr Val Tyr Tyr Leu Ala Asp Arg Asn Val Ser Gly
                930                 935                 940

Glu Thr Phe His Pro Ser Gly Gly Leu Arg Tyr Glu Arg Thr Pro Thr
945                 950                 955                 960
```

```
Gly Gly Glu Leu Phe Gly Leu Pro Ser Pro Glu Arg Leu Ala Glu Leu
            965                 970                 975

Val Gly Ser Thr Val Tyr Leu Ile Gly Glu His Leu Thr Glu His Leu
        980                 985                 990

Asn Leu Leu Ala Arg Ala Tyr Leu  Glu Arg Tyr Gly Ala  Arg Gln Val
            995                 1000                1005

Val Met  Ile Val Glu Thr Glu  Thr Gly Ala Glu Thr  Met Arg Arg
    1010                1015                1020

Leu Leu  His Asp His Val Glu  Ala Gly Arg Leu Met  Thr Ile Val
    1025                1030                1035

Ala Gly  Asp Gln Ile Glu Ala  Ala Ile Asp Gln Ala  Ile Thr Arg
    1040                1045                1050

Tyr Gly  Arg Pro Gly Pro Val  Val Cys Thr Pro Phe  Arg Pro Leu
    1055                1060                1065

Pro Thr  Val Pro Leu Val Gly  Arg Lys Asp Ser Asp  Trp Ser Thr
    1070                1075                1080

Val Leu  Ser Glu Ala Glu Phe  Ala Glu Leu Cys Glu  His Gln Leu
    1085                1090                1095

Thr His  His Phe Arg Val Ala  Arg Lys Ile Ala Leu  Ser Asp Gly
    1100                1105                1110

Ala Ser  Leu Ala Leu Val Thr  Pro Glu Thr Thr Ala  Thr Ser Thr
    1115                1120                1125

Thr Glu  Gln Phe Ala Leu Ala  Asn Phe Ile Lys Thr  Thr Leu His
    1130                1135                1140

Ala Phe  Thr Ala Thr Ile Gly  Val Glu Ser Glu Arg  Thr Ala Gln
    1145                1150                1155

Arg Ile  Leu Ile Asn Gln Val  Asp Leu Thr Arg Arg  Ala Arg Ala
    1160                1165                1170

Glu Glu  Pro Arg Asp Pro His  Glu Arg Gln Gln Glu  Leu Glu Arg
    1175                1180                1185

Phe Ile  Glu Ala Val Leu Leu  Val Thr Ala Pro Leu  Pro Pro Glu
    1190                1195                1200

Ala Asp  Thr Arg Tyr Ala Gly  Arg Ile His Arg Gly  Arg Ala Ile
    1205                1210                1215

Thr Val
    1220

<210> SEQ ID NO 2
<211> LENGTH: 1818
<212> TYPE: DNA
<213> ORGANISM: C. thermocellum

<400> SEQUENCE: 2
atgacatcaa caaacatgac aaaaaacaaa aaactgctgg attgggttaa ggaaatggct      60
gaaatgtgtc agcctgatga aatttattgg tgcgatggtt cggaggaaga aaatgagcgc     120
ttgataaagt tgatggtgga ttcaggtttg gctacgcctt tgaatcctga aaagcgacct     180
ggatgttatc tcttccgcag cgatccgtcc gacgttgccc gtgttgagga cagaactttt     240
attgcatcca aaccaaaga agatgcagga cctacaaaca actggataga tccggttgag     300
ctcaaggcaa ctatgaaaga gttgtacaag ggttgtatga agggaagaac aatgtatgtt     360
attccttcct ccatgggacc tatcggttca cccatttcaa aatcggcgt tgaattgacc     420 gacagccctt atgttgttgt taacatgcgc attatgactc gcataggcaa ggctgtgttg     480
```

```
gatcagctcg gagaagacgg agattttgta ccttgtctcc actcagtcgg tgctccgctc      540
aaagagggag aaaaggataa aggttggcca tgcgcaccaa tcgaaaagaa atacataagc      600
cacttcccgg aagaaaggac tatatggtca tatggttccg gatacggtgg aaatgcgctt      660
ttaggaaaga aatgctttgc acttcgtatt gcatctgtta tggcacgtga cgaaggttgg      720
cttgctgaac acatgcttat ccttcgcata acagaccctg aaggaaacaa gacatatgtt      780
acaggtgctt cccaagcgc atgcggaaag acgaacctgg ctatgcttat cctacaatt       840 cccggatgga agttgaaac aatcggtgac gatattgcat ggatgagatt tggaaaagac       900
ggccgtttgt atgctatcaa ccctgaagca ggattctttg gtgttgctcc gggtacatcc      960
atggattcaa atccgaacgc aatgcataca attaagaaaa atactatatt tacaaacgtt     1020
gcattgactg atgacggcga tgtttggtgg gaaggcatcg aactgaacc gccggctcat      1080 ctcatagact ggcagggtaa agactggact cctgattccg gaactttggc agcacatccc     1140
aacggacgtt ttacagcacc tgcaagtcag tgccctgtaa ttgctcctga atgggaggat     1200
ccggaaggtg tgccgatttc agcaatcctt atcggtggac gccgtccgaa caccattccg     1260
cttgttcatg aaagctttga ctggaaccat ggtgtattca tgggttcaat catgggttct     1320
gaaattacgg ctgccgcaat ttcaaacaaa atcggacagg tacgccgtga cccgtttgct     1380
atgctgcctt tcataggcta caacgtaaat gactatttgc agcactggtt gaacatgggt     1440
accaagactg acccaagcaa gcttcccaag atattctatg taaactggtt ccgcaaggac     1500
agcaacggta atggttgtg gcctggatac ggtgaaaaca gccgtgttct caagtggatt      1560
gttgaaagag tcaacggaaa aggtaaagca gtaaagacac ctataggata tatgcctaca     1620
gttgacgcta tcgacacaac cggccttgat gtaagcaaag aggatatgga agaactcttg     1680
agcgttaaca agaacagtg gctccaggaa gttgagtcaa taaaagaaca ttataagtca      1740
tacggagaaa aactgccgaa agaattgtgg gcacaattgg aggctcttga caacgtttg      1800 aaagagtata acggttaa                                                   1818

<210> SEQ ID NO 3
<211> LENGTH: 1632
<212> TYPE: DNA
<213> ORGANISM: T. saccharolyticum

<400> SEQUENCE: 3
atgattatga aaaatcaaa gaatgtttc aatctgaata ttgacgacaa agaaaccttg        60 aatactttg gaagttcgag aggagaattg tttatgatag atttagatga tgtatttaaa      120
aattctggca gtattcttta caatttacct gtttcagatt tgatagagga agccataaga     180
aataatgaag ggaaattgtt agaaaatggt gcattagatg tttttacagg taaatatacg     240
ggaagaatac caaaagataa atacattgta aatgaagaat ctattcataa tgatatttgg     300
tgggaaaata taattcaat ggaaaaagaa aatttttatta gagtttttaaa cagagtaatt      360 gattatttaa aaagagcag aaaattgtat gtttttaaag ttttgttgg cgcagacccg       420 cgatatagat atcaagtaac cgttattaat gaatatgcct atcaaaacgc ttttgtacat      480
caattattta ttaatcctaa aaatgaagaa gaacttaaaa aggaatccga ttttacagtt     540
atttgtgtgc cgaattttt agctgatcca atttatgatg gaactaattc tgaggcattt      600
attattataa gttttgaaga aaattaatt ttaattggtg gaacaagata ttcaggagaa       660
ataaaaaaat ctgtcttcac aatgatgaat tatttgatgt taaaaggaa tgtactgcct      720 atgcattgtg cagctaatat aggttccaat aatgatacag cgcttttttt tgggttgtcg     780
```

```
ggaaccggca agacaacttt atcaacggat ccagaaagat ttttaattgg cgacgatgaa    840
catggatggt cttcacatgg aattttaat tttgagggtg gatgctatgc aaagtgtata    900
aatttatccc catataatga acctgaaata tggaatgcaa ttagatttgg aacaatttta    960
gaaaatgtta tttatgatgt aaataatatg ccagtctata caagtagtaa aataactgaa   1020
aatacaagag cttcatatcc acttgagtac atccctagga aagcgtcaaa tggcattggc   1080
ggtaatccta aaattatatt tttcttggca gccgatgctt ttggagtatt gcctccaatt   1140
tctaagctga caaatgaaca ggctgttgac tatttcttat taggatatac gagcaaaata   1200
ccaggaacag aaaagggaat tgcgaaccaa caagcaacgt tttcatcatg ttttggagca   1260
ccatttttgc catcatatcc aatgaggtat gctgaattgt aaagaaaaa atcgcagaa    1320 aatgattcag ttgtttattt aataaatact ggatggatag gtggacatta tggaattggc   1380
aaaaggatag atttaaaata cacaagagaa atcataaaaa atgttttaaa tggtgaattg   1440 gaaaagcaa aatttaaaaa agatacagta tttgatttga tgataccaga aaagtgcaat   1500
aacattccag atgaattatt agatcctata aaaacatggg aagacaaaaa tgattacttc   1560
caaactgcta ataatttatt atctgcattt aaagcgagat tagattatat aaaaaatggg   1620
attcatcaat aa                                                      1632

<210> SEQ ID NO 4
<211> LENGTH: 1623
<212> TYPE: DNA
<213> ORGANISM: E. coli

<400> SEQUENCE: 4
atgcgcgtta caatggtttt gaccccgcaa gaactcgagg cttatggtat cagtgacgta     60
catgatatcg tttacaaccc aagctacgac ctgctgtatc aggaagagct cgatccgagc    120
ctgacaggtt atgagcgcgg ggtgttaact aatctgggtg ccgttgccgt cgataccggg    180
atcttcaccg gtcgttcacc aaaagataag tatatcgtcc gtgacgatac cactcgcgat    240
actttctggt gggcagacaa aggcaaaggt aagaacgaca caaacctct ctctccggaa    300 acctggcagc atctgaaagg cctggtgacc aggcagcttt ccggcaaacg tctgttcgtt    360
gtcgacgctt tctgtggtgc gaaccccgat actcgtcttt ccgtccgttt catcaccgaa    420
gtggcctggc aggcgcattt tgtcaaaaac atgtttattc gcccgagcga tgaagaactg    480
gcaggtttca aaccagactt tatcgttatg aacggcgcga agtgcactaa cccgcagtgg    540
aaagaacagg tctcaactc cgaaaacttc gtggcgttta acctgaccga gcgcatgcag    600
ctgattggcg gcacctggta cggcggcgaa atgaagaaag ggatgttctc gatgatgaac    660
tacctgctgc cgctgaaagg tatcgcttct atgcactgct ccgccaacgt tggtgagaaa    720
ggcgatgttg cggtgttctt cggcctttcc ggcaccggta aaaccaccct ttccaccgac    780
ccgaaacgtc gcctgattgg cgatgacgaa cacggctggg acgatgacgg cgtgtttaac    840
ttcgaaggcg gctgctacgc aaaaactatc aagctgtcga agaagcgga acctgaaatc    900 tacaacgcta tccgtcgtga tgcgttgctg gaaaacgtca ccgtgcgtga agatggcact    960
atcgactttg atgatggttc aaaaaccgag aacacccgcg tttcttatcc gatctatcac   1020
atcgataaca ttgttaagcc ggtttccaaa gcgggccacg cgactaaggt tatcttcctg   1080
actgctgatg ctttcggcgt gttgccgccg gtttctcgcc tgactgccga tcaaacccag   1140
tatcacttcc tctctggctt caccgccaaa ctggccggta ctgagcgtgg catcaccgaa   1200
```

-continued

```
ccgacgccaa ccttctccgc ttgcttcggc gcggcattcc tgtcgctgca cccgactcag    1260
tacgcagaag tgctggtgaa acgtatgcag gcggcgggcg cgcaggctta tctggttaac    1320
actggctgga acggcactgg caaacgtatc tcgattaaag atacccgcgc cattatcgac    1380
gccatcctca acggttcgct ggataatgca gaaaccttca ctctgccgat gtttaacctg    1440
gcgatcccaa ccgaactgcc gggcgtagac acgaagattc tcgatccgcg taacacctac    1500
gcttctccgg aacagtggca ggaaaaagcc gaaaccctgg cgaaactgtt tatcgacaac    1560
ttcgataaat acaccgacac ccctgcgggt gccgcgctgg tagcggctgg tccgaaactg    1620
taa                                                                  1623
```

<210> SEQ ID NO 5
<211> LENGTH: 1650
<212> TYPE: DNA
<213> ORGANISM: S. cerevisiae

<400> SEQUENCE: 5

```
atgtcccctt ctaaaatgaa tgctacagta ggatctactt ccgaagttga acaaaaaatc      60
agacaagaat tggctcttag tgacgaagtc accaccatca gacgcaatgc tccagctgcc     120
gttttgtatg aagatggtct aaaagaaaat aaaactgtca tttcatcaag cggtgcattg     180
atcgcttatt ccggtgttaa aaccggaaga tctccaaagg acaaacgtat tgttgaagaa     240
cctacctcga aagacgaaat ttggtggggt ccggtcaata aaccatgttc tgaaagaaca     300
tggtctatca accgtgaaag agctgcagat tacttgagaa caagagacca catttatatt     360
gtcgatgcat ttgcaggatg ggatccaaaa tacagaatca aagtccgcgt tgtttgtgcc     420
agggcttacc acgcttttat catgacaaat atgcttatta gacctacaga agaagaatta     480
gcccattttg gagaacctga ttttactgtc tggaacgctg gtcagttccc agccaattta     540
cacacccagg atatgtcttc aaagagtact atagaaatta acttcaaagc aatggaaatg     600
atcattttag gtaccgaata cgccggtgaa atgaaaaaag gtattttcac agttatgttt     660
tacttgatgc ctgtgcacca taacgtttta actttgcact cttccgccaa ccagggtatt     720
caaaacggtg acgttacttt attctttggc ctaagtggta ccgggaaaac cactttatcc     780
gcagacccac atagattgtt gatcggcgat gatgaacatt gttggtccga ccatggtgtc     840
ttcaatatcg aaggtggttg ttacgccaag tgtattaatt tatctgccga aaaggagcct     900
gaaattttcg acgctatcaa gtttggttct gtattagaaa acgttatcta tgacgagaag     960
tcgcatgtag tcgactatga cgactcttct attactgaaa atactagatg tgcctaccca    1020
attgactaca ttccaagtgc caagattcca tgtttggcgg actctcatcc aaagaacatt    1080
atcctgctaa cttgtgatgc ttcgggtgtt ttaccaccag tatctaaatt gactcctgaa    1140
caagtcatgt accatttcat ctctggttac acttctaaaa tggctggtac tgagcaaggt    1200
gtcactgaac ctgaaccaac attttcatct tgtttcggac aacccttcct agccttgcac    1260
cctattagat acgcaaccat gttagctaca agatgtctc aacataaagc taatgcgtac    1320
ttaatcaaca ccggctggac tggttcttcc tacgtatctg gtggtaaacg ttgcccattg    1380
aagtacacaa gggccattct ggattctatt catgatggtt cgttagccaa tgaaacgtac    1440
gaaactttac cgattttcaa tcttcaagta cctaccaagg ttaacggtgt tccagctgag    1500
cttttgaatc ctgctaaaaa ctggtctcaa ggtgaatcca atacagagg tgcagttacc    1560 aacttggcca acttgtttgt tcaaaatttc aagatttatc aagacagagc cacaccagat    1620
gtattagccg ctggtcctca attcgagtaa                                     1650
```

<210> SEQ ID NO 6
<211> LENGTH: 372
<212> TYPE: DNA
<213> ORGANISM: Propionibacterium freudenreichii

<400> SEQUENCE: 6

```
tcagccgatc ttgatgagac cctgaccgcc ctgcacggcg tcacgctcct tgacaaggac      60
cttctcgacc ttgccgtcgg tgggagcgtt gatctcggtc tccatcttca tggcctcgag     120
aacgagcacg gtctgaccag ccttgaccgt gtcaccctcc ttcacgagga tcttggagac     180
ggtgccggcc agcggagcgg gaatctcgcc ctctccggcc ttaccggcgc ctgcgccacc     240
tgctgcgcgc ggtgccggcg cgccgccggt gccgccgccg aacaggatgg tgcccatcgg     300
gttttcgtgt gacttgtcga cgtcaacgtc aacgtcatac gcagtgccgt tgactgttac     360
cttcagtttc at                                                         372
```

<210> SEQ ID NO 7
<211> LENGTH: 369
<212> TYPE: DNA
<213> ORGANISM: Propionibacterium freudenreichii

<400> SEQUENCE: 7

```
atgaaactga aggtaacagt caacggcact gcgtatgacg ttgacgttga cgtcgacaag      60
tcacacgaaa acccgatggg caccatcctg ttcggcggcg gcaccggcgg cgcgccggca     120
ccgcgcgcag caggtggcgc aggcgccggt aaggccggag agggcgagat tcccgctccg     180
ctggccggca ccgtctccaa gatcctcgtg aaggagggtg acacggtcaa ggctggtcag     240
accgtgctcg ttctcgaggc catgaagatg gagaccgaga tcaacgctcc caccgacggc     300
aaggtcgaga aggtccttgt caaggagcgt gacgccgtgc agggcggtca gggtctcatc     360
aagatcggc                                                             369
```

<210> SEQ ID NO 8
<211> LENGTH: 123
<212> TYPE: PRT
<213> ORGANISM: Propionibacterium freudenreichii

<400> SEQUENCE: 8

```
Met Lys Leu Lys Val Thr Val Asn Gly Thr Ala Tyr Asp Val Asp Val
  1               5                  10                  15

Asp Val Asp Lys Ser His Glu Asn Pro Met Gly Thr Ile Leu Phe Gly
             20                  25                  30

Gly Gly Thr Gly Gly Ala Pro Ala Pro Arg Ala Ala Gly Gly Ala Gly
         35                  40                  45

Ala Gly Lys Ala Gly Glu Gly Glu Ile Pro Ala Pro Leu Ala Gly Thr
     50                  55                  60

Val Ser Lys Ile Leu Val Lys Glu Gly Asp Thr Val Lys Ala Gly Gln
 65                  70                  75                  80

Thr Val Leu Val Leu Glu Ala Met Lys Met Glu Thr Glu Ile Asn Ala
                 85                  90                  95

Pro Thr Asp Gly Lys Val Glu Val Leu Val Lys Glu Arg Asp Ala
            100                 105                 110

Val Gln Gly Gly Gln Gly Leu Ile Lys Ile Gly
        115                 120
```

<210> SEQ ID NO 9

```
<211> LENGTH: 1518
<212> TYPE: DNA
<213> ORGANISM: Propionibacterium freudenreichii

<400> SEQUENCE: 9
tcacgcctgc tgaacggtga cttcgcggac ggttccgccc acgttcacgt tgtaggtgac      60
gggaccggcc acggcgagcg acttctcgtc gccctcggcc tcggccttca gctgggcatc     120
ggtgagagcc acgctgtgcg ggccctcggc gcgatgctcg aagaagaccg gagcgacctg     180
cgggaacagt gcataggtga gcacgtcctc gtcggtgccg ttgaagccct tgagggccgc     240
ggcctccttg gactgctcct cccactcggg gggcagcaga tcggccgggc gctgggtgat     300
cggcttcttg ccggactgct cctcggccaa cttgaccacc ttcggatcgc gatcggccgg     360
gctggcgccg tagtagccga gcatgatgtc ggcgaactcg ccggtcatcc tcttgtactc     420
gcccatcatc acgttgaaca cggcctgcgt gccgacgatc tggctggacg gggtgaccag     480
gggcgggaag ccggcggcct tgcggacgcg cggcacctct gccatgacct cgtccatctt     540
gtcctcggcg ccctgggcgc gcagctgcga ctccatgttg agagcatgc cgccggggat      600 ctgcgacttg aagatcgagg tgtcgacaag cgtcttcgac tcgaacttct tgtacttcgg     660
gcggatggcc ttgaagtgat cgcggatctt gtgcaggcga tcgtagtcaa ggttggtggt     720
gtacccggtg ccctcgagca tctcggcaac cgactcggtg gggttgtggc ccgggccgag     780
cgacatggac gagatggcgg tgtcgacgac gtcgacgccg gcctcgatgg ccttcatgag     840
ggagacctcg gtgacacccg tggtggagtg gcagtgcagg ttgatctgcg tcttctggcc     900
gtaggtgtcc ttgatggcct tgatgatgtc gtaggccggc tgcggcttga cagggcggc     960 catgtccttc agggcgatgg aatcagcacc catgtcgagc agctgaccag caagcttgac    1020
atagccctca acgtgtggga ccgggctgat cgtgtagcaa atggtgccct gcgcgtgctt    1080
gccggccttc ttgacggcag ccatggcgtg cgccatgttg cggggatcat tcatggcgtc    1140
gaagacacgg aacacgtcca tgccgttctc agcggacttg tcgacgaagc gatcgacgac    1200
ctcgtcgttg tagtggcggt aacccagcag gttctggcca cgcagcagca tctggagacg    1260
gctgttgggc atcagcttgc ggaacgtgcg cagacgctcc caaggatcct cgttgaggaa    1320
gcggatacac gagtcatacg tggcaccacc ccaacactcc actgaccagt acccggcagc    1380
atcaatgtct gcacaggcgc cgaccatgtc ttccattgcc attcgtgtgg ccatcaggct    1440
ctgatgggca tcgcgcagca cgagctcggt gataccaacc tcgcgcggct cggaaacctc    1500
aatttctcgc ggactcat                                                  1518

<210> SEQ ID NO 10
<211> LENGTH: 1518
<212> TYPE: DNA
<213> ORGANISM: Propionibacterium freudenreichii

<400> SEQUENCE: 10
atgagtccgc gagaaattga ggtttccgag ccgcgcgagg ttggtatcac cgagctcgtg      60
ctgcgcgatg cccatcagag cctgatggcc acacgaatgg caatggaaga catggtcggc     120
gcctgtgcag acattgatgc tgccgggtac tggtcagtgg agtgttgggg tggtgccacg     180
tatgactcgt gtatccgctt cctcaacgag gatccttggg agcgtctgcg cacgttccgc     240
aagctgatgc ccaacagccg ctccagatgc tgctgcgtg ccagaacct gctgggttac      300 cgccactaca acgacgaggt cgtcgatcgc ttcgtcgaca gtccgctga gaacggcatg      360 gacgtgttcc gtgtcttcga cgccatgaat gatccccgca acatggcgca cgccatggct     420
```

```
gccgtcaaga aggccggcaa gcacgcgcag ggcaccattt gctacacgat cagcccggtc    480
cacaccgttg agggctatgt caagcttgct ggtcagctgc tcgacatggg tgctgattcc    540
atcgccctga aggacatggc cgccctgctc aagccgcagc cggcctacga catcatcaag    600
gccatcaagg acacctacgg ccagaagacg cagatcaacc tgcactgcca ctccaccacg    660
ggtgtcaccg aggtctccct catgaaggcc atcgaggccg gcgtcgacgt cgtcgacacc    720
gccatctcgt ccatgtcgct cggcccgggc acaaccccca ccgagtcggt tgccgagatg    780
ctcgagggca ccgggtacac caccaacctt gactacgatc gcctgcacaa gatccgcgat    840
cacttcaagg ccatccgccc gaagtacaag aagttcgagt cgaagacgct tgtcgacacc    900
tcgatcttca gtcgcagat ccccggcggc atgctctcca acatggagtc gcagctgcgc    960
gcccagggcg ccgaggacaa gatggacgag gtcatggcag aggtgccgcg cgtccgcaag   1020
gccgccggct tcccgcccct ggtcaccccg tccagccaga tcgtcggcac gcaggccgtg   1080
ttcaacgtga tgatgggcga gtacaagagg atgaccggcg agttcgccga catcatgctc   1140
ggctactacg gcgccagccc ggccgatcgc gatccgaagg tggtcaagtt ggccgaggag   1200
cagtccggca agaagccgat cacccagcgc ccggccgatc tgctgccccc cgagtgggag   1260
gagcagtcca aggaggccgc ggccctcaag ggcttcaacg gcaccgacga ggacgtgctc   1320
acctatgcac tgttcccgca ggtcgctccg gtcttcttcg agcatcgcgc cgagggcccg   1380
cacagcgtgg ctctcaccga tgcccagctg aaggccgagc cgagggcga cgagaagtcg   1440 ctcgccgtgg ccggtcccgt cacctacaac gtgaacgtgg cggaaccgt ccgcgaagtc   1500 accgttcagc aggcgtga                                                1518
```

<210> SEQ ID NO 11
<211> LENGTH: 505
<212> TYPE: PRT
<213> ORGANISM: Propionibacterium freudenreichii

<400> SEQUENCE: 11

```
Met Ser Pro Arg Glu Ile Glu Val Ser Glu Pro Arg Glu Val Gly Ile
1               5                   10                  15

Thr Glu Leu Val Leu Arg Asp Ala His Gln Ser Leu Met Ala Thr Arg
                20                  25                  30

Met Ala Met Glu Asp Met Val Gly Ala Cys Ala Asp Ile Asp Ala Ala
            35                  40                  45

Gly Tyr Trp Ser Val Glu Cys Trp Gly Gly Ala Thr Tyr Asp Ser Cys
        50                  55                  60

Ile Arg Phe Leu Asn Glu Asp Pro Trp Glu Arg Leu Arg Thr Phe Arg
65                  70                  75                  80

Lys Leu Met Pro Asn Ser Arg Leu Gln Met Leu Leu Arg Gly Gln Asn
                85                  90                  95

Leu Leu Gly Tyr Arg His Tyr Asn Asp Glu Val Val Asp Arg Phe Val
            100                 105                 110

Asp Lys Ser Ala Glu Asn Gly Met Asp Val Phe Arg Val Phe Asp Ala
        115                 120                 125

Met Asn Asp Pro Arg Asn Met Ala His Ala Met Ala Ala Val Lys Lys
    130                 135                 140

Ala Gly Lys His Ala Gln Gly Thr Ile Cys Tyr Thr Ile Ser Pro Val
145                 150                 155                 160

His Thr Val Glu Gly Tyr Val Lys Leu Ala Gly Gln Leu Leu Asp Met
                165                 170                 175
```

Gly Ala Asp Ser Ile Ala Leu Lys Asp Met Ala Ala Leu Leu Lys Pro
            180                 185                 190

Gln Pro Ala Tyr Asp Ile Ile Lys Ala Ile Lys Asp Thr Tyr Gly Gln
            195                 200                 205

Lys Thr Gln Ile Asn Leu His Cys His Ser Thr Thr Gly Val Thr Glu
    210                 215                 220

Val Ser Leu Met Lys Ala Ile Glu Ala Gly Val Asp Val Val Asp Thr
225                 230                 235                 240

Ala Ile Ser Ser Met Ser Leu Gly Pro Gly His Asn Pro Thr Glu Ser
                245                 250                 255

Val Ala Glu Met Leu Glu Gly Thr Gly Tyr Thr Thr Asn Leu Asp Tyr
            260                 265                 270

Asp Arg Leu His Lys Ile Arg Asp His Phe Lys Ala Ile Arg Pro Lys
            275                 280                 285

Tyr Lys Lys Phe Glu Ser Lys Thr Leu Val Asp Thr Ser Ile Phe Lys
            290                 295                 300

Ser Gln Ile Pro Gly Gly Met Leu Ser Asn Met Glu Ser Gln Leu Arg
305                 310                 315                 320

Ala Gln Gly Ala Glu Asp Lys Met Asp Glu Val Met Ala Glu Val Pro
                325                 330                 335

Arg Val Arg Lys Ala Ala Gly Phe Pro Pro Leu Val Thr Pro Ser Ser
            340                 345                 350

Gln Ile Val Gly Thr Gln Ala Val Phe Asn Val Met Met Gly Glu Tyr
            355                 360                 365

Lys Arg Met Thr Gly Glu Phe Ala Asp Ile Met Leu Gly Tyr Tyr Gly
            370                 375                 380

Ala Ser Pro Ala Asp Arg Asp Pro Lys Val Val Lys Leu Ala Glu Glu
385                 390                 395                 400

Gln Ser Gly Lys Lys Pro Ile Thr Gln Arg Pro Ala Asp Leu Leu Pro
                405                 410                 415

Pro Glu Trp Glu Glu Gln Ser Lys Glu Ala Ala Leu Lys Gly Phe
            420                 425                 430

Asn Gly Thr Asp Glu Asp Val Leu Thr Tyr Ala Leu Phe Pro Gln Val
            435                 440                 445

Ala Pro Val Phe Phe Glu His Arg Ala Glu Gly Pro His Ser Val Ala
450                 455                 460

Leu Thr Asp Ala Gln Leu Lys Ala Glu Ala Glu Gly Asp Glu Lys Ser
465                 470                 475                 480

Leu Ala Val Ala Gly Pro Val Thr Tyr Asn Val Asn Val Gly Gly Thr
                485                 490                 495

Val Arg Glu Val Thr Val Gln Gln Ala
            500                 505

<210> SEQ ID NO 12
<211> LENGTH: 1575
<212> TYPE: DNA
<213> ORGANISM: Propionibacterium freudenreichii

<400> SEQUENCE: 12
tcagcagggg aagtttccat gcttcttcgc cgggcgggtc tgacgcttgg tggcgtacat     60
ctccagggcg gaagcaatct ttcgacgggt atcagccggg tcaatcacgt cgtcgacctg    120
accgcgggcg gcggccacgt acggcgtgtt gaacgcgttc tggtactcct cgatcttctc    180
ggcgcgcatg gcgtcgggat cgtcggcagc cttgatctcc ttgcggaaga tcacatttgc    240

```
cgcaccctcg gcgcccatca ccgcaatctc ggcgctgggc caggcgtaca cggcgtcggc      300
accaaggtca cggttgcaca tggccaggta ggagccgccg taggccttgc ggagcaccac      360
ggtgatcttc ggcacggtgg cctcggagta ggcgtacagc atcttcgcgc atggcgaat      420 gatgccgccg tactcctgct gcacgccggg caggaagccc ggcacgtcga ccagctgcac      480
cagcgggatg ttgaacgaat cgcagaaatt cacgaattcg gcggccttgt cagaggcgtt      540
gatgtcgagg caacccgaca tcaccgacgg ctgattggcc acgatgccca ccgaacgacc      600
attgacccgg gcgaaggcgg tcacgaggtt ggtggcatag ccggccttga cctcgaggta      660
gtcaccccag tcgacgatct tggcaatgac atcgcgcacg tcatagccct tcttgccgtc      720
aatcggaacg atgtcgcgca gctcggtatt ggggctgacg tcattgttcg ggttgacgaa      780
ggatgcttcc tcagtgttgt tctgcggaag gaagctcagc agcttcttgg caatgagctc      840
cgcggcgtcg tcgtcctcgg ccacgaagtg gatattgccc gagatggcca tgggcctc       900 agcgccaccg agttcgtcag cggtgacatc ctcgccggtg accgacttga tgacctgggg      960
gcccgtgatg aacatatggg ccttcttggt catgatgatg aagtcagtca gtgccggcga     1020
atacgaggcg ccaccggcac aggggccggc aatgatggcg atctgcggca cgacgcccga     1080
cagcttcacg ttggcgaaga acatcttgcc gtaaccgctc agcgagtcga tgccctcctg     1140
gatccgggcg ccgcccgaat cgtagaagaa caggaagggc gtgccggtga gcagcgcctg     1200
ttccatcgtc tcgacgacct tcgtggactg cgtctcgcca gccgaaccac ccatgaccgt     1260
gaagtcctgg gacgcggcgt gcacgggacg accaaggatg gtgccacggc cggtgaccac     1320
gccatctgcc gggacgacgg ccttgtccat gccgaacaac gtggtgcggt gcttgcggaa     1380
agcgccgacc tcgtcgaacg aatgggggatc gagcaggttg ttcaggcgct cacgagcggt     1440
ctgcttaccc tgggaatgtt gcttctcgac gcgacgttcg ccgccaccgg cttcgatcac     1500
ctggcgctgc tctgcgagct gctccacgcg accttccatg gtgctggcga gcttcaaatt     1560
gttgttttca gccat                                                      1575
```

<210> SEQ ID NO 13
<211> LENGTH: 1572
<212> TYPE: DNA
<213> ORGANISM: Propionibacterium freudenreichii

<400> SEQUENCE: 13

```
atggctgaaa acaacaattt gaagctcgcc agcaccatgg aaggtcgcgt ggagcagctc       60
gcagagcagc gccaggtgat cgaagccggt ggcggcgaac gtcgcgtcga aagcaacat      120 tcccagggta agcagaccgc tcgtgagcgc ctgaacaacc tgctcgatcc ccattcgttc      180
gacgaggtcg gcgctttccg caagcaccgc accacgttgt tcggcatgga caaggccgtc      240
gtcccggcag atggcgtggt caccggccgt ggcaccatcc ttggtcgtcc cgtgcacgcc      300
gcgtcccagg acttcacggt catggtggt tcggctggcg agacgcagtc cacgaaggtc      360
gtcgagacga tggaacaggc gctgctcacc ggcacgccct tcctgttctt ctacgattcg      420
ggcggcgccc ggatccagga gggcatcgac tcgctgagcg gttacggcaa gatgttcttc      480
gccaacgtga agctgtcggg cgtcgtgccg cagatcgcca tcattgccgg ccctgtgcc     540 ggtggcgcct cgtattcgcc ggcactgact gacttcatca tcatgaccaa gaaggcccat      600
atgttcatca cggccccca ggtcatcaag tcggtcaccg gcgaggatgt caccgctgac      660
gaactcggtg gcgctgaggc ccatatggcc atctcgggca atatccactt cgtggccgag      720
```

```
gacgacgacg ccgcggagct cattgccaag aagctgctga gcttccttcc gcagaacaac    780
actgaggaag catccttcgt caacccgaac aatgacgtca gccccaatac cgagctgcgc    840
gacatcgttc cgattgacgg caagaagggc tatgacgtgc gcgatgtcat tgccaagatc    900
gtcgactggg gtgactacct cgaggtcaag gccggctatg ccaccaacct cgtgaccgcc    960
ttcgcccggg tcaatggtcg ttcggtgggc atcgtggcca atcagccgtc ggtgatgtcg   1020
ggttgcctcg acatcaacgc ctctgacaag gccgccgaat cgtgaatttt ctgcgattcg   1080
ttcaacatcc cgctggtgca gctggtcgac gtgccgggct cctgcccgg cgtgcagcag    1140
gagtacggcg gcatcattcg ccatggcgcg aagatgctgt acgcctactc cgaggccacc   1200
gtgccgaaga tcaccgtggt gctccgcaag gcctacggcg gctcctacct ggccatgtgc   1260
aaccgtgacc ttggtgccga cgccgtgtac gcctggccca cgccgagat tgcggtgatg    1320
ggcgccgagg gtgcggcaaa tgtgatcttc cgcaaggaga tcaaggctgc cgacgatccc   1380
gacgccatgc gcgccgagaa gatcgaggag taccagaacg cgttcaacac gccgtacgtg   1440
gccgccgccc gcggtcaggt cgacgacgtg attgacccgg ctgataccg tcgaaagatt    1500
gcttccgccc tggagatgta cgccaccaag cgtcagaccc gccggcgaa gaagcatgga    1560
aacttcccct gc                                                       1572
```

```
<210> SEQ ID NO 14
<211> LENGTH: 524
<212> TYPE: PRT
<213> ORGANISM: Propionibacterium freudenreichii

<400> SEQUENCE: 14

Met Ala Glu Asn Asn Leu Lys Leu Ala Ser Thr Met Glu Gly Arg
1               5                   10                  15

Val Glu Gln Leu Ala Glu Gln Arg Gln Val Ile Glu Ala Gly Gly Gly
            20                  25                  30

Glu Arg Arg Val Glu Lys Gln His Ser Gln Gly Lys Gln Thr Ala Arg
        35                  40                  45

Glu Arg Leu Asn Asn Leu Leu Asp Pro His Ser Phe Asp Glu Val Gly
    50                  55                  60

Ala Phe Arg Lys His Arg Thr Thr Leu Phe Gly Met Asp Lys Ala Val
65                  70                  75                  80

Val Pro Ala Asp Gly Val Val Thr Gly Arg Gly Thr Ile Leu Gly Arg
                85                  90                  95

Pro Val His Ala Ala Ser Gln Asp Phe Thr Val Met Gly Gly Ser Ala
            100                 105                 110

Gly Glu Thr Gln Ser Thr Lys Val Val Glu Thr Met Glu Gln Ala Leu
        115                 120                 125

Leu Thr Gly Thr Pro Phe Leu Phe Phe Tyr Asp Ser Gly Gly Ala Arg
    130                 135                 140

Ile Gln Glu Gly Ile Asp Ser Leu Ser Gly Tyr Gly Lys Met Phe Phe
145                 150                 155                 160

Ala Asn Val Lys Leu Ser Gly Val Val Pro Gln Ile Ala Ile Ile Ala
                165                 170                 175

Gly Pro Cys Ala Gly Gly Ala Ser Tyr Ser Pro Ala Leu Thr Asp Phe
            180                 185                 190

Ile Ile Met Thr Lys Lys Ala His Met Phe Ile Thr Gly Pro Gln Val
        195                 200                 205

Ile Lys Ser Val Thr Gly Glu Asp Val Thr Ala Asp Glu Leu Gly Gly
    210                 215                 220
```

Ala Glu Ala His Met Ala Ile Ser Gly Asn Ile His Phe Val Ala Glu
225                 230                 235                 240

Asp Asp Asp Ala Ala Glu Leu Ile Ala Lys Lys Leu Leu Ser Phe Leu
            245                 250                 255

Pro Gln Asn Asn Thr Glu Glu Ala Ser Phe Val Asn Pro Asn Asn Asp
        260                 265                 270

Val Ser Pro Asn Thr Glu Leu Arg Asp Ile Val Pro Ile Asp Gly Lys
    275                 280                 285

Lys Gly Tyr Asp Val Arg Asp Val Ile Ala Lys Ile Val Asp Trp Gly
290                 295                 300

Asp Tyr Leu Glu Val Lys Ala Gly Tyr Ala Thr Asn Leu Val Thr Ala
305                 310                 315                 320

Phe Ala Arg Val Asn Gly Arg Ser Val Gly Ile Val Ala Asn Gln Pro
                325                 330                 335

Ser Val Met Ser Gly Cys Leu Asp Ile Asn Ala Ser Asp Lys Ala Ala
            340                 345                 350

Glu Phe Val Asn Phe Cys Asp Ser Phe Asn Ile Pro Leu Val Gln Leu
        355                 360                 365

Val Asp Val Pro Gly Phe Leu Pro Gly Val Gln Gln Glu Tyr Gly Gly
    370                 375                 380

Ile Ile Arg His Gly Ala Lys Met Leu Tyr Ala Tyr Ser Glu Ala Thr
385                 390                 395                 400

Val Pro Lys Ile Thr Val Val Leu Arg Lys Ala Tyr Gly Gly Ser Tyr
                405                 410                 415

Leu Ala Met Cys Asn Arg Asp Leu Gly Ala Asp Ala Val Tyr Ala Trp
            420                 425                 430

Pro Ser Ala Glu Ile Ala Val Met Gly Ala Glu Gly Ala Ala Asn Val
        435                 440                 445

Ile Phe Arg Lys Glu Ile Lys Ala Ala Asp Pro Asp Ala Met Arg
    450                 455                 460

Ala Glu Lys Ile Glu Glu Tyr Gln Asn Ala Phe Asn Thr Pro Tyr Val
465                 470                 475                 480

Ala Ala Ala Arg Gly Gln Val Asp Asp Val Ile Asp Pro Ala Asp Thr
                485                 490                 495

Arg Arg Lys Ile Ala Ser Ala Leu Glu Met Tyr Ala Thr Lys Arg Gln
            500                 505                 510

Thr Arg Pro Ala Lys Lys His Gly Asn Phe Pro Cys
        515                 520

<210> SEQ ID NO 15
<211> LENGTH: 246
<212> TYPE: DNA
<213> ORGANISM: P.freudenreichii

<400> SEQUENCE: 15
atggctgatg aggaagagaa ggacctgatg atcgccacgc tcaacaagcg cgtcgcgtca      60
ttggagtctg agttgggttc actccagagc gatacccagg gtgtcaccga ggacgtactg     120
acggccattt cggccgccgt tgcggcctat ctcggcaacg atggatcggc tgaggtcgtc     180
catttcgccc cgagcccgaa ctgggtccgc gagggtcgtc gggctctgca gaaccattcc     240
attcgt                                                                246

<210> SEQ ID NO 16
<211> LENGTH: 82

```
<212> TYPE: PRT
<213> ORGANISM: P.freudenreichii

<400> SEQUENCE: 16

Met Ala Asp Glu Glu Lys Asp Leu Met Ile Ala Thr Leu Asn Lys
1               5                   10                  15

Arg Val Ala Ser Leu Glu Ser Glu Leu Gly Ser Leu Gln Ser Asp Thr
            20                  25                  30

Gln Gly Val Thr Glu Asp Val Leu Thr Ala Ile Ser Ala Ala Val Ala
        35                  40                  45

Ala Tyr Leu Gly Asn Asp Gly Ser Ala Glu Val Val His Phe Ala Pro
    50                  55                  60

Ser Pro Asn Trp Val Arg Glu Gly Arg Arg Ala Leu Gln Asn His Ser
65                  70                  75                  80

Ile Arg

<210> SEQ ID NO 17
<211> LENGTH: 1575
<212> TYPE: DNA
<213> ORGANISM: P. acnes

<400> SEQUENCE: 17
atggctgaga agaaaccaat caagctggcc gataccatgg ccggccggat cgagcagctc      60
gccgacgagc gccacgctgt ggagcttggc gggggcgagg atcgcctgca aaagcagcgt     120
gacaggggca agcagacagc ccgtgaacgg atcgacaacc tcgttgatgc ttattccttc     180
gatgaggtgg gtgcgttccg taagcaccgc accacccttt tcggcatgga caaggccgaa     240
gttcccgccg acggcgtagt caccggtcgt gcgaccatcc atggtcgccc ggtccacatc     300
gcgtctcagg acttcaccgt catgggtggg tcggctggcg agacccagtc gacgaaggtc     360
gtcgagacga tggaacagtc cctgctgacc ggcactccgt ttctgttctt ctatgactcg     420
ggcggcgccc gaattcaaga aggcatcgac tcgctgtccg ggtacggcaa gatgttctac     480
gcgaacgtca agctgtcggg cgtcgtgccg cagatcgcca tcattgctgg ccctgcgcc     540
ggcggcgcct cctattcccc ggccctgacc gacttcatca tcatgacgaa gaaggcccac     600
atgttcatta cgggccccgg agtcatcaag tcggttaccg gtgaggaggt gactgctgac     660
gacctgggtg gtgcggatgc gcacatgtcc acctcgggca atatccactt cgtgccgaa      720
gatgacgacg ccgcagtgct catcgcgcag aagttgctga gcttcctgcc gcaaaacaac     780
actgaggacg cccagatctc caaccccaat gacgatgtct ccccgcagcc tgagctgcgc     840
gacatcgttc cgctggatgg taagaagggc tacgacgtcc gcgacgtcat ctccaagatc     900
gtcgactggg gcgactacct agaggtcaag gccggttggg cgaccaacat cgtcaccgcc     960
tttgcccggg tcaatggtcg taccgtcggc atcgtggcca accagccgaa ggtgatgtcg    1020
ggttgccttg acatcaatgc ttcggacaag gctgccgagt tcattacctt ctgcgactcg    1080
ttcaatattc cgttggtgca gttggttgac gttcctggct cctgcctggg tgtccagcag    1140
gagtacggcg gcatcatccg ccacggcgcg aagatgctgt atgcctactc gaggccacc     1200
gtcccgaaga tcaccgtggt gctgcgtaag gcttacggcg gctcctacct tgccatgtgc    1260
aaccgtgacc tgggtgctga cgccgtctat gcctggccga gcgcggagat gcggtgatg    1320
ggtgccgatg gcgctgccaa cgtcatttc cgtcgccaga tcaaggactc tgaggatccc    1380
gcagccaccc gtgccgcgaa gatcgaggag taccgcaacg ccttcaacac gccttacgtg    1440
gctgccgccc gtggacaggt tgacgacgtg atcgatcccg cggacacccg tcgcaagatc    1500
```

```
accgccgctc tggagaccta cgccactaag cgtcagtccc gtccggccaa gaagcacggc    1560
gtcatgcctt gctga                                                     1575

<210> SEQ ID NO 18
<211> LENGTH: 1494
<212> TYPE: DNA
<213> ORGANISM: P. acnes

<400> SEQUENCE: 18
atgagtccac gaaagattgg cgttaccgag ctcgtgctcc gcgacgcgca tcagagcctg      60
cttgccactc gcatggccat ggaggacatg gttgatgcct gtgccgacat tgatgcggca     120
ggcttctggt ccgttgaatg ctggggcgga gctaccttcg attcttgcat ccgattcctc     180
aacgaagacc catgggagcg tctgcgtact ttccgcaagc tgctgccgaa ctcccggttg     240
cagatgctgc tgcgtggcca aaaccttctg gctaccgcc actacaacga cgaggtcgtc      300
gacaagtttg tcgagaagtc ggccgagaac ggcatggacg tgttccgggt gttcgacgct     360
ctgaacgatc ctcgcaacct tgagcacgcg atggcagccg tcaagaagac cggcaagcac     420
gcccagggca ccatctgcta caccacttcc ccgattcaca ccccagagag cttcgtcaag     480
caggccgatc gtctcatcga catgggtgcc gactcgatcg ccttcaagga catggctgct     540
ttgctcaagc cgcagcctgc ctacgacatc atcaagggca ttaaggagaa ccatccggac     600
gtgcagatca acctgcactg ccactccacc acgggcgtca ccctggtcac cctgcagaag     660
gccatcgagg ctggtgtcga cgtcgtcgac accgctatct cgtcgatgtc gctcggcccg     720
gggcacaacc caaccgagtc tttggtcgag atgctcgagg caccgagta caccaccggc      780 ctcgacatgg atcgcctgct caagatccgc gaccacttca agaaggtgcg tccgaagtac     840
aagaagttcg agtcgaagac gctggtcaac accaacatct tccagtccca gatcccgggc     900
ggaatgctct ccaacatgga gtcccagctc gaggcccagg gtgctggaga ccgcatggat     960
gaggtcatga aggaggtgcc gcgcgttcgt aaggatgccg gctacccgcc gctggtcacc    1020
ccgtcctccc cgatcgtggg aaaccaggcg gtgttcaacg tcctgatggg caatggttcg    1080
tacaagaacc tcactgccga gttgccgac ctcatgcttg gctactacgg caagcccatt     1140
ggcgagctca atcccgagat cgttgagatg gccaagaagc agaccggcaa ggagccgatc    1200
gactgccgtc ccgccgacct gctcgagcct gagtgggacc agctggtcga gcaggccaag    1260
agtcttgagg gcttcgacgg ctccgacgag gacgttctta ccaacgccct gttcccggga    1320
gttgccccga agttcctcaa ggaacgcgca cagggcccga gagcgtcgc gatgaccgag     1380 gcacagctga aggccgagaa ggaaggcacc ggcgctgccg gcatcgccgg accggtcaac    1440
tacaacgtga cggtcggtgg caacagccac caggtgaccg tcgagcctgc gtga          1494

<210> SEQ ID NO 19
<211> LENGTH: 363
<212> TYPE: DNA
<213> ORGANISM: P. acnes

<400> SEQUENCE: 19
atgaagctca aggtgaccgt caatgacgtc gcatacgacg ttgacgttga cgttgataag      60
accgccaatg cgccgatggc gccgatcctc tttggtggcg gcgccggcgg cccgatgaag    120
gcatccggtg gcggcgccgg taaggccggt gagggcgagg ttcccgcacc gctagctggg    180
actgttgcca agatcctggt ggccgaagga gatgccgtca aggccggtca ggtgctcctg    240
```

```
accctcgagg ccatgaagat ggagaccgag atcaatgccc cggcggacgg aaccgtcaag      300
gggatcctgg tggctgtcgg tgacgccgtc cagggtggtc agggcctggt ggctctgggc      360
tga                                                                   363
```

<210> SEQ ID NO 20
<211> LENGTH: 1551
<212> TYPE: DNA
<213> ORGANISM: C. thermocellum

<400> SEQUENCE: 20

```
atggacaaag tagacaagat cggccttctc cgtgaaaaac tggcccaggt tgaacagggc       60
ggaggagctg aaaaaatcgc aaaacagcat gatgccggaa aaatgacagc aagagaaaga      120
atccaggctt tatttgatga aaacagcttt gttgagatcg acacatttgt tgagacaaga      180
agcattgact tcgatatgca aaaaagaaa gtcccgggag acggtgttgt aacagggtat      240
ggttccatag acggacgtct ggtctttgtt gcggcgcagg actttactgt aatcggtggg      300
tctttgggtg aaatgcatgc cgcaaaaatc accaaagtaa tggacatggc aatgaaaatg      360
ggcgcaccgt ttataagcat taatgattcc ggcggtgcaa gaattgaaga aggaattgac      420
gcactcaagg gatttggaga tatcttctac agaaatactt tggcttcagg tgtaattccc      480
cagatttcag ttatcatggg accatgcgca ggcggagcgg tatattctcc tgcaataacc      540
gactttatat ttatggttga caaaaccagt cagatgttta acgggacc ccaggtaatt      600 aagtccgtaa ccggagaaga cgtgactttt gaaaaacttg gcggtgcgga acccacaac      660 tccataagcg gtgttgctca cttcagaagt tcaagtgaaa aagaatgtat agagcaaatc      720
aaaaagctta ttagttatct tcctgataac aatctttccg atgttccgat tgttccaact      780
caggatgaca taaacagaat tactgacaac ctggtcgata tcattccgca ggactccaac      840
aagccttatg acatgatgga aataatcact tccgtagttg acaacggtga cttttttgaa      900
attcaaaaag actttgcaaa aaacattata ataggtttcg gcagaatgaa cggcggaacc      960
gtcggtatag tggcaaatca gccaaaagtt gccgcagggg ttttggatgt gaactcctct     1020
gacaaagccg caaggtttgt tcgtttctgt gatgcgttca acattccaat tataaccttt     1080
accgatgtac cgggggtatct gcccggagta ggccaggagc acagcggagt aataagacac     1140
ggtgcaaagc ttctttatgc tttctctgaa gccaccgttc aaaaatcaa tgttattgtc     1200 agaaaagctt acggcggtgc atatattgcc atgaacagca agcaccttgg agcggacatg     1260
gtatttgcgt ggccttcggc ggaaattgca gttatgggac cggaaggtgc ggcaaacatc     1320
attttcaaga aagatatagc tgctgccgat gacccaatgg aaacaagaaa gaggctcatt     1380
gaagaatatc gtgaaaaatt ctccaatccg tatgttgcag cttcaagggg ttatgttgat     1440
gatgtaattg atccggcaac aacaaggata agactgatta gtgcccttga aatgcttgca     1500
agtaagagag aaaacagacc tgccaaaaag catggaaata ttccattata a            1551
```

<210> SEQ ID NO 21
<211> LENGTH: 516
<212> TYPE: PRT
<213> ORGANISM: C. thermocellum

<400> SEQUENCE: 21

```
Met Asp Lys Val Asp Lys Ile Gly Leu Leu Arg Glu Lys Leu Ala Gln
1               5                   10                  15

Val Glu Gln Gly Gly Gly Ala Glu Lys Ile Ala Lys Gln His Asp Ala
            20                  25                  30
```

```
Gly Lys Met Thr Ala Arg Glu Arg Ile Gln Ala Leu Phe Asp Glu Asn
        35                  40                  45

Ser Phe Val Glu Ile Asp Thr Phe Val Glu Thr Arg Ser Ile Asp Phe
 50                  55                  60

Asp Met Gln Lys Lys Val Pro Gly Asp Gly Val Val Thr Gly Tyr
 65              70                  75                  80

Gly Ser Ile Asp Gly Arg Leu Val Phe Val Ala Ala Gln Asp Phe Thr
                 85                  90                  95

Val Ile Gly Gly Ser Leu Gly Glu Met His Ala Ala Lys Ile Thr Lys
                100                 105                 110

Val Met Asp Met Ala Met Lys Met Gly Ala Pro Phe Ile Ser Ile Asn
            115                 120                 125

Asp Ser Gly Gly Ala Arg Ile Gln Glu Gly Ile Asp Ala Leu Lys Gly
        130                 135                 140

Phe Gly Asp Ile Phe Tyr Arg Asn Thr Leu Ala Ser Gly Val Ile Pro
145                 150                 155                 160

Gln Ile Ser Val Ile Met Gly Pro Cys Ala Gly Gly Ala Val Tyr Ser
                165                 170                 175

Pro Ala Ile Thr Asp Phe Ile Phe Met Val Asp Lys Thr Ser Gln Met
            180                 185                 190

Phe Ile Thr Gly Pro Gln Val Ile Lys Ser Val Thr Gly Glu Asp Val
        195                 200                 205

Thr Phe Glu Lys Leu Gly Gly Ala Glu Thr His Asn Ser Ile Ser Gly
210                 215                 220

Val Ala His Phe Arg Ser Ser Glu Lys Glu Cys Ile Glu Gln Ile
225                 230                 235                 240

Lys Lys Leu Ile Ser Tyr Leu Pro Asp Asn Asn Leu Ser Asp Val Pro
                245                 250                 255

Ile Val Pro Thr Gln Asp Asp Ile Asn Arg Ile Thr Asp Asn Leu Val
            260                 265                 270

Asp Ile Ile Pro Gln Asp Ser Asn Lys Pro Tyr Asp Met Met Glu Ile
        275                 280                 285

Ile Thr Ser Val Val Asp Asn Gly Asp Phe Phe Glu Ile Gln Lys Asp
290                 295                 300

Phe Ala Lys Asn Ile Ile Ile Gly Phe Gly Arg Met Asn Gly Gly Thr
305                 310                 315                 320

Val Gly Ile Val Ala Asn Gln Pro Lys Val Ala Ala Gly Val Leu Asp
                325                 330                 335

Val Asn Ser Ser Asp Lys Ala Ala Arg Phe Val Arg Phe Cys Asp Ala
                340                 345                 350

Phe Asn Ile Pro Ile Ile Thr Phe Thr Asp Val Pro Gly Tyr Leu Pro
            355                 360                 365

Gly Val Gly Gln Glu His Ser Gly Val Ile Arg His Gly Ala Lys Leu
        370                 375                 380

Leu Tyr Ala Phe Ser Glu Ala Thr Val Pro Lys Ile Asn Val Ile Val
385                 390                 395                 400

Arg Lys Ala Tyr Gly Gly Ala Tyr Ile Ala Met Asn Ser Lys His Leu
                405                 410                 415

Gly Ala Asp Met Val Phe Ala Trp Pro Ser Ala Glu Ile Ala Val Met
            420                 425                 430

Gly Pro Glu Gly Ala Ala Asn Ile Ile Phe Lys Lys Asp Ile Ala Ala
        435                 440                 445
```

Ala Asp Asp Pro Met Glu Thr Arg Lys Arg Leu Ile Glu Glu Tyr Arg
    450                 455                 460

Glu Lys Phe Ser Asn Pro Tyr Val Ala Ser Arg Gly Tyr Val Asp
465                 470                 475                 480

Asp Val Ile Asp Pro Ala Thr Thr Arg Ile Arg Leu Ile Ser Ala Leu
                485                 490                 495

Glu Met Leu Ala Ser Lys Arg Glu Asn Arg Pro Ala Lys Lys His Gly
            500                 505                 510

Asn Ile Pro Leu
        515

<210> SEQ ID NO 22
<211> LENGTH: 399
<212> TYPE: DNA
<213> ORGANISM: C. thermocellum

<400> SEQUENCE: 22
atgaaaaagt ttttgataaa ggtaaacgga atcaatatg aggttgaagt tgaagaaatc        60
agagacggtg cttcagcacc acaggttact ctcagcacac cttcggctgc acctgcgcct      120
tcaccggcac cggctcagga acgaaaaca gctgcaccaa agaaagacag cacagtaccg       180
gcaggtgcta cggcaattaa agctccgatg ccgggtacca tactcgacat tcgtgtaaat     240
caaggggata cggtaaagaa aggccaagtt cttttaattc ttgaagcaat gaagatggaa     300
aatgaaatag ttgctccaaa tgacggtaca gttgcatcaa ttaatgtttc aaagggtgca     360
tctgtaaacg tcggagaggt tcttgtctca ttaaaatag                             399

<210> SEQ ID NO 23
<211> LENGTH: 132
<212> TYPE: PRT
<213> ORGANISM: C. thermocellum

<400> SEQUENCE: 23

Met Lys Lys Phe Leu Ile Lys Val Asn Gly Asn Gln Tyr Glu Val Glu
1               5                   10                  15

Val Glu Glu Ile Arg Asp Gly Ala Ser Ala Pro Gln Val Thr Leu Ser
            20                  25                  30

Thr Pro Ser Ala Ala Pro Ala Pro Ser Pro Ala Pro Ala Gln Glu Thr
        35                  40                  45

Lys Thr Ala Ala Pro Lys Lys Asp Ser Thr Val Pro Ala Gly Ala Thr
    50                  55                  60

Ala Ile Lys Ala Pro Met Pro Gly Thr Ile Leu Asp Ile Arg Val Asn
65                  70                  75                  80

Gln Gly Asp Thr Val Lys Lys Gly Gln Val Leu Leu Ile Leu Glu Ala
                85                  90                  95

Met Lys Met Glu Asn Glu Ile Val Ala Pro Asn Asp Gly Thr Val Ala
            100                 105                 110

Ser Ile Asn Val Ser Lys Gly Ala Ser Val Asn Val Gly Glu Val Leu
        115                 120                 125

Val Ser Leu Lys
    130

<210> SEQ ID NO 24
<211> LENGTH: 1398
<212> TYPE: DNA
<213> ORGANISM: C. thermocellum

<400> SEQUENCE: 24

```
atggctaagg taaaaattac cgaaacggcg ctgagggatg cccatcaatc tctcattgca    60
acaagaatga gaatagaaga gatgcttcct atcatagata aactggacga gatcggttat   120
cattctttgg aggtatgggg cggtgcaacc tttgatgcct gcctgagatt tttgaatgaa   180
gacccgtggg aaaggcttag aattataaaa agccactgca agaaaactcc ccttcaaatg   240
cttttaagag gccagaatct tttgggttac aagcattatg ccgatgacgt tgtggagtac   300
tttgtacaaa agagcgttgc aaacggtata acataataa gaattttcga cgccttgaat   360
gacaccagaa atatagaaac tgcaatcaaa gcctgcaaaa agaaggcgg tcatgctcag   420
ggaacggtat gttatacaat aagtcccgtt cacaatcttg aacttttgt caaagatgca   480
aagactcttg tggaaatggg agctgactcc atatgcgtaa aggatatggc aggacttctg   540
cttccatatg ttgcatatga ccttatcaaa gcattaaaag aaaacgtaaa agtgccgatt   600
caacttcata cccactatac gagcggtgtt gcttcaatga catatctgaa ggcaattgag   660
gcagggtgcg atgttgtgga ctgcgctatc tcaccaatgt caatgggaac atcccagcct   720
ccgacagaac ctcttgtggc aaccttaaaa ggcacgccgt acgataccgg acttgacctg   780
gataaattaa gtgaaatcgc agactacttc agacctctca agaaaagta tatttcagaa   840
ggacttcttg atgtaaaggt tatgggagtt gacgtaaaca ctctcaaata ccaggtaccc   900
ggtggaatgc tttcaaacct ggtgtctcag ttaaagcagt ccaatgcggt tgataaattc   960
gaagaggttc tgaaagaagt gccaagagta agagaagact tcggatatcc tccgttggtt  1020
acacctacaa gccagattgt aggtactcag gcagttttaa atgtggtaac gggtgaaaga  1080
tacaaaatgg ttccaaaaga atccaaggca ctgatcaagg gtgaatacgg cagaacaccg  1140
gctccggtca accctgaagt tcagaagaag atttaaaag atgaagagcc gattacagtt  1200
agacctgctg atttgataga gcccgagctt gacaagatca gaaatgaaat gaagaatac  1260
ctggaacaag acgaggacgt tttgtcctat gcactgttcc cgcaggtggc agagaagttc  1320
ttccaataca ggaaagctca aaatataag atagaaccgg acatggtcga ttacgaaaac  1380
agggttcatc cggtttaa                                                1398
```

<210> SEQ ID NO 25
<211> LENGTH: 465
<212> TYPE: PRT
<213> ORGANISM: C.thermocellum

<400> SEQUENCE: 25

```
Met Ala Lys Val Lys Ile Thr Glu Thr Ala Leu Arg Asp Ala His Gln
1               5                   10                  15

Ser Leu Ile Ala Thr Arg Met Arg Ile Glu Glu Met Leu Pro Ile Ile
            20                  25                  30

Asp Lys Leu Asp Glu Ile Gly Tyr His Ser Leu Glu Val Trp Gly Gly
        35                  40                  45

Ala Thr Phe Asp Ala Cys Leu Arg Phe Leu Asn Glu Asp Pro Trp Glu
    50                  55                  60

Arg Leu Arg Ile Ile Lys Ser His Cys Lys Lys Thr Pro Leu Gln Met
65                  70                  75                  80

Leu Leu Arg Gly Gln Asn Leu Leu Gly Tyr Lys His Tyr Ala Asp Asp
                85                  90                  95

Val Val Glu Tyr Phe Val Gln Lys Ser Val Ala Asn Gly Ile Asn Ile
            100                 105                 110

Ile Arg Ile Phe Asp Ala Leu Asn Asp Thr Arg Asn Ile Glu Thr Ala
```

```
        115                 120                 125
Ile Lys Ala Cys Lys Lys Glu Gly Gly His Ala Gln Gly Thr Val Cys
    130                 135                 140

Tyr Thr Ile Ser Pro Val His Asn Leu Glu Leu Phe Val Lys Asp Ala
145                 150                 155                 160

Lys Thr Leu Val Glu Met Gly Ala Asp Ser Ile Cys Val Lys Asp Met
                165                 170                 175

Ala Gly Leu Leu Leu Pro Tyr Val Ala Tyr Asp Leu Ile Lys Ala Leu
            180                 185                 190

Lys Glu Asn Val Lys Val Pro Ile Gln Leu His Thr His Tyr Thr Ser
        195                 200                 205

Gly Val Ala Ser Met Thr Tyr Leu Lys Ala Ile Glu Ala Gly Cys Asp
    210                 215                 220

Val Val Asp Cys Ala Ile Ser Pro Met Ser Met Gly Thr Ser Gln Pro
225                 230                 235                 240

Pro Thr Glu Pro Leu Val Ala Thr Leu Lys Gly Thr Pro Tyr Asp Thr
                245                 250                 255

Gly Leu Asp Leu Asp Lys Leu Ser Glu Ile Ala Asp Tyr Phe Arg Pro
            260                 265                 270

Leu Lys Glu Lys Tyr Ile Ser Glu Gly Leu Leu Asp Val Lys Val Met
        275                 280                 285

Gly Val Asp Val Asn Thr Leu Lys Tyr Gln Val Pro Gly Gly Met Leu
    290                 295                 300

Ser Asn Leu Val Ser Gln Leu Lys Gln Ser Asn Ala Val Asp Lys Phe
305                 310                 315                 320

Glu Glu Val Leu Lys Glu Val Pro Arg Val Arg Glu Asp Phe Gly Tyr
                325                 330                 335

Pro Pro Leu Val Thr Pro Thr Ser Gln Ile Val Gly Thr Gln Ala Val
            340                 345                 350

Leu Asn Val Val Thr Gly Glu Arg Tyr Lys Met Val Pro Lys Glu Ser
        355                 360                 365

Lys Ala Leu Ile Lys Gly Glu Tyr Gly Arg Thr Pro Ala Pro Val Asn
    370                 375                 380

Pro Glu Val Gln Lys Lys Ile Leu Lys Asp Glu Pro Ile Thr Val
385                 390                 395                 400

Arg Pro Ala Asp Leu Ile Glu Pro Glu Leu Asp Lys Ile Arg Asn Glu
                405                 410                 415

Met Lys Glu Tyr Leu Glu Gln Asp Glu Asp Val Leu Ser Tyr Ala Leu
            420                 425                 430

Phe Pro Gln Val Ala Glu Lys Phe Phe Gln Tyr Arg Lys Ala Gln Lys
        435                 440                 445

Tyr Lys Ile Glu Pro Asp Met Val Asp Tyr Glu Asn Arg Val His Pro
    450                 455                 460

Val
465

<210> SEQ ID NO 26
<211> LENGTH: 168
<212> TYPE: DNA
<213> ORGANISM: C.thermocellum

<400> SEQUENCE: 26
atgaaagagc aaataaatga agaaattatt ctggcaatat cagcggccat tgctgctttg      60
gaaacaagac ccggatacaa gcttgtagta agatcattta aaagaatacc ccaaacttct     120
```

```
cctgtatggt ccgctacagg aaaaatcgag agaatcagaa gaagtatg           168
```

<210> SEQ ID NO 27
<211> LENGTH: 56
<212> TYPE: PRT
<213> ORGANISM: C.thermocellum

<400> SEQUENCE: 27

```
Met Lys Glu Gln Ile Asn Glu Glu Ile Ile Leu Ala Ile Ser Ala Ala
1               5                   10                  15

Ile Ala Ala Leu Glu Thr Arg Pro Gly Tyr Lys Leu Val Val Arg Ser
            20                  25                  30

Phe Lys Arg Ile Pro Gln Thr Ser Pro Val Trp Ser Ala Thr Gly Lys
        35                  40                  45

Ile Glu Arg Ile Arg Arg Ser Met
    50                  55
```

<210> SEQ ID NO 28
<211> LENGTH: 1551
<212> TYPE: DNA
<213> ORGANISM: T. saccharolyticum

<400> SEQUENCE: 28

```
atgtcaatag atgataggat tgaagacctt cttagaagaa gagagatggt tttagaaggc    60
ggtggtttag ataaagtaga gaaacaacac caaaagggaa agcttaccgc aagagagagg   120
atatacaagc ttttagatga agatagcttt gtggaaatag atgcgtatgt tgagcacagg   180
tgtattgact ttggcatgga aaagcaaagg atacctggcg aaggcgtagt gacagggtat   240
gggacgatag atgaaggct tgtctacgtt tatgcacagg attttacggt tttaggagga   300
tcattaggcg agtatcatgc aaagaaaatc acaaaaatca tggatatggc tttaaagatg   360
ggagcaccgc tcattggatt aaatgattcc ggaggtgcca gaatacagga aggcgtcgat   420
gctttatcgg gatatggcaa catatttttc agaaacacgc tggcatcagg cgtaataccg   480
caaatatcgg tgataatggg gcccagcgct ggaggtgcag tttattcgcc tgctcttact   540
gactttatat tcatggtaga caagacaagt cagatgttta aactggacc gcaggtcata   600
aaagccgtca caggtgaaga tgtttcggca gaggagcttg gtggatcgat tactcacagc   660
acgaaaagcg gtgtggcgca ttttagggct gaaaacgacg aagagtgttt gaagatggtg   720
aggaagctat taagttaccct tccatcaaac aatttggaag atccgccaca gttggcgaca   780
gatgacgaca taaacagatt ttccgatagg cttattgaga taatcccaga tagtcctaat   840
aagccatacg atatgaaaga agtaatttcg gaaatagtgg atgaaggcgt gtattttgaa   900
tcacaggcaa tgtatgcgca aaacataata acggcatttg caaggcttaa tggaaggacg   960
gtagggataa tagcaaatca gcctaaagtt ttggctggat gtctcgacat caatgcgtct  1020
gataaggcat cgaggtttat aaggttttgc gatgcattta acatcccgct ctcaatata  1080
gtagatgttc caggatttt gcctggaacg aatcaagagt acggtggaat aatacgccat  1140
ggggcaaaga tgttgtacgc ttactctgag gctacagtgc caaaagtgac tctcattgtg  1200
aggaaagctt atggcggtgc ttaccttgcc atgtgcagca aagacttagg agctgatttt  1260
gttttggcat ggcctactgc tgaaatagcg gtcatgggac ctgatggggc agcaaacatc  1320
gtgtttaaaa atgaaataaa atcgtctgat gatcctgtgg ctgcaagaaa tgaaaagata  1380
aatgagtaca gggagaattt cgcaaatcca tacagggcag cagcgagagg atatgtagat  1440
```

```
gatgtagttc tgccgcaaga gacgagacct cgcctcatct cggcgttcga tatgcttatg    1500
agcaaaaggg agtcaaggcc cagcaaaaag catggcaatt ttcctgttta a             1551
```

<210> SEQ ID NO 29
<211> LENGTH: 516
<212> TYPE: PRT
<213> ORGANISM: T. saccharolyticum

<400> SEQUENCE: 29

| | | | | | | | | | | | | | | |
|---|---|---|---|---|---|---|---|---|---|---|---|---|---|---|
| Met | Ser | Ile | Asp | Asp | Arg | Ile | Glu | Asp | Leu | Leu | Arg | Arg | Glu | Met |
| 1 | | | | 5 | | | | | 10 | | | | | 15 |
| Val | Leu | Glu | Gly | Gly | Gly | Leu | Asp | Lys | Val | Glu | Lys | Gln | His | Gln | Lys |
| | | | 20 | | | | | 25 | | | | | 30 | | |
| Gly | Lys | Leu | Thr | Ala | Arg | Glu | Arg | Ile | Tyr | Lys | Leu | Leu | Asp | Glu | Asp |
| | | | 35 | | | | 40 | | | | | 45 | | | |
| Ser | Phe | Val | Glu | Ile | Asp | Ala | Tyr | Val | Glu | His | Arg | Cys | Ile | Asp | Phe |
| | 50 | | | | | 55 | | | | | 60 | | | | |
| Gly | Met | Glu | Lys | Gln | Arg | Ile | Pro | Gly | Glu | Gly | Val | Val | Thr | Gly | Tyr |
| 65 | | | | | 70 | | | | | 75 | | | | | 80 |
| Gly | Thr | Ile | Asp | Gly | Arg | Leu | Val | Tyr | Val | Ala | Gln | Asp | Phe | Thr |
| | | | | 85 | | | | | 90 | | | | | 95 |
| Val | Leu | Gly | Gly | Ser | Leu | Gly | Glu | Tyr | His | Ala | Lys | Lys | Ile | Thr | Lys |
| | | | | 100 | | | | | 105 | | | | | 110 | |
| Ile | Met | Asp | Met | Ala | Leu | Lys | Met | Gly | Ala | Pro | Leu | Ile | Gly | Leu | Asn |
| | | | 115 | | | | | 120 | | | | | 125 | | |
| Asp | Ser | Gly | Gly | Ala | Arg | Ile | Gln | Glu | Gly | Val | Asp | Ala | Leu | Ser | Gly |
| | 130 | | | | | 135 | | | | | 140 | | | | |
| Tyr | Gly | Asn | Ile | Phe | Phe | Arg | Asn | Thr | Leu | Ala | Ser | Gly | Val | Ile | Pro |
| 145 | | | | | 150 | | | | | 155 | | | | | 160 |
| Gln | Ile | Ser | Val | Ile | Met | Gly | Pro | Ser | Ala | Gly | Gly | Ala | Val | Tyr | Ser |
| | | | | 165 | | | | | 170 | | | | | 175 | |
| Pro | Ala | Leu | Thr | Asp | Phe | Ile | Phe | Met | Val | Asp | Lys | Thr | Ser | Gln | Met |
| | | | 180 | | | | | 185 | | | | | 190 | | |
| Phe | Ile | Thr | Gly | Pro | Gln | Val | Ile | Lys | Ala | Val | Thr | Gly | Glu | Asp | Val |
| | | | 195 | | | | | 200 | | | | | 205 | | |
| Ser | Ala | Glu | Glu | Leu | Gly | Gly | Ser | Ile | Thr | His | Ser | Thr | Lys | Ser | Gly |
| | 210 | | | | | 215 | | | | | 220 | | | | |
| Val | Ala | His | Phe | Arg | Ala | Glu | Asn | Asp | Glu | Glu | Cys | Leu | Lys | Met | Val |
| 225 | | | | | 230 | | | | | 235 | | | | | 240 |
| Arg | Lys | Leu | Leu | Ser | Tyr | Leu | Pro | Ser | Asn | Asn | Leu | Glu | Asp | Pro | Pro |
| | | | | 245 | | | | | 250 | | | | | 255 | |
| Gln | Leu | Ala | Thr | Asp | Asp | Ile | Asn | Arg | Phe | Ser | Asp | Arg | Leu | Ile |
| | | | 260 | | | | | 265 | | | | | 270 | | |
| Glu | Ile | Ile | Pro | Asp | Ser | Pro | Asn | Lys | Pro | Tyr | Asp | Met | Lys | Glu | Val |
| | | | 275 | | | | | 280 | | | | | 285 | | |
| Ile | Ser | Glu | Ile | Val | Asp | Glu | Gly | Val | Tyr | Phe | Glu | Ser | Gln | Ala | Met |
| | | | 290 | | | | | 295 | | | | | 300 | | |
| Tyr | Ala | Gln | Asn | Ile | Ile | Thr | Ala | Phe | Ala | Arg | Leu | Asn | Gly | Arg | Thr |
| 305 | | | | | 310 | | | | | 315 | | | | | 320 |
| Val | Gly | Ile | Ile | Ala | Asn | Gln | Pro | Lys | Val | Leu | Ala | Gly | Cys | Leu | Asp |
| | | | | 325 | | | | | 330 | | | | | 335 | |
| Ile | Asn | Ala | Ser | Asp | Lys | Ala | Ser | Arg | Phe | Ile | Arg | Phe | Cys | Asp | Ala |
| | | | 340 | | | | | 345 | | | | | 350 | | |
| Phe | Asn | Ile | Pro | Leu | Leu | Asn | Ile | Val | Asp | Val | Pro | Gly | Phe | Leu | Pro |

```
                355                 360                 365
Gly Thr Asn Gln Glu Tyr Gly Ile Ile Arg His Gly Ala Lys Met
        370                 375                 380

Leu Tyr Ala Tyr Ser Glu Ala Thr Val Pro Lys Val Thr Leu Ile Val
385                 390                 395                 400

Arg Lys Ala Tyr Gly Ala Tyr Leu Ala Met Cys Ser Lys Asp Leu
                405                 410                 415

Gly Ala Asp Phe Val Leu Ala Trp Pro Thr Ala Glu Ile Ala Val Met
                420                 425                 430

Gly Pro Asp Gly Ala Ala Asn Ile Val Phe Lys Asn Glu Ile Lys Ser
                435                 440                 445

Ser Asp Asp Pro Val Ala Ala Arg Asn Glu Lys Ile Asn Glu Tyr Arg
            450                 455                 460

Glu Asn Phe Ala Asn Pro Tyr Arg Ala Ala Arg Gly Tyr Val Asp
465                 470                 475                 480

Asp Val Val Leu Pro Gln Glu Thr Arg Pro Arg Leu Ile Ser Ala Phe
                485                 490                 495

Asp Met Leu Met Ser Lys Arg Glu Ser Arg Pro Ser Lys Lys His Gly
            500                 505                 510

Asn Phe Pro Val
        515

<210> SEQ ID NO 30
<211> LENGTH: 384
<212> TYPE: DNA
<213> ORGANISM: T. saccharolyticum

<400> SEQUENCE: 30
atgaaaaaat ttatagtaac tgtcaatgga aaaaaatacg atgtggaagt agaagaagta      60
aaagtcgacg tggcaagtga gaaaaaagca aagaagata ctgctgctaa aaatgcgtca      120
gatgcaagtg taaaaagcaa acaggttgaa gtaaaaaacg aagtcaaaga cggtttctca      180
atcaatgcac cgatgccggg aactatattg gatgtcaaaa taagccaagg ccagactgtc      240
agacgaggcg atgtgctttt aatactggaa gccatgaaga tggaaaatga atcacgtca      300 ccttacgatg gcacaataat atccataaat gtttcaaaag gtgcctctgt aaatacaggc      360
gatgtgcttt tgtacttaaa atga                                              384

<210> SEQ ID NO 31
<211> LENGTH: 127
<212> TYPE: PRT
<213> ORGANISM: T. saccharolyticum

<400> SEQUENCE: 31

Met Lys Lys Phe Ile Val Thr Val Asn Gly Lys Lys Tyr Asp Val Glu
1               5                   10                  15

Val Glu Glu Val Lys Val Asp Val Ala Ser Glu Lys Lys Ala Lys Glu
                20                  25                  30

Asp Thr Ala Ala Lys Asn Ala Ser Asp Ala Ser Val Lys Ser Lys Gln
            35                  40                  45

Val Glu Val Lys Asn Glu Val Lys Asp Gly Phe Ser Ile Asn Ala Pro
        50                  55                  60

Met Pro Gly Thr Ile Leu Asp Val Lys Ile Ser Gln Gly Gln Thr Val
65                  70                  75                  80

Arg Arg Gly Asp Val Leu Leu Ile Leu Glu Ala Met Lys Met Glu Asn
                85                  90                  95
```

Glu Ile Thr Ser Pro Tyr Asp Gly Thr Ile Ile Ser Ile Asn Val Ser
            100                 105                 110

Lys Gly Ala Ser Val Asn Thr Gly Asp Val Leu Leu Tyr Leu Lys
        115                 120                 125

<210> SEQ ID NO 32
<211> LENGTH: 1395
<212> TYPE: DNA
<213> ORGANISM: T. saccharolyticum

<400> SEQUENCE: 32
atgtctaaga taaaataac ggagactgtt ttaagagatg cacatcaatc gttgctggca     60
accagaatga caaccgatga aatgcttcct atagcagaaa aattagatga agttggtttt    120
ttctcgctgg aagcatgggg cggtgctaca tttgatgcat gtatgagatt tttgaatgaa    180
gacccatggg aaagattaag acttttaaag aaggcgatta agaagacacc tcttcaaatg    240
cttttaagag gtcaaaattt actcggatat aaacactatc ccgatgatgt cgtaaatgaa    300
tttataataa aatctgttga aaatggtata gataataaa gaattttttga tgcgttaaat    360
gatgtgagaa atttagaagt gccaataaaa tctgcaaaaa gtgcaggtgc tcatgtacag    420
gcagctattg tatatacagt tagtcctgta cataatacag atcattattt gaaagtggca    480
aagtctcttc aagatatggg tgcggattcc atatgcatta aggatatgtc tggaatatta    540
tcaccctatg ttgcatacga tttgattaaa tctctgaaaa gagcactttta cacgccaatt    600
caactgcata gccattatac agcaggactg gcttcaatga cttatttaaa agccatagaa    660
gctggtgtag acggggttga tacagctatt tcttcgcttg ccttaggaac atcacaacca    720
gctacagaat caatcgtggc tgcattgaaa gatacagaat atgatacagg ctagattta    780
aaattgcttg ctgagatagc tcagcatttt aatgtagtca aacagaatca caaaaatgac    840
agcgatatgt cttgcttat gtctgttgat gttaaagcat tagaaagtca ataccaggg    900
ggaatgttat caaatttggt ttcacagcta aagcagcaga atgcattaaa caaatatcaa    960
gacgtcttga agaagttcc aagggtacgc gaagatttgg gatatcctcc tcttgttact   1020
ccaatgagcc agatggttgg aacccaggct gttttaaatg ttattacagg ggagagatat   1080
aaaatcgttc ctaaagaaat taagattat gtcaaaggtt tatatgggat gccaccagct   1140
ccaattttcag attctatacg aaagaaaata atcggccgatg aagaagtaat ttcaaagagg   1200
ccagcagatt tactaagtcc tcaattggat gaatttaaaa atgagataaa ggaattata   1260
gagcaagatg aagatgttttt atcatatgca ttatttcctc aagtagcaag aagatttttc   1320
gagtataggc aagccaaaaa atacagaatt gattcaacat tattaaatat cgaagaaagg   1380
gttcatccga tataa                                                  1395

<210> SEQ ID NO 33
<211> LENGTH: 464
<212> TYPE: PRT
<213> ORGANISM: T. saccharolyticum

<400> SEQUENCE: 33

Met Ser Lys Ile Lys Ile Thr Glu Thr Val Leu Arg Asp Ala His Gln
1               5                   10                  15

Ser Leu Leu Ala Thr Arg Met Thr Thr Asp Glu Met Leu Pro Ile Ala
            20                  25                  30

Glu Lys Leu Asp Glu Val Gly Phe Phe Ser Leu Glu Ala Trp Gly Gly
        35                  40                  45

```
Ala Thr Phe Asp Ala Cys Met Arg Phe Leu Asn Glu Asp Pro Trp Glu
 50                  55                  60

Arg Leu Arg Leu Leu Lys Lys Ala Ile Lys Lys Thr Pro Leu Gln Met
 65                  70                  75                  80

Leu Leu Arg Gly Gln Asn Leu Leu Gly Tyr Lys His Tyr Pro Asp Asp
                 85                  90                  95

Val Val Asn Glu Phe Ile Ile Lys Ser Val Glu Asn Gly Ile Asp Ile
            100                 105                 110

Ile Arg Ile Phe Asp Ala Leu Asn Asp Val Arg Asn Leu Glu Val Pro
        115                 120                 125

Ile Lys Ser Ala Lys Ser Ala Gly Ala His Val Gln Ala Ala Ile Val
    130                 135                 140

Tyr Thr Val Ser Pro Val His Asn Thr Asp His Tyr Leu Lys Val Ala
145                 150                 155                 160

Lys Ser Leu Gln Asp Met Gly Ala Asp Ser Ile Cys Ile Lys Asp Met
                165                 170                 175

Ser Gly Ile Leu Ser Pro Tyr Val Ala Tyr Asp Leu Ile Lys Ser Leu
            180                 185                 190

Lys Arg Ala Leu Tyr Thr Pro Ile Gln Leu His Ser His Tyr Thr Ala
        195                 200                 205

Gly Leu Ala Ser Met Thr Tyr Leu Lys Ala Ile Glu Ala Gly Val Asp
    210                 215                 220

Gly Val Asp Thr Ala Ile Ser Ser Leu Ala Leu Gly Thr Ser Gln Pro
225                 230                 235                 240

Ala Thr Glu Ser Ile Val Ala Ala Leu Lys Asp Thr Glu Tyr Asp Thr
                245                 250                 255

Gly Leu Asp Leu Lys Leu Leu Ala Glu Ile Ala Gln His Phe Asn Val
            260                 265                 270

Val Lys Gln Asn His Lys Asn Asp Ser Asp Met Ser Leu Leu Met Ser
        275                 280                 285

Val Asp Val Lys Ala Leu Glu Ser Gln Ile Pro Gly Gly Met Leu Ser
    290                 295                 300

Asn Leu Val Ser Gln Leu Lys Gln Gln Asn Ala Leu Asn Lys Tyr Gln
305                 310                 315                 320

Asp Val Leu Lys Glu Val Pro Arg Val Arg Glu Asp Leu Gly Tyr Pro
                325                 330                 335

Pro Leu Val Thr Pro Met Ser Gln Met Val Gly Thr Gln Ala Val Leu
            340                 345                 350

Asn Val Ile Thr Gly Glu Arg Tyr Lys Ile Val Pro Lys Glu Ile Lys
        355                 360                 365

Asp Tyr Val Lys Gly Leu Tyr Gly Met Pro Pro Ala Pro Ile Ser Asp
    370                 375                 380

Ser Ile Arg Lys Lys Ile Ile Gly Asp Glu Val Ile Ser Lys Arg
385                 390                 395                 400

Pro Ala Asp Leu Leu Ser Pro Gln Leu Asp Glu Phe Lys Asn Glu Ile
                405                 410                 415

Lys Glu Phe Ile Glu Gln Asp Glu Asp Val Leu Ser Tyr Ala Leu Phe
            420                 425                 430

Pro Gln Val Ala Arg Arg Phe Phe Glu Tyr Arg Gln Ala Lys Lys Tyr
        435                 440                 445

Arg Ile Asp Ser Thr Leu Leu Asn Ile Glu Glu Arg Val His Pro Ile
    450                 455                 460
```

<210> SEQ ID NO 34
<211> LENGTH: 159
<212> TYPE: DNA
<213> ORGANISM: T. saccharolyticum

<400> SEQUENCE: 34

| | | |
|---|---|---|
| atggaagaga taaatgaaga aatagttgct gtcattgaag ctgcgattta cgcggcattt | 60 |
| ggtcagtacg aaaagaattt ccgcatcaag gtaataaaga gagtggactc aaatatgccg | 120 |
| gaatggagaa aagctggcct ttacaatcag atgagatag | 159 |

<210> SEQ ID NO 35
<211> LENGTH: 52
<212> TYPE: PRT
<213> ORGANISM: T. saccharolyticum

<400> SEQUENCE: 35

Met Glu Glu Ile Asn Glu Glu Ile Val Ala Val Ile Glu Ala Ala Ile
1               5                   10                  15

Tyr Ala Ala Phe Gly Gln Tyr Glu Lys Asn Phe Arg Ile Lys Val Ile
            20                  25                  30

Lys Arg Val Asp Ser Asn Met Pro Glu Trp Arg Lys Ala Gly Leu Tyr
        35                  40                  45

Asn Gln Met Arg
    50

<210> SEQ ID NO 36
<211> LENGTH: 1542
<212> TYPE: DNA
<213> ORGANISM: C. bescii

<400> SEQUENCE: 36

| | | |
|---|---|---|
| atgacaaaca agctcagaga gctcaagcaa aagagagaaa gaatactaaa gcttggtgga | 60 |
| gaagataaaa taaaaaaaca gcatgatagc aaaaaactta cttgtagaga gagaatagaa | 120 |
| tatttacttg accctggaag cttcaatgaa atagatatgt tgttgaaca cagatgtcaa | 180 |
| gaatttgata tgaaagatac atttgtcccc tgtgatggtg ttgtaacggg ttatggaaca | 240 |
| atcaatggca gaaaagtttt tgtttatgct caagatttta cttcgatagg cggttctctt | 300 |
| ggcgagatgc atgcaaaaaa gatttgtaaa gttttggact tagcattaaa atatggttgt | 360 |
| ccagtgatag gtataaatga ttctggtggt gcaagaattc aagaaggtgt tgatgcatta | 420 |
| gcaggatatg gtgaaatctt ctatagaaat accatggcat caggtgtaat tccacaaatt | 480 |
| gcagctataa tgggaccttg tgcaggtgga gctgtatact ctcctgctat tatggatttt | 540 |
| attttatgg tggacaaaac cagccaaatg tttgttacag acctcaggt tataaaagct | 600 |
| gtgactggag aggagatatc ctttgaagag cttggtggcg cttacactca cagctcaaag | 660 |
| agtggagttg ctcattttat tgcagaggat gagtatcacc tacttgatat gataaagtat | 720 |
| ttattgtcgt ttataccttc aaataacatg gaagacccac cttttataat gtcatctgat | 780 |
| tcagaaaaaa gatttgttcc cgagctcgaa atataattc cgcaagagcc aaacaaagct | 840 |
| tatgatgtaa aagaaataat ttataaagta gtagacaacc aagaattttt agaagtacaa | 900 |
| ccttattttg ctcaaaatgc tgttgtagga tttggtagaa taggggctt tagcgtagga | 960 |
| attgtagcaa atcagcccaa agtgaacgct ggagtgcttg attatgattc gtctgacaag | 1020 |
| atagcacgat ttgtaagatt ttgtgatgct tttaatattc ccataataac atttacagac | 1080 |
| gtgcctggat ttttgccagg tgttaaccaa gagcacaatg gaataattcg tcatgggct | 1140 |

-continued

```
aaggttttgt atgcatactc agaggcaaca gttccaaaga taaatgtaat tttgagaaaa    1200
gcatatggtg gggcttacat tgcaatgagc agcaaacaca ttggtgcaga ctttgtgttt    1260
gcatggccaa ctgccgagat agctgttatg ggaccagatg gcgcagcaaa tattatattt    1320
agaaaagaga tacaaagcgc tcaaaatccc gaagaggaaa gaaaaagaag atagaagag     1380 tatactcaaa gtttgcaaa tccatacatt gcagctgccc gtgggtatgt tgacgatgtg     1440
attgagccac agcttacccg taacaaaatc attgaggcgc tcaaaatttc cattacaaaa    1500
agagagcaaa ggccccaaa aaagcatggc aatattccat ta                       1542
```

<210> SEQ ID NO 37
<211> LENGTH: 514
<212> TYPE: PRT
<213> ORGANISM: C. bescii

<400> SEQUENCE: 37

```
Met Thr Asn Lys Leu Arg Glu Leu Lys Gln Lys Arg Glu Arg Ile Leu
1               5                   10                  15

Lys Leu Gly Gly Glu Asp Lys Ile Lys Lys Gln His Asp Ser Lys Lys
            20                  25                  30

Leu Thr Cys Arg Glu Arg Ile Glu Tyr Leu Leu Asp Pro Gly Ser Phe
        35                  40                  45

Asn Glu Ile Asp Met Phe Val Glu His Arg Cys Gln Glu Phe Asp Met
    50                  55                  60

Lys Asp Thr Phe Val Pro Cys Asp Gly Val Val Thr Gly Tyr Gly Thr
65                  70                  75                  80

Ile Asn Gly Arg Lys Val Phe Val Tyr Ala Gln Asp Phe Thr Ser Ile
                85                  90                  95

Gly Gly Ser Leu Gly Glu Met His Ala Lys Lys Ile Cys Lys Val Leu
            100                 105                 110

Asp Leu Ala Leu Lys Tyr Gly Cys Pro Val Ile Gly Ile Asn Asp Ser
        115                 120                 125

Gly Gly Ala Arg Ile Gln Glu Gly Val Asp Ala Leu Ala Gly Tyr Gly
    130                 135                 140

Glu Ile Phe Tyr Arg Asn Thr Met Ala Ser Gly Val Ile Pro Gln Ile
145                 150                 155                 160

Ala Ala Ile Met Gly Pro Cys Ala Gly Gly Ala Val Tyr Ser Pro Ala
                165                 170                 175

Ile Met Asp Phe Ile Phe Met Val Asp Lys Thr Ser Gln Met Phe Val
            180                 185                 190

Thr Gly Pro Gln Val Ile Lys Ala Val Thr Gly Glu Glu Ile Ser Phe
        195                 200                 205

Glu Glu Leu Gly Gly Ala Tyr Thr His Ser Ser Lys Ser Gly Val Ala
    210                 215                 220

His Phe Ile Ala Glu Asp Glu Tyr His Leu Leu Asp Met Ile Lys Tyr
225                 230                 235                 240

Leu Leu Ser Phe Ile Pro Ser Asn Asn Met Glu Asp Pro Pro Phe Ile
                245                 250                 255

Met Ser Ser Asp Ser Glu Lys Arg Phe Val Pro Glu Leu Glu Asn Ile
            260                 265                 270

Ile Pro Gln Glu Pro Asn Lys Ala Tyr Asp Val Lys Glu Ile Ile Tyr
        275                 280                 285

Lys Val Val Asp Asn Gln Glu Phe Leu Glu Val Gln Pro Tyr Phe Ala
    290                 295                 300
```

```
Gln Asn Ala Val Val Gly Phe Gly Arg Ile Gly Gly Phe Ser Val Gly
305                 310                 315                 320

Ile Val Ala Asn Gln Pro Lys Val Asn Ala Gly Val Leu Asp Tyr Asp
            325                 330                 335

Ser Ser Asp Lys Ile Ala Arg Phe Val Arg Phe Cys Asp Ala Phe Asn
        340                 345                 350

Ile Pro Ile Ile Thr Phe Thr Asp Val Pro Gly Phe Leu Pro Gly Val
    355                 360                 365

Asn Gln Glu His Asn Gly Ile Ile Arg His Gly Ala Lys Val Leu Tyr
370                 375                 380

Ala Tyr Ser Glu Ala Thr Val Pro Lys Ile Asn Val Ile Leu Arg Lys
385                 390                 395                 400

Ala Tyr Gly Gly Ala Tyr Ile Ala Met Ser Ser Lys His Ile Gly Ala
                405                 410                 415

Asp Phe Val Phe Ala Trp Pro Thr Ala Glu Ile Ala Val Met Gly Pro
            420                 425                 430

Asp Gly Ala Ala Asn Ile Ile Phe Arg Lys Glu Ile Gln Ser Ala Gln
        435                 440                 445

Asn Pro Glu Glu Glu Arg Lys Arg Arg Ile Glu Tyr Thr Gln Lys
    450                 455                 460

Phe Ala Asn Pro Tyr Ile Ala Ala Ala Arg Gly Tyr Val Asp Asp Val
465                 470                 475                 480

Ile Glu Pro Gln Leu Thr Arg Asn Lys Ile Ile Glu Ala Leu Lys Ile
            485                 490                 495

Ser Ile Thr Lys Arg Glu Gln Arg Pro Pro Lys Lys His Gly Asn Ile
                500                 505                 510

Pro Leu

<210> SEQ ID NO 38
<211> LENGTH: 381
<212> TYPE: DNA
<213> ORGANISM: C. bescii

<400> SEQUENCE: 38
atgagaaagt tcaaggtgaa gatcaatagc caagaatttg ttgtagaagt ggaagaaata      60
ggagttgaaa atgctacttc tgtcgtgcca aggcctaaga ttggccattt tgagccaaaa     120
caggaaaaac atgaggataa acaaaacaa agccctgtac tttcttctga taaaaattcg      180
gttgttgccc agcttccggg tactattgta aggctgctaa aaagtgaagg tgatgttgtt     240
gatgcaaatg aacctgtttt aattcttgaa gccatgaaaa tggaaaatga ataactgca      300 cctgtcaaag gaaaaattaa agaatacat gtaaaggaag ggcagaaggt agcaaaagga     360
gatttgctat ttgaaataga g                                                381

<210> SEQ ID NO 39
<211> LENGTH: 127
<212> TYPE: PRT
<213> ORGANISM: C. bescii

<400> SEQUENCE: 39

Met Arg Lys Phe Lys Val Lys Ile Asn Ser Gln Glu Phe Val Val Glu
1               5                   10                  15

Val Glu Glu Ile Gly Val Glu Asn Ala Thr Ser Val Val Pro Arg Pro
            20                  25                  30

Lys Ile Gly His Phe Glu Pro Lys Gln Glu Lys His Glu Asp Lys Thr
```

```
                35                  40                  45
Lys Gln Ser Pro Val Leu Ser Ser Asp Lys Asn Ser Val Val Ala Gln
         50                  55                  60

Leu Pro Gly Thr Ile Val Arg Leu Leu Lys Ser Glu Gly Asp Val Val
 65                  70                  75                  80

Asp Ala Asn Glu Pro Val Leu Ile Leu Glu Ala Met Lys Met Glu Asn
                 85                  90                  95

Glu Ile Thr Ala Pro Val Lys Gly Lys Ile Lys Arg Ile His Val Lys
                100                 105                 110

Glu Gly Gln Lys Val Ala Lys Gly Asp Leu Leu Phe Glu Ile Glu
        115                 120                 125

<210> SEQ ID NO 40
<211> LENGTH: 1389
<212> TYPE: DNA
<213> ORGANISM: C. bescii

<400> SEQUENCE: 40
atgggggtaa aaataacaga acaatactc agagatgctc atcagtcact cattgcaacc      60
cgcatgacaa ctgaacagat gcttgagatt gctcctgtgc ttgaccaagt tggttattat     120
tcggttgagt gctggggcgg tgctacattt gatgcgtgtc tgaggttttt caatgaagac     180
ccatgggaaa gattaaaaag actgagaact gcttttaaaa agacaaagct ccagatgctt     240
cttcgaggac aaaatcttgt tgggtataga cattattctg atgatgttgt tgaagagttt     300
gtaaaaaagg ccatatacta tggcattgat attataagaa tatttgatgc acttaatgac     360
atccggaata ttgaaatggc tctaaaaata acaaaaaaag aaaaaggaca tgcccaggtt     420
gccatatcat acactgtctc accttatcat actattgaaa actatgtaaa tttggcaaaa     480
caaatagaag aacttggggc agactcaatt tgtataaaag acatggctgg gcttctctct     540
ccatttgatg cttataaact tgtaaaagcg ttaaaagagc aggtaaaact tcctattcat     600
cttcatacac actacaccac aggatttgga tcaatgacat atttgaaagc tgtcgaagca     660
ggtgtggatg gtattgacac ggcttttatct ccgcttgcac tgggcacatc ccagcctcca     720
accgaaacaa ttgtatatgc acttgaaaat acagaatatg ctccaaaact tgatttagaa     780
aagatcaacg aggcaagcga atatttttaaa gtactcagag aagaatatat aagaaagggg    840
cttcttgacc cgaaagtatt aagtgttgat ataaacgctc ttcattatca atacctggt     900 ggaatgctat caaatcttat ttctcagcta aaagaacaag ggcaggaaga caagttagat     960
gaggttttaa aagaggtacc tgaggttcga aaagattttg gatatccgcc acttgtaact    1020
cctacgagtc aaattgtggg aacacaagct gttttgaatg ttatagcagg tgagagatac    1080
aaacttgtca caaagaaac aaaagcatat tttaaaggtg agtatgggaa acctccagct    1140
cctgtgaatg aagaggtaaa agaaaaatc ttgaaagacg aaaaagagat aacctgcaga    1200
cctgcagatt tgattttgcc agagcttgaa aatgcaaaag aaaagattaa ggagtatatt    1260
gaaaatgata ctgatgtggt aacttactgt ttattccctc aacttgcaga aaatttttc    1320 aaattaaggt tcgcaaaaaa atacaaggtt gacgctgatc ttgttcaggg taacaaagtg    1380
tatcctgtg                                                            1389

<210> SEQ ID NO 41
<211> LENGTH: 463
<212> TYPE: PRT
<213> ORGANISM: C. bescii
```

```
<400> SEQUENCE: 41

Met Gly Val Lys Ile Thr Glu Thr Ile Leu Arg Asp Ala His Gln Ser
1               5                   10                  15

Leu Ile Ala Thr Arg Met Thr Thr Glu Gln Met Leu Glu Ile Ala Pro
            20                  25                  30

Val Leu Asp Gln Val Gly Tyr Tyr Ser Val Glu Cys Trp Gly Gly Ala
        35                  40                  45

Thr Phe Asp Ala Cys Leu Arg Phe Phe Asn Glu Asp Pro Trp Glu Arg
    50                  55                  60

Leu Lys Arg Leu Arg Thr Ala Phe Lys Lys Thr Lys Leu Gln Met Leu
65              70                  75                  80

Leu Arg Gly Gln Asn Leu Val Gly Tyr Arg His Tyr Ser Asp Asp Val
                85                  90                  95

Val Glu Glu Phe Val Lys Lys Ala Ile Tyr Tyr Gly Ile Asp Ile Ile
            100                 105                 110

Arg Ile Phe Asp Ala Leu Asn Asp Ile Arg Asn Ile Glu Met Ala Leu
        115                 120                 125

Lys Ile Thr Lys Lys Glu Lys Gly His Ala Gln Val Ala Ile Ser Tyr
130             135                 140

Thr Val Ser Pro Tyr His Thr Ile Glu Asn Tyr Val Asn Leu Ala Lys
145                 150                 155                 160

Gln Ile Glu Glu Leu Gly Ala Asp Ser Ile Cys Ile Lys Asp Met Ala
                165                 170                 175

Gly Leu Leu Ser Pro Phe Asp Ala Tyr Lys Leu Val Lys Ala Leu Lys
            180                 185                 190

Glu Gln Val Lys Leu Pro Ile His Leu His Thr His Tyr Thr Thr Gly
        195                 200                 205

Phe Gly Ser Met Thr Tyr Leu Lys Ala Val Glu Ala Gly Val Asp Gly
    210                 215                 220

Ile Asp Thr Ala Leu Ser Pro Leu Ala Leu Gly Thr Ser Gln Pro Pro
225             230                 235                 240

Thr Glu Thr Ile Val Tyr Ala Leu Glu Asn Thr Glu Tyr Ala Pro Lys
                245                 250                 255

Leu Asp Leu Glu Lys Ile Asn Glu Ala Ser Glu Tyr Phe Lys Val Leu
            260                 265                 270

Arg Glu Glu Tyr Ile Arg Lys Gly Leu Leu Asp Pro Lys Val Leu Ser
        275                 280                 285

Val Asp Ile Asn Ala Leu His Tyr Gln Ile Pro Gly Gly Met Leu Ser
290             295                 300

Asn Leu Ile Ser Gln Leu Lys Glu Gln Gly Gln Glu Asp Lys Leu Asp
305                 310                 315                 320

Glu Val Leu Lys Glu Val Pro Glu Val Arg Lys Asp Phe Gly Tyr Pro
                325                 330                 335

Pro Leu Val Thr Pro Thr Ser Gln Ile Val Gly Thr Gln Ala Val Leu
            340                 345                 350

Asn Val Ile Ala Gly Glu Arg Tyr Lys Leu Val Thr Lys Glu Thr Lys
        355                 360                 365

Ala Tyr Phe Lys Gly Glu Tyr Gly Lys Pro Pro Ala Pro Val Asn Glu
    370                 375                 380

Glu Val Lys Arg Lys Ile Leu Lys Asp Glu Lys Glu Ile Thr Cys Arg
385                 390                 395                 400

Pro Ala Asp Leu Ile Leu Pro Glu Leu Glu Asn Ala Lys Glu Lys Ile
                405                 410                 415
```

```
Lys Glu Tyr Ile Glu Asn Asp Thr Asp Val Val Thr Tyr Cys Leu Phe
            420                 425                 430
Pro Gln Leu Ala Glu Asn Phe Phe Lys Leu Arg Phe Ala Lys Lys Tyr
        435                 440                 445
Lys Val Asp Ala Asp Leu Val Gln Gly Asn Lys Val Tyr Pro Val
    450                 455                 460

<210> SEQ ID NO 42
<211> LENGTH: 189
<212> TYPE: DNA
<213> ORGANISM: C. bescii

<400> SEQUENCE: 42
atgtatgctc aggtcagtac tatttcaacc attacaaaag aagaacttgc ttgtatttgt      60
gcatgtctgc acattgtgat gggtgaaggt caatataaaa ttaccaacat aactaaacag     120
caaaacaagt gggtcaaagg tgcaagagaa atgatgctca atcagtcaca gatgttttat     180
agatggagg                                                              189

<210> SEQ ID NO 43
<211> LENGTH: 63
<212> TYPE: PRT
<213> ORGANISM: C. bescii

<400> SEQUENCE: 43

Met Tyr Ala Gln Val Ser Thr Ile Ser Thr Ile Thr Lys Glu Glu Leu
1               5                   10                  15
Ala Cys Ile Cys Ala Cys Leu His Ile Val Met Gly Glu Gly Gln Tyr
            20                  25                  30
Lys Ile Thr Asn Ile Thr Lys Gln Gln Asn Lys Trp Val Lys Gly Ala
        35                  40                  45
Arg Glu Met Met Leu Asn Gln Ser Gln Met Phe Tyr Arg Trp Arg
    50                  55                  60

<210> SEQ ID NO 44
<211> LENGTH: 1548
<212> TYPE: DNA
<213> ORGANISM: C. cellulolyticum

<400> SEQUENCE: 44
atgtcacaaa ttgaaaagat acaaaattta aaaacatga aaaaaactat agctaaaggc       60
ggcggagaag agaaaatagc aaaaagacac gcagatggaa agctttctgc agagaaaga     120 atccatttgt tgtttgatga aacagtttt gttgaggtag atgcattcat agaatccaga     180
tgctttgact tggtatgca gaagaagaaa cttccaggtg acggggttgt taccggttac     240
ggaacagtta atggcagaaa ggtctttgtt tcatcacagg actttactgt tataggcggt     300
tcattgggag atgcacgc aaagaaaatt acaaaggtta tggatatggc tctgaaaatg     360
ggagcaccgt tcatagccat taatgattcc ggcggagctc gtattgagga aggtctggat     420
gctctttcag gttacggaga tattttttac aggaatactc ttgcatcagg cgttattccg     480
cagatatcag taataatggg gccatgtgca ggtggtgcgg tatattcccc ggccataact     540
gattttatat tcatggtgga aaaacaagt cagatgttta ttacaggccc acaggtaata     600
aagtctgtta cgggtgaaga tgtatcagtt gaaaatctgg gaggtgcaga tgttcatact     660
gctacaagcg gtgtagcaca tttcaaatct tcaagcgaag aagagtgtat agaagatata     720
aagaggcttt taagttttat tcccgataat aatgtatcag atactatgta ctacggagtg     780
```

```
tctgatgctg ccgacagatt agccgaaagc ctcaacagca ttattccaga agagtcaaac      840
aagccatatg acatgtttga cgtaatagca gaagtagtag atgatggaga tttctttgaa      900
gttcagagtt atttctctca gaatataata atcggatttg caagaatgaa tggcagaagt      960
gttggtattg ttgcaaacca gcctaagata atggcagggt cactagatat gaacgcggct     1020
gataaggcgg cacgtttcgt tcgtttctgt gatgcattta atattcctgt cgtttcatta     1080
accgatgtac ctgcattcct gcccggggta gcccaggagc ataacggcat aatacgtcac     1140
ggtgcaaaac tcctatatgc tttctctgaa gcaacagtac aaagataaa tgttattctt      1200 agaaaggcat atggaggagc atatattgct atgaacagta aaacaatagg tgccgatatg     1260
gttttggcat ggccatcagc tgaaattgca gttatgggac ctgacggagc agcaaatatt     1320
atatttaaaa aggatattgc tgcgtcggaa gatccagcag aaaccagaaa ggaaaagatt     1380
gcggaatata gagataaatt ctcaaatcct tatgtagcag catcaagagg gtatattgat     1440
gatgttatcg agccttctga aaccagagta aaaattataa ctgctctgga aatgctggat     1500
acaaagaggg aaaacaggcc ttcaaaaaaa catggaaaca ttccgcta                  1548
```

<210> SEQ ID NO 45
<211> LENGTH: 516
<212> TYPE: PRT
<213> ORGANISM: C. cellulolyticum

<400> SEQUENCE: 45

```
Met Ser Gln Ile Glu Lys Ile Gln Asn Leu Lys Asn Met Lys Lys Thr
 1               5                  10                  15

Ile Ala Lys Gly Gly Gly Glu Lys Ile Ala Lys Arg His Ala Asp
                20                  25                  30

Gly Lys Leu Ser Ala Arg Glu Arg Ile His Leu Leu Phe Asp Glu Asn
            35                  40                  45

Ser Phe Val Glu Val Asp Ala Phe Ile Glu Ser Arg Cys Phe Asp Phe
        50                  55                  60

Gly Met Gln Lys Lys Lys Leu Pro Gly Asp Gly Val Val Thr Gly Tyr
    65                  70                  75                  80

Gly Thr Val Asn Gly Arg Lys Val Phe Val Ser Ser Gln Asp Phe Thr
                85                  90                  95

Val Ile Gly Gly Ser Leu Gly Glu Met His Ala Lys Lys Ile Thr Lys
            100                 105                 110

Val Met Asp Met Ala Leu Lys Met Gly Ala Pro Phe Ile Ala Ile Asn
        115                 120                 125

Asp Ser Gly Gly Ala Arg Ile Glu Glu Gly Leu Asp Ala Leu Ser Gly
    130                 135                 140

Tyr Gly Asp Ile Phe Tyr Arg Asn Thr Leu Ala Ser Gly Val Ile Pro
145                 150                 155                 160

Gln Ile Ser Val Ile Met Gly Pro Cys Ala Gly Gly Ala Val Tyr Ser
                165                 170                 175

Pro Ala Ile Thr Asp Phe Ile Phe Met Val Glu Lys Thr Ser Gln Met
            180                 185                 190

Phe Ile Thr Gly Pro Gln Val Ile Lys Ser Val Thr Gly Glu Asp Val
        195                 200                 205

Ser Val Glu Asn Leu Gly Gly Ala Asp Val His Thr Ala Thr Ser Gly
    210                 215                 220

Val Ala His Phe Lys Ser Ser Glu Glu Glu Cys Ile Glu Asp Ile
225                 230                 235                 240
```

Lys Arg Leu Leu Ser Phe Ile Pro Asp Asn Asn Val Ser Asp Thr Met
            245                 250                 255

Tyr Tyr Gly Val Ser Asp Ala Ala Asp Arg Leu Ala Glu Ser Leu Asn
            260                 265                 270

Ser Ile Ile Pro Glu Glu Ser Asn Lys Pro Tyr Asp Met Phe Asp Val
            275                 280                 285

Ile Ala Glu Val Val Asp Asp Gly Asp Phe Phe Glu Val Gln Ser Tyr
            290                 295                 300

Phe Ser Gln Asn Ile Ile Ile Gly Phe Ala Arg Met Asn Gly Arg Ser
305                 310                 315                 320

Val Gly Ile Val Ala Asn Gln Pro Lys Ile Met Ala Gly Ser Leu Asp
            325                 330                 335

Met Asn Ala Ala Asp Lys Ala Ala Arg Phe Val Arg Phe Cys Asp Ala
            340                 345                 350

Phe Asn Ile Pro Val Val Ser Leu Thr Asp Val Pro Ala Phe Leu Pro
            355                 360                 365

Gly Val Ala Gln Glu His Asn Gly Ile Ile Arg His Gly Ala Lys Leu
            370                 375                 380

Leu Tyr Ala Phe Ser Glu Ala Thr Val Pro Lys Ile Asn Val Ile Leu
385                 390                 395                 400

Arg Lys Ala Tyr Gly Gly Ala Tyr Ile Ala Met Asn Ser Lys Thr Ile
            405                 410                 415

Gly Ala Asp Met Val Leu Ala Trp Pro Ser Ala Glu Ile Ala Val Met
            420                 425                 430

Gly Pro Asp Gly Ala Ala Asn Ile Phe Lys Lys Asp Ile Ala Ala
            435                 440                 445

Ser Glu Asp Pro Ala Glu Thr Arg Lys Glu Lys Ile Ala Glu Tyr Arg
            450                 455                 460

Asp Lys Phe Ser Asn Pro Tyr Val Ala Ala Ser Arg Gly Tyr Ile Asp
465                 470                 475                 480

Asp Val Ile Glu Pro Ser Glu Thr Arg Val Lys Ile Ile Thr Ala Leu
            485                 490                 495

Glu Met Leu Asp Thr Lys Arg Glu Asn Arg Pro Ser Lys Lys His Gly
            500                 505                 510

Asn Ile Pro Leu
            515

<210> SEQ ID NO 46
<211> LENGTH: 366
<212> TYPE: DNA
<213> ORGANISM: C. cellulolyticum

<400> SEQUENCE: 46
atgagtaaat atataataaa ggtaaacgga actccttatg aagtagaggt tgaagaagtg    60
ggcgggggaa ggcccatttc agctgctcca aagctaagag ctaccaagcc gggacatacc   120
tctgctgcaa aagcagcaca gccgcaggca ggtaaagcag gtgatgttgc tgctccaatg   180
ccgggaactg ttttaaaggt aaaggttgct atcggtgatg aagtaaagaa ggggcaggta   240
cttttaatac ttgaagctat gaaaatggag aatgaaatag ttgctccggc tgacggtaaa   300
gttacggcgt taaacgtcga ggccggaaag tctgttactg ctggagaact aatggtgtct   360
atagcc                                                             366

<210> SEQ ID NO 47

```
<211> LENGTH: 122
<212> TYPE: PRT
<213> ORGANISM: C. cellulolyticum

<400> SEQUENCE: 47

Met Ser Lys Tyr Ile Ile Lys Val Asn Gly Thr Pro Tyr Glu Val Glu
1               5                   10                  15

Val Glu Val Gly Gly Gly Arg Pro Ile Ser Ala Ala Pro Lys Leu
            20                  25                  30

Arg Ala Thr Lys Pro Gly His Thr Ser Ala Ala Lys Ala Ala Gln Pro
        35                  40                  45

Gln Ala Gly Lys Ala Gly Asp Val Ala Ala Pro Met Pro Gly Thr Val
    50                  55                  60

Leu Lys Val Lys Val Ala Ile Gly Asp Glu Val Lys Lys Gly Gln Val
65                  70                  75                  80

Leu Leu Ile Leu Glu Ala Met Lys Met Glu Asn Glu Ile Val Ala Pro
                85                  90                  95

Ala Asp Gly Lys Val Thr Ala Leu Asn Val Glu Ala Gly Lys Ser Val
            100                 105                 110

Thr Ala Gly Glu Leu Met Val Ser Ile Ala
        115                 120

<210> SEQ ID NO 48
<211> LENGTH: 1530
<212> TYPE: DNA
<213> ORGANISM: C. cellulolyticum

<400> SEQUENCE: 48
atgccaggcg taagaattac ggaaacagtt ttaagagatg ctcaccagtc ccttatagca      60
accagaatga agaccgaaga atgcttcca attgttgaga agcttgacaa tattggttac     120
cattcactgg aagcttgggg cggagctact tttgactcat gtatgagatt tttgaatgaa     180
gatccatgga tgagacttag aaaaataaaa gatgttgcaa agaaaacacc tctgcaaatg     240
cttcttaggg gccagaacct tttaggatac aaacactatg ccgatgatat agttgagtac     300
tttgttcaga aggctgttgc aaacggcatg gacattatga gaatattcga tgcactaaat     360
gatgccagga atatcgagac ggcaattaag gcatgtaaaa aggaaggcgg ccatgctcag     420
ggctgtattt gctatactat aagtcctgtt cacaatcttg agcttttttgt aaaagatgca     480 aagcagttgg agagcatggg agcagattct atctgtataa aagacatggc cggacttctg     540
gtgccgtatc aggcttatga actggtaaag gcttttgaaag aaagtgtaaa gataccgata     600
caattgcaca ctcactatac tagcggtgta gcatctatga cgtatttgaa ggctatagaa     660
gcaggtatag atattgttga ctgtgcaatt tcacctatgt caatgggaac gtcacagccg     720
cctacagagc ctttggtggc aactttaaag ggaactgatt tcgatactgg actggatttg     780
gaaaaactca gtgaaattgc agactatttc agacccctta agaaaaata tattgagagc     840 ggactattag acgttaaggt aatgggtgtt gacgttaaca ctcttattta tcaggtacct     900
ggtggaatgc tttcaaatct tgtttcacaa ttgaagcagt caaatgcttt ggataaatat     960
gaagaggttc tcaaggaagt tcccagagta agagccgatt cggctatcc tccgcttgta    1020 acaccatcaa gtcagatagt tggtacccaa gcggtactta atgtattgac tggtgagaga    1080
tacaagatgg taccaaagga atcaaaaggc gttgtaaagg gggaatacgg taaaaccct    1140 gcacctatta gtgatgaaat aaaagctaag attctgggcg atgaaaagcc tataacatgc    1200
agacctgctg accttattga acctgagctt gaaaagatta gagaagctgt taaggattat    1260
```

```
atagagcagg atgaagatgt actttcatac gcaatgcttc ctcaggttgc cgagaagttc    1320
tttaaacagc gtattgagga tagaaataag gctactgcac ccgcatcaga cgaaataaaa    1380
cccgaagttg tagcggcaat atcagccgta gtaaacgaaa tgggcgaaag agacggcaca    1440
cagtacagaa tcggaaatat ctctaagttg aaccagaatc agaacagatg gagtctgtat    1500
ggtatgcttg atagattcag aacaaaaatt                                     1530
```

<210> SEQ ID NO 49
<211> LENGTH: 510
<212> TYPE: PRT
<213> ORGANISM: C. cellulolyticum

<400> SEQUENCE: 49

```
Met Pro Gly Val Arg Ile Thr Glu Thr Val Leu Arg Asp Ala His Gln
1               5                   10                  15

Ser Leu Ile Ala Thr Arg Met Lys Thr Glu Met Leu Pro Ile Val
            20                  25                  30

Glu Lys Leu Asp Asn Ile Gly Tyr His Ser Leu Glu Ala Trp Gly Gly
        35                  40                  45

Ala Thr Phe Asp Ser Cys Met Arg Phe Leu Asn Glu Asp Pro Trp Met
    50                  55                  60

Arg Leu Arg Lys Ile Lys Asp Val Ala Lys Lys Thr Pro Leu Gln Met
65                  70                  75                  80

Leu Leu Arg Gly Gln Asn Leu Leu Gly Tyr Lys His Tyr Ala Asp Asp
                85                  90                  95

Ile Val Glu Tyr Phe Val Gln Lys Ala Val Ala Asn Gly Met Asp Ile
            100                 105                 110

Met Arg Ile Phe Asp Ala Leu Asn Asp Ala Arg Asn Ile Glu Thr Ala
        115                 120                 125

Ile Lys Ala Cys Lys Lys Glu Gly Gly His Ala Gln Gly Cys Ile Cys
    130                 135                 140

Tyr Thr Ile Ser Pro Val His Asn Leu Glu Leu Phe Val Lys Asp Ala
145                 150                 155                 160

Lys Gln Leu Glu Ser Met Gly Ala Asp Ser Ile Cys Ile Lys Asp Met
                165                 170                 175

Ala Gly Leu Leu Val Pro Tyr Gln Ala Tyr Glu Leu Val Lys Ala Leu
            180                 185                 190

Lys Glu Ser Val Lys Ile Pro Ile Gln Leu His Thr His Tyr Thr Ser
        195                 200                 205

Gly Val Ala Ser Met Thr Tyr Leu Lys Ala Ile Glu Ala Gly Ile Asp
    210                 215                 220

Ile Val Asp Cys Ala Ile Ser Pro Met Ser Met Gly Thr Ser Gln Pro
225                 230                 235                 240

Pro Thr Glu Pro Leu Val Ala Thr Leu Lys Gly Thr Asp Phe Asp Thr
                245                 250                 255

Gly Leu Asp Leu Glu Lys Leu Ser Glu Ile Ala Asp Tyr Phe Arg Pro
            260                 265                 270

Leu Lys Glu Lys Tyr Ile Glu Ser Gly Leu Leu Asp Val Lys Val Met
        275                 280                 285

Gly Val Asp Val Asn Thr Leu Ile Tyr Gln Val Pro Gly Gly Met Leu
    290                 295                 300

Ser Asn Leu Val Ser Gln Leu Lys Gln Ser Asn Ala Leu Asp Lys Tyr
305                 310                 315                 320
```

```
Glu Glu Val Leu Lys Glu Val Pro Arg Val Arg Ala Asp Phe Gly Tyr
                325                 330                 335
Pro Pro Leu Val Thr Pro Ser Ser Gln Ile Val Gly Thr Gln Ala Val
            340                 345                 350
Leu Asn Val Leu Thr Gly Glu Arg Tyr Lys Met Val Pro Lys Glu Ser
        355                 360                 365
Lys Gly Val Val Lys Gly Glu Tyr Gly Lys Thr Pro Ala Pro Ile Ser
    370                 375                 380
Asp Glu Ile Lys Ala Lys Ile Leu Gly Asp Glu Lys Pro Ile Thr Cys
385                 390                 395                 400
Arg Pro Ala Asp Leu Ile Glu Pro Glu Leu Glu Lys Ile Arg Glu Ala
                405                 410                 415
Val Lys Asp Tyr Ile Glu Gln Asp Glu Asp Val Leu Ser Tyr Ala Met
            420                 425                 430
Leu Pro Gln Val Ala Glu Lys Phe Phe Lys Gln Arg Ile Glu Asp Arg
        435                 440                 445
Asn Lys Ala Thr Ala Pro Ala Ser Asp Glu Ile Lys Pro Glu Val Val
    450                 455                 460
Ala Ala Ile Ser Ala Val Val Asn Glu Met Gly Glu Arg Asp Gly Thr
465                 470                 475                 480
Gln Tyr Arg Ile Gly Asn Ile Ser Lys Leu Asn Gln Asn Gln Asn Arg
                485                 490                 495
Trp Ser Leu Tyr Gly Met Leu Asp Arg Phe Arg Thr Lys Ile
            500                 505                 510
```

<210> SEQ ID NO 50
<211> LENGTH: 1581
<212> TYPE: DNA
<213> ORGANISM: C. kroppenstedtii

<400> SEQUENCE: 50

```
atgagtgagc aacctcacga tcccagcatg cctgagcgcc tcggacagct ggaagaagaa      60
agaaaccgca tccgactcgg cggcgggcag gcacgcctgg acaagcagca cgaccgcggc     120
aagatgaccg cccgcgagcg catcaccaag cttgtcgacg aagacacgtt ccaggaaacc     180
ggaatgttcg ccaagcaccg gacaacgcac ttcggcatgg acaaggccga cgcccccgcc     240
gacggcgtcg tcaccggatc cggcgcggtc tacggacggc cagtgcacat cgcgtcccag     300
gacttcagcg tcatgggcgg atctgctggc gaaatgcagt ccaacaaagt ggtcgccatg     360
atgaaggcgt ccgcgaccac cggcaccccc ttcgtcttta tcaacgactc cggcggagct     420
cgtgtccaag agggcatcga ctccctctcc ggatacggcc gcgtgttcta caacaacgtg     480
ctgctctccg gactcgtacc gcaggtctcc atcatcgccg gcccgtgcgc tggtggtgcg     540
gcctactcgc cggcactgac ggacttcatc atccagaccc gcaaggccaa catgttcatc     600
accggcccca aggtcatcga gtccgtgacc ggcgaaaaag tcacggccga cgaactcggt     660
ggtgccgatg cccacatgag cacagctggc aacattcact tcgtcgccga cgatgacgag     720
caagccatcc tgatcgcgca gaagctcctg agcttcctgc cgcaaaacaa caccgaagag     780
ccgcccatcg tcgatccgga cgaggttgtc gagcccgacg attccctccg cgacatcgtc     840
cccgtcgatg gccgcaaggg ctacgacgtc cgcgatatca tccgcaagat cgtcgactac     900
ggcgacttcc tcgaggtcca ggccggatac gcccaaaacc tcgtggtcgg atttgcccgc     960
gtcgttggcc ggacagtcgg tatcgtcgct aaccagtcgc aagtgatgtc cggcgttctg    1020
gacatcaact cgtcggacaa aggcgcaagc ttcgttcgct tctgcgactc cttcaatatt    1080
```

```
ccgctcctca ccctcgtcga cgtccccggc ttcatgccag gtgtcgcaca agagcatggc    1140
ggaatcattc gccacggcgc gaagatgctg ttcgcctact cggcggccac cgtgccgaag    1200
ctgaccgtgg tcctccgcaa atcctatggc ggatcgtacc tggccatgtg ctccaaggac    1260
cttggcgcgg accgcgtctg ggcgtggccc accgctgaaa ttgcggtcat gggtgccgac    1320
ggagccgtga acgtcgtctt ccgtaaggaa atcaagaaag cccaggaaga gggtggcgac    1380
gaagccgctg cagcaaagaa gagcgaactc gtccagctct acaaagacac cttctcgacg    1440
ccatacatgg cggcgtcccg aggcctcgtc gatgacatca tcgaccccgc ggacacacgt    1500
cgcgaaattg ctctggccct ggagttgctg accaacaagc gtgagaaccg gccgtccaag    1560
aagcacggcc tggcacccaa c                                              1581
```

<210> SEQ ID NO 51
<211> LENGTH: 527
<212> TYPE: PRT
<213> ORGANISM: C. kroppenstedtii

<400> SEQUENCE: 51

```
Met Ser Glu Gln Pro His Asp Pro Ser Met Pro Glu Arg Leu Gly Gln
1               5                   10                  15

Leu Glu Glu Glu Arg Asn Arg Ile Arg Leu Gly Gly Gly Gln Ala Arg
            20                  25                  30

Leu Asp Lys Gln His Asp Arg Gly Lys Met Thr Ala Arg Glu Arg Ile
        35                  40                  45

Thr Lys Leu Val Asp Glu Asp Thr Phe Gln Glu Thr Gly Met Phe Ala
    50                  55                  60

Lys His Arg Thr Thr His Phe Gly Met Asp Lys Ala Asp Ala Pro Ala
65                  70                  75                  80

Asp Gly Val Val Thr Gly Ser Gly Ala Val Tyr Gly Arg Pro Val His
                85                  90                  95

Ile Ala Ser Gln Asp Phe Ser Val Met Gly Gly Ser Ala Gly Glu Met
            100                 105                 110

Gln Ser Asn Lys Val Val Ala Met Met Lys Ala Ser Ala Thr Thr Gly
        115                 120                 125

Thr Pro Phe Val Phe Ile Asn Asp Ser Gly Gly Ala Arg Val Gln Glu
    130                 135                 140

Gly Ile Asp Ser Leu Ser Gly Tyr Gly Arg Val Phe Tyr Asn Asn Val
145                 150                 155                 160

Leu Leu Ser Gly Leu Val Pro Gln Val Ser Ile Ile Ala Gly Pro Cys
                165                 170                 175

Ala Gly Gly Ala Ala Tyr Ser Pro Ala Leu Thr Asp Phe Ile Ile Gln
            180                 185                 190

Thr Arg Lys Ala Asn Met Phe Ile Thr Gly Pro Lys Val Ile Glu Ser
        195                 200                 205

Val Thr Gly Glu Lys Val Thr Ala Asp Glu Leu Gly Gly Ala Asp Ala
    210                 215                 220

His Met Ser Thr Ala Gly Asn Ile His Phe Val Ala Asp Asp Glu
225                 230                 235                 240

Gln Ala Ile Leu Ile Ala Gln Lys Leu Leu Ser Phe Leu Pro Gln Asn
                245                 250                 255

Asn Thr Glu Glu Pro Pro Ile Val Asp Pro Asp Glu Val Val Glu Pro
            260                 265                 270

Asp Asp Ser Leu Arg Asp Ile Val Pro Val Asp Gly Arg Lys Gly Tyr
```

-continued

```
        275                 280                 285

Asp Val Arg Asp Ile Ile Arg Lys Ile Val Asp Tyr Gly Asp Phe Leu
    290                 295                 300
Glu Val Gln Ala Gly Tyr Ala Gln Asn Leu Val Val Gly Phe Ala Arg
305                 310                 315                 320
Val Val Gly Arg Thr Val Gly Ile Val Ala Asn Gln Ser Gln Val Met
                325                 330                 335
Ser Gly Val Leu Asp Ile Asn Ser Ser Asp Lys Gly Ala Ser Phe Val
            340                 345                 350
Arg Phe Cys Asp Ser Phe Asn Ile Pro Leu Leu Thr Leu Val Asp Val
        355                 360                 365
Pro Gly Phe Met Pro Gly Val Ala Gln Glu His Gly Gly Ile Ile Arg
    370                 375                 380
His Gly Ala Lys Met Leu Phe Ala Tyr Ser Ala Ala Thr Val Pro Lys
385                 390                 395                 400
Leu Thr Val Val Leu Arg Lys Ser Tyr Gly Gly Ser Tyr Leu Ala Met
                405                 410                 415
Cys Ser Lys Asp Leu Gly Ala Asp Arg Val Trp Ala Trp Pro Thr Ala
            420                 425                 430
Glu Ile Ala Val Met Gly Ala Asp Gly Ala Val Asn Val Val Phe Arg
        435                 440                 445

Lys Glu Ile Lys Lys Ala Gln Glu Glu Gly Gly Asp Glu Ala Ala Ala
    450                 455                 460
Ala Lys Lys Ser Glu Leu Val Gln Leu Tyr Lys Asp Thr Phe Ser Thr
465                 470                 475                 480
Pro Tyr Met Ala Ala Ser Arg Gly Leu Val Asp Asp Ile Ile Asp Pro
                485                 490                 495
Ala Asp Thr Arg Arg Glu Ile Ala Leu Ala Leu Glu Leu Leu Thr Asn
            500                 505                 510
Lys Arg Glu Asn Arg Pro Ser Lys Lys His Gly Leu Ala Pro Asn
        515                 520                 525

<210> SEQ ID NO 52
<211> LENGTH: 369
<212> TYPE: DNA
<213> ORGANISM: C. kroppenstedtii

<400> SEQUENCE: 52
atgaaactga cagttaccgt caacggcgtc ccctattccg tggacgtaga agttgaacac      60
gaagaacgcc ccacactcgg caccatcatc actggtggca acagcaacgg gccaacaccc     120
accgcgccga ccacctcatc tgtccagggt gtcagcgcca attcggtcac ggcacccctg     180
gctggttccg tcagcaaggt gcttgtggag gaaggccaag ccatcacggc cggcgaagtg     240
atcgttgtcc ttgaagccat gaagatggaa accgaaatta cggcccccaa cgacggcacc     300
gtcaccgcgc ttcacgtgca acccggcgac gccgttcagg gtggacagtc tctgctggag     360
atcggggac                                                             369

<210> SEQ ID NO 53
<211> LENGTH: 123
<212> TYPE: PRT
<213> ORGANISM: C. kroppenstedtii

<400> SEQUENCE: 53

Met Lys Leu Thr Val Thr Val Asn Gly Val Pro Tyr Ser Val Asp Val
1               5                   10                  15
```

```
Glu Val Glu His Glu Glu Arg Pro Thr Leu Gly Thr Ile Ile Thr Gly
            20                  25                  30

Gly Asn Ser Asn Gly Pro Thr Pro Thr Ala Pro Thr Thr Ser Ser Val
        35                  40                  45

Gln Gly Val Ser Ala Asn Ser Val Thr Ala Pro Leu Ala Gly Ser Val
    50                  55                  60

Ser Lys Val Leu Val Glu Glu Gly Gln Ala Ile Thr Ala Gly Glu Val
65                  70                  75                  80

Ile Val Val Leu Glu Ala Met Lys Met Glu Thr Glu Ile Thr Ala Pro
                85                  90                  95

Asn Asp Gly Thr Val Thr Ala Leu His Val Gln Pro Gly Asp Ala Val
            100                 105                 110

Gln Gly Gly Gln Ser Leu Leu Glu Ile Gly Asp
        115                 120

<210> SEQ ID NO 54
<211> LENGTH: 1494
<212> TYPE: DNA
<213> ORGANISM: C. kroppenstedtii

<400> SEQUENCE: 54
atgaccacgc gaaaaattgg agtgaccgaa ctggctctgc gtgatgctca ccagagcctc      60
atggcaacac gcatggccct cgaagacatg gtcgatgcct gtgaggatat agacaaagcc     120
gggtactgga gcgtggaatg ctggggcggg gcaaccttcg acgcctgcat tcgcttcctg     180
aacgaagacc cgtgggagag actgcgcaca ttccgcaagc tcatgcccaa ctcacgcctt     240
cagatgctgc ttcgtggcca gaatcttctg ggataccgtc actacgagga cggcgtcgtc     300
gataagtttg ttgaaaaatc cgctgaaaac ggcatggacg tcttcagggt tttcgacgcg     360
ctcaacgacc cccgcaacct cgagcacgcc atgcaagctg tgaaaaaagt gggcaagcac     420
gcgcagggca ccatctgcta caccgtgtcc ccgctacacg acgtgcaggg ctacattgat     480
ctagcagggc gtttgctgga catgggcgcg gattcgatcg cgctcaaaga catggcagcg     540
ctgctcaaac cacagcccgc ctacgacatt atccgtggca ttaaggacac ctacggcgag     600
gatacgcaga tcaacgtcca ctgccactcc accaccggcg tcacgatggt caccctcatg     660
aaggccattg aagccggtgc ggatgtcgtc gacaccgcca tttcctccat gtccctcggc     720
ccagggcata accccaccga gtctctcgtc gaaatgctcg aaggaaccga ctacgagacc     780
gggcttgaca tggatcggct cattaacatc cgcgaccact tcaagacagt gcgcccgaag     840
tacgcggagt ttgagtcgaa aacactggtc aacaccaata ttttccaatc gcagattccg     900
ggcggaatgc tctccaacat ggaatcgcag ctcaaagccc agggcgcggg cgaccgtatc     960
gacgaggtca tgaaagaagt ccccgtcgtt cggaaagctg ccggataccc gccgttggtg    1020
acgccatcgt cccagatcgt cggcacccag gccgtgttca acgtgctgat gggccgctac    1080
aaagtactca cggctgaatt cgccgacctc ctcctcgggt actacggcga agcaccaggt    1140
gagagggata aagacctcat cgagcaagcc aagaagcaga ccggcaaaga gcccatcacc    1200
gagcgtcctg ctgacctcct tgagcccgaa tgggacaacc tggttgagga agctgacgaa    1260
ctcgacggca ccgacgggtc cgacgaagac gtcctcacaa acgccctgtt cccgcaggtc    1320
gcgccgggat tcttcaagac tcgccccgac ggcccgaaga acgtcggcaa gactaaggaa    1380
cagctcgagc gcgaagaggc gaaggcctcc ggcgacgcca ctgccatccg cgaaccgatt    1440
atgtacaaag tcaccacagg cggccgcagc cacactgtct ccgtggaacc cgca          1494
```

<210> SEQ ID NO 55
<211> LENGTH: 498
<212> TYPE: PRT
<213> ORGANISM: C. kroppenstedtii

<400> SEQUENCE: 55

```
Met Thr Thr Arg Lys Ile Gly Val Thr Glu Leu Ala Leu Arg Asp Ala
1               5                   10                  15

His Gln Ser Leu Met Ala Thr Arg Met Ala Leu Glu Asp Met Val Asp
            20                  25                  30

Ala Cys Glu Asp Ile Asp Lys Ala Gly Tyr Trp Ser Val

```
    370                 375                 380

Asp Leu Ile Glu Gln Ala Lys Lys Gln Thr Gly Lys Glu Pro Ile Thr
385                 390                 395                 400

Glu Arg Pro Ala Asp Leu Leu Glu Pro Glu Trp Asp Asn Leu Val Glu
                405                 410                 415

Glu Ala Asp Glu Leu Asp Gly Thr Asp Gly Ser Asp Glu Asp Val Leu
            420                 425                 430

Thr Asn Ala Leu Phe Pro Gln Val Ala Pro Gly Phe Phe Lys Thr Arg
        435                 440                 445

Pro Asp Gly Pro Lys Asn Val Gly Lys Thr Lys Glu Gln Leu Glu Arg
    450                 455                 460

Glu Glu Ala Lys Ala Ser Gly Asp Ala Thr Ala Ile Arg Glu Pro Ile
465                 470                 475                 480

Met Tyr Lys Val Thr Thr Gly Gly Arg Ser His Thr Val Ser Val Glu
                485                 490                 495

Pro Ala

<210> SEQ ID NO 56
<211> LENGTH: 285
<212> TYPE: DNA
<213> ORGANISM: C. kroppenstedtii

<400> SEQUENCE: 56
atgaatacag acaatgcatc ctctgctgaa ctcagtcagt tgttggcccg cctgtccaac     60
caggtagaaa agctctcccg caacgtcacc aagctcgaaa atgaagttgc ggcactgaag    120
cagcgctctg acgaggaaat tcctgaagat gtcttgattg cgatcagtgc ggccgtatcc    180
gcctacatgg gtaaccgcgg aaccgtgcgc gcagttcact tcttgcgcca tcgcagctgg    240
tcacagcaag gtcggcaggc agttcagcac aaggcgaaat ggcaa                    285

<210> SEQ ID NO 57
<211> LENGTH: 95
<212> TYPE: PRT
<213> ORGANISM: C. kroppenstedtii

<400> SEQUENCE: 57

Met Asn Thr Asp Asn Ala Ser Ser Ala Glu Leu Ser Gln Leu Leu Ala
1               5                   10                  15

Arg Leu Ser Asn Gln Val Glu Lys Leu Ser Arg Asn Val Thr Lys Leu
            20                  25                  30

Glu Asn Glu Val Ala Ala Leu Lys Gln Arg Ser Asp Glu Glu Ile Pro
        35                  40                  45

Glu Asp Val Leu Ile Ala Ile Ser Ala Ala Val Ser Ala Tyr Met Gly
    50                  55                  60

Asn Arg Gly Thr Val Arg Ala Val His Phe Leu Arg His Arg Ser Trp
65                  70                  75                  80

Ser Gln Gln Gly Arg Gln Ala Val Gln His Lys Ala Lys Trp Gln
                85                  90                  95

<210> SEQ ID NO 58
<211> LENGTH: 1542
<212> TYPE: DNA
<213> ORGANISM: G. bemidjiensis

<400> SEQUENCE: 58
atgtccatag aagagaagat aaaagcgctg aacgacaaga agagcaagct gaagctgggc     60
```

```
ggcgggcgct cgaagatcga ccagcagcac gcccagggaa gcctgaccgc ccgggagcgg    120
atagaggcgc tggtggacaa ggacagcttc aggaaatcg gcatcttcgc caggcaccgc    180
tgcaccaatt tcggcatggc cgggaaggaa ctgccggccg aaggggtggt caccggcgca    240
gggagcgtgg gcgggaggat ggtgcacctg gcgagccagg atttcaccgt cgccggggga    300
tcggcgggcg aggtgcacag cgacaagatc gtgcaggcga tgctgggggtc gctgaagacc    360 ggaacccccct tcgtcttcat gaacgattcc ggcggcgcca ggatccagga agggatcgac    420
tcgttagccg gctacggcaa ggtcttctac cacaacgtga tgctcagcgg ggtggtgccg    480
cagatctcgc tcatctgcgg ccctgtgcc ggggcgcgg cctacagccc ggcgctcacc    540
gatttcatca tccagaccgc caaggcgcgc atgttcatca ccggcccttc cgtgatcaag    600
gaggcgaccg cgaagagat cagcgccgag gagctgggag gccactgtc gcagatgaac    660 catagcggcg tagcccattt cgtggcggag aacgacctgg tggcgcttcg catctgcaag    720
aagctccttt cctacctccc ctccaacaac atcgaggacc cgccgcagtt ggaaagcgac    780
gacgtcatcg tcccggacaa gacgttgaac agcatcgtgc cgtcggagca aagaaaggcc    840
tacgacgtga ggaacgtgat cacgcgcctg atcgacggcg cgacttcct ggaggtgcag    900 cctctgttcg ctgccaacat cgtggtcggg ttcggcagga tactcgggcg gagcgtcggc    960
atcgtcgcca tcagccgtc ggtcttggcg ggggcgctgg acatcaacgc ttcggacaag   1020
ggagccaggt tcgtccggtt ctgcaacgcc ttcaacatcc cgctggtgac cctggtggac   1080
gttccgggtt ttctccccgg ggtacagcag gagaagggg ggatcatccg ccacggcgcc   1140
aagatgctct tcgcctacgc cgcggccacc gtcccgaaga taaccgtcat catgcgcaag   1200
gcgtacggcg gcgccttcct cgccatgtgc ggcaaggagt tggagaccga tcgggttttc   1260
gcctggccca gcgccgagat cgcggtcatg ggaccgcagg gagcggtcaa cgtcatcttc   1320
cggaacgaga tcgcccaggc ggaagatccc aagaaaaagc gcgacgagct gatcgcttct   1380
taccagggaa ccttcgccac tcccctatgcg gccgcggcac gccgcgatgt ggacgacatc   1440
atcgagcccg ccgatacgag gcgccaccttc gccatgacgc tggacatcct gagcaccaag   1500
cgcgaattca ggcccatgaa gaagcatggc ctcattccgc tg                      1542
```

<210> SEQ ID NO 59
<211> LENGTH: 514
<212> TYPE: PRT
<213> ORGANISM: G. bemidjiensis

<400> SEQUENCE: 59

```
Met Ser Ile Glu Glu Lys Ile Lys Ala Leu Asn Asp Lys Lys Ser Lys
1               5                   10                  15

Leu Lys Leu Gly Gly Gly Arg Ser Lys Ile Asp Gln Gln His Ala Gln
            20                  25                  30

Gly Ser Leu Thr Ala Arg Glu Arg Ile Glu Ala Leu Val Asp Lys Asp
        35                  40                  45

Ser Phe Gln Glu Ile Gly Ile Phe Ala Arg His Arg Cys Thr Asn Phe
    50                  55                  60

Gly Met Ala Gly Lys Glu Leu Pro Ala Glu Gly Val Val Thr Gly Ala
65                  70                  75                  80

Gly Ser Val Gly Gly Arg Met Val His Leu Ala Ser Gln Asp Phe Thr
                85                  90                  95

Val Ala Gly Gly Ser Ala Gly Glu Val His Ser Asp Lys Ile Val Gln
            100                 105                 110
```

```
Ala Met Leu Gly Ser Leu Lys Thr Gly Thr Pro Phe Val Phe Met Asn
            115                 120                 125

Asp Ser Gly Gly Ala Arg Ile Gln Glu Gly Ile Asp Ser Leu Ala Gly
130                 135                 140

Tyr Gly Lys Val Phe Tyr His Asn Val Met Leu Ser Gly Val Val Pro
145                 150                 155                 160

Gln Ile Ser Leu Ile Cys Gly Pro Cys Ala Gly Ala Ala Tyr Ser
            165                 170                 175

Pro Ala Leu Thr Asp Phe Ile Ile Gln Thr Ala Lys Ala Arg Met Phe
            180                 185                 190

Ile Thr Gly Pro Ser Val Ile Lys Glu Ala Thr Gly Glu Glu Ile Ser
            195                 200                 205

Ala Glu Glu Leu Gly Gly Pro Leu Ser Gln Met Asn His Ser Gly Val
            210                 215                 220

Ala His Phe Val Ala Glu Asn Asp Leu Val Ala Leu Arg Ile Cys Lys
225                 230                 235                 240

Lys Leu Leu Ser Tyr Leu Pro Ser Asn Asn Ile Glu Asp Pro Pro Gln
            245                 250                 255

Leu Glu Ser Asp Asp Val Ile Val Pro Asp Lys Thr Leu Asn Ser Ile
            260                 265                 270

Val Pro Ser Glu Gln Lys Lys Ala Tyr Asp Val Arg Asn Val Ile Thr
            275                 280                 285

Arg Leu Ile Asp Gly Gly Asp Phe Leu Glu Val Gln Pro Leu Phe Ala
            290                 295                 300

Ala Asn Ile Val Val Gly Phe Gly Arg Ile Leu Gly Arg Ser Val Gly
305                 310                 315                 320

Ile Val Ala Asn Gln Pro Ser Val Leu Ala Gly Ala Leu Asp Ile Asn
            325                 330                 335

Ala Ser Asp Lys Gly Ala Arg Phe Val Arg Phe Cys Asn Ala Phe Asn
            340                 345                 350

Ile Pro Leu Val Thr Leu Val Asp Val Pro Gly Phe Leu Pro Gly Val
            355                 360                 365

Gln Gln Glu Lys Gly Gly Ile Ile Arg His Gly Ala Lys Met Leu Phe
            370                 375                 380

Ala Tyr Ala Ala Ala Thr Val Pro Lys Ile Thr Val Ile Met Arg Lys
385                 390                 395                 400

Ala Tyr Gly Gly Ala Phe Leu Ala Met Cys Gly Lys Glu Leu Glu Thr
                405                 410                 415

Asp Arg Val Phe Ala Trp Pro Ser Ala Glu Ile Ala Val Met Gly Pro
            420                 425                 430

Gln Gly Ala Val Asn Val Ile Phe Arg Asn Glu Ile Ala Gln Ala Glu
            435                 440                 445

Asp Pro Lys Lys Lys Arg Asp Glu Leu Ile Ala Ser Tyr Gln Gly Thr
            450                 455                 460

Phe Ala Thr Pro Tyr Ala Ala Ala Arg Arg Asp Val Asp Asp Ile
465                 470                 475                 480

Ile Glu Pro Ala Asp Thr Arg Arg His Leu Ala Met Thr Leu Asp Ile
            485                 490                 495

Leu Ser Thr Lys Arg Glu Phe Arg Pro Met Lys Lys His Gly Leu Ile
            500                 505                 510

Pro Leu

<210> SEQ ID NO 60
```

-continued

<211> LENGTH: 393
<212> TYPE: DNA
<213> ORGANISM: G. bemidjiensis

<400> SEQUENCE: 60
gtgcaactga ccatgaccat tgacggaaag aaataccggg tggacgtaga agtcgaggaa    60
ggggaagagg tgcgtacgga aggggccttc cctcccaccg cgactatgca ggcgtacccg   120
gtgtattcgg cgcatccaac cgcgaccccc ccgctggccg cgccaccccc ggcctccagt   180
tcggaaaaga tctgccgcag tcccatcgcg ggggtggttt tcaagatcgt ggcgcaggtg   240
ggtcaacacc tggagatgaa cgacctgctg gtcgtcctcg aggcgatgaa gatggagacc   300
aacatcaccg cgcacatgtc cgggaaggtg aaaaagattc tggtttccgt gggcgaagcg   360
gtgcagcctg gacaggcaat tgccgaattt gcc                                393

<210> SEQ ID NO 61
<211> LENGTH: 131
<212> TYPE: PRT
<213> ORGANISM: G. bemidjiensis

<400> SEQUENCE: 61

Val Gln Leu Thr Met Thr Ile Asp Gly Lys Lys Tyr Arg Val Asp Val
1               5                   10                  15

Glu Val Glu Glu Gly Glu Val Arg Thr Glu Gly Ala Phe Pro Pro
            20                  25                  30

Thr Ala Thr Met Gln Ala Tyr Pro Val Tyr Ser Ala His Pro Thr Ala
        35                  40                  45

Thr Pro Pro Leu Ala Ala Pro Thr Pro Ala Ser Ser Glu Lys Ile
    50                  55                  60

Cys Arg Ser Pro Ile Ala Gly Val Val Phe Lys Ile Val Ala Gln Val
65                  70                  75                  80

Gly Gln His Leu Glu Met Asn Asp Leu Leu Val Val Leu Glu Ala Met
                85                  90                  95

Lys Met Glu Thr Asn Ile Thr Ala His Met Ser Gly Lys Val Glu Lys
            100                 105                 110

Ile Leu Val Ser Val Gly Glu Ala Val Gln Pro Gly Gln Ala Ile Ala
        115                 120                 125

Glu Phe Ala
    130

<210> SEQ ID NO 62
<211> LENGTH: 1504
<212> TYPE: DNA
<213> ORGANISM: G. bemidjiensis

<400> SEQUENCE: 62
atggaccgca ttatcgacat aaccgaactg gctctgcgcg acgcgcacca gagccttatc    60
gctacgaggc tcgggataga cgacatggtt ccggtgtgcg aggacctgga ccaggcgggc   120
tactggtcca tcgagtgctg gggcggggcc acctatgacg cctgcatccg ctttctcaac   180
gaagatccgt gggtgaggct taggaccttc aaggagctga tgccgaaaac cccgctgcag   240
atgcttttgc gggggcagaa ccttttggga taccggcatt accaggacga ggtggtggac   300
cggttcgtcc agaagagcgc cgagaacggc atcgacgtgt tccggatctt cgatgcgctg   360
aacgatctga ggaacctgga gcggtcggtc caggcggtga agcagtgcgg aaagcacgcg   420
caggtcgcca tctcctatac catcagcccc attcacacca cggcgaaatt cgtggagcag   480

```
gcgaagcgcc tggtcgacat ggggtgcgac tccatctgca tcaaggacat ggcggcgctg    540
atcaagccgc acgcgacata cgacctggtg agagggatca agaggcctg cggcgaccgg     600
atccggatac agctgcatgc gcacgccacc agcggcgtga ccatggtgag ttacatgaag    660
gcggtggagg cgggcgtgga cggcgtggac acggcgtga gttccatgag cctcgggccc     720
ggacacaacc cgacggagag ctttgcggag atgctggaaa atacgggcta caccacgcgc    780
atcgacctcg gccgggtgaa caaggtgaag gagcatttcg ccaaggtgct ccccaggtac    840
tcagaattcc tctccaccat caccggcgcg gagacggaga tcttcaggag ccagattcca    900
ggcgggatgc tttccaacat ggagagccag ttgaagcagc aggggctgg ggaccggatg     960
cgcgacgtgc tggaagagat accgctggtg agaaaggaca cgggatacgt cccgctggta   1020
accccgacca gccagatcgt cgggacccag gcggtgctga acgtattgat ggggcgctac   1080
aaggtgctga ccggcgagtt cgccgacctg atgctcggct actacggcct cacgccggga   1140
gaacggaacc cggaggtggt ggagcaggcg cgccgccacg cgaataagga gccgatagag   1200
tgccgccccg cagatctatt ggagccggaa tgggcaagc tgcgggcggc ggcgctcccc    1260
ttggagggtt gcgacggcag cgacgaggac gtgctcacct acgccctctt ccgcaggtg    1320
gcgccgaagt tcttcgccac gaggagtgaa ggaccccgaa acctggggcg cgatcccgtc   1380
accggagctt cggaaaccag cattcccgaa gggcaccccg ggaagatcac cggccccgtc   1440
acctacacgg tcaccttgag cgggcagccg cacaaggtga cggttgcacc ctacggccag   1500
gaat                                                                1504
```

<210> SEQ ID NO 63
<211> LENGTH: 501
<212> TYPE: PRT
<213> ORGANISM: G. bemidjiensis

<400> SEQUENCE: 63

Met Asp Arg Ile Ile Asp Ile Thr Glu Leu Ala Leu Arg Asp Ala His
1               5                   10                  15

Gln Ser Leu Ile Ala Thr Arg Leu Gly Ile Asp Asp Met Val Pro Val
                20                  25                  30

Cys Glu Asp Leu Asp Gln Ala Gly Tyr Trp Ser Ile Glu Cys Trp Gly
            35                  40                  45

Gly Ala Thr Tyr Asp Ala Cys Ile Arg Phe Leu Asn Glu Asp Pro Trp
        50                  55                  60

Val Arg Leu Arg Thr Phe Lys Glu Leu Met Pro Lys Thr Pro Leu Gln
65                  70                  75                  80

Met Leu Leu Arg Gly Gln Asn Leu Leu Gly Tyr Arg His Tyr Gln Asp
                85                  90                  95

Glu Val Val Asp Arg Phe Val Gln Lys Ser Ala Glu Asn Gly Ile Asp
            100                 105                 110

Val Phe Arg Ile Phe Asp Ala Leu Asn Asp Leu Arg Asn Leu Glu Arg
        115                 120                 125

Ser Val Gln Ala Val Lys Gln Cys Gly Lys His Ala Gln Val Ala Ile
    130                 135                 140

Ser Tyr Thr Ile Ser Pro Ile His Thr Thr Ala Lys Phe Val Glu Gln
145                 150                 155                 160

Ala Lys Arg Leu Val Asp Met Gly Cys Asp Ser Ile Cys Ile Lys Asp
                165                 170                 175

Met Ala Ala Leu Ile Lys Pro His Ala Thr Tyr Asp Leu Val Arg Gly
            180                 185                 190

Ile Lys Glu Ala Cys Gly Asp Arg Ile Arg Ile Gln Leu His Ala His
    195                 200                 205

Ala Thr Ser Gly Val Thr Met Val Ser Tyr Met Lys Ala Val Glu Ala
    210                 215                 220

Gly Val Asp Gly Val Asp Thr Ala Val Ser Ser Met Ser Leu Gly Pro
225                 230                 235                 240

Gly His Asn Pro Thr Glu Ser Phe Ala Glu Met Leu Glu Asn Thr Gly
                245                 250                 255

Tyr Thr Thr Arg Ile Asp Leu Gly Arg Val Asn Lys Val Lys Glu His
                260                 265                 270

Phe Ala Lys Val Leu Pro Arg Tyr Ser Glu Phe Leu Ser Thr Ile Thr
            275                 280                 285

Gly Ala Glu Thr Glu Ile Phe Arg Ser Gln Ile Pro Gly Gly Met Leu
        290                 295                 300

Ser Asn Met Glu Ser Gln Leu Lys Gln Gly Ala Gly Asp Arg Met
305                 310                 315                 320

Arg Asp Val Leu Glu Glu Ile Pro Leu Val Arg Lys Asp Thr Gly Tyr
                325                 330                 335

Val Pro Leu Val Thr Pro Thr Ser Gln Ile Val Gly Thr Gln Ala Val
            340                 345                 350

Leu Asn Val Leu Met Gly Arg Tyr Lys Val Leu Thr Gly Glu Phe Ala
        355                 360                 365

Asp Leu Met Leu Gly Tyr Tyr Gly Leu Thr Pro Gly Glu Arg Asn Pro
    370                 375                 380

Glu Val Val Glu Gln Ala Arg Arg His Ala Asn Lys Glu Pro Ile Glu
385                 390                 395                 400

Cys Arg Pro Ala Asp Leu Leu Glu Pro Glu Trp Gly Lys Leu Arg Ala
                405                 410                 415

Ala Ala Leu Pro Leu Glu Gly Cys Asp Gly Ser Asp Glu Asp Val Leu
            420                 425                 430

Thr Tyr Ala Leu Phe Pro Gln Val Ala Pro Lys Phe Phe Ala Thr Arg
        435                 440                 445

Ser Glu Gly Pro Arg Asn Leu Gly Arg Asp Pro Val Thr Gly Ala Ser
    450                 455                 460

Glu Thr Ser Ile Pro Glu Gly His Pro Gly Lys Ile Thr Gly Pro Val
465                 470                 475                 480

Thr Tyr Thr Val Thr Leu Ser Gly Gln Pro His Lys Val Thr Val Ala
                485                 490                 495

Pro Tyr Gly Gln Glu
            500

<210> SEQ ID NO 64
<211> LENGTH: 195
<212> TYPE: DNA
<213> ORGANISM: G. bemidjiensis

<400> SEQUENCE: 64
gtggacgaag agatggagca ggaacacgat ccggaaatca cgcccgaact gctgatggtg      60
atgtccgccg cgatagccgc gtatctgggc aagaccgtga ggataaggcg ggccaggttc     120
gtcgacccga atctgatcaa cgcctgggga cagtcgagcc gcgtggtgct gcaggcgtcg     180
cacaacttga ggaga                                                      195

<210> SEQ ID NO 65

<211> LENGTH: 65
<212> TYPE: PRT
<213> ORGANISM: G. bemidjiensis

<400> SEQUENCE: 65

```
Val Asp Glu Glu Met Glu Gln Glu His Asp Pro Glu Ile Thr Pro Glu
1               5                   10                  15

Leu Leu Met Val Met Ser Ala Ala Ile Ala Ala Tyr Leu Gly Lys Thr
            20                  25                  30

Val Arg Ile Arg Arg Ala Arg Phe Val Asp Pro Asn Leu Ile Asn Ala
        35                  40                  45

Trp Gly Gln Ser Ser Arg Val Val Leu Gln Ala Ser His Asn Leu Arg
    50                  55                  60

Arg
65
```

<210> SEQ ID NO 66
<211> LENGTH: 1548
<212> TYPE: DNA
<213> ORGANISM: D. propionicus

<400> SEQUENCE: 66

| | |
|---|---:|
| atgagcacaa aggaaaaatt agagcagcta aagcaaaaaa gggccaaagc cttgctgggc | 60 |
| ggcggtcagg ataaaatcga caagatccac tcccagggca atataccgc cgtgagcgt | 120 |
| attcaactcc tcctcgaccc aggcaccttc gaggaatacg atgctttcaa gctccatcgc | 180 |
| tgctacaact tcggcatgga aaaaatcaag ttttttcggcg acggtatcgt caccggatat | 240 |
| ggcaagctgg ccggccggcc ggtttatatt tacgcgcagg acttttcggt cctcgccggt | 300 |
| tctctttccg gaaccttggc tgaaaaaata tgcaaaatca tggatctggg catgaaaaac | 360 |
| ggcattccgg tcatcggatt gaacgactcc ggtggcgccc gtatccagga aggtatcgag | 420 |
| gccctggcag gatataccga atcttcacc cgtaatgttc tcgcttcggg tgttgttccc | 480 |
| cagatttccg gtgttttcgg accctgcgcc ggtggcgccg tttactctcc tgccctgacc | 540 |
| gacttcatca tccaggtcaa gatccagtcc tacatgttcc tgacaggtcc caaggtcgtt | 600 |
| aagactgtgt taaacgagga cgtcaccacc gagcagttgg gtggtgcggc catgcatacc | 660 |
| accaagtccg gcgtcaccga ctatgctgcc gagaacgagg acgacgccat tcagtacatc | 720 |
| aaggatctga tgagctattt gccgcagaac aatctgagg atcctccgga tgcccctgc | 780 |
| gacgatccga tcacccgccg ctccgaactg ctcaacgaca tcattccgga caacccgaat | 840 |
| gccgcctacg acatgaaaaa ggtcatcacc gagacggcag acaacggtat cttctttgaa | 900 |
| atcaagaaga atttcgctcc gaacatcgtc atcggtttg cccgttatgg tggcaaggct | 960 |
| attggcatcg ttgccaacca gccgtcctac tacgccggtg ttctcgacat cgattcctcg | 1020 |
| atcaaaggtg cccgcttcat ccgcttctgc gactgcttca acattccgat ccttaccttc | 1080 |
| gtcgacgtcc ctggcttcct gcccggcact gcacaggaat cggcggcgt tatccgcaac | 1140 |
| ggcgccaaga tgctgtatgc ctacgccgaa tcgacagtgc caaaggtaac gattattacc | 1200 |
| cgtaaatcct atggcggcgc ctactgcgct atgtcgtcca agcacctgcg aaccgatatc | 1260 |
| aactactcct ggccgaccgg tgaaatcgcc gttatgggct ccaaaggcgc ggtcgaagtc | 1320 |
| ctgcacgcca agggcgctaa agcagcagaa gatcccagag cgttcctggc cgaaaaagaa | 1380 |
| aacgagtaca acgagcagtt ctccaatcca tattgtgcgg ccgagcgtgg ctatatcgac | 1440 |
| gatgtcattg aaccggccga aaccaggtac cgtatcatca acgcgtttga gtcgatctct | 1500 |

```
ggaaagcgtg acacgatccc gatgaagaaa cacggcaata tcccgctg                    1548
```

<210> SEQ ID NO 67
<211> LENGTH: 516
<212> TYPE: PRT
<213> ORGANISM: D. propionicus

<400> SEQUENCE: 67

| | | | | | | | | | | | | | | | |
|---|---|---|---|---|---|---|---|---|---|---|---|---|---|---|---|
| Met | Ser | Thr | Lys | Glu | Lys | Leu | Glu | Gln | Leu | Lys | Gln | Lys | Arg | Ala | Lys |
| 1 | | | | 5 | | | | | 10 | | | | | 15 | |
| Ala | Leu | Leu | Gly | Gly | Gly | Gln | Asp | Lys | Ile | Asp | Lys | Ile | His | Ser | Gln |
| | | | 20 | | | | | 25 | | | | | 30 | | |
| Gly | Lys | Tyr | Thr | Ala | Arg | Glu | Arg | Ile | Gln | Leu | Leu | Asp | Pro | Gly | |
| | | 35 | | | | | 40 | | | | | 45 | | | |
| Thr | Phe | Glu | Glu | Tyr | Asp | Ala | Phe | Lys | Leu | His | Arg | Cys | Tyr | Asn | Phe |
| | 50 | | | | | 55 | | | | | 60 | | | | |
| Gly | Met | Glu | Lys | Ile | Lys | Phe | Phe | Gly | Asp | Gly | Ile | Val | Thr | Gly | Tyr |
| 65 | | | | | 70 | | | | | 75 | | | | | 80 |
| Gly | Lys | Leu | Ala | Gly | Arg | Pro | Val | Tyr | Ile | Tyr | Ala | Gln | Asp | Phe | Ser |
| | | | | 85 | | | | | 90 | | | | | 95 | |
| Val | Leu | Ala | Gly | Ser | Leu | Ser | Gly | Thr | Leu | Ala | Glu | Lys | Ile | Cys | Lys |
| | | | 100 | | | | | 105 | | | | | 110 | | |
| Ile | Met | Asp | Leu | Gly | Met | Lys | Asn | Gly | Ile | Pro | Val | Ile | Gly | Leu | Asn |
| | | 115 | | | | | 120 | | | | | 125 | | | |
| Asp | Ser | Gly | Gly | Ala | Arg | Ile | Gln | Glu | Gly | Ile | Glu | Ala | Leu | Ala | Gly |
| | 130 | | | | | 135 | | | | | 140 | | | | |
| Tyr | Thr | Glu | Ile | Phe | Thr | Arg | Asn | Val | Leu | Ala | Ser | Gly | Val | Val | Pro |
| 145 | | | | | 150 | | | | | 155 | | | | | 160 |
| Gln | Ile | Ser | Gly | Val | Phe | Gly | Pro | Cys | Ala | Gly | Gly | Ala | Val | Tyr | Ser |
| | | | | 165 | | | | | 170 | | | | | 175 | |
| Pro | Ala | Leu | Thr | Asp | Phe | Ile | Ile | Gln | Val | Lys | Ile | Gln | Ser | Tyr | Met |
| | | | 180 | | | | | 185 | | | | | 190 | | |
| Phe | Leu | Thr | Gly | Pro | Lys | Val | Val | Lys | Thr | Val | Leu | Asn | Glu | Asp | Val |
| | | 195 | | | | | 200 | | | | | 205 | | | |
| Thr | Thr | Glu | Gln | Leu | Gly | Gly | Ala | Ala | Met | His | Thr | Thr | Lys | Ser | Gly |
| | 210 | | | | | 215 | | | | | 220 | | | | |
| Val | Thr | Asp | Tyr | Ala | Ala | Glu | Asn | Glu | Asp | Asp | Ala | Ile | Gln | Tyr | Ile |
| 225 | | | | | 230 | | | | | 235 | | | | | 240 |
| Lys | Asp | Leu | Met | Ser | Tyr | Leu | Pro | Gln | Asn | Asn | Leu | Glu | Asn | Pro | Pro |
| | | | | 245 | | | | | 250 | | | | | 255 | |
| Asp | Ala | Pro | Cys | Asp | Asp | Pro | Ile | Thr | Arg | Arg | Ser | Glu | Leu | Leu | Asn |
| | | | 260 | | | | | 265 | | | | | 270 | | |
| Asp | Ile | Ile | Pro | Asp | Asn | Pro | Asn | Ala | Ala | Tyr | Asp | Met | Lys | Lys | Val |
| | | 275 | | | | | 280 | | | | | 285 | | | |
| Ile | Thr | Glu | Thr | Ala | Asp | Asn | Gly | Ile | Phe | Phe | Glu | Ile | Lys | Lys | Asn |
| | 290 | | | | | 295 | | | | | 300 | | | | |
| Phe | Ala | Pro | Asn | Ile | Val | Ile | Gly | Phe | Ala | Arg | Tyr | Gly | Gly | Lys | Ala |
| 305 | | | | | 310 | | | | | 315 | | | | | 320 |
| Ile | Gly | Ile | Val | Ala | Asn | Gln | Pro | Ser | Tyr | Tyr | Ala | Gly | Val | Leu | Asp |
| | | | | 325 | | | | | 330 | | | | | 335 | |
| Ile | Asp | Ser | Ser | Ile | Lys | Gly | Ala | Arg | Phe | Ile | Arg | Phe | Cys | Asp | Cys |
| | | | 340 | | | | | 345 | | | | | 350 | | |
| Phe | Asn | Ile | Pro | Ile | Leu | Thr | Phe | Val | Asp | Val | Pro | Gly | Phe | Leu | Pro |
| | | 355 | | | | | 360 | | | | | 365 | | | |

```
Gly Thr Ala Gln Glu Phe Gly Gly Val Ile Arg Asn Gly Ala Lys Met
    370                 375                 380

Leu Tyr Ala Tyr Ala Glu Ser Thr Val Pro Lys Val Thr Ile Ile Thr
385                 390                 395                 400

Arg Lys Ser Tyr Gly Gly Ala Tyr Cys Ala Met Ser Ser Lys His Leu
                405                 410                 415

Arg Thr Asp Ile Asn Tyr Ser Trp Pro Thr Gly Glu Ile Ala Val Met
            420                 425                 430

Gly Ser Lys Gly Ala Val Glu Val Leu His Ala Lys Gly Ala Lys Ala
        435                 440                 445

Ala Glu Asp Pro Arg Ala Phe Leu Ala Glu Lys Glu Asn Glu Tyr Asn
450                 455                 460

Glu Gln Phe Ser Asn Pro Tyr Cys Ala Ala Glu Arg Gly Tyr Ile Asp
465                 470                 475                 480

Asp Val Ile Glu Pro Ala Glu Thr Arg Tyr Arg Ile Ile Asn Ala Phe
                485                 490                 495

Glu Ser Ile Ser Gly Lys Arg Asp Thr Ile Pro Met Lys Lys His Gly
            500                 505                 510

Asn Ile Pro Leu
        515

<210> SEQ ID NO 68
<211> LENGTH: 195
<212> TYPE: DNA
<213> ORGANISM: D. propionicus

<400> SEQUENCE: 68
atggcaaaaa tgaacaaaaa aatggctgcg gcccttgcag ccgttaatgc ctacctgatg      60
caggaagagg aggcggcata ccaggcccag ttgctggctg ccaaatctgt tgcaccagcc     120
gggccaagct atgggcaat tgccggccgt caggatatca tgaatttccg caggctgatt      180
caaatgaaag ccttc                                                      195

<210> SEQ ID NO 69
<211> LENGTH: 65
<212> TYPE: PRT
<213> ORGANISM: D. propionicus

<400> SEQUENCE: 69

Met Ala Lys Met Asn Lys Lys Met Ala Ala Ala Leu Ala Ala Val Asn
1               5                   10                  15

Ala Tyr Leu Met Gln Glu Glu Ala Ala Tyr Gln Ala Gln Leu Leu
                20                  25                  30

Ala Ala Lys Ser Val Ala Pro Ala Gly Pro Ser Leu Trp Ala Ile Ala
            35                  40                  45

Gly Arg Gln Asp Ile Met Asn Phe Arg Arg Leu Ile Gln Met Lys Ala
        50                  55                  60

Phe
65

<210> SEQ ID NO 70
<211> LENGTH: 1989
<212> TYPE: DNA
<213> ORGANISM: D. propionicus

<400> SEQUENCE: 70
atgagcgacc aagtgaaaat gaccgccatg aattatgcaa ctgaccggcc tgctgcagaa      60
```

-continued

```
aatccggtca aagttatgga cttgagcctt cgtgacggcc accagtctct gttcgccacc       120
cgcgggcgca ccgaggacat gattccgatc gcggaaatga tggacgagat cggcttctgg       180
gcagttgaga cctggggtgg cgccaccttt gacaccatgc accgcttcct caacgaggac       240
ccgtgggagc gtctccgcac cctgaaacgt tacatcaaga agaccccctt ctccatgttg       300
ctgcgcgcgc agaacctggt tggataccgt aactatgccg atgacttggc caccgccttt       360
gttgagcgcg ctgccgagaa cggtatggat atcttccgga cctttgacgc cctcaacgat       420
taccgtaact tcgagaccgt tgttaaacag atcaagaaga gcggcaagca cttccagggt       480
tgtatttgct attcgctgac cgaaccgcgt ctgggcgggg atgtttatga cctgaagtac       540
tatgtcgacc gcgccaaagc gcttgacgac atgggcgctg actccatctg catcaaggac       600
atggccggtc tgatcgcccc atacgacgcc tacgccatcg tcaaggctat caaggaagtc       660
accaagaccc cgatccacct gcacagccac ttcacctctg gtatggcgtc catgagtcat       720
ctgaaggcca ttgaggctgg cgtagatatc gttgacacct gcatgacccc gtacgctttc       780
cgtaccgccc atccggccat cgagccgttg gtcatggccc tgctcggcac caaccgcgac       840
accggtttcg acatcaagaa actggccgcc atcaacgagg tgctagagaa agaggttatg       900
ccgaaataca agcacctcat ggatgactcc aagtgctcaa tcatcgatat caacgttctt       960
ctccatcaga ccccgggcgg catgctctcc aacctggtca accagttgcg tgagatggat      1020
gctctggaca agatcgatca ggtctacaaa gagctgccga agttcggaa agacctcggc       1080 cagattccgc tggttacccc gaccagccag atcgttggca tccagaccgt gaacaacgtg      1140
ctgtttgaca ctcctgatga gcgctacaag atgatcaccg cccaggtcaa agacctgtgc      1200
tacggtctct atggtaaaac cgctgtgccg atcaaccctg aactgcagaa gaaggctctg      1260
aaaggctatc cgcgcggtga agagccgatc acctgccgtc cggcagaggt gcttgagccc      1320
gagttggaaa aggccaagaa agagattggc gatctcgcca aggatatcga tgacttggta      1380
ctctacgcca tctacccggt caccgggaag aagttccttg agtggaagta tggcattacc      1440
ccggcaccgc ccgaagtcaa gccgctcacc cttgaggatg tcaagaagcg tgatgaactg      1500
gtggccaagg ccaaggctgg caagctcatc gagcccaagc ccgctgctcc ggagaagacc      1560
gctaacgttc ggaccttcaa cgtcttcgtc gacggtgagt atttcaacgt tgaggtcgac      1620
ccgaccggtg acttccagcc gatggtcgcc gctgctccgc ggcctgccgc acctgccgct      1680
gcaccgaaag ctgctgcacc tgccgctgct gcacctgctg ccgcgccgaa ggctgctgca      1740
cctgccgccg ccgctccggc tccagccgct gttgagggag aaccccgct gttggccccc       1800 atgcccggca tgatcgtcaa gaatctggtc aatgttggtg atgcggtcaa agctggcgac      1860
cccatcctcg ttcttgaggc catgaagatg gagaacaatc tcggttctcc gtgcgatggt      1920
actgtgaagg cgcttaattt tggcagcggt gactcggttg ccaaggatac cgtcctggca      1980
atcatcgga                                                              1989
```

<210> SEQ ID NO 71
<211> LENGTH: 663
<212> TYPE: PRT
<213> ORGANISM: D. propionicus

<400> SEQUENCE: 71

```
Met Ser Asp Gln Val Lys Met Thr Ala Met Asn Tyr Ala Thr Asp Arg
1               5                   10                  15

Pro Ala Ala Glu Asn Pro Val Lys Val Met Asp Leu Ser Leu Arg Asp
            20                  25                  30
```

```
Gly His Gln Ser Leu Phe Ala Thr Arg Gly Arg Thr Glu Asp Met Ile
         35                  40                  45

Pro Ile Ala Glu Met Met Asp Glu Ile Gly Phe Trp Ala Val Glu Thr
 50                  55                  60

Trp Gly Gly Ala Thr Phe Asp Thr Met His Arg Phe Leu Asn Glu Asp
 65                  70                  75                  80

Pro Trp Glu Arg Leu Arg Thr Leu Lys Arg Tyr Ile Lys Lys Thr Pro
                 85                  90                  95

Phe Ser Met Leu Leu Arg Ala Gln Asn Leu Val Gly Tyr Arg Asn Tyr
                100                 105                 110

Ala Asp Asp Leu Ala Thr Ala Phe Val Glu Arg Ala Ala Glu Asn Gly
                115                 120                 125

Met Asp Ile Phe Arg Thr Phe Asp Ala Leu Asn Asp Tyr Arg Asn Phe
130                 135                 140

Glu Thr Val Val Lys Gln Ile Lys Lys Ser Gly Lys His Phe Gln Gly
145                 150                 155                 160

Cys Ile Cys Tyr Ser Leu Thr Glu Pro Arg Leu Gly Gly Asp Val Tyr
                165                 170                 175

Asp Leu Lys Tyr Tyr Val Asp Arg Ala Lys Ala Leu Asp Met Gly
                180                 185                 190

Ala Asp Ser Ile Cys Ile Lys Asp Met Ala Gly Leu Ile Ala Pro Tyr
                195                 200                 205

Asp Ala Tyr Ala Ile Val Lys Ala Ile Lys Glu Val Thr Lys Thr Pro
                210                 215                 220

Ile His Leu His Ser His Phe Thr Ser Gly Met Ala Ser Met Ser His
225                 230                 235                 240

Leu Lys Ala Ile Glu Ala Gly Val Asp Ile Val Asp Thr Cys Met Thr
                245                 250                 255

Pro Tyr Ala Phe Arg Thr Ala His Pro Ala Ile Glu Pro Leu Val Met
                260                 265                 270

Ala Leu Leu Gly Thr Asn Arg Asp Thr Gly Phe Asp Ile Lys Lys Leu
                275                 280                 285

Ala Ala Ile Asn Glu Val Leu Glu Lys Glu Val Met Pro Lys Tyr Lys
                290                 295                 300

His Leu Met Asp Asp Ser Lys Cys Ser Ile Ile Asp Ile Asn Val Leu
305                 310                 315                 320

Leu His Gln Thr Pro Gly Gly Met Leu Ser Asn Leu Val Asn Gln Leu
                325                 330                 335

Arg Glu Met Asp Ala Leu Asp Lys Ile Asp Gln Val Tyr Lys Glu Leu
                340                 345                 350

Pro Lys Val Arg Lys Asp Leu Gly Gln Ile Pro Leu Val Thr Pro Thr
                355                 360                 365

Ser Gln Ile Val Gly Ile Gln Thr Val Asn Asn Val Leu Phe Asp Thr
370                 375                 380

Pro Asp Glu Arg Tyr Lys Met Ile Thr Ala Gln Val Lys Asp Leu Cys
385                 390                 395                 400

Tyr Gly Leu Tyr Gly Lys Thr Ala Val Pro Ile Asn Pro Glu Leu Gln
                405                 410                 415

Lys Lys Ala Leu Lys Gly Tyr Pro Arg Gly Glu Pro Ile Thr Cys
                420                 425                 430

Arg Pro Ala Glu Val Leu Glu Pro Glu Leu Glu Lys Ala Lys Lys Glu
                435                 440                 445
```

```
Ile Gly Asp Leu Ala Lys Asp Ile Asp Asp Leu Val Leu Tyr Ala Ile
    450                 455                 460
Tyr Pro Val Thr Gly Lys Lys Phe Leu Glu Trp Lys Tyr Gly Ile Thr
465                 470                 475                 480
Pro Ala Pro Pro Glu Val Lys Pro Leu Thr Leu Glu Asp Val Lys Lys
                485                 490                 495
Arg Asp Glu Leu Val Ala Lys Ala Lys Ala Gly Lys Leu Ile Glu Pro
            500                 505                 510
Lys Pro Ala Ala Pro Glu Lys Thr Ala Asn Val Arg Thr Phe Asn Val
        515                 520                 525
Phe Val Asp Gly Glu Tyr Phe Asn Val Glu Val Asp Pro Thr Gly Asp
    530                 535                 540
Phe Gln Pro Met Val Ala Ala Pro Arg Pro Ala Ala Pro Ala Ala
545                 550                 555                 560
Ala Pro Lys Ala Ala Ala Pro Ala Ala Ala Pro Ala Ala Ala Pro
                565                 570                 575
Lys Ala Ala Ala Pro Ala Ala Ala Pro Ala Pro Ala Ala Val Glu
            580                 585                 590
Gly Gly Thr Pro Leu Leu Ala Pro Met Pro Gly Met Ile Val Lys Asn
        595                 600                 605
Leu Val Asn Val Gly Asp Ala Val Lys Ala Gly Asp Pro Ile Leu Val
    610                 615                 620
Leu Glu Ala Met Lys Met Glu Asn Asn Leu Gly Ser Pro Cys Asp Gly
625                 630                 635                 640
Thr Val Lys Ala Leu Asn Phe Gly Ser Gly Asp Ser Val Ala Lys Asp
                645                 650                 655
Thr Val Leu Ala Ile Ile Gly
            660

<210> SEQ ID NO 72
<211> LENGTH: 933
<212> TYPE: DNA
<213> ORGANISM: T. saccharolyticum

<400> SEQUENCE: 72
atgagcaagg tagcaataat aggatctggt tttgtaggtg caacatcggc atttacgctg      60
gcattaagtg ggactgtgac agatatcgtg ctggtggatt taaacaagga caaggctata     120
ggcgatgcac tggacataag ccatggcata ccgctaatac agcctgtaaa tgtgtatgca     180
ggtgactaca agatgtgaa aggcgcagat gtaatagttg tgacagcagg tgctgctcaa     240
aagccgggag agacacggct tgaccttgta agaaaaaata cagccatatt taagtccatg     300
atacctgagc ttttaaagta caatgacaag gccatatatt tgattgtgac aaatcccgta     360
gatatactga cgtacgttac atacaagatt tctggacttc catggggcag agttttttggt     420 tctggcaccg ttcttgacag ctcaaggttt agatacctt taagcaagca ctgcaatata     480
gatccgagaa atgtccacgg aaggataatc ggcgagcatg gtgacacaga gtttgcagca     540
tggagcataa caaacatatc gggtatatca tttaatgagt actgcagcat atgcggacgc     600
gtctgcaaca caaatttcag aaaggaagta gaagaagaag tcgtaaatgc tgcttacaag     660
ataatagaca aaaaaggtgc tacatactat gctgtggcag ttgcagtaag aaggattgtg     720
gagtgcatct taagagatga aaattccatc ctcacagtat catctccatt aaatggacag     780
tacggcgtga agatgtttc attaagcttg ccatctatcg taggcaggaa tggcgttgcc     840
aggattttgg acttgccttt atctgacgaa gaagtggaga agtttaggca ttcagcaagt     900
```
gtcatggcag atgtcataaa acaattagat ata    933

<210> SEQ ID NO 73
<211> LENGTH: 2577
<212> TYPE: DNA
<213> ORGANISM: T. saccharolyticum

<400> SEQUENCE: 73

| | |
|---|---:|
| atggcaacga caaaaacgga attagacgtt cagaagcaga tagatctact tgtgtcaaga | 60 |
| gcacaagagg ctcagaaaaa attcatgtct tacacgcaag agcaaatcga cgcaatagtt | 120 |
| aaggcaatgg ctttagcagg cgttgacaaa cacgtagagc tggcaaagat ggcgtacgaa | 180 |
| gagacaaaaa tgggtgtata cgaagataag ataacaaaaa atctcttcgc aacagagtac | 240 |
| gtgtaccacg acataaaaaa tgaaagact gtaggaatca taaacgagaa catagaagaa | 300 |
| aactacatgg aagtggcaga accgataggc gtaattgccg gtgtcacacc tgtcacaaac | 360 |
| ccaacatcta ccacgatgtt taaatgctta atatccataa agacgcgaaa tcctataata | 420 |
| ttcagcttcc atccaaaggc aataaagtgc agcatcgcag cagccaaagt gatgtatgaa | 480 |
| gctgcactaa aggcaggcgc acctgaagga tgcataggat ggatagaaac gccatcaatt | 540 |
| gaggccacac agcttctcat gacacatcca ggcgtatcgc tgatccttgc aacgggcggt | 600 |
| gcaggaatgg taaaagcggc atacagctca ggaaaaccgg cattaggcgt aggtcctggc | 660 |
| aatgtgccat gctacatcga aaaatcagca acataaaga gggctgtatc ggatctcata | 720 |
| ctaagcaaga catttgacaa tggagtaata tgcgcatcag agcaggccgt aataatagac | 780 |
| gaggaaatag cagatgaagt caaaaagctt atgaaagaat acggctgcta cttcttaaac | 840 |
| aaagatgaaa taagaagct tgagaaattt gcaattgatg agcaaagctg cgccatgagc | 900 |
| cctgcagtgg taggtcagcc agcggcgaag attgctgaaa tggcaggctt caaagtcccc | 960 |
| gaaggcacaa agatattagt ggcagagtac gaaggagtag gtccaaaata tcctctatca | 1020 |
| agggagaaac taagcccgat tcttgcttgc tacaccgtca aagactacaa tgaaggaatc | 1080 |
| aaaaagtgcg aggaaatgac tgaattcgga ggtttaggcc actctgctgt aatacactct | 1140 |
| gaaaatcaaa acgtcataaa tgaatttgca aggcgagtcc gcacaggaag acttatcgta | 1200 |
| aattcaccat catcacaggg agcaatagga gatatataca atacaaacac gccatcactt | 1260 |
| acattaggct gtggttctat gggaagaaac tcaacgacag acaatgtaag cgtcaagaac | 1320 |
| cttttgaata ttaagcgtgt cgtgataagg aatgatagaa tgaaatggtt caagattcca | 1380 |
| ccgaagattt actttgaaag cgggtcactc cagtacctgt gcaaagtcaa agaaaaaaaa | 1440 |
| gcgtttatcg tcacagatcc attcatggtt aagcttggct tcgtagacaa agtgacatat | 1500 |
| caattagaca aagcaaacat cgaatacgaa atattctcag aagtagagcc agatccatct | 1560 |
| gttgacacag tcatgaacgg cgtaaaaata tgaattcgt acaatcctga cttaataatc | 1620 |
| gctgtaggcg gtggctctgc aatagacgca gcaagggaa tgtggctttt ctacgaatat | 1680 |
| cctgatacag agtttgaaac attgaggctt aaatttgcag acatcagaaa aagggcattt | 1740 |
| aagttcccag aacttggcaa aaaagcgcta ttcatcgcaa taccgacaac aagcggcaca | 1800 |
| ggctcagaag tgacagcatt tgccgtaata accgacaaaa agagaaacat caagtatcca | 1860 |
| ctggcagact acgaacttac acctgacata gccataatag atcctgacct tacaaagact | 1920 |
| gtaccgccat ctgtaacagc agacacaggc atggatgtgc tgacacacgc catagaagca | 1980 |
| tacgtatcag taatggcatc agactacaca gatgcactgg cggaaaaggc tataaagatc | 2040 |

```
gtatttgaat acctgccaag ggcttataaa aacggcaatg atgaagaagc ccgcgaaaag    2100
atgcacaatg cttcctgcat ggctggtatg gcattcacaa atgcattctt aggaataaac    2160
cacagcatgg cacacatact gggcggaaag ttccacatac cacacggaag agcaaatgca    2220
atacttctgc cgtatgtaat aaggtacaat gcagaaaaac ctacaaagtt tgtggcattc    2280
ccacaatacg aatatccaaa agcagcagaa agatatgcgg aaatcgccaa attcttagga    2340
ctgcctgctt caactgttga agaaggcgta gaaagcttaa tagaagctat aaagaacctc    2400
atgaaagagc ttaacattcc gcttacactt aaagacgccg gcatcaacaa agaacagttt    2460
gaaaaagaaa tagaggaaat gtcagacatc gccttcaacg atcagtgcac agggacaaac    2520
ccgagaatgc ctctcacaaa agaaattgca gagatctaca gaaaagcata cggtgca       2577
```

<210> SEQ ID NO 74
<211> LENGTH: 1752
<212> TYPE: DNA
<213> ORGANISM: T. saccharolyticum

<400> SEQUENCE: 74

```
atgcgtagaa ctaagataat atgcacgatt ggtcctgcca gtgaaaaata tgagatattg     60
aaagagctta tagaaagcgg tcttaatatt tgcaggttga attttcaca tggggatcat     120 gaagagcatg gaagcagaat agacaatatt ataaagatta gagaagaact taagctgcct    180
attgcaatta tgcttgatac aaaagggcct gaaataagga ctggcagatt taaaggcggt    240
gttgcagagc ttaagaaagg ccagacattt acgataacat caagggaaat tgaaggagat    300
aacactattt gttctgtttc atacaagggg cttcctcaag atgtggagag aggttctcgc    360
atattgattg atgacggatt agtatcattg aaagtcaatg acgtaaaagg tgaagatata    420
gtatgcactg tggagaattc tggtacaata ggtgatcaca aaggtgtaaa tgtacctggt    480
acaaagctta atttgcctgc cataacgcaa aaagacgtgg atgatataga gtttggaata    540
aaaaaaggaa tcgacatgat tgcagcgtct tttgtcagaa aagcagcaga tgtaattgcc    600
ataaggagat tgttagaaga caatgacgct ggccatatac ttatcatatc aaaaattgaa    660
aatcgcgaag gcgtagaaaa tattgacgaa ataatcaaag tctctgatgg cataatggta    720
gcccgcggcg atttgggtgt cgaaattcct atagaggaaa tacctatcgt tcagaaaagg    780
ataattgaaa atgcaacaa agcaggtaaa ccagtagtta ctgctacaca gatgcttgac    840
tctatgataa gaaatccaag gccaacaagg gcagaagtaa cagatgtagc caatgctata    900
ttggatggca ctgatgcgat aatgttgtct ggtgaaacag cgcaaggcaa atatcctgta    960
gaggctttta gacgatgtc aaagatagct gaaaagattg agacgtatat aaattacaaa    1020
gaaaatttag ataaaaatgt ggattacaat atttctatga caaatgccat aagccatgct    1080
acgtgcacta ccgcgagaga tataggcgca actgccatta ttacatctac aatatcaggt    1140
tatactgcga gaatggtgtc taagtataga ccgtcagcac ctataatagc agtgacgcca    1200
aacaaagatg ttgcaagaag gcttagcatc gtgtggggtg tacatccatt gatatcacag    1260
gaagtcaatt ctacagatga aatgatagaa gtatcagtaa atacggcttt aaatgaagga    1320
ttaattcgaa atggcgatat tgtagtaata tcggcaggaa tacctgtcgc gactacaggc    1380
acaacaaata tgttgaaggt tcatattgtg ggagatgtaa tagtaaaagg cacaggcata    1440
ggcactaaat ccataagtgg tgttgttttcc atcataagag atccatacaa ggacaaagat    1500
aagttcagag aaggagatat catcgttgct caaaaaactg aaagggatta tatgcctata    1560
attgagaagg cttcagctat cataacagaa gaaggtggac taacgtccca tgctgcaata    1620
```

| | |
|---|---:|
| gttggattga actatggatt acctgtcatt gtaggctgtg aaggagtaac ttcaaagctt | 1680 |
| aaagatggaa tgacggtaac tctcgatact gccagaggat tggtctacaa aggtatagtg | 1740 |
| aatataaaat ag | 1752 |

<210> SEQ ID NO 75
<211> LENGTH: 2226
<212> TYPE: DNA
<213> ORGANISM: T. saccharolyticum

<400> SEQUENCE: 75

| | |
|---|---:|
| atgatcaatg aatggcgcgg gtttcaggag ggcaaatggc aaaagactat tgacgttcaa | 60 |
| gattttatcc agaaaaatta cacattatac gaaggcgatg atagttttt agaagggcct | 120 |
| acagaaaaga ctattaagct ttggaacaaa gttcttgagc taatgaagga agaactgaaa | 180 |
| aaaggtgtgt tagatattga tacaaaaact gtatcgtcta aacatccca tgatgcgggg | 240 |
| tatatagaca aagatcttga ggaaatagtt ggattgcaga cagacaaacc tcttaaaaga | 300 |
| gctataatgc cttacggtgg cataagaatg gtcaaaaaag cttgcgaagc ttatggatat | 360 |
| aaagtggacc caaaagtaga agagatattt acgaagtaca aaagacccca caatgatggt | 420 |
| gtatttgatg catatactcc agaaataaga gcagcaagac atgccggcat aataacaggt | 480 |
| cttccagatg catatggcag aggaagaatc ataggtgatt acagaagagt tgctctttat | 540 |
| ggaattgata gactcatcga agaaaaggaa aaagaaaaac ttgagcttga ttacgatgaa | 600 |
| tttgatgaag caactattcg cttgagagaa gaattgacag aacagataaa agcattaaac | 660 |
| gaaatgaaag agatggcttt aaagtacggt tatgacatat caaagcctgc aaaaaatgca | 720 |
| aaagaagctg tgcagtggac ttactttgcc ttccttgctg ctataaagga acaaaatggt | 780 |
| gccgctatgt cgctgggcag agtatctact tttttagata tatacattga agagatctt | 840 |
| aaagaaggaa cattgacaga aaacaagca caagagttaa tggatcactt tgtcatgaag | 900 |
| cttagaatgg tgaggttctt aaggactcct gattacaatg aactatttag tggcgatcct | 960 |
| gtttgggtga ctgaatcaat tggcggtgta ggcgtagacg aaagacctct tgtcactaaa | 1020 |
| aattcattca ggatattaaa tactttatat aacttaggtc ctgcacctga gccaaacttg | 1080 |
| acggttttat ggtccaaaaa ccttcctgaa aactttaaaa gattctgtgc caaggtatca | 1140 |
| atagatacaa gttctattca atatgaaaat gacgacttaa tgaggccaat atacaatgac | 1200 |
| gactatagca tcgcctgctg tgtgtcagct atgaagacgg gagaacagat gcaattttt | 1260 |
| ggagcaaggg caaatctcgc gaaggcgcta ctgtatgcta taacggcgg tatcgatgaa | 1320 |
| aggtataaaa cgcaagtggc accaaaattt aatcctataa cgtctgagta tttagactac | 1380 |
| gatgaggtaa tggcagcata tgacaatatg ttagagtggc ttgcaaaagt gtatgttaaa | 1440 |
| gctatgaata taatacacta catgcacgat aaatacgctt atgaaagatc ccttatggct | 1500 |
| ttgcatgata gagacatcgt aaggacgatg gcttttggaa tcgcaggtct ttctgttgcg | 1560 |
| gcagattcgt taagcgccat aaagtatgct aaagtaaaag ccataagaga tgaaaatggc | 1620 |
| atagcaatag attatgaagt ggaaggagat ttccctaagt ttggcaatga tgatgacagg | 1680 |
| gttgactcaa tagcagttga cattgtgaa agattcatga taagcttaa aaagcacaag | 1740 |
| acttacagaa actctatacc aacactgtct gttttgacaa taacgtcaaa tgtggtgtac | 1800 |
| ggcaaaaaga cgggtgctac acctgacgga agaaaagcgg agaaccttt tgcgccaggc | 1860 |
| gcaaatccga tgcacggcag agatacaaaa ggtgccatag catcaatgaa ttcagtatca | 1920 |

```
aaaatacctt atgacagttc attggatggt atatcataca catttacgat tgtaccaaat    1980
gcgcttggca aggatgacga agataaaatt aataatcttg taggactatt agatggatat    2040
gcatttaatg cggggcacca cataaacatc aatgttttaa acagagatat gttgcttgat    2100
gctatggagc atcctgaaaa atatccgcag cttactataa gggtttcagg gtatgctgtc    2160
aatttcaata aattaacgag agagcaacag ttggaggtta tatcccgcac ttttcacgaa    2220
tctatg                                                              2226

<210> SEQ ID NO 76
<211> LENGTH: 2285
<212> TYPE: DNA
<213> ORGANISM: T. saccharolyticum

<400> SEQUENCE: 76
gtgtatacaa tatatttctt cttagtaaga ggaatgtata aaaataaata ttttaaagga      60
agggacgatc ttatgagcat tattcaaaac atcattgaaa aagctaaaag cgataaaaag     120
aaaattgttc tgccagaagg tgcagaaccc aggacattaa aagctgctga atagttttta     180
aaagaaggga ttgcagattt agtgcttctt ggaaatgaag atgagataag aaatgctgca     240
aaagacttgg acatatccaa agctgaaatc attgaccctg taaagtctga atgtttgat      300 aggtatgcta atgatttcta tgagttaagg aagaacaaag gaatcacgtt ggaaaaagcc     360
agagaaacaa tcaaggataa tatctatttt ggatgtatga tggttaaaga aggttatgct     420
gatggattgg tatctggcgc tattcatgct actgcagatt tattaagacc tgcatttcag     480
ataattaaaa cggctccagg agcaaagata gtatcaagct ttttttataat ggaagtgcct    540 aattgtgaat atggtgaaaa tggtgtattc ttgtttgctg attgtgcggt caacccatcg     600
cctaatgcag aagaacttgc ttctattgcc gtacaatctg ctaatactgc aaagaatttg     660
ttgggctttg aaccaaaagt tgccatgcta tcatttcta caaaggtag tgcatcacat      720 gaattagtag ataaagtaag aaaagcgaca gagatagcaa agaattgat gccagatgtt     780 gctatcgacg gtgaattgca attggatgct gctcttgtta aagaagttgc agagctaaaa     840
gcgccgggaa gcaaagttgc gggatgtgca aatgtgctta tattccctga tttacaagct     900
ggtaatatag gatataagct tgtacagagg ttagctaagg caaatgcaat tggacctata     960
acacaaggaa tgggtgcacc ggttaatgat ttatcaagag gatgcagcta tagagatatt    1020
gttgacgtaa tagcaacaac agctgtgcag gctcaataaa atgtaaagta tggaggatga    1080
aaattatgaa aatactggtt attaattgcg gaagttcttc gctaaaatat caactgattg    1140
aatcaactga tggaaatgtg ttggcaaaag gccttgctga agaatcggc ataaatgatt     1200 ccatgttgac acataatgct aacggagaaa aaatcaagat aaaaaagac atgaaagatc     1260 acaaagacgc aataaaattg gttttagatg ctttggtaaa cagtgactac ggcgttataa    1320 agatatgtc tgagatagat gctgtaggac atagagttgt tcacggagga gaatcttta     1380 catcatcagt tctcataaat gatgaagtgt taaaagcgat aacagattgc atagaattag    1440
ctccactgca caatcctgct aatatagaag gaattaaagc ttgccagcaa atcatgccaa    1500
acgttccaat ggtggcgtaa tttgatacag ccttcatca acaatgcct gattatgcat     1560 atctttatcc aataccttat gaatactaca caaagtacag gattagaaga tatggatttc    1620
atggcacatc gcataaatat gttcaaata gggctgcaga gattttgaat aaacctattg    1680
aagatttgaa aatcataact tgtcatcttg gaaatggctc cagcattgct gctgtcaaat    1740
atggtaaatc aattgacaca agcatgggat ttacaccatt agaaggtttg gctatgggta    1800
```

```
cacgatctgg aagcatagac ccatccatca tttcgtatct tatggaaaaa gaaatataa    1860 gcgctgaaga agtagtaaat atattaaata aaaaatctgg tgtttacggt atttcaggaa   1920
taagcagcga ttttagagac ttagaagatg ccgcctttaa aaatggagat gaaagagctc   1980
agttggcttt aaatgtgttt gcatatcgag taaagaagac gattggcgct tatgcagcag   2040
ctatgggagg cgtcgatgtc attgtattta cagcaggtgt tggtgaaaat ggtcctgaga   2100
tacgagaatt tatacttgat ggattagagt ttttagggtt cagcttggat aaagaaaaaa   2160
ataaagtcag aggaaaagaa actattatat ctacgccgaa ttcaaaagtt agcgtgatgg   2220
ttgtgcctac taatgaagaa tacatgattg ctaaagatac tgaaaagatt gtaaagagta   2280
taaaa                                                              2285
```

<210> SEQ ID NO 77
<211> LENGTH: 38
<212> TYPE: DNA
<213> ORGANISM: Artificial
<220> FEATURE:
<223> OTHER INFORMATION: pMU433 construction; X01648

<400> SEQUENCE: 77

```
gtctttcgac tgagcctttc gttttatttg atgcctgg                            38
```

<210> SEQ ID NO 78
<211> LENGTH: 35
<212> TYPE: DNA
<213> ORGANISM: Artificial
<220> FEATURE:
<223> OTHER INFORMATION: pMU433 construction; X01649

<400> SEQUENCE: 78

```
aattgtagaa tacaatccac ttcacaatgg gcacg                               35
```

<210> SEQ ID NO 79
<211> LENGTH: 34
<212> TYPE: DNA
<213> ORGANISM: Artificial
<220> FEATURE:
<223> OTHER INFORMATION: pMU433 construction; X01654

<400> SEQUENCE: 79

```
aggggtcccg agcgcctacg aggaatttgt atcg                                34
```

<210> SEQ ID NO 80
<211> LENGTH: 35
<212> TYPE: DNA
<213> ORGANISM: Artificial
<220> FEATURE:
<223> OTHER INFORMATION: pMU433 construction; X01655

<400> SEQUENCE: 80

```
ccgtcagtag ctgaacagga gggacagctg ataga                               35
```

<210> SEQ ID NO 81
<211> LENGTH: 169
<212> TYPE: DNA
<213> ORGANISM: Artificial
<220> FEATURE:
<223> OTHER INFORMATION: adhE promoter

<400> SEQUENCE: 81

```
tcatataagt gtaaggtgat tgttaaatga ataacaaaaa ttatttacat cacacagtcc    60
```

```
aaaattcaat tcattcaagc gaatttcctg ttgaaatgct tgaaaaactg atacaatcac    120
ctgaaatgta gagatttatt gttaataaat taacacggag gtgtttatt                169

<210> SEQ ID NO 82
<211> LENGTH: 621
<212> TYPE: DNA
<213> ORGANISM: Artificial
<220> FEATURE:
<223> OTHER INFORMATION: cbp promoter

<400> SEQUENCE: 82
gagtcgtgac taagaacgtc aaagtaatta acaatacagc tattttctc atgcttttac      60 cccttcata aaattaatt ttatcgttat cataaaaaat tatagacgtt atattgcttg      120
ccgggatata gtgctgggca ttcgttggtg caaaatgttc ggagtaaggt ggatattgat    180
ttgcatgttg atctattgca ttgaaatgat tagttatccg taaatattaa ttaatcatat    240
cataaattaa ttatatcata attgttttga cgaatgaagg ttttggata aattatcaag    300 taaaggaacg ctaaaaattt tggcgtaaaa tatcaaaatg accacttgaa ttaatatggt    360
aaagtagata taatattttg gtaaacatgc cttcagcaag gttagattag ctgtttccgt    420
ataaattaac cgtatggtaa aacggcagtc agaaaaataa gtcataagat tccgttatga    480
aaatatactt cggtagttaa taataagaga tatgaggtaa gagatacaag ataagagata    540
taaggtacga atgtataaga tggtgctttt aggcacacta aataaaaaac aaataaacga    600
aaattttaag gaggacgaaa g                                              621

<210> SEQ ID NO 83
<211> LENGTH: 172
<212> TYPE: DNA
<213> ORGANISM: Artificial
<220> FEATURE:
<223> OTHER INFORMATION: pta promoter

<400> SEQUENCE: 83
gtattctaca attaaaccta atacgctcat aatatgcgcc tttctaaaaa attattaatt     60
gtacttatta ttttataaaa aatatgttaa aatgtaaaat gtgtatacaa tatatttctt    120
cttagtaaga ggaatgtata aaaataaata ttttaaagga agggacgatc tt            172

<210> SEQ ID NO 84
<211> LENGTH: 214
<212> TYPE: DNA
<213> ORGANISM: Artificial
<220> FEATURE:
<223> OTHER INFORMATION: hyd promoter

<400> SEQUENCE: 84
ataagcgaaa gggtaaattg ctttgattta gatgatttga atatggtagt cgactggatg     60
tgcaagtaaa gaaacatat caaattagtc gggattatca gaaaataaaa aaatttttat    120
ttttaactgt taaaaaaata attaacatat ggtataataa ttatgtccta ttttgcaatt    180
ttaaagatta attttttaa aaggagggta ttag                                 214

<210> SEQ ID NO 85
<211> LENGTH: 251
<212> TYPE: DNA
<213> ORGANISM: Artificial
<220> FEATURE:
<223> OTHER INFORMATION: hfs promoter

<400> SEQUENCE: 85
```

```
gctgtaattg tccttgatga cgataggaag ataaacattc caacaaaata tcttcccagc   60
aatattgctg aagaagatgc catagatatt tcattggatg tcaatgaaag aggacgaaaa  120
ttaaaaaagt tgattgaaga atcaagggag gaagactaat tttttaattt ttttaacgtt  180
aattgttaat aaattaacta ttgtttacac actttctttt atgtaataaa ataattgtat  240
acagtatacg g                                                      251
```

<210> SEQ ID NO 86
<211> LENGTH: 237
<212> TYPE: DNA
<213> ORGANISM: Artificial
<220> FEATURE:
<223> OTHER INFORMATION: ech promoter

<400> SEQUENCE: 86

```
tactgaatgg agaaactgca caaaaagctt gttgacggca gcagaggaga ttattcctct   60 gctattttg tgggaaaaac tgcaaaattc attgaaatat tgttaaataa taaacaaaat  120
taattaatat taaatacaat tgacttatca tttaattaga tttataatca aatgggtat   180 ttaaaaatgt atacaatata taatattcat taaatgaaat aaagaaggag tgaaaaa     237
```

<210> SEQ ID NO 87
<211> LENGTH: 1670
<212> TYPE: DNA
<213> ORGANISM: Acinetobacter sp.

<400> SEQUENCE: 87

```
cagaagatat ggttcggtta tcggttggga ttgaacatat tgatgatttg attgcagatc   60
tggaacaagc attggccaca gtttgagcgt aaatttttata aaaaacctct gcaatttcag  120 aggtttttt atatttgctt tattatcgta tgatgttcat aattgatcta gcaaataata  180
aaaattagag caattactct aaaaacattt gtaatttcag atacttaaca ctagatttt   240 taaccaaatc actttagatt aactttagtt ctggaaattt tatttcctt taaccgtctt   300 caatccaaat acaataatga cagcctttac agtttgatat caatcaggga aaaacgcgtg  360
aacaaaaaac ttgaagctct cttccgagag aatgtaaaag gtaaagtggc tttgatcact  420
ggtgcatcta gtggaatcgg tttgacgatt gcaaaagaa ttgctgcggc aggtgctcat  480
gtattattgg ttgcccgaac ccaagaaaca ctggaagaag tgaaagctgc aattgaacag  540 caaggggggac aggcctctat ttttccttgt gacctgactg acatgaatgc gattgaccag  600
ttatcacaac aaattatggc cagtgtcgat catgtcgatt cctgatcaa taatgcaggg   660 cgttcgattc gccgtgccgt acacgagtcg tttgatcgct tccatgattt tgaacgcacc  720
atgcagctga attactttgg tgcggtacgt ttagtgttaa atttactgcc acatatgatt  780
aagcgtaaaa atggccagat catcaatatc agctctattg gtgtattggc caatgcgacc  840
cgtttttctg cttatgtcgc gtctaaagct gcgctggatg ccttcagtcg ctgtctttca  900
gccgaggtac tcaagcataa aatctcaatt acctcgattt atatgccatt ggtgcgtacc  960
ccaatgatcg cacccaccaa aatttataaa tacgtgccca cgctttcccc agaagaagcc 1020
gcagatctca ttgtctacgc cattgtgaaa cgtccaacac gtattgcgac gcacttgggt 1080
cgtctggcgt caattaccta tgccatcgca ccagacatca ataatattct gatgtcgatt 1140
ggatttaacc tattcccaag ctcaacggct gcactgggtg aacaggaaaa attgaatctg 1200
ctacaacgtg cctatgcccg cttgttccca ggcgaacact ggtaaaattt ataaaagaag 1260
```

| cctctcatac cgagaggctt ttttatggtt acgaccatca gccagattta gaggaaattg | 1320 |
| actttttcctg tttttacatc ataaatcgca ccaacaatat caatttcttt gcgatccagc | 1380 |
| atatctttaa gtacagaact atgctgaata atgtattgaa tattatagtg aacattcata | 1440 |
| gcagtcacct gatcaataaa tgctttgctt aattcacgcg gttgcataat atcaaataca | 1500 |
| ctgccaaccg aatgcatgag tggcccaagc acgtattgga tgtgtggcat ttcctgaata | 1560 |
| tcggaaatct gcttatgttg caatcttaac tggcatgcgc tggtgaccgc accacagtcg | 1620 |
| gtatgtccca aaaccagaat cactttggaa cctttggctt gacaggcaaa | 1670 |

<210> SEQ ID NO 88
<211> LENGTH: 1188
<212> TYPE: DNA
<213> ORGANISM: Geobacillus thermodenitrificans

<400> SEQUENCE: 88

| ttacgccttg tgcggctcta cgatcgtccc ggcaaacgcg gcttcgtaaa tcgcacggat | 60 |
| gtcggcttcc aacagcggca acggactgcg ggcaagcaaa cgtttctgtt ggacagcatc | 120 |
| tttcgtcaag ctttctagcg cgcttttcggg gatgccaaat ccccccaatg ttttcggaat | 180 |
| gccgacatcg gcgacgaacc gttctagttc ctcgacgcac cgataagacg cttccacttc | 240 |
| ggacaaaaaa cttgagttgc cgccaagcgc gttgaaaata tcggccattc tcttcgtaca | 300 |
| gctttgacga atgtagccca tcacatacgg caacagcaca gcattcgatt caccatgagc | 360 |
| gatatgaaac tgaccaccga gcggataagc gagcgcatgc acaccggcta ccccggcgtt | 420 |
| gaaaaatgcc aagccggcca ataactgccg gttcgccata tcaatgcgcg cctgtttgtc | 480 |
| cgaaccgttg gccaccgctt tgcgcagtga gcgtgaaatc agccgaatag cggcaacggc | 540 |
| caatccatcc gatgttgggc tcgcattgac cgacacatac gcctcaactg catgggtgag | 600 |
| tgcatcaatt cccgttgcgg ccgttacccg cggtggaacg gaaacggtca gctgcggatc | 660 |
| aacgatcgcg acgtcggcca ataagtaatc gtgcgtcacg acatctttcg tcgtttccaa | 720 |
| agacaagaca gagatgtttg tcacttccga cccggtgccc gatgtcgtgg aatcaaaat | 780 |
| tttcggcaac ccttttttcct caagtgttcg cgttcctgtc aaatttaaat agtcagcgac | 840 |
| cgagccatca tgcaccgcca aaacagccgc cagtttcgcc aaatccagcg cgctgccacc | 900 |
| accaacaccg atgacaaggt caaactttcc gtcgcgggca aacgccactg ccttttcccc | 960 |
| tgtctcaagc ggcggctctg gcacaacatc cgtatacaca tgcacgctat acccttcttg | 1020 |
| acggagcggg gacgtcactt gatcgactag gccgatcttc acaagcatcg ggtcggtaat | 1080 |
| caccaaaata tgttttgctc ccaaccgctt cacttcagga actaactggt caagcgctcc | 1140 |
| ccagccgaca tggctgagcg gcggaaagac aatgcgggct acactcat | 1188 |

<210> SEQ ID NO 89
<211> LENGTH: 1164
<212> TYPE: DNA
<213> ORGANISM: Geobacillus thermodenitrificans

<400> SEQUENCE: 89

| ttataaagac gcacgcaaaa tggcgagcac atcatcacga tttaacgttt tgaaacggcc | 60 |
| aaactcacca aacgccatcg ctttatccgc catcagctcg agattttcct cgccgatgcc | 120 |
| ataatcagcc aatcgagacg gcgccccgag gctcgaccaa aacgcgcgca accgctcgat | 180 |
| gccctcaagc gccacgtcgc gctccgtttt gccgtcgga tcgacgtcaa agacgcgcac | 240 |
| cgccagttgg gcgaaacggc tgacatttc atcaagcaca tgtttcatcc aattcgggaa | 300 |

```
caaaatggcc aatccccgg cgtgcgggat atcgtataca gcagagaccg catgctcgat      360
atcatgcgtc gcccaatcac cgcgcacgcc catttgcaaa aagccgttta aggcgatcgt      420
gcccgagtac atgatcgtct cgcgcagctc gtagttctct aagtcgtcaa ccaattttgg      480
cgccgcctca atgaccgttt ttaacactgc ctcgcacatc cggtcttgca gcggcgtgtt      540
cggcgtatga tggaaatatt gctcaaacac atgggacatc atatcgacga tgccgtaaac      600
ggtatggtct ttcggcaccg tcatcgtgta cgtcggatcc aaaatcgaaa attgcgggaa      660
tgtcaccggg ctgccccagc cgtatttttc tttcgtctcc caattggtga tcaccgatcc      720
ggcgttcatt tccgagccgg tcgctgccag cgtcaggacc gtcccaaacg caacgcctc       780 agtgacagtc gctttttcg taatgaactc ccacggatcg ccatcaaact tcgcgccggc      840
tgcaatcgct ttcgtacagt cgatcacact gccgccgcca acggcaagca aaaattcaat      900
tccttcccgt ctgcaaatgt ctacccctt tttgacggtc gaaaggcgcg ggttcggttc       960
gacgcctggc agttcaacga cttcggcgcc aatgtccgtc aataggctca tgacttcatc     1020
atatagtccg tttcgtttaa tgctgccgcc cccatagaca agcagcactt ttttgccata     1080
tttcggcact tcttctttga gctgctcaat ttgtcctctc ccaaaaatga gtttggtcgg     1140
attgcgaaac gtaaaatttt gcat                                          1164
```

<210> SEQ ID NO 90
<211> LENGTH: 59
<212> TYPE: DNA
<213> ORGANISM: Artificial
<220> FEATURE:
<223> OTHER INFORMATION: X12312 primer

<400> SEQUENCE: 90

```
ttttgtctgt cttaattttt ggtatcatta taggatctat gtaacccagg aagcggcaa       59
```

<210> SEQ ID NO 91
<211> LENGTH: 48
<212> TYPE: DNA
<213> ORGANISM: Artificial
<220> FEATURE:
<223> OTHER INFORMATION: X12313 primer

<400> SEQUENCE: 91

```
acgagattac tgctgctgtg cagactttgc gttccattgc acggatca                   48
```

<210> SEQ ID NO 92
<211> LENGTH: 48
<212> TYPE: DNA
<213> ORGANISM: Artificial
<220> FEATURE:
<223> OTHER INFORMATION: X12314 primer

<400> SEQUENCE: 92

```
tgatccgtgc aatggaacgc aaagtctgca cagcagcagt aatctcgt                   48
```

<210> SEQ ID NO 93
<211> LENGTH: 59
<212> TYPE: DNA
<213> ORGANISM: Artificial
<220> FEATURE:
<223> OTHER INFORMATION: X12315 primer

<400> SEQUENCE: 93

```
gataacaatt tcacacagga aacagctatg accatacggc ctcttctccc ataccaaat       59
```

```
<210> SEQ ID NO 94
<211> LENGTH: 59
<212> TYPE: DNA
<213> ORGANISM: Artificial
<220> FEATURE:
<223> OTHER INFORMATION: X12316 primer

<400> SEQUENCE: 94
ttttgtctgt cttaattttt ggtatcatta taggaacgca gttgctggat atcagaggt      59

<210> SEQ ID NO 95
<211> LENGTH: 48
<212> TYPE: DNA
<213> ORGANISM: Artificial
<220> FEATURE:
<223> OTHER INFORMATION: X12317 primer

<400> SEQUENCE: 95
tactggtcag agcttctgct gtcaactcgt tcacctgttg caggtact                  48

<210> SEQ ID NO 96
<211> LENGTH: 48
<212> TYPE: DNA
<213> ORGANISM: Artificial
<220> FEATURE:
<223> OTHER INFORMATION: X12318 primer

<400> SEQUENCE: 96
agtacctgca acaggtgaac gagttgacag cagaagctct gaccagta                  48

<210> SEQ ID NO 97
<211> LENGTH: 59
<212> TYPE: DNA
<213> ORGANISM: Artificial
<220> FEATURE:
<223> OTHER INFORMATION: X12319 primer

<400> SEQUENCE: 97
gataacaatt tcacacagga aacagctatg accatttggg atgtgtgcat tacccaacg      59

<210> SEQ ID NO 98
<211> LENGTH: 59
<212> TYPE: DNA
<213> ORGANISM: Artificial
<220> FEATURE:
<223> OTHER INFORMATION: X12320 primer

<400> SEQUENCE: 98
ttttgtctgt cttaattttt ggtatcatta taggatactg gtaaacgtct gccgaccaa      59

<210> SEQ ID NO 99
<211> LENGTH: 48
<212> TYPE: DNA
<213> ORGANISM: Artificial
<220> FEATURE:
<223> OTHER INFORMATION: X12321 primer

<400> SEQUENCE: 99
acagcttagc gccttctaca gcttcgcgcg aacgttcaat gattcgat                  48

<210> SEQ ID NO 100
<211> LENGTH: 48
<212> TYPE: DNA
<213> ORGANISM: Artificial
<220> FEATURE:
<223> OTHER INFORMATION: X12322 primer
```

```
<400> SEQUENCE: 100
atcgaatcat tgaacgttcg cgcgaagctg tagaaggcgc taagctgt                  48

<210> SEQ ID NO 101
<211> LENGTH: 59
<212> TYPE: DNA
<213> ORGANISM: Artificial
<220> FEATURE:
<223> OTHER INFORMATION: X12323 primer

<400> SEQUENCE: 101
gataacaatt tcacacagga aacagctatg accatgctga cattggctat ccctgcatt     59

<210> SEQ ID NO 102
<211> LENGTH: 59
<212> TYPE: DNA
<213> ORGANISM: Artificial
<220> FEATURE:
<223> OTHER INFORMATION: X12324 primer

<400> SEQUENCE: 102
ttttgtctgt cttaattttt ggtatcatta taggagcggg tcaatttcca gataacgca     59

<210> SEQ ID NO 103
<211> LENGTH: 48
<212> TYPE: DNA
<213> ORGANISM: Artificial
<220> FEATURE:
<223> OTHER INFORMATION: X12325 primer

<400> SEQUENCE: 103
tcaggaacag gaatacgcga ccaagatcgg cttgaaaggt ttgcacga                  48

<210> SEQ ID NO 104
<211> LENGTH: 48
<212> TYPE: DNA
<213> ORGANISM: Artificial
<220> FEATURE:
<223> OTHER INFORMATION: X12326 primer

<400> SEQUENCE: 104
tcgtgcaaac ctttcaagcc gatcttggtc gcgtattcct gttcctga                  48

<210> SEQ ID NO 105
<211> LENGTH: 59
<212> TYPE: DNA
<213> ORGANISM: Artificial
<220> FEATURE:
<223> OTHER INFORMATION: X12327 primer

<400> SEQUENCE: 105
gataacaatt tcacacagga aacagctatg accatgcgaa acatgcactg ccttacctt     59

<210> SEQ ID NO 106
<211> LENGTH: 59
<212> TYPE: DNA
<213> ORGANISM: Artificial
<220> FEATURE:
<223> OTHER INFORMATION: X12328 primer

<400> SEQUENCE: 106
ttttgtctgt cttaattttt ggtatcatta taggatggac cgaatggacg atggagttt     59

<210> SEQ ID NO 107
```

```
<211> LENGTH: 48
<212> TYPE: DNA
<213> ORGANISM: Artificial
<220> FEATURE:
<223> OTHER INFORMATION: X12329 primer

<400> SEQUENCE: 107
agaatgcctt tcacgcgttc catgtcgttg ctttatagac acccgcct        48

<210> SEQ ID NO 108
<211> LENGTH: 48
<212> TYPE: DNA
<213> ORGANISM: Artificial
<220> FEATURE:
<223> OTHER INFORMATION: X12330 primer

<400> SEQUENCE: 108
aggcgggtgt ctataaagca acgacatgga acgcgtgaaa ggcattct        48

<210> SEQ ID NO 109
<211> LENGTH: 59
<212> TYPE: DNA
<213> ORGANISM: Artificial
<220> FEATURE:
<223> OTHER INFORMATION: X12331 primer

<400> SEQUENCE: 109
gataacaatt tcacacagga aacagctatg accatttccg ttaacgatac gcttcgggt     59

<210> SEQ ID NO 110
<211> LENGTH: 59
<212> TYPE: DNA
<213> ORGANISM: Artificial
<220> FEATURE:
<223> OTHER INFORMATION: X12332 primer

<400> SEQUENCE: 110
ttttgtctgt cttaattttt ggtatcatta taggaattca aacgttatgc ccgacgctg     59

<210> SEQ ID NO 111
<211> LENGTH: 48
<212> TYPE: DNA
<213> ORGANISM: Artificial
<220> FEATURE:
<223> OTHER INFORMATION: X12333 primer

<400> SEQUENCE: 111
agcgggtcgg tgtaaatatt ccgttccttg atggtttctc ccagcact        48

<210> SEQ ID NO 112
<211> LENGTH: 48
<212> TYPE: DNA
<213> ORGANISM: Artificial
<220> FEATURE:
<223> OTHER INFORMATION: X12334 primer

<400> SEQUENCE: 112
agtgctggga gaaaccatca aggaacggaa tatttacacc gacccgct        48

<210> SEQ ID NO 113
<211> LENGTH: 59
<212> TYPE: DNA
<213> ORGANISM: Artificial
<220> FEATURE:
<223> OTHER INFORMATION: X12335 primer

<400> SEQUENCE: 113
```

```
gataacaatt tcacacagga aacagctatg accatttgaa attagccagt ggcggcaag      59

<210> SEQ ID NO 114
<211> LENGTH: 59
<212> TYPE: DNA
<213> ORGANISM: Artificial
<220> FEATURE:
<223> OTHER INFORMATION: X12336 primer

<400> SEQUENCE: 114
ttttgtctgt cttaattttt ggtatcatta taggacagcc gctacattaa aggcaccaa      59

<210> SEQ ID NO 115
<211> LENGTH: 48
<212> TYPE: DNA
<213> ORGANISM: Artificial
<220> FEATURE:
<223> OTHER INFORMATION: X12337 primer

<400> SEQUENCE: 115
ccagcagcgg cagatcaaat tcaatggcgg ttcgacttta gcctgtat                   48

<210> SEQ ID NO 116
<211> LENGTH: 48
<212> TYPE: DNA
<213> ORGANISM: Artificial
<220> FEATURE:
<223> OTHER INFORMATION: X12338 primer

<400> SEQUENCE: 116
atacaggcta aagtcgaacc gccattgaat ttgatctgcc gctgctgg                   48

<210> SEQ ID NO 117
<211> LENGTH: 59
<212> TYPE: DNA
<213> ORGANISM: Artificial
<220> FEATURE:
<223> OTHER INFORMATION: X12339 primer

<400> SEQUENCE: 117
gataacaatt tcacacagga aacagctatg accatatggt ttagcggcta tttgcgtgc      59

<210> SEQ ID NO 118
<211> LENGTH: 59
<212> TYPE: DNA
<213> ORGANISM: Artificial
<220> FEATURE:
<223> OTHER INFORMATION: X12340 primer

<400> SEQUENCE: 118
ttttgtctgt cttaattttt ggtatcatta taggatggcg aatggcactc cctatgtta      59

<210> SEQ ID NO 119
<211> LENGTH: 48
<212> TYPE: DNA
<213> ORGANISM: Artificial
<220> FEATURE:
<223> OTHER INFORMATION: X12341 primer

<400> SEQUENCE: 119
tgacaatcac caggtcacca gacatccgaa tgaaataacg ccgcgatg                   48

<210> SEQ ID NO 120
<211> LENGTH: 48
<212> TYPE: DNA
```

<213> ORGANISM: Artificial
<220> FEATURE:
<223> OTHER INFORMATION: X12342 primer

<400> SEQUENCE: 120
catcgcggcg ttatttcatt cggatgtctg gtgacctggt gattgtca                    48

<210> SEQ ID NO 121
<211> LENGTH: 59
<212> TYPE: DNA
<213> ORGANISM: Artificial
<220> FEATURE:
<223> OTHER INFORMATION: X12343 primer

<400> SEQUENCE: 121
gataacaatt tcacacagga aacagctatg accattgttg atgagatgtt tgccaccgc        59

<210> SEQ ID NO 122
<211> LENGTH: 59
<212> TYPE: DNA
<213> ORGANISM: Artificial
<220> FEATURE:
<223> OTHER INFORMATION: X12344 primer

<400> SEQUENCE: 122
ttttgtctgt cttaatttttt ggtatcatta taggaatgct gtacgtaata cgcctgcga      59

<210> SEQ ID NO 123
<211> LENGTH: 48
<212> TYPE: DNA
<213> ORGANISM: Artificial
<220> FEATURE:
<223> OTHER INFORMATION: X12345 primer

<400> SEQUENCE: 123
tctttaacaa gctgcggcac aacgatggga gaaacttgct ttctgggc                    48

<210> SEQ ID NO 124
<211> LENGTH: 48
<212> TYPE: DNA
<213> ORGANISM: Artificial
<220> FEATURE:
<223> OTHER INFORMATION: X12346 primer

<400> SEQUENCE: 124
gcccagaaag caagtttctc ccatcgttgt gccgcagctt gttaaaga                    48

<210> SEQ ID NO 125
<211> LENGTH: 59
<212> TYPE: DNA
<213> ORGANISM: Artificial
<220> FEATURE:
<223> OTHER INFORMATION: X12347 primer

<400> SEQUENCE: 125
gataacaatt tcacacagga aacagctatg accatatctt tagcagcctg aacgtcgga        59

<210> SEQ ID NO 126
<211> LENGTH: 58
<212> TYPE: DNA
<213> ORGANISM: Artificial
<220> FEATURE:
<223> OTHER INFORMATION: X13802 primer

<400> SEQUENCE: 126
ttataggtta atgtcatgat aataatggtt tcttccgtca aagggcaaat caccgaaa         58

<210> SEQ ID NO 127
<211> LENGTH: 58
<212> TYPE: DNA
<213> ORGANISM: Artificial
<220> FEATURE:
<223> OTHER INFORMATION: X13803 primer

<400> SEQUENCE: 127
gggttccgcg cacatttccc cgaaaagtgc caccactcgg aataaccggt tcgggaaa    58

<210> SEQ ID NO 128
<211> LENGTH: 58
<212> TYPE: DNA
<213> ORGANISM: Artificial
<220> FEATURE:
<223> OTHER INFORMATION: X13804 primer

<400> SEQUENCE: 128
cgccttctat cgccttcttg acgagttctt ctgatacgac aaagcgttcg tcgcttca    58

<210> SEQ ID NO 129
<211> LENGTH: 58
<212> TYPE: DNA
<213> ORGANISM: Artificial
<220> FEATURE:
<223> OTHER INFORMATION: X13805 primer

<400> SEQUENCE: 129
actgttggga agggcgatcg gtgcgggcct cttcgaatga agcccagttc gcccattt    58

<210> SEQ ID NO 130
<211> LENGTH: 58
<212> TYPE: DNA
<213> ORGANISM: Artificial
<220> FEATURE:
<223> OTHER INFORMATION: X14576 primer

<400> SEQUENCE: 130
ttataggtta atgtcatgat aataatggtt tcttgcggat gcgaaggctt tgttgtat    58

<210> SEQ ID NO 131
<211> LENGTH: 48
<212> TYPE: DNA
<213> ORGANISM: Artificial
<220> FEATURE:
<223> OTHER INFORMATION: X14577 primer

<400> SEQUENCE: 131
tgggtagaaa aaataaacgg ctcagattcc tgtcacgaaa cggttgct    48

<210> SEQ ID NO 132
<211> LENGTH: 48
<212> TYPE: DNA
<213> ORGANISM: Artificial
<220> FEATURE:
<223> OTHER INFORMATION: X14578 primer

<400> SEQUENCE: 132
agcaaccgtt tcgtgacagg aatctgagcc gtttatttttt tctaccca    48

<210> SEQ ID NO 133
<211> LENGTH: 48
<212> TYPE: DNA
<213> ORGANISM: Artificial
<220> FEATURE:

<223> OTHER INFORMATION: X14579 primer

<400> SEQUENCE: 133
ggtcaaacca ttgttaacgc gcattttagt gctccgctaa tgtcaact            48

<210> SEQ ID NO 134
<211> LENGTH: 48
<212> TYPE: DNA
<213> ORGANISM: Artificial
<220> FEATURE:
<223> OTHER INFORMATION: X14580 primer

<400> SEQUENCE: 134
agttgacatt agcggagcac taaaatgcgc gttaacaatg gtttgacc            48

<210> SEQ ID NO 135
<211> LENGTH: 58
<212> TYPE: DNA
<213> ORGANISM: Artificial
<220> FEATURE:
<223> OTHER INFORMATION: X14581 primer

<400> SEQUENCE: 135
gggttccgcg cacatttccc cgaaaagtgc cacctagaag cgatacctttt cagcggca   58

<210> SEQ ID NO 136
<211> LENGTH: 58
<212> TYPE: DNA
<213> ORGANISM: Artificial
<220> FEATURE:
<223> OTHER INFORMATION: X14588 primer

<400> SEQUENCE: 136
ttataggtta atgtcatgat aataatggtt tctttctatg taacccagga agcggcaa   58

<210> SEQ ID NO 137
<211> LENGTH: 48
<212> TYPE: DNA
<213> ORGANISM: Artificial
<220> FEATURE:
<223> OTHER INFORMATION: X14589 primer

<400> SEQUENCE: 137
tgggtagaaa aaataaacgg ctcactttgc gttccattgc acggatca            48

<210> SEQ ID NO 138
<211> LENGTH: 48
<212> TYPE: DNA
<213> ORGANISM: Artificial
<220> FEATURE:
<223> OTHER INFORMATION: X14590 primer

<400> SEQUENCE: 138
tgatccgtgc aatggaacgc aaagtgagcc gtttattttt tctaccca            48

<210> SEQ ID NO 139
<211> LENGTH: 48
<212> TYPE: DNA
<213> ORGANISM: Artificial
<220> FEATURE:
<223> OTHER INFORMATION: X14591 primer

<400> SEQUENCE: 139
ataaagaact aagacaatct tcattttagt gctccgctaa tgtcaact            48

```
<210> SEQ ID NO 140
<211> LENGTH: 48
<212> TYPE: DNA
<213> ORGANISM: Artificial
<220> FEATURE:
<223> OTHER INFORMATION: X14592 primer

<400> SEQUENCE: 140
agttgacatt agcggagcac taaaatgaag attgtcttag ttctttat              48

<210> SEQ ID NO 141
<211> LENGTH: 48
<212> TYPE: DNA
<213> ORGANISM: Artificial
<220> FEATURE:
<223> OTHER INFORMATION: X14593 primer

<400> SEQUENCE: 141
acgagattac tgctgctgtg cagactattt cttatcgtgt ttaccgta              48

<210> SEQ ID NO 142
<211> LENGTH: 48
<212> TYPE: DNA
<213> ORGANISM: Artificial
<220> FEATURE:
<223> OTHER INFORMATION: X14594 primer

<400> SEQUENCE: 142
tacggtaaac acgataagaa atagtctgca cagcagcagt aatctcgt              48

<210> SEQ ID NO 143
<211> LENGTH: 58
<212> TYPE: DNA
<213> ORGANISM: Artificial
<220> FEATURE:
<223> OTHER INFORMATION: X14595 primer

<400> SEQUENCE: 143
gggttccgcg cacatttccc cgaaaagtgc caccacggcc tcttctccca taccaaat   58

<210> SEQ ID NO 144
<211> LENGTH: 58
<212> TYPE: DNA
<213> ORGANISM: Artificial
<220> FEATURE:
<223> OTHER INFORMATION: X15570 primer

<400> SEQUENCE: 144
ttataggtta atgtcatgat aataatggtt tctttgcgat ccgtagcaga caccataa   58

<210> SEQ ID NO 145
<211> LENGTH: 48
<212> TYPE: DNA
<213> ORGANISM: Artificial
<220> FEATURE:
<223> OTHER INFORMATION: X15571 primer

<400> SEQUENCE: 145
gaatactgcg ccagcgtttc acttcgttcc gcttgttctt cgatggtt              48

<210> SEQ ID NO 146
<211> LENGTH: 48
<212> TYPE: DNA
<213> ORGANISM: Artificial
<220> FEATURE:
<223> OTHER INFORMATION: X15572 primer
```

<400> SEQUENCE: 146
aaccatcgaa gaacaagcgg aacgaagtga aacgctggcg cagtattc					48

<210> SEQ ID NO 147
<211> LENGTH: 58
<212> TYPE: DNA
<213> ORGANISM: Artificial
<220> FEATURE:
<223> OTHER INFORMATION: X15573 primer

<400> SEQUENCE: 147
gggttccgcg cacatttccc cgaaaagtgc cacccatcaa tggcgatcac tttggcgt					58

<210> SEQ ID NO 148
<211> LENGTH: 58
<212> TYPE: DNA
<213> ORGANISM: Artificial
<220> FEATURE:
<223> OTHER INFORMATION: X15574 primer

<400> SEQUENCE: 148
ttataggtta atgtcatgat aataatggtt tcttaattga ccgccagttt gtcacacg					58

<210> SEQ ID NO 149
<211> LENGTH: 48
<212> TYPE: DNA
<213> ORGANISM: Artificial
<220> FEATURE:
<223> OTHER INFORMATION: X15575 primer

<400> SEQUENCE: 149
tcgccgtgca tttcaccatc aatcgagcgc ggcgacaact tcaataaa					48

<210> SEQ ID NO 150
<211> LENGTH: 48
<212> TYPE: DNA
<213> ORGANISM: Artificial
<220> FEATURE:
<223> OTHER INFORMATION: X15576 primer

<400> SEQUENCE: 150
tttattgaag ttgtcgccgc gctcgattga tggtgaaatg cacggcga					48

<210> SEQ ID NO 151
<211> LENGTH: 58
<212> TYPE: DNA
<213> ORGANISM: Artificial
<220> FEATURE:
<223> OTHER INFORMATION: X15577 primer

<400> SEQUENCE: 151
gggttccgcg cacatttccc cgaaaagtgc caccgccata atcaccaat gcaccgct					58

<210> SEQ ID NO 152
<211> LENGTH: 58
<212> TYPE: DNA
<213> ORGANISM: Artificial
<220> FEATURE:
<223> OTHER INFORMATION: X15578 primer

<400> SEQUENCE: 152
ttataggtta atgtcatgat aataatggtt tcttcagctg gcaggcagta aaccattt					58

<210> SEQ ID NO 153
<211> LENGTH: 48

```
<212> TYPE: DNA
<213> ORGANISM: Artificial
<220> FEATURE:
<223> OTHER INFORMATION: X15579 primer

<400> SEQUENCE: 153
tcaaatgcgc tcagggtacc gatattctga acctgaaggc agttgggt                48

<210> SEQ ID NO 154
<211> LENGTH: 48
<212> TYPE: DNA
<213> ORGANISM: Artificial
<220> FEATURE:
<223> OTHER INFORMATION: X15580 primer

<400> SEQUENCE: 154
acccaactgc cttcaggttc agaatatcgg taccctgagc gcatttga                 48

<210> SEQ ID NO 155
<211> LENGTH: 58
<212> TYPE: DNA
<213> ORGANISM: Artificial
<220> FEATURE:
<223> OTHER INFORMATION: X15581 primer

<400> SEQUENCE: 155
gggttccgcg cacatttccc cgaaaagtgc caccactggc ggtttaccta ccattcca      58

<210> SEQ ID NO 156
<211> LENGTH: 58
<212> TYPE: DNA
<213> ORGANISM: Artificial
<220> FEATURE:
<223> OTHER INFORMATION: X15586 primer

<400> SEQUENCE: 156
ttataggtta atgtcatgat aataatggtt tctttcgaca tcgctattgt caccacca      58

<210> SEQ ID NO 157
<211> LENGTH: 48
<212> TYPE: DNA
<213> ORGANISM: Artificial
<220> FEATURE:
<223> OTHER INFORMATION: X15587 primer

<400> SEQUENCE: 157
tttcggaagt ttgtgccaca acataatgct ctcctgataa tgttaaac                 48

<210> SEQ ID NO 158
<211> LENGTH: 48
<212> TYPE: DNA
<213> ORGANISM: Artificial
<220> FEATURE:
<223> OTHER INFORMATION: X15588 primer

<400> SEQUENCE: 158
gtttaacatt atcaggagag cattatgttg tggcacaaac ttccgaaa                 48

<210> SEQ ID NO 159
<211> LENGTH: 58
<212> TYPE: DNA
<213> ORGANISM: Artificial
<220> FEATURE:
<223> OTHER INFORMATION: X15589 primer

<400> SEQUENCE: 159
```

```
gggttccgcg cacatttccc cgaaaagtgc caccccaagt ggtcggcaat ttcagcat      58
```

```
<210> SEQ ID NO 160
<211> LENGTH: 24
<212> TYPE: DNA
<213> ORGANISM: Artificial
<220> FEATURE:
<223> OTHER INFORMATION: X12354 primer

<400> SEQUENCE: 160
ttgctgtatt tgacaccgcg ttcc                                            24
```

```
<210> SEQ ID NO 161
<211> LENGTH: 24
<212> TYPE: DNA
<213> ORGANISM: Artificial
<220> FEATURE:
<223> OTHER INFORMATION: X12355 primer

<400> SEQUENCE: 161
tttcacgaaa gaagcggtcg gact                                            24
```

```
<210> SEQ ID NO 162
<211> LENGTH: 24
<212> TYPE: DNA
<213> ORGANISM: Artificial
<220> FEATURE:
<223> OTHER INFORMATION: X12356 primer

<400> SEQUENCE: 162
ggcaagttta acgtcgcagt agca                                            24
```

```
<210> SEQ ID NO 163
<211> LENGTH: 24
<212> TYPE: DNA
<213> ORGANISM: Artificial
<220> FEATURE:
<223> OTHER INFORMATION: X12357 primer

<400> SEQUENCE: 163
tttatggcgg tgtcgtttgg cttg                                            24
```

```
<210> SEQ ID NO 164
<211> LENGTH: 24
<212> TYPE: DNA
<213> ORGANISM: Artificial
<220> FEATURE:
<223> OTHER INFORMATION: X12358 primer

<400> SEQUENCE: 164
atatctggaa gaagagggcg cgaa                                            24
```

```
<210> SEQ ID NO 165
<211> LENGTH: 24
<212> TYPE: DNA
<213> ORGANISM: Artificial
<220> FEATURE:
<223> OTHER INFORMATION: X12359 primer

<400> SEQUENCE: 165
gatgcattac gccgtgtggt tgaa                                            24
```

```
<210> SEQ ID NO 166
<211> LENGTH: 24
<212> TYPE: DNA
<213> ORGANISM: Artificial
```

```
<220> FEATURE:
<223> OTHER INFORMATION: X12360 primer

<400> SEQUENCE: 166
aacagcaatt gtagcagcgt gtcg                                          24

<210> SEQ ID NO 167
<211> LENGTH: 24
<212> TYPE: DNA
<213> ORGANISM: Artificial
<220> FEATURE:
<223> OTHER INFORMATION: X12361 primer

<400> SEQUENCE: 167
ttgtttgcca gcatcacgat accc                                          24

<210> SEQ ID NO 168
<211> LENGTH: 24
<212> TYPE: DNA
<213> ORGANISM: Artificial
<220> FEATURE:
<223> OTHER INFORMATION: X12362 primer

<400> SEQUENCE: 168
ctgggcgttt atgcttgccg tatt                                          24

<210> SEQ ID NO 169
<211> LENGTH: 24
<212> TYPE: DNA
<213> ORGANISM: Artificial
<220> FEATURE:
<223> OTHER INFORMATION: X12363 primer

<400> SEQUENCE: 169
agtcgtcagt tgtgagctcg actt                                          24

<210> SEQ ID NO 170
<211> LENGTH: 24
<212> TYPE: DNA
<213> ORGANISM: Artificial
<220> FEATURE:
<223> OTHER INFORMATION: X12364 project

<400> SEQUENCE: 170
tattcacggt ggcgacgctt ctaa                                          24

<210> SEQ ID NO 171
<211> LENGTH: 24
<212> TYPE: DNA
<213> ORGANISM: Artificial
<220> FEATURE:
<223> OTHER INFORMATION: X12365 primer

<400> SEQUENCE: 171
cgcctgttgc aggatttcaa tggt                                          24

<210> SEQ ID NO 172
<211> LENGTH: 24
<212> TYPE: DNA
<213> ORGANISM: Artificial
<220> FEATURE:
<223> OTHER INFORMATION: X12366 primer

<400> SEQUENCE: 172
aaagcgttag gtgcaaacct ggtg                                          24
```

-continued

```
<210> SEQ ID NO 173
<211> LENGTH: 24
<212> TYPE: DNA
<213> ORGANISM: Artificial
<220> FEATURE:
<223> OTHER INFORMATION: X12367 primer

<400> SEQUENCE: 173
attgccgtgc ctgctatcaa acag                                          24

<210> SEQ ID NO 174
<211> LENGTH: 24
<212> TYPE: DNA
<213> ORGANISM: Artificial
<220> FEATURE:
<223> OTHER INFORMATION: X12368

<400> SEQUENCE: 174
gctatggcac tggaagccaa tgtt                                          24

<210> SEQ ID NO 175
<211> LENGTH: 24
<212> TYPE: DNA
<213> ORGANISM: Artificial
<220> FEATURE:
<223> OTHER INFORMATION: X12369

<400> SEQUENCE: 175
agaacgtagt gaagctgaac gcga                                          24

<210> SEQ ID NO 176
<211> LENGTH: 24
<212> TYPE: DNA
<213> ORGANISM: Artificial
<220> FEATURE:
<223> OTHER INFORMATION: X12370

<400> SEQUENCE: 176
tgaagcttac cgcctcatcc tgaa                                          24

<210> SEQ ID NO 177
<211> LENGTH: 24
<212> TYPE: DNA
<213> ORGANISM: Artificial
<220> FEATURE:
<223> OTHER INFORMATION: X12371

<400> SEQUENCE: 177
agaatggtga accagagcaa ggga                                          24

<210> SEQ ID NO 178
<211> LENGTH: 24
<212> TYPE: DNA
<213> ORGANISM: Artificial
<220> FEATURE:
<223> OTHER INFORMATION: X12801

<400> SEQUENCE: 178
gattgattac gcggtgaaag cgca                                          24

<210> SEQ ID NO 179
<211> LENGTH: 24
<212> TYPE: DNA
<213> ORGANISM: Artificial
<220> FEATURE:
<223> OTHER INFORMATION: X12802
```

```
<400> SEQUENCE: 179
acacccggta tcaaaccctt ccat                                             24

<210> SEQ ID NO 180
<211> LENGTH: 24
<212> TYPE: DNA
<213> ORGANISM: Artificial
<220> FEATURE:
<223> OTHER INFORMATION: X14574

<400> SEQUENCE: 180
ccgtggcgat taacgtgaac aact                                             24

<210> SEQ ID NO 181
<211> LENGTH: 24
<212> TYPE: DNA
<213> ORGANISM: Artificial
<220> FEATURE:
<223> OTHER INFORMATION: X14575

<400> SEQUENCE: 181
agtcgatagt gccatcttca cgca                                             24

<210> SEQ ID NO 182
<211> LENGTH: 24
<212> TYPE: DNA
<213> ORGANISM: Artificial
<220> FEATURE:
<223> OTHER INFORMATION: X15590

<400> SEQUENCE: 182
actgttccct tcccgcgttt gata                                             24

<210> SEQ ID NO 183
<211> LENGTH: 24
<212> TYPE: DNA
<213> ORGANISM: Artificial
<220> FEATURE:
<223> OTHER INFORMATION: X15591

<400> SEQUENCE: 183
gcatcaactg ccgagttaaa cgca                                             24

<210> SEQ ID NO 184
<211> LENGTH: 24
<212> TYPE: DNA
<213> ORGANISM: Artificial
<220> FEATURE:
<223> OTHER INFORMATION: X15592

<400> SEQUENCE: 184
aggtcgaagc cagcttgatc agaa                                             24

<210> SEQ ID NO 185
<211> LENGTH: 24
<212> TYPE: DNA
<213> ORGANISM: Artificial
<220> FEATURE:
<223> OTHER INFORMATION: X15593

<400> SEQUENCE: 185
cgctgacggt ttgtgataac gctt                                             24

<210> SEQ ID NO 186
```

```
<211> LENGTH: 24
<212> TYPE: DNA
<213> ORGANISM: Artificial
<220> FEATURE:
<223> OTHER INFORMATION: X15594

<400> SEQUENCE: 186
taccttctgc tttgcccagt gagt                                              24

<210> SEQ ID NO 187
<211> LENGTH: 24
<212> TYPE: DNA
<213> ORGANISM: Artificial
<220> FEATURE:
<223> OTHER INFORMATION: X15595

<400> SEQUENCE: 187
tgaagcattg ctggtgggat ctga                                              24

<210> SEQ ID NO 188
<211> LENGTH: 24
<212> TYPE: DNA
<213> ORGANISM: Artificial
<220> FEATURE:
<223> OTHER INFORMATION: X15596

<400> SEQUENCE: 188
agtggcacca caccaatgct ttca                                              24

<210> SEQ ID NO 189
<211> LENGTH: 24
<212> TYPE: DNA
<213> ORGANISM: Artificial
<220> FEATURE:
<223> OTHER INFORMATION: X15597

<400> SEQUENCE: 189
tgaacgccag cttcacggat agat                                              24

<210> SEQ ID NO 190
<211> LENGTH: 58
<212> TYPE: DNA
<213> ORGANISM: Artificial
<220> FEATURE:
<223> OTHER INFORMATION: X16072

<400> SEQUENCE: 190
tctcagtagt agttgacatt agcggagcac taaaatgaag attgtcttag ttctttat        58

<210> SEQ ID NO 191
<211> LENGTH: 58
<212> TYPE: DNA
<213> ORGANISM: Artificial
<220> FEATURE:
<223> OTHER INFORMATION: X16073

<400> SEQUENCE: 191
cagtctttcg actgagcctt tcgttttacg gccgctattt cttatcgtgt ttaccgta        58

<210> SEQ ID NO 192
<211> LENGTH: 58
<212> TYPE: DNA
<213> ORGANISM: Artificial
<220> FEATURE:
<223> OTHER INFORMATION: X16082

<400> SEQUENCE: 192
```

```
tctcagtagt agttgacatt agcggagcac taaaatggca accgttctgt gtgttctg        58

<210> SEQ ID NO 193
<211> LENGTH: 58
<212> TYPE: DNA
<213> ORGANISM: Artificial
<220> FEATURE:
<223> OTHER INFORMATION: X16083

<400> SEQUENCE: 193
cagtctttcg actgagcctt tcgttttacg gccgttaggt cagacgatag ctctgtgc        58

<210> SEQ ID NO 194
<211> LENGTH: 59
<212> TYPE: DNA
<213> ORGANISM: Artificial
<220> FEATURE:
<223> OTHER INFORMATION: X16829

<400> SEQUENCE: 194
tgtgagcgga taacaatttc acacaggaaa cagctatgtc gaaggttatg aaaaccatg       59

<210> SEQ ID NO 195
<211> LENGTH: 48
<212> TYPE: DNA
<213> ORGANISM: Artificial
<220> FEATURE:
<223> OTHER INFORMATION: X16064

<400> SEQUENCE: 195
gctttcacac ctccaagatt tcgtctaatt ttgttcagca agcttctt                   48

<210> SEQ ID NO 196
<211> LENGTH: 48
<212> TYPE: DNA
<213> ORGANISM: Artificial
<220> FEATURE:
<223> OTHER INFORMATION: X16065

<400> SEQUENCE: 196
aagaagcttg ctgaacaaaa ttagacgaaa tcttggaggt gtgaaagc                   48

<210> SEQ ID NO 197
<211> LENGTH: 59
<212> TYPE: DNA
<213> ORGANISM: Artificial
<220> FEATURE:
<223> OTHER INFORMATION: X16830

<400> SEQUENCE: 197
cctcgaggtc gacggtatcg ataagcttga tatcttattc agccttaata gctcctgtt       59

<210> SEQ ID NO 198
<211> LENGTH: 59
<212> TYPE: DNA
<213> ORGANISM: Artificial
<220> FEATURE:
<223> OTHER INFORMATION: X16831

<400> SEQUENCE: 198
tgtgagcgga taacaatttc acacaggaaa cagctatggg aaagaaaatg atgacgact       59

<210> SEQ ID NO 199
<211> LENGTH: 50
<212> TYPE: DNA
```

<213> ORGANISM: Artificial
<220> FEATURE:
<223> OTHER INFORMATION: X16075

<400> SEQUENCE: 199
tacacctcct tatcttaata ggcgttctac ttcttcgtcc gcttgctgag            50

<210> SEQ ID NO 200
<211> LENGTH: 50
<212> TYPE: DNA
<213> ORGANISM: Artificial
<220> FEATURE:
<223> OTHER INFORMATION: X16076

<400> SEQUENCE: 200
ctcagcaagc ggacgaagaa gtagaacgcc tattaagata aggaggtgta            50

<210> SEQ ID NO 201
<211> LENGTH: 51
<212> TYPE: DNA
<213> ORGANISM: Artificial
<220> FEATURE:
<223> OTHER INFORMATION: X16077

<400> SEQUENCE: 201
cccgtctgat atttatggtt ctacgactta ctcttgaact ggagctccta c          51

<210> SEQ ID NO 202
<211> LENGTH: 51
<212> TYPE: DNA
<213> ORGANISM: Artificial
<220> FEATURE:
<223> OTHER INFORMATION: X16078

<400> SEQUENCE: 202
gtaggagctc cagttcaaga gtaagtcgta gaaccataaa tatcagacgg g          51

<210> SEQ ID NO 203
<211> LENGTH: 59
<212> TYPE: DNA
<213> ORGANISM: Artificial
<220> FEATURE:
<223> OTHER INFORMATION: X16832

<400> SEQUENCE: 203
ccctcgaggt cgacggtatc gataagcttg atatcctatt ggttctgccg gatatatat  59

<210> SEQ ID NO 204
<211> LENGTH: 59
<212> TYPE: DNA
<213> ORGANISM: Artificial
<220> FEATURE:
<223> OTHER INFORMATION: X16981

<400> SEQUENCE: 204
tgtgagcgga taacaatttc acacaggaaa cagctatgcc cgatatgaca aacgaatct  59

<210> SEQ ID NO 205
<211> LENGTH: 59
<212> TYPE: DNA
<213> ORGANISM: Artificial
<220> FEATURE:
<223> OTHER INFORMATION: X16982

<400> SEQUENCE: 205
ccctcgaggt cgacggtatc gataagcttg atatcttaaa caccagcttc gaagtcctt  59

<210> SEQ ID NO 206
<211> LENGTH: 5568
<212> TYPE: DNA
<213> ORGANISM: Artificial
<220> FEATURE:
<223> OTHER INFORMATION: Sequence of the PNO gene and flanking regions used to create FP66

<400> SEQUENCE: 206

| | | | | | |
|---|---|---|---|---|---|
| tgagccgttt | atttttttcta | cccatatcct | tgaagcggtg | ttataatgcc | gcgccctcga | 60 |
| tatggggatt | tttaacgacc | tgattttcgg | gtctcagtag | tagttgacat | tagcggagca | 120 |
| ctaaaatgaa | acagagcgtt | cgtccgatta | ttagcaatgt | tctgcgtaaa | gaagttgccc | 180 |
| tgtatagcac | cattattggt | caggataaag | gtaaagaacc | gacaggtcgt | acctatacca | 240 |
| gcggtccgaa | accggcaagc | catattgaag | ttccgcatca | tgttaccgtt | ccggcaaccg | 300 |
| atcgtacccc | gaatccggat | gcacagtttt | ttcagagcgt | tgatggtagc | caggcaacca | 360 |
| gccatgttgc | atatgccctg | agcgatacCg | catttatcta | tccgattacc | ccgagcagcg | 420 |
| ttatgggtga | actggcagat | gtttggatgg | cacagggtcg | taaaaatgcc | tttggtcagg | 480 |
| ttgttgatgt | tcgtgaaatg | cagagcgaag | ccggtgcagc | gggtgcactg | catggtgcac | 540 |
| tggcagccgg | tgcgattgca | accacccttta | ccgcaagcca | gggtctgctg | ctgatgattc | 600 |
| cgaatatgta | taaatcgca | ggcgaactga | tgccgagcgt | tattcatgtt | gcagcacgtg | 660 |
| agctggcagg | tcatgcactg | agcattttttg | gtggtcatgc | agatgttatg | gcagttcgtc | 720 |
| agaccggttg | ggcaatgctg | tgtagccata | ccgttcagca | gagccatgat | atggcactga | 780 |
| ttagccatgt | ggcaacccctg | aaaagcagca | ttccgtttgt | tcatttttttt | gatggttttc | 840 |
| gcaccagcca | cgaagtgaac | aaaatcaaaa | tgctgccgta | tgccgaactg | aaaaaactgg | 900 |
| ttccgcctgg | caccatggaa | cagcattggg | cacgtagcct | gaatccgatg | catccgacca | 960 |
| ttcgtggcac | caatcagagc | gcagatatct | atttcagaa | tatggaaagc | gccaaccagt | 1020 |
| attataccga | tctggcagaa | gttgttcaag | aaaccatgga | tgaagttgca | ccgtatattg | 1080 |
| gtcgtcatta | caaaatcttt | gagtatgttg | gtgcaccgga | tgcagaagag | gtgaccgttc | 1140 |
| tgatgggtag | cggtgccacc | accgttaatg | aagcagttga | tctgctggtt | aaacgcggta | 1200 |
| aaaaagttgg | tgcagttctg | gttcatctgt | atcgtccgtg | gtcaaccaaa | gcatttgaaa | 1260 |
| aagttctgcc | gaaaaccgtg | aaacgtattg | cagcactgga | tcgttgcaaa | gaagttaccg | 1320 |
| cactgggcga | accgctgtat | ctggatgtta | gcgccaccct | gaacctgttt | ccggaacgtc | 1380 |
| agaatgttaa | agttattggt | ggtcgttatg | gtctgggtag | caaagatttc | attccggaac | 1440 |
| atgcactggc | catttatgca | aatctggcaa | gcgaaaatcc | gattcagcgt | tttaccgttg | 1500 |
| gtattaccga | tgatgttacc | ggcaccagcg | tgccgtttgt | taatgaacgt | gttgataccc | 1560 |
| tgccggaagg | cacccgtcag | tgtgtttttt | ggggtattgg | tagtgatggc | accgttggtg | 1620 |
| caaatcgtag | cgcagttcgt | attattggtg | ataatagcga | tctgatggtg | caggcgtatt | 1680 |
| ttcagtttga | tgcatttaaa | agcggtggtg | ttaccagcag | ccatctgcgt | tttggtccta | 1740 |
| aaccgattac | cgcacagtat | ctggttacca | atgcagatta | tattgcctgc | cactttcaag | 1800 |
| agtatgtgaa | acgttttgat | atgctggatg | caattcgtga | aggtggcacc | tttgttctga | 1860 |
| atagccgttg | gaccaccgaa | gatatggaaa | agaaaattcc | ggcagatttt | cgtcgtaatg | 1920 |
| tggcacagaa | aaaagtgcgc | ttttataacg | ttgatgcccg | taaatttgc | gatagctttg | 1980 |
| gtctgggcaa | acgcattaac | atgctgatgc | aggcatgttt | ttcaaactg | agcggtgttc | 2040 |

```
tgccgctggc cgaagcacag cgtctgctga atgaaagcat tgttcatgag tatggcaaaa    2100
aaggtggtaa agtggtggaa atgaatcagg cagttgttaa tgcagtgttt gccggtgatc    2160
tgcctcaaga agttcaggtt ccggcagcat gggcaaatgc agttgatacc agcacccgca    2220
ccccgaccgg tattgaattt gttgataaaa tcatgcgtcc gctgatggat ttcaaaggtg    2280
atcagctgcc ggttagcgtt atgacaccgg gtggtacatt tccggttggc accacccagt    2340
atgcaaaacg tgcaattgcg gcatttattc cgcagtggat tccggcaaat tgtacccagt    2400
gtaattattg cagctatgtt tgtccgcatg caaccattcg tccgtttgtg ctgaccgatc    2460
aagaagtgca gctggcaccg aaagctttg ttacccgtaa agcaaaaggt gattatcagg    2520
gtatgaactt tcgtattcag gttgcaccgg aagattgtac cggttgtcag gtttgtgttg    2580
aaacctgtcc ggatgatgca ctggaaatga ccgatgcgtt taccgccaca ccggttcagc    2640
gtaccaattg ggaatttgca attaaagttc gaatcgtgg tacgatgacc gatcgctata    2700
gcctgaaagg tagccagttt cagcaaccgc tgctggaatt tagcggtgca tgtgaaggtt    2760
gtggtgaaac cccgtatgtt aaactgctga cccagctgtt tggtgaacgt accgttattg    2820
caaatgccac cggttgtagc agcatttggg gtggtacggc aggtctggct ccgtatacca    2880
ccaatgcaaa aggtcagggt ccggcatggg gtaatagcct gtttgaagat aatgccgaat    2940
ttggttttgg tattgcagtt gccaatgcac agaaacgtag ccgtgttcgt gattgtattc    3000
tgcaggccgt tgaaaaaaaa gtggccgatg aaggtctgac cacctgctg gcacagtggc    3060 tgcaggattg gaataccggt gataaaacac tgaaatatca ggaccagatt attgccggtc    3120
tggcacagca gcgtagtaaa gatcctctgc tggaacaaat ttatggcatg aaagatatgc    3180
tgccgaatat cagccagtgg attattggcg gtgatggttg ggccaatgat attggctttg    3240
gtggcctgga tcatgttctg cgcagcggtc agaatctgaa tgttctggtg ctggataccg    3300
aaatgtatag caatacaggt ggtcaggcaa gcaaaagcac ccatatggca agcgttgcaa    3360
aatttgccct gggtggtaaa cgtaccaaca aaaaaaacct gaccgaaatg gccatgagct    3420
atggtaatgt ttatgttgca accgttagcc atggtaatat ggcccagtgt gttaaagcct    3480
ttgttgaagc agaaagctat gatggtccga gcctgattgt tggttatgca ccgtgcattg    3540
aacatggtct gcgtgcaggt atggcacgta tggttcaaga atcagaagca gcaattgcaa    3600
ccggttattg gccactgtat cgttttgatc gcgtctggc aaccgaaggt aaaaacccgt    3660
ttcagctgga tagcaaacgt attaaaggta acctgcaaga atatctggat cgccagaatc    3720
gttatgtgaa cctgaaaaaa aacaatccga aaggtgccga tctgctgaaa gccagatgg    3780 cagataacat tacagcacgc tttaatcgtt atcgtcgtat gctggaaggt ccgaatacca    3840
aagcagcagc accgagcggt aatcatgtga ccattctgta tggtagtgaa accggtaata    3900
gcgaaggtct ggcaaaagaa ctggccaccg atttgaacg tcgtgaatat agcgttgcag    3960
ttcaggccct ggatgatatt gatgttgcg atctggaaaa tatgggctt gttgttattg    4020 ccgtttcaac ctgtggtcag ggccagtttc gcgtaatag tcagctgttt ggcgtgaac    4080 tgcagcgtga taaaccggaa ggttggctga aaatctgaa atacaccgtt tttggcctgg    4140
gtgatagcac ctattacttt tattgtcata ccgccaaaca aatcgatgca cgtctggcag    4200
cgctgggtgc acagcgtgtt gttccgattg gtttcggtga tgatggtgat gaagatatgt    4260
ttcataccgg cttcaataat tggattccga gcgtttggaa tgagctgaaa accaaaactc    4320
cggaagaagc actgtttacc ccgtcaattg ccgttcagct gaccccgaat gcaacaccgc    4380
aggattttca ttttgccaaa agcacaccgg tgctgagcat taccggtgca gaacgtatta    4440
```

```
caccggcaga tcatacccgc aattttgtta ccattcgttg gaaaaccgat ctgagctatc    4500
aggttggtga tagcctgggt gttttccag aaaatacccg tagcgttgtt gaagaattcc    4560
tgcagtatta tggcctgaac ccgaaagatg ttattaccat tgaaaataaa ggctcacgcg    4620
aactgccgca ttgtatggcc gttggtgacc tgtttaccaa agttctggat attctgggta    4680
aaccgaataa ccgcttctat aaaaccctga gctatttcgc cgttgataaa gcagaaaaag    4740
aacgcctgct gaaaattgca gaaatgggtc cggaatatag caacattctg tcagagatgt    4800
atcattatgc cgacatcttt catatgtttc cgagcgcacg tccgacactg cagtatctga    4860
ttgaaatgat cccgaacatt aaaccgcgtt attatagcat tagtagcgca ccgattcata    4920
ctccgggtga agtgcatagc ctggttctga ttgatacctg gattaccctg agcggtaaac    4980
atcgtacggg tctgacctgt accatgctgg aacatctgca ggcaggtcag gtggtggatg    5040
gttgtattca tccgaccgca atggaatttc cggatcatga aaaaccggtt gttatgtgtg    5100
caatgggttc aggtctggca ccttttgttg catttctgcg tgaacgtagc accctgcgta    5160
aacagggtaa aaaaacgggc aatatggcgc tgtattttgg caatcgttac gaaaaaaccg    5220
aatttctgat gaaagaggaa ctgaaaggcc atatcaatga tggtctgctg acactgcgtt    5280
gtgcatttag ccgtgatgat ccgaaaaaaa aagtctatgt gcaggatctg atcaaaatgg    5340
atgaaaaaat gatgtatgat tacctggtgg ttcagaaagg cagcatgtat tgttgtggta    5400
gccgtagttt tatcaaaccg gtgcaagaaa gcctgaaaca ttgttttatg aaagcgggtg    5460
gtctgaccgc agaacaggca gaaaatgaag ttattgatat gtttaccacg ggtcgctata    5520
acattgaagc gtggcggccg taaaacgaaa ggctcagtcg aaagactg                 5568
```

<210> SEQ ID NO 207
<211> LENGTH: 14039
<212> TYPE: DNA
<213> ORGANISM: Artificial
<220> FEATURE:
<223> OTHER INFORMATION: pMU2924

<400> SEQUENCE: 207

```
ctgacgggct tgtctgctcc cggcatccgc ttacagacaa gctgtgaccg tctccgggag     60
ctgcatgtgt cagaggtttt caccgtcatc accgaaacgc gcgagacgaa agggcctcgt    120
gatacgccta ttttttatagg ttaatgtcat gataataatg gtttcttacg cagttgctgg    180
atatcagagg ttaatgcgag agagagtttt ccctgccatt cctgccaggg agaaaaaatc    240
agtttatcga tattgatcca ggtgttaggc agcatggcct gccactgcgc gagtgttttt    300
ggagcggctg gcgattgctc cgtctgcggc aatttcgcca gacaagcaga atcaagttct    360
accgtgccga cgttcaataa ccagcggctg ggatgtgaaa ggctggcgtt ggtgatatgc    420
gcaagctgac aatctcccac cagataacgg gatcgggaa tgattaaacc tttacgcgta    480
atgcgtgggc tttcatctaa tgcaatacgt gtcccgagcg gtagccagat gcccgccagc    540
gtgggaaccc acagcccgag cgtcatcagc agcgtcaacg gcacaagaat aatcagtaat    600
aacagcgcga aacggcttt atatttaccc agcatgggta gttaatatcc tgatttagcg    660
aaaaattaag cattcaatac gggtattgtg gcatgtttaa ccgttcagtt gaaggttgcg    720
cctacactaa gcatagttgt tgatgaattt tcaatatcg ccatagcttt caattaaatt    780
tgaaattttg taaatatttt ttagtagctt aaatgtgatt caacatcact ggagaaagtc    840
ttatgaaact cgccgtttat agcacaaaac agtacgacaa gaagtacctg caacaggtga    900
```

```
acgagttgag ccgtttattt tttctaccca tatccttgaa gcggtgttat aatgccgcgc      960
cctcgatatg gggatttta acgacctgat tttcgggtct cagtagtagt tgacattagc     1020
ggagcactaa aatgtcaata gatgatagga ttgaagacct tcttagaaga agagagatgg     1080
ttttagaagg cggtggttta gataaagtag agaaacaaca ccaaaaggga aagcttaccg     1140
caagagagag gatatacaag cttttagatg aagatagctt tgtggaaata gatgcgtatg     1200
ttgagcacag gtgtattgac tttggcatgg aaaagcaaag gatacctggc gaaggcgtag     1260
tgacagggta tgggacgata gatggaaggc ttgtctacgt ttatgcacag gattttacgg     1320
ttttaggagg atcattaggc gagtatcatg caaagaaaat cacaaaaatc atggatatgg     1380
ctttaaagat gggagcaccg ctcattggat taaatgattc cggaggtgcc agaatacagg     1440
aaggcgtcga tgcttatcg ggatatggca acatattttt cagaaacacg ctggcatcag     1500
gcgtaatacc gcaaatatcg gtgataatgg ggcccagcgc tggaggtgca gtttattcgc     1560
ctgctcttac tgactttata ttcatggtag acaagacaag tcagatgttt ataactggac     1620
cgcaggtcat aaaagccgtc acaggtgaag atgtttcggc agaggagctt ggtggatcga     1680
ttactcacag cacgaaaagc ggtgtggcgc attttagggc tgaaaacgac gaagagtgtt     1740
tgaagatggt gaggaagcta ttaagttacc ttccatcaaa caatttggaa gatccgccac     1800
agttggcgac agatgacgac ataaacagat tttccgatag gcttattgag ataatcccag     1860
atagtcctaa taagccatac gatatgaaag aagtaatttc ggaaatagtg gatgaaggcg     1920
tgtatttga atcacaggca atgtatgcgc aaaacataat aacggcattt gcaaggctta     1980
atggaaggac ggtagggata atagcaaatc agcctaaagt tttggctgga tgtctcgaca     2040
tcaatgcgtc tgataaggca tcgaggttta aaggttttg cgatgcattt aacatcccgc     2100
ttctcaatat agtagatgtt ccaggatttt tgcctgaac gaatcaagag tacgtggaa      2160
taatacgcca tggggcaaag atgttgtacg cttactctga ggctacagtg ccaaaagtga     2220
ctctcattgt gaggaaagct tatggcggtc cttaccttgc catgtgcagc aaaagactta g    2280
gagctgattt tgttttggca tggcctactg ctgaaatagc ggtcatggga cctgatgggg      2340
cagcaaacat cgtgtttaaa aatgaaataa aatcgtctga tgatcctgtg gctgcaagaa      2400
atgaaaagat aaatgagtac agggagaatt tcgcaaatcc atacagggca gcagcgagag      2460
gatatgtaga tgatgtagtt ctgccgcaag agacgagacc tcgcctcatc tcggcgttcg      2520
atatgcttat gagcaaaagg gagtcaaggc ccagcaaaaa gcatggcaat tttcctgttt      2580
aaaatcgatt taaggggaag tgaaagaatg gaagagataa atgaagaaat agttgctgtc      2640
attgaagctg cgatttacgc ggcatttggt cagtacgaaa agaatttccg catcaaggta      2700
ataaagagag tggactcaaa tatgccggaa tggagaaaag ctggccttta caatcagatg      2760
agatagatga ggaggatgga aatgaaaaaa tttatagtaa ctgtcaatgg aaaaaaatac      2820
gatgtggaag tagaagaagt aaaagtcgac gtggcaagtg agaaaaaagc aaaagaagat      2880
actgctgcta aaaatgcgtc agatgcaagt gtaaaaagca aacaggttga agtaaaaaac      2940
gaagtcaaag acggtttctc aatcaatgca ccgatgccgg aactatatt ggatgtcaaa       3000
ataagccaag gccagactgt cagacgagcg gatgtgcttt taatactgga agccatgaag      3060
atggaaaatg aaatcacgtc accttacgat ggcacaataa tatccataaa tgtttcaaaa      3120
ggtgcctctg taaatacagg cgatgtgctt ttgtacttaa aatgagagta aaggaggagt      3180
tttaatgtct aagataaaaa taacggagac tgttttaaga gatgcacatc aatcgttgct      3240
ggcaaccaga atgacaaccg atgaaatgct tcctatagca gaaaaattag atgaagttgg      3300
```

```
tttttctcg ctggaagcat ggggcggtgc tacatttgat gcatgtatga gattttgaa    3360 tgaagaccca tgggaaagat taagactttt aagaaggcg attaagaaga cacctcttca    3420
aatgctttta agaggtcaaa atttactcgg atataaacac tatcccgatg atgtcgtaaa    3480
tgaatttata ataaaatctg ttgaaaatgg tatagatata ataagaattt ttgatgcgtt    3540
aaatgatgtg agaaatttag aagtgccaat aaaatctgca aaaagtgcag gtgctcatgt    3600
acaggcagct attgtatata cagttagtcc tgtacataat acagatcatt atttgaaagt    3660
ggcaaagtct cttcaagata tgggtgcgga ttccatatgc attaaggata tgtctggaat    3720
attatcaccc tatgttgcat acgatttgat taaatctctg aaaagagcac tttacacgcc    3780
aattcaactg catagccatt atacagcagg actggcttca atgacttatt taaaagccat    3840
agaagctggt gtagacgggg ttgatacagc tatttcttcg cttgccttag gaacatcaca    3900
accagctaca gaatcaatcg tggctgcatt gaaagataca gaatatgata cagggctaga    3960
tttaaaattg cttgctgaga tagctcagca ttttaatgta gtcaaacaga atcacaaaaa    4020
tgacagcgat atgtctttgc ttatgtctgt tgatgttaaa gcattagaaa gtcaaatacc    4080 aggggggaatt tatcaaatt tggtttcaca gctaaagcag cagaatgcat taaacaaata    4140
tcaagacgtc ttgaaagaag ttccaagggt acgcgaagat ttgggatatc ctcctcttgt    4200
tactccaatg agccagatgg ttggaaccca ggctgtttta atgttatta caggggagag    4260 atataaaatc gttcctaaag aaattaaaga ttatgtcaaa ggtttatatg ggatgccacc    4320
agctccaatt tcagattcta tacgaaagaa aataatcggc gatgaagaag taatttcaaa    4380
gaggccagca gatttactaa gtcctcaatt ggatgaattt aaaaatgaga taaggaatt    4440 tatagagcaa gatgaagatg ttttatcata tgcattattt cctcaagtag caagaagatt    4500
tttcgagtat aggcaagcca aaaaatacag aattgattca acattattaa atatcgaaga    4560
aagggttcat ccgatataac ggccgtaaaa cgaaaggctc agtcgaaaga ctgggccttt    4620
cgttttatct gttgtttgtc ggtgaacgct ctcctgagta ggacaaatcc gccgggagcg    4680
gatttgaacg ttgcgaagca acggcccgga gggtggcggg caggacgccc gccataaact    4740
gccaggcatc aaattaagca gaaggccatc ctgacggatg cctttttgc gtttctacaa    4800 actcttcctg tcgtcatatc tacaagccat ccccccacag atacggtaaa ctagcctcgt    4860
ttttgcatca ggaaagcagc tatgaaccac tcctccagcc aggacagaaa tgcctcgact    4920
tcgctgctgc ccaaggttgc cgggtgacgc acaccgtgga aacggatgaa ggcacgaacc    4980
cagtggacat aagcctgttc ggttcgtaag ctgtaatgca agtagcgtat gcgctcacgc    5040
aactggtcca gaaccttgac cgaacgcagc ggtggtaacg gcgcagtggc ggttttcatg    5100
gcttgttatg actgtttttt tggggtacag tctatgcctc gggcatccaa gcagcaagcg    5160
cgttacgccg tgggtcgatg tttgatgtta tggagcagca acgatgttac gcagcagggc    5220
agtcgcccta aaacaaagtt aaacatcatg agggaagcgg tgatcgccga agtatcgact    5280
caactatcag aggtagttgg cgtcatcgag cgccatctcg aaccgacgtt gctggccgta    5340
catttgtacg gctccgcagt ggatggcggc ctgaagccac acagtgatat tgatttgctg    5400
gttacggtga ccgtaaggct tgatgaaaca acgcggcgag ctttgatcaa cgaccttttg    5460
gaaacttcgg cttcccctgg agagagcgag attctccgcg ctgtagaagt caccattgtt    5520
gtgcacgacg acatcattcc gtggcgttat ccagctaagc gcgaactgca atttggagaa    5580
tggcagcgca atgacattct tgcaggtatc ttcgagccag ccacgatcga cattgatctg    5640
```

```
gctatcttgc tgacaaaagc aagagaacat agcgttgcct tggtaggtcc agcggcggag      5700
gaactctttg atccggttcc tgaacaggat ctatttgagg cgctaaatga aaccttaacg      5760
ctatggaact cgccgcccga ctgggctggc gatgagcgaa atgtagtgct tacgttgtcc      5820
cgcatttggt acagcgcagt aaccggcaaa atcgcgccga aggatgtcgc tgccgactgg      5880
gcaatggagc gcctgccggc ccagtatcag cccgtcatac ttgaagctag acaggcttat      5940
cttggacaag aagaagatcg cttggcctcg cgcgcagatc agttggaaga atttgtccac      6000
tacgtgaaag gcgagatcac caaggtagtc ggcaaataac cctcgagcca cccatgacca      6060
aaatccctta acgtgagtta cgcgtcgttc cactgtgaca gcagaagctc tgaccagtat      6120
ttctcagact acgctgcaaa acttaagcaa tctggaaaaa ggcgaaacct gcccgaacga      6180
actggtttaa tcttgccgct cccctgcatt ccaggggagc tgattcagat aatccccaat      6240
gacctttcat cctctattct aaaaatagtc ctgagtcaga aactgtaatt gagaaccaca      6300
atgaagaaag tagccgcgtt tgttgcgcta agcctgctga tggcgggatg tgtaagtaat      6360
gacaaaattg ctgttacgcc agaacagcta cagcatcatc gctttgtgct ggaaagcgta      6420
aacggtaagc ccgtgaccag cgataaaaat ccgccagaaa tcagctttgg tgaaaaaatg      6480
atgatttccg gcagcatgtg taaccgcttt agcggtgaag gcaaactgtc taatggtgaa      6540
ctgacagcca aagggctggc aatgacccgt atgatgtgcg ctaacccgca gcttaatgaa      6600
ctcgataaca ccattagcga aatgctgaaa gaaggtgcac aagtggatct gaccgcgaac      6660
cagttaacgc tggcgaccgc aaaacagaca ttaacttata agctggcgga tttaatgaat      6720
taatagctgc cacagctccc ggcggcaagt gactgttcgc tacagcgttt gccgttgggt      6780
aatgcacaca tcccaaggtg gcacttttcg gggaaatgtg cgcggaaccc ctatttgttt      6840 attttctaa atacattcaa atatgtatcc gctcatgaga caataaccct gataaatgct      6900
tcaataatat tgaaaaagga agagtatgag tattcaacat ttccgtgtcg cccttattcc      6960
cttttttgcg gcattttgcc ttcctgtttt tgctcaccca gaaacgctgg tgaaagtaaa      7020
agatgctgaa gatcagttgg gtgcacgagt gggttacatc gaactggatc tcaacagcgg      7080
taagatcctt gagagttttc gccccgaaga acgttttcca atgatgagca cttttaaagt      7140
tctgctatgt ggcgcggtat tatcccgtat tgacgccggg caagagcaac tcggtcgccg      7200
catacactat tctcagaatg acttggttga gtactcacca gtcacagaaa agcatcttac      7260
ggatggcatg acagtaagag aattatgcag tgctgccata accatgagtg ataacactgc      7320
ggccaactta cttctgacaa cgatcggagg accgaaggag ctaaccgctt ttttgcacaa      7380
catgggggat catgtaactc gccttgatcg ttgggaaccg gagctgaatg aagccatacc      7440
aaacgacgag cgtgacacca cgatgcctgt agcaatggca acaacgttgc gcaaactatt      7500
aactggcgaa ctacttactc tagcttcccg gcaacaatta atagactgga tggaggcgga      7560
taaagttgca ggaccacttc tgcgctcggc ccttccggct ggctggttta ttgctgataa      7620
atctggagcc ggtgagcgtg ggtctcgcgg tatcattgca gcactgggc cagatggtaa      7680 gccctcccgt atcgtagtta tctacacgac ggggagtcag gcaactatgg atgaacgaaa      7740
tagacagatc gctgagatag gtgcctcact gattaagcat tggtaagcga tgaaatgtga      7800
ggtgaatcag ggttttcacc cgattttgtg ctgatcagaa tttttttttct ttttcccct      7860 tgaaggggcg aagcctcatc cccatttctc tggtcaccag ccgggaaacc acgtaagctc      7920
cggcgtcacc cataacagat acggactttc tcaaggagag ttatcaatg aacatcaaaa      7980 agtttgcaaa acaagcaaca gtattaacct ttactaccgc actgctggca ggaggcgcaa      8040
```

```
ctcaagcgtt tgcgaaagaa acgaaccaaa agccatataa ggaaacatac ggcatttccc    8100
atattacacg ccatgatatg ctgcaaatcc ctgaacagca aaaaaatgaa aaatatcaag    8160
ttcctgagtt cgattcgtcc acaattaaaa atatctcttc tgcaaaaggc ctggacgttt    8220
gggacagctg gccattacaa aacgctgacg gcactgtcgc aaactatcac ggctaccaca    8280
tcgtctttgc attagccgga gatcctaaaa atgcggatga cacatcgatt tacatgttct    8340
atcaaaaagt cggcgaaact tctattgaca gctggaaaaa cgctggccgc gtctttaaag    8400
acagcgacaa attcgatgca aatgattcta tcctaaaaga ccaaacacaa gaatggtcag    8460
gttcagccac atttacatct gacggaaaaa tccgtttatt ctacactgat ttctccggta    8520
aacattacgg caaacaaaca ctgacaactg cacaagttaa cgtatcagca tcagacagct    8580 cttttgaacat caacggtgta gaggattata atcaatctt tgacggtgac ggaaaaacgt    8640
atcaaaatgt acagcagttc atcgatgaag gcaactacag ctcaggcgac aaccatacgc    8700
tgagagatcc tcactacgta gaagataaag gccacaaata cttagtattt gaagcaaaca    8760
ctggaactga agatggctac caaggcgaag aatctttatt taacaaagca tactatggca    8820
aaagcacatc attcttccgt caagaaagtc aaaaacttct gcaaagcgat aaaaaacgca    8880
cggctgagtt agcaaacggc gctctcggta tgattgagct aaacgatgat tacacactga    8940
aaaaagtgat gaaaccgctg attgcatcta acacagtaac agatgaaatt gaacgcgcga    9000
acgtctttaa aatgaacggc aaatggtatc tgttcactga ctcccgcgga tcaaaaatga    9060
cgattgacgg cattacgtct aacgatattt acatgcttgg ttatgtttct aattctttaa    9120
ctggcccata caagccgctg aacaaaactg gccttgtgtt aaaaatggat cttgatccta    9180
acgatgtaac ctttacttac tcacacttcg ctgtacctca agcgaaagga aacaatgtcg    9240
tgattacaag ctatatgaca aacagaggat tctacgcaga caaacaatca acgtttgcgc    9300
ctagcttcct gctgaacatc aaaggcaaga aaacatctgt tgtcaaagac agcatccttg    9360
aacaaggaca attaacagtt aacaaataac caggagctat ttaatggcaa cagttaacca    9420
gctggtacgc aaaccacgtg ctcgcaaagt tgcgaaaagc aacgtgcctg cgctggaagc    9480
atgcccgcaa aaacgtggcg tatgtactcg tgtatatact accactccta aaaaaccgaa    9540
ctccgcgctg cgtaaagtat gccgtgttcg tctgactaac ggtttcgaag tgacttccta    9600
catcggtggt gaaggtcaca acctgcagga gcactccgtg atcctgatcc gtggcggtcg    9660
tgttaaagac ctcccggggtg ttcgttacca caccgtacgt ggtgcgcttg actgctccgg    9720
cgttaaagac cgtaagcagg ctcgttccaa gtatggcgtg aagcgtccta aggcttaatg    9780
gttctccgtt aagtaaggcc aaatagagga tctgaagatc agcagttcaa cctgttgata    9840
gtacgtacta agctctcatg tttcacgtac taagctctca tgtttaacgt actaagctct    9900
catgtttaac gaactaaacc ctcatggcta acgtactaag ctctcatggc taacgtacta    9960
agctctcatg tttcacgtac taagctctca tgtttaacaa ataaaattaa tataaatcag   10020
caacttaaat agcctctaag gttttaagtt ttataagaaa aaaagaata tataaggctt   10080 ttaaagcttt taaggtttaa cggttgtgga caacaagcca gggatgtaac gcactgagaa   10140
gcccttagag cctctcaaag caattttcag tgacacagga acacttaacg ctgacagac   10200 gctgccgcaa gcactcaggg cgcaagggct gctaaaggaa gcggaacacg tagaaagcca   10260
gtccgcagaa acggtgctga ccccggatga atgtcagcta ctgggctatc tggacaaggg   10320
aaaacgcaag cgcaaagaga aagcaggtag cttgcagtgg gcttacatgg cgatagctag   10380
```

```
actgggcggt tttatggaca gcaagcgaac cggaattgcc agctggggcg ccctctggta    10440
aggttgggaa gccctgcaaa gtaaactgga tggctttctt gccgccaagg atctgatggc    10500
gcagggatc  aagatctgat caagagacag gatgaggatc gtttcgcatg attgaacaag    10560
atggattgca cgcaggttct ccggccgctt gggtggagag gctattcggc tatgactggg    10620
cacaacagac aatcggctgc tctgatgccg ccgtgttccg gctgtcagcg caggggcgcc    10680
cggttctttt tgtcaagacc gacctgtccg gtgccctgaa tgaactccaa gacgaggcag    10740
cgcggctatc gtggctggcc acgacgggcg ttccttgcgc agctgtgctc gacgttgtca    10800
ctgaagcggg aagggactgg ctgctattgg gcgaagtgcc ggggcaggat ctcctgtcat    10860
ctcaccttgc tcctgccgag aaagtatcca tcatggctga tgcaatgcgg cggctgcata    10920
cgcttgatcc ggctacctgc ccattcgacc accaagcgaa acatcgcatc gagcgagcac    10980
gtactcggat ggaagccggt cttgtcgatc aggatgatct ggacgaagag catcagggc     11040
tcgcgccagc cgaactgttc gccaggctca aggcgcggat gcccgacggc gaggatctcg    11100
tcgtgaccca tggcgatgcc tgcttgccga atatcatggt ggaaaatggc cgcttttctg    11160
gattcatcga ctgtggccgg ctgggtgtgg cggaccgcta tcaggacata gcgttggcta    11220
cccgtgatat tgctgaagag cttggcggcg aatgggctga ccgcttcctc gtgctttacg    11280
gtatcgccgc tcccgattcg cagcgcatcg ccttctatcg ccttcttgac gagttcttct    11340
gaattccgga tccgaagagg cccgcaccga tcgcccttcc caacagttgc gcagcctgaa    11400
tggcgaatgg cgcctgatgc ggtattttct ccttacgcat ctgtgcggta tttcacaccg    11460
catagggtaa taactgatat aattaaattg aagctctaat ttgtgagttt agtatacatg    11520
catttactta taatacagtt ttttagtttt gctggccgca tcttctcaaa tatgcttccc    11580
agcctgcttt tctgtaacgt tcaccctcta ccttagcatc ccttcccttt gcaaatagtc    11640
ctcttccaac aataataatg tcagatcctg tagagaccac atcatccacg gttctatact    11700
gttgacccaa tgcgtctccc ttgtcatcta aacccacacc gggtgtcata atcaaccaat    11760
cgtaaccttc atctcttcca cccatgtctc tttgagcaat aaagccgata acaaaatctt    11820
tgtcgctctt cgcaatgtca acagtaccct tagtatattc tccagtagat agggagccct    11880
tgcatgacaa ttctgctaac atcaaaaggc ctctaggttc ctttgttact tcttctgccg    11940
cctgcttcaa accgctaaca ataccctggg ccaccacacc gtgtgcattc gtaatgtctg    12000
cccattctgc tattctgtat acacccgcag agtactgcaa tttgactgta ttaccaatgt    12060
cagcaaattt tctgtcttcg aagagtaaaa aattgtactt ggcggataat gcctttagcg    12120
gcttaactgt gccctccatg gaaaaatcag tcaagatatc cacatgtgtt tttagtaaac    12180
aaatttttggg acctaatgct tcaactaact ccagtaattc cttggtggta cgaacatcca    12240
atgaagcaca caagtttgtt tgcttttcgt gcatgatatt aaatagcttg gcagcaacag    12300
gactaggatg agtagcagca cgttccttat atgtagcttt cgacatgatt tatcttcgtt    12360
tcggtttttg ttctgtgcag ttgggttaag aatactgggc aatttcatgt tcttcaaca     12420
ctacatatgc gtatatatac caatctaagt ctgtgctcct tccttcgttc ttccttctgt    12480
tcggagatta ccgaatcaaa aaatttcaa agaaaccgaa atcaaaaaaa agaataaaaa      12540
aaaaatgatg aattgaaaag ctcttgttac ccatcattga attttgaaca tccgaacctg    12600
ggagttttcc ctgaaacaga tagtatattt gaacctgtat aataatatat agtctagcgc    12660
tttacggaag acaatgtatg tatttcggtt cctggagaaa ctattgcatc tattgcatag    12720
gtaatcttgc acgtcgcatc cccggttcat tttctgcgtt tccatcttgc acttcaatag    12780
```

```
catatctttg ttaacgaagc atctgtgctt cattttgtag aacaaaaatg caacgcgaga    12840
gcgctaattt ttcaaacaaa gaatctgagc tgcattttta cagaacagaa atgcaacgcg    12900
aaagcgctat tttaccaacg aagaatctgt gcttcatttt tgtaaaacaa aaatgcaacg    12960
cgagagcgct aattttttcaa acaaagaatc tgagctgcat ttttacagaa cagaaatgca    13020
```
*Note: line 13020 — best reading.*
```
acgcgagagc gctattttac caacaaagaa tctatacttc ttttttgttc tacaaaaatg    13080
catcccgaga gcgctatttt tctaacaaag catcttagat tactttttt ctcctttgtg     13140 cgctctataa tgcagtctct tgataacttt ttgcactgta ggtccgttaa ggttagaaga    13200
aggctacttt ggtgtctatt ttctcttcca taaaaaagc ctgactccac ttcccgcgtt     13260
tactgattac tagcgaagct gcgggtgcat ttttcaaga taaggcatc cccgattata      13320 ttctataccg atgtggattg cgcatacttt gtgaacagaa agtgatagcg ttgatgattc    13380
ttcattggtc agaaaattat gaacggtttc ttctattttg tctctatata ctacgtatag    13440
gaaatgttta cattttcgta ttgttttcga ttcactctat gaatagttct tactacaatt    13500
tttttgtcta aagagtaata ctagagataa acataaaaaa tgtagaggtc gagtttagat    13560
gcaagttcaa ggagcgaaag gtggatgggt aggttatata gggatatagc acagagatat    13620
atagcaaaga gatacttttg agcaatgttt gtggaagcgg tattcgcaat attttagtag    13680
ctcgttacag tccggtgcgt ttttggtttt ttgaaagtgc gtcttcagag cgcttttggt    13740
tttcaaaagc gctctgaagt tcctatactt tctagctaga aataggaac ttcggaatag     13800 gaacttcaaa gcgtttccga aaacgagcgc ttccgaaaat gcaacgcgag ctgcgcacat    13860
acagctcact gttcacgtcg cacctatatc tgcgtgttgc ctgtatatat atatacatga    13920
gaagaacggc atagtgcgtg tttatgctta aatgcgttat ggtgcactct cagtacaatc    13980
tgctctgatg ccgcatagtt aagccagccc cgacacccgc caacacccgc tgacgcgcc    14039
```

<210> SEQ ID NO 208
<211> LENGTH: 14251
<212> TYPE: DNA
<213> ORGANISM: Artificial
<220> FEATURE:
<223> OTHER INFORMATION: pMU2969

<400> SEQUENCE: 208

```
agccccgaca cccgccaaca cccgctgacg cgccctgacg ggcttgtctg ctcccggcat      60
ccgcttacag acaagctgtg accgtctccg ggagctgcat gtgtcagagg ttttcaccgt     120
catcaccgaa acgcgcgaga cgaaagggcc tcgtgatacg cctatttta taggttaatg      180 tcatgataat aatggtttct tacgcagttg ctggatatca gaggttaatg cgagagagag     240 ttttcccctgc cattcctgcc agggagaaaa aatcagttta tcgatattga tccaggtgtt    300
aggcagcatg gcctgccact gcgcgagtgt ttttggagcg gctggcgatt gctccgtctg    360
cggcaatttc gccagacaag cagaatcaag ttctaccgtg ccgacgttca ataaccagcg    420
gctgggatgt gaaaggctgg cgttggtgat atgcgcaagc tgacaatctc ccaccagata    480
acggagatcg ggaatgatta aacctttacg cgtaatgcgt gggctttcat ctaatgcaat    540
acgtgtcccg agcggtagcc agatgcccgc cagcgtggga acccacagcc cgagcgtcat    600
cagcagcgtc aacggcacaa gaataatcag taataacagc gcgagaacgg ctttatattt    660
acccagcatg ggtagttaat atcctgattt agcgaaaaat taagcattca atacgggtat    720
tgtggcatgt ttaaccgttc agttgaaggt tgcgcctaca ctaagcatag ttgttgatga    780
```

```
attttttcaat atcgccatag cttttcaatta aatttgaaat tttgtaaaat attttttagta    840
gcttaaatgt gattcaacat cactggagaa agtcttatga aactcgccgt ttatagcaca       900
aaacagtacg acaagaagta cctgcaacag gtgaacgagt tgagccgttt atttttttcta     960
cccatatcct tgaagcggtg ttataatgcc gcgccctcga tatggggatt tttaacgacc      1020
tgattttcgg gtctcagtag tagttgacat tagcggagca ctaaaatgag tccgcgagaa      1080
attgaggttt ccgagccgcg cgaggttggt atcaccgagc tcgtgctgcg cgatgcccat      1140
cagagcctga tggccacacg aatggcaatg aaagacatgg tcggcgcctg tgcagacatt      1200
gatgctgccg ggtactggtc agtggagtgt tggggtggtg ccacgtatga ctcgtgtatc      1260
cgcttcctca acgaggatcc ttgggagcgt ctgcgcacgt tccgcaagct gatgcccaac      1320
agccgtctcc agatgctgct gcgtggccag aacctgctgg gttaccgcca ctacaacgac      1380
gaggtcgtcg atcgcttcgt cgacaagtcc gctgagaacg gcatggacgt gttccgtgtc      1440
ttcgacgcca tgaatgatcc ccgcaacatg gcgcacgcca tggctgccgt caagaaggcc      1500
ggcaagcacg cgcagggcac catttgctac acgatcagcc cggtccacac cgttgagggc      1560
tatgtcaagc ttgctggtca gctgctcgac atgggtgctg attccatcgc cctgaaggac      1620
atggccgccc tgctcaagcc gcagccggcc tacgacatca tcaaggccat caaggacacc      1680
tacggccaga agacgcagat caacctgcac tgccactcca ccacgggtgt caccgaggtc      1740
tccctcatga aggccatcga ggccggcgtc gacgtcgtcg acaccgccat ctcgtccatg      1800
tcgctcggcc cgggccacaa ccccaccgag tcggttgccg agatgctcga gggcaccggg      1860
tacaccacca accttgacta cgatcgcctg cacaagatcc gcgatcactt caaggccatc      1920
cgcccgaagt acaagaagtt cgagtcgaag acgcttgtcg cacctcgat cttcaagtcg       1980
cagatccccg gcggcatgct ctccaacatg gagtcgcagc tgcgcgccca gggcgccgag      2040
gacaagatgg acgaggtcat ggcagaggtg ccgcgcgtcc gcaaggccgc cggcttcccg      2100
cccctggtca ccccgtccag ccagatcgtc ggcacgcagg ccgtgttcaa cgtgatgatg      2160
ggcgagtaca agaggatgac cggcgagttc gccgacatca tgctcggcta ctacggcgcc      2220
agcccggccg atcgcgatcc gaaggtggtc aagttggccg aggagcagtc cggcaagaag      2280
ccgatcaccc agcgcccggc cgatctgctg cccccccgagt gggaggagca gtccaaggag      2340
gccgcggccc tcaagggctt caacggcacc gacgaggacg tgctcaccta tgcactgttc      2400
ccgcaggtcg ctccggtctt cttcgagcat cgcgccgagg gcccgcacag cgtggctctc      2460
accgatgccc agctgaaggc cgaggccgag ggcgacgaga agtcgctcgc cgtggccggt      2520
cccgtcacct acaacgtgaa cgtgggcgga accgtccgcg aagtcaccgt tcagcaggcg      2580
tgaggatgat tgccaatcat ggctgaaaac aacaatttga agctcgccag caccatggaa      2640
ggtcgcgtgg agcagctcgc agagcagcgc caggtgatcg aagccggtgg cggcgaacgt      2700
cgcgtcgaga agcaacattc ccagggtaag cagaccgctc gtgagcgcct gaacaacctg      2760
ctcgatcccc attcgttcga cgaggtcggc gctttccgca agcaccgcac cacgttgttc      2820
ggcatggaca aggccgtcgt cccggcagat ggcgtggtca ccggccgtgg caccatcctt      2880
ggtcgtcccg tgcacgccgc gtcccaggac ttcacggtca tgggtggttc ggctggcgag      2940
acgcagtcca cgaaggtcgt cgagacgatg gaacaggcgc tgctcaccgg cacgcccttc      3000
ctgttcttct acgattcggg cggcgcccgg atccaggagg gcatcgactc gctgagcggt      3060
tacggcaaga tgttcttcgc caacgtgaag ctgtcgggcg tcgtgccgca gatcgccatc      3120
attgccggcc cctgtgccgg tggcgcctcg tattcgccgg cactgactga cttcatcatc      3180
```

```
atgaccaaga aggcccatat gttcatcacg ggcccccagg tcatcaagtc ggtcaccggc    3240
gaggatgtca ccgctgacga actcggtggc gctgaggccc atatggccat ctcgggcaat    3300
atccacttcg tggccgagga cgacgacgcc gcggagctca ttgccaagaa gctgctgagc    3360
ttccttccgc agaacaacac tgaggaagca tccttcgtca acccgaacaa tgacgtcagc    3420
cccaataccg agctgcgcga catcgttccg attgacggca agaagggcta tgacgtgcgc    3480
gatgtcattg ccaagatcgt cgactggggt gactacctcg aggtcaaggc cggctatgcc    3540
accaacctcg tgaccgcctt cgcccgggtc aatggtcgtt cggtgggcat cgtggccaat    3600
cagccgtcgg tgatgtcggg ttgcctcgac atcaacgcct tgacaaggc cgccgaattc     3660
gtgaatttct gcgattcgtt caacatcccg ctggtgcagc tggtcgacgt gccgggcttc    3720
ctgcccggcg tgcagcagga gtacggcggc atcattcgcc atggcgcgaa gatgctgtac    3780
gcctactccg aggccaccgt gccgaagatc accgtggtgc tccgcaaggc ctacggcggc    3840
tcctacctgg ccatgtgcaa ccgtgacctt ggtgccgacg ccgtgtacgc ctggcccagc    3900
gccgagattg cggtgatggg cgccgagggt gcggcaaatg tgatcttccg caaggagatc    3960
aaggctgccg acgatcccga cgccatgcgc gccgagaaga tcgaggagta ccagaacgcg    4020
ttcaacacgc cgtacgtggc cgccgcccgc ggtcaggtcg acgacgtgat tgacccggct    4080
gatacccgtc gaaagattgc ttccgccctg gagatgtacg ccaccaagcg tcagacccgc    4140
ccggcgaaga agcatggaaa cttcccctgc tgagcgagga gagaaattat ggctgatgag    4200
gaagagaagg acctgatgat cgccacgctc aacaagcgcg tcgcgtcatt ggagtctgag    4260
ttgggttcac tccagagcga tacccagggt gtcaccgagg acgtactgac ggccatttcg    4320
gccgccgttg cggcctatct cggcaacgat ggatcggctg aggtcgtcca tttcgccccg    4380
agcccgaact gggtccgcga gggtcgtcgg gctctgcaga accattccat tcgttgatcc    4440
gggagtaact cacatgaaac tgaaggtaac agtcaacggc actgcgtatg acgttgacgt    4500
tgacgtcgac aagtcacacg aaaacccgat gggcaccatc ctgttcggcg gcggcaccgg    4560
cggcgcgccg gcaccgcgcg cagcaggtgg cgcaggcgcc ggtaaggccg agagggcga    4620
gattcccgct ccgctggccg gcaccgtctc caagatcctc gtgaaggagg gtgacacggt    4680
caaggctggt cagaccgtgc tcgttctcga ggccatgaag atggagaccg agatcaacgc    4740
tcccaccgac ggcaaggtcg agaaggtcct tgtcaaggag cgtgacgccg tgcagggcgg    4800
tcagggtctc atcaagatcg gctgacggcc gtaaaacgaa aggctcagtc gaaagactgg    4860
gcctttcgtt ttatctgttg tttgtcggtg aacgctctcc tgagtaggac aaatccgccg    4920
ggagcggatt tgaacgttgc gaagcaacgg cccggagggt ggcgggcagg acgcccgcca    4980
taaactgcca ggcatcaaat taagcagaag gccatcctga cggatggcct ttttgcgttt    5040
ctacaaactc ttcctgtcgt catatctaca agccatcccc ccacagatac ggtaaactag    5100
cctcgttttt gcatcaggaa agcagctatg aaccactcct ccagccagga cagaaatgcc    5160
tcgacttcgc tgctgcccaa ggttgccggg tgacgcacac cgtggaaacg gatgaaggca    5220
cgaacccagt ggacataagc ctgttcggtt cgtaagctgt aatgcaagta gcgtatgcgc    5280
tcacgcaact ggtccagaac cttgaccgaa cgcagcggtg gtaacggcgc agtggcggtt    5340
ttcatggctt gttatgactg ttttttggg gtacagtcta tgcctcgggc atccaagcag    5400
caagcgcgtt acgccgtggg tcgatgtttg atgttatgga gcagcaacga tgttacgcag    5460
cagggcagtc gccctaaaac aaagttaaac atcatgaggg aagcggtgat cgccgaagta    5520
```

```
tcgactcaac tatcagaggt agttggcgtc atcgagcgcc atctcgaacc gacgttgctg    5580
gccgtacatt tgtacggctc cgcagtggat ggcggcctga agccacacag tgatattgat    5640
ttgctggtta cggtgaccgt aaggcttgat gaaacaacgc ggcgagcttt gatcaacgac    5700
cttttggaaa cttcggcttc ccctggagag agcgagattc tccgcgctgt agaagtcacc    5760
attgttgtgc acgacgacat cattccgtgg cgttatccag ctaagcgcga actgcaattt    5820
ggagaatggc agcgcaatga cattcttgca ggtatcttcg agccagccac gatcgacatt    5880
gatctggcta tcttgctgac aaaagcaaga gaacatagcg ttgccttggt aggtccagcg    5940
gcggaggaac tctttgatcc ggttcctgaa caggatctat ttgaggcgct aaatgaaacc    6000
ttaacgctat ggaactcgcc gcccgactgg gctggcgatg agcgaaatgt agtgcttacg    6060
ttgtcccgca tttggtacag cgcagtaacc ggcaaaatcg cgccgaagga tgtcgctgcc    6120
gactgggcaa tggagcgcct gccggcccag tatcagcccg tcatacttga agctagacag    6180
gcttatcttg acaagaaga agatcgcttg gcctcgcgcg cagatcagtt ggaagaattt    6240
gtccactacg tgaaaggcga gatcaccaag gtagtcggca aataaccctc gagccaccca    6300
tgaccaaaat cccttaacgt gagttacgcg tcgttccact gtgacagcag aagtctgac    6360
cagtatttct cagactacgc tgcaaaactt aagcaatctg gaaaaggcg aaacctgccc    6420
gaacgaactg gtttaatctt gccgctcccc tgcattccag gggagctgat tcagataatc    6480
cccaatgacc tttcatcctc tattcttaaa atagtcctga gtcagaaact gtaattgaga    6540
accacaatga agaaagtagc gcgtttgtt gcgctaagcc tgctgatggc gggatgtgta    6600
agtaatgaca aaattgctgt tacgccagaa cagctacagc atcatcgctt tgtgctggaa    6660
agcgtaaacg gtaagcccgt gaccagcgat aaaaatccgc cagaaatcag ctttggtgaa    6720
aaaatgatga tttccggcag catgtgtaac cgctttagcg gtgaaggcaa actgtctaat    6780
ggtgaactga cagccaaagg gctggcaatg acccgtatga tgtgcgctaa cccgcagctt    6840
aatgaactcg ataacaccat tagcgaaatg ctgaaagaag gtgcacaagt ggatctgacc    6900
gcgaaccagt taacgctggc gaccgcaaaa cagacattaa cttataagct ggcggattta    6960
atgaattaat agctgccaca gctcccggcg gcaagtgact gttcgctaca gcgtttgccg    7020
ttgggtaatg cacacatccc aaggtggcac ttttcgggga aatgtgcgcg gaacccctat    7080
ttgttttattt ttctaaatac attcaaatat gtatccgctc atgagacaat aaccctgata    7140
aatgcttcaa taatattgaa aaaggaagag tatgagtatt caacatttcc gtgtcgccct    7200
tattccctttt tttgcggcat tttgccttcc tgttttttgct cacccagaaa cgctggtgaa    7260
agtaaaagat gctgaagatc agttgggtgc acgagtgggt tacatcgaac tggatctcaa    7320
cagcggtaag atccttgaga gttttcgccc cgaagaacgt tttccaatga tgagcacttt    7380
taaagttctg ctatgtggcg cggtattatc ccgtattgac gccgggcaag agcaactcgg    7440
tcgccgcata cactattctc agaatgactt ggttgagtac tcaccagtca cagaaaagca    7500
tcttacggat ggcatgacag taagagaatt atgcagtgct gccataacca tgagtgataa    7560
cactgcggcc aacttacttc tgacaacgat cggaggaccg aaggagctaa ccgcttttt    7620
gcacaacatg gggatcatg taactcgcct tgatcgttgg gaaccggagc tgaatgaagc    7680
cataccaaac gacgagcgtg acaccacgat gcctgtagca atggcaacaa cgttgcgcaa    7740
actattaact ggcgaactac ttactctagc ttcccggcaa caattaatag actggatgga    7800
ggcggataaa gttgcaggac cacttctgcg ctcggccctt ccggctggct ggtttattgc    7860
tgataaatct ggagccggtg agcgtgggtc tcgcggtatc attgcagcac tggggccaga    7920
```

```
tggtaagccc tcccgtatcg tagttatcta cacgacgggg agtcaggcaa ctatggatga   7980
acgaaataga cagatcgctg agataggtgc ctcactgatt aagcattggt aagcgatgaa   8040
atgtgaggtg aatcagggtt ttcacccgat tttgtgctga tcagaatttt ttttctttt    8100 cccccttgaa ggggcgaagc ctcatcccca tttctctggt caccagccgg gaaaccacgt   8160
aagctccggc gtcacccata acagatacgg actttctcaa aggagagtta tcaatgaaca   8220
tcaaaaagtt tgcaaaacaa gcaacagtat taacctttac taccgcactg ctggcaggag   8280
gcgcaactca agcgtttgcg aaagaaacga accaaaagcc atataaggaa acatacggca   8340
tttcccatat tacacgccat gatatgctgc aaatccctga acagcaaaaa aatgaaaaat   8400
atcaagttcc tgagttcgat tcgtccacaa ttaaaaatat ctcttctgca aaaggcctgg   8460
acgtttggga cagctggcca ttacaaaacg ctgacggcac tgtcgcaaac tatcacggct   8520
accacatcgt ctttgcatta gccggagatc ctaaaaatgc ggatgacaca tcgatttaca   8580
tgttctatca aaaagtcggc gaaacttcta ttgacagctg gaaaaacgct ggccgcgtct   8640
ttaaagacag cgacaaattc gatgcaaatg attctatcct aaaagaccaa acacaagaat   8700
ggtcaggttc agccacattt acatctgacg gaaaaatccg tttattctac actgatttct   8760
ccggtaaaca ttacggcaaa caaacactga caactgcaca agttaacgta tcagcatcag   8820
acagctcttt gaacatcaac ggtgtagagg attataaatc aatctttgac ggtgacggaa   8880
aaacgtatca aaatgtacag cagttcatcg atgaaggcaa ctacagctca ggcgacaacc   8940
atacgctgag agatcctcac tacgtagaag ataaaggcca caaatactta gtatttgaag   9000
caaacactgg aactgaagat ggctaccaag gcgaagaatc tttatttaac aaagcatact   9060
atggcaaaag cacatcattc ttccgtcaag aaagtcaaaa acttctgcaa agcgataaaa   9120
aacgcacggc tgagttagca aacggcgctc tcggtatgat tgagctaaac gatgattaca   9180
cactgaaaaa agtgatgaaa ccgctgattg catctaacac agtaacagat gaaattgaac   9240
gcgcgaacgt ctttaaaatg aacggcaaat ggtatctgtt cactgactcc cgcggatcaa   9300
aaatgacgat tgacggcatt acgtctaacg atatttacat gcttggttat gtttctaatt   9360
ctttaactgg cccatacaag ccgctgaaca aaactggcct tgtgttaaaa atggatcttg   9420
atcctaacga tgtaaccttt acttactcac acttcgctgt acctcaagcg aaaggaaaca   9480
atgtcgtgat tacaagctat atgacaaaca gaggattcta cgcagacaaa caatcaacgt   9540
ttgcgcctag cttcctgctg aacatcaaag gcaagaaaac atctgttgtc aaagacagca   9600
tccttgaaca aggacaatta acagttaaca ataaccagg agctatttaa tggcaacagt    9660
taaccagctg gtacgcaaac cacgtgctcg caaagttgcg aaaagcaacg tgcctgcgct   9720
ggaagcatgc ccgcaaaaac gtggcgtatg tactcgtgta tatactacca ctcctaaaaa   9780
accgaactcc gcgctgcgta aagtatgccg tgttcgtctg actaacggtt tcgaagtgac   9840
ttcctacatc ggtggtgaag gtcacaacct gcaggagcac tccgtgatcc tgatccgtgg   9900
cggtcgtgtt aaagacctcc cgggtgttcg ttaccacacc gtacgtggtg cgcttgactg   9960
ctccggcgtt aaagaccgta agcaggctcg ttccaagtat ggcgtgaagc gtcctaaggc  10020
ttaatggttc tccgttaagt aaggccaaat agaggatctg aagatcagca gttcaacctg  10080
ttgatagtac gtactaagct ctcatgtttc acgtactaag ctctcatgtt taacgtacta  10140
agctctcatg tttaacgaac taaaccctca tggctaacgt actaagctct catggctaac  10200
gtactaagct ctcatgtttc acgtactaag ctctcatgtt tgaacaataa aattaatata  10260
```

```
aatcagcaac ttaaatagcc tctaaggttt taagttttat aagaaaaaaa agaatatata    10320
aggcttttaa agcttttaag gtttaacggt tgtggacaac aagccaggga tgtaacgcac    10380
tgagaagccc ttagagcctc tcaaagcaat tttcagtgac acaggaacac ttaacggctg    10440
acagacgctg ccgcaagcac tcagggcgca agggctgcta aaggaagcgg aacacgtaga    10500
aagccagtcc gcagaaacgg tgctgacccc ggatgaatgt cagctactgg gctatctgga    10560
caagggaaaa cgcaagcgca aagagaaagc aggtagcttg cagtgggctt acatggcgat    10620
agctagactg ggcggtttta tggacagcaa gcgaaccgga attgccagct ggggcgccct    10680
ctggtaaggt tgggaagccc tgcaaagtaa actggatggc tttcttgccg ccaaggatct    10740
gatggcgcag gggatcaaga tctgatcaag agacaggatg aggatcgttt cgcatgattg    10800
aacaagatgg attgcacgca ggttctccgg ccgcttgggt ggagaggcta ttcggctatg    10860
actgggcaca acagacaatc ggctgctctg atgccgccgt gttccggctg tcagcgcagg    10920
ggcgcccggt tctttttgtc aagaccgacc tgtccggtgc cctgaatgaa ctccaagacg    10980
aggcagcgcg gctatcgtgg ctggccacga cgggcgttcc ttgcgcagct gtgctcgacg    11040
ttgtcactga agcgggaagg gactggctgc tattgggcga agtgccgggg caggatctcc    11100
tgtcatctca ccttgctcct gccgagaaag tatccatcat ggctgatgca atgcggcggc    11160
tgcatacgct tgatccggct acctgcccat tcgaccacca agcgaaacat cgcatcgagc    11220
gagcacgtac tcggatggaa gccggtcttg tcgatcagga tgatctggac gaagagcatc    11280
aggggctcgc gccagccgaa ctgttcgcca ggctcaaggc gcggatgccc gacggcgagg    11340
atctcgtcgt gacccatggc gatgcctgct tgccgaatat catggtggaa aatggccgct    11400
tttctggatt catcgactgt ggccggctgg gtgtggcgga ccgctatcag gacatagcgt    11460
tggctacccg tgatattgct gaagagcttg gcggcgaatg ggctgaccgc ttcctcgtgc    11520
tttacggtat cgccgctccc gattcgcagc gcatcgcctt ctatcgcctt cttgacgagt    11580
tcttctgaat tccggatccg aagaggcccg caccgatcgc ccttcccaac agttgcgcag    11640
cctgaatggc gaatggcgcc tgatgcggta ttttctcctt acgcatctgt gcggtatttc    11700
acaccgcata gggtaataac tgatataatt aaattgaagc tctaatttgt gagtttagta    11760
tacatgcatt tacttataat acagtttttt agttttgctg gccgcatctt ctcaaatatg    11820
cttcccagcc tgcttttctg taacgttcac cctctacctt agcatccctt ccctttgcaa    11880
atagtcctct tccaacaata taatgtcag atcctgtaga gaccacatca tccacggttc    11940
tatactgttg acccaatgcg tctcccttgt catctaaacc cacaccgggt gtcataatca    12000
accaatcgta accttcatct cttccaccca tgtctctttg agcaataaag ccgataacaa    12060
aatctttgtc gctcttcgca atgtcaacag taccccttagt atattctcca gtagatag    12120
agcccttgca tgacaattct gctaacatca aaaggcctct aggttccttt gttacttctt    12180
ctgccgcctg cttcaaaccg ctaacaatac ctgggcccac cacaccgtgt gcattcgtaa    12240
tgtctgccca ttctgctatt ctgtatacac ccgcagagta ctgcaatttg actgtattac    12300
caatgtcagc aaattttctg tcttcgaaga gtaaaaaatt gtacttggcg gataatgcct    12360
ttagcggctt aactgtgccc tccatggaaa aatcagtcaa gatatccaca tgtgttttta    12420
gtaaacaaat tttgggacct aatgcttcaa ctaactccag taattccttg gtggtacgaa    12480
catccaatga agcacacaag tttgtttgct tttcgtgcat gatattaaat agcttggcag    12540
caacaggact aggatgagta gcagcacgtt ccttatatgt agctttcgac atgatttatc    12600
ttcgtttcgg ttttttgttct gtgcagttgg gttaagaata ctgggcaatt tcatgtttct    12660
```

```
tcaacactac atatgcgtat ataccaat ctaagtctgt gctccttcct tcgttcttcc    12720
ttctgttcgg agattaccga atcaaaaaaa tttcaaagaa accgaaatca aaaaaaagaa    12780
taaaaaaaaa atgatgaatt gaaaagctct tgttacccat cattgaattt tgaacatccg    12840
aacctgggag ttttccctga aacagatagt atatttgaac ctgtataata atatatagtc    12900
tagcgcttta cggaagacaa tgtatgtatt tcggttcctg agaaactat tgcatctatt    12960 gcataggtaa tcttgcacgt cgcatccccg gttcattttc tgcgtttcca tcttgcactt    13020
caatagcata tctttgttaa cgaagcatct gtgcttcatt ttgtagaaca aaaatgcaac    13080
gcgagagcgc taattttca aacaaagaat ctgagctgca tttttacaga acagaaatgc    13140
aacgcgaaag cgctatttta ccaacgaaga atctgtgctt cattttgta aacaaaaat    13200 gcaacgcgag agcgctaatt tttcaaacaa agaatctgag ctgcattttt acagaacaga    13260
aatgcaacgc gagagcgcta ttttaccaac aaagaatcta tacttctttt tgttctaca    13320 aaaatgcatc ccgagagcgc tatttttcta acaaagcatc ttagattact ttttttctcc    13380
tttgtgcgct ctataatgca gtctcttgat aacttttgc actgtaggtc cgttaaggtt    13440
agaagaaggc tactttggtg tctattttct cttccataaa aaagcctga ctccacttcc    13500 cgcgtttact gattactagc gaagctgcgg gtgcattttt tcaagataaa ggcatccccg    13560
attatattct ataccgatgt ggattgcgca tactttgtga acagaaagtg atagcgttga    13620
tgattcttca ttggtcagaa aattatgaac ggtttcttct atttgtctc tatatactac    13680 gtataggaaa tgtttacatt ttcgtattgt tttcgattca ctctatgaat agttcttact    13740 acaattttt tgtctaaaga gtaatactag agataaacat aaaaaatgta gaggtcgagt    13800
ttagatgcaa gttcaaggag cgaaaggtgg atgggtaggt tatataggga tatagcacag    13860
agatatatag caaagagata cttttgagca atgtttgtgg aagcggtatt cgcaatattt    13920
tagtagctcg ttacagtccg gtgcgttttt ggttttttga aagtgcgtct tcagagcgct    13980
tttggttttc aaaagcgctc tgaagttcct atactttcta gctagagaat aggaacttcg    14040
gaataggaac ttcaaagcgt ttccgaaaac gagcgcttcc gaaaatgcaa cgcgagctgc    14100
gcacatacag ctcactgttc acgtcgcacc tatatctgcg tgttgcctgt atatatatat    14160
acatgagaag aacggcatag tgcgtgttta tgcttaaatg cgttatggtg cactctcagt    14220
acaatctgct ctgatgccgc atagttaagc c                                   14251
```

<210> SEQ ID NO 209
<211> LENGTH: 910
<212> TYPE: PRT
<213> ORGANISM: B. adolescentis

<400> SEQUENCE: 209

Met Ala Asp Ala Lys Lys Lys Glu Glu Pro Thr Lys Pro Thr Pro Glu
1               5                   10                  15

Glu Lys Leu Ala Ala Ala Glu Ala Glu Val Asp Ala Leu Val Lys Lys
            20                  25                  30

Gly Leu Lys Ala Leu Asp Glu Phe Glu Lys Leu Asp Gln Lys Gln Val
        35                  40                  45

Asp His Ile Val Ala Lys Ala Ser Val Ala Ala Leu Asn Lys His Leu
    50                  55                  60

Val Leu Ala Lys Met Ala Val Glu Glu Thr His Arg Gly Leu Val Glu
65                  70                  75                  80

Asp Lys Ala Thr Lys Asn Ile Phe Ala Cys Glu His Val Thr Asn Tyr

```
                     85                  90                  95
Leu Ala Gly Gln Lys Thr Val Gly Ile Ile Arg Glu Asp Asp Val Leu
                100                 105                 110
Gly Ile Asp Glu Ile Ala Glu Pro Val Gly Val Val Ala Gly Val Thr
                115                 120                 125
Pro Val Thr Asn Pro Thr Ser Thr Ala Ile Phe Lys Ser Leu Ile Ala
                130                 135                 140
Leu Lys Thr Arg Cys Pro Ile Ile Phe Gly Phe His Pro Gly Ala Gln
145                 150                 155                 160
Asn Cys Ser Val Ala Ala Ala Lys Ile Val Arg Asp Ala Ala Ile Ala
                165                 170                 175
Ala Gly Ala Pro Glu Asn Cys Ile Gln Trp Ile Glu His Pro Ser Ile
                180                 185                 190
Glu Ala Thr Gly Ala Leu Met Lys His Asp Gly Val Ala Thr Ile Leu
                195                 200                 205
Ala Thr Gly Gly Pro Gly Met Val Lys Ala Ala Tyr Ser Ser Gly Lys
                210                 215                 220
Pro Ala Leu Gly Val Gly Ala Gly Asn Ala Pro Ala Tyr Val Asp Lys
225                 230                 235                 240
Asn Val Asp Val Val Arg Ala Ala Asn Asp Leu Ile Leu Ser Lys His
                245                 250                 255
Phe Asp Tyr Gly Met Ile Cys Ala Thr Glu Gln Ala Ile Ile Ala Asp
                260                 265                 270
Lys Asp Ile Tyr Ala Pro Leu Val Lys Glu Leu Lys Arg Arg Lys Ala
                275                 280                 285
Tyr Phe Val Asn Ala Asp Glu Lys Ala Lys Leu Glu Gln Tyr Met Phe
                290                 295                 300
Gly Cys Thr Ala Tyr Ser Gly Gln Thr Pro Lys Leu Asn Ser Val Val
305                 310                 315                 320
Pro Gly Lys Ser Pro Gln Tyr Ile Ala Lys Ala Ala Gly Phe Glu Ile
                325                 330                 335
Pro Glu Asp Ala Thr Ile Leu Ala Ala Glu Cys Lys Glu Val Gly Glu
                340                 345                 350
Asn Glu Pro Leu Thr Met Glu Lys Leu Ala Pro Val Gln Ala Val Leu
                355                 360                 365
Lys Ser Asp Asn Lys Glu Gln Ala Phe Glu Met Cys Glu Ala Met Leu
                370                 375                 380
Lys His Gly Ala Gly His Thr Ala Ala Ile His Thr Asn Asp Arg Asp
385                 390                 395                 400
Leu Val Arg Glu Tyr Gly Gln Arg Met His Ala Cys Arg Ile Ile Trp
                405                 410                 415
Asn Ser Pro Ser Ser Leu Gly Gly Val Gly Asp Ile Tyr Asn Ala Ile
                420                 425                 430
Ala Pro Ser Leu Thr Leu Gly Cys Gly Ser Tyr Gly Gly Asn Ser Val
                435                 440                 445
Ser Gly Asn Val Gln Ala Val Asn Leu Ile Asn Ile Lys Arg Ile Ala
                450                 455                 460
Arg Arg Asn Asn Asn Met Gln Trp Phe Lys Ile Pro Ala Lys Thr Tyr
465                 470                 475                 480
Phe Glu Pro Asn Ala Ile Lys Tyr Leu Arg Asp Met Tyr Gly Ile Glu
                485                 490                 495
Lys Ala Val Ile Val Cys Asp Lys Val Met Glu Gln Leu Gly Ile Val
                500                 505                 510
```

Asp Lys Ile Ile Asp Gln Leu Arg Ala Arg Ser Asn Arg Val Thr Phe
            515                 520                 525

Arg Ile Ile Asp Tyr Val Glu Pro Glu Pro Ser Val Glu Thr Val Glu
            530                 535                 540

Arg Gly Ala Ala Met Met Arg Glu Glu Phe Glu Pro Asp Thr Ile Ile
545                 550                 555                 560

Ala Val Gly Gly Gly Ser Pro Met Asp Ala Ser Lys Ile Met Trp Leu
                565                 570                 575

Leu Tyr Glu His Pro Glu Ile Ser Phe Ser Asp Val Arg Glu Lys Phe
            580                 585                 590

Phe Asp Ile Arg Lys Arg Ala Phe Lys Ile Pro Pro Leu Gly Lys Lys
            595                 600                 605

Ala Lys Leu Val Cys Ile Pro Thr Ser Ser Gly Thr Gly Ser Glu Val
            610                 615                 620

Thr Pro Phe Ala Val Ile Thr Asp His Lys Thr Gly Tyr Lys Tyr Pro
625                 630                 635                 640

Ile Thr Asp Tyr Ala Leu Thr Pro Ser Val Ala Ile Val Asp Pro Val
                645                 650                 655

Leu Ala Arg Thr Gln Pro Arg Lys Leu Ala Ser Asp Ala Gly Phe Asp
            660                 665                 670

Ala Leu Thr His Ala Phe Glu Ala Tyr Val Ser Val Tyr Ala Asn Asp
            675                 680                 685

Phe Thr Asp Gly Met Ala Leu His Ala Ala Lys Leu Val Trp Asp Asn
            690                 695                 700

Leu Ala Glu Ser Val Asn Gly Glu Pro Gly Glu Lys Thr Arg Ala
705                 710                 715                 720

Gln Glu Lys Met His Asn Ala Thr Met Ala Gly Met Ala Phe Gly
            725                 730                 735

Ser Ala Phe Leu Gly Met Cys His Gly Met Ala His Thr Ile Gly Ala
                740                 745                 750

Leu Cys His Val Ala His Gly Arg Thr Asn Ser Ile Leu Leu Pro Tyr
            755                 760                 765

Val Ile Arg Tyr Asn Gly Ser Val Pro Glu Glu Pro Thr Ser Trp Pro
            770                 775                 780

Lys Tyr Asn Lys Tyr Ile Ala Pro Glu Arg Tyr Gln Glu Ile Ala Lys
785                 790                 795                 800

Asn Leu Gly Val Asn Pro Gly Lys Thr Pro Glu Glu Gly Val Glu Asn
                805                 810                 815

Leu Ala Lys Ala Val Glu Asp Tyr Arg Asp Asn Lys Leu Gly Met Asn
            820                 825                 830

Lys Ser Phe Gln Glu Cys Gly Val Asp Glu Asp Tyr Tyr Trp Ser Ile
            835                 840                 845

Ile Asp Gln Ile Gly Met Arg Ala Tyr Glu Asp Gln Cys Ala Pro Ala
850                 855                 860

Asn Pro Arg Ile Pro Gln Ile Glu Asp Met Lys Asp Ile Ala Ile Ala
865                 870                 875                 880

Ala Tyr Tyr Gly Val Ser Gln Ala Glu Gly His Lys Leu Arg Val Gln
                885                 890                 895

Arg Gln Gly Glu Ala Ala Thr Glu Glu Ala Ser Glu Arg Ala
            900                 905                 910

<210> SEQ ID NO 210
<211> LENGTH: 292

<212> TYPE: PRT
<213> ORGANISM: B. adolescentis

<400> SEQUENCE: 210

Met Ser Glu His Ile Phe Arg Ser Thr Thr Arg His Met Leu Arg Asp
1               5                   10                  15

Ser Lys Asp Tyr Val Asn Gln Thr Leu Met Gly Gly Leu Ser Gly Phe
            20                  25                  30

Glu Ser Pro Ile Gly Leu Asp Arg Leu Asp Arg Ile Lys Ala Leu Lys
        35                  40                  45

Ser Gly Asp Ile Gly Phe Val His Ser Trp Asp Ile Asn Thr Ser Val
    50                  55                  60

Asp Gly Pro Gly Thr Arg Met Thr Val Phe Met Ser Gly Cys Pro Leu
65                  70                  75                  80

Arg Cys Gln Tyr Cys Gln Asn Pro Asp Thr Trp Lys Met Arg Asp Gly
                85                  90                  95

Lys Pro Val Tyr Tyr Glu Ala Met Val Lys Lys Ile Glu Arg Tyr Ala
            100                 105                 110

Asp Leu Phe Lys Ala Thr Gly Gly Ile Thr Phe Ser Gly Gly Glu
        115                 120                 125

Ser Met Met Gln Pro Ala Phe Val Ser Arg Val Phe His Ala Ala Lys
    130                 135                 140

Gln Met Gly Val His Thr Cys Leu Asp Thr Ser Gly Phe Leu Gly Ala
145                 150                 155                 160

Ser Tyr Thr Asp Asp Met Val Asp Ile Asp Leu Cys Leu Leu Asp
                165                 170                 175

Val Lys Ser Gly Asp Glu Glu Thr Tyr His Lys Val Thr Gly Gly Ile
            180                 185                 190

Leu Gln Pro Thr Ile Asp Phe Gly Gln Arg Leu Ala Lys Ala Gly Lys
        195                 200                 205

Lys Ile Trp Val Arg Phe Val Leu Val Pro Gly Leu Thr Ser Ser Glu
    210                 215                 220

Glu Asn Val Glu Asn Val Ala Lys Ile Cys Glu Thr Phe Gly Asp Ala
225                 230                 235                 240

Leu Glu His Ile Asp Val Leu Pro Phe His Gln Leu Gly Arg Pro Lys
                245                 250                 255

Trp His Met Leu Asn Ile Pro Tyr Pro Leu Glu Asp Gln Lys Gly Pro
            260                 265                 270

Ser Ala Ala Met Lys Gln Arg Val Val Glu Gln Phe Gln Ser His Gly
        275                 280                 285

Phe Thr Val Tyr
    290

<210> SEQ ID NO 211
<211> LENGTH: 791
<212> TYPE: PRT
<213> ORGANISM: B. adolescentis

<400> SEQUENCE: 211

Met Ala Ala Val Asp Ala Thr Ala Val Ser Gln Glu Glu Leu Glu Ala
1               5                   10                  15

Lys Ala Trp Glu Gly Phe Thr Glu Gly Asn Trp Gln Lys Asp Ile Asp
            20                  25                  30

Val Arg Asp Phe Ile Gln Lys Asn Tyr Thr Pro Tyr Glu Gly Asp Glu
        35                  40                  45

```
Ser Phe Leu Ala Asp Ala Thr Asp Lys Thr Lys His Leu Trp Lys Tyr
 50                  55                  60

Leu Asp Asp Asn Tyr Leu Ser Val Glu Arg Lys Gln Arg Val Tyr Asp
 65                  70                  75                  80

Val Asp Thr His Thr Pro Ala Gly Ile Asp Ala Phe Pro Ala Gly Tyr
                 85                  90                  95

Ile Asp Ser Pro Glu Val Asp Asn Val Ile Val Gly Leu Gln Thr Asp
                100                 105                 110

Val Pro Cys Lys Arg Ala Met Met Pro Asn Gly Gly Trp Arg Met Val
            115                 120                 125

Glu Gln Ala Ile Lys Glu Ala Gly Lys Glu Pro Asp Pro Glu Ile Lys
    130                 135                 140

Lys Ile Phe Thr Lys Tyr Arg Lys Thr His Asn Asp Gly Val Phe Gly
145                 150                 155                 160

Val Tyr Thr Lys Gln Ile Lys Val Ala Arg His Asn Lys Ile Leu Thr
                165                 170                 175

Gly Leu Pro Asp Ala Tyr Gly Arg Gly Arg Ile Ile Gly Asp Tyr Arg
            180                 185                 190

Arg Val Ala Leu Tyr Gly Val Asn Ala Leu Ile Lys Phe Lys Gln Arg
        195                 200                 205

Asp Lys Asp Ser Ile Pro Tyr Arg Asn Asp Phe Thr Glu Pro Glu Ile
    210                 215                 220

Glu His Trp Ile Arg Phe Arg Glu Glu His Asp Glu Gln Ile Lys Ala
225                 230                 235                 240

Leu Lys Gln Leu Ile Asn Leu Gly Asn Glu Tyr Gly Leu Asp Leu Ser
                245                 250                 255

Arg Pro Ala Gln Thr Ala Gln Glu Ala Val Gln Trp Thr Tyr Met Gly
            260                 265                 270

Tyr Leu Ala Ser Val Lys Ser Gln Asp Gly Ala Ala Met Ser Phe Gly
        275                 280                 285

Arg Val Ser Thr Phe Phe Asp Val Tyr Phe Glu Arg Asp Leu Lys Ala
    290                 295                 300

Gly Lys Ile Thr Glu Thr Asp Ala Gln Glu Ile Ile Asp Asn Leu Val
305                 310                 315                 320

Met Lys Leu Arg Ile Val Arg Phe Leu Arg Thr Lys Asp Tyr Asp Ala
                325                 330                 335

Ile Phe Ser Gly Asp Pro Tyr Trp Ala Thr Trp Ser Asp Ala Gly Phe
            340                 345                 350

Gly Asp Asp Gly Arg Thr Met Val Thr Lys Thr Ser Phe Arg Leu Leu
        355                 360                 365

Asn Thr Leu Thr Leu Glu His Leu Gly Pro Gly Pro Glu Pro Asn Ile
    370                 375                 380

Thr Ile Phe Trp Asp Pro Lys Leu Pro Glu Ala Tyr Lys Arg Phe Cys
385                 390                 395                 400

Ala Arg Ile Ser Ile Asp Thr Ser Ala Ile Gln Tyr Glu Ser Asp Lys
                405                 410                 415

Glu Ile Arg Ser His Trp Gly Asp Asp Ala Ala Ile Ala Cys Cys Val
            420                 425                 430

Ser Pro Met Arg Val Gly Lys Gln Met Gln Phe Phe Ala Ala Arg Val
        435                 440                 445

Asn Ser Ala Lys Ala Leu Leu Tyr Ala Ile Asn Gly Gly Arg Asp Glu
    450                 455                 460

Met Thr Gly Met Gln Val Ile Asp Lys Gly Val Ile Asp Pro Ile Lys
```

```
            465                 470                 475                 480
        Pro Glu Ala Asp Gly Thr Leu Asp Tyr Glu Lys Val Lys Ala Asn Tyr
                        485                 490                 495

Glu Lys Ala Leu Glu Trp Leu Ser Glu Thr Tyr Val Met Ala Leu Asn
                        500                 505                 510

Ile Ile His Tyr Met His Asp Lys Tyr Ala Tyr Glu Ser Ile Glu Met
                        515                 520                 525

Ala Leu His Asp Lys Glu Val Tyr Arg Thr Leu Gly Cys Gly Met Ser
        530                 535                 540

Gly Leu Ser Ile Ala Ala Asp Ser Leu Ser Ala Cys Lys Tyr Ala Lys
        545                 550                 555                 560

Val Tyr Pro Ile Tyr Asn Lys Asp Ala Lys Thr Thr Pro Gly His Glu
                        565                 570                 575

Asn Glu Tyr Val Glu Gly Ala Asp Asp Leu Ile Val Gly Tyr Arg
                        580                 585                 590

Thr Glu Gly Asp Phe Pro Leu Tyr Gly Asn Asp Asp Arg Ala Asp
                        595                 600                 605

Asp Ile Ala Lys Trp Val Val Ser Thr Val Met Gly Gln Val Lys Arg
        610                 615                 620

Leu Pro Val Tyr Arg Asp Ala Val Pro Thr Gln Ser Ile Leu Thr Ile
        625                 630                 635                 640

Thr Ser Asn Val Glu Tyr Gly Lys Ala Thr Gly Ala Phe Pro Ser Gly
                        645                 650                 655

His Lys Lys Gly Thr Pro Tyr Ala Pro Gly Ala Asn Pro Glu Asn Gly
                        660                 665                 670

Met Asp Ser His Gly Met Leu Pro Ser Met Phe Ser Val Gly Lys Ile
                        675                 680                 685

Asp Tyr Asn Asp Ala Leu Asp Gly Ile Ser Leu Thr Asn Thr Ile Thr
                        690                 695                 700

Pro Asp Gly Leu Gly Arg Asp Glu Glu Arg Ile Gly Asn Leu Val
        705                 710                 715                 720

Gly Ile Leu Asp Ala Gly Asn Gly His Gly Leu Tyr His Ala Asn Ile
                        725                 730                 735

Asn Val Leu Arg Lys Glu Gln Leu Glu Asp Ala Val Glu His Pro Glu
                        740                 745                 750

Lys Tyr Pro His Leu Thr Val Arg Val Ser Gly Tyr Ala Val Asn Phe
                        755                 760                 765

Val Lys Leu Thr Lys Glu Gln Gln Leu Asp Val Ile Ser Arg Thr Phe
                        770                 775                 780

His Gln Gly Ala Val Val Asp
        785                 790

<210> SEQ ID NO 212
<211> LENGTH: 26
<212> TYPE: DNA
<213> ORGANISM: Artificial
<220> FEATURE:
<223> OTHER INFORMATION: X11316

<400> SEQUENCE: 212
gtaatacatc acctcgatga aagaga                                          26

<210> SEQ ID NO 213
<211> LENGTH: 29
<212> TYPE: DNA
<213> ORGANISM: Artificial
```

```
<220> FEATURE:
<223> OTHER INFORMATION: X11816

<400> SEQUENCE: 213
gcagtcatca ggatcgtagg agataagca                                29

<210> SEQ ID NO 214
<211> LENGTH: 30
<212> TYPE: DNA
<213> ORGANISM: Artificial
<220> FEATURE:
<223> OTHER INFORMATION: X11821

<400> SEQUENCE: 214
tcacaagagt gtgcagaaat aggaggtgga                               30

<210> SEQ ID NO 215
<211> LENGTH: 59
<212> TYPE: DNA
<213> ORGANISM: Artificial
<220> FEATURE:
<223> OTHER INFORMATION: X11822

<400> SEQUENCE: 215
gttgggggaa aaagaggcaa caggaaagat cagagacagc aagcattgat aaggaaggg    59

<210> SEQ ID NO 216
<211> LENGTH: 59
<212> TYPE: DNA
<213> ORGANISM: Artificial
<220> FEATURE:
<223> OTHER INFORMATION: X11823

<400> SEQUENCE: 216
cccttcctta tcaatgcttg ctgtctctga tctttcctgt tgcctctttt tcccccaac    59

<210> SEQ ID NO 217
<211> LENGTH: 29
<212> TYPE: DNA
<213> ORGANISM: Artificial
<220> FEATURE:
<223> OTHER INFORMATION: X11824

<400> SEQUENCE: 217
aagcctacag gcgcaagata acacatcac                                29

<210> SEQ ID NO 218
<211> LENGTH: 35
<212> TYPE: DNA
<213> ORGANISM: Artificial
<220> FEATURE:
<223> OTHER INFORMATION: X11829

<400> SEQUENCE: 218
ctcagcattg atcttagcag attcaggatc taggt                         35

<210> SEQ ID NO 219
<211> LENGTH: 59
<212> TYPE: DNA
<213> ORGANISM: Artificial
<220> FEATURE:
<223> OTHER INFORMATION: X11830

<400> SEQUENCE: 219
tatgttatct ttctccaata aatctaatct tcatgtagac tatcagcagc agcagacat    59
```

<210> SEQ ID NO 220
<211> LENGTH: 59
<212> TYPE: DNA
<213> ORGANISM: Artificial
<220> FEATURE:
<223> OTHER INFORMATION: X11831

<400> SEQUENCE: 220
gataatataa agatgtctgc tgctgctgat agtctacatg aagattagat ttattggag        59

<210> SEQ ID NO 221
<211> LENGTH: 30
<212> TYPE: DNA
<213> ORGANISM: Artificial
<220> FEATURE:
<223> OTHER INFORMATION: X11845

<400> SEQUENCE: 221
ttacttgtga aactgtctcc gctatgtcag        30

<210> SEQ ID NO 222
<211> LENGTH: 59
<212> TYPE: DNA
<213> ORGANISM: Artificial
<220> FEATURE:
<223> OTHER INFORMATION: X14775

<400> SEQUENCE: 222 cccctccac aaacacaaat attgataata taaagatggc agacgcaaag aagaaggaa        59

<210> SEQ ID NO 223
<211> LENGTH: 34
<212> TYPE: DNA
<213> ORGANISM: Artificial
<220> FEATURE:
<223> OTHER INFORMATION: X14778

<400> SEQUENCE: 223
atttattgga gaaagataac atatcatact ttcc        34

<210> SEQ ID NO 224
<211> LENGTH: 59
<212> TYPE: DNA
<213> ORGANISM: Artificial
<220> FEATURE:
<223> OTHER INFORMATION: X14829

<400> SEQUENCE: 224
gaaagtatga tatgttatct ttctccaata aatctagtct tctaggcggg ttatctact        59

<210> SEQ ID NO 225
<211> LENGTH: 59
<212> TYPE: DNA
<213> ORGANISM: Artificial
<220> FEATURE:
<223> OTHER INFORMATION: X14835

<400> SEQUENCE: 225
caaattctaa ccaacttcaa aatgacatag tacctcatct ataatttta ccctgatct        59

<210> SEQ ID NO 226
<211> LENGTH: 59
<212> TYPE: DNA
<213> ORGANISM: Artificial
<220> FEATURE:
<223> OTHER INFORMATION: X14836

<400> SEQUENCE: 226
agttagatca gggtaaaaat tatagatgag gtactatgtc attttgaagt tggttagaa    59

<210> SEQ ID NO 227
<211> LENGTH: 59
<212> TYPE: DNA
<213> ORGANISM: Artificial
<220> FEATURE:
<223> OTHER INFORMATION: X14837

<400> SEQUENCE: 227
ggtccatgta aaatgattgc tccaatgatt gaaattgatt caggtcaaaa tggattcag    59

<210> SEQ ID NO 228
<211> LENGTH: 59
<212> TYPE: DNA
<213> ORGANISM: Artificial
<220> FEATURE:
<223> OTHER INFORMATION: X14838

<400> SEQUENCE: 228
acgtccctga atccattttg acctgaatca atttcaatca ttggagcaat cattttaca    59

<210> SEQ ID NO 229
<211> LENGTH: 59
<212> TYPE: DNA
<213> ORGANISM: Artificial
<220> FEATURE:
<223> OTHER INFORMATION: X14843

<400> SEQUENCE: 229
ggtggaacca tttactgtat tttcaatgta acgctagaga ataaattcaa gttaaaaga    59

<210> SEQ ID NO 230
<211> LENGTH: 59
<212> TYPE: DNA
<213> ORGANISM: Artificial
<220> FEATURE:
<223> OTHER INFORMATION: X14844

<400> SEQUENCE: 230
catcatcttt taacttgaat ttattctcta gcgttacatt gaaaatacag taaatggtt    59

<210> SEQ ID NO 231
<211> LENGTH: 26
<212> TYPE: DNA
<213> ORGANISM: Artificial
<220> FEATURE:
<223> OTHER INFORMATION: X15380

<400> SEQUENCE: 231
taggtctaga gatctgttta gcttgc    26

<210> SEQ ID NO 232
<211> LENGTH: 23
<212> TYPE: DNA
<213> ORGANISM: Artificial
<220> FEATURE:
<223> OTHER INFORMATION: X15382

<400> SEQUENCE: 232
gagactacat gatagtccaa aga    23

<210> SEQ ID NO 233

```
<211> LENGTH: 59
<212> TYPE: DNA
<213> ORGANISM: Artificial
<220> FEATURE:
<223> OTHER INFORMATION: X15546

<400> SEQUENCE: 233
ggacgaggca agctaaacag atctctagac ctactttata ttatcaatat ttgtgtttg      59

<210> SEQ ID NO 234
<211> LENGTH: 59
<212> TYPE: DNA
<213> ORGANISM: Artificial
<220> FEATURE:
<223> OTHER INFORMATION: X15547

<400> SEQUENCE: 234
ccgtttcttt tctttggact atcatgtagt ctcatttatt ggagaaagat aacatatca      59

<210> SEQ ID NO 235
<211> LENGTH: 59
<212> TYPE: DNA
<213> ORGANISM: Artificial
<220> FEATURE:
<223> OTHER INFORMATION: X15548

<400> SEQUENCE: 235
ggacgaggca agctaaacag atctctagac ctatgataag aaggggagc gaaggaaaa       59

<210> SEQ ID NO 236
<211> LENGTH: 59
<212> TYPE: DNA
<213> ORGANISM: Artificial
<220> FEATURE:
<223> OTHER INFORMATION: X15549

<400> SEQUENCE: 236
ccgtttcttt tctttggact atcatgtagt ctcctctgat ctttcctgtt gcctcttt       59

<210> SEQ ID NO 237
<211> LENGTH: 59
<212> TYPE: DNA
<213> ORGANISM: Artificial
<220> FEATURE:
<223> OTHER INFORMATION: X15552

<400> SEQUENCE: 237
ccgtttcttt tctttggact atcatgtagt ctcgagtgat tatgagtatt tgtgagcag      59

<210> SEQ ID NO 238
<211> LENGTH: 31
<212> TYPE: DNA
<213> ORGANISM: Artificial
<220> FEATURE:
<223> OTHER INFORMATION: X15553

<400> SEQUENCE: 238
accagcgtct ggtggacaaa cggccttcaa c                                    31

<210> SEQ ID NO 239
<211> LENGTH: 59
<212> TYPE: DNA
<213> ORGANISM: Artificial
<220> FEATURE:
<223> OTHER INFORMATION: X15554

<400> SEQUENCE: 239
```

```
ggacgaggca agctaaacag atctctagac ctaattaatt ttcagctgtt atttcgatt        59

<210> SEQ ID NO 240
<211> LENGTH: 59
<212> TYPE: DNA
<213> ORGANISM: Artificial
<220> FEATURE:
<223> OTHER INFORMATION: X15555

<400> SEQUENCE: 240
ccgtttcttt tctttggact atcatgtagt ctcgagtgat tatgagtatt tgtgagcag        59

<210> SEQ ID NO 241
<211> LENGTH: 25
<212> TYPE: DNA
<213> ORGANISM: Artificial
<220> FEATURE:
<223> OTHER INFORMATION: X15559

<400> SEQUENCE: 241
ggaaggcacc gatactagaa ctccg                                             25

<210> SEQ ID NO 242
<211> LENGTH: 59
<212> TYPE: DNA
<213> ORGANISM: Artificial
<220> FEATURE:
<223> OTHER INFORMATION: X15564

<400> SEQUENCE: 242
ctaatcaaat caaaataaca gctgaaaatt aatctactta ttcccttcga gattatatc        59

<210> SEQ ID NO 243
<211> LENGTH: 59
<212> TYPE: DNA
<213> ORGANISM: Artificial
<220> FEATURE:
<223> OTHER INFORMATION: X15565

<400> SEQUENCE: 243
gttcctagat ataatctcga agggaataag tagattaatt ttcagctgtt attttgatt        59

<210> SEQ ID NO 244
<211> LENGTH: 59
<212> TYPE: DNA
<213> ORGANISM: Artificial
<220> FEATURE:
<223> OTHER INFORMATION: X15566

<400> SEQUENCE: 244
tcggatcagt agataacccg cctagaagac taggagtgat tatgagtatt tgtgagcag        59

<210> SEQ ID NO 245
<211> LENGTH: 59
<212> TYPE: DNA
<213> ORGANISM: Artificial
<220> FEATURE:
<223> OTHER INFORMATION: X15567

<400> SEQUENCE: 245
aaaacttctg ctcacaaata ctcataatca ctcctagtct tctaggcggg ttatctact        59

<210> SEQ ID NO 246
<211> LENGTH: 59
<212> TYPE: DNA
```

```
<213> ORGANISM: Artificial
<220> FEATURE:
<223> OTHER INFORMATION: X15870

<400> SEQUENCE: 246
ctaatcaaat caaaataaca gctgaaaatt aatgagtgat tatgagtatt tgtgagcag      59

<210> SEQ ID NO 247
<211> LENGTH: 59
<212> TYPE: DNA
<213> ORGANISM: Artificial
<220> FEATURE:
<223> OTHER INFORMATION: X15871

<400> SEQUENCE: 247
aaaacttctg ctcacaaata ctcataatca ctcattaatt ttcagctgtt attttgatt      59

<210> SEQ ID NO 248
<211> LENGTH: 30
<212> TYPE: DNA
<213> ORGANISM: Artificial
<220> FEATURE:
<223> OTHER INFORMATION: X16096

<400> SEQUENCE: 248
catggtgctt agcagcagat gaaagtgtca                                      30

<210> SEQ ID NO 249
<211> LENGTH: 59
<212> TYPE: DNA
<213> ORGANISM: Artificial
<220> FEATURE:
<223> OTHER INFORMATION: X16097

<400> SEQUENCE: 249
gttcctagat ataatctcga agggaataag tagattaatt ttcagctgtt atttcgatt      59

<210> SEQ ID NO 250
<211> LENGTH: 59
<212> TYPE: DNA
<213> ORGANISM: Artificial
<220> FEATURE:
<223> OTHER INFORMATION: X16098

<400> SEQUENCE: 250
ctaatcaaat cgaaataaca gctgaaaatt aatctactta ttcccttcga gattatatc      59

<210> SEQ ID NO 251
<211> LENGTH: 59
<212> TYPE: DNA
<213> ORGANISM: Artificial
<220> FEATURE:
<223> OTHER INFORMATION: X16099

<400> SEQUENCE: 251
aaaacttctg ctcacaaata ctcataatca ctcctagtct tctaggcggg ttatctact      59

<210> SEQ ID NO 252
<211> LENGTH: 59
<212> TYPE: DNA
<213> ORGANISM: Artificial
<220> FEATURE:
<223> OTHER INFORMATION: X16100

<400> SEQUENCE: 252
tcggatcagt agataacccg cctagaagac taggagtgat tatgagtatt tgtgagcag      59
```

```
<210> SEQ ID NO 253
<211> LENGTH: 25
<212> TYPE: DNA
<213> ORGANISM: Artificial
<220> FEATURE:
<223> OTHER INFORMATION: X16463

<400> SEQUENCE: 253
cagagtttga agatatccaa atggt                                              25

<210> SEQ ID NO 254
<211> LENGTH: 29
<212> TYPE: DNA
<213> ORGANISM: Artificial
<220> FEATURE:
<223> OTHER INFORMATION: X16464

<400> SEQUENCE: 254
tttgttcttc ttgttattgt attgtgttg                                          29

<210> SEQ ID NO 255
<211> LENGTH: 30
<212> TYPE: DNA
<213> ORGANISM: Artificial
<220> FEATURE:
<223> OTHER INFORMATION: X16465

<400> SEQUENCE: 255
gctaattaac ataaaactca tgattcaacg                                         30

<210> SEQ ID NO 256
<211> LENGTH: 27
<212> TYPE: DNA
<213> ORGANISM: Artificial
<220> FEATURE:
<223> OTHER INFORMATION: X16466

<400> SEQUENCE: 256
acataggttt gcaagcttta taatctg                                            27

<210> SEQ ID NO 257
<211> LENGTH: 59
<212> TYPE: DNA
<213> ORGANISM: Artificial
<220> FEATURE:
<223> OTHER INFORMATION: X16467

<400> SEQUENCE: 257
agaacaacac aatacaataa caagaagaac aaataggtct agagatctgt ttagcttgc         59

<210> SEQ ID NO 258
<211> LENGTH: 59
<212> TYPE: DNA
<213> ORGANISM: Artificial
<220> FEATURE:
<223> OTHER INFORMATION: X16468

<400> SEQUENCE: 258
aaacgttgaa tcatgagttt tatgttaatt agcgagacta catgatagtc caaagaaaa        59

<210> SEQ ID NO 259
<211> LENGTH: 59
<212> TYPE: DNA
<213> ORGANISM: Artificial
<220> FEATURE:
```

<223> OTHER INFORMATION: X16469

<400> SEQUENCE: 259
agaacaacac aatacaataa caagaagaac aaactactta ttcccttcga gattatatc     59

<210> SEQ ID NO 260
<211> LENGTH: 59
<212> TYPE: DNA
<213> ORGANISM: Artificial
<220> FEATURE:
<223> OTHER INFORMATION: X16470

<400> SEQUENCE: 260
aaacgttgaa tcatgagttt tatgttaatt agcctagtct tctaggcggg ttatctact     59

<210> SEQ ID NO 261
<211> LENGTH: 25
<212> TYPE: DNA
<213> ORGANISM: Artificial
<220> FEATURE:
<223> OTHER INFORMATION: X16471

<400> SEQUENCE: 261
aagaatctgt tagttcgaac tccag                                          25

<210> SEQ ID NO 262
<211> LENGTH: 30
<212> TYPE: DNA
<213> ORGANISM: Artificial
<220> FEATURE:
<223> OTHER INFORMATION: X16472

<400> SEQUENCE: 262
tttgttggca atatgttttt gctatattac                                     30

<210> SEQ ID NO 263
<211> LENGTH: 25
<212> TYPE: DNA
<213> ORGANISM: Artificial
<220> FEATURE:
<223> OTHER INFORMATION: X16473

<400> SEQUENCE: 263
gccattagta gtgtactcaa acgaa                                          25

<210> SEQ ID NO 264
<211> LENGTH: 24
<212> TYPE: DNA
<213> ORGANISM: Artificial
<220> FEATURE:
<223> OTHER INFORMATION: X16474

<400> SEQUENCE: 264
acgactcaac atatgtatgt tgct                                           24

<210> SEQ ID NO 265
<211> LENGTH: 59
<212> TYPE: DNA
<213> ORGANISM: Artificial
<220> FEATURE:
<223> OTHER INFORMATION: X16475

<400> SEQUENCE: 265
cacgtaatat agcaaaaaca tattgccaac aaataggtct agagatctgt ttagcttgc     59

```
<210> SEQ ID NO 266
<211> LENGTH: 59
<212> TYPE: DNA
<213> ORGANISM: Artificial
<220> FEATURE:
<223> OTHER INFORMATION: X16476

<400> SEQUENCE: 266
aacaataatt cgtttgagta cactactaat ggcgagacta catgatagtc caaagaaaa    59

<210> SEQ ID NO 267
<211> LENGTH: 59
<212> TYPE: DNA
<213> ORGANISM: Artificial
<220> FEATURE:
<223> OTHER INFORMATION: X16477

<400> SEQUENCE: 267
cacgtaatat agcaaaaaca tattgccaac aaactactta ttcccttcga gattatatc    59

<210> SEQ ID NO 268
<211> LENGTH: 59
<212> TYPE: DNA
<213> ORGANISM: Artificial
<220> FEATURE:
<223> OTHER INFORMATION: X16478

<400> SEQUENCE: 268
aacaataatt cgtttgagta cactactaat ggcctagtct tctaggcggg ttatctact    59

<210> SEQ ID NO 269
<211> LENGTH: 31
<212> TYPE: DNA
<213> ORGANISM: Artificial
<220> FEATURE:
<223> OTHER INFORMATION: X16951

<400> SEQUENCE: 269
atgttccgct gatgtgatgt gcaagataaa c                                  31

<210> SEQ ID NO 270
<211> LENGTH: 59
<212> TYPE: DNA
<213> ORGANISM: Artificial
<220> FEATURE:
<223> OTHER INFORMATION: X16952

<400> SEQUENCE: 270
gaggcaagct aaacagatct ctagacctat ttgattgatt tgactgtgtt attttgcgt    59

<210> SEQ ID NO 271
<211> LENGTH: 59
<212> TYPE: DNA
<213> ORGANISM: Artificial
<220> FEATURE:
<223> OTHER INFORMATION: X16953

<400> SEQUENCE: 271
ataacctcac gcaaaataac acagtcaaat caatcaaata ggtctagaga tctgtttag    59

<210> SEQ ID NO 272
<211> LENGTH: 59
<212> TYPE: DNA
<213> ORGANISM: Artificial
<220> FEATURE:
<223> OTHER INFORMATION: X16954
```

```
<400> SEQUENCE: 272
aaaactttaa ctaataatta gagattaaat cgcttagaga ctacatgata gtccaaaga       59

<210> SEQ ID NO 273
<211> LENGTH: 59
<212> TYPE: DNA
<213> ORGANISM: Artificial
<220> FEATURE:
<223> OTHER INFORMATION: X16955

<400> SEQUENCE: 273 gtcccccccgt ttcttttctt tggactatca tgtagtctct aagcgattta atctctaat      59

<210> SEQ ID NO 274
<211> LENGTH: 36
<212> TYPE: DNA
<213> ORGANISM: Artificial
<220> FEATURE:
<223> OTHER INFORMATION: X16956

<400> SEQUENCE: 274
tcggtcattg ggtgagttta agcattagca gcaatg                                36

<210> SEQ ID NO 275
<211> LENGTH: 59
<212> TYPE: DNA
<213> ORGANISM: Artificial
<220> FEATURE:
<223> OTHER INFORMATION: X16957

<400> SEQUENCE: 275
taaaacttta actaataatt agagattaaa tcgcttattt gattgatttg actgtgtta       59

<210> SEQ ID NO 276
<211> LENGTH: 59
<212> TYPE: DNA
<213> ORGANISM: Artificial
<220> FEATURE:
<223> OTHER INFORMATION: X16958

<400> SEQUENCE: 276
cacgcaaaat aacacagtca atcaatcaa ataagcgatt taatctctaa ttattagtt        59

<210> SEQ ID NO 277
<211> LENGTH: 1128
<212> TYPE: DNA
<213> ORGANISM: S. cerevisiae

<400> SEQUENCE: 277
atgtcgaagg gaaaggtttt gctggttctt tacgaaggtg gtaagcatgc tgaagagcag      60
gaaaagttat tggggtgtat tgaaaatgaa cttggtatca gaaatttcat tgaagaacag     120
ggatacgagt tggttactac cattgacaag gaccctgagc aacctcaac ggtagacagg      180 gagttgaaag acgctgaaat tgtcattact acgcccttt tccccgccta catctcgaga      240
aacaggattg cagaagctcc taacctgaag ctctgtgtaa ccgctggcgt cggttcagac     300
catgtcgatt tagaagctgc aaatgaacgg aaaatcacgg tcaccgaagt tactggttct     360
aacgtcgttt ctgtcgcaga gcacgttatg gccacaattt tggttttgat aagaaactat     420
aatggtggtc atcaacaagc aattaatggt gagtgggata ttgccggcgt ggctaaaaat    480
gagtatgatc tggaagacaa aataatttca acggtaggtg ccggtagaat tggatatagg     540
gttctggaaa gattggtcgc atttaatccg aagaagttac tgtactacga ctaccaggaa     600
```

```
ctacctgcgg aagcaatcaa tagattgaac gaggccagca agcttttcaa tggcagaggt    660
gatattgttc agagagtaga gaaattggag gatatggttg ctcagtcaga tgttgttacc    720
atcaactgtc cattgcacaa ggactcaagg ggtttattca ataaaaagct tatttcccac    780
atgaaagatg gtgcatactt ggtgaatacc gctagaggtg ctatttgtgt cgcagaagat    840
gttgccgagg cagtcaagtc tggtaaattg gctggctatg gtggtgatgt ctgggataag    900
caaccagcac caaagaccca tccctggagg actatggaca ataaggacca cgtgggaaac    960
gcaatgactg ttcatatcag tggcacatct ctggatgctc aaaagaggta cgctcaggga   1020
gtaaagaaca tcctaaatag ttacttttcc aaaaagtttg attaccgtcc acaggatatt   1080
attgtgcaga atggttctta tgccaccaga gcttatggac agaagaaa                1128
```

<210> SEQ ID NO 278
<211> LENGTH: 376
<212> TYPE: PRT
<213> ORGANISM: S. cerevisiae

<400> SEQUENCE: 278

```
Met Ser Lys Gly Lys Val Leu Leu Val Leu Tyr Glu Gly Gly Lys His
1               5                   10                  15

Ala Glu Glu Gln Glu Lys Leu Leu Gly Cys Ile Glu Asn Glu Leu Gly
                20                  25                  30

Ile Arg Asn Phe Ile Glu Glu Gln Gly Tyr Glu Leu Val Thr Thr Ile
            35                  40                  45

Asp Lys Asp Pro Glu Pro Thr Ser Thr Val Asp Arg Glu Leu Lys Asp
        50                  55                  60

Ala Glu Ile Val Ile Thr Thr Pro Phe Phe Pro Ala Tyr Ile Ser Arg
65                  70                  75                  80

Asn Arg Ile Ala Glu Ala Pro Asn Leu Lys Leu Cys Val Thr Ala Gly
                85                  90                  95

Val Gly Ser Asp His Val Asp Leu Glu Ala Ala Asn Glu Arg Lys Ile
            100                 105                 110

Thr Val Thr Glu Val Thr Gly Ser Asn Val Val Ser Val Ala Glu His
        115                 120                 125

Val Met Ala Thr Ile Leu Val Leu Ile Arg Asn Tyr Asn Gly Gly His
    130                 135                 140

Gln Gln Ala Ile Asn Gly Glu Trp Asp Ile Ala Gly Val Ala Lys Asn
145                 150                 155                 160

Glu Tyr Asp Leu Glu Asp Lys Ile Ile Ser Thr Val Gly Ala Gly Arg
                165                 170                 175

Ile Gly Tyr Arg Val Leu Glu Arg Leu Val Ala Phe Asn Pro Lys Lys
            180                 185                 190

Leu Leu Tyr Tyr Asp Tyr Gln Glu Leu Pro Ala Glu Ala Ile Asn Arg
        195                 200                 205

Leu Asn Glu Ala Ser Lys Leu Phe Asn Gly Arg Gly Asp Ile Val Gln
    210                 215                 220

Arg Val Glu Lys Leu Glu Asp Met Val Ala Gln Ser Asp Val Val Thr
225                 230                 235                 240

Ile Asn Cys Pro Leu His Lys Asp Ser Arg Gly Leu Phe Asn Lys Lys
                245                 250                 255

Leu Ile Ser His Met Lys Asp Gly Ala Tyr Leu Val Asn Thr Ala Arg
            260                 265                 270

Gly Ala Ile Cys Val Ala Glu Asp Val Ala Glu Ala Val Lys Ser Gly
```

```
            275                 280                 285
Lys Leu Ala Gly Tyr Gly Gly Asp Val Trp Asp Lys Gln Pro Ala Pro
    290                 295                 300
Lys Asp His Pro Trp Arg Thr Met Asp Asn Lys Asp His Val Gly Asn
305                 310                 315                 320
Ala Met Thr Val His Ile Ser Gly Thr Ser Leu Asp Ala Gln Lys Arg
                325                 330                 335
Tyr Ala Gln Gly Val Lys Asn Ile Leu Asn Ser Tyr Phe Ser Lys Lys
            340                 345                 350
Phe Asp Tyr Arg Pro Gln Asp Ile Ile Val Gln Asn Gly Ser Tyr Ala
        355                 360                 365
Thr Arg Ala Tyr Gly Gln Lys Lys
    370                 375
```

<210> SEQ ID NO 279
<211> LENGTH: 1158
<212> TYPE: DNA
<213> ORGANISM: B. stabilis

<400> SEQUENCE: 279

```
atggctaccg ttttgtgtgt cttgtatcca gatccagttg atggttatcc accacattat      60
gttagagata ccattccagt tattaccaga tacgctgatg tcaaactgc tccaactcca      120
gctggtccac caggttttag accaggtgaa ttggttggtt ctgtttctgg tgctttgggt     180
ttgagaggtt atttggaagc tcatggtcat actttgatcg ttacctctga taaggatggt    240
ccagattctg aattcgaaag aagattgcca gacgccgatg ttgttatttc tcaaccattt    300
tggccagctt acttgaccgc tgaaagaatt gctagagcac aaaattgag attggctttg     360
actgctggta ttggttctga tcatgttgat ttggatgctg ctgctagagc ccatattact    420
gttgctgaag ttactggttc caactctatt tcagttgccg aacacgttgt tatgactact    480
ttggctttgg tcagaaacta cttgccatct catgctattg ctcaacaagg tggttggaat    540
attgctgatt gtgtctctag atcctacgat gttgaaggta tgcattttgg tactgttggt    600
gctggtagaa ttggtttggc tgttttgaga agattgaagc catttggttt acacttgcac    660
tacacccaaa gacatagatt ggatgcagct atcgaacaag aattgggttt aacttatcat    720
gctgatccag cttcattggc tgctgctgtt gatatagtta acttgcaaat cccattatac    780
ccatccaccg aacatttgtt tgatgctgct atgattgcta gaatgaagag aggtgcatac    840
ttgattaaca ccgctagagc taaattggtt gatagagatg ctgttgttag agctgttact    900
tctggtcatt tggctggtta tggtggtgat gtttggtttc cacaaccagc tccagctgat    960
catccttgga gagctatgcc ttttaatggt atgactccac atatctccgg tacatctttg   1020
tctgctcaag ctagatatgc tgctggtact ttggaaatat gcaatgttg gtttgacggt    1080
agaccaatca gaaacgaata tttgattgtc gacggtggta ctttagctgg tactggtgct   1140
caatcttaca gattaact                                                 1158
```

<210> SEQ ID NO 280
<211> LENGTH: 386
<212> TYPE: PRT
<213> ORGANISM: B. stabilis

<400> SEQUENCE: 280

```
Met Ala Thr Val Leu Cys Val Leu Tyr Pro Asp Pro Val Asp Gly Tyr
1               5                   10                  15
```

Pro Pro His Tyr Val Arg Asp Thr Ile Pro Val Ile Thr Arg Tyr Ala
                20                  25                  30

Asp Gly Gln Thr Ala Pro Thr Pro Ala Gly Pro Pro Gly Phe Arg Pro
            35                  40                  45

Gly Glu Leu Val Gly Ser Val Ser Gly Ala Leu Gly Leu Arg Gly Tyr
        50                  55                  60

Leu Glu Ala His Gly His Thr Leu Ile Val Thr Ser Asp Lys Asp Gly
65                  70                  75                  80

Pro Asp Ser Glu Phe Glu Arg Arg Leu Pro Asp Ala Asp Val Val Ile
                85                  90                  95

Ser Gln Pro Phe Trp Pro Ala Tyr Leu Thr Ala Glu Arg Ile Ala Arg
            100                 105                 110

Ala Pro Lys Leu Arg Leu Ala Leu Thr Ala Gly Ile Gly Ser Asp His
        115                 120                 125

Val Asp Leu Asp Ala Ala Arg Ala His Ile Thr Val Ala Glu Val
    130                 135                 140

Thr Gly Ser Asn Ser Ile Ser Val Ala Glu His Val Val Met Thr Thr
145                 150                 155                 160

Leu Ala Leu Val Arg Asn Tyr Leu Pro Ser His Ala Ile Ala Gln Gln
                165                 170                 175

Gly Gly Trp Asn Ile Ala Asp Cys Val Ser Arg Ser Tyr Asp Val Glu
            180                 185                 190

Gly Met His Phe Gly Thr Val Gly Ala Gly Arg Ile Gly Leu Ala Val
        195                 200                 205

Leu Arg Arg Leu Lys Pro Phe Gly Leu His Leu His Tyr Thr Gln Arg
210                 215                 220

His Arg Leu Asp Ala Ala Ile Glu Gln Glu Leu Gly Leu Thr Tyr His
225                 230                 235                 240

Ala Asp Pro Ala Ser Leu Ala Ala Val Asp Ile Val Asn Leu Gln
                245                 250                 255

Ile Pro Leu Tyr Pro Ser Thr Glu His Leu Phe Asp Ala Ala Met Ile
            260                 265                 270

Ala Arg Met Lys Arg Gly Ala Tyr Leu Ile Asn Thr Ala Arg Ala Lys
        275                 280                 285

Leu Val Asp Arg Asp Ala Val Val Arg Ala Val Thr Ser Gly His Leu
290                 295                 300

Ala Gly Tyr Gly Gly Asp Val Trp Phe Pro Gln Pro Ala Pro Ala Asp
305                 310                 315                 320

His Pro Trp Arg Ala Met Pro Phe Asn Gly Met Thr Pro His Ile Ser
                325                 330                 335

Gly Thr Ser Leu Ser Ala Gln Ala Arg Tyr Ala Ala Gly Thr Leu Glu
            340                 345                 350

Ile Leu Gln Cys Trp Phe Asp Gly Arg Pro Ile Arg Asn Glu Tyr Leu
        355                 360                 365

Ile Val Asp Gly Gly Thr Leu Ala Gly Thr Gly Ala Gln Ser Tyr Arg
370                 375                 380

Leu Thr
385

<210> SEQ ID NO 281
<211> LENGTH: 1647
<212> TYPE: DNA
<213> ORGANISM: S. cerevisiae

<400> SEQUENCE: 281

-continued

```
atgtcccctt ctaaaatgaa tgctacagta ggatctactt ccgaagttga caaaaaatc      60
agacaagaat tggctcttag tgacgaagtc accaccatca gacgcaatgc tccagctgcc    120
gttttgtatg aagatggtct aaaagaaaat aaaactgtca tttcatcaag cggtgcattg    180
atcgcttatt ccggtgttaa aaccggaaga tctccaaagg acaaacgtat tgttgaagaa    240
cctacctcga aagacgaaat ttggtggggt ccggtcaata accatgttc tgaaagaaca     300
tggtctatca accgtgaaag agctgcagat tacttgagaa caagagacca catttatatt    360
gtcgatgcat ttgcaggatg ggatccaaaa tacagaatca agtccgcgt tgtttgtgcc     420
agggcttacc acgctttatt catgacaaat atgcttatta gacctacaga agaagaatta    480
gcccattttg agaacctga ttttactgtc tggaacgctg gtcagttccc agccaattta     540
cacacccagg atatgtcttc aaagagtact atagaaatta acttcaaagc aatgaaatg     600
atcattttag gtaccgaata cgccggtgaa atgaaaaaag gtattttcac agttatgttt    660
tacttgatgc ctgtgcacca taacgtttta actttgcact cttccgccaa ccagggtatt    720
caaaacggtg acgttacttt attctttggc ctaagtggta ccgggaaaac cactttatcc    780
gcagacccac atagattgtt gatcggcgat gatgaacatt gttggtccga ccatggtgtc    840
ttcaatatcg aaggtggttg ttacgccaag tgtattaatt tatctgccga aaaggagcct    900
gaaattttcg acgctatcaa gtttggttct gtattagaaa acgttatcta tgacgagaag    960
tcgcatgtag tcgactatga cgactcttct attactgaaa atactagatg tgcctaccca   1020
attgactaca ttccaagtgc caagattcca tgtttggcgg actctcatcc aaagaacatt   1080
atcctgctaa cttgtgatgc ttcgggtgtt ttaccaccag tatctaaatt gactcctgaa   1140
caagtcatgt accatttcat ctctggttac acttctaaaa tggctggtac tgagcaaggt   1200
gtcactgaac ctgaaccaac attttcatct tgtttcggac aacccttcct agccttgcac   1260
cctattagat acgcaaccat gttagctaca aagatgtctc aacataaagc taatgcgtac   1320
ttaatcaaca ccggctggac tggttcttcc tacgtatctg gtggtaaacg ttgcccattg   1380
aagtacacaa gggccattct ggattctatt catgatggtt cgttagccaa tgaaacgtac   1440
gaaactttac cgattttcaa tcttcaagta cctaccaagg ttaacggtgt tccagctgag   1500
cttttgaatc ctgctaaaaa ctggtctcaa ggtgaatcca atacagagg tgcagttacc    1560
aacttggcca acttgtttgt tcaaaatttc aagatttatc aagacagagc cacaccagat   1620
gtattagccg ctggtcctca attcgag                                        1647
```

<210> SEQ ID NO 282
<211> LENGTH: 549
<212> TYPE: PRT
<213> ORGANISM: S. cerevisiae

<400> SEQUENCE: 282

```
Met Ser Pro Ser Lys Met Asn Ala Thr Val Gly Ser Thr Ser Glu Val
1               5                   10                  15

Glu Gln Lys Ile Arg Gln Glu Leu Ala Leu Ser Asp Glu Val Thr Thr
            20                  25                  30

Ile Arg Arg Asn Ala Pro Ala Ala Val Leu Tyr Glu Asp Gly Leu Lys
        35                  40                  45

Glu Asn Lys Thr Val Ile Ser Ser Gly Ala Leu Ile Ala Tyr Ser
    50                  55                  60

Gly Val Lys Thr Gly Arg Ser Pro Lys Asp Lys Arg Ile Val Glu Glu
65                  70                  75                  80
```

-continued

```
Pro Thr Ser Lys Asp Glu Ile Trp Trp Gly Pro Val Asn Lys Pro Cys
                 85                  90                  95

Ser Glu Arg Thr Trp Ser Ile Asn Arg Glu Arg Ala Ala Asp Tyr Leu
            100                 105                 110

Arg Thr Arg Asp His Ile Tyr Ile Val Asp Ala Phe Ala Gly Trp Asp
        115                 120                 125

Pro Lys Tyr Arg Ile Lys Val Arg Val Cys Ala Arg Ala Tyr His
    130                 135                 140

Ala Leu Phe Met Thr Asn Met Leu Ile Arg Pro Thr Glu Glu Leu
145                 150                 155                 160

Ala His Phe Gly Glu Pro Asp Phe Thr Val Trp Asn Ala Gly Gln Phe
                165                 170                 175

Pro Ala Asn Leu His Thr Gln Asp Met Ser Ser Lys Ser Thr Ile Glu
            180                 185                 190

Ile Asn Phe Lys Ala Met Glu Met Ile Ile Leu Gly Thr Glu Tyr Ala
        195                 200                 205

Gly Glu Met Lys Lys Gly Ile Phe Thr Val Met Phe Tyr Leu Met Pro
    210                 215                 220

Val His His Asn Val Leu Thr Leu His Ser Ser Ala Asn Gln Gly Ile
225                 230                 235                 240

Gln Asn Gly Asp Val Thr Leu Phe Phe Gly Leu Ser Gly Thr Gly Lys
                245                 250                 255

Thr Thr Leu Ser Ala Asp Pro His Arg Leu Leu Ile Gly Asp Asp Glu
            260                 265                 270

His Cys Trp Ser Asp His Gly Val Phe Asn Ile Glu Gly Gly Cys Tyr
        275                 280                 285

Ala Lys Cys Ile Asn Leu Ser Ala Glu Lys Glu Pro Glu Ile Phe Asp
    290                 295                 300

Ala Ile Lys Phe Gly Ser Val Leu Glu Asn Val Ile Tyr Asp Glu Lys
305                 310                 315                 320

Ser His Val Val Asp Tyr Asp Asp Ser Ser Ile Thr Glu Asn Thr Arg
                325                 330                 335

Cys Ala Tyr Pro Ile Asp Tyr Ile Pro Ser Ala Lys Ile Pro Cys Leu
            340                 345                 350

Ala Asp Ser His Pro Lys Asn Ile Ile Leu Leu Thr Cys Asp Ala Ser
        355                 360                 365

Gly Val Leu Pro Pro Val Ser Lys Leu Thr Pro Glu Gln Val Met Tyr
    370                 375                 380

His Phe Ile Ser Gly Tyr Thr Ser Lys Met Ala Gly Thr Glu Gln Gly
385                 390                 395                 400

Val Thr Glu Pro Glu Pro Thr Phe Ser Ser Cys Phe Gly Gln Pro Phe
                405                 410                 415

Leu Ala Leu His Pro Ile Arg Tyr Ala Thr Met Leu Ala Thr Lys Met
            420                 425                 430

Ser Gln His Lys Ala Asn Ala Tyr Leu Ile Asn Thr Gly Trp Thr Gly
        435                 440                 445

Ser Ser Tyr Val Ser Gly Gly Lys Arg Cys Pro Leu Lys Tyr Thr Arg
    450                 455                 460

Ala Ile Leu Asp Ser Ile His Asp Gly Ser Leu Ala Asn Glu Thr Tyr
465                 470                 475                 480

Glu Thr Leu Pro Ile Phe Asn Leu Gln Val Pro Thr Lys Val Asn Gly
                485                 490                 495
```

Val Pro Ala Glu Leu Leu Asn Pro Ala Lys Asn Trp Ser Gln Gly Glu
            500                 505                 510

Ser Lys Tyr Arg Gly Ala Val Thr Asn Leu Ala Asn Leu Phe Val Gln
        515                 520                 525

Asn Phe Lys Ile Tyr Gln Asp Arg Ala Thr Pro Asp Val Leu Ala Ala
    530                 535                 540

Gly Pro Gln Phe Glu
545

<210> SEQ ID NO 283
<211> LENGTH: 903
<212> TYPE: DNA
<213> ORGANISM: A. thaliana

<400> SEQUENCE: 283

| | | | | | |
|---|---|---|---|---|---|
| atgcttgatt | ggaaacctag | gcgttctgac | atgctggtgg | atccttttgg | tataggggaga | 60 |
| attgttcagg | atggccttgt | gttccgtcag | aattttttcta | ttaggtcata | tgaaataggt | 120 |
| gctgatcgct | ctgcatctat | agaaaccgtc | atgaatcatc | tgcaggaaac | ggcgcttaat | 180 |
| catgttaaga | ctgctggatt | gcttggagat | gggtttggct | ctacacctga | gatgtttaag | 240 |
| aagaacttga | tatgggttgt | cactcgtatg | caggttgtgg | ttgataaata | tcctacttgg | 300 |
| ggagatgttg | ttgaagtaga | cacctgggtc | agtcaatctg | gaagaatgg | tatgcgtcgt | 360 |
| gattggctag | ttcgggattg | taatactgga | gaaaccttaa | cacgagcatc | aagtgtgtgg | 420 |
| gtgatgatga | ataaactgac | aaggagattg | tcaaagattc | ctgaagaggt | tcgaggggaa | 480 |
| atagagccctt | attttgtgaa | ttctgatcct | gtccttgccg | aggacagcag | aaagttaaca | 540 |
| aaaattgatg | acaagactgc | tgactatgtt | cgatctggtc | tcactcctcg | atggagtgac | 600 |
| ctagatgtta | accagcatgt | gaataatgta | aagtacattg | ggtggatcct | ggagagtgct | 660 |
| ccagtgggaa | taatggagag | gcagaagctg | aaaagcatga | ctctggagta | tcggagggaa | 720 |
| tgcgggagag | acagtgtgct | tcagtccctc | actgcagtta | cgggttgcga | tatcggtaac | 780 |
| ctggcaacag | cggggggatgt | ggaatgtcag | catttgctcc | gactccagga | tggagcggaa | 840 |
| gtggtgagag | aagaacaga | gtggagtagt | aaaacaccaa | caacaacttg | gggaactgca | 900 |
| ccg | | | | | | 903 |

<210> SEQ ID NO 284
<211> LENGTH: 301
<212> TYPE: PRT
<213> ORGANISM: A. thaliana

<400> SEQUENCE: 284

Met Leu Asp Trp Lys Pro Arg Arg Ser Asp Met Leu Val Asp Pro Phe
1               5                   10                  15

Gly Ile Gly Arg Ile Val Gln Asp Gly Leu Val Phe Arg Gln Asn Phe
            20                  25                  30

Ser Ile Arg Ser Tyr Glu Ile Gly Ala Asp Arg Ser Ala Ser Ile Glu
        35                  40                  45

Thr Val Met Asn His Leu Gln Glu Thr Ala Leu Asn His Val Lys Thr
    50                  55                  60

Ala Gly Leu Leu Gly Asp Gly Phe Gly Ser Thr Pro Glu Met Phe Lys
65                  70                  75                  80

Lys Asn Leu Ile Trp Val Val Thr Arg Met Gln Val Val Val Asp Lys
                85                  90                  95

Tyr Pro Thr Trp Gly Asp Val Val Glu Val Asp Thr Trp Val Ser Gln

|  |  |  | 100 |  |  |  | 105 |  |  |  | 110 |  |
|---|---|---|---|---|---|---|---|---|---|---|---|---|

Ser Gly Lys Asn Gly Met Arg Arg Asp Trp Leu Val Arg Asp Cys Asn
     115               120              125

Thr Gly Glu Thr Leu Thr Arg Ala Ser Ser Val Trp Val Met Met Asn
130               135              140

Lys Leu Thr Arg Arg Leu Ser Lys Ile Pro Glu Val Arg Gly Glu
145               150              155              160

Ile Glu Pro Tyr Phe Val Asn Ser Asp Pro Val Leu Ala Glu Asp Ser
             165              170              175

Arg Lys Leu Thr Lys Ile Asp Asp Lys Thr Ala Asp Tyr Val Arg Ser
     180               185              190

Gly Leu Thr Pro Arg Trp Ser Asp Leu Asp Val Asn Gln His Val Asn
             195              200              205

Asn Val Lys Tyr Ile Gly Trp Ile Leu Glu Ser Ala Pro Val Gly Ile
     210               215              220

Met Glu Arg Gln Lys Leu Lys Ser Met Thr Leu Glu Tyr Arg Arg Glu
225               230              235              240

Cys Gly Arg Asp Ser Val Leu Gln Ser Leu Thr Ala Val Thr Gly Cys
             245              250              255

Asp Ile Gly Asn Leu Ala Thr Ala Gly Asp Val Glu Cys Gln His Leu
         260               265              270

Leu Arg Leu Gln Asp Gly Ala Glu Val Val Arg Gly Arg Thr Glu Trp
     275               280              285

Ser Ser Lys Thr Pro Thr Thr Thr Trp Gly Thr Ala Pro
     290               295              300

<210> SEQ ID NO 285
<211> LENGTH: 12309
<212> TYPE: DNA
<213> ORGANISM: Artificial
<220> FEATURE:
<223> OTHER INFORMATION: pMU2737

<400> SEQUENCE: 285

| | | |
|---|---|---|
| tctccgggag ctgcatgtgt cagaggtttt caccgtcatc accgaaacgc gcgagacgaa | 60 |
| agggcctcgt gatacgccta tttttatagg ttaatgtcat gataataatg gtttcttgtg | 120 |
| acattggcgc aacgaaggta tattttgttt tttgccggag gatagcagca gatcgctgca | 180 |
| caatgtccgt caagtctaac attgacactc tggggcaaaa tagaccggcg tcccggcctg | 240 |
| ctggaattta tcgctatgca tacagctgtc ggggcatacg ctttacagac ggcggtgaaa | 300 |
| cgcctgtcac aatcacacta aacaaagagt acggaaccca ctcatggata ttcgtaagat | 360 |
| taaaaaactg atcgagctgg ttgaagaatc aggcatctcc gaactggaaa tttctgaagg | 420 |
| cgaagagtca gtacgcatta gccgtgcagc tcctgccgca gtttccctg tgatgcaaca | 480 |
| agcttacgct gcaccaatga tgcagcagcc agctcaatct aacgcagccg ctccggcgac | 540 |
| cgttccttcc atggaagcgc cagcagcagc ggaaatcagt ggtcacatcg tacgttcccc | 600 |
| gatggttggt actttctacc gcaccccaag cccggacgca aaagcgttca tcgaagtggg | 660 |
| tcagaaagtc aacgtgggcg ataccctgtg catcgttgaa gccatgaaaa tgatgaacca | 720 |
| gatcgaagcg gacaaatccg gtaccgtgaa agcaattctg gtcgaaagtg acaaccggt | 780 |
| agaatttgac gagccgctgg tcgtcatcga gtaacgaggc gaacacggcc tgatggtcaa | 840 |
| ctatctctac aagctcgacg acatcgtggc caaccacgag gctctggcgc agcgcggcga | 900 |
| agtgattgcc tcgcctgctg tcaaaagcct gctcaaccag aacgacgaag gccgcagtgg | 960 |

```
cggcaatggc cagcaaggct cccggccatt cgcacagata gtgaattcaa cgcttggagg   1020
agggcgaaag tgagcaacca tcttttcgac gccatgcggg ccgccgcgcc cggtaacgca   1080
ccattcatcc ggatcgataa cacgcgcaca tggacctatg acgacgcctt cgctctttcc   1140
ggccgcattg ccagcgcgat ggacgcgctc ggcattcgcc ccggcgaccg cgttgcggtg   1200
caggtcgaga aaagtgccga ggcattgatc ctctatctcg cctgtcttcg aagcggcgcc   1260
gtctacctgc cgctcaacac cgcctatacg ctggctgagc tcgattattt tatcggcgat   1320
gcggagccgc gtttggtggt tgtcgcatcg tcggctcgag cgggcgtgga dacaatcgcc   1380 aagcccgcg gtgcgatcgt cgaaactctc gacgctgctg gcagcggctc gttgctggat   1440
ctcgcccgcg acgagccggc cgactttgtc gatgcctcgc gctccgccga tgatctggcg   1500
gcgatcctct acacgtccgg aacgacggga cgctccaagg gggcgatgct cacgcatggg   1560
aacctgctct cgaacgccct gaccttgcga gattttttggc gcgtcaccgc cggcgatcga   1620
ctgatccatg ccttgccgat cttccacacg catggactgt tcgtcgccac gaacgtcaca   1680
ctgctcgccg gcgcctcgat gttcctgctg tcgaagttcg acccggagga gatcctgtcg   1740
ctgatgccgc aggcaacgat gctgatgggc gtgccgacct tctacgtgcg cctcctgcag   1800
agcccgcgcc tcgacaagca agcggtcgcc aacatccgcc tcttcatttc cggttcggct   1860
ccactgcttg cagaaacaca taccgagttc caggcacgta ccggtcacgc cattctcgag   1920
cgctacggca tgacggaaac caatatgaac acgtccaacc cttatgaggg gaaacggatt   1980
gccggaacgg tcggcttccc gctgcctgat gtgacggtgc gcgtcaccga tcccgccacc   2040
gggctcgcgc tgccgcccga caaaccggc atgatcgaga tcaaggggcc gaacgttttc   2100
aagggctatt ggcgcatgcc cgaaaaaacc gcggccgaat tcaccgccga cggtttcttc   2160
atcagcggcg atctcggcaa gatcgaccgc gacggttatg tccacatcgt cggccgcggc   2220
aaggatctgg tgatttcggg tggatacaac atctatccga aagaggttga gggcgagatc   2280
gaccagatcg agggtgtggt tgagagcgct gtgatcggcg tgccgcatcc cgatttcgga   2340
gaaggcgtaa cggccgtcgt cgtgcgcaag cccggcgctg ccctcgatga aaaggccatc   2400
gtcagcgccc tccaggaccg gctcgcgcgc tacaaacaac ccaagcgcat catctttgca   2460
gaggacttgc cgcgcaacac gatgggtaag gttcagaaaa acatcctgcg gcagcaatac   2520
gccgatcttt ataccaggac gtaaggcgac cgcgctctct gggaggagag tgcgtcgaca   2580
tcccgcatca atcttgaaaa cagcaactgc gacgcggagg cgtcggaggg aggggaatca   2640
tgggtattga attactgtcc ataggcctgc tgatcgccat gttcatcatt gcgacgatcc   2700
agccaatcaa catgggtgcg ctcgcctttg ccggcgcctt cgtgctcggc tcgatgatca   2760
tcgggatgaa aaccaacgaa atatttgccg gctttccgag tgatctgttc ctgacgctcg   2820
tcgccgtcac ctacctcttc gccatagcgc agatcaacgg cacgatcgac tggctcgtcg   2880
aatgtgccgt ccgcctggta cgcgggcgga tcggcttgat tccctgggtg atgttccttg   2940
tcgccgccat cattactggc ttcggtgcac ttgggcctgc tgcggtcgcc attctcgcac   3000
ccgtcgcgtt gagctttgcc gtgcagtacc gcattcatcc ggtgatgatg ggtctgatgg   3060
tgatccacgg cgcgcaggca ggcggcttct cgccgatcag catctatggc ggaatcacca   3120
accagatcgt tgcgaaggcc ggcctgcctt tcgctccgac ctcgctgttt ctttccagct   3180
tcttctttaa cctggcgatc gcggtgctgg tgttcttcgt gttcggcggc gcgagggtga   3240
tgaagcacga tcccgcatca cttggcccct tgcccgaact ccatcccgag ggcgtatcgg   3300
```

```
cgtcgatcag aggccacggc ggcacgccgg caaaaccgat cagagagcat gcctatggta   3360
cggcggccga taccgcgacg acgttgcgtc tgaacaatga gagaattacc accttgatcg   3420
gcctgacggc gctcggcatc ggcgccctgg ttttcaagtt caatgttggc ctcgtcgcca   3480
tgaccgtcgc cgtcgtcctc gcgctgctgt caccgaagac ccagaaggcc gcaatcgaca   3540
aggtcagttg gtcgaccgtg ctgctgattg ccggcatcat cacctatgtc ggcgtcatgg   3600
agaaggccgg tacggtcgac tacgtggcga atggcatatc cagtctcggc atgccgctac   3660
tggtagcgct cctgctttgc tttacgggcg ccatcgtctc ggccttttgct cctcgaccg    3720
cgctgctcgg cgcgatcatc ccgcttgccg ttccattcct cctgcaaggg cacatcagcg   3780
ccatcggtgt ggtcgcggcg atcgccatct cgacgacgat cgtcgacacc agcccattct   3840
ccaccaacgg cgcccttgtc gtcgccaatg cgccggacga cagccgtgag caggtgttgc   3900
gacagctact gatctacagc gccttgatcg ctatcatcgg tccgatcgtt gcctggttgg   3960
tgttcgtcgt gcccgggctg gtttgacgac gggctgctcc cagcgaaaag tgtgccgagc   4020
cctgttcggc acacttggag accgtggatg tcccaattac ggaactcggt cttcaggaaa   4080
aataagactg ctaaagcgtc aaaaggccgg atttccggc cttttttatt actggggatc      4140
gacaaccccc ataaggtaca atccccgctt tcttcaccca tcaggacaa aaaatggaca     4200
ctcgttttgt tcaggcccat aaagaggcgc gctgggcgct ggggctgacc cttttgtatc   4260
tggcagtttg gttagtagcc gcttacttat ctggcgttgc ccccggtttt accggctttc   4320
cgcgctggtt tgagatggcc tgcatcctga cgccgctgct gtttattgga ctgtgctggg   4380
cgatggtgaa atttatctat cgcgatatcc cactggagga tgacgatgca gcttgaagta   4440
attctaccgc tggtcgccta tctggtggtg gtgttcggta tctcggttta tgcgatgcgt   4500
aaacggagca ccggcacctt ccttaatgag tatttcctcg gcagccgctc tatgggcggt   4560
attgtgctgg cgatgacgct caccgcgacc tatatcagtg ccagttcgtt tatcggcggg   4620
ccaggagctg cttataaata cgggctgggc tgggtattgc tggcgatgat tcagcttcct   4680
gcagtctggc tttcactcgg tattctcggc aagaagtttg cgattcttgc gcgccgctac   4740
aatgcagtga cgctgaacga tatgctgttt gcccgctacc agagtcgtct tctggtgtgg   4800
ctggcgagtt tgagtttgct ggttgcgttc gttggtgcga tgaccgtgca gtttatcggc   4860
ggtgcgcgcc tgctggaaac cgcggcgggt attccttatg aaaccgggct gctgattttt   4920
ggtatcagca ttgcgttata taccgccttt ggtggctttc gccagcgt gctgaacgac     4980
accatgcaag gcttgtgat gctgattggc accgttggtg gcacttttcg gggaaatgtg    5040
cgcggaaccc ctatttgttt attttttctaa atacattcaa atatgtatcc gctcatgaga   5100
caataaccct gataaatgct tcaataatat tgaaaaagga gagtatgag tattcaacat    5160
ttccgtgtcg cccttattcc cttttttgcg gcattttgcc ttcctgtttt tgctcaccca   5220
gaaacgctgg tgaaagtaaa agatgctgaa gatcagttgg gtgcacgagt gggttacatc   5280
gaactggatc tcaacagcgg taagatcctt gagagttttc gccccgaaga acgttttcca   5340
atgatgagca cttttaaagt tctgctatgt ggcgcggtat tatcccgtat tgacgccggg   5400
caagagcaac tcggtcgccg catacactat tctcagaatg acttggttga gtactcacca   5460
gtcacagaaa agcatcttac ggatggcatg acagtaagag aattatgcag tgctgccata   5520
accatgagtg ataacactgc ggccaactta cttctgacaa cgatcggagg accgaaggag   5580
ctaaccgctt ttttgcacaa catgggggat catgtaactc gccttgatcg ttgggaaccg   5640
gagctgaatg aagccatacc aaacgacgag cgtgacacca cgatgcctgt agcaatggca   5700
```

```
acaacgttgc gcaaactatt aactggcgaa ctacttactc tagcttcccg gcaacaatta    5760
atagactgga tggaggcgga taaagttgca ggaccacttc tgcgctcggc ccttccggct    5820
ggctggttta ttgctgataa atctggagcc ggtgagcgtg ggtctcgcgg tatcattgca    5880
gcactggggc cagatggtaa gccctcccgt atcgtagtta tctacacgac ggggagtcag    5940
gcaactatgg atgaacgaaa tagacagatc gctgagatag gtgcctcact gattaagcat    6000
tggtaagcga tgaaatgtga ggtgaatcag ggttttcacc cgattttgtg ctgatcagaa    6060
ttttttttct ttttccccct tgaaggggcg aagcctcatc cccatttctc tggtcaccag    6120
ccgggaaacc acgtaagctc cggcgtcacc cataacagat acggactttc tcaaaggaga    6180
gttatcaatg aacatcaaaa agtttgcaaa acaagcaaca gtattaacct ttactaccgc    6240
actgctggca ggaggcgcaa ctcaagcgtt tgcgaaagaa acgaaccaaa agccatataa    6300
ggaaacatac ggcatttccc atattacacg ccatgatatg ctgcaaatcc ctgaacagca    6360 aaaaatgaa aaatatcaag ttcctgagtt cgattcgtcc acaattaaaa atatctcttc    6420
tgcaaaaggc ctggacgttt gggacagctg gccattacaa aacgctgacg gcactgtcgc    6480
aaactatcac ggctaccaca tcgtctttgc attagccgga gatcctaaaa atgcggatga    6540
cacatcgatt tacatgttct atcaaaaagt cggcgaaact tctattgaca gctggaaaaa    6600
cgctggccgc gtctttaaag acagcgacaa attcgatgca aatgattcta tcctaaaaga    6660
ccaaacacaa gaatggtcag gttcagccac atttacatct gacggaaaaa tccgtttatt    6720
ctacactgat ttctccggta acattacgg caaacaaaca ctgacaactg cacaagttaa    6780
cgtatcagca tcagacagct cttttgaacat caacggtgta gaggattata aatcaatctt    6840
tgacggtgac ggaaaaacgt atcaaaatgt acagcagttc atcgatgaag gcaactacag    6900
ctcaggcgac aaccatacgc tgagagatcc tcactacgta aagataaag gccacaaata    6960 cttagtattt gaagcaaaca ctggaactga agatggctac caaggcgaag aatctttatt    7020
taacaaagca tactatggca aaagcacatc attcttccgt caagaaagtc aaaaacttct    7080
gcaaagcgat aaaaaacgca cggctgagtt agcaaacggc gctctcggta tgattgagct    7140
aaacgatgat tacacactga aaaaagtgat gaaaccgctg attgcatcta acacagtaac    7200
agatgaaatt gaacgcgcga acgtctttaa aatgaacggc aaatggtatc tgttcactga    7260
ctcccgcgga tcaaaaatga cgattgacgg cattacgtct aacgatattt acatgcttgg    7320
ttatgtttct aattctttaa ctggcccata caagccgctg aacaaaactg gccttgtgtt    7380
aaaaatggat cttgatccta acgatgtaac ctttacttac tcacacttcg ctgtacctca    7440
agcgaaagga aacaatgtcg tgattacaag ctatatgaca aacagaggat tctacgcaga    7500
caaacaatca acgtttgcgc ctagcttcct gctgaacatc aaaggcaaga aaacatctgt    7560
tgtcaaagac agcatccttg aacaaggaca attaacagtt aacaaataac caggagctat    7620
ttaatggcaa cagttaacca gctggtacgc aaaccacgtg ctcgcaaagt tgcgaaaagc    7680
aacgtgcctg cgctggaagc atgcccgcaa aaacgtggcg tatgtactcg tgtatatact    7740
accactccta aaaaaccgaa ctccgcgctg cgtaaagtat gccgtgttcg tctgactaac    7800
ggtttcgaag tgacttccta catcggtggt gaaggtcaca acctgcagga gcactccgtg    7860
atcctgatcc gtggcggtcg tgttaaagac ctcccgggtg ttcgttacca caccgtacgt    7920
ggtgcgcttg actgctccgg cgttaaagac cgtaagcagg ctcgttccaa gtatggcgtg    7980
aagcgtccta aggcttaatg gttctccgtt aagtaaggcc aaatagagga tctgaagatc    8040
```

```
agcagttcaa cctgttgata gtacgtacta agctctcatg tttcacgtac taagctctca    8100
tgtttaacgt actaagctct catgtttaac gaactaaacc ctcatggcta acgtactaag    8160
ctctcatggc taacgtacta agctctcatg tttcacgtac taagctctca tgtttgaaca    8220
ataaaattaa tataaatcag caacttaaat agcctaag gttttaagtt ttataagaaa       8280
aaaaagaata tataaggctt ttaaagcttt taaggtttaa cggttgtgga caacaagcca    8340
gggatgtaac gcactgagaa gcccttagag cctctcaaag caattttcag tgacacagga    8400
acacttaacg gctgacagac gctgccgcaa gcactcaggg cgcaagggct gctaaaggaa    8460
gcggaacacg tagaaagcca gtccgcagaa acggtgctga ccccggatga atgtcagcta    8520
ctgggctatc tggacaaggg aaaacgcaag cgcaaagaga aagcaggtag cttgcagtgg    8580
gcttacatgg cgatagctag actgggcggt tttatggaca gcaagcgaac cggaattgcc    8640
agctggggcg ccctctggta aggttgggaa gccctgcaaa gtaaactgga tggcttttctt   8700
gccgccaagg atctgatggc gcaggggatc aagatctgat caagagacag gatgaggatc    8760
gtttcgcatg attgaacaag atggattgca cgcaggttct ccggccgctt gggtggagag    8820
gctattcggc tatgactggg cacaacagac aatcggctgc tctgatgccg ccgtgttccg    8880
gctgtcagcg caggggcgcc cggttctttt tgtcaagacc gacctgtccg gtgccctgaa    8940
tgaactccaa gacgaggcag cgcggctatc gtggctggcc acgacgggcg ttccttgcgc    9000
agctgtgctc gacgttgtca ctgaagcggg aagggactgg ctgctattgg gcgaagtgcc    9060
ggggcaggat ctcctgtcat ctcaccttgc tcctgccgag aaagtatcca tcatggctga    9120
tgcaatgcgg cggctgcata cgcttgatcc ggctacctgc ccattcgacc accaagcgaa    9180
acatcgcatc gagcgagcac gtactcggat ggaagccggt cttgtcgatc aggatgatct    9240
ggacgaagag catcaggggc tcgcgccagc cgaactgttc gccaggctca aggcgcggat    9300
gcccgacggc gaggatctcg tcgtgaccca tggcgatgcc tgcttgccga atatcatggt    9360
ggaaaatggc cgcttttctg gattcatcga ctgtggccgg ctgggtgtgg cggaccgcta    9420
tcaggacata gcgttggcta cccgtgatat tgctgaagag cttggcggcg aatgggctga    9480
ccgcttcctc gtgctttacg gtatcgccgc tcccgattcg cagcgcatcg ccttctatcg    9540
ccttcttgac gagttcttct gaattccgga tccgaagagg cccgcaccga tcgcccttcc    9600
caacagttgc gcagcctgaa tggcgaatgg cgcctgatgc ggtatttct ccttacgcat     9660
ctgtgcggta tttcacaccg catagggtaa taactgatat aattaaattg aagctctaat    9720
ttgtgagttt agtatacatg catttactta taatacagtt ttttagtttt gctggccgca    9780
tcttctcaaa tatgcttccc agcctgcttt tctgtaacgt tcaccctcta ccttagcatc    9840
ccttcccttt gcaaatagtc ctcttccaac aataataatg tcagatcctg tagagaccac    9900
atcatccacg gttctatact gttgacccaa tgcgtctccc ttgtcatcta aacccacacc    9960
gggtgtcata atcaaccaat cgtaaccttc atctcttcca cccatgtctc tttgagcaat    10020
aaagccgata acaaaatctt tgtcgctctt cgcaatgtca acagtaccct tagtatattc    10080
tccagtagat agggagccct tgcatgacaa ttctgctaac atcaaaaggc ctctaggttc    10140
ctttgttact tcttctgccg cctgcttcaa accgctaaca atacctgggc ccaccacacc    10200
gtgtgcattc gtaatgtctg cccattctgc tattctgtat acacccgcag agtactgcaa    10260
tttgactgta ttaccaatgt cagcaaattt tctgtcttcg aagagtaaaa aattgtactt    10320
ggcggataat gcctttagcg gcttaactgt gccctccatg gaaaaatcag tcaagatatc    10380
cacatgtgtt tttagtaaac aaattttggg acctaatgct tcaactaact ccagtaattc    10440
```

```
cttggtggta cgaacatcca atgaagcaca caagtttgtt tgcttttcgt gcatgatatt    10500
aaatagcttg gcagcaacag gactaggatg agtagcagca cgttccttat atgtagcttt    10560
cgacatgatt tatcttcgtt tcggttttg ttctgtgcag ttgggttaag aatactgggc     10620
aatttcatgt ttcttcaaca ctacatatgc gtatatatac caatctaagt ctgtgctcct    10680
tccttcgttc ttccttctgt tcggagatta ccgaatcaaa aaatttcaa agaaaccgaa      10740 atcaaaaaaa agaataaaaa aaaaatgatg aattgaaaag ctcttgttac ccatcattga     10800
attttgaaca tccgaacctg ggagttttcc ctgaaacaga tagtatattt gaacctgtat     10860
aataatatat agtctagcgc tttacggaag acaatgtatg tatttcggtt cctggagaaa    10920
ctattgcatc tattgcatag gtaatcttgc acgtcgcatc cccggttcat tttctgcgtt    10980
tccatcttgc acttcaatag catatctttg ttaacgaagc atctgtgctt cattttgtag    11040
aacaaaaatg caacgcgaga gcgctaattt ttcaaacaaa gaatctgagc tgcattttta    11100
cagaacagaa atgcaacgcg aaagcgctat tttaccaacg aagaatctgt gcttcatttt    11160
tgtaaaacaa aaatgcaacg cgagagcgct aattttttcaa acaaagaatc tgagctgcat   11220
ttttacagaa cagaaatgca acgcgagagc gctattttac caacaaagaa tctatacttc    11280
ttttttgttc tacaaaaatg catcccgaga gcgctatttt tctaacaaag catcttagat    11340
tacttttttt ctcctttgtg cgctctataa tgcagtctct tgataacttt ttgcactgta    11400
ggtccgttaa ggttagaaga aggctacttt ggtgtctatt ttctcttcca taaaaaaagc    11460
ctgactccac ttcccgcgtt tactgattac tagcgaagct gcgggtgcat tttttcaaga    11520
taaaggcatc cccgattata ttctataccg atgtggattg cgcatacttt gtgaacagaa    11580
agtgatagcg ttgatgattc ttcattggtc agaaaattat gaacggtttc ttctattttg    11640
tctctatata ctacgtatag gaaatgttta cattttcgta ttgttttcga ttcactctat    11700
gaatagttct tactacaatt ttttttgtcta aagagtaata ctagagataa acataaaaaa    11760
tgtagaggtc gagtttagat gcaagttcaa ggagcgaaag gtggatgggt aggttatata    11820
gggatatagc acagagatat atagcaaaga gatactttg agcaatgttt gtggaagcgg      11880
tattcgcaat attttagtag ctcgttacag tccggtgcgt ttttggtttt ttgaaagtgc    11940
gtcttcagag cgcttttggt tttcaaaagc gctctgaagt tcctatactt tctagctaga    12000
gaataggaac ttcggaatag gaacttcaaa gcgtttccga aaacgagcgc ttccgaaaat    12060
gcaacgcgag ctgcgcacat acagctcact gttcacgtcg cacctatatc tgcgtgttgc    12120
ctgtatatat atatacatga gaagaacggc atagtgcgtg tttatgctta aatgcgttat    12180
ggtgcactct cagtacaatc tgctctgatg ccgcatagtt aagccagccc cgacacccgc    12240
caacacccgc tgacgcgccc tgacgggctt gtctgctccc ggcatccgct tacagacaag    12300
ctgtgaccg                                                            12309
```

<210> SEQ ID NO 286
<211> LENGTH: 8500
<212> TYPE: DNA
<213> ORGANISM: Artificial
<220> FEATURE:
<223> OTHER INFORMATION: pMU2898

<400> SEQUENCE: 286

```
cagggggggcg agcctatgg aaaaacgcca gcaacgcggc cttttacgg ttcctggcct       60 tttgctggcc ttttgtgagc cgtttatttt ttctacccat atccttgaag cggtgttata     120
```

-continued

```
atgccgcgcc ctcgatatgg ggattttaa cgacctgatt ttcgggtctc agtagtagtt    180
gacattagcg gagcactaaa atgtcacaaa ttgaaaagat acaaaattta aaaaacatga    240
aaaaaactat agctaaaggc ggcggagaag agaaaatagc aaaaagacac gcagatggaa    300
agctttctgc cagagaaaga atccatttgt tgtttgatga aaacagtttt gttgaggtag    360
atgcattcat agaatccaga tgctttgact ttggtatgca gaagaagaaa cttccaggtg    420
acggggttgt taccggttac ggaacagtta atggcagaaa ggtctttgtt tcatcacagg    480
actttactgt tataggcggt tcattgggag agatgcacgc aaagaaaatt acaaaggtta    540
tggatatggc tctgaaaatg ggagcaccgt tcatagccat taatgattcc ggcggagctc    600
gtattgagga aggtctggat gctctttcag gttacggaga tattttttac aggaatactc    660
ttgcatcagg cgttattccg cagatatcag taataatggg gccatgtgca ggtggtgcgg    720
tatattcccc ggccataact gattttatat tcatggtgga aaaaacaagt cagatgttta    780
ttacaggccc acaggtaata aagtctgtta cgggtgaaga tgtatcagtt gaaaatctgg    840
gaggtgcaga tgttcatact gctacaagcg gtgtagcaca tttcaaatct tcaagcgaag    900
aagagtgtat agaagatata aagaggcttt taagttttat tcccgataat aatgtatcag    960
atactatgta ctacgagtg tctgatgctg ccgacagatt agccgaaagc ctcaacagca   1020
ttattccaga agagtcaaac aagccatatg acatgtttga cgtaatagca gaagtagtag   1080
atgatggaga tttctttgaa gttcagagtt atttctctca gaatataata tcggatttg    1140 caagaatgaa tggcagaagt gttggtattg ttgcaaacca gcctaagata atggcagggt   1200
cactagatat gaacgcggct gataaggcgg cacgtttcgt tcgtttctgt gatgcattta   1260
atattcctgt cgtttcatta accgatgtac ctgcattcct gcccggggta gcccaggagc   1320
ataacggcat aatacgtcac ggtgcaaaac tcctatatgc tttctctgaa gcaacagtac   1380
caaagataaa tgttattctt agaaaggcat atggaggagc atatattgct atgaacagta   1440
aaacaatagg tgccgatatg gttttggcat ggccatcagc tgaaattgca gttatgggac   1500
ctgacggagc agcaaatatt atatttaaaa aggatattgc tgcgtcggaa gatccagcag   1560
aaaccagaaa ggaaaagatt gcggaatata gagataaatt ctcaaatcct tatgtagcag   1620
catcaagagg gtatattgat gatgttatcg agccttctga aaccagagta aaaattataa   1680
ctgctctgga aatgctggat acaaagaggg aaaacaggcc ttcaaaaaaa catgaaaaca   1740
ttccgctata atatagtata ggaaacaaaa tatctggagg atgagtgtaa tgagtaaata   1800
tataataaag gtaaacggaa ctccttatga agtagaggtt gaagaagtgg gcgggggaag   1860
gcccatttca gctgctccaa agctaagagc taccaagccg ggacatacct ctgctgcaaa   1920
agcagcacag ccgcaggcag gtaaagcagg tgatgttgct gctccaatgc cgggaactgt   1980 tttaaggta aaggttgcta tcggtgatga agtaaagaag gggcaggtac ttttaatact   2040
tgaagctatg aaaatggaga atgaaatagt tgctccggct gacggtaaag ttacggcgtt   2100
aaacgtcgag gccggaaagt ctgttactgc tggagaacta atggtgtcta tagcctaaaa   2160
ggctgactta ccgcaaagga gatggaaaaa tgccaggcgt aagaattacg gaaacagttt   2220
taagagatgc tcaccagtcc cttatagcaa ccagaatgaa gaccgaagaa atgcttccaa   2280
ttgttgagaa gcttgacaat attggttacc attcactgga agcttggggc ggagctactt   2340
ttgactcatg tatgagattt ttgaatgaag atccatggat gagacttaga aaaataaaag   2400
atgttgcaaa gaaaacacct ctgcaaatgc ttccttaggg ccagaacctt ttaggataca   2460
aacactatgc cgatgatata gttgagtact ttgttcagaa ggctgttgca aacggcatgg   2520
```

```
acattatgag aatattcgat gcactaaatg atgccaggaa tatcgagacg gcaattaagg    2580
catgtaaaaa ggaaggcggc catgctcagg gctgtatttg ctatactata agtcctgttc    2640
acaatcttga gcttttttgta aaagatgcaa agcagttgga gagcatggga gcagattcta   2700
tctgtataaa agacatggcc ggacttctgg tgccgtatca ggcttatgaa ctggtaaagg    2760
ctttgaaaga aagtgtaaag ataccgatac aattgcacac tcactatact agcggtgtag    2820
catctatgac gtatttgaag gctatagaag caggtataga tattgttgac tgtgcaattt    2880
cacctatgtc aatgggaacg tcacagccgc ctacagagcc tttggtggca acttttaaagg   2940 gaactgattt cgatactgga ctggatttgg aaaaactcag tgaaattgca gactatttca    3000
gaccccttaa agaaaaatat attgagagcg gactattaga cgttaaggta atgggtgttg    3060
acgttaacac tcttatttat caggtacctg gtggaatgct ttcaaatctt gtttcacaat    3120
tgaagcagtc aaatgctttg gataaatatg aagaggttct caaggaagtt cccagagtaa    3180
gagccgattt cggctatcct ccgcttgtaa caccatcaag tcagatagtt ggtacccaag    3240
cggtacttaa tgtattgact ggtgagagat acaagatggt accaaaggaa tcaaaaggcg    3300
ttgtaaaggg ggaatacggt aaaacccctg cacctattag tgatgaaata aaagctaaga    3360
ttctgggcga tgaaaagcct ataacatgca gacctgctga ccttattgaa cctgagcttg    3420
aaaagattag agaagctgtt aaggattata tagagcagga tgaagatgta ctttcatacg    3480
caatgcttcc tcaggttgcc gagaagttct ttaaacagcg tattgaggat agaaataagg    3540
ctactgcacc cgcatcagac gaaataaaac ccgaagttgt agcggcaata tcagccgtag    3600
taaacgaaat gggcgaaaga gacggcacac agtacagaat cggaaatatc tctaagttga    3660
accagaatca gaacagatgg agtctgtatg gtatgcttga tagattcaga acaaaaattt    3720
aacggccgta aaacgaaagg ctcagtcgaa agactgggcc tttcgtttta tctgttgttt    3780
gtcggtgaac gctctcctga gtaggacaaa tccgccggga gcggatttga acgttgcgaa    3840
gcaacggccc ggagggtggc gggcaggacg cccgccataa actgccaggc atcaaattaa    3900
gcagaaggcc atcctgacgg atggcctttt tgcgtttcta caaactcttc ctgtcgtcat    3960
atctacaagc catcccccca cagatacggt aaactagcct cgttttttgca tcaggaaagc    4020 agctatgaac cactccttat aattaaattg aagctctaat ttgtgagttt agtatacatg    4080
catttactta taatacagtt ttttagtttt gctggccgca tcttctcaaa tatgcttccc    4140
agcctgcttt tctgtaacgt tcaccctcta ccttagcatc ccttccctt gcaaatagtc    4200 ctcttccaac aataataatg tcagatcctg tagagaccac atcatccacg gttctatact    4260
gttgacccaa tgcgtctccc ttgtcatcta aacccacacc gggtgtcata atcaaccaat    4320
cgtaaccttc atctcttcca cccatgtctc tttgagcaat aaagccgata acaaaatctt    4380
tgtcgctctt cgcaatgtca acagtaccct tagtatattc tccagtagat agggagccct    4440
tgcatgacaa ttctgctaac atcaaaaggc ctctaggttc ctttgttact tcttctgccg    4500
cctgcttcaa accgctaaca atacctgggc ccaccacacc gtgtgcattc gtaatgtctg    4560
cccattctgc tattctgtat acacccgcag agtactgcaa tttgactgta ttaccaatgt    4620
cagcaaattt tctgtcttcg aagagtaaaa aattgtactt ggcggataat gcctttagcg    4680
gcttaactgt gccctccatg gaaaaatcag tcaagatatc cacatgtgtt tttagtaaac    4740
aaattttggg acctaatgct tcaactaact ccagtaattc cttggtggta cgaacatcca    4800
atgaagcaca caagtttgtt tgcttttcgt gcatgatatt aaatagcttg gcagcaacag    4860
```

```
gactaggatg agtagcagca cgttccttat atgtagcttt cgacatgatt tatcttcgtt    4920
tcggttttttg ttctgtgcag ttgggttaag aatactgggc aatttcatgt ttcttcaaca    4980
ctacatatgc gtatatatac caatctaagt ctgtgctcct tccttcgttc ttccttctgt    5040
tcggagatta ccgaatcaaa aaatttcaa agaaaccgaa atcaaaaaaa agaataaaaa    5100
aaaaatgatg aattgaaaag ctcttgttac ccatcattga attttgaaca tccgaacctg    5160
ggagttttcc ctgaaacaga tagtatattt gaacctgtat aataatatat agtctagcgc    5220
tttacggaag acaatgtatg tatttcggtt cctggagaaa ctattgcatc tattgcatag    5280
gtaatcttgc acgtcgcatc cccggttcat tttctgcgtt tccatcttgc acttcaatag    5340
catatctttg ttaacgaagc atctgtgctt cattttgtag aacaaaaatg caacgcgaga    5400
gcgctaattt ttcaaacaaa gaatctgagc tgcattttta cagaacagaa atgcaacgcg    5460
aaagcgctat tttaccaacg aagaatctgt gcttcatttt tgtaaaacaa aaatgcaacg    5520
cgagagcgct aatttttcaa acaaagaatc tgagctgcat tttacagaa cagaaatgca    5580
acgcgagagc gctattttac caacaaagaa tctatacttc ttttttgttc tacaaaaatg    5640
catcccgaga gcgctatttt tctaacaaag catcttagat tactttttttt ctcctttgtg    5700
cgctctataa tgcagtctct tgataacttt ttgcactgta ggtccgttaa ggttagaaga    5760
aggctacttt ggtgtctatt ttctcttcca taaaaaaagc ctgactccac ttcccgcgtt    5820
tactgattac tagcgaagct gcgggtgcat tttttcaaga taaaggcatc cccgattata    5880
ttctataccg atgtggattg cgcatacttt gtgaacagaa agtgatagcg ttgatgattc    5940
ttcattggtc agaaaattat gaacggtttc ttctatttttg tctctatata ctacgtatag    6000
gaaatgttta cattttcgta ttgttttcga ttcactctat gaatagttct tactacaatt    6060
tttttgtcta aagagtaata ctagagataa acataaaaaa tgtagaggtc gagtttagat    6120
gcaagttcaa ggagcgaaag gtggatgggt aggttatata gggatatagc acagagatat    6180
atagcaaaga gatactttg agcaatgttt gtggaagcgg tattcgcaat attttagtag    6240
ctcgttacag tccggtgcgt ttttggtttt ttgaaagtgc gtcttcagag cgcttttggt    6300
tttcaaaagc gctctgaagt tcctatactt tctagctaga gaataggaac ttcggaatag    6360
gaacttcaaa gcgtttccga aaacgagcgc ttccgaaaat gcaacgcgag ctgcgcacat    6420
acagctcact gttcacgtcg cacctatatc tgcgtgttgc ctgtatatat atatacatga    6480
gaagaacggc atagtgcgtg tttatgctta aatgcgttat ggtgcactct cagtacaatc    6540
tgctctgatg ccgcatagtt aagccagccc cgacacccgc caacacccgc tgacgcgccc    6600
tgacgggctt gtctgctccc ggcatccgct tacagacaag ctgtgaccgt ctccgggagc    6660
tgcatgtgtc agaggttttc accgtcatca ccgaaacgcg cgagacgaaa gggcctcgtg    6720
atacgcctat ttttataggt taatgtcatg ataataatgg tttcttagac gtcaggtggc    6780
acttttcggg gaaatgtgcg cggaaccccct atttgtttat ttttctaaat acattcaaat    6840
atgtatccgc tcatgagaca ataaccctga taaatgcttc aataatattg aaaaaggaag    6900
agtatgagta ttcaacattt ccgtgtcgcc cttattccct ttttttgcggc attttgcctt    6960
cctgtttttg ctcacccaga aacgctggtg aaagtaaaag atgctgaaga tcagttgggt    7020
gcacgagtgg gttacatcga actggatctc aacagcggta agatccttga gagttttcgc    7080
cccgaagaac gttttccaat gatgagcact tttaaagttc tgctatgtgg cgcggtatta    7140
tcccgtattg acgccgggca agagcaactc ggtcgccgca tacactattc tcagaatgac    7200
ttggttgagt actcaccagt cacagaaaag catcttacgg atggcatgac agtaagagaa    7260
```

```
ttatgcagtg ctgccataac catgagtgat aacactgcgg ccaacttact tctgacaacg      7320
atcggaggac cgaaggagct aaccgctttt ttgcacaaca tgggggatca tgtaactcgc      7380
cttgatcgtt gggaaccgga gctgaatgaa gccataccaa acgacgagcg tgacaccacg      7440
atgcctgtag caatggcaac aacgttgcgc aaactattaa ctggcgaact acttactcta      7500
gcttcccggc aacaattaat agactggatg gaggcggata agttgcagg accacttctg       7560 cgctcggccc ttccggctgg ctggtttatt gctgataaat ctggagccgg tgagcgtggg      7620
tctcgcggta tcattgcagc actggggcca gatggtaagc cctcccgtat cgtagttatc      7680
tacacgacgg ggagtcaggc aactatggat gaacgaaata gacagatcgc tgagataggt      7740
gcctcactga ttaagcattg gtaactgtca gaccaagttt actcatatat actttagatt      7800
gatttaaaac ttcatttta atttaaaagg atctaggtga agatccttt tgataatctc       7860 atgaccaaaa tcccttaacg tgagttttcg ttccactgag cgtcagaccc cgtagaaaag     7920
atcaaaggat cttcttgaga tcctttttt ctgcgcgtaa tctgctgctt gcaaacaaaa      7980
aaaccaccgc taccagcggt ggtttgtttg ccggatcaag agctaccaac tcttttccg      8040 aaggtaactg gcttcagcag agcgcagata ccaaatactg tccttctagt gtagccgtag     8100
ttaggccacc acttcaagaa ctctgtagca ccgcctacat acctcgctct gctaatcctg     8160
ttaccagtgg ctgctgccag tggcgataag tcgtgtctta ccgggttgga ctcaagacga     8220
tagttaccgg ataaggcgca gcggtcgggc tgaacggggg gttcgtgcac acagcccagc     8280
ttggagcgaa cgacctacac cgaactgaga tacctacagc gtgagcattg agaaagcgcc     8340
acgcttcccg aagggagaaa ggcggacagg tatccggtaa gcggcagggt cggaacagga     8400
gagcgcacga gggagcttcc aggggggaaac gcctggtatc tttatagtcc tgtcgggttt     8460
cgccacctct gacttgagcg tcgatttttg tgatgctcgt                            8500

<210> SEQ ID NO 287
<211> LENGTH: 8563
<212> TYPE: DNA
<213> ORGANISM: Artificial
<220> FEATURE:
<223> OTHER INFORMATION: pMU2899

<400> SEQUENCE: 287
ttgagcgtcg attttgtga tgctcgtcag gggggcggag cctatggaaa aacgccagca       60
acgcggcctt tttacggttc ctggcctttt gctggccttt tgtgagccgt ttatttttc      120 tacccatatc cttgaagcgg tgttataatg ccgcgccctc gatatgggga ttttttaacga    180 cctgattttc gggtctcagt agtagttgac attagcggag cactaaaatg acaaacaagc     240
tcagagagct caagcaaaag agagaaagaa tactaaagct tggtggagaa gataaaataa     300
aaaaacagca tgatagcaaa aaacttactt gtagagagag aatagaatat ttacttgacc     360
ctggaagctt caatgaaata gatatgtttg ttgaacacag atgtcaagaa tttgatatga     420
aagatacatt tgtcccctgt gatggtgttg taacgggtta tggaacaatc aatggcagaa     480 aagttttgt ttatgctcaa gatttttact cgataggcgg ttctcttggc gagatgcatg      540
caaaaaagat ttgtaaagtt ttggacttag cattaaaata tggttgtcca gtgataggta     600
taaatgattc tggtggtgca agaattcaag aaggtgttga tgcattagca ggatatggtg     660
aaatcttcta tagaaatacc atggcatcag gtgtaattcc acaaattgca gctataatgg     720
gaccttgtgc aggtggagct gtatactctc ctgctattat ggattttatt tttatggtgg     780
```

```
acaaaaccag ccaaatgttt gttacaggac ctcaggttat aaaagctgtg actggagagg      840
agatatcctt tgaagagctt ggtggcgctt acactcacag ctcaaagagt ggagttgctc      900
attttattgc agaggatgag tatcacctac ttgatatgat aaagtattta ttgtcgttta      960
taccttcaaa taacatggaa gacccacctt ttataatgtc atctgattca gaaaaaagat     1020
ttgttcccga gctcgaaaat ataattccgc aagagccaaa caaagcttat gatgtaaaag     1080
aaataattta taaagtagta gacaaccaag aattttttaga agtacaacct tattttgctc     1140
aaaatgctgt tgtaggattt ggtagaatag ggggctttag cgtaggaatt gtagcaaatc     1200
agcccaaagt gaacgctgga gtgcttgatt atgattcgtc tgacaagata gcacgatttg     1260
taagattttg tgatgctttt aatattccca taataacatt tacagacgtg cctggatttt     1320
tgccaggtgt taaccaagag cacaatggaa taattcgtca tggggctaag gttttgtatg     1380
catactcaga ggcaacagtt ccaaagataa atgtaatttt gagaaaagca tatggtgggg     1440
cttacattgc aatgagcagc aaacacattg gtgcagactt tgtgtttgca tggccaactg     1500
ccgagatagc tgttatggga ccagatggcg cagcaaatat tatatttaga aaagagatac     1560
aaagcgctca aaatcccgaa gaggaaagaa aagaaggat agaagagtat actcaaaagt     1620
ttgcaaatcc atacattgca gctgcccgtg ggtatgttga cgatgtgatt gagccacagc     1680
ttacccgtaa caaaatcatt gaggcgctca aaatttccat tacaaaaaga gagcaaaggc     1740
cccccaaaaaa gcatggcaat attccattat aaaatgtatt tttgtaaaaa aaggagagtg     1800
tttttaaaaat gtatgctcag gtcagtacta tttcaaccat tacaaaagaa gaacttgctt     1860
gtatttgtgc atgtctgcac attgtgatgg gtgaaggtca atataaaatt accaacataa     1920
ctaaacagca aaacaagtgg gtcaaaggtg caagagaaat gatgctcaat cagtcacaga     1980
tgttttatag atggaggtaa agcttgtgat gagaaagttc aaggtgaaga tcaatagcca     2040
agaatttgtt gtagaagtgg aagaaatagg agttgaaaat gctacttctg tcgtgccaag     2100
gcctaagatt ggccatttttg agccaaaaca ggaaaaacat gaggataaaa caaaacaaag     2160
ccctgtactt tcttctgata aaaattcggt tgttgcccag cttccgggta ctattgtaag     2220
gctgctaaaa agtgaaggtg atgttgttga tgcaaatgaa cctgttttaa ttcttgaagc     2280
catgaaaatg gaaaatgaaa taactgcacc tgtcaaagga aaaattaaaa gaatacatgt     2340
aaaggaaggg cagaaggtag caaaaggaga tttgctattt gaaatagagt aagaaaaatt     2400
ttctggaggt tttaaaaata tgggggtaa aaataacaga aacaatactc agagatgctc     2460
atcagtcact cattgcaacc cgcatgacaa ctgaacagat gcttgagatt gctcctgtgc     2520
ttgaccaagt tggttattat tcggttgagt gctggggcgg tgctacattt gatgcgtgtc     2580
tgaggttttt caatgaagac ccatgggaaa gattaaaaag actgagaact gcttttaaaa     2640
agacaaagct ccagatgctt cttcgaggac aaaatcttgt tgggtataga cattattctg     2700
atgatgttgt tgaagagttt gtaaaaaagg ccatatacta tggcattgat attataagaa     2760
tatttgatgc acttaatgac atccggaata ttgaaatggc tctaaaaata acaaaaaaag     2820
aaaaaggaca tgcccaggtt gccatatcat acactgtctc accttatcat actattgaaa     2880
actatgtaaa tttggcaaaa caaatagaag aacttgggc agactcaatt tgtataaaag     2940
acatggctgg gcttctctct ccatttgatg cttataaact tgtaaaagcg ttaaaagagc     3000
aggtaaaaact tcctattcat cttcatacac actacaccac aggatttgga tcaatgacat     3060
atttgaaagc tgtcgaagca ggtgtggatg gtattgacac ggctttatct ccgcttgcac     3120
tgggcacatc ccagcctcca accgaaacaa ttgtatatgc acttgaaaat acagaatatg     3180
```

```
ctccaaaact tgatttagaa aagatcaacg aggcaagcga atattttaaa gtactcagag    3240
aagaatatat aagaaaaggg cttcttgacc cgaaagtatt aagtgttgat ataaacgctc    3300
ttcattatca aatacctggt ggaatgctat caaatcttat ttctcagcta aaagaacaag    3360
ggcaggaaga caagttagat gaggttttaa agaggtacc tgaggttcga aaagattttg     3420
gatatccgcc acttgtaact cctacgagtc aaattgtggg aacacaagct gttttgaatg    3480
ttatagcagg tgagagatac aaacttgtca caaaagaaac aaaagcatat tttaaaggtg    3540
agtatgggaa acctccagct cctgtgaatg aagaggtaaa aagaaaaatc ttgaaagacg    3600
aaaaagagat aacctgcaga cctgcagatt tgattttgcc agagcttgaa aatgcaaaag    3660
aaaagattaa ggagtatatt gaaaatgata ctgatgtggt aacttactgt ttattccctc    3720
aacttgcaga aaattttttc aaattaaggt tcgcaaaaaa atacaaggtt gacgctgatc    3780
ttgttcaggg taacaaagtg tatcctgtgt aacggccgta aaacgaaagg ctcagtcgaa    3840
agactgggcc tttcgtttta tctgttgttt gtcggtgaac gctctcctga gtaggacaaa    3900
tccgccggga gcggatttga acgttgcgaa gcaacggccc ggagggtggc gggcaggacg    3960
cccgccataa actgccaggc atcaaattaa gcagaaggcc atcctgacgg atggcctttt    4020
tgcgtttcta caaactcttc ctgtcgtcat atctacaagc catcccccca cagatacggt    4080
aaactagcct cgttttttgca tcaggaaagc agctatgaac cactccttat aattaaattg    4140
aagctctaat ttgtgagttt agtatacatg catttactta taatacagtt ttttagtttt    4200
gctggccgca tcttctcaaa tatgcttccc agcctgcttt tctgtaacgt tcaccctcta    4260
ccttagcatc ccttcccttt gcaaatagtc ctcttccaac aataataatg tcagatcctg    4320
tagagaccac atcatccacg gttctatact gttgacccaa tgcgtctccc ttgtcatcta    4380
aacccacacc gggtgtcata atcaaccaat cgtaaccttc atctcttcca cccatgtctc    4440
tttgagcaat aaagccgata acaaaatctt tgtcgctctt cgcaatgtca acagtaccct    4500
tagtatattc tccagtagat agggagccct tgcatgacaa ttctgctaac atcaaaaggc    4560
ctctaggttc ctttgttact tcttctgccg cctgcttcaa accgctaaca atacctgggc    4620
ccaccacacc gtgtgcattc gtaatgtctg cccattctgc tattctgtat acacccgcag    4680
agtactgcaa tttgactgta ttaccaatgt cagcaaattt tctgtcttcg aagagtaaaa    4740
aattgtactt ggcggataat gcctttagcg gcttaactgt gccctccatg gaaaaatcag    4800
tcaagatatc cacatgtgtt tttagtaaac aaattttggg acctaatgct tcaactaact    4860
ccagtaattc cttggtggta cgaacatcca atgaagcaca caagtttgtt tgcttttcgt    4920
gcatgatatt aaatagcttg gcagcaacag gactaggatg agtagcagca cgttccttat    4980
atgtagcttt cgacatgatt tatcttcgtt tcggttttttg ttctgtgcag ttgggttaag    5040
aatactgggc aatttcatgt ttcttcaaca ctacatatgc gtatatatac caatctaagt    5100
ctgtgctcct tccttcgttc ttccttctgt tcggagatta ccgaatcaaa aaatttcaa     5160 agaaaccgaa atcaaaaaaa agaataaaaa aaaaatgatg aattgaaaag ctcttgttac    5220
ccatcattga attttgaaca tccgaacctg ggagttttcc ctgaaacaga tagtatattt    5280
gaacctgtat aataatatat agtctagcgc tttacggaag acaatgtatg tatttcggtt    5340
cctggagaaa ctattgcatc tattgcatag gtaatcttgc acgtcgcatc cccggttcat    5400
tttctgcgtt tccatcttgc acttcaatag catatctttg ttaacgaagc atctgtgctt    5460
cattttgtag aacaaaaatg caacgcgaga gcgctaattt ttcaaacaaa gaatctgagc    5520
```

```
tgcattttta cagaacagaa atgcaacgcg aaagcgctat tttaccaacg aagaatctgt    5580
gcttcatttt tgtaaaacaa aaatgcaacg cgagagcgct aattttttcaa acaaagaatc   5640 tgagctgcat ttttacagaa cagaaatgca acgcgagagc gctattttac caacaaagaa   5700
tctatacttc ttttttgttc tacaaaaatg catcccgaga cgctatttt tctaacaaag    5760 catcttagat tactttttt ctcctttgtg cgctctataa tgcagtctct tgataacttt    5820
ttgcactgta ggtccgttaa ggttagaaga aggctacttt ggtgtctatt ttctcttcca   5880 taaaaaagc ctgactccac ttcccgcgtt tactgattac tagcgaagct gcgggtgcat    5940
tttttcaaga taaggcatc cccgattata ttctataccg atgtggattg cgcatacttt    6000
gtgaacagaa agtgatagcg ttgatgattc ttcattggtc agaaaattat gaacggtttc   6060
ttctattttg tctctatata ctacgtatag gaaatgttta catttcgta ttgttttcga    6120 ttcactctat gaatagttct tactacaatt ttttgtcta aagagtaata ctagagataa    6180
acataaaaaa tgtagaggtc gagtttagat gcaagttcaa ggagcgaaag gtggatgggt   6240
aggttatata gggatatagc acagagatat atagcaaaga gatactttg agcaatgttt    6300 gtggaagcgg tattcgcaat attttagtag ctcgttacag tccggtgcgt ttttggtttt   6360
ttgaaagtgc gtcttcagag cgcttttggt tttcaaaagc gctctgaagt tcctatactt   6420
tctagctaga gataggaac ttcggaatag gaacttcaaa gcgtttccga aaacgagcgc    6480
ttccgaaaat gcaacgcgag ctgcgcacat acagctcact gttcacgtcg cacctatatc   6540
tgcgtgttgc ctgtatatat atatacatga aagaacggc atagtgcgtg tttatgctta    6600
aatgcgttat ggtgcactct cagtacaatc tgctctgatg ccgcatagtt aagccagccc   6660
cgacacccgc caacacccgc tgacgcgccc tgacgggctt gtctgctccc ggcatccgct   6720
tacagacaag ctgtgaccgt ctccgggagc tgcatgtgtc agaggttttc accgtcatca   6780
ccgaaacgcg cgagacgaaa gggcctcgtg atacgcctat ttttataggt taatgtcatg   6840
ataataatgg tttcttagac gtcaggtggc acttttcggg gaaatgtgcg cggaacccct   6900
atttgtttat ttttctaaat acattcaaat atgtatccgc tcatgagaca ataaccctga   6960
taaatgcttc aataatattg aaaaaggaag agtatgagta ttcaacattt ccgtgtcgcc   7020
cttattccct tttttgcggc attttgcctt cctgtttttg ctcacccaga aacgctggtg   7080
aaagtaaaag atgctgaaga tcagttgggt gcacgagtgg gttacatcga actggatctc   7140
aacagcggta agatccttga gagttttcgc cccgaagaac gttttccaat gatgagcact   7200
tttaaagttc tgctatgtgg cgcggtatta tcccgtattg acgccgggca agagcaactc   7260
ggtcgccgca tacactattc tcagaatgac ttggttgagt actcaccagt cacagaaaag   7320
catcttacgg atggcatgac agtaagagaa ttatgcagtg ctgccataac catgagtgat   7380
aacactgcgg ccaacttact tctgacaacg atcggaggac cgaaggagct aaccgctttt   7440
ttgcacaaca tgggggatca tgtaactcgc cttgatcgtt gggaaccgga gctgaatgaa   7500
gccataccaa acgacgagcg tgacaccacg atgcctgtag caatggcaac aacgttgcgc   7560
aaactattaa ctggcgaact acttactcta gcttcccggc aacaattaat agactggatg   7620
gaggcggata aagttgcagg accacttctg cgctcggccc ttccggctgg ctggtttatt   7680
gctgataaat ctggagccgg tgagcgtggg tctcgcggta tcattgcagc actggggcca   7740
gatggtaagc cctcccgtat cgtagttatc tacacgacgg ggagtcaggc aactatggat   7800
gaacgaaata gacagatcgc tgagataggt gcctcactga ttaagcattg gtaactgtca   7860
gaccaagttt actcatatat actttagatt gatttaaaac ttcatttta atttaaaagg   7920
```

```
atctaggtga agatcctttt tgataatctc atgaccaaaa tcccttaacg tgagttttcg      7980
ttccactgag cgtcagaccc cgtagaaaag atcaaaggat cttcttgaga tcctttttt      8040 ctgcgcgtaa tctgctgctt gcaaacaaaa aaaccaccgc taccagcggt ggtttgtttg      8100
ccggatcaag agctaccaac tcttttccg  aaggtaactg gcttcagcag agcgcagata      8160
ccaaatactg tccttctagt gtagccgtag ttaggccacc acttcaagaa ctctgtagca      8220
ccgcctacat acctcgctct gctaatcctg ttaccagtgg ctgctgccag tggcgataag      8280
tcgtgtctta ccgggttgga ctcaagacga tagttaccgg ataaggcgca gcggtcgggc      8340
tgaacggggg gttcgtgcac acagcccagc ttggagcgaa cgacctacac cgaactgaga      8400
tacctacagc gtgagcattg agaaagcgcc acgcttcccg aagggagaaa ggcggacagg      8460
tatccggtaa cgcagggt cggaacagga gagcgcacga gggagcttcc aggggaaac       8520 gcctggtatc tttatagtcc tgtcgggttt cgccacctct gac                       8563
```

<210> SEQ ID NO 288
<211> LENGTH: 8652
<212> TYPE: DNA
<213> ORGANISM: Artificial
<220> FEATURE:
<223> OTHER INFORMATION: pMU2900

<400> SEQUENCE: 288

```
tttgtgatgc tcgtcagggg ggcggagcct atggaaaaac gccagcaacg cggcctttt       60 acggttcctg gccttttgct ggccttttgt gagccgttta ttttttctac ccatatcctt      120
gaagcggtgt tataatgccg cgccctcgat atggggattt ttaacgacct gattttcggg      180
tctcagtagt agttgacatt agcggagcac taaaatgtca atagatgata ggattgaaga      240
ccttcttaga agaagagaga tggttttaga aggcggtggt ttagataaag tagagaaaca      300
acaccaaaag ggaaagctta ccgcaagaga gaggatatac aagctttag  atgaagatag      360 cttttgtggaa atagatgcgt atgttgagca caggtgtatt gactttggca tggaaaagca      420 aaggataccct ggcgaaggcg tagtgacagg gtatgggacg atagatggaa ggcttgtcta      480
cgtttatgca caggatttta cggttttagg aggatcatta ggcgagtatc atgcaaagaa      540
aatcacaaaa atcatggata tggctttaaa gatgggagca ccgctcattg gattaaatga      600
ttccggaggt gccagaatac aggaaggcgt cgatgcttta tcgggatatg caacatatt      660 tttcagaaac acgctggcat caggcgtaat accgcaaata tcggtgataa tggggcccag      720
cgctggaggt gcagtttatt cgcctgctct tactgacttt atattcatgg tagacaagac      780
aagtcagatg tttataactg gaccgcaggt cataaaagcc gtcacaggtg aagatgtttc      840
ggcagaggag cttggtggat cgattactca cagcacgaaa agcggtgtgg cgcatttag       900 ggctgaaaac gacgaagagt gtttgaagat ggtgaggaag ctattaagtt accttccatc      960
aaacaatttg gaagatccgc cacagttggc gacagatgac gacataaaca gattttccga      1020
taggcttatt gagataatcc cagatagtcc taataagcca tacgatatga agaagtaat       1080 ttcggaaata gtggatgaag gcgtgtattt tgaatcacag gcaatgtatg cgcaaaacat      1140
aataacggca tttgcaaggc ttaatggaag gacggtaggg ataatagcaa atcagcctaa      1200
agttttggct ggatgtctcg acatcaatgc gtctgataag gcatcgaggt ttataaggtt      1260
ttgcgatgca tttaacatcc cgcttctcaa tatagtagat gttccaggat ttttgcctgg      1320
aacgaatcaa gagtacggtg gaataatacg ccatggggca aagatgttgt acgcttactc      1380
```

```
tgaggctaca gtgccaaaag tgactctcat tgtgaggaaa gcttatggcg gtgcttacct    1440
tgccatgtgc agcaaagact taggagctga ttttgttttg gcatggccta ctgctgaaat    1500
agcggtcatg ggacctgatg gggcagcaaa catcgtgttt aaaaatgaaa taaaatcgtc    1560
tgatgatcct gtggctgcaa gaaatgaaaa gataaatgag tacagggaga atttcgcaaa    1620
tccatacagg gcagcagcga gaggatatgt agatgatgta gttctgccgc aagagacgag    1680
acctcgcctc atctcggcgt tcgatatgct tatgagcaaa agggagtcaa ggcccagcaa    1740
aaagcatggc aattttcctg tttaaaatcg atttaagggg aagtgaaaga atggaagaga    1800
taaatgaaga aatagttgct gtcattgaag ctgcgattta cgcggcattt ggtcagtacg    1860
aaaagaattt ccgcatcaag gtaataaaga gagtggactc aaatatgccg gaatgggagaa   1920 aagctggcct ttacaatcag atgagataga tgaggaggat ggaaatgaaa aaatttatag    1980
taactgtcaa tggaaaaaaa tacgatgtgg aagtagaaga agtaaaagtc gacgtggcaa    2040
gtgagaaaaa agcaaagaa gatactgctg ctaaaaatgc gtcagatgca agtgtaaaaa     2100
gcaaacaggt tgaagtaaaa aacgaagtca aagacggttt ctcaatcaat gcaccgatgc    2160
cgggaactat attggatgtc aaaataagcc aaggccagac tgtcagacga ggcgatgtgc    2220
ttttaatact ggaagccatg aagatggaaa atgaaatcac gtcaccttac gatggcacaa    2280
taatatccat aaatgtttca aaaggtgcct ctgtaaatac aggcgatgtg cttttgtact    2340
taaaatgaga gtaaaggagg agttttaatg tctaagataa aaataacgga gactgtttta    2400
agagatgcac atcaatcgtt gctggcaacc agaatgacaa ccgatgaaat gcttcctata    2460
gcagaaaaat tagatgaagt tggttttttc tcgctggaag catggggcgg tgctacattt    2520
gatgcatgta tgagattttt gaatgaagac ccatgggaaa gattaagact tttaaagaag    2580
gcgattaaga agacacctct tcaaatgctt ttaagaggtc aaaatttact cggatataaa    2640
cactatcccg atgatgtcgt aaatgaattt ataataaaat ctgttgaaaa tggtatagat    2700
ataataagaa tttttgatgc gttaaatgat gtgagaaatt tagaagtgcc aataaaatct    2760
gcaaaaagtg caggtgctca tgtacaggca gctattgtat atacagttag tcctgtacat    2820
aatacagatc attatttgaa agtggcaaag tctcttcaag atatgggtgc ggattccata    2880
tgcattaagg atatgtctgg aatattatca ccctatgttg catacgattt gattaaatct    2940
ctgaaaagag cactttacac gccaattcaa ctgcatagcc attatacagc aggactggct    3000
tcaatgactt atttaaaagc catagaagct ggtgtagacg gggttgatac agctatttct    3060
tcgcttgcct taggaacatc acaaccagct acagaatcaa tcgtggctgc attgaaagat    3120
acagaatatg atacagggct agatttaaaa ttgcttgctg agatagctca gcattttaat    3180
gtagtcaaac agaatcacaa aaatgacagc gatatgtctt tgcttatgtc tgttgatgtt    3240
aaagcattag aaagtcaaat accaggggga atgttatcaa atttggtttc acagctaaag    3300
cagcagaatg cattaaacaa atatcaagac gtcttgaaag aagttccaag ggtacgcgaa    3360
gatttgggat atcctcctct tgttactcca atgagccaga tggttggaac ccaggctgtt    3420
ttaaatgtta ttacaggga gagatataaa atcgttccta agaaattaa agattatgtc      3480 aaaggtttat atgggatgcc accagctcca atttcagatt ctatacgaaa gaaaataatc    3540
ggcgatgaag aagtaatttc aaagaggcca gcagatttac taagtcctca attggatgaa    3600
tttaaaaatg agataaagga atttatagag caagatgaag atgttttatc atatgcatta    3660
tttcctcaag tagcaagaag atttttcgag tataggcaag ccaaaaaata cagaattgat    3720
tcaacattat taaatatcga agaagggtt catccgatat aacggccgta aaacgaaagg     3780
```

```
ctcagtcgaa agactgggcc tttcgtttta tctgttgttt gtcggtgaac gctctcctga    3840
gtaggacaaa tccgccggga gcggatttga acgttgcgaa gaacggccc ggagggtggc    3900 gggcaggacg cccgccataa actgccaggc atcaaattaa gcagaaggcc atcctgacgg    3960
atggcctttt tgcgtttcta caaactcttc ctgtcgtcat atctacaagc catcccccca    4020
cagatacggt aaactagcct cgttttgca tcaggaaagc agctatgaac cactcctgcg    4080
aagaggcccg caccgatcgc ccttcccaac agttgcgcag cctgaatggc gaatggcgcc    4140
tgatgcggta ttttctcctt acgcatctgt gcggtatttc acaccgcata gggtaataac    4200
tgatataatt aaattgaagc tctaatttgt gagtttagta tacatgcatt tacttataat    4260
acagtttttt agttttgctg gccgcatctt ctcaaatatg cttcccagcc tgcttttctg    4320
taacgttcac cctctacctt agcatccctt ccctttgcaa atagtcctct tccaacaata    4380
ataatgtcag atcctgtaga gaccacatca tccacggttc tatactgttg acccaatgcg    4440
tctcccttgt catctaaacc cacaccgggt gtcataatca accaatcgta accttcatct    4500
cttccaccca tgtctctttg agcaataaag ccgataacaa aatctttgtc gctcttcgca    4560
atgtcaacag tacccttagt atattctcca gtagataggg agcccttgca tgacaattct    4620
gctaacatca aaaggcctct aggttccttt gttacttctt ctgccgcctg cttcaaaccg    4680
ctaacaatac ctgggcccac cacaccgtgt gcattcgtaa tgtctgccca ttctgctatt    4740
ctgtatacac ccgcagagta ctgcaatttg actgtattac caatgtcagc aaattttctg    4800
tcttcgaaga gtaaaaaatt gtacttggcg gataatgcct ttagcggctt aactgtgccc    4860
tccatggaaa aatcagtcaa gatatccaca tgtgttttta gtaaacaaat tttgggacct    4920
aatgcttcaa ctaactccag taattccttg gtggtacgaa catccaatga agcacacaag    4980
tttgtttgct tttcgtgcat gatattaaat agcttggcag caacaggact aggatgagta    5040
gcagcacgtt cctatatgt agcttttcgac atgatttatc ttcgtttcgg ttttttgttct    5100 gtgcagttgg gttaagaata ctgggcaatt tcatgtttct tcaacactac atatgcgtat    5160
atataccaat ctaagtctgt gctccttcct tcgttcttcc ttctgttcgg agattaccga    5220
atcaaaaaaa tttcaaagaa accgaaatca aaaaaaagaa taaaaaaaaa atgatgaatt    5280
gaaaagctct tgttacccat cattgaattt tgaacatccg aacctgggag ttttccctga    5340
aacagatagt atatttgaac ctgtataata atatatagtc tagcgcttta cggaagacaa    5400
tgtatgtatt tcggttcctg gagaaactat tgcatctatt gcataggtaa tcttgcacgt    5460
cgcatccccg gttcattttc tgcgttcca tcttgcactt caatagcata tctttgttaa    5520
cgaagcatct gtgcttcatt ttgtagaaca aaaatgcaac gcgagagcgc taattttttca    5580 aacaaagaat ctgagctgca ttttacaga acagaaatgc aacgcgaaag cgcttatttta    5640 ccaacgaaga atctgtgctt cattttgta aaacaaaaat gcaacgcgag agcgctaatt    5700
tttcaaacaa agaatctgag ctgcattttt acagaacaga atgcaacgc gagagcgcta    5760 ttttaccaac aaagaatcta tacttcttt tgttctaca aaatgcatc ccgagagcgc    5820 tattttcta caaagcatc ttagattact ttttttctcc tttgtgcgct ctataatgca    5880
gtctcttgat aacttttgc actgtaggtc cgttaaggtt agaagaaggc tactttggtg    5940
tctattttct cttccataaa aaaagcctga ctccacttcc cgcgtttact gattactagc    6000
gaagctgcgg gtgcattttt tcaagataaa ggcatcccg attatattct ataccgatgt    6060
ggattgcgca tactttgtga acagaaagtg atagcgttga tgattcttca ttggtcagaa    6120
```

```
aattatgaac ggtttcttct attttgtctc tatatactac gtataggaaa tgtttacatt    6180
ttcgtattgt tttcgattca ctctatgaat agttcttact acaatttttt tgtctaaaga    6240
gtaatactag agataaacat aaaaaatgta gaggtcgagt ttagatgcaa gttcaaggag    6300
cgaaaggtgg atgggtaggt tatataggga tatagcacag agatatatag caaagagata    6360
cttttgagca atgtttgtgg aagcggtatt cgcaatattt tagtagctcg ttacagtccg    6420
gtgcgttttt ggtttttga aagtgcgtct tcagagcgct tttggttttc aaaagcgctc    6480
tgaagttcct atactttcta gctagagaat aggaacttcg gaataggaac ttcaaagcgt    6540
ttccgaaaac gagcgcttcc gaaaatgcaa cgcgagctgc gcacatacag ctcactgttc    6600
acgtcgcacc tatatctgcg tgttgcctgt atatatatat acatgagaag aacggcatag    6660
tgcgtgttta tgcttaaatg cgttatggtg cactctcagt acaatctgct ctgatgccgc    6720
atagttaagc cagccccgac acccgccaac acccgctgac gcgccctgac gggcttgtct    6780
gctcccggca tccgcttaca gacaagctgt gaccgtctcc gggagctgca tgtgtcagag    6840
gttttcaccg tcatcaccga aacgcgcgag acgaaagggc ctcgtgatac gcctattttt    6900
ataggttaat gtcatgataa taatggtttc ttagacgtca ggtggcactt tcggggaaa    6960
tgtgcgcgga acccctattt gtttattttt ctaaatacat tcaaatatgt atccgctcat    7020
gagacaataa ccctgataaa tgcttcaata atattgaaaa aggaagagta tgagtattca    7080
acatttccgt gtcgccctta ttcccttttt tgcggcattt tgccttcctg tttttgctca    7140
cccagaaacg ctggtgaaag taaaagatgc tgaagatcag ttgggtgcac gagtgggtta    7200
catcgaactg gatctcaaca gcggtaagat ccttgagagt tttcgccccg aagaacgttt    7260
tccaatgatg agcactttta aagttctgct atgtggcgcg gtattatccc gtattgacgc    7320
cgggcaagag caactcggtc gccgcataca ctattctcag aatgacttgg ttgagtactc    7380
accagtcaca gaaaagcatc ttacggatgg catgacagta agagaattat gcagtgctgc    7440
cataaccatg agtgataaca ctgcggccaa cttacttctg acaacgatcg gaggaccgaa    7500
ggagctaacc gcttttttgc acaacatggg ggatcatgta actcgccttg atcgttggga    7560
accggagctg aatgaagcca taccaaacga cgagcgtgac accacgatgc ctgtagcaat    7620
ggcaacaacg ttgcgcaaac tattaactgg cgaactactt actctagctt cccggcaaca    7680
attaatagac tggatggagg cggataaagt tgcaggacca cttctgcgct cggcccttcc    7740
ggctggctgg tttattgctg ataaatctgg agccggtgag cgtgggtctc gcggtatcat    7800
tgcagcactg gggccagatg gtaagccctc ccgtatcgta gttatctaca cgacggggag    7860
tcaggcaact atggatgaac gaaatagaca gatcgctgag ataggtgcct cactgattaa    7920
gcattggtaa ctgtcagacc aagtttactc atatatactt tagattgatt taaaacttca    7980
tttttaattt aaaaggatct aggtgaagat cctttttgat aatctcatga ccaaaatccc    8040
ttaacgtgag ttttcgttcc actgagcgtc agacccgta gaaaagatca aaggatcttc    8100
ttgagatcct ttttttctgc gcgtaatctg ctgcttgcaa acaaaaaaac caccgctacc    8160
agcggtggtt tgtttgccgg atcaagagct accaactctt tttccgaagg taactggctt    8220
cagcagagcg cagataccaa atactgtcct tctagtgtag ccgtagttag gccaccactt    8280
caagaactct gtagcaccgc ctacatacct cgctctgcta atcctgttac cagtggctgc    8340
tgccagtggc gataagtcgt gtcttaccgg gttggactca agacgatagt taccggataa    8400
ggcgcagcgg tcgggctgaa cggggggttc gtgcacacag cccagcttgg agcgaacgac    8460
ctacaccgaa ctgagatacc tacagcgtga gcattgagaa agcgccacgc ttcccgaagg    8520
```

-continued

| | |
|---|---|
| gagaaaggcg acaggtatc cggtaagcgg cagggtcgga acaggagagc gcacgaggga | 8580 |
| gcttccaggg ggaaacgcct ggtatcttta tagtcctgtc gggtttcgcc acctctgact | 8640 |
| tgagcgtcga tt | 8652 |

<210> SEQ ID NO 289
<211> LENGTH: 8864
<212> TYPE: DNA
<213> ORGANISM: Artificial
<220> FEATURE:
<223> OTHER INFORMATION: pMU2901

<400> SEQUENCE: 289

| | |
|---|---|
| ctcgtcaggg gggcggagcc tatggaaaaa cgccagcaac gcggccttt tacggttcct | 60 |
| ggccttttgc tggccttttg tgagccgttt attttttcta cccatatcct tgaagcggtg | 120 |
| ttataatgcc gcgccctcga tatggggatt tttaacgacc tgattttcgg gtctcagtag | 180 |
| tagttgacat tagcggagca ctaaaatgag tccgcgagaa attgaggttt ccgagccgcg | 240 |
| cgaggttggt atcaccgagc tcgtgctgcg cgatgcccat cagagcctga tggccacacg | 300 |
| aatggcaatg aagacatgg tcggcgcctg tgcagacatt gatgctgccg ggtactggtc | 360 |
| agtggagtgt tggggtggtg ccacgtatga ctcgtgtatc cgcttcctca acgaggatcc | 420 |
| ttgggagcgt ctgcgcacgt tccgcaagct gatgcccaac agccgtctcc agatgctgct | 480 |
| gcgtggccag aacctgctgg gttaccgcca ctacaacgac gaggtcgtcg atcgcttcgt | 540 |
| cgacaagtcc gctgagaacg gcatggacgt gttccgtgtc ttcgacgcca tgaatgatcc | 600 |
| ccgcaacatg gcgcacgcca tggctgccgt caagaaggcc ggcaagcacg cgcagggcac | 660 |
| catttgctac acgatcagcc cggtccacac cgttgagggc tatgtcaagc ttgctggtca | 720 |
| gctgctcgac atgggtgctg attccatcgc cctgaaggac atggccgccc tgctcaagcc | 780 |
| gcagccggcc tacgacatca tcaaggccat caaggacacc tacggccaga agacgcagat | 840 |
| caacctgcac tgccactcca ccacgggtgt caccgaggtc tccctcatga aggccatcga | 900 |
| ggccggcgtc gacgtcgtcg acaccgccat ctcgtccatg tcgctcggcc gggccacaa | 960 |
| ccccaccgag tcggttgccg agatgctcga gggcaccggg tacaccacca accttgacta | 1020 |
| cgatcgcctg cacaagatcc gcgatcactt caaggccatc cgcccgaagt acaagaagtt | 1080 |
| cgagtcgaag acgcttgtcg acacctcgat cttcaagtcg cagatccccg gcggcatgct | 1140 |
| ctccaacatg gagtcgcagc tgcgcgccca gggcgccgag gacaagatgg acgaggtcat | 1200 |
| ggcagaggtg ccgcgcgtcc gcaaggccgc cggcttcccg cccctggtca ccccgtccag | 1260 |
| ccagatcgtc ggcacgcagg ccgtgttcaa cgtgatgatg ggcgagtaca gaggatgac | 1320 |
| cggcgagttc gccgacatca tgctcggcta ctacggcgcc agcccggccg atcgcgatcc | 1380 |
| gaaggtggtc aagttggccg aggagcagtc cggcaagaag ccgatcaccc agcgcccggc | 1440 |
| cgatctgctg ccccccgagt gggaggagca gtccaaggag gccgcggccc tcaagggctt | 1500 |
| caacggcacc gacgaggacg tgctcaccta tgcactgttc ccgcaggtcg ctccggtctt | 1560 |
| cttcgagcat cgcgccgagg gcccgcacag cgtggctctc accgatgccc agctgaaggc | 1620 |
| cgaggccgag ggcgacgaga gtcgctcgc cgtggccggt cccgtcacct acaacgtgaa | 1680 |
| cgtgggcgga accgtccgcg aagtcaccgt tcagcaggcg tgaggatgat tgccaatcat | 1740 |
| ggctgaaaac aacaatttga agctcgccag caccatggaa ggtcgcgtgg agcagctcgc | 1800 |
| agagcagcgc caggtgatcg aagccggtgg cggcgaacgt cgcgtcgaga gcaacattc | 1860 |

```
ccagggtaag cagaccgctc gtgagcgcct gaacaacctg ctcgatcccc attcgttcga    1920
cgaggtcggc gctttccgca agcaccgcac cacgttgttc ggcatggaca aggccgtcgt    1980
cccggcagat ggcgtggtca ccggccgtgg caccatcctt ggtcgtcccg tgcacgccgc    2040
gtcccaggac ttcacggtca tgggtggttc ggctggcgag acgcagtcca cgaaggtcgt    2100
cgagacgatg gaacaggcgc tgctcaccgg cacgcccttc ctgttcttct acgattcggg    2160
cggcgcccgg atccaggagg gcatcgactc gctgagcggt tacggcaaga tgttcttcgc    2220
caacgtgaag ctgtcgggcg tcgtgccgca gatcgccatc attgccggcc cctgtgccgg    2280
tggcgcctcg tattcgccgg cactgactga cttcatcatc atgaccaaga aggcccatat    2340
gttcatcacg ggcccccagg tcatcaagtc ggtcaccggc gaggatgtca ccgctgacga    2400
actcggtggc gctgaggccc atatggccat ctcgggcaat atccacttcg tggccgagga    2460
cgacgacgcc gcggagctca ttgccaagaa gctgctgagc ttccttccgc agaacaacac    2520
tgaggaagca tccttcgtca acccgaacaa tgacgtcagc cccaatacccg agctgcgcga    2580
catcgttccg attgacggca agaagggcta tgacgtgcgc gatgtcattg ccaagatcgt    2640
cgactggggt gactacctcg aggtcaaggc cggctatgcc accaacctcg tgaccgcctt    2700
cgcccgggtc aatggtcgtt cggtgggcat cgtggccaat cagccgtcgg tgatgtcggg    2760
ttgcctcgac atcaacgcct ctgacaaggc cgccgaattc gtgaatttct gcgattcgtt    2820
caacatcccg ctggtgcagc tggtcgacgt gccgggcttc ctgcccggcg tgcagcagga    2880
gtacggcggc atcattcgcc atggcgcgaa gatgctgtac gcctactccg aggccaccgt    2940
gccgaagatc accgtggtgc tccgcaaggc ctacggcggc tcctacctgg ccatgtgcaa    3000
ccgtgacctt ggtgccgacg ccgtgtacgc ctggcccagc gccgagattg cggtgatggg    3060
cgccgagggt gcggcaaatg tgatcttccg caaggagatc aaggctgccg acgatcccga    3120
cgccatgcgc gccgagaaga tcgaggagta ccagaacgcg ttcaacacgc cgtacgtggc    3180
cgccgcccgc ggtcaggtcg acgacgtgat tgacccggct gatacccgtc gaaagattgc    3240
ttccgccctg agatgtacg ccaccaagcg tcagacccgc ccggcgaaga agcatggaaa    3300
cttcccctgc tgagcgagga gagaaattat ggctgatgag gaagagaagg acctgatgat    3360
cgccacgctc aacaagcgcg tcgcgtcatt ggagtctgag ttgggttcac tccagagcga    3420
tacccagggt gtcaccgagg acgtactgac ggccatttcg gccgccgttg cggcctatct    3480
cggcaacgat ggatcggctg aggtcgtcca tttcgccccg agcccgaact gggtccgcga    3540
gggtcgtcgg gctctgcaga accattccat tcgttgatcc gggagtaact cacatgaaac    3600
tgaaggtaac agtcaacggc actgcgtatg acgttgacgt tgacgtcgac aagtcacacg    3660
aaaacccgat gggcaccatc ctgttcggcg gcggcaccgg cggcgcgccg caccgcgcg    3720
cagcaggtgg cgcaggcgcc ggtaaggccg gagagggcga gattcccgct ccgctggccg    3780
gcaccgtctc caagatcctc gtgaaggagg gtgacacggt caaggctggt cagaccgtgc    3840
tcgttctcga ggccatgaag atggagaccg agatcaacgc tcccaccgac ggcaaggtcg    3900
agaaggtcct tgtcaaggag cgtgacgccg tgcagggcgg tcagggtctc atcaagatcg    3960
gctgacggcc gtaaaacgaa aggctcagtc gaaagactgg gcctttcgtt ttatctgttg    4020
tttgtcggtg aacgctctcc tgagtaggac aaatccgccg ggagcggatt tgaacgttgc    4080
gaagcaacgg cccggagggt ggcgggcagg acgcccgcca taaactgcca ggcatcaaat    4140
taagcagaag gccatcctga cggatggcct ttttgcgttt ctacaaactc ttcctgtcgt    4200
catatctaca agccatcccc ccacagatac ggtaaactag cctcgttttt gcatcaggaa    4260
```

-continued

```
agcagctatg aaccactcct gcgaagaggc ccgcaccgat cgcccttccc aacagttgcg   4320
cagcctgaat ggcgaatggc gcctgatgcg gtatttctc cttacgcatc tgtgcggtat   4380
ttcacaccgc atagggtaat aactgatata attaaattga agctctaatt tgtgagttta   4440
gtatacatgc atttacttat aatacagttt tttagttttg ctggccgcat cttctcaaat   4500
atgcttccca gcctgctttt ctgtaacgtt caccctctac cttagcatcc cttccctttg   4560
caaatagtcc tcttccaaca ataataatgt cagatcctgt agagaccaca tcatccacgg   4620
ttctatactg ttgacccaat gcgtctccct tgtcatctaa acccacaccg ggtgtcataa   4680
tcaaccaatc gtaaccttca tctcttccac ccatgtctct ttgagcaata aagccgataa   4740
caaaatcttt gtcgctcttc gcaatgtcaa cagtacccct agtatattct ccagtagata   4800
gggagcccct tgcatgacaat tctgctaaca tcaaaaggcc tctaggttcc tttgttactt   4860
cttctgccgc ctgcttcaaa ccgctaacaa tacctgggcc caccacaccg tgtgcattcg   4920
taatgtctgc ccattctgct attctgtata caccgcaga gtactgcaat ttgactgtat    4980
taccaatgtc agcaaatttt ctgtcttcga agagtaaaaa attgtacttg gcggataatg   5040
cctttagcgg cttaactgtg ccctccatgg aaaaatcagt caagatatcc acatgtgttt   5100
ttagtaaaca aattttggga cctaatgctt caactaactc cagtaattcc ttggtggtac   5160
gaacatccaa tgaagcacac aagtttgttt gcttttcgtg catgatatta aatagcttgg   5220
cagcaacagg actaggatga gtagcagcac gttccttata tgtagctttc gacatgattt   5280
atcttcgttt cggtttttgt tctgtgcagt tgggttaaga atactgggca atttcatgtt   5340
tcttcaacac tacatatgcg tatatatacc aatctaagtc tgtgctcctt ccttcgttct   5400
tccttctgtt cggagattac cgaatcaaaa aaatttcaaa gaaaccgaaa tcaaaaaaaa   5460
gaataaaaaa aaaatgatga attgaaaagc tcttgttacc catcattgaa ttttgaacat   5520
ccgaacctgg gagttttccc tgaaacagat agtatatttg aacctgtata ataatatata   5580
gtctagcgct ttacggaaga caatgtatgt atttcggttc ctggagaaac tattgcatct   5640
attgcatagg taatcttgca cgtcgcatcc ccggttcatt ttctgcgttt ccatcttgca   5700
cttcaatagc atatctttgt taacgaagca tctgtgcttc attttgtaga acaaaaatgc   5760
aacgcgagag cgctaatttt tcaaacaaag aatctgagct gcatttttac agaacagaaa   5820
tgcaacgcga aagcgctatt ttaccaacga agaatctgtg cttcattttt gtaaacaaa    5880 aatgcaacgc gagagcgcta attttttcaaa caaagaatct gagctgcatt tttacagaac   5940
agaaatgcaa cgcgagagcg ctattttacc aacaaagaat ctatacttct tttttgttct   6000
acaaaaatgc atcccgagag cgctattttt ctaacaaagc atcttagatt acttttttc    6060 tcctttgtgc gctctataat gcagtctctt gataactttt tgcactgtag gtccgttaag   6120
gttagaagaa ggctactttg gtgtctattt tctcttccat aaaaaaagcc tgactccact   6180
tcccgcgttt actgattact agcgaagctg cgggtgcatt ttttcaagat aaaggcatcc   6240
ccgattatat tctataccga tgtggattgc gcatactttg tgaacagaaa gtgatagcgt   6300
tgatgattct tcattggtca gaaaattatg aacggtttct tctatttttgt ctctatatac   6360 tacgtatagg aaatgtttac attttcgtat tgttttcgat tcactctatg aatagttctt   6420
actacaattt ttttgtctaa agagtaaatac tagagataaa cataaaaaat gtagaggtcg   6480
agtttagatg caagttcaag gagcgaaagg tggatgggta ggttatatag ggatatagca   6540
cagagatata tagcaaagag atactttgga gcaatgtttg tggaagcggt attcgcaata   6600
```

```
ttttagtagc tcgttacagt ccggtgcgtt tttggttttt tgaaagtgcg tcttcagagc    6660
gcttttggtt ttcaaaagcg ctctgaagtt cctatacttt ctagctagag aataggaact    6720
tcggaatagg aacttcaaag cgtttccgaa aacgagcgct tccgaaaatg caacgcgagc    6780
tgcgcacata cagctcactg ttcacgtcgc acctatatct gcgtgttgcc tgtatatata    6840
tatacatgag aagaacggca tagtgcgtgt ttatgcttaa atgcgttatg gtgcactctc    6900
agtacaatct gctctgatgc cgcatagtta agccagcccc gacacccgcc aacacccgct    6960
gacgcgccct gacgggcttg tctgctcccg gcatccgctt acagacaagc tgtgaccgtc    7020
tccgggagct gcatgtgtca gaggttttca ccgtcatcac cgaaacgcgc gagacgaaag    7080
ggcctcgtga tacgcctatt tttataggtt aatgtcatga taataatggt tcttagacg     7140 tcaggtggca cttttcgggg aaatgtgcgc ggaaccccta tttgtttatt tttctaaata    7200
cattcaaata tgtatccgct catgagacaa taaccctgat aaatgcttca ataatattga    7260
aaaaggaaga gtatgagtat tcaacatttc cgtgtcgccc ttattccctt ttttgcggca    7320
ttttgccttc ctgtttttgc tcacccagaa acgctggtga agtaaaagat gctgaagat    7380 cagttgggtg cacgagtggg ttacatcgaa ctggatctca acagcggtaa gatccttgag    7440
agttttcgcc ccgaagaacg ttttccaatg atgagcactt taaagttct gctatgtggc     7500 gcggtattat cccgtattga cgccgggcaa gagcaactcg gtcgccgcat acactattct    7560
cagaatgact tggttgagta ctcaccagtc acagaaaagc atcttacgga tggcatgaca    7620
gtaagagaat tatgcagtgc tgccataacc atgagtgata acactgcggc caacttactt    7680
ctgacaacga tcggaggacc gaaggagcta accgcttttt tgcacaacat ggggatcat    7740 gtaactcgcc ttgatcgttg gaaccggag ctgaatgaag ccataccaaa cgacgagcgt     7800
gacaccacga tgcctgtagc aatggcaaca acgttgcgca aactattaac tggcgaacta    7860
cttactctag cttcccggca acaattaata gactggatgg aggcggataa agttgcagga    7920
ccacttctgc gctcggccct tccggctggc tggtttattg ctgataaatc tggagccggt    7980
gagcgtgggt ctcgcggtat cattgcagca ctggggccag atggtaagcc ctcccgtatc    8040
gtagttatct acacgacggg gagtcaggca actatggatg aacgaaatag acagatcgct    8100
gagataggtg cctcactgat taagcattgg taactgtcag accaagttta ctcatatata    8160
ctttagattg atttaaaact tcattttaa tttaaaagga tctaggtgaa gatcctttt     8220 gataatctca tgaccaaaat cccttaacgt gagttttcgt tccactgagc gtcagacccc    8280
gtagaaaaga tcaaaggatc ttcttgagat cctttttttc tgcgcgtaat ctgctgcttg    8340
caaacaaaaa aaccaccgct accagcggtg gtttgtttgc cggatcaaga gctaccaact    8400
ctttttccga aggtaactgg cttcagcaga gcgcagatac caaatactgt ccttctagtg    8460
tagccgtagt taggccacca cttcaagaac tctgtagcac cgcctacata cctcgctctg    8520
ctaatcctgt taccagtggc tgctgccagt ggcgataagt cgtgtcttac cgggttggac    8580
tcaagacgat agttaccgga taaggcgcag cggtcgggct gaacggggg ttcgtgcaca    8640 cagcccagct tggagcgaac gacctacacc gaactgagat acctacagcg tgagcattga    8700
gaaagcgcca cgcttcccga agggagaaag gcggacaggt atccggtaag cggcagggtc    8760
ggaacaggag agcgcacgag ggagcttcca gggggaaacg cctggtatct ttatagtcct    8820
gtcgggtttc gccacctctg acttgagcgt cgatttttgt gatg                     8864
```

<210> SEQ ID NO 290
<211> LENGTH: 1220

<212> TYPE: PRT
<213> ORGANISM: C. aurantiacus

<400> SEQUENCE: 290

Met Ser Gly Thr Gly Arg Leu Ala Gly Lys Ile Ala Leu Ile Thr Gly
1               5                   10                  15

Gly Ala Gly Asn Ile Gly Ser Glu Leu Thr Arg Arg Phe Leu Ala Glu
            20                  25                  30

Gly Ala Thr Val Ile Ile Ser Gly Arg Asn Arg Ala Lys Leu Thr Ala
        35                  40                  45

Leu Ala Glu Arg Met Gln Ala Glu Ala Gly Val Pro Ala Lys Arg Ile
    50                  55                  60

Asp Leu Glu Val Met Asp Gly Ser Asp Pro Val Ala Val Arg Ala Gly
65                  70                  75                  80

Ile Glu Ala Ile Val Ala Arg His Gly Gln Ile Asp Ile Leu Val Asn
                85                  90                  95

Asn Ala Gly Ser Ala Gly Ala Gln Arg Arg Leu Ala Glu Ile Pro Leu
            100                 105                 110

Thr Glu Ala Glu Leu Gly Pro Gly Ala Glu Glu Thr Leu His Ala Ser
        115                 120                 125

Ile Ala Asn Leu Leu Gly Met Gly Trp His Leu Met Arg Ile Ala Ala
    130                 135                 140

Pro His Met Pro Val Gly Ser Ala Val Ile Asn Val Ser Thr Ile Phe
145                 150                 155                 160

Ser Arg Ala Glu Tyr Tyr Gly Arg Ile Pro Tyr Val Thr Pro Lys Ala
                165                 170                 175

Ala Leu Asn Ala Leu Ser Gln Leu Ala Ala Arg Glu Leu Gly Ala Arg
            180                 185                 190

Gly Ile Arg Val Asn Thr Ile Phe Pro Gly Pro Ile Glu Ser Asp Arg
        195                 200                 205

Ile Arg Thr Val Phe Gln Arg Met Asp Gln Leu Lys Gly Arg Pro Glu
    210                 215                 220

Gly Asp Thr Ala His His Phe Leu Asn Thr Met Arg Leu Cys Arg Ala
225                 230                 235                 240

Asn Asp Gln Gly Ala Leu Glu Arg Arg Phe Pro Ser Val Gly Asp Val
                245                 250                 255

Ala Asp Ala Ala Val Phe Leu Ala Ser Ala Glu Ser Ala Ala Leu Ser
            260                 265                 270

Gly Glu Thr Ile Glu Val Thr His Gly Met Glu Leu Pro Ala Cys Ser
        275                 280                 285

Glu Thr Ser Leu Leu Ala Arg Thr Asp Leu Arg Thr Ile Asp Ala Ser
    290                 295                 300

Gly Arg Thr Thr Leu Ile Cys Ala Gly Asp Gln Ile Glu Glu Val Met
305                 310                 315                 320

Ala Leu Thr Gly Met Leu Arg Thr Cys Gly Ser Glu Val Ile Ile Gly
                325                 330                 335

Phe Arg Ser Ala Ala Ala Leu Ala Gln Phe Glu Gln Ala Val Asn Glu
            340                 345                 350

Ser Arg Arg Leu Ala Gly Ala Asp Phe Thr Pro Pro Ile Ala Leu Pro
        355                 360                 365

Leu Asp Pro Arg Asp Pro Ala Thr Ile Asp Ala Val Phe Asp Trp Gly
    370                 375                 380

Ala Gly Glu Asn Thr Gly Gly Ile His Ala Ala Val Ile Leu Pro Ala
385                 390                 395                 400

```
Thr Ser His Glu Pro Ala Pro Cys Val Ile Glu Val Asp Asp Glu Arg
            405                 410                 415

Val Leu Asn Phe Leu Ala Asp Glu Ile Thr Gly Thr Ile Val Ile Ala
        420                 425                 430

Ser Arg Leu Ala Arg Tyr Trp Gln Ser Gln Arg Leu Thr Pro Gly Ala
    435                 440                 445

Arg Ala Arg Gly Pro Arg Val Ile Phe Leu Ser Asn Gly Ala Asp Gln
450                 455                 460

Asn Gly Asn Val Tyr Gly Arg Ile Gln Ser Ala Ala Ile Gly Gln Leu
465                 470                 475                 480

Ile Arg Val Trp Arg His Glu Ala Glu Leu Asp Tyr Gln Arg Ala Ser
                485                 490                 495

Ala Ala Gly Asp His Val Leu Pro Pro Val Trp Ala Asn Gln Ile Val
            500                 505                 510

Arg Phe Ala Asn Arg Ser Leu Glu Gly Leu Glu Phe Ala Cys Ala Trp
        515                 520                 525

Thr Ala Gln Leu Leu His Ser Gln Arg His Ile Asn Glu Ile Thr Leu
    530                 535                 540

Asn Ile Pro Ala Asn Ile Ser Ala Thr Thr Gly Ala Arg Ser Ala Ser
545                 550                 555                 560

Val Gly Trp Ala Glu Ser Leu Ile Gly Leu His Leu Gly Lys Val Ala
                565                 570                 575

Leu Ile Thr Gly Gly Ser Ala Gly Ile Gly Gly Gln Ile Gly Arg Leu
            580                 585                 590

Leu Ala Leu Ser Gly Ala Arg Val Met Leu Ala Ala Arg Asp Arg His
        595                 600                 605

Lys Leu Glu Gln Met Gln Ala Met Ile Gln Ser Glu Leu Ala Glu Val
    610                 615                 620

Gly Tyr Thr Asp Val Glu Asp Arg Val His Ile Ala Pro Gly Cys Asp
625                 630                 635                 640

Val Ser Ser Glu Ala Gln Leu Ala Asp Leu Val Glu Arg Thr Leu Ser
                645                 650                 655

Ala Phe Gly Thr Val Asp Tyr Leu Ile Asn Asn Ala Gly Ile Ala Gly
            660                 665                 670

Val Glu Glu Met Val Ile Asp Met Pro Val Glu Gly Trp Arg His Thr
        675                 680                 685

Leu Phe Ala Asn Leu Ile Ser Asn Tyr Ser Leu Met Arg Lys Leu Ala
    690                 695                 700

Pro Leu Met Lys Lys Gln Gly Ser Gly Tyr Ile Leu Asn Val Ser Ser
705                 710                 715                 720

Tyr Phe Gly Gly Glu Lys Asp Ala Ala Ile Pro Tyr Pro Asn Arg Ala
                725                 730                 735

Asp Tyr Ala Val Ser Lys Ala Gly Gln Arg Ala Met Ala Glu Val Phe
            740                 745                 750

Ala Arg Phe Leu Gly Pro Glu Ile Gln Ile Asn Ala Ile Ala Pro Gly
        755                 760                 765

Pro Val Glu Gly Asp Arg Leu Arg Gly Thr Gly Glu Arg Pro Gly Leu
    770                 775                 780

Phe Ala Arg Arg Ala Arg Leu Ile Leu Glu Asn Lys Arg Leu Asn Glu
785                 790                 795                 800

Leu His Ala Ala Leu Ile Ala Ala Arg Thr Asp Glu Arg Ser Met
                805                 810                 815
```

```
His Glu Leu Val Glu Leu Leu Pro Asn Asp Val Ala Ala Leu Glu
            820                 825                 830

Gln Asn Pro Ala Ala Pro Thr Ala Leu Arg Glu Leu Ala Arg Arg Phe
            835                 840                 845

Arg Ser Glu Gly Asp Pro Ala Ala Ser Ser Ser Ala Leu Leu Asn
    850                 855                 860

Arg Ser Ile Ala Ala Lys Leu Leu Ala Arg Leu His Asn Gly Gly Tyr
865                 870                 875                 880

Val Leu Pro Ala Asp Ile Phe Ala Asn Leu Pro Asn Pro Pro Asp Pro
                885                 890                 895

Phe Phe Thr Arg Ala Gln Ile Asp Arg Glu Ala Arg Lys Val Arg Asp
            900                 905                 910

Gly Ile Met Gly Met Leu Tyr Leu Gln Arg Met Pro Thr Glu Phe Asp
            915                 920                 925

Val Ala Met Ala Thr Val Tyr Tyr Leu Ala Asp Arg Asn Val Ser Gly
            930                 935                 940

Glu Thr Phe His Pro Ser Gly Gly Leu Tyr Glu Arg Thr Pro Thr
945                 950                 955                 960

Gly Gly Glu Leu Phe Gly Leu Pro Ser Pro Glu Arg Leu Ala Glu Leu
                965                 970                 975

Val Gly Ser Thr Val Tyr Leu Ile Gly Glu His Leu Thr Glu His Leu
            980                 985                 990

Asn Leu Leu Ala Arg Ala Tyr Leu Glu Arg Tyr Gly Ala Arg Gln Val
                995                 1000                1005

Val Met Ile Val Glu Thr Glu Thr Gly Ala Glu Thr Met Arg Arg
    1010                1015                1020

Leu Leu His Asp His Val Glu Ala Gly Arg Leu Met Thr Ile Val
    1025                1030                1035

Ala Gly Asp Gln Ile Glu Ala Ala Ile Asp Gln Ala Ile Thr Arg
    1040                1045                1050

Tyr Gly Arg Pro Gly Pro Val Val Cys Thr Pro Phe Arg Pro Leu
    1055                1060                1065

Pro Thr Val Pro Leu Val Gly Arg Lys Asp Ser Asp Trp Ser Thr
    1070                1075                1080

Val Leu Ser Glu Ala Glu Phe Ala Glu Leu Cys Glu His Gln Leu
    1085                1090                1095

Thr His His Phe Arg Val Ala Arg Lys Ile Ala Leu Ser Asp Gly
    1100                1105                1110

Ala Ser Leu Ala Leu Val Thr Pro Glu Thr Thr Ala Thr Ser Thr
    1115                1120                1125

Thr Glu Gln Phe Ala Leu Ala Asn Phe Ile Lys Thr Thr Leu His
    1130                1135                1140

Ala Phe Thr Ala Thr Ile Gly Val Glu Ser Glu Arg Thr Ala Gln
    1145                1150                1155

Arg Ile Leu Ile Asn Gln Val Asp Leu Thr Arg Arg Ala Arg Ala
    1160                1165                1170

Glu Glu Pro Arg Asp Pro His Glu Arg Gln Gln Glu Leu Glu Arg
    1175                1180                1185

Phe Ile Glu Ala Val Leu Leu Val Thr Ala Pro Leu Pro Pro Glu
    1190                1195                1200

Ala Asp Thr Arg Tyr Ala Gly Arg Ile His Arg Gly Arg Ala Ile
    1205                1210                1215

Thr Val
```

-continued

1220

<210> SEQ ID NO 291
<211> LENGTH: 1219
<212> TYPE: PRT
<213> ORGANISM: C. aurantiacus

<400> SEQUENCE: 291

```
Met Ser Gly Thr Gly Arg Leu Ala Gly Lys Ile Ala Leu Ile Thr Gly
1               5                   10                  15

Gly Ala Gly Asn Ile Gly Ser Glu Leu Thr Arg Arg Phe Leu Ala Glu
            20                  25                  30

Gly Ala Thr Val Ile Ile Ser Gly Arg Asn Arg Ala Lys Leu Thr Ala
        35                  40                  45

Leu Ala Glu Arg Met Gln Ala Glu Ala Gly Val Pro Ala Lys Arg Ile
    50                  55                  60

Asp Leu Glu Val Met Asp Gly Ser Asp Pro Val Ala Val Arg Ala Gly
65                  70                  75                  80

Ile Glu Ala Ile Val Ala Arg His Gly Gln Ile Asp Ile Leu Val Asn
                85                  90                  95

Asn Ala Gly Ser Ala Gly Ala Gln Arg Arg Leu Ala Glu Ile Pro Leu
            100                 105                 110

Thr Glu Ala Glu Leu Gly Pro Gly Ala Glu Glu Thr Leu His Ala Ser
        115                 120                 125

Ile Ala Asn Leu Leu Gly Met Gly Trp His Leu Met Arg Ile Ala Ala
    130                 135                 140

Pro His Met Pro Val Gly Ser Ala Val Ile Asn Val Ser Thr Ile Phe
145                 150                 155                 160

Ser Arg Ala Glu Tyr Tyr Gly Arg Ile Pro Tyr Val Thr Pro Lys Ala
                165                 170                 175

Ala Leu Asn Ala Leu Ser Gln Leu Ala Ala Arg Glu Leu Gly Ala Arg
            180                 185                 190

Gly Ile Arg Val Asn Thr Ile Phe Pro Gly Pro Ile Glu Ser Asp Arg
        195                 200                 205

Ile Arg Thr Val Phe Gln Arg Met Asp Gln Leu Lys Gly Arg Pro Glu
    210                 215                 220

Gly Asp Thr Ala His His Phe Leu Asn Thr Met Arg Leu Cys Arg Ala
225                 230                 235                 240

Asn Asp Gln Gly Ala Leu Glu Arg Arg Phe Pro Ser Val Gly Asp Val
                245                 250                 255

Ala Asp Ala Ala Val Phe Leu Ala Ser Ala Glu Ser Ala Ala Leu Ser
            260                 265                 270

Gly Glu Thr Ile Glu Val Thr His Gly Met Glu Leu Pro Ala Cys Ser
        275                 280                 285

Glu Thr Ser Leu Leu Ala Arg Thr Asp Leu Arg Thr Ile Asp Ala Ser
    290                 295                 300

Gly Arg Thr Thr Leu Ile Cys Ala Gly Asp Gln Ile Glu Glu Val Met
305                 310                 315                 320

Ala Leu Thr Gly Met Leu Arg Thr Cys Gly Ser Glu Val Ile Ile Gly
                325                 330                 335

Phe Arg Ser Ala Ala Ala Leu Ala Gln Phe Glu Gln Ala Val Asn Glu
            340                 345                 350

Ser Arg Arg Leu Ala Gly Ala Asp Phe Thr Pro Pro Ile Ala Leu Pro
        355                 360                 365
```

```
Leu Asp Pro Arg Asp Pro Ala Thr Ile Asp Ala Val Phe Asp Trp Ala
    370                 375                 380
Gly Glu Asn Thr Gly Gly Ile His Ala Ala Val Ile Leu Pro Ala Thr
385                 390                 395                 400
Ser His Glu Pro Ala Pro Cys Val Ile Glu Val Asp Asp Glu Arg Val
                405                 410                 415
Leu Asn Phe Leu Ala Asp Glu Ile Thr Gly Thr Ile Val Ile Ala Ser
            420                 425                 430
Arg Leu Ala Arg Tyr Trp Gln Ser Gln Arg Leu Thr Pro Gly Ala Arg
        435                 440                 445
Ala Arg Gly Pro Arg Val Ile Phe Leu Ser Asn Gly Ala Asp Gln Asn
450                 455                 460
Gly Asn Val Tyr Gly Arg Ile Gln Ser Ala Ala Ile Gly Gln Leu Ile
465                 470                 475                 480
Arg Val Trp Arg His Glu Ala Glu Leu Asp Tyr Gln Arg Ala Ser Ala
                485                 490                 495
Ala Gly Asp His Val Leu Pro Pro Val Trp Ala Asn Gln Ile Val Arg
            500                 505                 510
Phe Ala Asn Arg Ser Leu Glu Gly Leu Glu Phe Ala Cys Ala Trp Thr
        515                 520                 525
Ala Gln Leu Leu His Ser Gln Arg His Ile Asn Glu Ile Thr Leu Asn
530                 535                 540
Ile Pro Ala Asn Ile Ser Ala Thr Thr Gly Ala Arg Ser Ala Ser Val
545                 550                 555                 560
Gly Trp Ala Glu Ser Leu Ile Gly Leu His Leu Gly Lys Val Ala Leu
                565                 570                 575
Ile Thr Gly Gly Ser Ala Gly Ile Gly Gly Gln Ile Gly Arg Leu Leu
            580                 585                 590
Ala Leu Ser Gly Ala Arg Val Met Leu Ala Ala Arg Asp Arg His Lys
        595                 600                 605
Leu Glu Gln Met Gln Ala Met Ile Gln Ser Glu Leu Ala Glu Val Gly
610                 615                 620
Tyr Thr Asp Val Glu Asp Arg Val His Ile Ala Pro Gly Cys Asp Val
625                 630                 635                 640
Ser Ser Glu Ala Gln Leu Ala Asp Leu Val Glu Arg Thr Leu Ser Ala
                645                 650                 655
Phe Gly Thr Val Asp Tyr Leu Ile Asn Asn Ala Gly Ile Ala Gly Val
            660                 665                 670
Glu Glu Met Val Ile Asp Met Pro Val Glu Gly Trp Arg His Thr Leu
        675                 680                 685
Phe Ala Asn Leu Ile Ser Asn Tyr Ser Leu Met Arg Lys Leu Ala Pro
690                 695                 700
Leu Met Lys Lys Gln Gly Ser Gly Tyr Ile Leu Asn Val Ser Ser Tyr
705                 710                 715                 720
Phe Gly Gly Glu Lys Asp Ala Ala Ile Pro Tyr Pro Asn Arg Ala Asp
                725                 730                 735
Tyr Ala Val Ser Lys Ala Gly Gln Arg Ala Met Ala Glu Val Phe Ala
            740                 745                 750
Arg Phe Leu Gly Pro Glu Ile Gln Ile Asn Ala Ile Ala Pro Gly Pro
        755                 760                 765
Val Glu Gly Asp Arg Leu Arg Gly Thr Gly Glu Arg Pro Gly Leu Phe
770                 775                 780
Ala Arg Arg Ala Arg Leu Ile Leu Glu Asn Lys Arg Leu Asn Glu Leu
```

-continued

```
            785                 790                 795                 800
His Ala Ala Leu Ile Ala Ala Arg Thr Asp Glu Arg Ser Met His
                805                 810                 815

Glu Leu Val Glu Leu Leu Pro Asn Asp Val Ala Ala Leu Glu Gln
                820                 825                 830

Asn Pro Ala Ala Pro Thr Ala Leu Arg Glu Leu Ala Arg Phe Arg
                835                 840                 845

Ser Glu Gly Asp Pro Ala Ala Ser Ser Ser Ala Leu Leu Asn Arg
    850                 855                 860

Ser Ile Ala Ala Lys Leu Leu Ala Arg Leu His Asn Gly Gly Tyr Val
865                 870                 875                 880

Leu Pro Ala Asp Ile Phe Ala Asn Leu Pro Asn Pro Asp Pro Phe
                885                 890                 895

Phe Thr Arg Ala Gln Ile Asp Arg Glu Ala Arg Lys Val Arg Asp Gly
                900                 905                 910

Ile Met Gly Met Leu Tyr Leu Gln Arg Met Pro Thr Glu Phe Asp Val
                915                 920                 925

Ala Met Ala Thr Val Tyr Tyr Leu Ala Asp Arg Asn Val Ser Gly Glu
    930                 935                 940

Thr Phe His Pro Ser Gly Gly Leu Arg Tyr Glu Arg Thr Pro Thr Gly
945                 950                 955                 960

Gly Glu Leu Phe Gly Leu Pro Ser Pro Glu Arg Leu Ala Glu Leu Val
                965                 970                 975

Gly Ser Thr Val Tyr Leu Ile Gly Glu His Leu Thr Glu His Leu Asn
                980                 985                 990

Leu Leu Ala Arg Ala Tyr Leu Glu  Arg Tyr Gly Ala Arg  Gln Val Val
        995                 1000                1005

Met Ile  Val Glu Thr Glu Thr  Gly Ala Glu Thr  Met Arg Arg Leu
    1010                1015                1020

Leu His Asp His Val Glu Ala  Gly Arg Leu Met Thr  Ile Val Ala
    1025                1030                1035

Gly Asp  Gln Ile Glu Ala Ala  Ile Asp Gln Ala Ile  Thr Arg Tyr
    1040                1045                1050

Gly Arg  Pro Gly Pro Val Val  Cys Thr Pro Phe Arg  Pro Leu Pro
    1055                1060                1065

Thr Val  Pro Leu Val Gly Arg  Lys Asp Ser Asp Trp  Ser Thr Val
    1070                1075                1080

Leu Ser  Glu Ala Glu Phe Ala  Glu Leu Cys Glu His  Gln Leu Thr
    1085                1090                1095

His His  Phe Arg Val Ala Arg  Lys Ile Ala Leu Ser  Asp Gly Ala
    1100                1105                1110

Ser Leu  Ala Leu Val Thr Pro  Glu Thr Thr Ala Thr  Ser Thr Thr
    1115                1120                1125

Glu Gln  Phe Ala Leu Ala Asn  Phe Ile Lys Thr Thr  Leu His Ala
    1130                1135                1140

Phe Thr  Ala Thr Ile Gly Val  Glu Ser Glu Arg Thr  Ala Gln Arg
    1145                1150                1155

Ile Leu  Ile Asn Gln Val Asp  Leu Thr Arg Arg Ala  Arg Ala Glu
    1160                1165                1170

Glu Pro  Arg Asp Pro His Glu  Arg Gln Gln Glu Leu  Glu Arg Phe
    1175                1180                1185

Ile Glu  Ala Val Leu Leu Val  Thr Ala Pro Leu Pro  Pro Glu Ala
    1190                1195                1200
```

Asp Thr Arg Tyr Ala Gly Arg Ile His Arg Gly Arg Ala Ile Thr
    1205                1210                1215
Val

<210> SEQ ID NO 292
<211> LENGTH: 1219
<212> TYPE: PRT
<213> ORGANISM: Chloroflexus sp.

<400> SEQUENCE: 292

Met Ser Gly Thr Gly Arg Leu Ala Gly Lys Ile Ala Leu Ile Thr Gly
1               5                   10                  15

Gly Ala Gly Asn Ile Gly Ser Glu Leu Thr Arg Arg Phe Leu Ala Glu
            20                  25                  30

Gly Ala Thr Val Ile Ile Ser Gly Arg Asn Arg Ala Lys Leu Thr Ala
        35                  40                  45

Leu Ala Glu Arg Met Gln Ala Glu Ala Gly Val Pro Ala Lys Arg Ile
50                  55                  60

Asp Leu Glu Val Met Asp Gly Ser Asp Pro Val Ala Val Arg Ala Gly
65                  70                  75                  80

Ile Glu Ala Ile Val Ala Arg His Gly Gln Ile Asp Ile Leu Val Asn
                85                  90                  95

Asn Ala Gly Ser Ala Gly Ala Gln Arg Arg Leu Ala Glu Ile Pro Leu
            100                 105                 110

Thr Glu Ala Glu Leu Gly Pro Gly Ala Glu Glu Thr Leu His Ala Ser
        115                 120                 125

Ile Ala Asn Leu Leu Gly Met Gly Trp His Leu Met Arg Ile Ala Ala
130                 135                 140

Pro His Met Pro Val Gly Ser Ala Val Ile Asn Val Ser Thr Ile Phe
145                 150                 155                 160

Ser Arg Ala Glu Tyr Tyr Gly Arg Ile Pro Tyr Val Thr Pro Lys Ala
                165                 170                 175

Ala Leu Asn Ala Leu Ser Gln Leu Ala Ala Arg Glu Leu Gly Ala Arg
            180                 185                 190

Gly Ile Arg Val Asn Thr Ile Phe Pro Gly Pro Ile Glu Ser Asp Arg
        195                 200                 205

Ile Arg Thr Val Phe Gln Arg Met Asp Gln Leu Lys Gly Arg Pro Glu
210                 215                 220

Gly Asp Thr Ala His His Phe Leu Asn Thr Met Arg Leu Cys Arg Ala
225                 230                 235                 240

Asn Asp Gln Gly Ala Leu Glu Arg Arg Phe Pro Ser Val Gly Asp Val
                245                 250                 255

Ala Asp Ala Ala Val Phe Leu Ala Ser Ala Glu Ser Ala Ala Leu Ser
            260                 265                 270

Gly Glu Thr Ile Glu Val Thr His Gly Met Glu Leu Pro Ala Cys Ser
        275                 280                 285

Glu Thr Ser Leu Leu Ala Arg Thr Asp Leu Arg Thr Ile Asp Ala Ser
290                 295                 300

Gly Arg Thr Thr Leu Ile Cys Ala Gly Asp Gln Ile Glu Glu Val Met
305                 310                 315                 320

Ala Leu Thr Gly Met Leu Arg Thr Cys Gly Ser Glu Val Ile Ile Gly
                325                 330                 335

Phe Arg Ser Ala Ala Ala Leu Ala Gln Phe Glu Gln Ala Val Asn Glu
            340                 345                 350

```
Ser Arg Arg Leu Ala Gly Ala Asp Phe Thr Pro Pro Ile Ala Leu Pro
        355                 360                 365

Leu Asp Pro Arg Asp Pro Ala Thr Ile Asp Ala Val Phe Asp Trp Ala
        370                 375                 380

Gly Glu Asn Thr Gly Gly Ile His Ala Ala Val Ile Leu Pro Ala Thr
385                 390                 395                 400

Ser His Glu Pro Ala Pro Cys Val Ile Glu Val Asp Asp Glu Arg Val
            405                 410                 415

Leu Asn Phe Leu Ala Asp Glu Ile Thr Gly Thr Ile Val Ile Ala Ser
                420                 425                 430

Arg Leu Ala Arg Tyr Trp Gln Ser Gln Arg Leu Thr Pro Gly Ala Arg
        435                 440                 445

Ala Arg Gly Pro Arg Val Ile Phe Leu Ser Asn Gly Ala Asp Gln Asn
        450                 455                 460

Gly Asn Val Tyr Gly Arg Ile Gln Ser Ala Ala Ile Gly Gln Leu Ile
465                 470                 475                 480

Arg Val Trp Arg His Glu Ala Glu Leu Asp Tyr Gln Arg Ala Ser Ala
            485                 490                 495

Ala Gly Asp His Val Leu Pro Pro Val Trp Ala Asn Gln Ile Val Arg
            500                 505                 510

Phe Ala Asn Arg Ser Leu Glu Gly Leu Glu Phe Ala Cys Ala Trp Thr
        515                 520                 525

Ala Gln Leu Leu His Ser Gln Arg His Ile Asn Glu Ile Thr Leu Asn
        530                 535                 540

Ile Pro Ala Asn Ile Ser Ala Thr Thr Gly Ala Arg Ser Ala Ser Val
545                 550                 555                 560

Gly Trp Ala Glu Ser Leu Ile Gly Leu His Leu Gly Lys Val Ala Leu
            565                 570                 575

Ile Thr Gly Gly Ser Ala Gly Ile Gly Gly Gln Ile Gly Arg Leu Leu
            580                 585                 590

Ala Leu Ser Gly Ala Arg Val Met Leu Ala Ala Arg Asp Arg His Lys
        595                 600                 605

Leu Glu Gln Met Gln Ala Met Ile Gln Ser Glu Leu Ala Glu Val Gly
        610                 615                 620

Tyr Thr Asp Val Glu Asp Arg Val His Ile Ala Pro Gly Cys Asp Val
625                 630                 635                 640

Ser Ser Glu Ala Gln Leu Ala Asp Leu Val Glu Arg Thr Leu Ser Ala
            645                 650                 655

Phe Gly Thr Val Asp Tyr Leu Ile Asn Asn Ala Gly Ile Ala Gly Val
            660                 665                 670

Glu Glu Met Val Ile Asp Met Pro Val Glu Gly Trp Arg His Thr Leu
        675                 680                 685

Phe Ala Asn Leu Ile Ser Asn Tyr Ser Leu Met Arg Lys Leu Ala Pro
        690                 695                 700

Leu Met Lys Lys Gln Gly Ser Gly Tyr Ile Leu Asn Val Ser Ser Tyr
705                 710                 715                 720

Phe Gly Gly Glu Lys Asp Ala Ala Ile Pro Tyr Pro Asn Arg Ala Asp
            725                 730                 735

Tyr Ala Val Ser Lys Ala Gly Gln Arg Ala Met Ala Glu Val Phe Ala
            740                 745                 750

Arg Phe Leu Gly Pro Glu Ile Gln Ile Asn Ala Ile Ala Pro Gly Pro
        755                 760                 765
```

```
Val Glu Gly Asp Arg Leu Arg Gly Thr Gly Glu Arg Pro Gly Leu Phe
    770                 775                 780

Ala Arg Arg Ala Arg Leu Ile Leu Glu Asn Lys Arg Leu Asn Glu Leu
785                 790                 795                 800

His Ala Ala Leu Ile Ala Ala Arg Thr Asp Glu Arg Ser Met His
                805                 810                 815

Glu Leu Val Glu Leu Leu Pro Asn Asp Val Ala Ala Leu Glu Gln
            820                 825                 830

Asn Pro Ala Ala Pro Thr Ala Leu Arg Glu Leu Ala Arg Phe Arg
                835                 840                 845

Ser Glu Gly Asp Pro Ala Ala Ser Ser Ser Ala Leu Leu Asn Arg
    850                 855                 860

Ser Ile Ala Ala Lys Leu Leu Ala Arg Leu His Asn Gly Gly Tyr Val
865                 870                 875                 880

Leu Pro Ala Asp Ile Phe Ala Asn Leu Pro Asn Pro Asp Pro Phe
                885                 890                 895

Phe Thr Arg Ala Gln Ile Asp Arg Glu Ala Arg Lys Val Arg Asp Gly
                900                 905                 910

Ile Met Gly Met Leu Tyr Leu Gln Arg Met Pro Thr Glu Phe Asp Val
                915                 920                 925

Ala Met Ala Thr Val Tyr Tyr Leu Ala Asp Arg Asn Val Ser Gly Glu
930                 935                 940

Thr Phe His Pro Ser Gly Gly Leu Arg Tyr Glu Arg Thr Pro Thr Gly
945                 950                 955                 960

Gly Glu Leu Phe Gly Leu Pro Ser Pro Glu Arg Leu Ala Glu Leu Val
                965                 970                 975

Gly Ser Thr Val Tyr Leu Ile Gly Glu His Leu Thr Glu His Leu Asn
                980                 985                 990

Leu Leu Ala Arg Ala Tyr Leu Glu  Arg Tyr Gly Ala Arg Gln Val Val
            995                1000                1005

Met Ile Val Glu Thr Glu Thr  Gly Ala Glu Thr Met  Arg Arg Leu
    1010                1015                1020

Leu His Asp His Val Glu Ala  Gly Arg Leu Met Thr  Ile Val Ala
    1025                1030                1035

Gly Asp Gln Ile Glu Ala Ala  Ile Asp Gln Ala Ile  Thr Arg Tyr
    1040                1045                1050

Gly Arg Pro Gly Pro Val Val  Cys Thr Pro Phe Arg  Pro Leu Pro
    1055                1060                1065

Thr Val Pro Leu Val Gly Arg  Lys Asp Ser Asp Trp  Ser Thr Val
    1070                1075                1080

Leu Ser Glu Ala Glu Phe Ala  Glu Leu Cys Glu His  Gln Leu Thr
    1085                1090                1095

His His Phe Arg Val Ala Arg  Lys Ile Ala Leu Ser  Asp Gly Ala
    1100                1105                1110

Ser Leu Ala Leu Val Thr Pro  Glu Thr Thr Ala Thr  Ser Thr Thr
    1115                1120                1125

Glu Gln Phe Ala Leu Ala Asn  Phe Ile Lys Thr  Leu His Ala
    1130                1135                1140

Phe Thr Ala Thr Ile Gly Val  Glu Ser Glu Arg Thr  Ala Gln Arg
    1145                1150                1155

Ile Leu Ile Asn Gln Val Asp  Leu Thr Arg Arg Ala  Arg Ala Glu
    1160                1165                1170

Glu Pro Arg Asp Pro His Glu  Arg Gln Gln Glu Leu  Glu Arg Phe
```

```
                1175                1180                1185
Ile Glu Ala Val Leu Leu Val Thr Ala Pro Leu Pro Pro Glu Ala
        1190                1195                1200

Asp Thr Arg Tyr Ala Gly Arg Ile His Arg Gly Arg Ala Ile Thr
        1205                1210                1215

Val

<210> SEQ ID NO 293
<211> LENGTH: 1219
<212> TYPE: PRT
<213> ORGANISM: C. aggregans

<400> SEQUENCE: 293

Met Ser Val Thr Gly Arg Leu Ala Gly Lys Ile Ala Leu Ile Thr Gly
1               5                   10                  15

Gly Ala Gly Asn Ile Gly Ser Glu Met Thr Arg Arg Phe Leu Ala Glu
                20                  25                  30

Gly Ala Thr Val Ile Ile Ser Gly Arg Asn Ser Ala Lys Leu Ala Ala
            35                  40                  45

Leu Ala Glu Arg Leu Arg Ser Glu Ala Gly Val Pro Ala Lys Arg Ile
50                  55                  60

Asp Leu Glu Val Met Asp Gly Ser Asp Pro Ala Ala Val Arg Ala Gly
65                  70                  75                  80

Val Ala Ala Ile Ile Gly Arg His Gly His Ile Asp Ile Leu Val Asn
                85                  90                  95

Asn Ala Gly Ser Thr Gly Ala Gln Arg Arg Leu Ala Glu Ile Pro Leu
            100                 105                 110

Asn Glu Thr Asp Arg Asp Leu Asp Asp Glu Glu Ala Leu Ser Thr Ser
        115                 120                 125

Val Ala Asn Leu Leu Gly Met Ala Trp His Leu Met Arg Ile Leu Ser
130                 135                 140

Pro His Met Pro Pro Gly Ser Ala Ile Ile Asn Ile Ser Thr Ile Phe
145                 150                 155                 160

Ser Arg Ala Glu Tyr Tyr Gly Arg Ile Pro Tyr Val Val Pro Lys Ala
                165                 170                 175

Ala Leu Asn Thr Leu Thr Gln Ile Ala Ala Arg Glu Leu Gly Ile Arg
            180                 185                 190

Gly Ile Arg Val Asn Thr Ile Phe Pro Gly Pro Ile Glu Ser Glu Arg
        195                 200                 205

Ile Gln Thr Val Phe Gln Arg Met Asp Gln Leu Lys Gly Arg Pro Glu
210                 215                 220

Gly Asp Thr Ala Ser Gln Phe Leu Ala Thr Met Arg Leu Tyr Arg Ala
225                 230                 235                 240

Asn Asp Gln Gly Gln Leu Glu Arg Arg Phe Pro Thr Ile Cys Asp Val
                245                 250                 255

Ala Asp Ala Ala Val Phe Leu Ala Ser Asp Glu Ala Ala Ala Leu Thr
            260                 265                 270

Gly Glu Thr Ile Glu Val Thr His Gly Met Glu Leu Pro Thr Ser Ser
        275                 280                 285

Glu Thr Ser Leu Leu Ala Arg Thr Asp Leu Arg Thr Ile Asp Ala Asn
290                 295                 300

Gly Arg Thr Thr Leu Ile Cys Ala Gly Asp Gln Ile Glu Glu Val Met
305                 310                 315                 320

Ala Leu Thr Gly Met Leu Arg Thr Cys Gly Ser Glu Val Ile Ile Gly
```

```
                    325                 330                 335
Phe Arg Ser Glu Ala Ala Leu Ala Gln Phe Glu Gln Ala Ile Gly Glu
                340                 345                 350
Ser Arg Arg Leu Ala Gly Glu Ser Phe Ile Pro Pro Ile Ala Leu Pro
                355                 360                 365
Ile Asp Leu Arg Asn Pro Ser Thr Ile Asp Ala Leu Phe Asp Trp Ala
            370                 375                 380
Gly Glu Asn Thr Gly Gly Ile His Ala Ala Val Ile Leu Pro Ala Ser
385                 390                 395                 400
Gly Arg Glu Pro Ala Thr Gln Val Ile Asp Ile Asp Asp Ala His Val
                405                 410                 415
Gln Ala Phe Leu Asn Asp Glu Ile Val Gly Ser Ile Ile Ala Ser
                420                 425                 430
Arg Leu Ala Arg Tyr Trp Gln Ala Gln Arg Ile Ala Pro Gly Ala Arg
                435                 440                 445
Ala Arg Glu Pro Arg Val Ile Phe Leu Ser Asn Gly Ala Ser Thr Ala
                450                 455                 460
Gly Asn Pro Tyr Gly Arg Ile Gln Ser Ala Ala Ile Glu Gln Leu Ile
465                 470                 475                 480
Arg Val Trp Arg His Glu Ala Ala Leu Asp Tyr Glu Arg Ala Thr Ala
                485                 490                 495
Ala Gly Glu Arg Val Leu Pro Ala Val Trp Ala Ser Gln Ile Val Arg
                500                 505                 510
Phe Ala Asn Arg Ser Leu Glu Gly Leu Glu Phe Ala Cys Ala Trp Thr
                515                 520                 525
Ala Gln Leu Leu His Ser Gln Arg Arg Ile Asn Glu Ile Thr Leu Thr
                530                 535                 540
Ile Pro Ala Asp Ile Ser Ala Thr Thr Gly Ala Arg Ser Ala Ser Val
545                 550                 555                 560
Gly Trp Ala Glu Ser Leu Ile Gly Leu His Leu Gly Lys Val Ala Leu
                565                 570                 575
Ile Thr Gly Gly Ser Ala Gly Ile Gly Gly Gln Ile Gly Arg Leu Leu
                580                 585                 590
Ala Leu Ser Gly Ala Arg Val Met Leu Ala Ala Arg Asp Pro His Lys
            595                 600                 605
Leu Glu Gln Ile Gln Ala Thr Ile Arg Ala Glu Leu Ala Glu Val Gly
            610                 615                 620
Tyr Thr Asp Val Glu Glu Arg Val Gln Ile Ala Pro Gly Cys Asp Val
625                 630                 635                 640
Ser Ser Glu Glu Gln Leu Val Asp Leu Val Glu Arg Thr Leu Ala Ala
                645                 650                 655
Phe Gly Thr Val Asp Tyr Leu Ile Asn Asn Ala Gly Ile Ala Gly Val
                660                 665                 670
Glu Glu Met Val Ile Asp Met Pro Val Glu Gly Trp Arg Asn Thr Leu
            675                 680                 685
Tyr Ala Asn Leu Ile Ser Asn Tyr Ser Leu Met Arg Lys Leu Ala Pro
            690                 695                 700
Leu Met Lys Lys Gln Gly Ser Gly Tyr Val Leu Asn Val Ser Ser Tyr
705                 710                 715                 720
Phe Gly Gly Glu Lys Asp Ala Ala Ile Pro Tyr Pro Asn Arg Ala Asp
                725                 730                 735
Tyr Ala Val Ser Lys Ala Gly Gln Arg Ala Met Ala Glu Val Phe Ala
                740                 745                 750
```

```
Arg Phe Leu Gly Pro Glu Ile Gln Ile Asn Ala Ile Ala Pro Gly Pro
        755                 760                 765

Val Glu Gly Asp Arg Leu Arg Gly Thr Gly Glu Arg Pro Gly Leu Phe
770                 775                 780

Ala Arg Arg Ala Arg Leu Ile Leu Glu Asn Lys Arg Leu Asn Glu Leu
785                 790                 795                 800

His Ala Ala Leu Ile Thr Ala Ala Arg Thr Asp Asn Arg Pro Met Arg
                805                 810                 815

Glu Leu Val Glu Leu Leu Pro Asn Asp Val Ala Ala Leu Ala Gln
                820                 825                 830

His Pro Ala Ala Pro Asp Val Leu Arg Thr Leu Ala Lys Arg Phe Gln
                835                 840                 845

Ser Glu Gly Asp Pro Ala Ala Ser Ser Ser Phe Leu Leu Asn Arg
    850                 855                 860

Ser Ile Ala Ala Lys Leu Leu Ala Arg Leu Ile Asn Gly Gly Tyr Asp
865                 870                 875                 880

Leu Pro Ala Asp Ile Phe Ala Asn Leu Ala Val Pro Pro Asp Pro Phe
                885                 890                 895

Phe Thr Arg Ala Gln Ile Asp Arg Glu Ala Arg Lys Val Arg Asp Gly
                900                 905                 910

Ile Met Gly Met Leu Tyr Leu Gln Arg Met Pro Thr Glu Phe Asp Val
                915                 920                 925

Ala Met Ala Thr Val Tyr Tyr Leu Ala Asp Arg Asn Val Ser Gly Glu
930                 935                 940

Thr Phe His Pro Ser Gly Gly Leu Arg Tyr Glu Arg Thr Pro Thr Gly
945                 950                 955                 960

Gly Glu Leu Phe Gly Leu Pro Ala Pro Glu Arg Leu Ala Glu Leu Val
                965                 970                 975

Gly Ser Thr Val Tyr Leu Ile Gly Glu His Leu Thr Glu His Leu Asn
                980                 985                 990

Leu Leu Ala Arg Ala Tyr Leu Glu Arg Tyr Gly Ala Arg Gln Val Val
        995                 1000                1005

Met Ile Val Glu Thr Glu Ala Gly Ala Glu Lys Met Arg His Leu
    1010                1015                1020

Leu His Asp His Val Glu Ala Gly Arg Leu Pro Ile Ile Val Ala
    1025                1030                1035

Gly Asp Gln Ile Glu Ala Ala Ile Asp Gln Ala Ile Ala Asn Tyr
    1040                1045                1050

Gly Arg Pro Gly Pro Val Val Cys Thr Pro Phe Arg Pro Leu Pro
    1055                1060                1065

Ser Ala Pro Leu Val Gly Arg Lys Asp Ser Asp Trp Ser Thr Val
    1070                1075                1080

Leu Ser Glu Ala Glu Phe Ala Glu Leu Cys Glu His Gln Leu Thr
    1085                1090                1095

His His Phe Arg Val Ala Arg Lys Ile Ala Leu Ser Asp Gly Ala
    1100                1105                1110

Ser Leu Ala Leu Val Thr Pro Glu Thr Thr Ala Thr Ser Ser Thr
    1115                1120                1125

Glu Gln Phe Ala Leu Ala Asn Phe Val Lys Thr Thr Leu His Ala
    1130                1135                1140

Phe Thr Ala Thr Ile Gly Val Glu Ser Glu Arg Thr Ala Gln Arg
    1145                1150                1155
```

```
Ile Leu Ile Asn Gln Val Asp Leu Thr Arg Arg Ala Arg Ala Glu
    1160                1165                1170

Glu Pro Arg Asp Pro Arg Glu Arg Gln Gln Glu Leu Glu Arg Phe
    1175                1180                1185

Ile Glu Ala Val Leu Leu Val Thr Ala Pro Leu Pro Pro Glu Ala
    1190                1195                1200

Asp Thr Arg Tyr Ala Gly Arg Ile His Arg Gly Arg Ala Ile Thr
    1205                1210                1215

Val

<210> SEQ ID NO 294
<211> LENGTH: 1221
<212> TYPE: PRT
<213> ORGANISM: O. trichoides

<400> SEQUENCE: 294

Met Phe Met Thr Arg Leu Asn Asp Lys Ile Ala Leu Ile Thr Gly Gly
1               5                   10                  15

Ala Gly Thr Ile Gly Glu Val Ile Thr Arg Arg Tyr Leu Glu Glu Gly
                20                  25                  30

Ala Thr Val Val Met Ala Gly Arg Asn Arg Asp Lys Leu Asp Arg Tyr
            35                  40                  45

Arg Glu Arg Leu Ile Thr Glu Phe His Ala Leu Pro Glu Arg Val Met
        50                  55                  60

Val Val Arg Met Asp Gly Ser Ser Asn Ala Glu Val Arg Met Gly Ile
65                  70                  75                  80

Ala Ala Val Val Ala His Phe Gly Arg Ile Asp Ile Leu Val Asn Asn
                85                  90                  95

Ala Gly Ser Ala Gly Ala Arg Gln Arg Leu Pro Ala Ile Pro Leu Leu
            100                 105                 110

Arg Ser Glu Leu Gln Ala Asp Glu Thr Glu Thr Leu Ala Asp Ser Ile
        115                 120                 125

Gly Asn Leu Ile Gly Ile Thr Trp Asn Leu Ile Arg Ala Ala Ala Pro
    130                 135                 140

Phe Met Pro Ala Gly Ser Ser Val Ile Asn Ile Ser Thr Ile Phe Ala
145                 150                 155                 160

Arg Thr Asp Tyr Tyr Gly Arg Ile Pro Tyr Val Val Pro Lys Ala Ala
                165                 170                 175

Leu His Ala Leu Thr Leu Ala Ala Thr Glu Leu Gly Glu Arg Gly
            180                 185                 190

Ile Arg Val Asn Gln Ile Asn Pro Gly Pro Ile Asp Ser Asp Arg Ile
        195                 200                 205

Arg Thr Val Phe Arg Arg Met Asp Glu Leu Lys Gly Val Pro Glu Gln
    210                 215                 220

Ser Thr Ala Asp Gly Phe Phe Gln Met Met Arg Leu Arg Arg Pro Asn
225                 230                 235                 240

Ala Glu Gly Asp Leu Val Lys Gly Phe Pro Lys Thr Leu Asp Val Ala
                245                 250                 255

Asn Val Ala Val Phe Leu Gly Ser Ala Glu Ser Ala Ala Leu Ser Gly
            260                 265                 270

Glu Thr Leu Asp Val Thr His Gly Met Ala Val Pro Thr Glu Ser Arg
        275                 280                 285

Thr Thr Leu Thr Ser Arg Pro Gly Leu Arg Ala Val Asp Gly Ser Gly
    290                 295                 300
```

```
His Thr Thr Leu Ile Cys Val Gly Asp Gln Ile Glu Glu Ala Ala Ala
305                 310                 315                 320

Leu Thr Gly Val Leu Arg Ala Cys Gly Ala Glu Val Val Ile Gly Phe
            325                 330                 335

Arg Ser Arg Ala Ala Ile Ala Arg Phe Asp His Leu Ile Glu Arg Gly
            340                 345                 350

Arg His Leu Pro Ser Gln Glu His Val Ala Pro Val Leu Leu Tyr Leu
            355                 360                 365

Asn Pro Thr Glu Pro Glu Ser Ile Asp Gln Ala Leu Arg Trp Met Ala
            370                 375                 380

Thr Asn Leu Asp Leu Pro Thr Ser Val Ile Ile Leu Pro Ala Gln Arg
385                 390                 395                 400

Gln Pro Leu Pro Pro Ser Val Val Arg Ala Ser Asp Glu Val Ala
            405                 410                 415

Tyr Phe Leu Arg Asp Glu Leu Ser Gly Met Ile Val Leu Ala Ser Arg
            420                 425                 430

Leu Ala Arg Phe Trp Gln Gln Ala Thr Leu Ala Pro Gly Asn Ala Pro
            435                 440                 445

Ile Gln Pro Arg Val Leu Phe Met Thr Asn Pro Asp Asp Gly Gln Gly
450                 455                 460

Asn Leu Tyr Ala Glu Ile Leu Arg Ala Gly Val Glu Gln Leu Cys Arg
465                 470                 475                 480

Val Trp Arg His Glu Ser Gln Leu Asp Tyr Thr Arg Leu Ala Gln Met
            485                 490                 495

Asp Ala His Pro Pro His Ile Arg Pro Val Trp Ala Asn Gln Leu Val
            500                 505                 510

Arg Phe Ala Asn Asn Glu Gln Glu Asn Leu Glu Tyr Cys Cys Ala Trp
            515                 520                 525

Val Ala Lys Ile Leu Leu Ser Glu Arg Thr Ile Glu Glu Leu Asn Leu
530                 535                 540

Tyr Leu Pro Arg Gln Ile Gly Ser Thr Thr Gly Ser Arg Gln Pro Ser
545                 550                 555                 560

Phe Gly Trp Ala Glu Asn Leu Ile Gly Leu His Leu Gly Lys Thr Ala
            565                 570                 575

Leu Ile Thr Gly Gly Ser Ala Gly Ile Gly Ser Gln Ile Ala Arg Leu
            580                 585                 590

Leu Ala Leu Ser Gly Ala Arg Val Met Leu Cys Ala Arg Asp Glu Arg
            595                 600                 605

Lys Leu Ile Gln Met Arg Asp Met Ile Ile Ala Glu Leu Thr Glu Val
            610                 615                 620

Gly Tyr Asn Gln Val Glu Ser Arg Val Gln Ile Cys Ala Gly Cys Asp
625                 630                 635                 640

Val Gly Glu Glu Glu Gln Leu Glu Ile Ala Val Gln Arg Thr Leu Asp
            645                 650                 655

Leu Phe Gly His Val Asp Tyr Leu Ile Asn Asn Ala Gly Ile Ala Gly
            660                 665                 670

Ala Glu Glu Met Val Leu Asp Leu Pro Leu Glu Ala Trp Gln Arg Thr
            675                 680                 685

Leu Arg Thr Asn Leu Ile Ser Asn Tyr Ser Leu Ile Arg Lys Leu Ala
            690                 695                 700

Pro Gln Met Lys Ser Arg Gly Ser Gly Tyr Ile Leu Asn Val Ser Ser
705                 710                 715                 720

Tyr Phe Gly Gly Glu Lys Tyr Ala Ala Ile Pro Tyr Pro Asn Arg Ala
```

```
                725                 730                 735
Asp Tyr Ala Val Ser Lys Ala Gly Gln Arg Ala Leu Gly Glu Ala Leu
                740                 745                 750
Ala Arg Leu Leu Gly Pro Glu Val Gln Ile Asn Ala Met Ala Pro Gly
                755                 760                 765
Pro Val Glu Gly Glu Arg Leu Arg Gly Ser Gly Asp Arg Pro Gly Leu
                770                 775                 780
Phe Leu Arg Arg Gly Arg Leu Ile Leu Glu Asn Lys Arg Leu Asn Asp
785                 790                 795                 800
Leu His Ala Thr Leu Ile Ala Ala Glu Arg Glu Thr Gln Val Gly Met
                805                 810                 815
Arg Asp Leu Leu Ala Arg Leu Leu His Asn Asp Val Cys Ala Leu Ile
                820                 825                 830
Asp Asp Pro Ala Ala Pro Thr His Leu Arg Ala Leu Ala Glu Arg Ile
                835                 840                 845
Trp Glu Gln Ser Asp Pro Asn Ser Tyr Ala Arg Ala Phe Phe Met Asn
                850                 855                 860
Ala Asn Ile Ala Thr Lys Leu Leu Ala Arg Leu Phe Asn Ala Asp Gln
865                 870                 875                 880
Ile Asp Ala Gln Thr Phe His Thr Ser Gln Pro Asn Leu Pro Pro Glu
                885                 890                 895
Pro Phe Phe Ala Arg Thr Gln Ile Asp Arg Glu Ala Arg Arg Val Arg
                900                 905                 910
Asp Gly Val Met Ser Met Leu Tyr Leu Gln Arg Met Pro Thr Glu Phe
                915                 920                 925
Asp Val Ala Leu Ala Thr Val Tyr Tyr Leu Asn Asp Arg Ser Val Ser
                930                 935                 940
Gly Glu Thr Phe His Pro Ser Gly Gly Leu Arg His Glu Arg Thr Pro
945                 950                 955                 960
Thr Gly Ala Glu Leu Tyr Gly Ser Pro Ala Pro Gln Arg Leu Ala Ser
                965                 970                 975
Leu Ala Gly Ser Thr Val Tyr Leu Ile Gly Glu Ser Met Ala Ala His
                980                 985                 990
Leu Glu Ala Leu Ala Arg Ala Tyr Ile Glu Arg Tyr Ala Ala Thr Arg
                995                1000                1005
Val Val Leu Ile Cys Ala Thr Pro Ala Gly Val Glu Arg Phe Ser
                1010                1015                1020
His His Leu Ala Asp His Leu Ala Ser Gly Ala Leu Ala Ile Leu
                1025                1030                1035
Ser Ala Glu Glu Gly Ile Glu Ala Ala Leu Ser Glu Ala Leu Arg
                1040                1045                1050
Arg Phe Gly Pro Pro Gly Pro Val Val Ser Thr Pro Phe Gln Pro
                1055                1060                1065
Leu Pro Ser Gln Pro Leu Ile Gly Arg Asn Asp Ser Asp Trp Ser
                1070                1075                1080
Thr Val Leu Asp Val Ala Gly Phe Ser Ala Met Cys Glu Gln Gln
                1085                1090                1095
Leu Thr His His Phe Arg Val Thr Arg Lys Leu Ser Leu Val Ala
                1100                1105                1110
Gly Val Ser Leu Val Leu Val Thr Pro Glu Thr Asp Ser His Ser
                1115                1120                1125
Ser Thr Glu Gln Phe Ala Leu Ala Asn Phe Val Lys Thr Thr Leu
                1130                1135                1140
```

```
His Ala Phe Thr Ala Thr Val Gly Val Glu Cys Glu Arg Thr Ala
    1145                1150                1155

His Arg Ile Leu Val Asn Gln Val Asp Leu Gly Arg Gln Ala Arg
    1160                1165                1170

Ala Glu Glu Pro Arg Ser Pro Ala Glu Gln Ala Gln Glu Met Glu
    1175                1180                1185

Arg Phe Ile Asp Ala Ile Met Leu Thr Thr Ala Pro Ile Pro Ala
    1190                1195                1200

Glu Glu Asp Asn Arg Tyr Thr Gly Arg Ile Tyr Arg Gly Arg Ala
    1205                1210                1215

Ile Thr Val
    1220

<210> SEQ ID NO 295
<211> LENGTH: 1229
<212> TYPE: PRT
<213> ORGANISM: R. castenholzii

<400> SEQUENCE: 295

Met Ser Thr Val Arg Arg Leu Glu Gly Lys Val Ala Leu Ile Thr Gly
1               5                   10                  15

Gly Ala Gly Asn Ile Gly Glu Val Ile Thr Arg Arg Phe Leu Ala Glu
                20                  25                  30

Gly Ala Thr Val Val Ile Thr Gly Arg Asn Ala Glu Lys Leu Ala Val
            35                  40                  45

Tyr Arg Arg Arg Leu Ile Asp Glu Glu Arg Val Ala Pro Glu Arg Val
50                  55                  60

Val Ala Leu Arg Met Asp Gly Ser Asp Ile Ala Gln Val Arg Ala Gly
65                  70                  75                  80

Val Ala Gln Ile Val His Gly Gly Thr Asp Val Pro Ile Pro Leu His
                85                  90                  95

Arg Ile Asp Ile Leu Val Asn Asn Ala Gly Ser Ala Gly Pro Arg Arg
                100                 105                 110

Arg Leu Val Asp Ile Pro Leu Glu Pro Ser Glu Val Gln Pro Pro Asp
            115                 120                 125

Ser Glu Thr Leu Ala Gln Ala Val Gly Asn Leu Val Gly Ile Thr Trp
130                 135                 140

Asn Leu Thr Arg Ala Ala Ala Pro His Met Pro Ser Gly Ser Ser Val
145                 150                 155                 160

Ile Asn Ile Ser Thr Ile Phe Ser Arg Thr Asp Tyr Tyr Gly Arg Ile
                165                 170                 175

Ala Tyr Val Ala Pro Lys Ala Ala Leu Asn Ala Leu Ser Asp Gly Leu
            180                 185                 190

Ala Arg Glu Leu Gly Val Arg Gly Ile Arg Val Asn Thr Ile Tyr Pro
        195                 200                 205

Gly Pro Ile Glu Ser Glu Arg Ile Tyr Thr Met Phe Gln Ala Met Asp
210                 215                 220

Ala Leu Lys Gly Gln Pro Glu Gly Asp Thr Ala Ser Gly Phe Leu Arg
225                 230                 235                 240

Met Met Arg Leu Ser Arg Ile Asp Gln Asn Gly Glu Val Val Lys Arg
                245                 250                 255

Phe Pro Ser Pro Val Asp Val Ala Asn Thr Ala Val Phe Leu Ala Ser
            260                 265                 270

Asp Glu Ser Ala Ala Phe Thr Gly His Ala Phe Glu Val Thr His Gly
```

```
                275                 280                 285
Met Glu Val Pro Thr Glu Ser Arg Thr Thr Phe Val Ser Arg Pro Gly
    290                 295                 300

Leu Arg Ser Val Asp Ala Thr Gly Lys Val Ile Leu Ile Cys Ala Gly
305                 310                 315                 320

Asp Gln Val Asp Ala Val Ala Leu Ala Asp Thr Leu Arg Ser Cys
                325                 330                 335

Arg Ala Thr Val Ile Gly Phe Arg Asp Pro Arg Ala Leu Glu Lys
            340                 345                 350

Ala Ser Val Leu Leu Arg Glu Pro Arg His Ala Leu Ala Asp Met
        355                 360                 365

Tyr Gly Arg Pro Thr Met Thr Ala Glu Ala Arg Leu Val Arg Leu Asp
    370                 375                 380

Pro Leu Asp Pro Arg Ala Ala Gln Thr Leu Glu Gln Ile His Ala
385                 390                 395                 400

Glu Leu Gly Ala Ile His His Ala Val Val Leu Pro Gly Gln Ser Arg
                405                 410                 415

His Ala Pro Ser Ala Ser Leu Ile Glu Val Asp Asp Gln Val Val Glu
                420                 425                 430

Arg Phe Leu His Gln Glu Leu Val Gly Thr Ile Ala Leu Ala Arg Glu
            435                 440                 445

Leu Ala Arg Phe Trp Glu Glu Tyr Pro Ser Gly Ser Ser Met His Arg
450                 455                 460

Val Leu Phe Val Ser Asn Pro Asp Asp Gln Gln Gly Asn Gln Tyr Ser
465                 470                 475                 480

His Ile Leu Arg Ala Ala Val Glu Gln Leu Val Arg Val Trp Arg His
                485                 490                 495

Glu Ser Glu Tyr Asp Ser Val Asn Pro Ala His Gln Gln Glu Gly Gln
                500                 505                 510

Ser Ser Ala Ala Val Trp Ala Asn Gln Leu Ile Arg Tyr Val Asn Asn
            515                 520                 525

Glu Met Ala Asn Leu Asp Phe Thr Cys Ala Trp Val Ala Lys Leu Leu
    530                 535                 540

Gly Ser Asp Arg Arg Ile Ala Glu Ile Asn Leu Tyr Leu Pro Glu Glu
545                 550                 555                 560

Ile Val Gly Thr Ile Gly Val His Asn Pro Gly Phe Gly Trp Ala Glu
                565                 570                 575

Ser Leu Phe Gly Leu His Met Gly Lys Val Ala Leu Ile Thr Gly Gly
                580                 585                 590

Ser Ala Gly Ile Gly Gly Gln Ile Gly Arg Leu Leu Ala Leu Ser Gly
            595                 600                 605

Ala His Val Met Leu Ala Ala Arg Asn Ala Asp Gln Leu Glu Gln Met
        610                 615                 620

Arg Ala Ser Ile Val Arg Glu Val Arg Asp Ala Ser Tyr Pro Asp Ala
625                 630                 635                 640

Glu Ser Arg Val Ala Ile Phe Pro Gly Ser Asp Val Ser Asp Ile Asp
                645                 650                 655

Gly Leu Glu Arg Leu Val Asn His Thr Val Arg Val Phe Gly Lys Val
                660                 665                 670

Asp Tyr Leu Ile Asn Asn Ala Gly Ile Ala Gly Ala Glu Glu Met Val
            675                 680                 685

Ile Asp Met Pro Val Asp Ala Trp Arg His Thr Leu Arg Ala Asn Leu
        690                 695                 700
```

```
Ile Ser Asn Tyr Ala Leu Leu Arg Arg Leu Ala Pro Gln Met Lys Ala
705                 710                 715                 720

Ala Gly Gly Ala Tyr Val Leu Asn Val Ser Ser Tyr Phe Gly Gly Glu
            725                 730                 735

Lys Tyr Val Ala Ile Pro Tyr Pro Asn Arg Ser Asp Tyr Ala Val Ser
        740                 745                 750

Lys Ala Gly Gln Arg Ala Met Val Glu Ser Leu Ala Arg Phe Leu Gly
    755                 760                 765

Pro Glu Ile Gln Ile Asn Ala Ile Ala Pro Gly Pro Val Glu Gly Glu
770                 775                 780

Arg Leu Lys Gly Ala Gly Ser Arg Pro Gly Leu Phe Met Arg Arg Ala
785                 790                 795                 800

Arg Leu Ile Leu Glu Asn Lys Arg Leu Asn Glu Val Phe Ala Ala Leu
                805                 810                 815

Leu Ala Ala Arg His Glu Gly Ala Thr Ile Ala Asp Leu Leu Pro Asp
            820                 825                 830

Leu Phe Ala Asn Asp Ile Gln Ser Ile Ala Asn Ser Ala Ala Met Pro
        835                 840                 845

Ala Pro Leu Arg Arg Leu Ala Thr Met Leu Arg Glu Thr Ser Asp Ala
    850                 855                 860

Gly Gly Ser Ala Gln Ser Tyr Leu Met Asn Ala Thr Ile Ala Arg Lys
865                 870                 875                 880

Leu Leu Asn Arg Leu Glu Asn Gly Gly Tyr Ile Thr Leu His Asp Arg
                885                 890                 895

Arg Ala Leu Thr Val Glu Pro Pro Glu Pro Phe Phe Thr Glu Ala Gln
            900                 905                 910

Ile Glu Arg Glu Ala Ile Lys Val Arg Asp Gly Ile Leu Gly Met Leu
        915                 920                 925

His Leu Gln Arg Met Pro Thr Glu Phe Asp Val Ala Leu Ala Thr Val
    930                 935                 940

Phe Tyr Leu Ala Asp Arg Asn Val Thr Gly Glu Thr Phe His Pro Ser
945                 950                 955                 960

Gly Gly Leu Arg Phe Glu Arg Thr Val Thr Gly Glu Leu Phe Gly
                965                 970                 975

Lys Pro Gly Gln Gln Arg Leu Glu Arg Leu Lys Gly Ser Val Val Tyr
            980                 985                 990

Leu Ile Gly Glu His Leu Arg Gln His Leu Val Leu Leu Ala Arg Thr
        995                 1000                1005

Phe Leu Asp Glu Ile His Val Ala Arg Val Val Leu Leu Thr Glu
    1010                1015                1020

Thr Thr Gln Ala Ala Thr Asp Leu Ala Ala Glu Leu Ser Asp Tyr
    1025                1030                1035

Glu Ala Ala Gly Arg Phe Val Val Ile Pro Thr Cys Gly Asp Ile
    1040                1045                1050

Glu Gly Gly Ile Asp Arg Ala Met Ala Glu Tyr Gly Arg Pro Gly
    1055                1060                1065

Pro Val Ile Ser Thr Pro Phe Arg Pro Leu Pro Asp Arg Ala Leu
    1070                1075                1080

Ser Ala Arg Asn Gly Asp Trp Ser Ser Val Leu Thr Thr Ala Glu
    1085                1090                1095

Phe Glu Glu Leu Val Glu Gln Gln Ile Thr His His Phe Arg Val
    1100                1105                1110
```

```
Ala Arg Lys Ala Gly Leu Ile Glu Gly Ala Asn Val Thr Leu Val
    1115                1120                1125

Thr Pro Pro Thr Ser Ala Arg Ser Thr Ser Glu Glu Phe Ala Leu
    1130                1135                1140

Ala Asn Phe Val Lys Thr Thr Leu His Ala Leu Thr Ala Thr Ala
    1145                1150                1155

Gly Ala Glu Ser Glu Arg Thr Val Pro His Val Pro Val Asn Gln
    1160                1165                1170

Val Asp Leu Thr Arg Arg Ala Arg Ser Glu Glu Pro Arg Thr Pro
    1175                1180                1185

Ser Glu Glu Glu Glu Leu Gln Arg Phe Val Asn Ala Val Leu
    1190                1195                1200

Leu Thr Ser Ala Pro Leu Pro Thr Pro Leu Glu Ser Arg Tyr Arg
    1205                1210                1215

Ala Arg Ile Tyr Arg Gly Asn Ala Ile Thr Val
    1220                1225

<210> SEQ ID NO 296
<211> LENGTH: 1232
<212> TYPE: PRT
<213> ORGANISM: Roseiflexus sp.

<400> SEQUENCE: 296

Met Ser Thr Thr Arg Arg His Asp Arg Leu Glu Gly Lys Val Ala Leu
1               5                   10                  15

Ile Thr Gly Gly Ala Gly Asn Ile Gly Glu Val Ile Thr Arg Arg Phe
            20                  25                  30

Leu Ala Glu Gly Ala Thr Val Val Ile Thr Gly Arg Asn Val Glu Lys
        35                  40                  45

Leu Ala Ala Tyr Arg Arg Arg Leu Ile Asp Glu Glu Arg Ile Ala Pro
    50                  55                  60

Asp Arg Val Val Ala Leu Arg Met Asp Gly Ser Asp Met Ala Gln Val
65                  70                  75                  80

Arg Ala Ala Ile Ala Gln Ile Val His Gly Gly Ala Asp Val Pro Thr
                85                  90                  95

Pro Leu Lys Arg Ile Asp Ile Leu Val Asn Asn Ala Gly Ser Ala Gly
            100                 105                 110

Pro Arg Arg Arg Leu Val Asp Ile Pro Leu Glu Pro Ser Glu Val His
        115                 120                 125

Pro Pro Asp Thr Glu Thr Leu Ala Gln Ala Val Gly Asn Leu Val Gly
    130                 135                 140

Val Ala Trp Asn Leu Thr Arg Ala Ala Ala Pro Tyr Met Pro Pro Gly
145                 150                 155                 160

Ser Ser Ile Ile Asn Val Ser Thr Ile Phe Ser Arg Thr Asp Tyr Tyr
                165                 170                 175

Gly Arg Ile Ala Tyr Val Val Pro Lys Ala Ala Leu Asn Ala Leu Ser
            180                 185                 190

Gln Gly Leu Ala Arg Glu Leu Gly Val Arg Gly Ile Arg Val Asn Thr
        195                 200                 205

Ile Tyr Pro Gly Pro Ile Glu Ser Glu Arg Ile His Thr Val Phe Gln
    210                 215                 220

Ala Met Asp Ala Leu Lys Gly Gln Pro Glu Gly Glu Thr Ala Arg Ser
225                 230                 235                 240

Phe Leu Arg Leu Met Arg Leu Ser Arg Ala Asp Thr Gln Gly Glu Val
                245                 250                 255
```

```
Thr Lys Arg Phe Pro Leu Pro Val Asp Val Ala Asn Thr Ala Val Phe
            260                 265                 270

Leu Ala Ser Glu Glu Ser Ala Ala Phe Thr Gly His Ala Phe Glu Val
            275                 280                 285

Thr His Gly Met Glu Ala Pro Val Glu Ser Arg Thr Thr Phe Val Ser
290                 295                 300

Arg Pro Gly Leu Arg Ser Val Asp Ala Thr Gly Asn Val Ile Leu Ile
305                 310                 315                 320

Cys Ala Gly Asp Gln Val Asp Ala Ile Ala Leu Ser Asp Thr Leu
            325                 330                 335

Arg Ser Cys Arg Ala Thr Val Val Val Gly Phe Arg Asp Val Gln Ala
            340                 345                 350

Leu Glu Lys Ala Ser Ala Leu Leu Arg Glu Pro Arg His Val Ala Pro
            355                 360                 365

Ala Asp Met Tyr Gly Arg Pro Thr Met Val Ala Glu Thr Arg Leu Val
            370                 375                 380

His Leu Asp Pro Leu Asp Ser Arg Ala Ala Gln Thr Leu Glu Arg
385                 390                 395                 400

Ile Arg Ala Glu Leu Gly Thr Leu His His Ala Val Ile Leu Pro Ala
                    405                 410                 415

Ser Leu Arg His Ala Pro Thr Glu Ser Leu Ile Asp Val Asp Asp Arg
            420                 425                 430

Ile Ile Asp Arg Phe Leu Glu Gln Glu Leu Val Gly Ala Ile Ala Leu
            435                 440                 445

Ala Arg Glu Leu Ala Arg Phe Trp Glu Glu His Pro Ala Gly Ser Arg
450                 455                 460

Ala His Arg Val Leu Phe Val Ser Asn Pro Asp Asp Gln Gln Gly Asn
465                 470                 475                 480

Arg Tyr Ala Asp Ile Leu Arg Ala Ala Val Glu Gln Leu Ala Arg Val
                    485                 490                 495

Trp Arg His Glu Ser Glu Tyr Asp Ala Ala Asn Pro Ala His Arg His
            500                 505                 510

Glu Asp Gln Pro Gly Ala Ala Val Trp Ala Asn Gln Leu Ile Arg Tyr
            515                 520                 525

Val Asn Ser Glu Ser Ala Asn Leu Asp Phe Thr Cys Ala Trp Val Ala
530                 535                 540

Lys Leu Leu Gly Ser Asp Arg Arg Ile Ala Glu Ile Asn Leu Tyr Leu
545                 550                 555                 560

Pro Glu Gln Ile Val Ser Thr Ile Gly Val His Asn Pro Gly Phe Gly
                    565                 570                 575

Trp Ala Glu Ser Leu Phe Gly Leu His Met Gly Lys Val Ala Leu Ile
            580                 585                 590

Thr Gly Gly Ser Ala Gly Ile Gly Ala Gln Ile Gly Arg Leu Leu Ala
            595                 600                 605

Leu Ser Gly Ala His Val Met Leu Ala Ala Arg Asn Ala Glu Gln Leu
610                 615                 620

Glu Gln Met Arg Ala Leu Ile Val Arg Glu Val Arg Asp Ala Ser Tyr
625                 630                 635                 640

Pro Asp Ala Glu Ser Arg Val Ala Ile Phe Pro Asn Ser Asp Val Ser
                    645                 650                 655

Asp Ile Asp Gly Leu Glu Arg Leu Val Asn His Thr Leu Arg Val Phe
            660                 665                 670
```

-continued

```
Gly Lys Val Asp Tyr Leu Ile Asn Asn Ala Gly Ile Ala Gly Ala Glu
            675                 680                 685
Glu Met Val Ile Asp Met Pro Val Asp Ala Trp Arg His Thr Leu Arg
690                 695                 700
Ala Asn Leu Ile Ser Asn Tyr Ala Leu Leu Arg Arg Leu Ala Pro Gln
705                 710                 715                 720
Met Lys Ala Ala Gly Ala Tyr Val Leu Asn Val Ser Ser Tyr Phe
            725                 730                 735
Gly Gly Glu Lys Tyr Val Ala Ile Pro Tyr Pro Asn Arg Ala Asp Tyr
            740                 745                 750
Ala Val Ser Lys Ala Gly Gln Arg Ala Met Val Glu Ser Leu Ala Arg
            755                 760                 765
Phe Leu Gly Pro Glu Ile Gln Ile Asn Ala Ile Ala Pro Gly Pro Val
770                 775                 780
Glu Gly Glu Arg Leu Lys Gly Ala Ala Asn Arg Pro Gly Leu Phe Met
785                 790                 795                 800
Arg Arg Ala Arg Leu Ile Leu Glu Asn Lys Arg Leu Asn Glu Val Phe
            805                 810                 815
Ala Ala Leu Leu Ala Ala Arg His Glu Gly Ala Val Ile Ala Ala Leu
            820                 825                 830
Leu Pro Asp Leu Phe Val Asn Asp Leu Gln Thr Ile Ala Asp Asn Pro
            835                 840                 845
Ala Met Pro Ala Pro Val Arg Arg Leu Ala Thr Met Leu Arg Glu Thr
            850                 855                 860
Thr Asp Ala Gly Gly Ser Ala Gln Ser Tyr Leu Met Asn Ala Thr Ile
865                 870                 875                 880
Ala Arg Lys Leu Leu Asn Arg Leu Glu Asn Gly Gly Tyr Ile Thr Ala
            885                 890                 895
Gly Asp Arg Arg Ala Leu Thr Asn Glu Pro Pro Asp Pro Phe Phe Thr
            900                 905                 910
Glu Ala Gln Ile Glu Arg Glu Ala Ile Lys Val Arg Asp Gly Ile Leu
            915                 920                 925
Gly Met Leu His Leu Gln Arg Met Pro Thr Glu Phe Asp Val Ala Leu
930                 935                 940
Ala Thr Val Phe Tyr Leu Ala Asp Arg Asn Val Thr Gly Glu Thr Phe
945                 950                 955                 960
His Pro Ser Gly Gly Leu Arg Phe Glu Arg Thr Val Thr Glu Gly Glu
            965                 970                 975
Leu Phe Gly Lys Pro Gly Arg Gln Arg Leu Glu Arg Met Ala Gly Ser
            980                 985                 990
Val Val Tyr Leu Ile Gly Glu His Leu Arg Gln His Leu Leu Leu Leu
            995                 1000                1005
Ala Arg Thr Phe Leu Asp Glu Ile His Val Ala Arg Val Val Leu
    1010                1015                1020
Leu Thr Glu Thr Glu Gln Ala Ala Ala Glu Leu Ala Thr Val Phe
    1025                1030                1035
Ala Asp Glu Glu Ala Ala Gly Arg Phe Val Ile Ile Pro Thr Gly
    1040                1045                1050
Gly Asp Ile Glu Gly Gly Ile Asp Arg Ala Met Ala Glu Tyr Gly
    1055                1060                1065
Arg Pro Gly Pro Val Ile Ser Thr Pro Phe Arg Pro Leu Pro Ser
    1070                1075                1080
Arg Ala Leu Ser Ala Gln Asn Gly Asp Trp Ser Asn Val Leu Thr
```

```
               1085                1090                1095

Thr Pro Glu Phe Glu Glu Leu Val Glu Gln His Ile Thr His His
    1100                1105                1110

Phe Arg Val Val Arg Lys Ala Gly Leu Ile Glu Gly Ala Asn Val
    1115                1120                1125

Thr Leu Val Thr Pro Pro Thr Ser Ala Arg Ser Thr Ala Glu Glu
    1130                1135                1140

Phe Ala Leu Ala Asn Phe Ile Lys Thr Thr Leu His Ala Leu Thr
    1145                1150                1155

Ala Thr Ala Gly Ala Glu Ser Glu Arg Thr Met Pro His Val Pro
    1160                1165                1170

Val Asn Gln Val Asp Leu Thr Arg Arg Ala Arg Ser Glu Glu Pro
    1175                1180                1185

Arg Thr Pro Ala Glu Glu Glu Glu Leu Gln Arg Phe Val Asn
    1190                1195                1200

Ala Val Leu Leu Thr Ser Ala Pro Leu Pro Thr Pro Leu Glu Ser
    1205                1210                1215

Arg Tyr Arg Ala Arg Ile Tyr Arg Gly Asn Ala Ile Thr Val
    1220                1225                1230

<210> SEQ ID NO 297
<211> LENGTH: 1217
<212> TYPE: PRT
<213> ORGANISM: Erythrobacter sp

<400> SEQUENCE: 297

Met Ser Lys Glu Gly Asn Ala Ala Lys Gly Arg Leu Glu Gly Lys Val
1               5                   10                  15

Ala Leu Ile Thr Gly Ala Ala Gly Asn Leu Gly Asn Glu Ile Ser Arg
            20                  25                  30

Ala Phe Ala Arg Glu Gly Ala Phe Val Val Met Thr Gly Arg Thr Glu
        35                  40                  45

Glu Arg Ile Ser Ala Ala Arg Glu Gln Leu Ile Ala Asp Thr Gly Val
    50                  55                  60

Ala Pro Glu Arg Ile Asp Thr Ala Val Leu Asp Gly Gly Asn Pro Asp
65                  70                  75                  80

Ser Ile Arg Ala Ala Met Ala Lys Leu Arg Lys Glu Tyr Gly Arg Ile
                85                  90                  95

Asp Ile Leu Ile Asn Asn Ala Gly Ser Ala Gly Pro Lys Gln Pro Leu
            100                 105                 110

His Asn Val Pro Leu Ser Pro Gln Glu Met Glu Ala Cys Gly Asp Thr
        115                 120                 125

Glu Thr Val Arg Asp Ala Met Leu Asn Ile Leu Gly Val Thr Trp Asn
    130                 135                 140

Met Ala Arg Ile Val Ala Pro Met Met Pro Val Gly Gly Ala Met Val
145                 150                 155                 160

Asn Ile Ser Thr Ile Phe Ser His Thr Arg Tyr Tyr Gly Arg Thr Ala
                165                 170                 175

Tyr Val Val Pro Lys Ala Ala Leu Asn Ala Leu Ser Asn Gln Leu Ala
            180                 185                 190

Ser Glu Leu Gly Pro Arg Gly Ile Arg Val Asn Thr Val Phe Pro Gly
        195                 200                 205

Pro Ile Glu Ser Asp Arg Ile Arg Thr Val Phe Ala Ala Met Asp Glu
    210                 215                 220
```

```
Val Gln Ser Gln Pro Lys Asp Thr Thr Ala Asn Tyr Phe Thr Gly Arg
225                 230                 235                 240

Met Ala Leu Thr Arg Ser Val Asn Gly Lys Val Asp Gly Lys Pro Leu
            245                 250                 255

Pro Asn Pro Lys Asp Ile Ala Gly Thr Cys Leu Phe Leu Ala Ser Glu
        260                 265                 270

Glu Ala Ala Gly Ile Ala Gly Glu Glu Val Asp Val Thr His Gly Leu
    275                 280                 285

Ser Ala Asn Arg Thr Ser Ala Ser Thr Tyr Met Thr Arg Pro Ser Met
290                 295                 300

Arg Ser Leu Asp Gly Ala Gly Leu Asn Ile Phe Ile Val Ser Gly Glu
305                 310                 315                 320

Asn Trp Asp Asp Ala Leu Val Ala Ala His Thr Leu Ile Gly Ser Gly
            325                 330                 335

Ala Lys Val Arg Leu Gly Leu Ala Arg Asn Ala Asp Val Ala Gln Ala
        340                 345                 350

Asn Ala Arg Leu Lys Ala Gln Gly Ile Gly Glu Glu Leu Thr Val Thr
    355                 360                 365

Arg Phe Asn Arg Ala Glu Pro Asp Ala Met Glu Asp Ala Leu Ala Ala
370                 375                 380

Phe Ser Gly Asp Val Asp Gly Ala Ile Thr Gly Ala Ile Ile Leu Pro
385                 390                 395                 400

Val Lys Pro Ser Gly His Phe Thr Gly Ser Leu Leu Ala Ala Asp Asp
            405                 410                 415

Asp Thr Val Thr Lys Phe Met Asp Thr Glu Leu Val Gly Ala Ile Ala
        420                 425                 430

Val Ser Arg Ser Leu Ala Arg Tyr Trp His Gly Arg Glu Asp Leu Gln
    435                 440                 445

Ser Pro Pro Arg Cys Val Phe Met Thr Asn Pro Gly Asp Pro Leu Gly
450                 455                 460

Asn Ser Phe Ala Ser Val Leu Ser Ala Gly Ile Thr Gln Leu Ile Arg
465                 470                 475                 480

Ile Trp Arg Asp Glu Glu Arg Val Gln Ala Gly Asn Gly Ser Thr Glu
            485                 490                 495

His Ala Val Trp Ser Asn Gln Ile Val Arg His Thr Asn Thr Glu Asp
        500                 505                 510

Glu Asn Thr Arg Phe Ala Ser Gly His Ala Thr Arg Val Leu Phe Arg
    515                 520                 525

Glu Gln His Ile Ala Glu Ile Asp Leu Lys Leu Pro Ala Asn Ile Ser
530                 535                 540

Glu Glu Thr Gly Ser Arg Lys Ala Met Val Gly Phe Ala Glu Asn Ile
545                 550                 555                 560

Thr Gly Leu His Leu Gly Lys Val Ala Phe Ile Thr Gly Gly Ser Ala
            565                 570                 575

Gly Ile Gly Gly Gln Val Ala Arg Leu Leu Ala Leu Ala Gly Ala Lys
        580                 585                 590

Val Met Met Val Ala Arg Arg Glu Ser Glu Leu Val Ala Ala Arg Asp
    595                 600                 605

Arg Ile Val Gly Glu Leu Gln Asp Ile Gly Phe Ala Gly Val Glu Arg
610                 615                 620

Arg Val Lys Tyr Met Ala Asp Ile Asp Val Ser Asp Phe Ala Ser Leu
625                 630                 635                 640

Asp Lys Ala Val Asp Ala Thr Leu Glu Glu Phe Gly Arg Ile Asp Tyr
```

-continued

```
                645                 650                 655
Leu Ile Asn Asn Ala Gly Val Ala Gly Ala Glu Asp Met Val Ile Asp
            660                 665                 670
Met Glu Pro Glu Ala Trp Arg Phe Thr Leu Asp Ala Asn Leu Ile Ser
            675                 680                 685
Asn Tyr His Leu Met Gln Arg Val Val Pro Leu Met Lys Glu Gln Gly
            690                 695                 700
Ser Gly Tyr Val Leu Asn Val Ser Ser Tyr Phe Gly Gly Glu Lys Phe
705                 710                 715                 720
Leu Ala Val Ala Tyr Pro Asn Arg Ala Asp Tyr Gly Leu Ser Lys Ala
                725                 730                 735
Gly Gln Arg Ala Met Val Glu Ala Phe Ser Pro Phe Leu Gly Pro Glu
            740                 745                 750
Val Gln Cys Asn Ala Ile Ala Pro Gly Pro Val Asp Gly Asp Arg Leu
            755                 760                 765
Ser Gly Thr Gly Gly Lys Pro Gly Leu Phe Gln Arg Arg Ala Lys Leu
            770                 775                 780
Ile Leu Glu Asn Lys Arg Leu Asn Ala Val Tyr Ser Ala Val Ile His
785                 790                 795                 800
Ala Ile Arg Glu Gly Gly Asp Ala Ala Lys Ile Leu Thr Arg Leu Ser
                805                 810                 815
Arg Asn Ser Thr Ser Thr Leu Ser His Asp Ala Glu Ala Pro Glu Glu
            820                 825                 830
Leu Arg Lys Leu Ala Leu Asp Phe Ala Ser Gln Gly Asp Gly Leu Cys
            835                 840                 845
Thr Trp Asp Gln Tyr Leu Leu Thr Asp Ala Met Ala Gln Arg Leu Leu
850                 855                 860
Val Arg Leu Gln Leu Gly Gly Phe Leu Leu Gly Ser Asn Glu Trp Ala
865                 870                 875                 880
Ser Leu Ser Ser Ser Glu Gln Thr Trp Leu Lys Leu Ser Pro Pro Asp
                885                 890                 895
Asp Lys Pro Phe Leu Pro Ala Ala Gln Val Asp Lys Val Ala Asn Gly
            900                 905                 910
Val Gly Lys Gly Val Ile Ser Gln Leu His Leu Gly Ala Met Pro Thr
            915                 920                 925
Glu Ala Glu Val Ala Gln Ala Thr Val Phe Leu Ala Asp Arg Ala
            930                 935                 940
Val Ser Gly Glu Thr Phe Met Pro Ser Gly Gly Leu Arg Val Glu Arg
945                 950                 955                 960
Ser Asn Thr Glu Arg Glu Met Phe Gly Ser Pro Lys Gln Glu Arg Ile
                965                 970                 975
Asp Lys Met Lys Gly Lys Thr Val Trp Ile Ile Gly Glu His Leu Ser
            980                 985                 990
Asp Tyr Val Ala Ala Thr Ile Glu Glu Leu Val Ser Gly Cys Gly Val
            995                 1000                1005
Ala Lys Val Val Leu Ile Ala Lys Asp Lys Ser Gly Glu Lys Ala
        1010                1015                1020
Val Arg Asp Gln Leu Pro Asn Asp Leu Ser Lys Asp Ala Leu Glu
        1025                1030                1035
Val Leu Ile Ala Gly Asp Gly Leu Glu Glu Ala Met Asp Glu Ala
        1040                1045                1050
Leu Gly His Trp Gly Lys Pro Thr Thr Val Leu Ser Met Pro Gly
        1055                1060                1065
```

```
Glu Pro Leu Pro Asp His Leu Phe Gly Gly Asn Pro Leu Ser
        1070                1075                1080

Thr Lys Asp Phe Ala His Met Val Glu Ala Asn Ile Thr Arg His
    1085                1090                1095

Tyr Arg Val Thr Arg Lys Ala Ser Leu Tyr Asp Gly Cys Gln Val
    1100                1105                1110

Val Leu Val Ser Pro Asp Val Pro Tyr Gly Ser Asp Gly Pro Gly
    1115                1120                1125

Val Ala Leu Ala Asn Phe Val Lys Thr Ser Leu His Ala Phe Thr
    1130                1135                1140

Ala Thr Val Ala Val Glu Asn Glu Arg Leu Val His Asp Val Pro
    1145                1150                1155

Val Asn Gln Ile Asn Leu Thr Arg Arg Val Ser Ser Glu Glu Pro
    1160                1165                1170

Arg Asp Ala Asp Glu His Ala Glu Glu Leu Arg Arg Phe Thr Arg
    1175                1180                1185

Ala Val Leu Leu Val Gly Ala Pro Leu Pro Asp Ala Gln Asp Ser
    1190                1195                1200

Arg Tyr Arg Ser Lys Ile Tyr Arg Gly Thr Ser Met Thr Val
    1205                1210                1215

<210> SEQ ID NO 298
<211> LENGTH: 1210
<212> TYPE: PRT
<213> ORGANISM: Artificial
<220> FEATURE:
<223> OTHER INFORMATION: gamma proteobacterium NOR51-B

<400> SEQUENCE: 298

Met Asn Thr Glu Thr Arg Thr Thr Ser Gly Gly Arg Leu His Asp Lys
1               5                   10                  15

Val Val Ile Leu Thr Gly Ala Ala Gly Asn Ile Gly Ser Tyr Ile Ser
                20                  25                  30

Arg Ser Leu Leu Arg Glu Gly Ala Asn Leu Val Met Thr Gly Arg Asn
            35                  40                  45

Glu Pro Lys Leu Gln Ala Phe Val Gly Leu Val Glu Glu Gly Phe
        50                  55                  60

Asp Arg Asp Asn Ile Leu Ile Ala Ile Gly Asp Ser Ala Lys Ala Asp
65                  70                  75                  80

Ile Cys Arg Glu Ile Val Lys Ala Thr Val Asn His Phe Gly Asn Ile
                85                  90                  95

Asp Val Leu Val Asn Asn Ala Gly Gly Ala Gly Pro Arg Arg Thr Leu
            100                 105                 110

Arg Asp Ile Pro Phe Ser Glu Ser Glu Arg Leu Ala Arg Gly Asp Asp
        115                 120                 125

Glu Thr Met Leu Asp Ala Ala Met Asn Leu Leu Ala Gly Ala Trp Asn
    130                 135                 140

Met Thr Arg Ala Ala Val Pro His Met Ser Glu Gly Gly Ser Ile Val
145                 150                 155                 160

Asn Val Ser Thr Ile Phe Ser Arg Thr His Tyr Tyr Gly Arg Ile Pro
                165                 170                 175

Tyr Val Val Pro Lys Ser Gly Leu Asn Ala Leu Ser Ile Gly Leu Ala
            180                 185                 190

Lys Glu Leu Gly Glu Glu His Gly Ile Arg Val Asn Thr Leu Phe Pro
        195                 200                 205
```

```
Gly Pro Ile Glu Ser Glu Arg Ile Asp Thr Val Phe Gly Asn Met Asp
210                 215                 220

Ala Leu Gln Ser Ala Pro Ala Gly Ala Thr Ser Gln Glu Phe Arg Asp
225                 230                 235                 240

Leu Met Ile Thr Arg Arg Glu Asn Pro Asp Gly Glu Tyr Glu Tyr Arg
                245                 250                 255

Tyr Pro Thr Pro Asn Asp Val Ala Ser Thr Val Thr Trp Leu Ala Ser
                260                 265                 270

Glu Glu Ser Ala Ala Leu Ser Gly His His Ile Glu Val Thr Asn Gly
            275                 280                 285

Met Gln Val Pro Ala Gln Ser Arg Ser Lys Leu Val Ser Trp Pro Asp
290                 295                 300

Lys Arg Leu Glu Asp Leu Ser Gly Gln Val Val Phe Leu Leu Ala Gly
305                 310                 315                 320

Ser Asp Tyr Glu Asp Ala Leu Ala Phe Ala Glu Arg His Met Val Ser
                325                 330                 335

Gly Ala Lys Val Val Leu Ala Phe Arg Ser Leu Glu Ser Leu Gly Leu
                340                 345                 350

Ala Arg Ser Leu Cys Ala Ser Arg Asp Leu Glu Ser Ile His Leu Leu
            355                 360                 365

His Leu Glu Pro Leu Arg Arg Glu Ser Ala Asp Arg Cys Phe Asp Tyr
370                 375                 380

Ile Arg Asp His Phe Gly Arg Leu Asp Gly Ile Val Val Leu Pro Arg
385                 390                 395                 400

Ser Gly Asn Gly Glu His Gly Tyr Ser Leu Ser Thr Ala Gly Asp Asp
                405                 410                 415

Asp Val Glu Ala Phe Val Arg Asp Glu Ile Ile Ser Pro Val Ala Phe
                420                 425                 430

Ala Ala Ala Leu Ala Ile Asn Leu Asp Arg Trp Gly Ile Leu Glu Glu
            435                 440                 445

Ala Pro Ala Leu Thr Tyr Val Thr Asn Pro Thr Asp Gly His Gly Asp
450                 455                 460

Tyr Leu Asn Glu Val Lys Arg Ala Ala Ile Glu Ala Leu Ile Arg Ile
465                 470                 475                 480

Trp Arg His Glu Asp Arg Gln Met Arg Lys Lys Gly Glu Arg Glu Trp
                485                 490                 495

Ala Met Leu Pro Asn Gln Leu Val Arg Tyr Asp Asn Asn Glu Glu Asp
                500                 505                 510

Asn Leu Thr Phe Thr Ala Asp Trp Ala Ala Thr Leu Thr Asn Arg Val
            515                 520                 525

Arg Arg Met Asp Pro Ile Asn Leu Trp Val Pro Glu Ser Ile Met Arg
530                 535                 540

Ala Thr Gly Lys Ser Gly Met Pro Gln Ser Ile Gln Arg Val Leu Pro
545                 550                 555                 560

Gly Leu His Lys Gly Arg Thr Ala Val Ile Thr Gly Gly Ser Leu Gly
                565                 570                 575

Ile Gly Leu Gln Leu Gly Arg Phe Leu Ala Ile Ala Gly Ala Arg Val
                580                 585                 590

Leu Leu Ser Ala Arg Ser Lys Glu Lys Leu Glu Glu Ala Arg His Glu
            595                 600                 605

Ile Val Glu Glu Leu Arg Gly Val Gly Tyr Pro Asn Ala His Gln Arg
610                 615                 620
```

```
Val His Ile Leu Pro Asp Ile Asp Val Gly Asp Glu Glu Ala Leu Glu
625                 630                 635                 640

Arg Leu Tyr Asn His Ser Ile Glu Leu Phe Gly Asn Val Asp Phe Leu
            645                 650                 655

Ile Asn Asn Ala Gly Ile Ser Gly Ala Glu Glu Met Val Val Asp Met
                660                 665                 670

Ser Leu Glu Ala Trp Asn Arg Thr Met Tyr Ala Asn Leu Ile Ser Asn
675                 680                 685

Tyr Ser Leu Ile Arg Lys Tyr Ala Pro Lys Met Lys Ala Asn Gly Tyr
    690                 695                 700

Gly Val Val Leu Asn Val Ser Ser Tyr Phe Gly Gly Glu Lys Tyr Val
705                 710                 715                 720

Ala Val Ala Tyr Pro Asn Arg Ala Asp Tyr Ala Val Ser Lys Ala Gly
            725                 730                 735

Gln Arg Val Leu Ala Glu Ile Leu Ser Arg His Leu Gly Pro Glu Ile
                740                 745                 750

Arg Ile Asn Ala Leu Ala Pro Gly Pro Val Asp Gly Ala Arg Leu Arg
                755                 760                 765

Gly Leu Gly Gly Ala Pro Gly Leu Phe Glu Arg Arg Gly Arg Leu Val
770                 775                 780

Leu Glu Asn Lys Arg Leu Asn Ser Val His Lys Ala Val Leu Ala Ala
785                 790                 795                 800

Leu Arg Glu Gly Ala Thr Pro Glu Val Ile Met Ala Leu Ser Arg Asn
                805                 810                 815

Ala Leu Gly Asp Ala Lys Pro Thr Ala Gly Gln Ser Lys Ala Leu Asp
                820                 825                 830

Lys Leu Phe Ala Gln Val Glu Asp Ser Pro Glu Gly Gly Asn Ser Thr
            835                 840                 845

Ala Phe Leu Leu Asn Arg Asp Leu Ala Glu Lys Leu Met Asn Arg Leu
850                 855                 860

Val Thr Gly Gly Leu Phe Thr Pro Glu Ser Ala Thr Gln Phe Met Glu
865                 870                 875                 880

Gly Phe Val Asp Ala Pro Ala Ile Phe Phe Asp Glu Lys Ser Val Asn
                885                 890                 895

Lys Ala Ala Ala Gly Ile Glu Ala Gly Ile Leu Asn Arg Leu His Leu
                900                 905                 910

His Lys Met Pro Thr Asp Glu Gln Ile Gly Leu Ser Thr Val Phe His
            915                 920                 925

Leu Ala Asp Asp Ile Ala Ser Gly Glu Thr Phe His Pro Ser Gly Gly
    930                 935                 940

Leu Lys Phe Asp Arg Ser Val Thr Glu Gly Glu Leu Leu Pro Pro
945                 950                 955                 960

Asp Arg Asp Ser Leu Ala Lys Leu Lys Gly Lys Arg Val Val Leu Ile
            965                 970                 975

Gly Asp Ser Met Arg Glu Glu Leu Ser Ala Ile Gly Asn Gly Phe Ile
    980                 985                 990

Asn Gln Gly Val Ala Ser Leu Thr Val Leu Thr Arg Ser Pro Glu Ala
        995                 1000                1005

Cys Glu Glu Val Gln His Ser Leu Gln Lys Ser Asn Ser Val Thr
        1010                1015                1020

Leu Asp Val Arg Cys Ile Glu Asp Asn Ile Glu Asp Ala Leu Asp
        1025                1030                1035

Asp Leu Leu Gln Asn Gln Gly Gly Phe Asp Val Val  Val Ser Ala
```

```
                1040                1045                1050

Pro Phe Ser Arg Leu Pro Tyr Asn Pro Leu Ala Ala Glu Arg Glu
    1055                1060                1065

Gly Ser Trp Asn Arg Val Leu Ser His Thr Asp Phe Ala Arg Leu
    1070                1075                1080

Ile Asp Glu Gln Leu Thr His His Phe Arg Val Ala Arg Arg Ala
    1085                1090                1095

Ala Leu Val Pro Asn Cys Gln Ile Val Leu Leu Thr Pro Asp Thr
    1100                1105                1110

Ser Phe Val Ser Ser Arg Glu Glu Phe Ala Leu Ala Leu Phe Val
    1115                1120                1125

Lys Asn Ser Leu His Ala Phe Thr Val Thr Leu Gly Val Glu Thr
    1130                1135                1140

Glu Arg Leu Pro Thr Val Pro Ala Val Asn Gln Val Gln Leu Thr
    1145                1150                1155

Arg Arg Ala Arg Ala Glu Glu Pro Ala Thr Glu Ser Glu Leu Gln
    1160                1165                1170

Glu Glu Met Glu Arg Leu Val Ser Ala Val Leu Gln Cys Ala Val
    1175                1180                1185

Pro Ala Pro Ser Pro Ser Glu Ser Arg Tyr Leu Ala Arg Ile Phe
    1190                1195                1200

Arg Gly Asn Ala Val Thr Val
    1205                1210

<210> SEQ ID NO 299
<211> LENGTH: 10
<212> TYPE: PRT
<213> ORGANISM: T. saccharolyticum

<400> SEQUENCE: 299

Met Lys Lys Phe Ile Val Thr Val Asn Gly
1               5                   10

<210> SEQ ID NO 300
<211> LENGTH: 24
<212> TYPE: DNA
<213> ORGANISM: Artificial
<220> FEATURE:
<223> OTHER INFORMATION: X13673 primer

<400> SEQUENCE: 300
atacgggata taccgcgcc acat                                         24

<210> SEQ ID NO 301
<211> LENGTH: 24
<212> TYPE: DNA
<213> ORGANISM: Artificial
<220> FEATURE:
<223> OTHER INFORMATION: X13674 primer

<400> SEQUENCE: 301
ccattcgacc accaagcgaa acat                                        24
```

What is claimed is:

1. A recombinant yeast microorganism comprising one or more engineered metabolic pathways to convert a carbohydrate source to a malonyl-CoA derived product, wherein the one or more engineered metabolic pathways comprises
(a) the conversion of phosphoenolpyruvate to oxaloacetate by a phosphoenolpyruvate carboxykinase and
(b) the conversion of oxaloacetate and acetyl-CoA to malonyl-CoA and pyruvate by a heterologous transcarboxylase Enzyme Commission Number 2.1.3.1;
wherein the one or more engineered metabolic pathways further comprises downregulation or deletion of native pyruvate decarboxylase, and wherein the one or more engineered metabolic pathway further comprises heterologous pyruvate formate lyase.

2. The recombinant yeast microorganism of claim 1, wherein the conversion of a carbohydrate source to a malonyl-CoA derived product is under anaerobic or microaerophilic conditions.

3. The recombinant yeast microorganism of claim 1, wherein at least one of said engineered metabolic pathways produces net ATP.

4. The recombinant yeast microorganism of claim 1, wherein said product is a polyketide or an organic acid.

5. The recombinant yeast microorganism of claim 4, wherein said polyketide is an antibiotic, antitumor, antifungal, or immunosuppressive.

6. The recombinant yeast microorganism of claim 4, wherein said organic acid is 3-hydroxypropionic acid.

7. The recombinant yeast microorganism of claim 6, wherein one of said engineered metabolic pathways comprises the following steps: (a) conversion of malonyl-CoA to malonate semialdehyde and coA; and (b) conversion of malonate semialdehyde to 3-hydroxypropanoate.

8. The recombinant yeast microorganism of claim 7, wherein said malonyl-CoA is converted to malonate semialdehyde and coA by a malonyl-CoA reductase.

9. The recombinant yeast microorganism of claim 8, wherein said malonyl-CoA reductase is encoded by a polynucleotide from a *C. aurantiacus*.

10. The recombinant yeast microorganism of claim 7, wherein said malonate semialdehyde is converted to 3-hydroxypropanoate by a 3-hydroxypropionate dehydrogenase.

11. The recombinant yeast microorganism of claim 6, wherein said malonyl-CoA is converted to 3-hydroxypropanoate by a bifunctional dehydrogenase.

12. The recombinant yeast microorganism of claim 4, wherein said organic acid is adipic acid.

13. The recombinant yeast microorganism of claim 1, wherein said carbohydrate source is a lignocellulosic material.

14. The recombinant yeast microorganism of claim 1, wherein one of said engineered metabolic pathways further comprises the conversion of pyruvate and CoA-SH into acetyl-CoA and $CO_2$ and NAD(P)H.

15. The recombinant yeast microorganism of claim 1, wherein said phosphoenolpyruvate carboxykinase is encoded by a polynucleotide from a *Thermoanaerobacter* species, *E. coli*, *S. cerevisiae*, or *C. thermocellum*.

16. The recombinant yeast microorganism of claim 1, wherein the one or more engineered metabolic pathways further comprises downregulation or deletion of native enzymes selected from the group consisting of: (a) a pyruvate carboxykinase; (b) a hydrogenase; (c) a lactate dehydrogenase; (d) a phosphotransacetylase; (e) an acetate kinase; (f) an acetaldehyde dehydrogenase; (g) an alcohol dehydrogenase; (h) an enzyme involved in degradation of fatty acids and their derivatives; and (i) combinations of (a)-(i).

17. The recombinant yeast microorganism of claim 1, wherein the one or more engineered metabolic pathways further comprises downregulation or deletion of native enzymes selected from the group consisting of: (a) a lactate dehydrogenase; (b) a phosphate acetyltransferase; (c) an acetaldehyde dehydrogenase/alcohol dehydrogenase; (d) a pyruvate carboxykinase; (e) a malate dehydrogenase; (f) a PEP-protein phosphotransferase of PTS system; and (g) combinations of (a)-(f).

18. A process for converting a carbohydrate source to a malonyl-CoA derived product comprising contacting the carbohydrate source with a recombinant yeast microorganism according to claim 1.

19. The process of claim 18, wherein said carbohydrate source comprises lignocellulosic biomass.

20. An engineered metabolic pathway for producing a malonyl-CoA derived product in a consolidated bioprocessing (CBP) organism according to claim 1.

21. The recombinant yeast microorganism of claim 1, wherein the conversion of a carbohydrate source to a malonyl-CoA derived product is redox neutral.

22. The recombinant yeast microorganism of claim 1, wherein one of said engineered metabolic pathways further comprises one or more formate dehydrogenases capable of converting formate to $CO_2$ and NAD(P)H.

23. The recombinant yeast microorganism of claim 22, wherein said formate dehydrogenase is encoded by an *S. cerevisiae* NAD+FDH1, a *B. stabilis* NADP+FDH, or both.

24. The recombinant yeast microorganism of claim 1, wherein one of said engineered metabolic pathways further comprises an enzyme encoding a palmitoyl-acyl carrier protein thioesterase (FatB1).

25. The recombinant yeast microorganism of claim 24, wherein said palmitoyl-acyl carrier protein thioesterase (FatB1) is from *A. thaliana*.

26. The recombinant yeast microorganism of claim 1, wherein the one or more engineered metabolic pathways further comprises downregulation or deletion of native enzymes selected from a glycerol-3-phosphate dehydrogenase 1 (GPD1), a glycerol-3-phosphate dehydrogenase 2 (GPD2), a formate dehydrogenase 1 (FDH1), a formate dehydrogenase 2 (FDH2), or a combination thereof.

27. The recombinant yeast microorganism of claim 26, wherein said native enzyme is downregulated or deleted by insertion of a heterologous enzyme at the locus of the native enzyme.

28. The recombinant yeast microorganism of claim 1, wherein said heterologous pyruvate formate lyase enzyme is a pyruvate formate lyase A (PFLA), a pyruvate formate lyase B (PFLB), or a combination thereof.

29. The recombinant yeast microorganism of claim 1, wherein said pyruvate decarboxylase is a pyruvate decarboxylase 5 (PDC5), a pyruvate decarboxylase 6 (PDC6), a pyruvate decarboxylase 1 (PDC1), or a combination thereof.

30. The recombinant yeast microorganism of claim 1, wherein said yeast microorganism is selected from the group consisting of *Saccharomyces cerevisiae, Kluyveromyces lactis, Kluyveromyces marxianus, Pichia pastoris, Yarrowia lipolytica, Hansenula polymorpha, Phaffia rhodozyma, Candida utliis, Arxula adeninivorans, Pichia stipitis, Debaryomyces hansenit, Debaryomyces polymorphus, Schizosaccharomyces pombe, Candida albicans,* and *Schwanniomyces occidentalis*.

* * * * *